United States Patent
Stahl et al.

(10) Patent No.: US 7,417,134 B2
(45) Date of Patent: *Aug. 26, 2008

(54) IL-1 RECEPTOR BASED CYTOKINE TRAPS AND METHOD OF USING

(75) Inventors: Neil Stahl, Carmel, NY (US); George D. Yancopoulos, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 354 days.

This patent is subject to a terminal disclaimer.

(21) Appl. No.: 11/134,114

(22) Filed: May 20, 2005

(65) Prior Publication Data

US 2005/0222033 A1 Oct. 6, 2005

Related U.S. Application Data

(63) Continuation of application No. 10/282,162, filed on Oct. 28, 2002, now Pat. No. 6,927,044, which is a continuation-in-part of application No. 09/787,835, filed as application No. PCT/US99/22045 on Sep. 22, 1999, now abandoned, which is a continuation of application No. 09/313,942, filed on May 19, 1999, now Pat. No. 6,472,179.

(60) Provisional application No. 60/101,858, filed on Sep. 25, 1998.

(51) Int. Cl.
  *C07H 21/04* (2006.01)
  *C12N 15/00* (2006.01)
  *A61K 38/20* (2006.01)

(52) U.S. Cl. .................... 536/23.4; 536/23.1; 536/23.5; 435/69.1; 435/69.52; 435/69.7; 435/320.1; 424/85.2

(58) Field of Classification Search ........................ None
See application file for complete search history.

(56) References Cited

U.S. PATENT DOCUMENTS 5,470,952 A  11/1995 Stahl et al.
6,610,750 B1 *  8/2003 Charbit et al. .............. 514/734

FOREIGN PATENT DOCUMENTS

| EP | 0835939 A2 | 6/1991 |
|---|---|---|
| EP | 0533006 A1 | 9/1992 |
| WO | WO93/19163 | 9/1993 |
| WO | WO93/19777 | 10/1993 |
| WO | WO94/22914 | 10/1994 |
| WO | WO95/06737 | 3/1995 |
| WO | WO96/11213 | 4/1996 |
| WO | WO96/23881 | 8/1996 |
| WO | WO96/35783 | 11/1996 |
| WO | WO97/15669 | 5/1997 |
| WO | WO97/31946 | 9/1997 |
| WO | WO99/37772 | 7/1999 |

OTHER PUBLICATIONS

Greenfeeder, S.A., et al., (1995) J. Biol. Chem. 270(23):13757-13765.
Seipelt, I., et al., (1997) Biochem. Biophys. Res. Comm. 293:534-542.
Stahl, N., et al., (1999) FASEB J. Abstract, 1457.
U.S. Appl. No. 60/101,858, filed Sep. 25, 1998, Stahl,N. & Yancopoulos,G.D.
U.S. Appl. No. 09/313,942, filed May 19, 1999, Stahl,N. & Yancopoulos,G.D.
J. of Biol. Chem., 1995, Greenfeeder, S.A., et. al., "Molecular Cloning and Characterization of a Second Subunit of the Interleukin 1 Receptor Complex", 270(23):13757-13765.
Biochem and Biophys Res Comm, 1997, Seipelt, I., et al., "Overexpression, Purification, and Use of a Soluble Human Interleukin-4 Receptor α-chain/Igγ1 Fusion Protein for Ligand Binding Studies," 239:534-542.
FASEB Journal, 1999, Stahl,N., et al., "Cytokine Traps: Heteromeric Receptor-Based Protein Therapeutics that Function as High-Affinity Blockers of Cytokine Action," Abstract, 1457.

* cited by examiner

*Primary Examiner*—Christine J Saoud
*Assistant Examiner*—Jegatheesan Seharaseyon
(74) *Attorney, Agent, or Firm*—Valeta Gregg, Esq.

(57) ABSTRACT

The present invention provides a fusion polypeptide capable of binding interleukin-1 (O:-1) to form a nonfunctional complex. It also provides a nucleic acid sequence encoding the fusion polypeptide and methods of using the fusion polypeptide.

13 Claims, 174 Drawing Sheets

Figure 4A

Amino acid sequence of human gp130-Fc-His6

```
Sequence Range: 1 to 861

10          20          30          40          50          60
           *           *           *           *           *           *
MVTLQTWVVQALFIFLTTES TGELLDPCGYISPESPVVQL HSNFTAVCVLKEKCMDYFHV 70          80          90         100         110         120
           *           *           *           *           *           *
NANYIVWKTNHFTIPKEQYT IINRTASSVTFTDIASLNIQ LTCNILTFGQLEQNVYGITI 130         140         150         160         170         180
           *           *           *           *           *           *
ISGLPPEKPKNLSCIVNEGK KMRCEWDGGRETHLETNFTL KSEWATHKFADCKAKRDTPT 190         200         210         220         230         240
           *           *           *           *           *           *
SCTVDYSTVYFVNIEVWVEA ENALGKVTSDHINFDPVYKV KPNPPHNLSVINSEELSSIL 250         260         270         280         290         300
           *           *           *           *           *           *
KLTWTNPSIKSVIILKYNIQ YRTKDASTWSQIPPEDTAST RSSFTVQDLKPFTEYVFRIR 310         320         330         340         350         360
           *           *           *           *           *           *
CMKEDGKGYWSDWSEEASGI TYEDRPSKAPSFWYKIDPSH TQGYRTVQLVWKTLPPFEAN 370         380         390         400         410         420
           *           *           *           *           *           *
GKILDYEVTLTRWKSHLQNY TVNATKLTVNLTNDRYLATL TVRNLVGKSDAAVLTIPACD 430         440         450         460         470         480
           *           *           *           *           *           *
FQATHPVMDLKAFPKDNMLW VEWTTPRESVKKYILEWCVL SDKAPCITDWQQEDGTVHRT 490         500         510         520         530         540
           *           *           *           *           *           *
YLRGNLAESKCYLITVTPVY ADGPGSPESIKAYLKQAPPS KGPTVRTKKVGKNEAVLEWD 550         560         570         580         590         600
           *           *           *           *           *           *
QLPVDVQNGFIRNYTIFYRT IIGNETAVNVDSSHTEYTLS SLTSDTLYMVRMAAYTDEGG 610         620         630         640         650         660
           *           *         * † †       *           *
KDGPEFTFTTPKFAQGEIES GEPKSCDKTHTCPPCPAPEL LGGPSVFLFPPKPKDTLMIS 670         680         690         700         710         720
           *           *           *           *           *           *
RTPEVTCVVVDVSHEDPEVK FNWYVDGVEVHNAKTKPREE QYNSTYRVVSVLTVLHQDWL 730         740         750         760         770         780
           *           *           *           *           *           *
```

Figure 4B

NGKEYKCKVSNKALPAPIEK TISKAKGQPREPQVYTLPPS RDELTKNQVSLTCLVKGFYP

```
      790            800            810            820            830            840
       *              *              *              *              *              *
SDIAVEWESNGQPENNYKTT PPVLDSDGSFFLYSKLTVDK SRWQQGNVFSCSVMHEALHN 850            860
       *              *
HYTQKSLSLSPGKHHHHHH.
```

Fig.5.

The amino acid sequence of human IL-6Rα-Fc

Sequence Range: 1 to 594

```
       10             20             30             40             50             60
        *              *              *              *              *              *
MVAVGCALLAALLAAPGAAL APRRCPAQEVARGVLTSLPG DSVTLTCPGVEPEDNATVHW 70             80             90            100            110            120
        *              *              *              *              *              *
VLRKPAAGSHPSRWAGMGRR LLLRSVQLHDSGNYSCYRAG RPAGTVHLLVDVPPEEPQLS 130            140            150            160            170            180
        *              *              *              *              *              *
CFRKSPLSNVVCEWGPRSTP SLTTKAVLLVRKFQNSPAED FQEPCQYSQESQKFSCQLAV 190            200            210            220            230            240
        *              *              *              *              *              *
PEGDSSFYIVSMCVASSVGS KFSKTQTFQGCGILQPDPPA NITVTAVARNPRWLSVTWQD 250            260            270            280            290            300
        *              *              *              *              *              *
PHSWNSSFYRLRFELRYRAE RSKTFTTWMVKDLQHHCVIH DAWSGLRHVVQLRAQEEFGQ 310            320            330            340            350            360
        *              *              *              *              *              *
GEWSEWSPEAMGTPWTESRS PPAENEVSTPMQALTTNKDD DNILFRDSANATSLPVQDAG 370            380            390            400            410            420
       *†     †        *              *              *              *              *
EPKSCDKTHTCPPCPAPELL GGPSVFLFPPKPKDTLMISR TPEVTCVVVDVSHEDPEVKF 430            440            450            460            470            480
        *              *              *              *              *              *
NWYVDGVEVHNAKTKPREEQ YNSTYRVVSVLTVLHQDWLN GKEYKCKVSNKALPAPIEKT 490            500            510            520            530            540
        *              *              *              *              *              *
ISKAKGQPREPQVYTLPPSR DELTKNQVSLTCLVKGFYPS DIAVEWESNGQPENNYKTTP 550            560            570            580            590
        *              *              *              *              *
PVLDSDGSFFLYSKLTVDKS RWQQGNVFSCSVMHEALHNH YTQKSLSLSPGK.
```

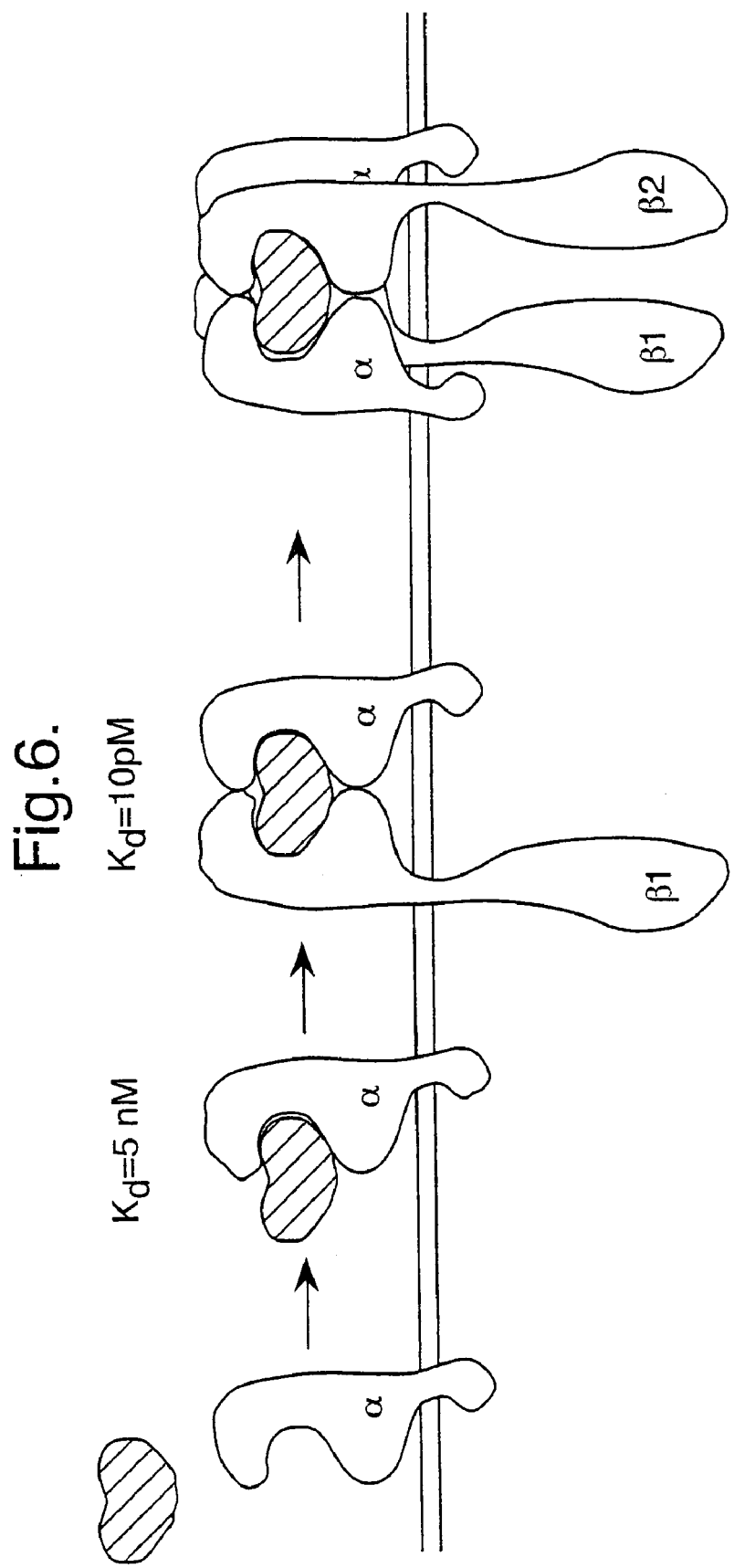

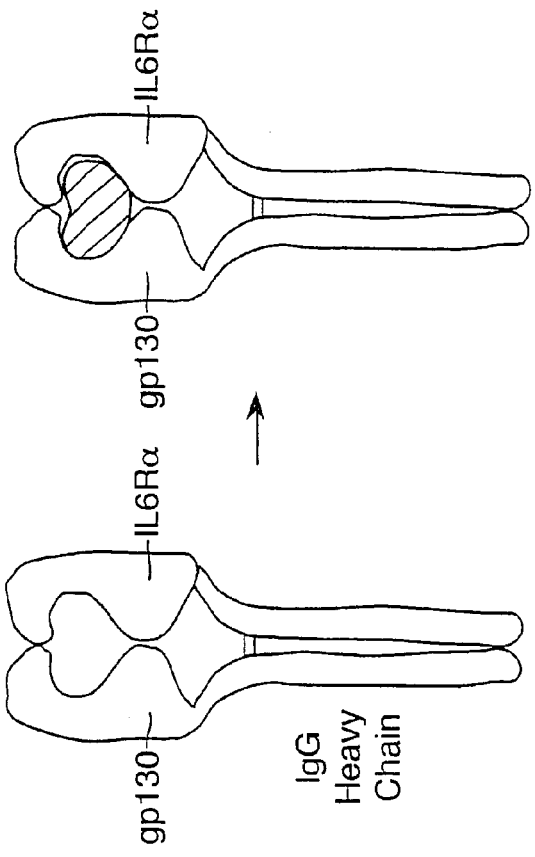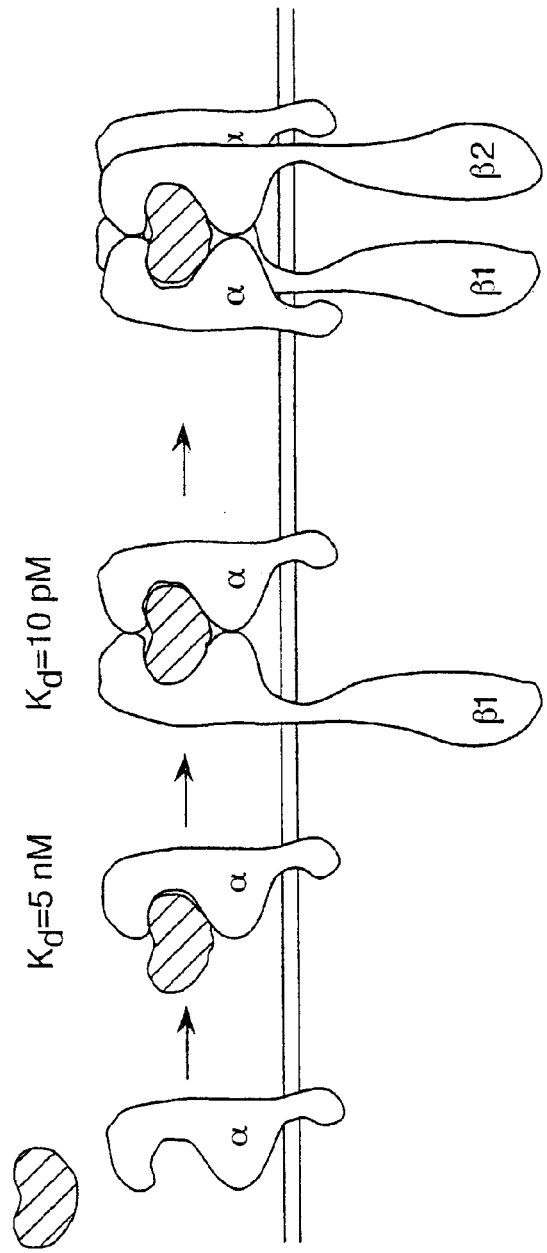
Fig. 7.

Immunoglobulin Heavy/Light Chain receptor Fusions

Figure 9A

Amino acid sequence of gp130-Cγ1

Sequence Range: 1 to 952

```
         10          20          30          40          50          60
          *           *           *           *           *           *
MVTLQTWVVQALFIFLTTES TGELLDPCGYISPESPVVQL HSNFTAVCVLKEKCMDYFHV 70          80          90         100         110         120
          *           *           *           *           *           *
NANYIVWKTNHFTIPKEQYT IINRTASSVTFTDIASLNIQ LTCNILTFGQLEQNVYGITI 130         140         150         160         170         180
          *           *           *           *           *           *
ISGLPPEKPKNLSCIVNEGK KMRCEWDGGRETHLETNFTL KSEWATHKFADCKAKRDTPT 190         200         210         220         230         240
          *           *           *           *           *           *
SCTVDYSTVYFVNIEVWVEA ENALGKVTSDHINFDPVYKV KPNPPHNLSVINSEELSSIL 250         260         270         280         290         300
          *           *           *           *           *           *
KLTWTNPSIKSVIILKYNIQ YRTKDASTWSQIPPEDTAST RSSFTVQDLKPFTEYVFRIR 310         320         330         340         350         360
          *           *           *           *           *           *
CMKEDGKGYWSDWSEEASGI TYEDRPSKAPSFWYKIDPSH TQGYRTVQLVWKTLPPFEAN 370         380         390         400         410         420
          *           *           *           *           *           *
GKILDYEVTLTRWKSHLQNY TVNATKLTVNLTNDRYLATL TVRNLVGKSDAAVLTIPACD 430         440         450         460         470         480
          *           *           *           *           *           *
FQATHPVMDLKAFPKDNMLW VEWTTPRESVKKYILEWCVL SDKAPCITDWQQEDGTVHRT 490         500         510         520         530         540
          *           *           *           *           *           *
YLRGNLAESKCYLITVTPVY ADGPGSPESIKAYLKQAPPS KGPTVRTKKVGKNEAVLEWD 550         560         570         580         590         600
          *           *           *           *           *           *
QLPVDVQNGFIRNYTIFYRT IIGNETAVNVDSSHTEYTLS SLTSDTLYMVRMAAYTDEGG 610         620         630         640         650         660
          *           *           *           *           *           *
KDGPEFTFTTPKFAQGEIES GASTKGPSVFPLAPSSKSTS GGTAALGCLVKDYFPEPVTV 670         680         690         700         710         720
          *           *           *           *           *           *
SWNSGALTSGVHTFPAVLQS SGLYSLSSVVTVPSSSLGTQ TYICNVNHKPSNTKVDKKVE 730         740         750         760         770         780
          *           *           *           *           *           *
PKSCDKTHTCPPCPAPELLG GPSVFLFPPKPKDTLMISRT PEVTCVVVDVSHEDPEVKFN
```

Figure 9B

```
         790         800         810         820         830         840
          *           *           *           *           *           *
WYVDGVEVHNAKTKPREEQY NSTYRVVSVLTVLHQDWLNG KEYKCKVSNKALPAPIEKTI 850         860         870         880         890         900
          *           *           *           *           *           *
SKAKGQPREPQVYTLPPSRD ELTKNQVSLTCLVKGFYPSD IAVEWESNGQPENNYKTTPP 910         920         930         940         950
          *           *           *           *           *
VLDSDGSFFLYSKLTVDKSR WQQGNVFSCSVMHEALHNHY TQKSLSLSPGK*
```

Fig. 10.

Amino acid sequence of gp130Δ3fibro

Sequence Range: 1 to 332

```
         10          20          30          40          50          60
          *           *           *           *           *           *
MVTLQTWVVQALFIFLTTES TGELLDPCGYISPESPVVQL HSNFTAVCVLKEKCMDYFHV 70          80          90         100         110         120
          *           *           *           *           *           *
NANYIVWKTNHFTIPKEQYT IINRTASSVTFTDIASLNIQ LTCNILTFGQLEQNVYGITI 130         140         150         160         170         180
          *           *           *           *           *           *
ISGLPPEKPKNLSCIVNEGK KMRCEWDGGRETHLETNFTL KSEWATHKFADCKAKRDTPT 190         200         210         220         230         240
          *           *           *           *           *           *
SCTVDYSTVYFVNIEVWVEA ENALGKVTSDHINFDPVYKV KPNPPHNLSVINSEELSSIL 250         260         270         280         290         300
          *           *           *           *           *           *
KLTWTNPSIKSVIILKYNIQ YRTKDASTWSQIPPEDTAST RSSFTVQDLKPFTEYVFRIR 310         320         330
          *           *           *
CMKEDGKGYWSDWSEEASGI TYEDRPSKAPSG
```

Fig. 11.
Amino acid sequence of J-CH1

Sequence Range: 1 to 121

```
         10          20          30          40          50          60
          *           *           *           *           *           *
SGGQGTLVTVSSASTKGPSV FPLAPSSKSTSGGTAALGCL VKDYFPEPVTVSWNSGALTS 70          80          90         100         110         120
          *           *           *           *           *           *
GVHTFPAVLQSSGLYSLSSV VTVPSSSLGTQTYICNVNHK PSNTKVDKKVEPKSCDKTHT*
```

Fig. 12.
Amino acid sequence of Cγ4

Sequence Range: 1 to 330

```
         10          20          30          40          50          60
          *           *           *           *           *           *
SGASTKGPSVFPLAPCSRST SESTAALGCLVKDYFPEPVT VSWNSGALTSGVHTFPAVLQ 70          80          90         100         110         120
          *           *           *           *           *           *
SSGLYSLSSVVTVPSSSLGT KTYTCNVDHKPSNTKVDKRV ESKYGPPCPSCPAPEFLGGP 130         140         150         160         170         180
          *           *           *           *           *           *
SVFLFPPKPKDTLMISRTPE VTCVVVDVSQEDPEVQFNWY VDGVEVHNAKTKPREEQFNS 190         200         210         220         230         240
          *           *           *           *           *           *
TYRVVSVLTVLHQDWLNGKE YKCKVSNKGLPSSIEKTISK AKGQPREPQVYTLPPSQEEM 250         260         270         280         290         300
          *           *           *           *           *           *
TKNQVSLTCLVKGFYPSDIA VEWESNGQPENNYKTTPPVL DSDGSFFLYSRLTVDKSRWQ 310         320         330
          *           *           *
EGNVFSCSVMHEALHNHYTQ KSLSLSLGK*
```

Fig.13.

Amino acid sequence of κ-domain

Sequence Range: 1 to 108

```
          10          20          30          40          50          60
          *           *           *           *           *           *
SGTVAAPSVFIFPPSDEQLK SGTASVVCLLNNFYPREAKV QWKVDNALQSGNSQESVTEQ 70          80          90         100
          *           *           *           *
DSKDSTYSLSSTLTLSKADY EKHKVYACEVTHQGLSSPVT KSFNRGEC*
```

Fig.14.

Amino acid sequence of λ-domain:

Sequence Range: 1 to 107

```
          10          20          30          40          50          60
          *           *           *           *           *           *
SGPKAAPSVTLFPPSSEELQ ANKATLVCLISDFYPGAVTV AWKADSSPVKAGVETTTPSK 70          80          90         100
          *           *           *           *
QSNNKYAASSYLSLTPEQWK SHRSYSCQVTHEGSTVEKTV APTECS*
```

Fig. 15.
Amino acid sequence of the soluble IL-6Rα domain

Sequence Range: 1 to 360

```
          10          20          30          40          50          60
           *           *           *           *           *           *
MVAVGCALLAALLAAPGAAL APRRCPAQEVARGVLTSLPG DSVTLTCPGVEPEDNATVHW 70          80          90         100         110         120
           *           *           *           *           *           *
VLRKPAAGSHPSRWAGMGRR LLLRSVQLHDSGNYSCYRAG RPAGTVHLLVDVPPEEPQLS 130         140         150         160         170         180
           *           *           *           *           *           *
CFRKSPLSNVVCEWGPRSTP SLTTKAVLLVRKFQNSPAED FQEPCQYSQESQKFSCQLAV 190         200         210         220         230         240
           *           *           *           *           *           *
PEGDSSFYIVSMCVASSVGS KFSKTQTFQGCGILQPDPPA NITVTAVARNPRWLSVTWQD 250         260         270         280         290         300
           *           *           *           *           *           *
PHSWNSSFYRLRFELRYRAE RSKTFTTWMVKDLQHHCVIH DAWSGLRHVVQLRAQEEFGQ 310         320         330         340         350         360
           *           *           *           *           *           *
GEWSEWSPEAMGTPWTESRS PPAENEVSTPMQALTTNKDD DNILFRDSANATSLPVQDAG
```

Fig. 16.
Amino acid sequence of the soluble IL-6kα313 domain

Sequence Range: 1 to 315

```
          10          20          30          40          50          60
           *           *           *           *           *           *
MVAVGCALLAALLAAPGAAL APRRCPAQEVARGVLTSLPG DSVTLTCPGVEPEDNATVHW 70          80          90         100         110         120
           *           *           *           *           *           *
VLRKPAAGSHPSRWAGMGRR LLLRSVQLHDSGNYSCYRAG RPAGTVHLLVDVPPEEPQLS 130         140         150         160         170         180
           *           *           *           *           *           *
CFRKSPLSNVVCEWGPRSTP SLTTKAVLLVRKFQNSPAED FQEPCQYSQESQKFSCQLAV 190         200         210         220         230         240
           *           *           *           *           *           *
PEGDSSFYIVSMCVASSVGS KFSKTQTFQGCGILQPDPPA NITVTAVARNPRWLSVTWQD 250         260         270         280         290         300
           *           *           *           *           *           *
PHSWNSSFYRLRFELRYRAE RSKTFTTWMVKDLQHHCVIH DAWSGLRHVVQLRAQEEFGQ

310
           *
GEWSEWSPEAMGTTG
```

Figure 19 A
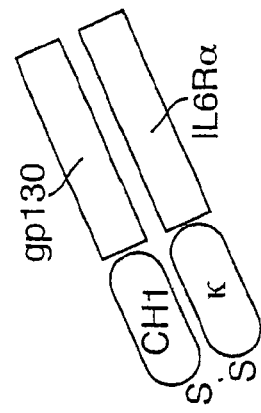
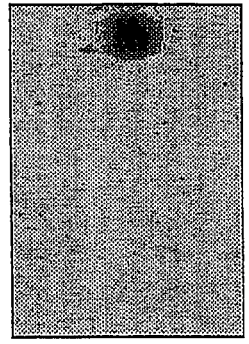
Does IL-6 Induce Complex Formation ?
No Protein A binding
Protein A binding — GF6F
Figure 19B
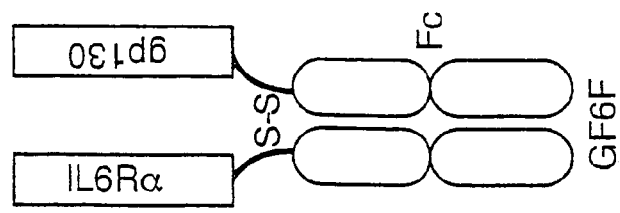
IP: Prot A
Blot: α-kappa

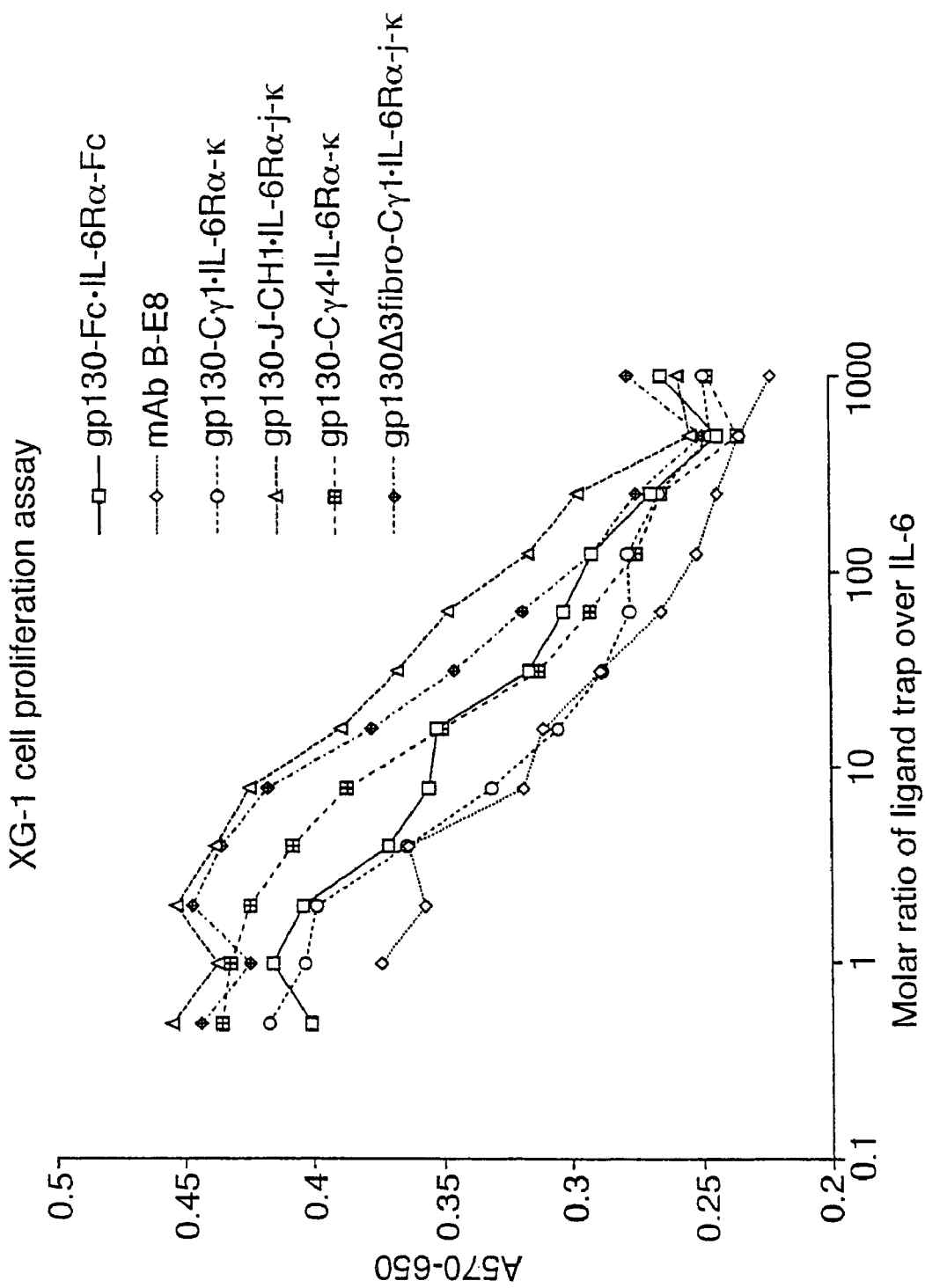

Fig.21A.

```
          10            20            30            40
           *             *             *             *
ATG GTG AAG CCA TCA TTA CCA TTC ACA TCC CTC TTA TTC CTG CAG CTG
Met Val Lys Pro Ser Leu Pro Phe Thr Ser Leu Leu Phe Leu Gln Leu>

50            60            70            80            90
   *             *             *             *             *
CCC CTG CTG GGA GTG GGG CTG AAC ACG ACA ATT CTG ACG CCC AAT GGG
Pro Leu Leu Gly Val Gly Leu Asn Thr Thr Ile Leu Thr Pro Asn Gly>

100           110           120           130           140
      *             *             *             *             *
AAT GAA GAC ACC ACA GCT GAT TTC TTC CTG ACC ACT ATG CCC ACT GAC
Asn Glu Asp Thr Thr Ala Asp Phe Phe Leu Thr Thr Met Pro Thr Asp>

150           160           170           180           190
      *             *             *             *             *
TCC CTC AGT GTT TCC ACT CTG CCC CTC CCA GAG GTT CAG TGT TTT GTG
Ser Leu Ser Val Ser Thr Leu Pro Leu Pro Glu Val Gln Cys Phe Val>

200           210           220           230           240
         *             *             *             *             *
TTC AAT GTC GAG TAC ATG AAT TGC ACT TGG AAC AGC AGC TCT GAG CCC
Phe Asn Val Glu Tyr Met Asn Cys Thr Trp Asn Ser Ser Ser Glu Pro>

250           260           270           280
            *             *             *             *
CAG CCT ACC AAC CTC ACT CTG CAT TAT TGG TAC AAG AAC TCG GAT AAT
Gln Pro Thr Asn Leu Thr Leu His Tyr Trp Tyr Lys Asn Ser Asp Asn>

290           300           310           320           330
 *             *             *             *             *
GAT AAA GTC CAG AAG TGC AGC CAC TAT CTA TTC TCT GAA GAA ATC ACT
Asp Lys Val Gln Lys Cys Ser His Tyr Leu Phe Ser Glu Glu Ile Thr>

340           350           360           370           380
    *             *             *             *             *
TCT GGC TGT CAG TTG CAA AAA AAG GAG ATC CAC CTC TAC CAA ACA TTT
Ser Gly Cys Gln Leu Gln Lys Lys Glu Ile His Leu Tyr Gln Thr Phe>

390           400           410           420           430
    *             *             *             *             *
GTT GTT CAG CTC CAG GAC CCA CGG GAA CCC AGG AGA CAG GCC ACA CAG
Val Val Gln Leu Gln Asp Pro Arg Glu Pro Arg Arg Gln Ala Thr Gln>

440           450           460           470           480
       *             *             *             *             *
ATG CTA AAA CTG CAG AAT CTG GTG ATC CCC TGG GCT CCA GAG AAC CTA
Met Leu Lys Leu Gln Asn Leu Val Ile Pro Trp Ala Pro Glu Asn Leu>

490           500           510           520
          *             *             *             *
ACA CTT CAC AAA CTG AGT GAA TCC CAG CTA GAA CTG AAC TGG AAC AAC
Thr Leu His Lys Leu Ser Glu Ser Gln Leu Glu Leu Asn Trp Asn Asn>

530           540           550           560           570
 *             *             *             *             *
AGA TTC TTG AAC CAC TGT TTG GAG CAC TTG GTG CAG TAC CGG ACT GAC
Arg Phe Leu Asn His Cys Leu Glu His Leu Val Gln Tyr Arg Thr Asp>
```

Fig.21B.

```
     580            590            600            610            620
      *              *              *              *              *
TGG GAC CAC AGC TGG ACT GAA CAA TCA GTG GAT TAT AGA CAT AAG TTC
Trp Asp His Ser Trp Thr Glu Gln Ser Val Asp Tyr Arg His Lys Phe>

630            640            650            660            670
           *              *              *              *              *
TCC TTG CCT AGT GTG GAT GGG CAG AAA CGC TAC ACG TTT CGT GTT CGG
Ser Leu Pro Ser Val Asp Gly Gln Lys Arg Tyr Thr Phe Arg Val Arg>

680            690            700            710            720
           *              *              *              *              *
AGC CGC TTT AAC CCA CTC TGT GGA AGT GCT CAG CAT TGG AGT GAA TGG
Ser Arg Phe Asn Pro Leu Cys Gly Ser Ala Gln His Trp Ser Glu Trp>

730            740            750            760
           *              *              *              *              *
AGC CAC CCA ATC CAC TGG GGG AGC AAT ACT TCA AAA GAG AAC GCG TCG
Ser His Pro Ile His Trp Gly Ser Asn Thr Ser Lys Glu Asn Ala Ser>

770            780            790            800            810
 *              *              *              *              *              *
TCT GGG AAC ATG AAG GTC CTG CAG GAG CCC ACC TGC GTC TCC GAC TAC
Ser Gly Asn Met Lys Val Leu Gln Glu Pro Thr Cys Val Ser Asp Tyr>

820            830            840            850            860
       *              *              *              *              *
ATG AGC ATC TCT ACT TGC GAG TGG AAG ATG AAT GGT CCC ACC AAT TGC
Met Ser Ile Ser Thr Cys Glu Trp Lys Met Asn Gly Pro Thr Asn Cys>

870            880            890            900            910
           *              *              *              *              *
AGC ACC GAG CTC CGC CTG TTG TAC CAG CTG GTT TTT CTG CTC TCC GAA
Ser Thr Glu Leu Arg Leu Leu Tyr Gln Leu Val Phe Leu Leu Ser Glu>

920            930            940            950            960
               *              *              *              *              *
GCC CAC ACG TGT ATC CCT GAG AAC AAC GGA GGC GCG GGG TGC GTG TGC
Ala His Thr Cys Ile Pro Glu Asn Asn Gly Gly Ala Gly Cys Val Cys>

970            980            990            1000
               *              *              *              *              *
CAC CTG CTC ATG GAT GAC GTG GTC AGT GCG GAT AAC TAT ACA CTG GAC
His Leu Leu Met Asp Asp Val Val Ser Ala Asp Asn Tyr Thr Leu Asp>

1010           1020           1030           1040           1050
  *              *              *              *              *              *
CTG TGG GCT GGG CAG CAG CTG CTG TGG AAG GGC TCC TTC AAG CCC AGC
Leu Trp Ala Gly Gln Gln Leu Leu Trp Lys Gly Ser Phe Lys Pro Ser>

1060           1070           1080           1090           1100
       *              *              *              *              *
GAG CAT GTG AAA CCC AGG GCC CCA GGA AAC CTG ACA GTT CAC ACC AAT
Glu His Val Lys Pro Arg Ala Pro Gly Asn Leu Thr Val His Thr Asn>

1110           1120           1130           1140           1150
           *              *              *              *              *
GTC TCC GAC ACT CTG CTG CTG ACC TGG AGC AAC CCG TAT CCC CCT GAC
Val Ser Asp Thr Leu Leu Leu Thr Trp Ser Asn Pro Tyr Pro Pro Asp>

```
AAT TAC CTG TAT AAT CAT CTC ACC TAT GCA GTC AAC ATT TGG AGT GAA
Asn Tyr Leu Tyr Asn His Leu Thr Tyr Ala Val Asn Ile Trp Ser Glu>
            1210        1220        1230        1240
             *           *           *           *           *
AAC GAC CCG GCA GAT TTC AGA ATC TAT AAC GTG ACC TAC CTA GAA CCC
Asn Asp Pro Ala Asp Phe Arg Ile Tyr Asn Val Thr Tyr Leu Glu Pro>
   1250        1260        1270        1280        1290
    *           *           *           *           *           *
TCC CTC CGC ATC GCA GCC AGC ACC CTG AAG TCT GGG ATT TCC TAC AGG
Ser Leu Arg Ile Ala Ala Ser Thr Leu Lys Ser Gly Ile Ser Tyr Arg>
       1300        1310        1320        1330        1340
        *           *           *           *           *
GCA CGG GTG AGG GCC TGG GCT CAG TGC TAT AAC ACC ACC TGG AGT GAG
Ala Arg Val Arg Ala Trp Ala Gln Cys Tyr Asn Thr Thr Trp Ser Glu>
          1350        1360        1370        1380        1390
           *           *           *           *           *
TGG AGC CCC AGC ACC AAG TGG CAC AAC TCC TAC AGG GAG CCC TTC GAG
Trp Ser Pro Ser Thr Lys Trp His Asn Ser Tyr Arg Glu Pro Phe Glu>
              1400        1410        1420        1430        1440
               *           *           *           *           *
CAG TCC GGA GAC AAA ACT CAC ACA TGC CCA CCG TGC CCA GCA CCT GAA
Gln Ser Gly Asp Lys Thr His Thr Cys Pro Pro Cys Pro Ala Pro Glu>
                 1450        1460        1470        1480
                  *           *           *           *           *
CTC CTG GGG GGA CCG TCA GTC TTC CTC TTC CCC CCA AAA CCC AAG GAC
Leu Leu Gly Gly Pro Ser Val Phe Leu Phe Pro Pro Lys Pro Lys Asp>
   1490        1500        1510        1520        1530
    *           *           *           *           *           *
ACC CTC ATG ATC TCC CGG ACC CCT GAG GTC ACA TGC GTG GTG GTG GAC
Thr Leu Met Ile Ser Arg Thr Pro Glu Val Thr Cys Val Val Val Asp>
       1540        1550        1560        1570        1580
        *           *           *           *           *
GTG AGC CAC GAA GAC CCT GAG GTC AAG TTC AAC TGG TAC GTG GAC GGC
Val Ser His Glu Asp Pro Glu Val Lys Phe Asn Trp Tyr Val Asp Gly>
          1590        1600        1610        1620        1630
           *           *           *           *           *
GTG GAG GTG CAT AAT GCC AAG ACA AAG CCG CGG GAG GAG CAG TAC AAC
Val Glu Val His Asn Ala Lys Thr Lys Pro Arg Glu Glu Gln Tyr Asn>
              1640        1650        1660        1670        1680
               *           *           *           *           *
AGC ACG TAC CGT GTG GTC AGC GTC CTC ACC GTC CTG CAC CAG GAC TGG
Ser Thr Tyr Arg Val Val Ser Val Leu Thr Val Leu His Gln Asp Trp>
                 1690        1700        1710        1720
                  *           *           *           *           *
CTG AAT GGC AAG GAG TAC AAG TGC AAG GTC TCC AAC AAA GCC CTC CCA
Leu Asn Gly Lys Glu Tyr Lys Cys Lys Val Ser Asn Lys Ala Leu Pro>
   1730        1740        1750        1760        1770
    *           *           *           *           *           *
GCC CCC ATC GAG AAA ACC ATC TCC AAA GCC AAA GGG CAG CCC CGA GAA
Ala Pro Ile Glu Lys Thr Ile Ser Lys Ala Lys Gly Gln Pro Arg Glu>
```

Fig.21D.

```
       1780            1790            1800            1810            1820
         *               *               *               *               *
CCA CAG GTG TAC ACC CTG CCC CCA TCC CGG GAG GAG ATG ACC AAG AAC
Pro Gln Val Tyr Thr Leu Pro Pro Ser Arg Glu Glu Met Thr Lys Asn>

1830            1840            1850            1860            1870
  *      *        *      *        *      *        *      *        *      *
CAG GTC AGC CTG ACC TGC CTG GTC AAA GGC TTC TAT CCC AGC GAC ATC
Gln Val Ser Leu Thr Cys Leu Val Lys Gly Phe Tyr Pro Ser Asp Ile>

1880            1890            1900            1910            1920
  *      *        *      *        *      *        *      *        *      *
GCC GTG GAG TGG GAG AGC AAT GGG CAG CCG GAG AAC AAC TAC AAG ACC
Ala Val Glu Trp Glu Ser Asn Gly Gln Pro Glu Asn Asn Tyr Lys Thr>

1930            1940            1950            1960
         *      *        *      *        *      *        *      *        *
ACG CCT CCC GTG CTG GAC TCC GAC GGC TCC TTC TTC CTC TAT AGC AAG
Thr Pro Pro Val Leu Asp Ser Asp Gly Ser Phe Phe Leu Tyr Ser Lys>

1970           1980            1990            2000            2010
  *      *        *      *        *      *        *      *        *      *
CTC ACC GTG GAC AAG AGC AGG TGG CAG CAG GGG AAC GTC TTC TCA TGC
Leu Thr Val Asp Lys Ser Arg Trp Gln Gln Gly Asn Val Phe Ser Cys>

2020            2030            2040            2050            2060
         *               *               *               *               *
TCC GTG ATG CAT GAG GCT CTG CAC AAC CAC TAC ACG CAG AAG AGC CTC
Ser Val Met His Glu Ala Leu His Asn His Tyr Thr Gln Lys Ser Leu>

2070            2080
         *               *        *
TCC CTG TCT CCG GGT AAA TGA
Ser Leu Ser Pro Gly Lys ***>
```

Fig.22A.

```
            10                  20                  30                  40
            *                   *                   *                   *
ATG GTG AAG CCA TCA TTA CCA TTC ACA TCC CTC TTA TTC CTG CAG CTG
Met Val Lys Pro Ser Leu Pro Phe Thr Ser Leu Leu Phe Leu Gln Leu>

50                  60                  70                  80                  90
 *                   *                   *                   *                   *
CCC CTG CTG GGA GTG GGG CTG AAC ACG ACA ATT CTG ACG CCC AAT GGG
Pro Leu Leu Gly Val Gly Leu Asn Thr Thr Ile Leu Thr Pro Asn Gly>

100                 110                 120                 130                 140
        *                   *                   *                   *                   *
AAT GAA GAC ACC ACA GCT GAT TTC TTC CTG ACC ACT ATG CCC ACT GAC
Asn Glu Asp Thr Thr Ala Asp Phe Phe Leu Thr Thr Met Pro Thr Asp>

150                 160                 170                 180                 190
        *                   *                   *                   *                   *
TCC CTC AGT GTT TCC ACT CTG CCC CTC CCA GAG GTT CAG TGT TTT GTG
Ser Leu Ser Val Ser Thr Leu Pro Leu Pro Glu Val Gln Cys Phe Val>

200                 210                 220                 230                 240
            *                   *                   *                   *                   *
TTC AAT GTC GAG TAC ATG AAT TGC ACT TGG AAC AGC AGC TCT GAG CCC
Phe Asn Val Glu Tyr Met Asn Cys Thr Trp Asn Ser Ser Ser Glu Pro>

250                 260                 270                 280
            *                   *                   *                   *
CAG CCT ACC AAC CTC ACT CTG CAT TAT TGG TAC AAG AAC TCG GAT AAT
Gln Pro Thr Asn Leu Thr Leu His Tyr Trp Tyr Lys Asn Ser Asp Asn>

290                 300                 310                 320                 330
*                   *                   *                   *                   *
GAT AAA GTC CAG AAG TGC AGC CAC TAT CTA TTC TCT GAA GAA ATC ACT
Asp Lys Val Gln Lys Cys Ser His Tyr Leu Phe Ser Glu Glu Ile Thr>

340                 350                 360                 370                 380
    *                   *                   *                   *                   *
TCT GGC TGT CAG TTG CAA AAA AAG GAG ATC CAC CTC TAC CAA ACA TTT
Ser Gly Cys Gln Leu Gln Lys Lys Glu Ile His Leu Tyr Gln Thr Phe>

390                 400                 410                 420                 430
            *                   *                   *                   *                   *
GTT GTT CAG CTC CAG GAC CCA CGG GAA CCC AGG AGA CAG GCC ACA CAG
Val Val Gln Leu Gln Asp Pro Arg Glu Pro Arg Arg Gln Ala Thr Gln>

440                 450                 460                 470                 480
            *                   *                   *                   *                   *
ATG CTA AAA CTG CAG AAT CTG GTG ATC CCC TGG GCT CCA GAG AAC CTA
Met Leu Lys Leu Gln Asn Leu Val Ile Pro Trp Ala Pro Glu Asn Leu>

490                 500                 510                 520
            *                   *                   *                   *
ACA CTT CAC AAA CTG AGT GAA TCC CAG CTA GAA CTG AAC TGG AAC AAC
Thr Leu His Lys Leu Ser Glu Ser Gln Leu Glu Leu Asn Trp Asn Asn>

530                 540                 550                 560                 570
*                   *                   *                   *                   *
AGA TTC TTG AAC CAC TGT TTG GAG CAC TTG GTG CAG TAC CGG ACT GAC
Arg Phe Leu Asn His Cys Leu Glu His Leu Val Gln Tyr Arg Thr Asp>
```

Fig.22B.

```
       580             590             600             610             620
        *       *       *       *       *       *       *       *       *
TGG GAC CAC AGC TGG ACT GAA CAA TCA GTG GAT TAT AGA CAT AAG TTC
Trp Asp His Ser Trp Thr Glu Gln Ser Val Asp Tyr Arg His Lys Phe>

630             640             650             660             670
        *       *       *       *       *       *       *       *       *
TCC TTG CCT AGT GTG GAT GGG CAG AAA CGC TAC ACG TTT CGT GTT CGG
Ser Leu Pro Ser Val Asp Gly Gln Lys Arg Tyr Thr Phe Arg Val Arg>

680             690             700             710             720
        *       *       *       *       *       *       *       *       *
AGC CGC TTT AAC CCA CTC TGT GGA AGT GCT CAG CAT TGG AGT GAA TGG
Ser Arg Phe Asn Pro Leu Cys Gly Ser Ala Gln His Trp Ser Glu Trp>

730             740             750             760
        *       *       *       *       *       *       *       *       *
AGC CAC CCA ATC CAC TGG GGG AGC AAT ACT TCA AAA GAG AAC GGG AAC
Ser His Pro Ile His Trp Gly Ser Asn Thr Ser Lys Glu Asn Gly Asn>

770             780             790             800             810
 *       *       *       *       *       *       *       *       *       *
ATG AAG GTC CTG CAG GAG CCC ACC TGC GTC TCC GAC TAC ATG AGC ATC
Met Lys Val Leu Gln Glu Pro Thr Cys Val Ser Asp Tyr Met Ser Ile>

820             830             840             850             860
        *       *       *       *       *       *       *       *       *
TCT ACT TGC GAG TGG AAG ATG AAT GGT CCC ACC AAT TGC AGC ACC GAG
Ser Thr Cys Glu Trp Lys Met Asn Gly Pro Thr Asn Cys Ser Thr Glu>

870             880             890             900             910
        *       *       *       *       *       *       *       *       *
CTC CGC CTG TTG TAC CAG CTG GTT TTT CTG CTC TCC GAA GCC CAC ACG
Leu Arg Leu Leu Tyr Gln Leu Val Phe Leu Leu Ser Glu Ala His Thr>

920             930             940             950             960
        *       *       *       *       *       *       *       *       *
TGT ATC CCT GAG AAC AAC GGA GGC GCG GGG TGC GTG TGC CAC CTG CTC
Cys Ile Pro Glu Asn Asn Gly Gly Ala Gly Cys Val Cys His Leu Leu>

970             980             990             1000
        *       *       *       *       *       *       *       *       *
ATG GAT GAC GTG GTC AGT GCG GAT AAC TAT ACA CTG GAC CTG TGG GCT
Met Asp Asp Val Val Ser Ala Asp Asn Tyr Thr Leu Asp Leu Trp Ala>

1010            1020            1030            1040            1050
 *       *       *       *       *       *       *       *       *       *
GGG CAG CAG CTG CTG TGG AAG GGC TCC TTC AAG CCC AGC GAG CAT GTG
Gly Gln Gln Leu Leu Trp Lys Gly Ser Phe Lys Pro Ser Glu His Val>

1060            1070            1080            1090            1100
        *       *       *       *       *       *       *       *       *
AAA CCC AGG GCC CCA GGA AAC CTG ACA GTT CAC ACC AAT GTC TCC GAC
Lys Pro Arg Ala Pro Gly Asn Leu Thr Val His Thr Asn Val Ser Asp>

1110            1120            1130            1140            1150
        *       *       *       *       *       *       *       *       *
ACT CTG CTG CTG ACC TGG AGC AAC CCG TAT CCC CCT GAC AAT TAC CTG
Thr Leu Leu Leu Thr Trp Ser Asn Pro Tyr Pro Pro Asp Asn Tyr Leu>

```
        TAT AAT CAT CTC ACC TAT GCA GTC AAC ATT TGG AGT GAA AAC GAC CCG
        Tyr Asn His Leu Thr Tyr Ala Val Asn Ile Trp Ser Glu Asn Asp Pro>

1210        1220        1230        1240
               *           *           *           *           *
        GCA GAT TTC AGA ATC TAT AAC GTG ACC TAC CTA GAA CCC TCC CTC CGC
        Ala Asp Phe Arg Ile Tyr Asn Val Thr Tyr Leu Glu Pro Ser Leu Arg>

1250        1260        1270        1280        1290
    *           *           *           *           *           *
        ATC GCA GCC AGC ACC CTG AAG TCT GGG ATT TCC TAC AGG GCA CGG GTG
        Ile Ala Ala Ser Thr Leu Lys Ser Gly Ile Ser Tyr Arg Ala Arg Val>

1300        1310        1320        1330        1340
           *           *           *           *           *
        AGG GCC TGG GCT CAG AGC TAT AAC ACC ACC TGG AGT GAG TGG AGC CCC
        Arg Ala Trp Ala Gln Ser Tyr Asn Thr Thr Trp Ser Glu Trp Ser Pro>

1350        1360        1370        1380        1390
               *           *           *           *           *           *
        AGC ACC AAG TGG CAC AAC TCC TAC AGG GAG CCC TTC GAG CAG TCC GGA
        Ser Thr Lys Trp His Asn Ser Tyr Arg Glu Pro Phe Glu Gln Ser Gly>

1400        1410        1420        1430        1440
               *           *           *           *           *           *
        GAC AAA ACT CAC ACA TGC CCA CCG TGC CCA GCA CCT GAA CTC CTG GGG
        Asp Lys Thr His Thr Cys Pro Pro Cys Pro Ala Pro Glu Leu Leu Gly>

1450        1460        1470        1480
               *           *           *           *           *
        GGA CCG TCA GTC TTC CTC TTC CCC CCA AAA CCC AAG GAC ACC CTC ATG
        Gly Pro Ser Val Phe Leu Phe Pro Pro Lys Pro Lys Asp Thr Leu Met>

1490        1500        1510        1520        1530
    *           *           *           *           *           *
        ATC TCC CGG ACC CCT GAG GTC ACA TGC GTG GTG GTG GAC GTG AGC CAC
        Ile Ser Arg Thr Pro Glu Val Thr Cys Val Val Val Asp Val Ser His>

1540        1550        1560        1570        1580
           *           *           *           *           *
        GAA GAC CCT GAG GTC AAG TTC AAC TGG TAC GTG GAC GGC GTG GAG GTG
        Glu Asp Pro Glu Val Lys Phe Asn Trp Tyr Val Asp Gly Val Glu Val>

1590        1600        1610        1620        1630
               *           *           *           *           *           *
        CAT AAT GCC AAG ACA AAG CCG CGG GAG GAG CAG TAC AAC AGC ACG TAC
        His Asn Ala Lys Thr Lys Pro Arg Glu Glu Gln Tyr Asn Ser Thr Tyr>

1640        1650        1660        1670        1680
               *           *           *           *           *           *
        CGT GTG GTC AGC GTC CTC ACC GTC CTG CAC CAG GAC TGG CTG AAT GGC
        Arg Val Val Ser Val Leu Thr Val Leu His Gln Asp Trp Leu Asn Gly>

1690        1700        1710        1720
               *           *           *           *           *
        AAG GAG TAC AAG TGC AAG GTC TCC AAC AAA GCC CTC CCA GCC CCC ATC
        Lys Glu Tyr Lys Cys Lys Val Ser Asn Lys Ala Leu Pro Ala Pro Ile>

1730        1740        1750        1760        1770
    *           *           *           *           *           *
        GAG AAA ACC ATC TCC AAA GCC AAA GGG CAG CCC CGA GAA CCA CAG GTG
        Glu Lys Thr Ile Ser Lys Ala Lys Gly Gln Pro Arg Glu Pro Gln Val>
```

Fig.22D.

```
      1780            1790            1800            1810            1820
   *       *       *       *       *       *       *       *       *       *
TAC ACC CTG CCC CCA TCC CGG GAT GAG CTG ACC AAG AAC CAG GTC AGC
Tyr Thr Leu Pro Pro Ser Arg Asp Glu Leu Thr Lys Asn Gln Val Ser>

1830            1840            1850            1860            1870
   *       *       *       *       *       *       *       *       *       *
CTG ACC TGC CTG GTC AAA GGC TTC TAT CCC AGC GAC ATC GCC GTG GAG
Leu Thr Cys Leu Val Lys Gly Phe Tyr Pro Ser Asp Ile Ala Val Glu>

1880            1890            1900            1910            1920
   *       *       *       *       *       *       *       *       *       *
TGG GAG AGC AAT GGG CAG CCG GAG AAC AAC TAC AAG ACC ACG CCT CCC
Trp Glu Ser Asn Gly Gln Pro Glu Asn Asn Tyr Lys Thr Thr Pro Pro>

1930            1940            1950            1960
   *       *       *       *       *       *       *       *       *
GTG CTG GAC TCC GAC GGC TCC TTC TTC CTC TAT AGC AAG CTC ACC GTG
Val Leu Asp Ser Asp Gly Ser Phe Phe Leu Tyr Ser Lys Leu Thr Val>

1970          1980            1990          2000            2010
   *       *       *       *       *       *       *       *       *       *
GAC AAG AGC AGG TGG CAG CAG GGG AAC GTC TTC TCA TGC TCC GTG ATG
Asp Lys Ser Arg Trp Gln Gln Gly Asn Val Phe Ser Cys Ser Val Met>

2020            2030            2040            2050            2060
   *       *       *       *       *       *       *       *       *
CAT GAG GCT CTG CAC AAC CAC TAC ACG CAG AAG AGC CTC TCC CTG TCT
His Glu Ala Leu His Asn His Tyr Thr Gln Lys Ser Leu Ser Leu Ser>

2070
   *       *       *
CCG GGT AAA TGA
Pro Gly Lys ***>
```

Fig.23A.

```
            10           20            30              40
             *            *             *               *
  *           *            *    *        *       *       *     *
ATG GTG AAG CCA TCA TTA CCA TTC ACA TCC CTC TTA TTC CTG CAG CTG
Met Val Lys Pro Ser Leu Pro Phe Thr Ser Leu Leu Phe Leu Gln Leu>

50              60           70            80           90
   *       *       *    *       *    *        *    *       *     *
CCC CTG CTG GGA GTG GGG CTG AAC ACG ACA ATT CTG ACG CCC AAT GGG
Pro Leu Leu Gly Val Gly Leu Asn Thr Thr Ile Leu Thr Pro Asn Gly>

100           110          120          130          140
       *     *       *    *       *    *       *    *       *
AAT GAA GAC ACC ACA GCT GAT TTC TTC CTG ACC ACT ATG CCC ACT GAC
Asn Glu Asp Thr Thr Ala Asp Phe Phe Leu Thr Thr Met Pro Thr Asp>

150          160         170          180         190
          *    *       *    *      *    *       *    *      *    *
TCC CTC AGT GTT TCC ACT CTG CCC CTC CCA GAG GTT CAG TGT TTT GTG
Ser Leu Ser Val Ser Thr Leu Pro Leu Pro Glu Val Gln Cys Phe Val>

200          210          220          230          240
   *     *    *       *    *       *    *       *    *       *    *
TTC AAT GTC GAG TAC ATG AAT TGC ACT TGG AAC AGC AGC TCT GAG CCC
Phe Asn Val Glu Tyr Met Asn Cys Thr Trp Asn Ser Ser Ser Glu Pro>

250          260          270          280
             *    *       *    *       *    *       *    *     *
CAG CCT ACC AAC CTC ACT CTG CAT TAT TGG TAC AAG AAC TCG GAT AAT
Gln Pro Thr Asn Leu Thr Leu His Tyr Trp Tyr Lys Asn Ser Asp Asn>

290          300          310          320          330
  *    *       *     *      *    *       *    *       *     *
GAT AAA GTC CAG AAG TGC AGC CAC TAT CTA TTC TCT GAA GAA ATC ACT
Asp Lys Val Gln Lys Cys Ser His Tyr Leu Phe Ser Glu Glu Ile Thr>

340          350          360          370          380
   *     *    *       *    *       *    *       *    *       *
TCT GGC TGT CAG TTG CAA AAA AAG GAG ATC CAC CTC TAC CAA ACA TTT
Ser Gly Cys Gln Leu Gln Lys Lys Glu Ile His Leu Tyr Gln Thr Phe>

390          400          410          420          430
             *    *       *    *       *    *       *    *       *
GTT GTT CAG CTC CAG GAC CCA CGG GAA CCC AGG AGA CAG GCC ACA CAG
Val Val Gln Leu Gln Asp Pro Arg Glu Pro Arg Arg Gln Ala Thr Gln>

440          450          460          470          480
             *    *       *    *       *    *       *    *       *
ATG CTA AAA CTG CAG AAT CTG GTG ATC CCC TGG GCT CCA GAG AAC CTA
Met Leu Lys Leu Gln Asn Leu Val Ile Pro Trp Ala Pro Glu Asn Leu>

490          500          510          520
             *    *       *    *       *    *       *     *
ACA CTT CAC AAA CTG AGT GAA TCC CAG CTA GAA CTG AAC TGG AAC AAC
Thr Leu His Lys Leu Ser Glu Ser Gln Leu Glu Leu Asn Trp Asn Asn>

530          540          550          560          570
  *    *       *    *       *    *       *    *       *     *
AGA TTC TTG AAC CAC TGT TTG GAG CAC TTG GTG CAG TAC CGG ACT GAC
Arg Phe Leu Asn His Cys Leu Glu His Leu Val Gln Tyr Arg Thr Asp>
```

Fig.23B.

```
       580           590           600           610           620
  *     *     *     *     *     *     *     *     *     *
TGG   GAC   CAC   AGC   TGG   ACT   GAA   CAA   TCA   GTG   GAT   TAT   AGA   CAT   AAG   TTC
Trp   Asp   His   Ser   Trp   Thr   Glu   Gln   Ser   Val   Asp   Tyr   Arg   His   Lys   Phe>

630           640           650           660           670
  *     *     *     *     *     *     *     *     *     *
TCC   TTG   CCT   AGT   GTG   GAT   GGG   CAG   AAA   CGC   TAC   ACG   TTT   CGT   GTT   CGG
Ser   Leu   Pro   Ser   Val   Asp   Gly   Gln   Lys   Arg   Tyr   Thr   Phe   Arg   Val   Arg>

680           690           700           710           720
  *     *     *     *     *     *     *     *     *     *
AGC   CGC   TTT   AAC   CCA   CTC   TGT   GGA   AGT   GCT   CAG   CAT   TGG   AGT   GAA   TGG
Ser   Arg   Phe   Asn   Pro   Leu   Cys   Gly   Ser   Ala   Gln   His   Trp   Ser   Glu   Trp>

730           740           750           760
  *     *     *     *     *     *     *     *     *     *
AGC   CAC   CCA   ATC   CAC   TGG   GGG   AGC   AAT   ACT   TCA   AAA   GAG   AAC   GCG   TCG
Ser   His   Pro   Ile   His   Trp   Gly   Ser   Asn   Thr   Ser   Lys   Glu   Asn   Ala   Ser>

770           780           790           800           810
  *     *     *     *     *     *     *     *     *     *
TCT   GGG   AAC   ATG   AAG   GTC   CTG   CAG   GAG   CCC   ACC   TGC   GTC   TCC   GAC   TAC
Ser   Gly   Asn   Met   Lys   Val   Leu   Gln   Glu   Pro   Thr   Cys   Val   Ser   Asp   Tyr>

820           830           840           850           860
  *     *     *     *     *     *     *     *     *     *
ATG   AGC   ATC   TCT   ACT   TGC   GAG   TGG   AAG   ATG   AAT   GGT   CCC   ACC   AAT   TGC
Met   Ser   Ile   Ser   Thr   Cys   Glu   Trp   Lys   Met   Asn   Gly   Pro   Thr   Asn   Cys>

870           880           890           900           910
  *     *     *     *     *     *     *     *     *     *
AGC   ACC   GAG   CTC   CGC   CTG   TTG   TAC   CAG   CTG   GTT   TTT   CTG   CTC   TCC   GAA
Ser   Thr   Glu   Leu   Arg   Leu   Leu   Tyr   Gln   Leu   Val   Phe   Leu   Leu   Ser   Glu>

920           930           940           950           960
  *     *     *     *     *     *     *     *     *     *
GCC   CAC   ACG   TGT   ATC   CCT   GAG   AAC   AAC   GGA   GGC   GCG   GGG   TGC   GTG   TGC
Ala   His   Thr   Cys   Ile   Pro   Glu   Asn   Asn   Gly   Gly   Ala   Gly   Cys   Val   Cys>

970           980           990           1000
  *     *     *     *     *     *     *     *     *     *
CAC   CTG   CTC   ATG   GAT   GAC   GTG   GTC   AGT   GCG   GAT   AAC   TAT   ACA   CTG   GAC
His   Leu   Leu   Met   Asp   Asp   Val   Val   Ser   Ala   Asp   Asn   Tyr   Thr   Leu   Asp>

1010          1020          1030          1040          1050
  *     *     *     *     *     *     *     *     *     *
CTG   TGG   GCT   GGG   CAG   CAG   CTG   CTG   TGG   AAG   GGC   TCC   TTC   AAG   CCC   AGC
Leu   Trp   Ala   Gly   Gln   Gln   Leu   Leu   Trp   Lys   Gly   Ser   Phe   Lys   Pro   Ser>

1060          1070          1080          1090          1100
  *     *     *     *     *     *     *     *     *     *
GAG   CAT   GTG   AAA   CCC   AGG   GCC   CCA   GGA   AAC   CTG   ACA   GTT   CAC   ACC   AAT
Glu   His   Val   Lys   Pro   Arg   Ala   Pro   Gly   Asn   Leu   Thr   Val   His   Thr   Asn>

1110          1120          1130          1140          1150
  *     *     *     *     *     *     *     *     *     *
GTC   TCC   GAC   ACT   CTG   CTG   CTG   ACC   TGG   AGC   AAC   CCG   TAT   CCC   CCT   GAC
Val   Ser   Asp   Thr   Leu   Leu   Leu   Thr   Trp   Ser   Asn   Pro   Tyr   Pro   Pro   Asp>

```
         AAT TAC CTG TAT AAT CAT CTC ACC TAT GCA GTC AAC ATT TGG AGT GAA
         Asn Tyr Leu Tyr Asn His Leu Thr Tyr Ala Val Asn Ile Trp Ser Glu>
                   1210        1220        1230        1240
                    *           *           *           *           *
         AAC GAC CCG GCA GAT TTC AGA ATC TAT AAC GTG ACC TAC CTA GAA CCC
         Asn Asp Pro Ala Asp Phe Arg Ile Tyr Asn Val Thr Tyr Leu Glu Pro>
  1250        1260        1270        1280        1290
    *           *           *           *           *           *
         TCC CTC CGC ATC GCA GCC AGC ACC CTG AAG TCT GGG ATT TCC TAC AGG
         Ser Leu Arg Ile Ala Ala Ser Thr Leu Lys Ser Gly Ile Ser Tyr Arg>
         1300        1310        1320        1330        1340
          *           *           *           *           *
         GCA CGG GTG AGG GCC TGG GCT CAG AGC TAT AAC ACC ACC TGG AGT GAG
         Ala Arg Val Arg Ala Trp Ala Gln Ser Tyr Asn Thr Thr Trp Ser Glu>
                   1350        1360        1370        1380        1390
                    *           *           *           *           *
         TGG AGC CCC AGC ACC AAG TGG CAC AAC TCC TAC AGG GAG CCC TTC GAG
         Trp Ser Pro Ser Thr Lys Trp His Asn Ser Tyr Arg Glu Pro Phe Glu>
         1400        1410        1420        1430        1440
          *           *           *           *           *
         CAG TCC GGA GAC AAA ACT CAC ACA TGC CCA CCG TGC CCA GCA CCT GAA
         Gln Ser Gly Asp Lys Thr His Thr Cys Pro Pro Cys Pro Ala Pro Glu>
                   1450        1460        1470        1480
                    *           *           *           *           *
         CTC CTG GGG GGA CCG TCA GTC TTC CTC TTC CCC CCA AAA CCC AAG GAC
         Leu Leu Gly Gly Pro Ser Val Phe Leu Phe Pro Pro Lys Pro Lys Asp>
  1490        1500        1510        1520        1530
    *           *           *           *           *           *
         ACC CTC ATG ATC TCC CGG ACC CCT GAG GTC ACA TGC GTG GTG GTG GAC
         Thr Leu Met Ile Ser Arg Thr Pro Glu Val Thr Cys Val Val Val Asp>
         1540        1550        1560        1570        1580
          *           *           *           *           *
         GTG AGC CAC GAA GAC CCT GAG GTC AAG TTC AAC TGG TAC GTG GAC GGC
         Val Ser His Glu Asp Pro Glu Val Lys Phe Asn Trp Tyr Val Asp Gly>
                   1590        1600        1610        1620        1630
                    *           *           *           *           *
         GTG GAG GTG CAT AAT GCC AAG ACA AAG CCG CGG GAG GAG CAG TAC AAC
         Val Glu Val His Asn Ala Lys Thr Lys Pro Arg Glu Glu Gln Tyr Asn>
         1640        1650        1660        1670        1680
          *           *           *           *           *
         AGC ACG TAC CGT GTG GTC AGC GTC CTC ACC GTC CTG CAC CAG GAC TGG
         Ser Thr Tyr Arg Val Val Ser Val Leu Thr Val Leu His Gln Asp Trp>
                   1690        1700        1710        1720
                    *           *           *           *           *
         CTG AAT GGC AAG GAG TAC AAG TGC AAG GTC TCC AAC AAA GCC CTC CCA
         Leu Asn Gly Lys Glu Tyr Lys Cys Lys Val Ser Asn Lys Ala Leu Pro>
  1730        1740        1750        1760        1770
    *           *           *           *           *           *
         GCC CCC ATC GAG AAA ACC ATC TCC AAA GCC AAA GGG CAG CCC CGA GAA
         Ala Pro Ile Glu Lys Thr Ile Ser Lys Ala Lys Gly Gln Pro Arg Glu>
```

Fig.23D.

```
      1780          1790          1800          1810          1820
  *      *      *      *      *      *      *      *      *
CCA CAG GTG TAC ACC CTG CCC CCA TCC CGG GAT GAG CTG ACC AAG AAC
Pro Gln Val Tyr Thr Leu Pro Pro Ser Arg Asp Glu Leu Thr Lys Asn>

1830          1840          1850          1860          1870
  *      *      *      *      *      *      *      *      *      *
CAG GTC AGC CTG ACC TGC CTG GTC AAA GGC TTC TAT CCC AGC GAC ATC
Gln Val Ser Leu Thr Cys Leu Val Lys Gly Phe Tyr Pro Ser Asp Ile>

1880          1890          1900          1910          1920
  *      *      *      *      *      *      *      *      *      *
GCC GTG GAG TGG GAG AGC AAT GGG CAG CCG GAG AAC AAC TAC AAG ACC
Ala Val Glu Trp Glu Ser Asn Gly Gln Pro Glu Asn Asn Tyr Lys Thr>

1930          1940          1950          1960
  *      *      *      *      *      *      *      *      *
ACG CCT CCC GTG CTG GAC TCC GAC GGC TCC TTC TTC CTC TAT AGC AAG
Thr Pro Pro Val Leu Asp Ser Asp Gly Ser Phe Phe Leu Tyr Ser Lys>

1970          1980          1990          2000          2010
  *      *      *      *      *      *      *      *      *      *
CTC ACC GTG GAC AAG AGC AGG TGG CAG CAG GGG AAC GTC TTC TCA TGC
Leu Thr Val Asp Lys Ser Arg Trp Gln Gln Gly Asn Val Phe Ser Cys>

2020          2030          2040          2050          2060
  *      *      *      *      *      *      *      *      *
TCC GTG ATG CAT GAG GCT CTG CAC AAC CAC TAC ACG CAG AAG AGC CTC
Ser Val Met His Glu Ala Leu His Asn His Tyr Thr Gln Lys Ser Leu>

2070          2080
  *      *      *      *      *
TCC CTG TCT CCG GGT AAA TGA
Ser Leu Ser Pro Gly Lys ***>
```

Fig.24A.

```
         10              20              30              40
          *       *       *       *       *       *       *       *       *
ATG GTG GCC GTC GGC TGC GCG CTG CTG GCT GCC CTG CTG GCC GCG CCG
Met Val Ala Val Gly Cys Ala Leu Leu Ala Ala Leu Leu Ala Ala Pro>

50              60              70              80              90
  *       *       *       *       *       *       *       *       *       *
GGA GCG GCG CTG GCC CCA AGG CGC TGC CCT GCG CAG GAG GTG GCA AGA
Gly Ala Ala Leu Ala Pro Arg Arg Cys Pro Ala Gln Glu Val Ala Arg>

100             110             120             130             140
  *       *       *       *       *       *       *       *       *       *
GGC GTG CTG ACC AGT CTG CCA GGA GAC AGC GTG ACT CTG ACC TGC CCG
Gly Val Leu Thr Ser Leu Pro Gly Asp Ser Val Thr Leu Thr Cys Pro>

150             160             170             180             190
  *       *       *       *       *       *       *       *       *       *
GGG GTA GAG CCG GAA GAC AAT GCC ACT GTT CAC TGG GTG CTC AGG AAG
Gly Val Glu Pro Glu Asp Asn Ala Thr Val His Trp Val Leu Arg Lys>

200             210             220             230             240
          *       *       *       *       *       *       *       *       *       *
CCG GCT GCA GGC TCC CAC CCC AGC AGA TGG GCT GGC ATG GGA AGG AGG
Pro Ala Ala Gly Ser His Pro Ser Arg Trp Ala Gly Met Gly Arg Arg>

250             260             270             280
          *       *       *       *       *       *       *       *       *
CTG CTG CTG AGG TCG GTG CAG CTC CAC GAC TCT GGA AAC TAT TCA TGC
Leu Leu Leu Arg Ser Val Gln Leu His Asp Ser Gly Asn Tyr Ser Cys>

290             300             310             320             330
  *       *       *       *       *       *       *       *       *       *
TAC CGG GCC GGC CGC CCA GCT GGG ACT GTG CAC TTG CTG GTG GAT GTT
Tyr Arg Ala Gly Arg Pro Ala Gly Thr Val His Leu Leu Val Asp Val>

340             350             360             370             380
  *       *       *       *       *       *       *       *       *
CCC CCC GAG GAG CCC CAG CTC TCC TGC TTC CGG AAG AGC CCC CTC AGC
Pro Pro Glu Glu Pro Gln Leu Ser Cys Phe Arg Lys Ser Pro Leu Ser>

390             400             410             420             430
  *       *       *       *       *       *       *       *       *       *
AAT GTT GTT TGT GAG TGG GGT CCT CGG AGC ACC CCA TCC CTG ACG ACA
Asn Val Val Cys Glu Trp Gly Pro Arg Ser Thr Pro Ser Leu Thr Thr>

440             450             460             470             480
          *       *       *       *       *       *       *       *       *       *
AAG GCT GTG CTC TTG GTG AGG AAG TTT CAG AAC AGT CCG GCC GAA GAC
Lys Ala Val Leu Leu Val Arg Lys Phe Gln Asn Ser Pro Ala Glu Asp>

490             500             510             520
          *       *       *       *       *       *       *       *       *
TTC CAG GAG CCG TGC CAG TAT TCC CAG GAG TCC CAG AAG TTC TCC TGC
Phe Gln Glu Pro Cys Gln Tyr Ser Gln Glu Ser Gln Lys Phe Ser Cys>

530             540             550             560             570
  *       *       *       *       *       *       *       *       *       *
CAG TTA GCA GTC CCG GAG GGA GAC AGC TCT TTC TAC ATA GTG TCC ATG
Gln Leu Ala Val Pro Glu Gly Asp Ser Ser Phe Tyr Ile Val Ser Met>
```

Fig.24B.

```
       580            590           600           610           620
   *     *       *     *      *      *      *      *      *      *
 TGC   GTC   GCC   AGT   AGT   GTC   GGG   AGC   AAG   TTC   AGC   AAA   ACT   CAA   ACC   TTT
 Cys   Val   Ala   Ser   Ser   Val   Gly   Ser   Lys   Phe   Ser   Lys   Thr   Gln   Thr   Phe>

630           640           650           660           670
   *     *      *      *      *      *      *      *      *      *
 CAG   GGT   TGT   GGA   ATC   TTG   CAG   CCT   GAT   CCG   CCT   GCC   AAC   ATC   ACA   GTC
 Gln   Gly   Cys   Gly   Ile   Leu   Gln   Pro   Asp   Pro   Pro   Ala   Asn   Ile   Thr   Val>

680           690           700           710           720
   *     *      *      *      *      *      *      *      *      *
 ACT   GCC   GTG   GCC   AGA   AAC   CCC   CGC   TGG   CTC   AGT   GTC   ACC   TGG   CAA   GAC
 Thr   Ala   Val   Ala   Arg   Asn   Pro   Arg   Trp   Leu   Ser   Val   Thr   Trp   Gln   Asp>

730           740           750           760
   *     *      *      *      *      *      *      *      *      *
 CCC   CAC   TCC   TGG   AAC   TCA   TCT   TTC   TAC   AGA   CTA   CGG   TTT   GAG   CTC   AGA
 Pro   His   Ser   Trp   Asn   Ser   Ser   Phe   Tyr   Arg   Leu   Arg   Phe   Glu   Leu   Arg>

770           780           790           800           810
   *     *      *      *      *      *      *      *      *      *
 TAT   CGG   GCT   GAA   CGG   TCA   AAG   ACA   TTC   ACA   ACA   TGG   ATG   GTC   AAG   GAC
 Tyr   Arg   Ala   Glu   Arg   Ser   Lys   Thr   Phe   Thr   Thr   Trp   Met   Val   Lys   Asp>

820           830           840           850           860
   *     *      *      *      *      *      *      *      *      *
 CTC   CAG   CAT   CAC   TGT   GTC   ATC   CAC   GAC   GCC   TGG   AGC   GGC   CTG   AGG   CAC
 Leu   Gln   His   His   Cys   Val   Ile   His   Asp   Ala   Trp   Ser   Gly   Leu   Arg   His>

870           880           890           900           910
   *     *      *      *      *      *      *      *      *      *
 GTG   GTG   CAG   CTT   CGT   GCC   CAG   GAG   GAG   TTC   GGG   CAA   GGC   GAG   TGG   AGC
 Val   Val   Gln   Leu   Arg   Ala   Gln   Glu   Glu   Phe   Gly   Gln   Gly   Glu   Trp   Ser>

920           930           940           950           960
   *     *      *      *      *      *      *      *      *      *
 GAG   TGG   AGC   CCG   GAG   GCC   ATG   GGC   ACG   CCT   TGG   ACA   GAA   TCC   AGG   AGT
 Glu   Trp   Ser   Pro   Glu   Ala   Met   Gly   Thr   Pro   Trp   Thr   Glu   Ser   Arg   Ser>

970           980           990          1000
   *     *      *      *      *      *      *      *      *      *
 CCT   CCA   GCT   GAG   AAC   GAG   GTG   TCC   ACC   CCC   ATG   ACC   GGT   GGC   GCG   CCT
 Pro   Pro   Ala   Glu   Asn   Glu   Val   Ser   Thr   Pro   Met   Thr   Gly   Gly   Ala   Pro>

1010          1020          1030          1040          1050
   *     *      *      *      *      *      *      *      *      *
 TCA   GGT   GCT   CAG   CTG   GAA   CTT   CTA   GAC   CCA   TGT   GGT   TAT   ATC   AGT   CCT
 Ser   Gly   Ala   Gln   Leu   Glu   Leu   Leu   Asp   Pro   Cys   Gly   Tyr   Ile   Ser   Pro>

1060          1070          1080          1090          1100
   *     *      *      *      *      *      *      *      *      *
 GAA   TCT   CCA   GTT   GTA   CAA   CTT   CAT   TCT   AAT   TTC   ACT   GCA   GTT   TGT   GTG
 Glu   Ser   Pro   Val   Val   Gln   Leu   His   Ser   Asn   Phe   Thr   Ala   Val   Cys   Val>

1110          1120          1130          1140          1150
   *     *      *      *      *      *      *      *      *      *
 CTA   AAG   GAA   AAA   TGT   ATG   GAT   TAT   TTT   CAT   GTA   AAT   GCT   AAT   TAC   ATT
 Leu   Lys   Glu   Lys   Cys   Met   Asp   Tyr   Phe   His   Val   Asn   Ala   Asn   Tyr   Ile>

```
    GTC TGG AAA ACA AAC CAT TTT ACT ATT CCT AAG GAG CAA TAT ACT ATC
    Val Trp Lys Thr Asn His Phe Thr Ile Pro Lys Glu Gln Tyr Thr Ile>

1210        1220        1230        1240
          *     *     *     *     *     *     *     *     *     *
    ATA AAC AGA ACA GCA TCC AGT GTC ACC TTT ACA GAT ATA GCT TCA TTA
    Ile Asn Arg Thr Ala Ser Ser Val Thr Phe Thr Asp Ile Ala Ser Leu>

1250        1260        1270        1280        1290
  *     *     *     *     *     *     *     *     *     *
    AAT ATT CAG CTC ACT TGC AAC ATT CTT ACA TTC GGA CAG CTT GAA CAG
    Asn Ile Gln Leu Thr Cys Asn Ile Leu Thr Phe Gly Gln Leu Glu Gln>

1300        1310        1320        1330        1340
      *     *     *     *     *     *     *     *     *     *
    AAT GTT TAT GGA ATC ACA ATA ATT TCA GGC TTG CCT CCA GAA AAA CCT
    Asn Val Tyr Gly Ile Thr Ile Ile Ser Gly Leu Pro Pro Glu Lys Pro>

1350        1360        1370        1380        1390
          *     *     *     *     *     *     *     *     *     *
    AAA AAT TTG AGT TGC ATT GTG AAC GAG GGG AAG AAA ATG AGG TGT GAG
    Lys Asn Leu Ser Cys Ile Val Asn Glu Gly Lys Lys Met Arg Cys Glu>

1400        1410        1420        1430        1440
              *     *     *     *     *     *     *     *     *     *
    TGG GAT GGT GGA AGG GAA ACA CAC TTG GAG ACA AAC TTC ACT TTA AAA
    Trp Asp Gly Gly Arg Glu Thr His Leu Glu Thr Asn Phe Thr Leu Lys>

1450        1460        1470        1480
              *     *     *     *     *     *     *     *     *
    TCT GAA TGG GCA ACA CAC AAG TTT GCT GAT TGC AAA GCA AAA CGT GAC
    Ser Glu Trp Ala Thr His Lys Phe Ala Asp Cys Lys Ala Lys Arg Asp>

1490        1500        1510        1520        1530
  *     *     *     *     *     *     *     *     *     *
    ACC CCC ACC TCA TGC ACT GTT GAT TAT TCT ACT GTG TAT TTT GTC AAC
    Thr Pro Thr Ser Cys Thr Val Asp Tyr Ser Thr Val Tyr Phe Val Asn>

1540        1550        1560        1570        1580
          *     *     *     *     *     *     *     *     *
    ATT GAA GTC TGG GTA GAA GCA GAG AAT GCC CTT GGG AAG GTT ACA TCA
    Ile Glu Val Trp Val Glu Ala Glu Asn Ala Leu Gly Lys Val Thr Ser>

1590        1600        1610        1620        1630
              *     *     *     *     *     *     *     *     *     *
    GAT CAT ATC AAT TTT GAT CCT GTA TAT AAA GTG AAG CCC AAT CCG CCA
    Asp His Ile Asn Phe Asp Pro Val Tyr Lys Val Lys Pro Asn Pro Pro>

1640        1650        1660        1670        1680
                  *     *     *     *     *     *     *     *     *     *
    CAT AAT TTA TCA GTG ATC AAC TCA GAG GAA CTG TCT AGT ATC TTA AAA
    His Asn Leu Ser Val Ile Asn Ser Glu Glu Leu Ser Ser Ile Leu Lys>

1690        1700        1710        1720
              *     *     *     *     *     *     *     *     *
    TTG ACA TGG ACC AAC CCA AGT ATT AAG AGT GTT ATA ATA CTA AAA TAT
    Leu Thr Trp Thr Asn Pro Ser Ile Lys Ser Val Ile Ile Leu Lys Tyr>

1730        1740        1750        1760        1770
  *     *     *     *     *     *     *     *     *     *
    AAC ATT CAA TAT AGG ACC AAA GAT GCC TCA ACT TGG AGC CAG ATT CCT
    Asn Ile Gln Tyr Arg Thr Lys Asp Ala Ser Thr Trp Ser Gln Ile Pro>
```

Fig.24D.

```
     1780        1790        1800        1810        1820
      *    *     *    *      *    *      *    *      *    *
CCT GAA GAC ACA GCA TCC ACC CGA TCT TCA TTC ACT GTC CAA GAC CTT
Pro Glu Asp Thr Ala Ser Thr Arg Ser Ser Phe Thr Val Gln Asp Leu>

1830        1840        1850        1860        1870
      *    *     *    *      *    *      *    *      *    *
AAA CCT TTT ACA GAA TAT GTG TTT AGG ATT CGC TGT ATG AAG GAA GAT
Lys Pro Phe Thr Glu Tyr Val Phe Arg Ile Arg Cys Met Lys Glu Asp>

1880        1890        1900        1910        1920
      *    *     *    *      *    *      *    *      *    *
GGT AAG GGA TAC TGG AGT GAC TGG AGT GAA GAA GCA AGT GGG ATC ACC
Gly Lys Gly Tyr Trp Ser Asp Trp Ser Glu Glu Ala Ser Gly Ile Thr>

1930        1940        1950        1960
      *    *     *    *      *    *      *    *
TAT GAA GAT AGA CCA TCT AAA GCA CCA AGT TTC TGG TAT AAA ATA GAT
Tyr Glu Asp Arg Pro Ser Lys Ala Pro Ser Phe Trp Tyr Lys Ile Asp>

1970        1980        1990        2000        2010
 *    *     *    *      *    *      *    *      *    *
CCA TCC CAT ACT CAA GGC TAC AGA ACT GTA CAA CTC GTG TGG AAG ACA
Pro Ser His Thr Gln Gly Tyr Arg Thr Val Gln Leu Val Trp Lys Thr>

2020        2030        2040        2050        2060
      *    *     *    *      *    *      *    *      *    *
TTG CCT CCT TTT GAA GCC AAT GGA AAA ATC TTG GAT TAT GAA GTG ACT
Leu Pro Pro Phe Glu Ala Asn Gly Lys Ile Leu Asp Tyr Glu Val Thr>

2070        2080        2090        2100        2110
      *    *     *    *      *    *      *    *      *    *
CTC ACA AGA TGG AAA TCA CAT TTA CAA AAT TAC ACA GTT AAT GCC ACA
Leu Thr Arg Trp Lys Ser His Leu Gln Asn Tyr Thr Val Asn Ala Thr>

2120        2130        2140        2150        2160
      *    *     *    *      *    *      *    *      *    *
AAA CTG ACA GTA AAT CTC ACA AAT GAT CGC TAT CTA GCA ACC CTA ACA
Lys Leu Thr Val Asn Leu Thr Asn Asp Arg Tyr Leu Ala Thr Leu Thr>

2170        2180        2190        2200
      *    *     *    *      *    *      *    *
GTA AGA AAT CTT GTT GGC AAA TCA GAT GCA GCT GTT TTA ACT ATC CCT
Val Arg Asn Leu Val Gly Lys Ser Asp Ala Ala Val Leu Thr Ile Pro>

2210        2220        2230        2240        2250
 *    *     *    *      *    *      *    *      *    *
GCC TGT GAC TTT CAA GCT ACT CAC CCT GTA ATG GAT CTT AAA GCA TTC
Ala Cys Asp Phe Gln Ala Thr His Pro Val Met Asp Leu Lys Ala Phe>

2260        2270        2280        2290        2300
      *    *     *    *      *    *      *    *      *    *
CCC AAA GAT AAC ATG CTT TGG GTG GAA TGG ACT ACT CCA AGG GAA TCT
Pro Lys Asp Asn Met Leu Trp Val Glu Trp Thr Thr Pro Arg Glu Ser>

2310        2320        2330        2340        2350
      *    *     *    *      *    *      *    *      *    *
GTA AAG AAA TAT ATA CTT GAG TGG TGT GTG TTA TCA GAT AAA GCA CCC
Val Lys Lys Tyr Ile Leu Glu Trp Cys Val Leu Ser Asp Lys Ala Pro>

```
      *         *         *         *         *         *         *         *         *         *
TGT ATC ACA GAC TGG CAA CAA GAA GAT GGT ACC GTG CAT CGC ACC TAT
Cys Ile Thr Asp Trp Gln Gln Glu Asp Gly Thr Val His Arg Thr Tyr>

2410          2420          2430          2440
          *         *         *         *         *         *         *         *
TTA AGA GGG AAC TTA GCA GAG AGC AAA TGC TAT TTG ATA ACA GTT ACT
Leu Arg Gly Asn Leu Ala Glu Ser Lys Cys Tyr Leu Ile Thr Val Thr>

2450          2460          2470          2480          2490
    *         *         *         *         *         *         *         *         *         *
CCA GTA TAT GCT GAT GGA CCA GGA AGC CCT GAA TCC ATA AAG GCA TAC
Pro Val Tyr Ala Asp Gly Pro Gly Ser Pro Glu Ser Ile Lys Ala Tyr>

2500          2510          2520          2530          2540
    *         *         *         *         *         *         *         *         *
CTT AAA CAA GCT CCA CCT TCC AAA GGA CCT ACT GTT CGG ACA AAA AAA
Leu Lys Gln Ala Pro Pro Ser Lys Gly Pro Thr Val Arg Thr Lys Lys>

2550          2560          2570          2580          2590
    *         *         *         *         *         *         *         *         *         *
GTA GGG AAA AAC GAA GCT GTC TTA GAG TGG GAC CAA CTT CCT GTT GAT
Val Gly Lys Asn Glu Ala Val Leu Glu Trp Asp Gln Leu Pro Val Asp>

2600          2610          2620          2630          2640
          *         *         *         *         *         *         *         *         *
GTT CAG AAT GGA TTT ATC AGA AAT TAT ACT ATA TTT TAT AGA ACC ATC
Val Gln Asn Gly Phe Ile Arg Asn Tyr Thr Ile Phe Tyr Arg Thr Ile>

2650          2660          2670          2680
              *         *         *         *         *         *         *         *         *
ATT GGA AAT GAA ACT GCT GTG AAT GTG GAT TCT TCC CAC ACA GAA TAT
Ile Gly Asn Glu Thr Ala Val Asn Val Asp Ser Ser His Thr Glu Tyr>

2690          2700          2710          2720          2730
    *         *         *         *         *         *         *         *         *         *
ACA TTG TCC TCT TTG ACT AGT GAC ACA TTG TAC ATG GTA CGA ATG GCA
Thr Leu Ser Ser Leu Thr Ser Asp Thr Leu Tyr Met Val Arg Met Ala>

2740          2750          2760          2770          2780
    *         *         *         *         *         *         *         *         *
GCA TAC ACA GAT GAA GGT GGG AAG GAT GGT CCA GAA TTC ACT TTT ACT
Ala Tyr Thr Asp Glu Gly Gly Lys Asp Gly Pro Glu Phe Thr Phe Thr>

2790          2800          2810          2820          2830
    *         *         *         *         *         *         *         *         *         *
ACC CCA AAG TTT GCT CAA GGA GAA ATT GAA TCC GGG GGC GAC AAA ACT
Thr Pro Lys Phe Ala Gln Gly Glu Ile Glu Ser Gly Gly Asp Lys Thr>

2840          2850          2860          2870          2880
          *         *         *         *         *         *         *         *         *         *
CAC ACA TGC CCA CCG TGC CCA GCA CCT GAA CTC CTG GGG GGA CCG TCA
His Thr Cys Pro Pro Cys Pro Ala Pro Glu Leu Leu Gly Gly Pro Ser>

2890          2900          2910          2920
              *         *         *         *         *         *         *         *         *
GTC TTC CTC TTC CCC CCA AAA CCC AAG GAC ACC CTC ATG ATC TCC CGG
Val Phe Leu Phe Pro Pro Lys Pro Lys Asp Thr Leu Met Ile Ser Arg>

2930          2940          2950          2960          2970
    *         *         *         *         *         *         *         *         *
ACC CCT GAG GTC ACA TGC GTG GTG GTG GAC GTG AGC CAC GAA GAC CCT
```

Fig.24F.

```
                                  Thr Pro Glu Val Thr Cys Val Val Val Asp Val Ser His Glu Asp Pro>
       2980           2990           3000           3010           3020
         *       *     *       *     *       *     *       *     *
GAG GTC AAG TTC AAC TGG TAC GTG GAC GGC GTG GAG GTG CAT AAT GCC
Glu Val Lys Phe Asn Trp Tyr Val Asp Gly Val Glu Val His Asn Ala>
       3030           3040           3050           3060           3070
         *       *     *       *     *       *     *       *     *
AAG ACA AAG CCG CGG GAG GAG CAG TAC AAC AGC ACG TAC CGT GTG GTC
Lys Thr Lys Pro Arg Glu Glu Gln Tyr Asn Ser Thr Tyr Arg Val Val>
       3080           3090           3100           3110           3120
         *       *     *       *     *       *     *       *     *
AGC GTC CTC ACC GTC CTG CAC CAG GAC TGG CTG AAT GGC AAG GAG TAC
Ser Val Leu Thr Val Leu His Gln Asp Trp Leu Asn Gly Lys Glu Tyr>
            3130           3140           3150           3160
         *       *     *       *     *       *     *       *     *
AAG TGC AAG GTC TCC AAC AAA GCC CTC CCA GCC CCC ATC GAG AAA ACC
Lys Cys Lys Val Ser Asn Lys Ala Leu Pro Ala Pro Ile Glu Lys Thr>
3170          3180           3190           3200           3210
   *       *     *       *     *       *     *       *     *       *
ATC TCC AAA GCC AAA GGG CAG CCC CGA GAA CCA CAG GTG TAC ACC CTG
Ile Ser Lys Ala Lys Gly Gln Pro Arg Glu Pro Gln Val Tyr Thr Leu>
    3220          3230           3240           3250          3260
      *       *     *       *     *       *     *       *     *
CCC CCA TCC CGG GAT GAG CTG ACC AAG AAC CAG GTC AGC CTG ACC TGC
Pro Pro Ser Arg Asp Glu Leu Thr Lys Asn Gln Val Ser Leu Thr Cys>
         3270           3280           3290           3300          3310
      *       *     *       *     *       *     *       *     *       *
CTG GTC AAA GGC TTC TAT CCC AGC GAC ATC GCC GTG GAG TGG GAG AGC
Leu Val Lys Gly Phe Tyr Pro Ser Asp Ile Ala Val Glu Trp Glu Ser>
            3320          3330           3340           3350          3360
         *       *     *       *     *       *     *       *     *       *
AAT GGG CAG CCG GAG AAC AAC TAC AAG ACC ACG CCT CCC GTG CTG GAC
Asn Gly Gln Pro Glu Asn Asn Tyr Lys Thr Thr Pro Pro Val Leu Asp>
               3370           3380           3390          3400
            *       *     *       *     *       *     *       *     *
TCC GAC GGC TCC TTC TTC CTC TAC AGC AAG CTC ACC GTG GAC AAG AGC
Ser Asp Gly Ser Phe Phe Leu Tyr Ser Lys Leu Thr Val Asp Lys Ser>
3410          3420           3430           3440          3450
   *       *     *       *     *       *     *       *     *       *
AGG TGG CAG CAG GGG AAC GTC TTC TCA TGC TCC GTG ATG CAT GAG GCT
Arg Trp Gln Gln Gly Asn Val Phe Ser Cys Ser Val Met His Glu Ala>
    3460          3470           3480           3490          3500
      *       *     *       *     *       *     *       *     *
CTG CAC AAC CAC TAC ACG CAG AAG AGC CTC TCC CTG TCT CCG GGT AAA
Leu His Asn His Tyr Thr Gln Lys Ser Leu Ser Leu Ser Pro Gly Lys>
   *
TGA
***>
```

Fig.25A.

```
          10                  20                  30                  40
           *         *         *         *         *         *         *         *
ATG GTG GCC GTC GGC TGC GCG CTG CTG GCT GCC CTG CTG GCC GCG CCG
Met Val Ala Val Gly Cys Ala Leu Leu Ala Ala Leu Leu Ala Ala Pro>

50                  60                  70                  80                  90
    *         *         *         *         *         *         *         *         *
GGA GCG GCG CTG GCC CCA AGG CGC TGC CCT GCG CAG GAG GTG GCA AGA
Gly Ala Ala Leu Ala Pro Arg Arg Cys Pro Ala Gln Glu Val Ala Arg>

100                 110                 120                 130                 140
       *         *         *         *         *         *         *         *         *
GGC GTG CTG ACC AGT CTG CCA GGA GAC AGC GTG ACT CTG ACC TGC CCG
Gly Val Leu Thr Ser Leu Pro Gly Asp Ser Val Thr Leu Thr Cys Pro>

150                 160                 170                 180                 190
          *         *         *         *         *         *         *         *         *
GGG GTA GAG CCG GAA GAC AAT GCC ACT GTT CAC TGG GTG CTC AGG AAG
Gly Val Glu Pro Glu Asp Asn Ala Thr Val His Trp Val Leu Arg Lys>

200                 210                 220                 230                 240
             *         *         *         *         *         *         *         *         *
CCG GCT GCA GGC TCC CAC CCC AGC AGA TGG GCT GGC ATG GGA AGG AGG
Pro Ala Ala Gly Ser His Pro Ser Arg Trp Ala Gly Met Gly Arg Arg>

250                 260                 270                 280
                *         *         *         *         *         *         *         *
CTG CTG CTG AGG TCG GTG CAG CTC CAC GAC TCT GGA AAC TAT TCA TGC
Leu Leu Leu Arg Ser Val Gln Leu His Asp Ser Gly Asn Tyr Ser Cys>

290                 300                 310                 320                 330
 *         *         *         *         *         *         *         *         *
TAC CGG GCC GGC CGC CCA GCT GGG ACT GTG CAC TTG CTG GTG GAT GTT
Tyr Arg Ala Gly Arg Pro Ala Gly Thr Val His Leu Leu Val Asp Val>

340                 350                 360                 370                 380
    *         *         *         *         *         *         *         *         *
CCC CCC GAG GAG CCC CAG CTC TCC TGC TTC CGG AAG AGC CCC CTC AGC
Pro Pro Glu Glu Pro Gln Leu Ser Cys Phe Arg Lys Ser Pro Leu Ser>

390                 400                 410                 420                 430
       *         *         *         *         *         *         *         *         *
AAT GTT GTT TGT GAG TGG GGT CCT CGG AGC ACC CCA TCC CTG ACG ACA
Asn Val Val Cys Glu Trp Gly Pro Arg Ser Thr Pro Ser Leu Thr Thr>

440                 450                 460                 470                 480
          *         *         *         *         *         *         *         *         *
AAG GCT GTG CTC TTG GTG AGG AAG TTT CAG AAC AGT CCG GCC GAA GAC
Lys Ala Val Leu Leu Val Arg Lys Phe Gln Asn Ser Pro Ala Glu Asp>

490                 500                 510                 520
             *         *         *         *         *         *         *         *
TTC CAG GAG CCG TGC CAG TAT TCC CAG GAG TCC CAG AAG TTC TCC TGC
Phe Gln Glu Pro Cys Gln Tyr Ser Gln Glu Ser Gln Lys Phe Ser Cys>

530                 540                 550                 560                 570
 *         *         *         *         *         *         *         *         *
CAG TTA GCA GTC CCG GAG GGA GAC AGC TCT TTC TAC ATA GTG TCC ATG
Gln Leu Ala Val Pro Glu Gly Asp Ser Ser Phe Tyr Ile Val Ser Met>
```

Fig.25B.

```
            580             590             600             610             620
              *               *               *               *               *
          *               *               *               *               *
      TGC GTC GCC AGT AGT GTC GGG AGC AAG TTC AGC AAA ACT CAA ACC TTT
      Cys Val Ala Ser Ser Val Gly Ser Lys Phe Ser Lys Thr Gln Thr Phe>

630             640             650             660             670
              *               *               *               *               *
          *               *               *               *               *
      CAG GGT TGT GGA ATC TTG CAG CCT GAT CCG CCT GCC AAC ATC ACA GTC
      Gln Gly Cys Gly Ile Leu Gln Pro Asp Pro Pro Ala Asn Ile Thr Val>

680             690             700             710             720
              *               *               *               *               *
          *               *               *               *               *
      ACT GCC GTG GCC AGA AAC CCC CGC TGG CTC AGT GTC ACC TGG CAA GAC
      Thr Ala Val Ala Arg Asn Pro Arg Trp Leu Ser Val Thr Trp Gln Asp>

730             740             750             760
              *               *               *               *
          *               *               *               *               *
      CCC CAC TCC TGG AAC TCA TCT TTC TAC AGA CTA CGG TTT GAG CTC AGA
      Pro His Ser Trp Asn Ser Ser Phe Tyr Arg Leu Arg Phe Glu Leu Arg>

770             780             790             800             810
        *               *               *               *               *
          *               *               *               *               *
      TAT CGG GCT GAA CGG TCA AAG ACA TTC ACA ACA TGG ATG GTC AAG GAC
      Tyr Arg Ala Glu Arg Ser Lys Thr Phe Thr Thr Trp Met Val Lys Asp>

820             830             840             850             860
              *               *               *               *               *
          *               *               *               *               *
      CTC CAG CAT CAC TGT GTC ATC CAC GAC GCC TGG AGC GGC CTG AGG CAC
      Leu Gln His His Cys Val Ile His Asp Ala Trp Ser Gly Leu Arg His>

870             880             890             900             910
              *               *               *               *               *
          *               *               *               *               *
      GTG GTG CAG CTT CGT GCC CAG GAG GAG TTC GGG CAA GGC GAG TGG AGC
      Val Val Gln Leu Arg Ala Gln Glu Glu Phe Gly Gln Gly Glu Trp Ser>

920             930             940             950             960
              *               *               *               *               *
          *               *               *               *               *
      GAG TGG AGC CCG GAG GCC ATG GGC ACG CCT TGG ACA GAA TCG CGA TCG
      Glu Trp Ser Pro Glu Ala Met Gly Thr Pro Trp Thr Glu Ser Arg Ser>

970             980             990             1000
              *               *               *               *
          *               *               *               *               *
      CCT CCA GCT GAG AAC GAG GTG TCC ACC CCC ATG GAA CTT CTA GAC CCA
      Pro Pro Ala Glu Asn Glu Val Ser Thr Pro Met Glu Leu Leu Asp Pro>

1010            1020            1030            1040            1050
        *               *               *               *               *
          *               *               *               *               *
      TGT GGT TAT ATC AGT CCT GAA TCT CCA GTT GTA CAA CTT CAT TCT AAT
      Cys Gly Tyr Ile Ser Pro Glu Ser Pro Val Val Gln Leu His Ser Asn>

1060            1070            1080            1090            1100
              *               *               *               *               *
          *               *               *               *               *
      TTC ACT GCA GTT TGT GTG CTA AAG GAA AAA TGT ATG GAT TAT TTT CAT
      Phe Thr Ala Val Cys Val Leu Lys Glu Lys Cys Met Asp Tyr Phe His>

1110            1120            1130            1140            1150
              *               *               *               *               *
          *               *               *               *               *
      GTA AAT GCT AAT TAC ATT GTC TGG AAA ACA AAC CAT TTT ACT ATT CCT
      Val Asn Ala Asn Tyr Ile Val Trp Lys Thr Asn His Phe Thr Ile Pro>

```
            AAG GAG CAA TAT ACT ATC ATA AAC AGA ACA GCA TCC AGT GTC ACC TTT
            Lys Glu Gln Tyr Thr Ile Ile Asn Arg Thr Ala Ser Ser Val Thr Phe>
                    1210        1220        1230        1240
              *       *    *      *    *      *    *      *    *      *
            ACA GAT ATA GCT TCA TTA AAT ATT CAG CTC ACT TGC AAC ATT CTT ACA
            Thr Asp Ile Ala Ser Leu Asn Ile Gln Leu Thr Cys Asn Ile Leu Thr>
   1250        1260        1270        1280        1290
     *    *      *    *      *    *      *    *      *    *      *
            TTC GGA CAG CTT GAA CAG AAT GTT TAT GGA ATC ACA ATA ATT TCA GGC
            Phe Gly Gln Leu Glu Gln Asn Val Tyr Gly Ile Thr Ile Ile Ser Gly>
                1300        1310        1320        1330        1340
              *    *      *    *      *    *      *    *      *    *
            TTG CCT CCA GAA AAA CCT AAA AAT TTG AGT TGC ATT GTG AAC GAG GGG
            Leu Pro Pro Glu Lys Pro Lys Asn Leu Ser Cys Ile Val Asn Glu Gly>
                    1350        1360        1370        1380        1390
              *       *    *      *    *      *    *      *    *      *
            AAG AAA ATG AGG TGT GAG TGG GAT GGT GGA AGG GAA ACA CAC TTG GAG
            Lys Lys Met Arg Cys Glu Trp Asp Gly Gly Arg Glu Thr His Leu Glu>
                    1400        1410        1420        1430        1440
              *       *    *      *    *      *    *      *    *      *
            ACA AAC TTC ACT TTA AAA TCT GAA TGG GCA ACA CAC AAG TTT GCT GAT
            Thr Asn Phe Thr Leu Lys Ser Glu Trp Ala Thr His Lys Phe Ala Asp>
                    1450        1460        1470        1480
              *       *    *      *    *      *    *      *    *
            TGC AAA GCA AAA CGT GAC ACC CCC ACC TCA TGC ACT GTT GAT TAT TCT
            Cys Lys Ala Lys Arg Asp Thr Pro Thr Ser Cys Thr Val Asp Tyr Ser>
   1490        1500        1510        1520        1530
     *    *      *    *      *    *      *    *      *    *      *
            ACT GTG TAT TTT GTC AAC ATT GAA GTC TGG GTA GAA GCA GAG AAT GCC
            Thr Val Tyr Phe Val Asn Ile Glu Val Trp Val Glu Ala Glu Asn Ala>
                1540        1550        1560        1570        1580
              *    *      *    *      *    *      *    *      *
            CTT GGG AAG GTT ACA TCA GAT CAT ATC AAT TTT GAT CCT GTA TAT AAA
            Leu Gly Lys Val Thr Ser Asp His Ile Asn Phe Asp Pro Val Tyr Lys>
                    1590        1600        1610        1620        1630
              *       *    *      *    *      *    *      *    *      *
            GTG AAG CCC AAT CCG CCA CAT AAT TTA TCA GTG ATC AAC TCA GAG GAA
            Val Lys Pro Asn Pro Pro His Asn Leu Ser Val Ile Asn Ser Glu Glu>
                    1640        1650        1660        1670        1680
              *       *    *      *    *      *    *      *    *      *
            CTG TCT AGT ATC TTA AAA TTG ACA TGG ACC AAC CCA AGT ATT AAG AGT
            Leu Ser Ser Ile Leu Lys Leu Thr Trp Thr Asn Pro Ser Ile Lys Ser>
                        1690        1700        1710        1720
                  *       *    *      *    *      *    *      *
            GTT ATA ATA CTA AAA TAT AAC ATT CAA TAT AGG ACC AAA GAT GCC TCA
            Val Ile Ile Leu Lys Tyr Asn Ile Gln Tyr Arg Thr Lys Asp Ala Ser>
   1730        1740        1750        1760        1770
     *    *      *    *      *    *      *    *      *    *      *
            ACT TGG AGC CAG ATT CCT CCT GAA GAC ACA GCA TCC ACC CGA TCT TCA
            Thr Trp Ser Gln Ile Pro Pro Glu Asp Thr Ala Ser Thr Arg Ser Ser>
```

Fig.25D.

```
          1780                1790                1800                1810                1820
            *        *          *        *           *       *          *        *          *       *
          TTC ACT GTC CAA GAC CTT AAA CCT TTT ACA GAA TAT GTG TTT AGG ATT
          Phe Thr Val Gln Asp Leu Lys Pro Phe Thr Glu Tyr Val Phe Arg Ile>

1830                1840                1850                1860                1870
            *        *          *        *           *       *          *        *          *       *
          CGC TGT ATG AAG GAA GAT GGT AAG GGA TAC TGG AGT GAC TGG AGT GAA
          Arg Cys Met Lys Glu Asp Gly Lys Gly Tyr Trp Ser Asp Trp Ser Glu>

1880                1890                1900                1910                1920
            *        *          *        *           *       *          *        *          *       *
          GAA GCA AGT GGG ATC ACC TAT GAA GAT AGA CCA TCT AAA GCA CCA AGT
          Glu Ala Ser Gly Ile Thr Tyr Glu Asp Arg Pro Ser Lys Ala Pro Ser>

1930                1940                1950                1960
                   *        *          *        *           *       *          *        *         *
                 TTC TGG TAT AAA ATA GAT CCA TCC CAT ACT CAA GGC TAC AGA ACT GTA
                 Phe Trp Tyr Lys Ile Asp Pro Ser His Thr Gln Gly Tyr Arg Thr Val>

1970                1980                1990                2000                2010
     *        *          *        *           *       *          *        *          *       *
   CAA CTC GTG TGG AAG ACA TTG CCT CCT TTT GAA GCC AAT GGA AAA ATC
   Gln Leu Val Trp Lys Thr Leu Pro Pro Phe Glu Ala Asn Gly Lys Ile>

2020                2030                2040                2050                2060
            *        *          *        *           *       *          *        *          *       *
          TTG GAT TAT GAA GTG ACT CTC ACA AGA TGG AAA TCA CAT TTA CAA AAT
          Leu Asp Tyr Glu Val Thr Leu Thr Arg Trp Lys Ser His Leu Gln Asn>

2070                2080                2090                2100                2110
            *        *          *        *           *       *          *        *          *       *
          TAC ACA GTT AAT GCC ACA AAA CTG ACA GTA AAT CTC ACA AAT GAT CGC
          Tyr Thr Val Asn Ala Thr Lys Leu Thr Val Asn Leu Thr Asn Asp Arg>

2120                2130                2140                2150                2160
            *        *          *        *           *       *          *        *          *       *
          TAT CTA GCA ACC CTA ACA GTA AGA AAT CTT GTT GGC AAA TCA GAT GCA
          Tyr Leu Ala Thr Leu Thr Val Arg Asn Leu Val Gly Lys Ser Asp Ala>

2170                2180                2190                2200
                   *        *          *        *           *       *          *        *         *
                 GCT GTT TTA ACT ATC CCT GCC TGT GAC TTT CAA GCT ACT CAC CCT GTA
                 Ala Val Leu Thr Ile Pro Ala Cys Asp Phe Gln Ala Thr His Pro Val>

2210                2220                2230                2240                2250
     *        *          *        *           *       *          *        *          *       *
   ATG GAT CTT AAA GCA TTC CCC AAA GAT AAC ATG CTT TGG GTG GAA TGG
   Met Asp Leu Lys Ala Phe Pro Lys Asp Asn Met Leu Trp Val Glu Trp>

2260                2270                2280                2290                2300
            *        *          *        *           *       *          *        *          *       *
          ACT ACT CCA AGG GAA TCT GTA AAG AAA TAT ATA CTT GAG TGG TGT GTG
          Thr Thr Pro Arg Glu Ser Val Lys Lys Tyr Ile Leu Glu Trp Cys Val>

2310                2320                2330                2340                2350
                   *        *          *        *           *       *          *        *          *       *
                 TTA TCA GAT AAA GCA CCC TGT ATC ACA GAC TGG CAA CAA GAA GAT GGT
                 Leu Ser Asp Lys Ala Pro Cys Ile Thr Asp Trp Gln Gln Glu Asp Gly>

```
         *         *         *         *         *         *         *         *         *         *
ACC GTG CAT CGC ACC TAT TTA AGA GGG AAC TTA GCA GAG AGC AAA TGC
Thr Val His Arg Thr Tyr Leu Arg Gly Asn Leu Ala Glu Ser Lys Cys>

2410          2420          2430          2440
         *         *         *         *         *         *         *         *         *
TAT TTG ATA ACA GTT ACT CCA GTA TAT GCT GAT GGA CCA GGA AGC CCT
Tyr Leu Ile Thr Val Thr Pro Val Tyr Ala Asp Gly Pro Gly Ser Pro>

2450          2460          2470          2480          2490
    *         *         *         *         *         *         *         *         *         *
GAA TCC ATA AAG GCA TAC CTT AAA CAA GCT CCA CCT TCC AAA GGA CCT
Glu Ser Ile Lys Ala Tyr Leu Lys Gln Ala Pro Pro Ser Lys Gly Pro>

2500          2510          2520          2530          2540
    *         *         *         *         *         *         *         *         *
ACT GTT CGG ACA AAA AAA GTA GGG AAA AAC GAA GCT GTC TTA GAG TGG
Thr Val Arg Thr Lys Lys Val Gly Lys Asn Glu Ala Val Leu Glu Trp>

2550          2560          2570          2580          2590
    *         *         *         *         *         *         *         *         *         *
GAC CAA CTT CCT GTT GAT GTT CAG AAT GGA TTT ATC AGA AAT TAT ACT
Asp Gln Leu Pro Val Asp Val Gln Asn Gly Phe Ile Arg Asn Tyr Thr>

2600          2610          2620          2630          2640
    *         *         *         *         *         *         *         *         *         *
ATA TTT TAT AGA ACC ATC ATT GGA AAT GAA ACT GCT GTG AAT GTG GAT
Ile Phe Tyr Arg Thr Ile Ile Gly Asn Glu Thr Ala Val Asn Val Asp>

2650          2660          2670          2680
    *         *         *         *         *         *         *         *         *
TCT TCC CAC ACA GAA TAT ACA TTG TCC TCT TTG ACT AGT GAC ACA TTG
Ser Ser His Thr Glu Tyr Thr Leu Ser Ser Leu Thr Ser Asp Thr Leu>

2690          2700          2710          2720          2730
    *         *         *         *         *         *         *         *         *         *
TAC ATG GTA CGA ATG GCA GCA TAC ACA GAT GAA GGT GGG AAG GAT GGT
Tyr Met Val Arg Met Ala Ala Tyr Thr Asp Glu Gly Gly Lys Asp Gly>

2740          2750          2760          2770          2780
    *         *         *         *         *         *         *         *         *
CCA GAA TTC ACT TTT ACT ACC CCA AAG TTT GCT CAA GGA GAA ATT GAA
Pro Glu Phe Thr Phe Thr Thr Pro Lys Phe Ala Gln Gly Glu Ile Glu>

2790          2800          2810          2820          2830
    *         *         *         *         *         *         *         *         *         *
TCC GGG GGC GAC AAA ACT CAC ACA TGC CCA CCG TGC CCA GCA CCT GAA
Ser Gly Gly Asp Lys Thr His Thr Cys Pro Pro Cys Pro Ala Pro Glu>

2840          2850          2860          2870          2880
    *         *         *         *         *         *         *         *         *         *
CTC CTG GGG GGA CCG TCA GTC TTC CTC TTC CCC CCA AAA CCC AAG GAC
Leu Leu Gly Gly Pro Ser Val Phe Leu Phe Pro Pro Lys Pro Lys Asp>

2890          2900          2910          2920
    *         *         *         *         *         *         *         *         *
ACC CTC ATG ATC TCC CGG ACC CCT GAG GTC ACA TGC GTG GTG GTG GAC
Thr Leu Met Ile Ser Arg Thr Pro Glu Val Thr Cys Val Val Val Asp>

2930          2940          2950          2960          2970
    *         *         *         *         *         *         *         *         *         *
GTG AGC CAC GAA GAC CCT GAG GTC AAG TTC AAC TGG TAC GTG GAC GGC
```

Fig.25F.

```
                     Val Ser His Glu Asp Pro Glu Val Lys Phe Asn Trp Tyr Val Asp Gly>
        2980          2990          3000          3010          3020
         *     *     *     *     *     *     *     *     *     *
        GTG GAG GTG CAT AAT GCC AAG ACA AAG CCG CGG GAG GAG CAG TAC AAC
        Val Glu Val His Asn Ala Lys Thr Lys Pro Arg Glu Glu Gln Tyr Asn>
           3030          3040          3050          3060          3070
         *     *     *     *     *     *     *     *     *     *
        AGC ACG TAC CGT GTG GTC AGC GTC CTC ACC GTC CTG CAC CAG GAC TGG
        Ser Thr Tyr Arg Val Val Ser Val Leu Thr Val Leu His Gln Asp Trp>
           3080          3090          3100          3110          3120
         *     *     *     *     *     *     *     *     *     *
        CTG AAT GGC AAG GAG TAC AAG TGC AAG GTC TCC AAC AAA GCC CTC CCA
        Leu Asn Gly Lys Glu Tyr Lys Cys Lys Val Ser Asn Lys Ala Leu Pro>
              3130          3140          3150          3160
         *     *     *     *     *     *     *     *     *
        GCC CCC ATC GAG AAA ACC ATC TCC AAA GCC AAA GGG CAG CCC CGA GAA
        Ala Pro Ile Glu Lys Thr Ile Ser Lys Ala Lys Gly Gln Pro Arg Glu>
  3170          3180          3190          3200          3210
   *     *     *     *     *     *     *     *     *     *
  CCA CAG GTG TAC ACC CTG CCC CCA TCC CGG GAT GAG CTG ACC AAG AAC
  Pro Gln Val Tyr Thr Leu Pro Pro Ser Arg Asp Glu Leu Thr Lys Asn>
     3220          3230          3240          3250          3260
   *     *     *     *     *     *     *     *     *
  CAG GTC AGC CTG ACC TGC CTG GTC AAA GGC TTC TAT CCC AGC GAC ATC
  Gln Val Ser Leu Thr Cys Leu Val Lys Gly Phe Tyr Pro Ser Asp Ile>
     3270          3280          3290          3300          3310
   *     *     *     *     *     *     *     *     *     *
  GCC GTG GAG TGG GAG AGC AAT GGG CAG CCG GAG AAC AAC TAC AAG ACC
  Ala Val Glu Trp Glu Ser Asn Gly Gln Pro Glu Asn Asn Tyr Lys Thr>
        3320          3330          3340          3350          3360
         *     *     *     *     *     *     *     *     *     *
        ACG CCT CCC GTG CTG GAC TCC GAC GGC TCC TTC TTC CTC TAC AGC AAG
        Thr Pro Pro Val Leu Asp Ser Asp Gly Ser Phe Phe Leu Tyr Ser Lys>
           3370          3380          3390          3400
         *     *     *     *     *     *     *     *     *
        CTC ACC GTG GAC AAG AGC AGG TGG CAG CAG GGG AAC GTC TTC TCA TGC
        Leu Thr Val Asp Lys Ser Arg Trp Gln Gln Gly Asn Val Phe Ser Cys>
  3410          3420          3430          3440          3450
   *     *     *     *     *     *     *     *     *     *
  TCC GTG ATG CAT GAG GCT CTG CAC AAC CAC TAC ACG CAG AAG AGC CTC
  Ser Val Met His Glu Ala Leu His Asn His Tyr Thr Gln Lys Ser Leu>
     3460          3470
   *     *     *     *
  TCC CTG TCT CCG GGT AAA TGA
  Ser Leu Ser Pro Gly Lys ***>
```

Fig.26A.

```
          10              20              30              40
           *               *               *               *        *
ATG GTG CTT CTG TGG TGT GTA GTG AGT CTC TAC TTT TAT GGA ATC CTG
Met Val Leu Leu Trp Cys Val Val Ser Leu Tyr Phe Tyr Gly Ile Leu>

50              60              70              80              90
  *               *               *               *               *        *
CAA AGT GAT GCC TCA GAA CGC TGC GAT GAC TGG GGA CTA GAC ACC ATG
Gln Ser Asp Ala Ser Glu Arg Cys Asp Asp Trp Gly Leu Asp Thr Met>

100             110             120             130             140
     *               *               *               *               *
AGG CAA ATC CAA GTG TTT GAA GAT GAG CCA GCT CGC ATC AAG TGC CCA
Arg Gln Ile Gln Val Phe Glu Asp Glu Pro Ala Arg Ile Lys Cys Pro>

150             160             170             180             190
  *       *       *       *       *       *       *       *       *       *
CTC TTT GAA CAC TTC TTG AAA TTC AAC TAC AGC ACA GCC CAT TCA GCT
Leu Phe Glu His Phe Leu Lys Phe Asn Tyr Ser Thr Ala His Ser Ala>

200             210             220             230             240
     *               *               *               *               *        *
GGC CTT ACT CTG ATC TGG TAT TGG ACT AGG CAG GAC CGG GAC CTT GAG
Gly Leu Thr Leu Ile Trp Tyr Trp Thr Arg Gln Asp Arg Asp Leu Glu>

250             260             270             280
          *       *       *       *       *       *       *       *       *
GAG CCA ATT AAC TTC CGC CTC CCC GAG AAC CGC ATT AGT AAG GAG AAA
Glu Pro Ile Asn Phe Arg Leu Pro Glu Asn Arg Ile Ser Lys Glu Lys>

290             300             310             320             330
 *               *               *       *               *               *
GAT GTG CTG TGG TTC CGG CCC ACT CTC CTC AAT GAC ACT GGC AAC TAT
Asp Val Leu Trp Phe Arg Pro Thr Leu Leu Asn Asp Thr Gly Asn Tyr>

340             350             360             370             380
     *       *       *       *       *       *       *       *       *
ACC TGC ATG TTA AGG AAC ACT ACA TAT TGC AGC AAA GTT GCA TTT CCC
Thr Cys Met Leu Arg Asn Thr Thr Tyr Cys Ser Lys Val Ala Phe Pro>

390             400             410             420             430
  *       *       *       *       *       *       *       *       *       *
TTG GAA GTT GTT CAA AAA GAC AGC TGT TTC AAT TCC CCC ATG AAA CTC
Leu Glu Val Val Gln Lys Asp Ser Cys Phe Asn Ser Pro Met Lys Leu>

440             450             460             470             480
     *       *       *       *       *       *       *       *       *       *
CCA GTG CAT AAA CTG TAT ATA GAA TAT GGC ATT CAG AGG ATC ACT TGT
Pro Val His Lys Leu Tyr Ile Glu Tyr Gly Ile Gln Arg Ile Thr Cys>

490             500             510             520
          *       *       *       *       *       *       *       *       *
CCA AAT GTA GAT GGA TAT TTT CCT TCC AGT GTC AAA CCG ACT ATC ACT
Pro Asn Val Asp Gly Tyr Phe Pro Ser Ser Val Lys Pro Thr Ile Thr>

530             540             550             560             570
 *       *       *       *       *       *       *       *       *       *
TGG TAT ATG GGC TGT TAT AAA ATA CAG AAT TTT AAT AAT GTA ATA CCC
Trp Tyr Met Gly Cys Tyr Lys Ile Gln Asn Phe Asn Asn Val Ile Pro>
```

Fig. 26B.

```
       580            590            600            610            620
        *      *       *      *       *      *       *      *       *
GAA GGT ATG AAC TTG AGT TTC CTC ATT GCC TTA ATT TCA AAT AAT GGA
Glu Gly Met Asn Leu Ser Phe Leu Ile Ala Leu Ile Ser Asn Asn Gly>

630            640            650            660            670
  *      *       *      *       *      *       *      *       *
AAT TAC ACA TGT GTT GTT ACA TAT CCA GAA AAT GGA CGT ACG TTT CAT
Asn Tyr Thr Cys Val Val Thr Tyr Pro Glu Asn Gly Arg Thr Phe His>

680            690            700            710            720
  *      *       *      *       *      *       *      *       *
CTC ACC AGG ACT CTG ACT GTA AAG GTA GTA GGC TCT CCA AAA AAT GCA
Leu Thr Arg Thr Leu Thr Val Lys Val Val Gly Ser Pro Lys Asn Ala>

730            740            750            760
    *      *       *      *       *      *       *      *
GTG CCC CCT GTG ATC CAT TCA CCT AAT GAT CAT GTG GTC TAT GAG AAA
Val Pro Pro Val Ile His Ser Pro Asn Asp His Val Val Tyr Glu Lys>

770            780            790            800            810
  *      *       *      *       *      *       *      *       *
GAA CCA GGA GAG GAG CTA CTC ATT CCC TGT ACG GTC TAT TTT AGT TTT
Glu Pro Gly Glu Glu Leu Leu Ile Pro Cys Thr Val Tyr Phe Ser Phe>

820            830            840            850            860
    *      *       *      *       *      *       *      *       *
CTG ATG GAT TCT CGC AAT GAG GTT TGG TGG ACC ATT GAT GGA AAA AAA
Leu Met Asp Ser Arg Asn Glu Val Trp Trp Thr Ile Asp Gly Lys Lys>

870            880            890            900            910
   *       *      *       *      *       *      *       *      *
CCT GAT GAC ATC ACT ATT GAT GTC ACC ATT AAC GAA AGT ATA AGT CAT
Pro Asp Asp Ile Thr Ile Asp Val Thr Ile Asn Glu Ser Ile Ser His>

920            930            940            950            960
    *      *       *      *       *      *       *      *       *
AGT AGA ACA GAA GAT GAA ACA AGA ACT CAG ATT TTG AGC ATC AAG AAA
Ser Arg Thr Glu Asp Glu Thr Arg Thr Gln Ile Leu Ser Ile Lys Lys>

970            980            990            1000
    *       *      *       *      *       *      *       *
GTT ACC TCT GAG GAT CTC AAG CGC AGC TAT GTC TGT CAT GCT AGA AGT
Val Thr Ser Glu Asp Leu Lys Arg Ser Tyr Val Cys His Ala Arg Ser>

1010           1020           1030           1040           1050
  *      *       *      *       *      *       *      *       *
GCC AAA GGC GAA GTT GCC AAA GCA GCC AAG GTG AAG CAG AAA GTG CCA
Ala Lys Gly Glu Val Ala Lys Ala Ala Lys Val Lys Gln Lys Val Pro>

1060           1070           1080           1090           1100
    *       *      *       *      *       *      *       *      *
GCT CCA AGA TAC ACA GTG TCC GGT GGC GCG CCT ATG CTG AGC GAG GCT
Ala Pro Arg Tyr Thr Val Ser Gly Gly Ala Pro Met Leu Ser Glu Ala>

1110           1120           1130           1140           1150
    *       *      *       *      *       *      *       *      *
GAT AAA TGC AAG GAA CGT GAA GAA AAA ATA ATT TTA GTG TCA TCT GCA
Asp Lys Cys Lys Glu Arg Glu Glu Lys Ile Ile Leu Val Ser Ser Ala>

```
    AAT GAA ATT GAT GTT CGT CCC TGT CCT CTT AAC CCA AAT GAA CAC AAA
    Asn Glu Ile Asp Val Arg Pro Cys Pro Leu Asn Pro Asn Glu His Lys>

1210        1220        1230        1240
           *     *     *     *     *     *     *     *     *
    GGC ACT ATA ACT TGG TAT AAG GAT GAC AGC AAG ACA CCT GTA TCT ACA
    Gly Thr Ile Thr Trp Tyr Lys Asp Asp Ser Lys Thr Pro Val Ser Thr>

1250        1260        1270        1280        1290
  *     *     *     *     *     *     *     *     *     *
    GAA CAA GCC TCC AGG ATT CAT CAA CAC AAA GAG AAA CTT TGG TTT GTT
    Glu Gln Ala Ser Arg Ile His Gln His Lys Glu Lys Leu Trp Phe Val>

1300        1310        1320        1330        1340
        *     *     *     *     *     *     *     *     *
    CCT GCT AAG GTG GAG GAT TCA GGA CAT TAC TAT TGC GTG GTA AGA AAT
    Pro Ala Lys Val Glu Asp Ser Gly His Tyr Tyr Cys Val Val Arg Asn>

1350        1360        1370        1380        1390
           *     *     *     *     *     *     *     *     *     *
    TCA TCT TAC TGC CTC AGA ATT AAA ATA AGT GCA AAA TTT GTG GAG AAT
    Ser Ser Tyr Cys Leu Arg Ile Lys Ile Ser Ala Lys Phe Val Glu Asn>

1400        1410        1420        1430        1440
               *     *     *     *     *     *     *     *     *     *
    GAG CCT AAC TTA TGT TAT AAT GCA CAA GCC ATA TTT AAG CAG AAA CTA
    Glu Pro Asn Leu Cys Tyr Asn Ala Gln Ala Ile Phe Lys Gln Lys Leu>

1450        1460        1470        1480
                   *     *     *     *     *     *     *     *     *
    CCC GTT GCA GGA GAC GGA GGA CTT GTG TGC CCT TAT ATG GAG TTT TTT
    Pro Val Ala Gly Asp Gly Gly Leu Val Cys Pro Tyr Met Glu Phe Phe>

1490        1500        1510        1520        1530
  *     *     *     *     *     *     *     *     *     *
    AAA AAT GAA AAT AAT GAG TTA CCT AAA TTA CAG TGG TAT AAG GAT TGC
    Lys Asn Glu Asn Asn Glu Leu Pro Lys Leu Gln Trp Tyr Lys Asp Cys>

1540        1550        1560        1570        1580
        *     *     *     *     *     *     *     *     *
    AAA CCT CTA CTT CTT GAC AAT ATA CAC TTT AGT GGA GTC AAA GAT AGG
    Lys Pro Leu Leu Leu Asp Asn Ile His Phe Ser Gly Val Lys Asp Arg>

1590        1600        1610        1620        1630
           *     *     *     *     *     *     *     *     *     *
    CTC ATC GTG ATG AAT GTG GCT GAA AAG CAT AGA GGG AAC TAT ACT TGT
    Leu Ile Val Met Asn Val Ala Glu Lys His Arg Gly Asn Tyr Thr Cys>

1640        1650        1660        1670        1680
               *     *     *     *     *     *     *     *     *     *
    CAT GCA TCC TAC ACA TAC TTG GGC AAG CAA TAT CCT ATT ACC CGG GTA
    His Ala Ser Tyr Thr Tyr Leu Gly Lys Gln Tyr Pro Ile Thr Arg Val>

1690        1700        1710        1720
                   *     *     *     *     *     *     *     *
    ATA GAA TTT ATT ACT CTA GAG GAA AAC AAA CCC ACA AGG CCT GTG ATT
    Ile Glu Phe Ile Thr Leu Glu Glu Asn Lys Pro Thr Arg Pro Val Ile>

1730        1740        1750        1760        1770
  *     *     *     *     *     *     *     *     *     *
    GTG AGC CCA GCT AAT GAG ACA ATG GAA GTA GAC TTG GGA TCC CAG ATA
    Val Ser Pro Ala Asn Glu Thr Met Glu Val Asp Leu Gly Ser Gln Ile>
```

Fig.26D.

```
        1780          1790          1800          1810          1820
          *             *             *             *             *
     *         *         *     *         *     *         *     *         *
    CAA TTG ATC TGT AAT GTC ACC GGC CAG TTG AGT GAC ATT GCT TAC TGG
    Gln Leu Ile Cys Asn Val Thr Gly Gln Leu Ser Asp Ile Ala Tyr Trp>

1830          1840          1850          1860          1870
          *             *             *             *             *
     *         *     *         *     *         *     *         *     *
    AAG TGG AAT GGG TCA GTA ATT GAT GAA GAT GAC CCA GTG CTA GGG GAA
    Lys Trp Asn Gly Ser Val Ile Asp Glu Asp Asp Pro Val Leu Gly Glu>

1880          1890          1900          1910          1920
          *             *             *             *             *
     *         *     *         *     *         *     *         *     *
    GAC TAT TAC AGT GTG GAA AAT CCT GCA AAC AAA AGA AGG AGT ACC CTC
    Asp Tyr Tyr Ser Val Glu Asn Pro Ala Asn Lys Arg Arg Ser Thr Leu>

1930          1940          1950          1960
          *             *             *             *             *
     *         *     *         *     *         *     *         *     *
    ATC ACA GTG CTT AAT ATA TCG GAA ATT GAG AGT AGA TTT TAT AAA CAT
    Ile Thr Val Leu Asn Ile Ser Glu Ile Glu Ser Arg Phe Tyr Lys His>

1970          1980          1990          2000          2010
  *             *             *             *             *
     *         *     *         *     *         *     *         *     *
    CCA TTT ACC TGT TTT GCC AAG AAT ACA CAT GGT ATA GAT GCA GCA TAT
    Pro Phe Thr Cys Phe Ala Lys Asn Thr His Gly Ile Asp Ala Ala Tyr>

2020          2030          2040          2050          2060
          *             *             *             *             *
     *         *     *         *     *         *     *         *     *
    ATC CAG TTA ATA TAT CCA GTC ACT AAT TCC GGA GAC AAA ACT CAC ACA
    Ile Gln Leu Ile Tyr Pro Val Thr Asn Ser Gly Asp Lys Thr His Thr>

2070          2080          2090          2100          2110
          *             *             *             *             *
     *         *     *         *     *         *     *         *     *
    TGC CCA CCG TGC CCA GCA CCT GAA CTC CTG GGG GGA CCG TCA GTC TTC
    Cys Pro Pro Cys Pro Ala Pro Glu Leu Leu Gly Gly Pro Ser Val Phe>

2120          2130          2140          2150          2160
          *             *             *             *             *
     *         *     *         *     *         *     *         *     *
    CTC TTC CCC CCA AAA CCC AAG GAC ACC CTC ATG ATC TCC CGG ACC CCT
    Leu Phe Pro Pro Lys Pro Lys Asp Thr Leu Met Ile Ser Arg Thr Pro>

2170          2180          2190          2200
          *             *             *             *             *
     *         *     *         *     *         *     *         *     *
    GAG GTC ACA TGC GTG GTG GTG GAC GTG AGC CAC GAA GAC CCT GAG GTC
    Glu Val Thr Cys Val Val Val Asp Val Ser His Glu Asp Pro Glu Val>

2210          2220          2230          2240          2250
  *             *             *             *             *
     *         *     *         *     *         *     *         *     *
    AAG TTC AAC TGG TAC GTG GAC GGC GTG GAG GTG CAT AAT GCC AAG ACA
    Lys Phe Asn Trp Tyr Val Asp Gly Val Glu Val His Asn Ala Lys Thr>

2260          2270          2280          2290          2300
          *             *             *             *             *
     *         *     *         *     *         *     *         *     *
    AAG CCG CGG GAG GAG CAG TAC AAC AGC ACG TAC CGT GTG GTC AGC GTC
    Lys Pro Arg Glu Glu Gln Tyr Asn Ser Thr Tyr Arg Val Val Ser Val>

2310          2320          2330          2340          2350
          *             *             *             *             *
     *         *     *         *     *         *     *         *     *
    CTC ACC GTC CTG CAC CAG GAC TGG CTG AAT GGC AAG GAG TAC AAG TGC
    Leu Thr Val Leu His Gln Asp Trp Leu Asn Gly Lys Glu Tyr Lys Cys>

```
               *         *         *         *         *         *         *         *         *         *
            AAG GTC TCC AAC AAA GCC CTC CCA GCC CCC ATC GAG AAA ACC ATC TCC
            Lys Val Ser Asn Lys Ala Leu Pro Ala Pro Ile Glu Lys Thr Ile Ser>

2410          2420          2430          2440
               *         *         *         *         *         *         *         *         *
            AAA GCC AAA GGG CAG CCC CGA GAA CCA CAG GTG TAC ACC CTG CCC CCA
            Lys Ala Lys Gly Gln Pro Arg Glu Pro Gln Val Tyr Thr Leu Pro Pro>

2450          2460          2470          2480          2490
         *       *       *       *       *       *       *       *       *       *
      TCC CGG GAG GAG ATG ACC AAG AAC CAG GTC AGC CTG ACC TGC CTG GTC
      Ser Arg Glu Glu Met Thr Lys Asn Gln Val Ser Leu Thr Cys Leu Val>

2500          2510          2520          2530          2540
            *         *         *         *         *         *         *         *         *
         AAA GGC TTC TAT CCC AGC GAC ATC GCC GTG GAG TGG GAG AGC AAT GGG
         Lys Gly Phe Tyr Pro Ser Asp Ile Ala Val Glu Trp Glu Ser Asn Gly>

2550          2560          2570          2580          2590
               *       *       *       *       *       *       *       *       *       *
            CAG CCG GAG AAC AAC TAC AAG ACC ACG CCT CCC GTG CTG GAC TCC GAC
            Gln Pro Glu Asn Asn Tyr Lys Thr Thr Pro Pro Val Leu Asp Ser Asp>

2600          2610          2620          2630          2640
                  *       *       *       *       *       *       *       *       *       *
               GGC TCC TTC TTC CTC TAT AGC AAG CTC ACC GTG GAC AAG AGC AGG TGG
               Gly Ser Phe Phe Leu Tyr Ser Lys Leu Thr Val Asp Lys Ser Arg Trp>

2650          2660          2670          2680
                  *       *       *       *       *       *       *       *       *
               CAG CAG GGG AAC GTC TTC TCA TGC TCC GTG ATG CAT GAG GCT CTG CAC
               Gln Gln Gly Asn Val Phe Ser Cys Ser Val Met His Glu Ala Leu His>

2690          2700          2710          2720          2730
         *       *       *       *       *       *       *       *       *
      AAC CAC TAC ACG CAG AAG AGC CTC TCC CTG TCT CCG GGT AAA TGA
      Asn His Tyr Thr Gln Lys Ser Leu Ser Leu Ser Pro Gly Lys ***>
```

Fig.31A.

```
              10            20            30            40
         *     *     *     *     *     *     *     *     *
       ATG   GTG   TGG   CTT   TGC   TCT   GGG   CTC   CTG   TTC   CCT   GTG   AGC   TGC   CTG   GTC
       TAC   CAC   ACC   GAA   ACG   AGA   CCC   GAG   GAC   AAG   GGA   CAC   TCG   ACG   GAC   CAG
       Met   Val   Trp   Leu   Cys   Ser   Gly   Leu   Leu   Phe   Pro   Val   Ser   Cys   Leu   Val>

50            60            70            80            90
         *     *     *     *     *     *     *     *     *     *
       CTG   CTG   CAG   GTG   GCA   AGC   TCT   GGG   AAC   ATG   AAG   GTC   TTG   CAG   GAG   CCC
       GAC   GAC   GTC   CAC   CGT   TCG   AGA   CCC   TTG   TAC   TTC   CAG   AAC   GTC   CTC   GGG
       Leu   Leu   Gln   Val   Ala   Ser   Ser   Gly   Asn   Met   Lys   Val   Leu   Gln   Glu   Pro>

100           110           120           130           140
         *     *     *     *     *     *     *     *     *
       ACC   TGC   GTC   TCC   GAC   TAC   ATG   AGC   ATC   TCT   ACT   TGC   GAG   TGG   AAG   ATG
       TGG   ACG   CAG   AGG   CTG   ATG   TAC   TCG   TAG   AGA   TGA   ACG   CTC   ACC   TTC   TAC
       Thr   Cys   Val   Ser   Asp   Tyr   Met   Ser   Ile   Ser   Thr   Cys   Glu   Trp   Lys   Met>

150           160           170           180           190
         *     *     *     *     *     *     *     *     *     *
       AAT   GGT   CCC   ACC   AAT   TGC   AGC   ACC   GAG   CTC   CGC   CTG   TTG   TAC   CAG   CTG
       TTA   CCA   GGG   TGG   TTA   ACG   TCG   TGG   CTC   GAG   GCG   GAC   AAC   ATG   GTC   GAC
       Asn   Gly   Pro   Thr   Asn   Cys   Ser   Thr   Glu   Leu   Arg   Leu   Leu   Tyr   Gln   Leu>

200           210           220           230           240
         *     *     *     *     *     *     *     *     *     *
       GTT   TTT   CTG   CTC   TCC   GAA   GCC   CAC   ACG   TGT   ATC   CCT   GAG   AAC   AAC   GGA
       CAA   AAA   GAC   GAG   AGG   CTT   CGG   GTG   TGC   ACA   TAG   GGA   CTC   TTG   TTG   CCT
       Val   Phe   Leu   Leu   Ser   Glu   Ala   His   Thr   Cys   Ile   Pro   Glu   Asn   Asn   Gly>

250           260           270           280
         *     *     *     *     *     *     *     *     *
       GGC   GCG   GGG   TGC   GTG   TGC   CAC   CTG   CTC   ATG   GAT   GAC   GTG   GTC   AGT   GCG
       CCG   CGC   CCC   ACG   CAC   ACG   GTG   GAC   GAG   TAC   CTA   CTG   CAC   CAG   TCA   CGC
       Gly   Ala   Gly   Cys   Val   Cys   His   Leu   Leu   Met   Asp   Asp   Val   Val   Ser   Ala>

290           300           310           320           330
         *     *     *     *     *     *     *     *     *     *
       GAT   AAC   TAT   ACA   CTG   GAC   CTG   TGG   GCT   GGG   CAG   CAG   CTG   CTG   TGG   AAG
       CTA   TTG   ATA   TGT   GAC   CTG   GAC   ACC   CGA   CCC   GTC   GTC   GAC   GAC   ACC   TTC
       Asp   Asn   Tyr   Thr   Leu   Asp   Leu   Trp   Ala   Gly   Gln   Gln   Leu   Leu   Trp   Lys>

340           350           360           370           380
         *     *     *     *     *     *     *     *     *     *
       GGC   TCC   TTC   AAG   CCC   AGC   GAG   CAT   GTG   AAA   CCC   AGG   GCC   CCA   GGA   AAC
       CCG   AGG   AAG   TTC   GGG   TCG   CTC   GTA   CAC   TTT   GGG   TCC   CGG   GGT   CCT   TTG
       Gly   Ser   Phe   Lys   Pro   Ser   Glu   His   Val   Lys   Pro   Arg   Ala   Pro   Gly   Asn>
```

Fig.31B.

```
       390            400           410           420           430
    *     *      *     *      *     *      *     *      *     *
   CTG ACA GTT CAC ACC AAT GTC TCC GAC ACT CTG CTG CTG ACC TGG AGC
   GAC TGT CAA GTG TGG TTA CAG AGG CTG TGA GAC GAC GAC TGG ACC TCG
   Leu Thr Val His Thr Asn Val Ser Asp Thr Leu Leu Leu Thr Trp Ser>

440           450           460           470           480
      *     *      *     *      *     *      *     *      *     *
   AAC CCG TAT CCC CCT GAC AAT TAC CTG TAT AAT CAT CTC ACC TAT GCA
   TTG GGC ATA GGG GGA CTG TTA ATG GAC ATA TTA GTA GAG TGG ATA CGT
   Asn Pro Tyr Pro Pro Asp Asn Tyr Leu Tyr Asn His Leu Thr Tyr Ala>

490           500           510           520
         *     *      *     *      *     *      *     *      *
   GTC AAC ATT TGG AGT GAA AAC GAC CCG GCA GAT TTC AGA ATC TAT AAC
   CAG TTG TAA ACC TCA CTT TTG CTG GGC CGT CTA AAG TCT TAG ATA TTG
   Val Asn Ile Trp Ser Glu Asn Asp Pro Ala Asp Phe Arg Ile Tyr Asn>

530           540           550           560           570
    *     *      *     *      *     *      *     *      *     *
   GTG ACC TAC CTA GAA CCC TCC CTC CGC ATC GCA GCC AGC ACC CTG AAG
   CAC TGG ATG GAT CTT GGG AGG GAG GCG TAG CGT CGG TCG TGG GAC TTC
   Val Thr Tyr Leu Glu Pro Ser Leu Arg Ile Ala Ala Ser Thr Leu Lys>

580           590           600           610           620
      *     *      *     *      *     *      *     *      *
   TCT GGG ATT TCC TAC AGG GCA CGG GTG AGG GCC TGG GCT CAG AGC TAT
   AGA CCC TAA AGG ATG TCC CGT GCC CAC TCC CGG ACC CGA GTC TCG ATA
   Ser Gly Ile Ser Tyr Arg Ala Arg Val Arg Ala Trp Ala Gln Ser Tyr>

630           640           650           660           670
      *     *      *     *      *     *      *     *      *     *
   AAC ACC ACC TGG AGT GAG TGG AGC CCC AGC ACC AAG TGG CAC AAC TCC
   TTG TGG TGG ACC TCA CTC ACC TCG GGG TCG TGG TTC ACC GTG TTG AGG
   Asn Thr Thr Trp Ser Glu Trp Ser Pro Ser Thr Lys Trp His Asn Ser>

680           690           700           710           720
      *     *      *     *      *     *      *     *      *     *
   TAC AGG GAG CCC TTC GAG CAG TCC GGT GGG GGC GGG GGC GCC GCG CCT
   ATG TCC CTC GGG AAG CTC GTC AGG CCA CCC CCG CCC CCG CGG CGC GGA
   Tyr Arg Glu Pro Phe Glu Gln Ser Gly Gly Gly Gly Ala Ala Pro>

730           740           750           760
      *     *      *     *      *     *      *     *
   ACG GAA ACT CAG CCA CCT GTG ACA AAT TTG AGT GTC TCT GTT GAA AAC
   TGC CTT TGA GTC GGT GGA CAC TGT TTA AAC TCA CAG AGA CAA CTT TTG
   Thr Glu Thr Gln Pro Pro Val Thr Asn Leu Ser Val Ser Val Glu Asn>
```

Fig.31C.

```
       770            780            790            800            810
        *       *      *       *      *       *      *       *      *       *
       CTC TGC ACA GTA ATA TGG ACA TGG AAT CCA CCC GAG GGA GCC AGC TCA
       GAG ACG TGT CAT TAT ACC TGT ACC TTA GGT GGG CTC CCT CGG TCG AGT
       Leu Cys Thr Val Ile Trp Thr Trp Asn Pro Pro Glu Gly Ala Ser Ser>

820            830            840            850            860
        *       *      *       *      *       *      *       *      *
       AAT TGT AGT CTA TGG TAT TTT AGT CAT TTT GGC GAC AAA CAA GAT AAG
       TTA ACA TCA GAT ACC ATA AAA TCA GTA AAA CCG CTG TTT GTT CTA TTC
       Asn Cys Ser Leu Trp Tyr Phe Ser His Phe Gly Asp Lys Gln Asp Lys>

870            880            890            900            910
        *       *      *       *      *       *      *       *      *       *
       AAA ATA GCT CCG GAA ACT CGT CGT TCA ATA GAA GTA CCC CTG AAT GAG
       TTT TAT CGA GGC CTT TGA GCA GCA AGT TAT CTT CAT GGG GAC TTA CTC
       Lys Ile Ala Pro Glu Thr Arg Arg Ser Ile Glu Val Pro Leu Asn Glu>

920            930            940            950            960
               *       *      *       *      *       *      *       *      *       *
              AGG ATT TGT CTG CAA GTG GGG TCC CAG TGT AGC ACC AAT GAG AGT GAG
              TCC TAA ACA GAC GTT CAC CCC AGG GTC ACA TCG TGG TTA CTC TCA CTC
              Arg Ile Cys Leu Gln Val Gly Ser Gln Cys Ser Thr Asn Glu Ser Glu>

970            980            990           1000
                      *       *      *       *      *       *      *       *      *
                     AAG CCT AGC ATT TTG GTT GAA AAA TGC ATC TCA CCC CCA GAA GGT GAT
                     TTC GGA TCG TAA AAC CAA CTT TTT ACG TAG AGT GGG GGT CTT CCA CTA
                     Lys Pro Ser Ile Leu Val Glu Lys Cys Ile Ser Pro Pro Glu Gly Asp>

1010           1020           1030           1040           1050
        *       *      *       *      *       *      *       *      *       *
       CCT GAG TCT GCT GTG ACT GAG CTT CAA TGC ATT TGG CAC AAC CTG AGC
       GGA CTC AGA CGA CAC TGA CTC GAA GTT ACG TAA ACC GTG TTG GAC TCG
       Pro Glu Ser Ala Val Thr Glu Leu Gln Cys Ile Trp His Asn Leu Ser>

1060           1070           1080           1090           1100
               *       *      *       *      *       *      *       *      *
              TAC ATG AAG TGT TCT TGG CTC CCT GGA AGG AAT ACC AGT CCC GAC ACT
              ATG TAC TTC ACA AGA ACC GAG GGA CCT TCC TTA TGG TCA GGG CTG TGA
              Tyr Met Lys Cys Ser Trp Leu Pro Gly Arg Asn Thr Ser Pro Asp Thr>

1110           1120           1130           1140           1150
                      *       *      *       *      *       *      *       *      *       *
                     AAC TAT ACT CTC TAC TAT TGG CAC AGA AGC CTG GAA AAA ATT CAT CAA
                     TTG ATA TGA GAG ATG ATA ACC GTG TCT TCG GAC CTT TTT TAA GTA GTT
                     Asn Tyr Thr Leu Tyr Tyr Trp His Arg Ser Leu Glu Lys Ile His Gln>
```

Fig.31D.

```
             1160           1170           1180            1190           1200
              *        *      *       *      *        *      *       *      *        *
         TGT GAA AAC ATC TTT AGA GAA GGC CAA TAC TTT GGT TGT TCC TTT GAT
         ACA CTT TTG TAG AAA TCT CTT CCG GTT ATG AAA CCA ACA AGG AAA CTA
         Cys Glu Asn Ile Phe Arg Glu Gly Gln Tyr Phe Gly Cys Ser Phe Asp>

1210           1220           1230           1240
              *      *       *      *       *      *       *      *       *      *
         CTG ACC AAA GTG AAG GAT TCC AGT TTT GAA CAA CAC AGT GTC CAA ATA
         GAC TGG TTT CAC TTC CTA AGG TCA AAA CTT GTT GTG TCA CAG GTT TAT
         Leu Thr Lys Val Lys Asp Ser Ser Phe Glu Gln His Ser Val Gln Ile>

1250           1260           1270           1280           1290
         *      *       *      *       *      *       *      *       *      *
     ATG GTC AAG GAT AAT GCA GGA AAA ATT AAA CCA TCC TTC AAT ATA GTG
     TAC CAG TTC CTA TTA CGT CCT TTT TAA TTT GGT AGG AAG TTA TAT CAC
     Met Val Lys Asp Asn Ala Gly Lys Ile Lys Pro Ser Phe Asn Ile Val>

1300           1310           1320           1330           1340
              *      *       *      *       *      *       *      *       *
         CCT TTA ACT TCC CGT GTG AAA CCT GAT CCT CCA CAT ATT AAA AAC CTC
         GGA AAT TGA AGG GCA CAC TTT GGA CTA GGA GGT GTA TAA TTT TTG GAG
         Pro Leu Thr Ser Arg Val Lys Pro Asp Pro Pro His Ile Lys Asn Leu>

1350           1360           1370           1380           1390
              *      *       *      *       *      *       *      *       *      *
         TCC TTC CAC AAT GAT GAC CTA TAT GTG CAA TGG GAG AAT CCA CAG AAT
         AGG AAG GTG TTA CTA CTG GAT ATA CAC GTT ACC CTC TTA GGT GTC TTA
         Ser Phe His Asn Asp Asp Leu Tyr Val Gln Trp Glu Asn Pro Gln Asn>

1400           1410           1420           1430           1440
              *      *       *      *       *      *       *      *       *      *
         TTT ATT AGC AGA TGC CTA TTT TAT GAA GTA GAA GTC AAT AAC AGC CAA
         AAA TAA TCG TCT ACG GAT AAA ATA CTT CAT CTT CAG TTA TTG TCG GTT
         Phe Ile Ser Arg Cys Leu Phe Tyr Glu Val Glu Val Asn Asn Ser Gln>

1450           1460           1470           1480
              *      *       *      *       *      *       *      *       *
         ACT GAG ACA CAT AAT GTT TTC TAC GTC CAA GAG GCT AAA TGT GAG AAT
         TGA CTC TGT GTA TTA CAA AAG ATG CAG GTT CTC CGA TTT ACA CTC TTA
         Thr Glu Thr His Asn Val Phe Tyr Val Gln Glu Ala Lys Cys Glu Asn>

1490           1500           1510           1520           1530
         *      *       *      *       *      *       *      *       *      *
     CCA GAA TTT GAG AGA AAT GTG GAG AAT ACA TCT TGT TTC ATG GTC CCT
     GGT CTT AAA CTC TCT TTA CAC CTC TTA TGT AGA ACA AAG TAC CAG GGA
     Pro Glu Phe Glu Arg Asn Val Glu Asn Thr Ser Cys Phe Met Val Pro>
```

Fig.31E.

```
        1540          1550          1560          1570          1580
          *       *     *       *     *       *     *      *      *
        GGT GTT CTT CCT GAT ACT TTG AAC ACA GTC AGA ATA AGA GTC AAA ACA
        CCA CAA GAA GGA CTA TGA AAC TTG TGT CAG TCT TAT TCT CAG TTT TGT
        Gly Val Leu Pro Asp Thr Leu Asn Thr Val Arg Ile Arg Val Lys Thr>

1590          1600          1610          1620          1630
               *       *     *       *     *       *     *       *     *       *
             AAT AAG TTA TGC TAT GAG GAT GAC AAA CTC TGG AGT AAT TGG AGC CAA
             TTA TTC AAT ACG ATA CTC CTA CTG TTT GAG ACC TCA TTA ACC TCG GTT
             Asn Lys Leu Cys Tyr Glu Asp Asp Lys Leu Trp Ser Asn Trp Ser Gln>

1640          1650          1660          1670          1680
                   *       *     *       *     *       *     *       *     *       *
                 GAA ATG AGT ATA GGT AAG AAG CGC AAT TCC ACA ACC GGA GAC AAA ACT
                 CTT TAC TCA TAT CCA TTC TTC GCG TTA AGG TGT TGG CCT CTG TTT TGA
                 Glu Met Ser Ile Gly Lys Lys Arg Asn Ser Thr Thr Gly Asp Lys Thr>

1690          1700          1710          1720
                        *       *     *       *     *       *     *       *     *
                      CAC ACA TGC CCA CCG TGC CCA GCA CCT GAA CTC CTG GGG GGA CCG TCA
                      GTG TGT ACG GGT GGC ACG GGT CGT GGA CTT GAG GAC CCC CCT GGC AGT
                      His Thr Cys Pro Pro Cys Pro Ala Pro Glu Leu Leu Gly Gly Pro Ser>

1730          1740          1750          1760          1770
          *       *     *       *     *       *     *       *     *       *
        GTC TTC CTC TTC CCC CCA AAA CCC AAG GAC ACC CTC ATG ATC TCC CGG
        CAG AAG GAG AAG GGG GGT TTT GGG TTC CTG TGG GAG TAC TAG AGG GCC
        Val Phe Leu Phe Pro Pro Lys Pro Lys Asp Thr Leu Met Ile Ser Arg>

1780          1790          1800          1810          1820
               *       *     *       *     *       *     *       *     *
             ACC CCT GAG GTC ACA TGC GTG GTG GTG GAC GTG AGC CAC GAA GAC CCT
             TGG GGA CTC CAG TGT ACG CAC CAC CAC CTG CAC TCG GTG CTT CTG GGA
             Thr Pro Glu Val Thr Cys Val Val Val Asp Val Ser His Glu Asp Pro>

1830          1840          1850          1860          1870
                   *       *     *       *     *       *     *       *     *       *
                 GAG GTC AAG TTC AAC TGG TAC GTG GAC GGC GTG GAG GTG CAT AAT GCC
                 CTC CAG TTC AAG TTG ACC ATG CAC CTG CCG CAC CTC CAC GTA TTA CGG
                 Glu Val Lys Phe Asn Trp Tyr Val Asp Gly Val Glu Val His Asn Ala>

1880          1890          1900          1910          1920
                        *       *     *       *     *       *     *       *     *       *
                      AAG ACA AAG CCG CGG GAG GAG CAG TAC AAC AGC ACG TAC CGT GTG GTC
                      TTC TGT TTC GGC GCC CTC CTC GTC ATG TTG TCG TGC ATG GCA CAC CAG
                      Lys Thr Lys Pro Arg Glu Glu Gln Tyr Asn Ser Thr Tyr Arg Val Val>
```

Fig.31F.

```
            1930              1940              1950              1960
         *     *     *     *     *     *     *     *     *     *
       AGC   GTC   CTC   ACC   GTC   CTG   CAC   CAG   GAC   TGG   CTG   AAT   GGC   AAG   GAG   TAC
       TCG   CAG   GAG   TGG   CAG   GAC   GTG   GTC   CTG   ACC   GAC   TTA   CCG   TTC   CTC   ATG
       Ser   Val   Leu   Thr   Val   Leu   His   Gln   Asp   Trp   Leu   Asn   Gly   Lys   Glu   Tyr>

1970              1980              1990              2000              2010
    *     *     *     *     *     *     *     *     *     *
  AAG   TGC   AAG   GTC   TCC   AAC   AAA   GCC   CTC   CCA   GCC   CCC   ATC   GAG   AAA   ACC
  TTC   ACG   TTC   CAG   AGG   TTG   TTT   CGG   GAG   GGT   CGG   GGG   TAG   CTC   TTT   TGG
  Lys   Cys   Lys   Val   Ser   Asn   Lys   Ala   Leu   Pro   Ala   Pro   Ile   Glu   Lys   Thr>

2020              2030              2040              2050              2060
         *     *     *     *     *     *     *     *     *
       ATC   TCC   AAA   GCC   AAA   GGG   CAG   CCC   CGA   GAA   CCA   CAG   GTG   TAC   ACC   CTG
       TAG   AGG   TTT   CGG   TTT   CCC   GTC   GGG   GCT   CTT   GGT   GTC   CAC   ATG   TGG   GAC
       Ile   Ser   Lys   Ala   Lys   Gly   Gln   Pro   Arg   Glu   Pro   Gln   Val   Tyr   Thr   Leu>

2070              2080              2090              2100              2110
    *     *     *     *     *     *     *     *     *     *
  CCC   CCA   TCC   CGG   GAG   GAG   ATG   ACC   AAG   AAC   CAG   GTC   AGC   CTG   ACC   TGC
  GGG   GGT   AGG   GCC   CTC   CTC   TAC   TGG   TTC   TTG   GTC   CAG   TCG   GAC   TGG   ACG
  Pro   Pro   Ser   Arg   Glu   Glu   Met   Thr   Lys   Asn   Gln   Val   Ser   Leu   Thr   Cys>

2120              2130              2140              2150              2160
             *     *     *     *     *     *     *     *     *     *
           CTG   GTC   AAA   GGC   TTC   TAT   CCC   AGC   GAC   ATC   GCC   GTG   GAG   TGG   GAG   AGC
           GAC   CAG   TTT   CCG   AAG   ATA   GGG   TCG   CTG   TAG   CGG   CAC   CTC   ACC   CTC   TCG
           Leu   Val   Lys   Gly   Phe   Tyr   Pro   Ser   Asp   Ile   Ala   Val   Glu   Trp   Glu   Ser>

2170              2180              2190              2200
             *     *     *     *     *     *     *     *     *
           AAT   GGG   CAG   CCG   GAG   AAC   AAC   TAC   AAG   ACC   ACG   CCT   CCC   GTG   CTG   GAC
           TTA   CCC   GTC   GGC   CTC   TTG   TTG   ATG   TTC   TGG   TGC   GGA   GGG   CAC   GAC   CTG
           Asn   Gly   Gln   Pro   Glu   Asn   Asn   Tyr   Lys   Thr   Thr   Pro   Pro   Val   Leu   Asp>

2210              2220              2230              2240              2250
    *     *     *     *     *     *     *     *     *     *
  TCC   GAC   GGC   TCC   TTC   TTC   CTC   TAT   AGC   AAG   CTC   ACC   GTG   GAC   AAG   AGC
  AGG   CTG   CCG   AGG   AAG   AAG   GAG   ATA   TCG   TTC   GAG   TGG   CAC   CTG   TTC   TCG
  Ser   Asp   Gly   Ser   Phe   Phe   Leu   Tyr   Ser   Lys   Leu   Thr   Val   Asp   Lys   Ser>

2260              2270              2280              2290              2300
         *     *     *     *     *     *     *     *     *
       AGG   TGG   CAG   CAG   GGG   AAC   GTC   TTC   TCA   TGC   TCC   GTG   ATG   CAT   GAG   GCT
       TCC   ACC   GTC   GTC   CCC   TTG   CAG   AAG   AGT   ACG   AGG   CAC   TAC   GTA   CTC   CGA
       Arg   Trp   Gln   Gln   Gly   Asn   Val   Phe   Ser   Cys   Ser   Val   Met   His   Glu   Ala>
```

Fig.31G.

```
     2310           2320           2330           2340           2350
  *     *       *     *       *     *       *     *       *     *
CTG CAC AAC CAC TAC ACG CAG AAG AGC CTC TCC CTG TCT CCG GGT AAA
GAC GTG TTG GTG ATG TGC GTC TTC TCG GAG AGG GAC AGA GGC CCA TTT
Leu His Asn His Tyr Thr Gln Lys Ser Leu Ser Leu Ser Pro Gly Lys>

*
TGA
ACT
***>
```

Fig.32A.

```
            10           20           30           40
             *            *            *            *            *
ATG GTG TGG CCG GCG CGG CTC TGC GGG CTG TGG GCG CTG CTG CTC TGC
TAC CAC ACC GGC CGC GCC GAG ACG CCC GAC ACC CGC GAC GAC GAG ACG
Met Val Trp Pro Ala Arg Leu Cys Gly Leu Trp Ala Leu Leu Leu Cys>

50           60           70           80           90
        *            *            *            *            *            *
GCC GGC GGC GGG GGC GGG GGC GGG GGC GCC GCG CCT ACG GAA ACT CAG
CGG CCG CCG CCC CCG CCC CCG CCC CCG CGG CGC GGA TGC CTT TGA GTC
Ala Gly Gly Gly Gly Gly Gly Gly Ala Ala Pro Thr Glu Thr Gln>

100          110          120          130          140
          *            *            *            *            *            *
CCA CCT GTG ACA AAT TTG AGT GTC TCT GTT GAA AAC CTC TGC ACA GTA
GGT GGA CAC TGT TTA AAC TCA CAG AGA CAA CTT TTG GAG ACG TGT CAT
Pro Pro Val Thr Asn Leu Ser Val Ser Val Glu Asn Leu Cys Thr Val>

150          160          170          180          190
          *            *            *            *            *            *
ATA TGG ACA TGG AAT CCA CCC GAG GGA GCC AGC TCA AAT TGT AGT CTA
TAT ACC TGT ACC TTA GGT GGG CTC CCT CGG TCG AGT TTA ACA TCA GAT
Ile Trp Thr Trp Asn Pro Pro Glu Gly Ala Ser Ser Asn Cys Ser Leu>

200          210          220          230          240
          *            *            *            *            *            *
TGG TAT TTT AGT CAT TTT GGC GAC AAA CAA GAT AAG AAA ATA GCT CCG
ACC ATA AAA TCA GTA AAA CCG CTG TTT GTT CTA TTC TTT TAT CGA GGC
Trp Tyr Phe Ser His Phe Gly Asp Lys Gln Asp Lys Lys Ile Ala Pro>

250          260          270          280
          *            *            *            *            *
GAA ACT CGT CGT TCA ATA GAA GTA CCC CTG AAT GAG AGG ATT TGT CTG
CTT TGA GCA GCA AGT TAT CTT CAT GGG GAC TTA CTC TCC TAA ACA GAC
Glu Thr Arg Arg Ser Ile Glu Val Pro Leu Asn Glu Arg Ile Cys Leu>

290          300          310          320          330
     *            *            *            *            *            *
CAA GTG GGG TCC CAG TGT AGC ACC AAT GAG AGT GAG AAG CCT AGC ATT
GTT CAC CCC AGG GTC ACA TCG TGG TTA CTC TCA CTC TTC GGA TCG TAA
Gln Val Gly Ser Gln Cys Ser Thr Asn Glu Ser Glu Lys Pro Ser Ile>

340          350          360          370          380
     *            *            *            *            *
TTG GTT GAA AAA TGC ATC TCA CCC CCA GAA GGT GAT CCT GAG TCT GCT
AAC CAA CTT TTT ACG TAG AGT GGG GGT CTT CCA CTA GGA CTC AGA CGA
Leu Val Glu Lys Cys Ile Ser Pro Pro Glu Gly Asp Pro Glu Ser Ala>
```

Fig.32B.

```
       390            400           410           420           430
        *       *      *      *       *      *     *      *      *      *
GTG ACT GAG CTT CAA TGC ATT TGG CAC AAC CTG AGC TAC ATG AAG TGT
CAC TGA CTC GAA GTT ACG TAA ACC GTG TTG GAC TCG ATG TAC TTC ACA
Val Thr Glu Leu Gln Cys Ile Trp His Asn Leu Ser Tyr Met Lys Cys>

440            450           460           470           480
        *       *      *      *       *      *     *      *      *      *
TCT TGG CTC CCT GGA AGG AAT ACC AGT CCC GAC ACT AAC TAT ACT CTC
AGA ACC GAG GGA CCT TCC TTA TGG TCA GGG CTG TGA TTG ATA TGA GAG
Ser Trp Leu Pro Gly Arg Asn Thr Ser Pro Asp Thr Asn Tyr Thr Leu>

490           500           510           520
        *       *      *      *       *      *     *      *      *
TAC TAT TGG CAC AGA AGC CTG GAA AAA ATT CAT CAA TGT GAA AAC ATC
ATG ATA ACC GTG TCT TCG GAC CTT TTT TAA GTA GTT ACA CTT TTG TAG
Tyr Tyr Trp His Arg Ser Leu Glu Lys Ile His Gln Cys Glu Asn Ile>

530           540           550           560           570
   *      *      *      *      *      *      *      *      *      *
TTT AGA GAA GGC CAA TAC TTT GGT TGT TCC TTT GAT CTG ACC AAA GTG
AAA TCT CTT CCG GTT ATG AAA CCA ACA AGG AAA CTA GAC TGG TTT CAC
Phe Arg Glu Gly Gln Tyr Phe Gly Cys Ser Phe Asp Leu Thr Lys Val>

580           590           600           610           620
         *      *      *      *       *      *     *      *      *
AAG GAT TCC AGT TTT GAA CAA CAC AGT GTC CAA ATA ATG GTC AAG GAT
TTC CTA AGG TCA AAA CTT GTT GTG TCA CAG GTT TAT TAC CAG TTC CTA
Lys Asp Ser Ser Phe Glu Gln His Ser Val Gln Ile Met Val Lys Asp>

630           640           650           660           670
         *      *      *      *       *      *     *      *      *
AAT GCA GGA AAA ATT AAA CCA TCC TTC AAT ATA GTG CCT TTA ACT TCC
TTA CGT CCT TTT TAA TTT GGT AGG AAG TTA TAT CAC GGA AAT TGA AGG
Asn Ala Gly Lys Ile Lys Pro Ser Phe Asn Ile Val Pro Leu Thr Ser>

680           690           700           710           720
         *      *      *      *       *      *     *      *      *
CGT GTG AAA CCT GAT CCT CCA CAT ATT AAA AAC CTC TCC TTC CAC AAT
GCA CAC TTT GGA CTA GGA GGT GTA TAA TTT TTG GAG AGG AAG GTG TTA
Arg Val Lys Pro Asp Pro Pro His Ile Lys Asn Leu Ser Phe His Asn>

730           740           750           760
        *       *      *      *       *      *     *      *      *
GAT GAC CTA TAT GTG CAA TGG GAG AAT CCA CAG AAT TTT ATT AGC AGA
CTA CTG GAT ATA CAC GTT ACC CTC TTA GGT GTC TTA AAA TAA TCG TCT
Asp Asp Leu Tyr Val Gln Trp Glu Asn Pro Gln Asn Phe Ile Ser Arg>
```

Fig.32C.

```
        770           780           790           800           810
         *     *       *     *       *     *       *     *       *     *
        TGC   CTA     TTT   TAT     GAA   GTA     GAA   GTC     AAT   AAC   AGC   CAA   ACT   GAG   ACA   CAT
        ACG   GAT     AAA   ATA     CTT   CAT     CTT   CAG     TTA   TTG   TCG   GTT   TGA   CTC   TGT   GTA
        Cys   Leu     Phe   Tyr     Glu   Val     Glu   Val     Asn   Asn   Ser   Gln   Thr   Glu   Thr   His>

820           830           840           850           860
         *     *       *     *       *     *       *     *       *
        AAT   GTT     TTC   TAC     GTC   CAA     GAG   GCT     AAA   TGT   GAG   AAT   CCA   GAA   TTT   GAG
        TTA   CAA     AAG   ATG     CAG   GTT     CTC   CGA     TTT   ACA   CTC   TTA   GGT   CTT   AAA   CTC
        Asn   Val     Phe   Tyr     Val   Gln     Glu   Ala     Lys   Cys   Glu   Asn   Pro   Glu   Phe   Glu>

870           880           890           900           910
         *     *       *     *       *     *       *     *       *     *
        AGA   AAT     GTG   GAG     AAT   ACA     TCT   TGT     TTC   ATG   GTC   CCT   GGT   GTT   CTT   CCT
        TCT   TTA     CAC   CTC     TTA   TGT     AGA   ACA     AAG   TAC   CAG   GGA   CCA   CAA   GAA   GGA
        Arg   Asn     Val   Glu     Asn   Thr     Ser   Cys     Phe   Met   Val   Pro   Gly   Val   Leu   Pro>

920           930           940           950           960
         *     *     *       *     *       *     *       *     *       *     *
        GAT   ACT   TTG     AAC   ACA     GTC   AGA     ATA   AGA     GTC   AAA   ACA   AAT   AAG   TTA   TGC
        CTA   TGA   AAC     TTG   TGT     CAG   TCT     TAT   TCT     CAG   TTT   TGT   TTA   TTC   AAT   ACG
        Asp   Thr   Leu     Asn   Thr     Val   Arg     Ile   Arg     Val   Lys   Thr   Asn   Lys   Leu   Cys>

970           980           990           1000
         *     *     *       *     *     *       *     *       *     *     *
        TAT   GAG   GAT     GAC   AAA   CTC     TGG   AGT     AAT   TGG   AGC   CAA   GAA   ATG   AGT   ATA
        ATA   CTC   CTA     CTG   TTT   GAG     ACC   TCA     TTA   ACC   TCG   GTT   CTT   TAC   TCA   TAT
        Tyr   Glu   Asp     Asp   Lys   Leu     Trp   Ser     Asn   Trp   Ser   Gln   Glu   Met   Ser   Ile>

1010          1020          1030          1040          1050
         *     *       *     *     *       *     *     *       *     *       *
        GGT   AAG     AAG   CGC   AAT     TCC   ACA   GGC     GCG   CCT     AGT   GGT   GGA   GGT   GGC   CGG
        CCA   TTC     TTC   GCG   TTA     AGG   TGT   CCG     CGC   GGA     TCA   CCA   CCT   CCA   CCG   GCC
        Gly   Lys     Lys   Arg   Asn     Ser   Thr   Gly     Ala   Pro     Ser   Gly   Gly   Gly   Gly   Arg>

1060          1070          1080          1090          1100
         *     *       *     *       *     *     *       *     *       *
        CCC   GCA     AGC   TCT     GGG   AAC   ATG     AAG   GTC     TTG   CAG   GAG   CCC   ACC   TGC   GTC
        GGG   CGT     TCG   AGA     CCC   TTG   TAC     TTC   CAG     AAC   GTC   CTC   GGG   TGG   ACG   CAG
        Pro   Ala     Ser   Ser     Gly   Asn   Met     Lys   Val     Leu   Gln   Glu   Pro   Thr   Cys   Val>

1110          1120          1130          1140          1150
         *     *       *     *       *     *       *     *       *     *
        TCC   GAC     TAC   ATG     AGC   ATC     TCT   ACT     TGC   GAG   TGG   AAG   ATG   AAT   GGT   CCC
        AGG   CTG     ATG   TAC     TCG   TAG     AGA   TGA     ACG   CTC   ACC   TTC   TAC   TTA   CCA   GGG
        Ser   Asp     Tyr   Met     Ser   Ile     Ser   Thr     Cys   Glu   Trp   Lys   Met   Asn   Gly   Pro>
```

Fig.32D.

```
         1160          1170          1180          1190          1200
           *        *     *        *     *        *     *        *     *    *
      ACC AAT TGC AGC ACC GAG CTC CGC CTG TTG TAC CAG CTG GTT TTT CTG
      TGG TTA ACG TCG TGG CTC GAG GCG GAC AAC ATG GTC GAC CAA AAA GAC
      Thr Asn Cys Ser Thr Glu Leu Arg Leu Leu Tyr Gln Leu Val Phe Leu>

1210          1220          1230          1240
            *     *        *     *        *     *        *     *     *
         CTC TCC GAA GCC CAC ACG TGT ATC CCT GAG AAC AAC GGA GGC GCG GGG
         GAG AGG CTT CGG GTG TGC ACA TAG GGA CTC TTG TTG CCT CCG CGC CCC
         Leu Ser Glu Ala His Thr Cys Ile Pro Glu Asn Asn Gly Gly Ala Gly>

1250          1260          1270          1280          1290
    *        *     *        *     *        *     *        *     *        *
 TGC GTG TGC CAC CTG CTC ATG GAT GAC GTG GTC AGT GCG GAT AAC TAT
 ACG CAC ACG GTG GAC GAG TAC CTA CTG CAC CAG TCA CGC CTA TTG ATA
 Cys Val Cys His Leu Leu Met Asp Asp Val Val Ser Ala Asp Asn Tyr>

1300          1310          1320          1330          1340
           *        *     *        *     *        *     *        *     *
      ACA CTG GAC CTG TGG GCT GGG CAG CAG CTG CTG TGG AAG GGC TCC TTC
      TGT GAC CTG GAC ACC CGA CCC GTC GTC GAC GAC ACC TTC CCG AGG AAG
      Thr Leu Asp Leu Trp Ala Gly Gln Gln Leu Leu Trp Lys Gly Ser Phe>

1350          1360          1370          1380          1390
            *     *        *     *        *     *        *     *        *     *
         AAG CCC AGC GAG CAT GTG AAA CCC AGG GCC CCA GGA AAC CTG ACA GTT
         TTC GGG TCG CTC GTA CAC TTT GGG TCC CGG GGT CCT TTG GAC TGT CAA
         Lys Pro Ser Glu His Val Lys Pro Arg Ala Pro Gly Asn Leu Thr Val>

1400          1410          1420          1430          1440
               *        *     *        *     *        *     *        *     *    *
            CAC ACC AAT GTC TCC GAC ACT CTG CTG CTG ACC TGG AGC AAC CCG TAT
            GTG TGG TTA CAG AGG CTG TGA GAC GAC GAC TGG ACC TCG TTG GGC ATA
            His Thr Asn Val Ser Asp Thr Leu Leu Leu Thr Trp Ser Asn Pro Tyr>

1450          1460          1470          1480
                  *     *        *     *        *     *        *     *     *
               CCC CCT GAC AAT TAC CTG TAT AAT CAT CTC ACC TAT GCA GTC AAC ATT
               GGG GGA CTG TTA ATG GAC ATA TTA GTA GAG TGG ATA CGT CAG TTG TAA
               Pro Pro Asp Asn Tyr Leu Tyr Asn His Leu Thr Tyr Ala Val Asn Ile>

1490          1500          1510          1520          1530
    *        *     *        *     *        *     *        *     *        *
 TGG AGT GAA AAC GAC CCG GCA GAT TTC AGA ATC TAT AAC GTG ACC TAC
 ACC TCA CTT TTG CTG GGC CGT CTA AAG TCT TAG ATA TTG CAC TGG ATG
 Trp Ser Glu Asn Asp Pro Ala Asp Phe Arg Ile Tyr Asn Val Thr Tyr>
```

Fig.32E.

```
      1540          1550          1560          1570          1580
        *       *     *       *     *       *     *       *     *
CTA GAA CCC TCC CTC CGC ATC GCA GCC AGC ACC CTG AAG TCT GGG ATT
GAT CTT GGG AGG GAG GCG TAG CGT CGG TCG TGG GAC TTC AGA CCC TAA
Leu Glu Pro Ser Leu Arg Ile Ala Ala Ser Thr Leu Lys Ser Gly Ile>

1590          1600          1610          1620          1630
       *     *       *     *       *     *       *     *       *     *
TCC TAC AGG GCA CGG GTG AGG GCC TGG GCT CAG TGC TAT AAC ACC ACC
AGG ATG TCC CGT GCC CAC TCC CGG ACC CGA GTC ACG ATA TTG TGG TGG
Ser Tyr Arg Ala Arg Val Arg Ala Trp Ala Gln Cys Tyr Asn Thr Thr>

1640          1650          1660          1670          1680
          *     *       *     *       *     *       *     *       *     *
TGG AGT GAG TGG AGC CCC AGC ACC AAG TGG CAC AAC TCC TAC AGG GAG
ACC TCA CTC ACC TCG GGG TCG TGG TTC ACC GTG TTG AGG ATG TCC CTC
Trp Ser Glu Trp Ser Pro Ser Thr Lys Trp His Asn Ser Tyr Arg Glu>

1690          1700          1710          1720
          *     *       *     *       *     *       *     *       *
CCC TTC GAG CAG TCC GGA GAC AAA ACT CAC ACA TGC CCA CCG TGC CCA
GGG AAG CTC GTC AGG CCT CTG TTT TGA GTG TGT ACG GGT GGC ACG GGT
Pro Phe Glu Gln Ser Gly Asp Lys Thr His Thr Cys Pro Pro Cys Pro>

1730          1740          1750          1760          1770
   *       *     *       *     *       *     *       *     *       *
GCA CCT GAA CTC CTG GGG GGA CCG TCA GTC TTC CTC TTC CCC CCA AAA
CGT GGA CTT GAG GAC CCC CCT GGC AGT CAG AAG GAG AAG GGG GGT TTT
Ala Pro Glu Leu Leu Gly Gly Pro Ser Val Phe Leu Phe Pro Pro Lys>

1780          1790          1800          1810          1820
      *       *     *       *     *       *     *       *     *
CCC AAG GAC ACC CTC ATG ATC TCC CGG ACC CCT GAG GTC ACA TGC GTG
GGG TTC CTG TGG GAG TAC TAG AGG GCC TGG GGA CTC CAG TGT ACG CAC
Pro Lys Asp Thr Leu Met Ile Ser Arg Thr Pro Glu Val Thr Cys Val>

1830          1840          1850          1860          1870
         *       *     *       *     *       *     *       *     *
GTG GTG GAC GTG AGC CAC GAA GAC CCT GAG GTC AAG TTC AAC TGG TAC
CAC CAC CTG CAC TCG GTG CTT CTG GGA CTC CAG TTC AAG TTG ACC ATG
Val Val Asp Val Ser His Glu Asp Pro Glu Val Lys Phe Asn Trp Tyr>

1880          1890          1900          1910          1920
            *       *     *       *     *       *     *       *     *
GTG GAC GGC GTG GAG GTG CAT AAT GCC AAG ACA AAG CCG CGG GAG GAG
CAC CTG CCG CAC CTC CAC GTA TTA CGG TTC TGT TTC GGC GCC CTC CTC
Val Asp Gly Val Glu Val His Asn Ala Lys Thr Lys Pro Arg Glu Glu>
```

Fig.32F.

```
         1930           1940           1950            1960
           *      *       *      *       *      *       *      *       *
       CAG TAC AAC AGC ACG TAC CGT GTG GTC AGC GTC CTC ACC GTC CTG CAC
       GTC ATG TTG TCG TGC ATG GCA CAC CAG TCG CAG GAG TGG CAG GAC GTG
       Gln Tyr Asn Ser Thr Tyr Arg Val Val Ser Val Leu Thr Val Leu His>

1970           1980           1990           2000           2010
    *      *       *      *       *      *       *      *       *      *
  CAG GAC TGG CTG AAT GGC AAG GAG TAC AAG TGC AAG GTC TCC AAC AAA
  GTC CTG ACC GAC TTA CCG TTC CTC ATG TTC ACG TTC CAG AGG TTG TTT
  Gln Asp Trp Leu Asn Gly Lys Glu Tyr Lys Cys Lys Val Ser Asn Lys>

2020           2030           2040           2050           2060
            *      *       *      *       *      *       *      *       *
        GCC CTC CCA GCC CCC ATC GAG AAA ACC ATC TCC AAA GCC AAA GGG CAG
        CGG GAG GGT CGG GGG TAG CTC TTT TGG TAG AGG TTT CGG TTT CCC GTC
        Ala Leu Pro Ala Pro Ile Glu Lys Thr Ile Ser Lys Ala Lys Gly Gln>

2070           2080           2090           2100           2110
            *      *       *      *       *      *       *      *       *
        CCC CGA GAA CCA CAG GTG TAC ACC CTG CCC CCA TCC CGG GAG GAG ATG
        GGG GCT CTT GGT GTC CAC ATG TGG GAC GGG GGT AGG GCC CTC CTC TAC
        Pro Arg Glu Pro Gln Val Tyr Thr Leu Pro Pro Ser Arg Glu Glu Met>

2120           2130           2140           2150           2160
            *      *       *      *       *      *       *      *       *
        ACC AAG AAC CAG GTC AGC CTG ACC TGC CTG GTC AAA GGC TTC TAT CCC
        TGG TTC TTG GTC CAG TCG GAC TGG ACG GAC CAG TTT CCG AAG ATA GGG
        Thr Lys Asn Gln Val Ser Leu Thr Cys Leu Val Lys Gly Phe Tyr Pro>

2170           2180           2190           2200
            *      *       *      *       *      *       *      *
        AGC GAC ATC GCC GTG GAG TGG GAG AGC AAT GGG CAG CCG GAG AAC AAC
        TCG CTG TAG CGG CAC CTC ACC CTC TCG TTA CCC GTC GGC CTC TTG TTG
        Ser Asp Ile Ala Val Glu Trp Glu Ser Asn Gly Gln Pro Glu Asn Asn>

2210           2220           2230           2240           2250
   *      *       *      *       *      *       *      *       *      *
 TAC AAG ACC ACG CCT CCC GTG CTG GAC TCC GAC GGC TCC TTC TTC CTC
 ATG TTC TGG TGC GGA GGG CAC GAC CTG AGG CTG CCG AGG AAG AAG GAG
 Tyr Lys Thr Thr Pro Pro Val Leu Asp Ser Asp Gly Ser Phe Phe Leu>

2260           2270           2280           2290           2300
           *      *       *      *       *      *       *      *       *
       TAT AGC AAG CTC ACC GTG GAC AAG AGC AGG TGG CAG CAG GGG AAC GTC
       ATA TCG TTC GAG TGG CAC CTG TTC TCG TCC ACC GTC GTC CCC TTG CAG
       Tyr Ser Lys Leu Thr Val Asp Lys Ser Arg Trp Gln Gln Gly Asn Val>
```

```
         2310            2320            2330            2340            2350
  *        *       *       *       *       *       *       *       *       *
TTC     TCA     TGC     TCC     GTG     ATG     CAT     GAG     GCT     CTG     CAC     AAC     CAC     TAC     ACG     CAG
AAG     AGT     ACG     AGG     CAC     TAC     GTA     CTC     CGA     GAC     GTG     TTG     GTG     ATG     TGC     GTC
Phe     Ser     Cys     Ser     Val     Met     His     Glu     Ala     Leu     His     Asn     His     Tyr     Thr     Gln>

2360            2370            2380
         *       *       *       *       *       *
AAG     AGC     CTC     TCC     CTG     TCT     CCG     GGT     AAA     TGA
TTC     TCG     GAG     AGG     GAC     AGA     GGC     CCA     TTT     ACT
Lys     Ser     Leu     Ser     Leu     Ser     Pro     Gly     Lys     ***>
```

Figure 38A

```
             10             20             30             40
         *        *      *       *      *        *      *        *
ATG GTG TTA CTC AGA CTT ATT TGT TTC ATA GCT CTA CTG ATT
TAC CAC AAT GAG TCT GAA TAA ACA AAG TAT CGA GAT GAC TAA
Met Val Leu Leu Arg Leu Ile Cys Phe Ile Ala Leu Leu Ile>
_____SIGNAL PEPTIDE_____>
_____IL-1RI_____>

50             60             70             80
         *        *      *       *      *        *      *        *
TCT TCT CTG GAG GCT GAT AAA TGC AAG GAA CGT GAA GAA AAA
AGA AGA GAC CTC CGA CTA TTT ACG TTC CTT GCA CTT CTT TTT
Ser Ser Leu Glu Ala Asp>
____SIGNAL PEPTIDE_____>
                        Lys Cys Lys Glu Arg Glu Glu Lys>
                        _____IL-1RI_____>

90            100            110            120
         *        *      *       *      *        *      *        *
ATA ATT TTA GTG TCA TCT GCA AAT GAA ATT GAT GTT CGT CCC
TAT TAA AAT CAC AGT AGA CGT TTA CTT TAA CTA CAA GCA GGG
Ile Ile Leu Val Ser Ser Ala Asn Glu Ile Asp Val Arg Pro>
_____IL-1RI_____>

130            140            150            160
         *        *      *       *      *        *      *        *
TGT CCT CTT AAC CCA AAT GAA CAC AAA GGC ACT ATA ACT TGG
ACA GGA GAA TTG GGT TTA CTT GTG TTT CCG TGA TAT TGA ACC
Cys Pro Leu Asn Pro Asn Glu His Lys Gly Thr Ile Thr Trp>
_____IL-1RI_____>

170            180            190            200            210
     *        *      *        *      *        *      *        *      *
TAT AAG GAT GAC AGC AAG ACA CCT GTA TCT ACA GAA CAA GCC
ATA TTC CTA CTG TCG TTC TGT GGA CAT AGA TGT CTT GTT CGG
Tyr Lys Asp Asp Ser Lys Thr Pro Val Ser Thr Glu Gln Ala>
_____IL-1RI_____>

220            230            240            250
         *        *      *       *      *        *      *        *
TCC AGG ATT CAT CAA CAC AAA GAG AAA CTT TGG TTT GTT CCT
AGG TCC TAA GTA GTT GTG TTT CTC TTT GAA ACC AAA CAA GGA
Ser Arg Ile His Gln His Lys Glu Lys Leu Trp Phe Val Pro>
_____IL-1RI_____>

260            270            280            290
         *        *      *       *      *        *      *
GCT AAG GTG GAG GAT TCA GGA CAT TAC TAT TGC GTG GTA AGA
CGA TTC CAC CTC CTA AGT CCT GTA ATG ATA ACG CAC CAT TCT
Ala Lys Val Glu Asp Ser Gly His Tyr Tyr Cys Val Val Arg>
_____IL-1RI_____>
```

Figure 38B

```
         300            310            320            330
   *      *      *      *      *      *      *      *      *
  AAT    TCA    TCT    TAC    TGC    CTC    AGA    ATT    AAA    ATA    AGT    GCA    AAA    TTT
  TTA    AGT    AGA    ATG    ACG    GAG    TCT    TAA    TTT    TAT    TCA    CGT    TTT    AAA
  Asn    Ser    Ser    Tyr    Cys    Leu    Arg    Ile    Lys    Ile    Ser    Ala    Lys    Phe>
  _____IL-1RI_____>

340            350            360            370
   *      *      *      *      *      *      *      *      *
  GTG    GAG    AAT    GAG    CCT    AAC    TTA    TGT    TAT    AAT    GCA    CAA    GCC    ATA
  CAC    CTC    TTA    CTC    GGA    TTG    AAT    ACA    ATA    TTA    CGT    GTT    CGG    TAT
  Val    Glu    Asn    Glu    Pro    Asn    Leu    Cys    Tyr    Asn    Ala    Gln    Ala    Ile>
  _____IL-1RI_____>

380            390            400            410            420
   *      *      *      *      *      *      *      *      *
  TTT    AAG    CAG    AAA    CTA    CCC    GTT    GCA    GGA    GAC    GGA    GGA    CTT    GTG
  AAA    TTC    GTC    TTT    GAT    GGG    CAA    CGT    CCT    CTG    CCT    CCT    GAA    CAC
  Phe    Lys    Gln    Lys    Leu    Pro    Val    Ala    Gly    Asp    Gly    Gly    Leu    Val>
  _____IL-1RI_____>

430            440            450            460
   *      *      *      *      *      *      *      *
  TGC    CCT    TAT    ATG    GAG    TTT    TTT    AAA    AAT    GAA    AAT    AAT    GAG    TTA
  ACG    GGA    ATA    TAC    CTC    AAA    AAA    TTT    TTA    CTT    TTA    TTA    CTC    AAT
  Cys    Pro    Tyr    Met    Glu    Phe    Phe    Lys    Asn    Glu    Asn    Asn    Glu    Leu>
  _____IL-1RI_____>

470            480            490            500
   *      *      *      *      *      *      *      *
  CCT    AAA    TTA    CAG    TGG    TAT    AAG    GAT    TGC    AAA    CCT    CTA    CTT    CTT
  GGA    TTT    AAT    GTC    ACC    ATA    TTC    CTA    ACG    TTT    GGA    GAT    GAA    GAA
  Pro    Lys    Leu    Gln    Trp    Tyr    Lys    Asp    Cys    Lys    Pro    Leu    Leu    Leu>
  _____IL-1RI_____>

510            520            530            540
   *      *      *      *      *      *      *      *      *
  GAC    AAT    ATA    CAC    TTT    AGT    GGA    GTC    AAA    GAT    AGG    CTC    ATC    GTG
  CTG    TTA    TAT    GTG    AAA    TCA    CCT    CAG    TTT    CTA    TCC    GAG    TAG    CAC
  Asp    Asn    Ile    His    Phe    Ser    Gly    Val    Lys    Asp    Arg    Leu    Ile    Val>
  _____IL-1RI_____>

550            560            570            580
   *      *      *      *      *      *      *      *
  ATG    AAT    GTG    GCT    GAA    AAG    CAT    AGA    GGG    AAC    TAT    ACT    TGT    CAT
  TAC    TTA    CAC    CGA    CTT    TTC    GTA    TCT    CCC    TTG    ATA    TGA    ACA    GTA
  Met    Asn    Val    Ala    Glu    Lys    His    Arg    Gly    Asn    Tyr    Thr    Cys    His>
  _____IL-1RI_____>

590            600            610            620            630
   *      *      *      *      *      *      *      *      *
  GCA    TCC    TAC    ACA    TAC    TTG    GGC    AAG    CAA    TAT    CCT    ATT    ACC    CGG
  CGT    AGG    ATG    TGT    ATG    AAC    CCG    TTC    GTT    ATA    GGA    TAA    TGG    GCC
  Ala    Ser    Tyr    Thr    Tyr    Leu    Gly    Lys    Gln    Tyr    Pro    Ile    Thr    Arg>
  _____IL-1RI_____>
```

Figure 38C

```
          640           650           660           670
       *    *       *    *       *    *       *    *
GTA ATA GAA TTT ATT ACT CTA GAG GAA AAC AAA CCC ACA AGG
CAT TAT CTT AAA TAA TGA GAT CTC CTT TTG TTT GGG TGT TCC
Val Ile Glu Phe Ile Thr Leu Glu Glu Asn Lys Pro Thr Arg>
                         IL-1RI                          >

680           690           700           710
       *    *       *    *       *    *       *    *
CCT GTG ATT GTG AGC CCA GCT AAT GAG ACA ATG GAA GTA GAC
GGA CAC TAA CAC TCG GGT CGA TTA CTC TGT TAC CTT CAT CTG
Pro Val Ile Val Ser Pro Ala Asn Glu Thr Met Glu Val Asp>
                         IL-1RI                          >

720           730           740           750
       *    *       *    *       *    *       *    *
TTG GGA TCC CAG ATA CAA TTG ATC TGT AAT GTC ACC GGC CAG
AAC CCT AGG GTC TAT GTT AAC TAG ACA TTA CAG TGG CCG GTC
Leu Gly Ser Gln Ile Gln Leu Ile Cys Asn Val Thr Gly Gln>
                         IL-1RI                          >

760           770           780           790
       *    *       *    *       *    *       *    *
TTG AGT GAC ATT GCT TAC TGG AAG TGG AAT GGG TCA GTA ATT
AAC TCA CTG TAA CGA ATG ACC TTC ACC TTA CCC AGT CAT TAA
Leu Ser Asp Ile Ala Tyr Trp Lys Trp Asn Gly Ser Val Ile>
                         IL-1RI                          >

800           810           820           830           840
   *       *    *       *    *       *    *       *    *
GAT GAA GAT GAC CCA GTG CTA GGG GAA GAC TAT TAC AGT GTG
CTA CTT CTA CTG GGT CAC GAT CCC CTT CTG ATA ATG TCA CAC
Asp Glu Asp Asp Pro Val Leu Gly Glu Asp Tyr Tyr Ser Val>
                         IL-1RI                          >

850           860           870           880
       *    *       *    *       *    *       *    *
GAA AAT CCT GCA AAC AAA AGA AGG AGT ACC CTC ATC ACA GTG
CTT TTA GGA CGT TTG TTT TCT TCC TCA TGG GAG TAG TGT CAC
Glu Asn Pro Ala Asn Lys Arg Arg Ser Thr Leu Ile Thr Val>
                         IL-1RI                          >

890           900           910           920
       *    *       *    *       *    *       *    *
CTT AAT ATA TCG GAA ATT GAG AGT AGA TTT TAT AAA CAT CCA
GAA TTA TAT AGC CTT TAA CTC TCA TCT AAA ATA TTT GTA GGT
Leu Asn Ile Ser Glu Ile Glu Ser Arg Phe Tyr Lys His Pro>
                         IL-1RI                          >

930           940           950           960
       *    *       *    *       *    *       *    *
TTT ACC TGT TTT GCC AAG AAT ACA CAT GGT ATA GAT GCA GCA
AAA TGG ACA AAA CGG TTC TTA TGT GTA CCA TAT CTA CGT CGT
Phe Thr Cys Phe Ala Lys Asn Thr His Gly Ile Asp Ala Ala>
                         IL-1RI                          >
```

Figure 38D

```
       970         980         990        1000
        *     *     *     *     *     *     *     *
TAT ATC CAG TTA ATA TAT CCA GTC ACT AAT TCA GAA CGC TGC
ATA TAG GTC AAT TAT ATA GGT CAG TGA TTA AGT CTT GCG ACG
Tyr Ile Gln Leu Ile Tyr Pro Val Thr Asn>
_____IL-1RI_____>
                                    Ser Glu Arg Cys>
                                    ___IL-1RAcP____>

1010        1020        1030        1040        1050
   *     *     *     *     *     *     *     *     *
GAT GAC TGG GGA CTA GAC ACC ATG AGG CAA ATC CAA GTG TTT
CTA CTG ACC CCT GAT CTG TGG TAC TCC GTT TAG GTT CAC AAA
Asp Asp Trp Gly Leu Asp Thr Met Arg Gln Ile Gln Val Phe>
_____IL-1RAcP_____>

1060        1070        1080        1090
        *     *     *     *     *     *     *     *
GAA GAT GAG CCA GCT CGC ATC AAG TGC CCA CTC TTT GAA CAC
CTT CTA CTC GGT CGA GCG TAG TTC ACG GGT GAG AAA CTT GTG
Glu Asp Glu Pro Ala Arg Ile Lys Cys Pro Leu Phe Glu His>
_____IL-1RAcP_____>

1100        1110        1120        1130
        *     *     *     *     *     *     *     *
TTC TTG AAA TTC AAC TAC AGC ACA GCC CAT TCA GCT GGC CTT
AAG AAC TTT AAG TTG ATG TCG TGT CGG GTA AGT CGA CCG GAA
Phe Leu Lys Phe Asn Tyr Ser Thr Ala His Ser Ala Gly Leu>
_____IL-1RAcP_____>

1140        1150        1160        1170
   *     *     *     *     *     *     *     *     *
ACT CTG ATC TGG TAT TGG ACT AGG CAG GAC CGG GAC CTT GAG
TGA GAC TAG ACC ATA ACC TGA TCC GTC CTG GCC CTG GAA CTC
Thr Leu Ile Trp Tyr Trp Thr Arg Gln Asp Arg Asp Leu Glu>
_____IL-1RAcP_____>

1180        1190        1200        1210
   *     *     *     *     *     *     *     *
GAG CCA ATT AAC TTC CGC CTC CCC GAG AAC CGC ATT AGT AAG
CTC GGT TAA TTG AAG GCG GAG GGG CTC TTG GCG TAA TCA TTC
Glu Pro Ile Asn Phe Arg Leu Pro Glu Asn Arg Ile Ser Lys>
_____IL-1RAcP_____>

1220        1230        1240        1250        1260
   *     *     *     *     *     *     *     *     *
GAG AAA GAT GTG CTG TGG TTC CGG CCC ACT CTC CTC AAT GAC
CTC TTT CTA CAC GAC ACC AAG GCC GGG TGA GAG GAG TTA CTG
Glu Lys Asp Val Leu Trp Phe Arg Pro Thr Leu Leu Asn Asp>
_____IL-1RAcP_____>
```

Figure 38E

```
              1270          1280          1290          1300
         *      *      *      *      *      *      *      *
       ACT GGC AAC TAT ACC TGC ATG TTA AGG AAC ACT ACA TAT TGC
       TGA CCG TTG ATA TGG ACG TAC AAT TCC TTG TGA TGT ATA ACG
       Thr Gly Asn Tyr Thr Cys Met Leu Arg Asn Thr Thr Tyr Cys>
                              ___IL-1RAcP_____>

1310          1320          1330          1340
         *      *      *      *      *      *      *      *
       AGC AAA GTT GCA TTT CCC TTG GAA GTT GTT CAA AAA GAC AGC
       TCG TTT CAA CGT AAA GGG AAC CTT CAA CAA GTT TTT CTG TCG
       Ser Lys Val Ala Phe Pro Leu Glu Val Val Gln Lys Asp Ser>
                              ___IL-1RAcP_____>

1350          1360          1370          1380
         *    *       *    *      *      *      *      *      *
       TGT TTC AAT TCC CCC ATG AAA CTC CCA GTG CAT AAA CTG TAT
       ACA AAG TTA AGG GGG TAC TTT GAG GGT CAC GTA TTT GAC ATA
       Cys Phe Asn Ser Pro Met Lys Leu Pro Val His Lys Leu Tyr>
                              ___IL-1RAcP_____>

1390          1400          1410          1420
         *      *      *      *    *      *      *      *
       ATA GAA TAT GGC ATT CAG AGG ATC ACT TGT CCA AAT GTA GAT
       TAT CTT ATA CCG TAA GTC TCC TAG TGA ACA GGT TTA CAT CTA
       Ile Glu Tyr Gly Ile Gln Arg Ile Thr Cys Pro Asn Val Asp>
                              ___IL-1RAcP_____>

1430          1440          1450          1460          1470
       *      *      *      *      *      *      *      *      *
       GGA TAT TTT CCT TCC AGT GTC AAA CCG ACT ATC ACT TGG TAT
       CCT ATA AAA GGA AGG TCA CAG TTT GGC TGA TAG TGA ACC ATA
       Gly Tyr Phe Pro Ser Ser Val Lys Pro Thr Ile Thr Trp Tyr>
                              ___IL-1RAcP_____>

1480          1490          1500          1510
         *      *      *      *      *      *      *      *
       ATG GGC TGT TAT AAA ATA CAG AAT TTT AAT AAT GTA ATA CCC
       TAC CCG ACA ATA TTT TAT GTC TTA AAA TTA TTA CAT TAT GGG
       Met Gly Cys Tyr Lys Ile Gln Asn Phe Asn Asn Val Ile Pro>
                              ___IL-1RAcP_____>

1520          1530          1540          1550
         *      *      *      *      *      *      *      *
       GAA GGT ATG AAC TTG AGT TTC CTC ATT GCC TTA ATT TCA AAT
       CTT CCA TAC TTG AAC TCA AAG GAG TAA CGG AAT TAA AGT TTA
       Glu Gly Met Asn Leu Ser Phe Leu Ile Ala Leu Ile Ser Asn>
                              ___IL-1RAcP_____>

1560          1570          1580          1590
         *      *      *      *      *      *      *      *      *
       AAT GGA AAT TAC ACA TGT GTT GTT ACA TAT CCA GAA AAT GGA
       TTA CCT TTA ATG TGT ACA CAA CAA TGT ATA GGT CTT TTA CCT
       Asn Gly Asn Tyr Thr Cys Val Val Thr Tyr Pro Glu Asn Gly>
                              ___IL-1RAcP_____>
```

Figure 38F

```
          1600              1610              1620              1630
            *         *       *         *       *         *       *         *
         CGT ACG TTT CAT CTC ACC AGG ACT CTG ACT GTA AAG GTA GTA
         GCA TGC AAA GTA GAG TGG TCC TGA GAC TGA CAT TTC CAT CAT
         Arg Thr Phe His Leu Thr Arg Thr Leu Thr Val Lys Val Val>
         _____IL-1RAcP_____>

1640              1650              1660              1670              1680
    *         *       *         *       *         *       *         *       *
 GGC TCT CCA AAA AAT GCA GTG CCC CCT GTG ATC CAT TCA CCT
 CCG AGA GGT TTT TTA CGT CAC GGG GGA CAC TAG GTA AGT GGA
 Gly Ser Pro Lys Asn Ala Val Pro Pro Val Ile His Ser Pro>
 _____IL-1RAcP_____>

1690              1700              1710              1720
            *         *       *         *       *         *       *         *
         AAT GAT CAT GTG GTC TAT GAG AAA GAA CCA GGA GAG GAG CTA
         TTA CTA GTA CAC CAG ATA CTC TTT CTT GGT CCT CTC CTC GAT
         Asn Asp His Val Val Tyr Glu Lys Glu Pro Gly Glu Glu Leu>
         _____IL-1RAcP_____>

1730              1740              1750              1760
            *         *       *         *       *         *       *         *
         CTC ATT CCC TGT ACG GTC TAT TTT AGT TTT CTG ATG GAT TCT
         GAG TAA GGG ACA TGC CAG ATA AAA TCA AAA GAC TAC CTA AGA
         Leu Ile Pro Cys Thr Val Tyr Phe Ser Phe Leu Met Asp Ser>
         _____IL-1RAcP_____>

1770              1780              1790              1800
            *         *       *         *       *         *       *         *
         CGC AAT GAG GTT TGG TGG ACC ATT GAT GGA AAA AAA CCT GAT
         GCG TTA CTC CAA ACC ACC TGG TAA CTA CCT TTT TTT GGA CTA
         Arg Asn Glu Val Trp Trp Thr Ile Asp Gly Lys Lys Pro Asp>
         _____IL-1RAcP_____>

1810              1820              1830              1840
            *         *       *         *       *         *       *         *
         GAC ATC ACT ATT GAT GTC ACC ATT AAC GAA AGT ATA AGT CAT
         CTG TAG TGA TAA CTA CAG TGG TAA TTG CTT TCA TAT TCA GTA
         Asp Ile Thr Ile Asp Val Thr Ile Asn Glu Ser Ile Ser His>
         _____IL-1RAcP_____>

1850              1860              1870              1880              1890
    *         *       *         *       *         *       *         *       *
 AGT AGA ACA GAA GAT GAA ACA AGA ACT CAG ATT TTG AGC ATC
 TCA TCT TGT CTT CTA CTT TGT TCT TGA GTC TAA AAC TCG TAG
 Ser Arg Thr Glu Asp Glu Thr Arg Thr Gln Ile Leu Ser Ile>
 _____IL-1RAcP_____>

1900              1910              1920              1930
            *         *       *         *       *         *       *         *
         AAG AAA GTT ACC TCT GAG GAT CTC AAG CGC AGC TAT GTC TGT
         TTC TTT CAA TGG AGA CTC CTA GAG TTC GCG TCG ATA CAG ACA
         Lys Lys Val Thr Ser Glu Asp Leu Lys Arg Ser Tyr Val Cys>
         _____IL-1RAcP_____>
```

Figure 38G

```
         1940          1950          1960          1970
  *       *     *       *     *       *     *       *
CAT GCT AGA AGT GCC AAA GGC GAA GTT GCC AAA GCA GCC AAG
GTA CGA TCT TCA CGG TTT CCG CTT CAA CGG TTT CGT CGG TTC
His Ala Arg Ser Ala Lys Gly Glu Val Ala Lys Ala Ala Lys>
                         ____IL-1RAcP_____>

1980          1990          2000          2010
  *       *     *       *     *       *     *       *     *
GTG AAG CAG AAA GTG CCA GCT CCA AGA TAC ACA GTG GAA TCC
CAC TTC GTC TTT CAC GGT CGA GGT TCT ATG TGT CAC CTT AGG
Val Lys Gln Lys Val Pro Ala Pro Arg Tyr Thr Val Glu>
                         ____IL-1RAcP_____>
                                                       Ser>
                                                       ___>

2020          2030          2040          2050
  *       *     *       *     *       *     *       *
GGA GAC AAA ACT CAC ACA TGC CCA CCG TGC CCA GCA CCT GAA
CCT CTG TTT TGA GTG TGT ACG GGT GGC ACG GGT CGT GGA CTT
Gly Asp Lys Thr His Thr Cys Pro Pro Cys Pro Ala Pro Glu>
                         ____FC-IgG1_____>

2060          2070          2080          2090          2100
  *       *     *       *     *       *     *       *     *
CTC CTG GGG GGA CCG TCA GTC TTC CTC TTC CCC CCA AAA CCC
GAG GAC CCC CCT GGC AGT CAG AAG GAG AAG GGG GGT TTT GGG
Leu Leu Gly Gly Pro Ser Val Phe Leu Phe Pro Pro Lys Pro>
                         ____FC-IgG1_____>

2110          2120          2130          2140
  *       *     *       *     *       *     *       *
AAG GAC ACC CTC ATG ATC TCC CGG ACC CCT GAG GTC ACA TGC
TTC CTG TGG GAG TAC TAG AGG GCC TGG GGA CTC CAG TGT ACG
Lys Asp Thr Leu Met Ile Ser Arg Thr Pro Glu Val Thr Cys>
                         ____FC-IgG1_____>

2150          2160          2170          2180
  *       *     *       *     *       *     *       *
GTG GTG GTG GAC GTG AGC CAC GAA GAC CCT GAG GTC AAG TTC
CAC CAC CAC CTG CAC TCG GTG CTT CTG GGA CTC CAG TTC AAG
Val Val Val Asp Val Ser His Glu Asp Pro Glu Val Lys Phe>
                         ____FC-IgG1_____>

2190          2200          2210          2220
  *       *     *       *     *       *     *       *
AAC TGG TAC GTG GAC GGC GTG GAG GTG CAT AAT GCC AAG ACA
TTG ACC ATG CAC CTG CCG CAC CTC CAC GTA TTA CGG TTC TGT
Asn Trp Tyr Val Asp Gly Val Glu Val His Asn Ala Lys Thr>
                         ____FC-IgG1_____>
```

Figure 38H

```
           2230           2240           2250           2260
            *              *       *       *       *       *       *       *
          AAG CCG CGG GAG GAG CAG TAC AAC AGC ACG TAC CGT GTG GTC
          TTC GGC GCC CTC CTC GTC ATG TTG TCG TGC ATG GCA CAC CAG
          Lys Pro Arg Glu Glu Gln Tyr Asn Ser Thr Tyr Arg Val Val>
                                   __FC-IgG1_____>

2270           2280           2290           2300           2310
   *       *       *       *       *       *       *       *       *
  AGC GTC CTC ACC GTC CTG CAC CAG GAC TGG CTG AAT GGC AAG
  TCG CAG GAG TGG CAG GAC GTG GTC CTG ACC GAC TTA CCG TTC
  Ser Val Leu Thr Val Leu His Gln Asp Trp Leu Asn Gly Lys>
                     __FC-IgG1_____>

2320           2330           2340           2350
            *       *       *       *       *       *       *       *
          GAG TAC AAG TGC AAG GTC TCC AAC AAA GCC CTC CCA GCC CCC
          CTC ATG TTC ACG TTC CAG AGG TTG TTT CGG GAG GGT CGG GGG
          Glu Tyr Lys Cys Lys Val Ser Asn Lys Ala Leu Pro Ala Pro>
                                   __FC-IgG1_____>

2360           2370           2380           2390
            *       *       *       *       *       *       *       *
          ATC GAG AAA ACC ATC TCC AAA GCC AAA GGG CAG CCC CGA GAA
          TAG CTC TTT TGG TAG AGG TTT CGG TTT CCC GTC GGG GCT CTT
          Ile Glu Lys Thr Ile Ser Lys Ala Lys Gly Gln Pro Arg Glu>
                                   __FC-IgG1_____>

2400           2410           2420           2430
            *       *       *       *       *       *       *       *
          CCA CAG GTG TAC ACC CTG CCC CCA TCC CGG GAG GAG ATG ACC
          GGT GTC CAC ATG TGG GAC GGG GGT AGG GCC CTC CTC TAC TGG
          Pro Gln Val Tyr Thr Leu Pro Pro Ser Arg Glu Glu Met Thr>
                                   __FC-IgG1_____>

2440           2450           2460           2470
   *       *       *       *       *       *       *       *
  AAG AAC CAG GTC AGC CTG ACC TGC CTG GTC AAA GGC TTC TAT
  TTC TTG GTC CAG TCG GAC TGG ACG GAC CAG TTT CCG AAG ATA
  Lys Asn Gln Val Ser Leu Thr Cys Leu Val Lys Gly Phe Tyr>
                     __FC-IgG1_____>

2480           2490           2500           2510           2520
 *       *       *       *       *       *       *       *       *
CCC AGC GAC ATC GCC GTG GAG TGG GAG AGC AAT GGG CAG CCG
GGG TCG CTG TAG CGG CAC CTC ACC CTC TCG TTA CCC GTC GGC
Pro Ser Asp Ile Ala Val Glu Trp Glu Ser Asn Gly Gln Pro>
                 __FC-IgG1_____>

2530           2540           2550           2560
            *       *       *       *       *       *       *       *
          GAG AAC AAC TAC AAG ACC ACG CCT CCC GTG CTG GAC TCC GAC
          CTC TTG TTG ATG TTC TGG TGC GGA GGG CAC GAC CTG AGG CTG
          Glu Asn Asn Tyr Lys Thr Thr Pro Pro Val Leu Asp Ser Asp>
                                   __FC-IgG1_____>
```

Figure 38I

```
          2570              2580              2590              2600
   *       *       *       *       *       *       *       *
  GGC     TCC     TTC     TTC     CTC     TAT     AGC     AAG     CTC     ACC     GTG     GAC     AAG     AGC
  CCG     AGG     AAG     AAG     GAG     ATA     TCG     TTC     GAG     TGG     CAC     CTG     TTC     TCG
  Gly     Ser     Phe     Phe     Leu     Tyr     Ser     Lys     Leu     Thr     Val     Asp     Lys     Ser>
                                     ____FC-IgG1_____>

2610              2620              2630              2640
   *       *       *       *       *       *       *       *       *
  AGG     TGG     CAG     CAG     GGG     AAC     GTC     TTC     TCA     TGC     TCC     GTG     ATG     CAT
  TCC     ACC     GTC     GTC     CCC     TTG     CAG     AAG     AGT     ACG     AGG     CAC     TAC     GTA
  Arg     Trp     Gln     Gln     Gly     Asn     Val     Phe     Ser     Cys     Ser     Val     Met     His>
                                     ____FC-IgG1_____>

2650              2660              2670              2680
   *       *       *       *       *       *       *       *
  GAG     GCT     CTG     CAC     AAC     CAC     TAC     ACG     CAG     AAG     AGC     CTC     TCC     CTG
  CTC     CGA     GAC     GTG     TTG     GTG     ATG     TGC     GTC     TTC     TCG     GAG     AGG     GAC
  Glu     Ala     Leu     His     Asn     His     Tyr     Thr     Gln     Lys     Ser     Leu     Ser     Leu>
                                     ____FC-IgG1_____>

2690            2700
   *       *       *
  TCT     CCG     GGT     AAA     TGA
  AGA     GGC     CCA     TTT     ACT
  Ser     Pro     Gly     Lys     ***>
      ____FC-IgG1_____>
```

Figure 39A

```
             10            20            30            40
              *             *             *             *
ATG GTG TTA CTC AGA CTT ATT TGT TTC ATA GCT CTA CTG ATT
TAC CAC AAT GAG TCT GAA TAA ACA AAG TAT CGA GAT GAC TAA
Met Val Leu Leu Arg Leu Ile Cys Phe Ile Ala Leu Leu Ile>
                    SIGNAL PEPTIDE                     >
                         IL-1RI                        >

50            60            70            80
        *             *             *             *
TCT TCT CTG GAG GCT GAT AAA TGC AAG GAA CGT GAA GAA AAA
AGA AGA GAC CTC CGA CTA TTT ACG TTC CTT GCA CTT CTT TTT
Ser Ser Leu Glu Ala Asp>
    SIGNAL PEPTIDE     >
                 Lys Cys Lys Glu Arg Glu Glu Lys>
                        IL-1RI                    >

90           100           110           120
      *             *             *             *
ATA ATT TTA GTG TCA TCT GCA AAT GAA ATT GAT GTT CGT CCC
TAT TAA AAT CAC AGT AGA CGT TTA CTT TAA CTA CAA GCA GGG
Ile Ile Leu Val Ser Ser Ala Asn Glu Ile Asp Val Arg Pro>
                         IL-1RI                        >

130           140           150           160
       *             *             *             *
TGT CCT CTT AAC CCA AAT GAA CAC AAA GGC ACT ATA ACT TGG
ACA GGA GAA TTG GGT TTA CTT GTG TTT CCG TGA TAT TGA ACC
Cys Pro Leu Asn Pro Asn Glu His Lys Gly Thr Ile Thr Trp>
                         IL-1RI                        >

170           180           190           200           210
  *             *             *             *             *
TAT AAG GAT GAC AGC AAG ACA CCT GTA TCT ACA GAA CAA GCC
ATA TTC CTA CTG TCG TTC TGT GGA CAT AGA TGT CTT GTT CGG
Tyr Lys Asp Asp Ser Lys Thr Pro Val Ser Thr Glu Gln Ala>
                         IL-1RI                        >

220           230           240           250
        *             *             *             *
TCC AGG ATT CAT CAA CAC AAA GAG AAA CTT TGG TTT GTT CCT
AGG TCC TAA GTA GTT GTG TTT CTC TTT GAA ACC AAA CAA GGA
Ser Arg Ile His Gln His Lys Glu Lys Leu Trp Phe Val Pro>
                         IL-1RI                        >

260           270           280           290
        *             *             *             *
GCT AAG GTG GAG GAT TCA GGA CAT TAC TAT TGC GTG GTA AGA
CGA TTC CAC CTC CTA AGT CCT GTA ATG ATA ACG CAC CAT TCT
Ala Lys Val Glu Asp Ser Gly His Tyr Tyr Cys Val Val Arg>
                         IL-1RI                        >
```

Figure 39B

```
         300           310           320           330
          *     *       *     *       *     *       *     *       *
        AAT TCA TCT TAC TGC CTC AGA ATT AAA ATA AGT GCA AAA TTT
        TTA AGT AGA ATG ACG GAG TCT TAA TTT TAT TCA CGT TTT AAA
        Asn Ser Ser Tyr Cys Leu Arg Ile Lys Ile Ser Ala Lys Phe>
        _____IL-1RI_____>

340           350           360           370
               *     *       *     *       *     *       *     *
         GTG GAG AAT GAG CCT AAC TTA TGT TAT AAT GCA CAA GCC ATA
         CAC CTC TTA CTC GGA TTG AAT ACA ATA TTA CGT GTT CGG TAT
         Val Glu Asn Glu Pro Asn Leu Cys Tyr Asn Ala Gln Ala Ile>
         _____IL-1RI_____>

380           390           400           410           420
         *     *       *     *       *     *       *     *       *
        TTT AAG CAG AAA CTA CCC GTT GCA GGA GAC GGA GGA CTT GTG
        AAA TTC GTC TTT GAT GGG CAA CGT CCT CTG CCT CCT GAA CAC
        Phe Lys Gln Lys Leu Pro Val Ala Gly Asp Gly Gly Leu Val>
        _____IL-1RI_____>

430           440           450           460
                 *     *       *     *       *     *       *     *
           TGC CCT TAT ATG GAG TTT TTT AAA AAT GAA AAT AAT GAG TTA
           ACG GGA ATA TAC CTC AAA AAA TTT TTA CTT TTA TTA CTC AAT
           Cys Pro Tyr Met Glu Phe Phe Lys Asn Glu Asn Asn Glu Leu>
           _____IL-1RI_____>

470           480           490           500
                 *     *       *     *       *     *       *     *
           CCT AAA TTA CAG TGG TAT AAG GAT TGC AAA CCT CTA CTT CTT
           GGA TTT AAT GTC ACC ATA TTC CTA ACG TTT GGA GAT GAA GAA
           Pro Lys Leu Gln Trp Tyr Lys Asp Cys Lys Pro Leu Leu Leu>
           _____IL-1RI_____>

510           520           530           540
               *     *       *     *       *     *       *     *       *
         GAC AAT ATA CAC TTT AGT GGA GTC AAA GAT AGG CTC ATC GTG
         CTG TTA TAT GTG AAA TCA CCT CAG TTT CTA TCC GAG TAG CAC
         Asp Asn Ile His Phe Ser Gly Val Lys Asp Arg Leu Ile Val>
         _____IL-1RI_____>

550           560           570           580
               *     *       *     *       *     *       *     *
         ATG AAT GTG GCT GAA AAG CAT AGA GGG AAC TAT ACT TGT CAT
         TAC TTA CAC CGA CTT TTC GTA TCT CCC TTG ATA TGA ACA GTA
         Met Asn Val Ala Glu Lys His Arg Gly Asn Tyr Thr Cys His>
         _____IL-1RI_____>

590           600           610           620           630
         *     *       *     *       *     *       *     *       *
        GCA TCC TAC ACA TAC TTG GGC AAG CAA TAT CCT ATT ACC CGG
        CGT AGG ATG TGT ATG AAC CCG TTC GTT ATA GGA TAA TGG GCC
        Ala Ser Tyr Thr Tyr Leu Gly Lys Gln Tyr Pro Ile Thr Arg>
        _____IL-1RI_____>
```

Figure 39C

```
              640           650           660           670
               *     *       *     *       *     *       *     *
         GTA ATA GAA TTT ATT ACT CTA GAG GAA AAC AAA CCC ACA AGG
         CAT TAT CTT AAA TAA TGA GAT CTC CTT TTG TTT GGG TGT TCC
         Val Ile Glu Phe Ile Thr Leu Glu Glu Asn Lys Pro Thr Arg>
         _____IL-1RI_____>

680           690           700           710
               *     *       *     *       *     *       *     *
         CCT GTG ATT GTG AGC CCA GCT AAT GAG ACA ATG GAA GTA GAC
         GGA CAC TAA CAC TCG GGT CGA TTA CTC TGT TAC CTT CAT CTG
         Pro Val Ile Val Ser Pro Ala Asn Glu Thr Met Glu Val Asp>
         _____IL-1RI_____>

720           730           740           750
               *     *       *     *       *     *       *     *
         TTG GGA TCC CAG ATA CAA TTG ATC TGT AAT GTC ACC GGC CAG
         AAC CCT AGG GTC TAT GTT AAC TAG ACA TTA CAG TGG CCG GTC
         Leu Gly Ser Gln Ile Gln Leu Ile Cys Asn Val Thr Gly Gln>
         _____IL-1RI_____>

760           770           780           790
               *     *       *     *       *     *       *     *
         TTG AGT GAC ATT GCT TAC TGG AAG TGG AAT GGG TCA GTA ATT
         AAC TCA CTG TAA CGA ATG ACC TTC ACC TTA CCC AGT CAT TAA
         Leu Ser Asp Ile Ala Tyr Trp Lys Trp Asn Gly Ser Val Ile>
         _____IL-1RI_____>

800           810           820           830           840
          *     *       *     *       *     *       *     *       *
         GAT GAA GAT GAC CCA GTG CTA GGG GAA GAC TAT TAC AGT GTG
         CTA CTT CTA CTG GGT CAC GAT CCC CTT CTG ATA ATG TCA CAC
         Asp Glu Asp Asp Pro Val Leu Gly Glu Asp Tyr Tyr Ser Val>
         _____IL-1RI_____>

850           860           870           880
               *     *       *     *       *     *       *     *
         GAA AAT CCT GCA AAC AAA AGA AGG AGT ACC CTC ATC ACA GTG
         CTT TTA GGA CGT TTG TTT TCT TCC TCA TGG GAG TAG TGT CAC
         Glu Asn Pro Ala Asn Lys Arg Arg Ser Thr Leu Ile Thr Val>
         _____IL-1RI_____>

890           900           910           920
               *     *       *     *       *     *       *     *
         CTT AAT ATA TCG GAA ATT GAG AGT AGA TTT TAT AAA CAT CCA
         GAA TTA TAT AGC CTT TAA CTC TCA TCT AAA ATA TTT GTA GGT
         Leu Asn Ile Ser Glu Ile Glu Ser Arg Phe Tyr Lys His Pro>
         _____IL-1RI_____>

930           940           950           960
               *     *       *     *       *     *       *     *
         TTT ACC TGT TTT GCC AAG AAT ACA CAT GGT ATA GAT GCA GCA
         AAA TGG ACA AAA CGG TTC TTA TGT GTA CCA TAT CTA CGT CGT
         Phe Thr Cys Phe Ala Lys Asn Thr His Gly Ile Asp Ala Ala>
         _____IL-1RI_____>
```

Figure 39D

```
       970           980           990          1000
        *      *      *      *      *      *      *      *
   TAT ATC CAG TTA ATA TAT CCA GTC ACT AAT TCA GAA CGC TGC
   ATA TAG GTC AAT TAT ATA GGT CAG TGA TTA AGT CTT GCG ACG
   Tyr Ile Gln Leu Ile Tyr Pro Val Thr Asn>
   _____IL-1RI_____>
                                             Ser Glu Arg Cys>
                                             ___IL-1RAcP____>

1010          1020          1030          1040          1050
      *      *      *      *      *      *      *      *      *
   GAT GAC TGG GGA CTA GAC ACC ATG AGG CAA ATC CAA GTG TTT
   CTA CTG ACC CCT GAT CTG TGG TAC TCC GTT TAG GTT CAC AAA
   Asp Asp Trp Gly Leu Asp Thr Met Arg Gln Ile Gln Val Phe>
   _____IL-1RAcP_____>

1060          1070          1080          1090
        *      *      *      *      *      *      *      *
   GAA GAT GAG CCA GCT CGC ATC AAG TGC CCA CTC TTT GAA CAC
   CTT CTA CTC GGT CGA GCG TAG TTC ACG GGT GAG AAA CTT GTG
   Glu Asp Glu Pro Ala Arg Ile Lys Cys Pro Leu Phe Glu His>
   _____IL-1RAcP_____>

1100          1110          1120          1130
        *      *      *      *      *      *      *      *
   TTC TTG AAA TTC AAC TAC AGC ACA GCC CAT TCA GCT GGC CTT
   AAG AAC TTT AAG TTG ATG TCG TGT CGG GTA AGT CGA CCG GAA
   Phe Leu Lys Phe Asn Tyr Ser Thr Ala His Ser Ala Gly Leu>
   _____IL-1RAcP_____>

1140          1150          1160          1170
        *      *      *      *      *      *      *      *      *
   ACT CTG ATC TGG TAT TGG ACT AGG CAG GAC CGG GAC CTT GAG
   TGA GAC TAG ACC ATA ACC TGA TCC GTC CTG GCC CTG GAA CTC
   Thr Leu Ile Trp Tyr Trp Thr Arg Gln Asp Arg Asp Leu Glu>
   _____IL-1RAcP_____>

1180          1190          1200          1210
        *      *      *      *      *      *      *      *
   GAG CCA ATT AAC TTC CGC CTC CCC GAG AAC CGC ATT AGT AAG
   CTC GGT TAA TTG AAG GCG GAG GGG CTC TTG GCG TAA TCA TTC
   Glu Pro Ile Asn Phe Arg Leu Pro Glu Asn Arg Ile Ser Lys>
   _____IL-1RAcP_____>

1220          1230          1240          1250          1260
    *      *      *      *      *      *      *      *      *
   GAG AAA GAT GTG CTG TGG TTC CGG CCC ACT CTC CTC AAT GAC
   CTC TTT CTA CAC GAC ACC AAG GCC GGG TGA GAG GAG TTA CTG
   Glu Lys Asp Val Leu Trp Phe Arg Pro Thr Leu Leu Asn Asp>
   _____IL-1RAcP_____>
```

Figure 39E

```
           1270            1280            1290            1300
     *       *       *       *       *       *       *       *
    ACT GGC AAC TAT ACC TGC ATG TTA AGG AAC ACT ACA TAT TGC
    TGA CCG TTG ATA TGG ACG TAC AAT TCC TTG TGA TGT ATA ACG
    Thr Gly Asn Tyr Thr Cys Met Leu Arg Asn Thr Thr Tyr Cys>
                              __IL-1RAcP_____>

1310            1320            1330            1340
     *       *       *       *       *       *       *       *
    AGC AAA GTT GCA TTT CCC TTG GAA GTT GTT CAA AAA GAC AGC
    TCG TTT CAA CGT AAA GGG AAC CTT CAA CAA GTT TTT CTG TCG
    Ser Lys Val Ala Phe Pro Leu Glu Val Val Gln Lys Asp Ser>
    _____IL-1RAcP_____>

1350            1360            1370            1380
   *       *       *       *       *       *       *       *       *
   TGT TTC AAT TCC CCC ATG AAA CTC CCA GTG CAT AAA CTG TAT
   ACA AAG TTA AGG GGG TAC TTT GAG GGT CAC GTA TTT GAC ATA
   Cys Phe Asn Ser Pro Met Lys Leu Pro Val His Lys Leu Tyr>
   _____IL-1RAcP_____>

1390            1400            1410            1420
     *       *       *       *       *       *       *       *
    ATA GAA TAT GGC ATT CAG AGG ATC ACT TGT CCA AAT GTA GAT
    TAT CTT ATA CCG TAA GTC TCC TAG TGA ACA GGT TTA CAT CTA
    Ile Glu Tyr Gly Ile Gln Arg Ile Thr Cys Pro Asn Val Asp>
    _____IL-1RAcP_____>

1430            1440            1450            1460            1470
   *       *       *       *       *       *       *       *       *
  GGA TAT TTT CCT TCC AGT GTC AAA CCG ACT ATC ACT TGG TAT
  CCT ATA AAA GGA AGG TCA CAG TTT GGC TGA TAG TGA ACC ATA
  Gly Tyr Phe Pro Ser Ser Val Lys Pro Thr Ile Thr Trp Tyr>
  _____IL-1RAcP_____>

1480            1490            1500            1510
      *       *       *       *       *       *       *       *
     ATG GGC TGT TAT AAA ATA CAG AAT TTT AAT AAT GTA ATA CCC
     TAC CCG ACA ATA TTT TAT GTC TTA AAA TTA TTA CAT TAT GGG
     Met Gly Cys Tyr Lys Ile Gln Asn Phe Asn Asn Val Ile Pro>
     _____IL-1RAcP_____>

1520            1530            1540            1550
     *       *       *       *       *       *       *       *
    GAA GGT ATG AAC TTG AGT TTC CTC ATT GCC TTA ATT TCA AAT
    CTT CCA TAC TTG AAC TCA AAG GAG TAA CGG AAT TAA AGT TTA
    Glu Gly Met Asn Leu Ser Phe Leu Ile Ala Leu Ile Ser Asn>
                             ___IL-1RAcP_____>

1560            1570            1580            1590
      *       *       *       *       *       *       *       *       *
     AAT GGA AAT TAC ACA TGT GTT GTT ACA TAT CCA GAA AAT GGA
     TTA CCT TTA ATG TGT ACA CAA CAA TGT ATA GGT CTT TTA CCT
     Asn Gly Asn Tyr Thr Cys Val Val Thr Tyr Pro Glu Asn Gly>
     _____IL-1RAcP_____>
```

Figure 39F

```
        1600            1610            1620           1630
         *       *       *       *       *       *       *       *
        CGT ACG TTT CAT CTC ACC AGG ACT CTG ACT GTA AAG GTA GTA
        GCA TGC AAA GTA GAG TGG TCC TGA GAC TGA CAT TTC CAT CAT
        Arg Thr Phe His Leu Thr Arg Thr Leu Thr Val Lys Val Val>
        _____IL-1RAcP_____>

1640            1650            1660           1670            1680
 *       *       *       *       *       *       *       *       *
GGC TCT CCA AAA AAT GCA GTG CCC CCT GTG ATC CAT TCA CCT
CCG AGA GGT TTT TTA CGT CAC GGG GGA CAC TAG GTA AGT GGA
Gly Ser Pro Lys Asn Ala Val Pro Pro Val Ile His Ser Pro>
_____IL-1RAcP_____>

1690            1700            1710           1720
         *       *       *       *       *       *       *       *
        AAT GAT CAT GTG GTC TAT GAG AAA GAA CCA GGA GAG GAG CTA
        TTA CTA GTA CAC CAG ATA CTC TTT CTT GGT CCT CTC CTC GAT
        Asn Asp His Val Val Tyr Glu Lys Glu Pro Gly Glu Glu Leu>
        _____IL-1RAcP_____>

1730            1740            1750           1760
         *       *       *       *       *       *       *       *
        CTC ATT CCC TGT ACG GTC TAT TTT AGT TTT CTG ATG GAT TCT
        GAG TAA GGG ACA TGC CAG ATA AAA TCA AAA GAC TAC CTA AGA
        Leu Ile Pro Cys Thr Val Tyr Phe Ser Phe Leu Met Asp Ser>
        _____IL-1RAcP_____>

1770            1780            1790           1800
         *       *       *       *       *       *       *       *       *
        CGC AAT GAG GTT TGG TGG ACC ATT GAT GGA AAA AAA CCT GAT
        GCG TTA CTC CAA ACC ACC TGG TAA CTA CCT TTT TTT GGA CTA
        Arg Asn Glu Val Trp Trp Thr Ile Asp Gly Lys Lys Pro Asp>
        _____IL-1RAcP_____>

1810            1820            1830           1840
         *       *       *       *       *       *       *       *
        GAC ATC ACT ATT GAT GTC ACC ATT AAC GAA AGT ATA AGT CAT
        CTG TAG TGA TAA CTA CAG TGG TAA TTG CTT TCA TAT TCA GTA
        Asp Ile Thr Ile Asp Val Thr Ile Asn Glu Ser Ile Ser His>
        _____IL-1RAcP_____>

1850            1860            1870           1880            1890
 *       *       *       *       *       *       *       *       *
AGT AGA ACA GAA GAT GAA ACA AGA ACT CAG ATT TTG AGC ATC
TCA TCT TGT CTT CTA CTT TGT TCT TGA GTC TAA AAC TCG TAG
Ser Arg Thr Glu Asp Glu Thr Arg Thr Gln Ile Leu Ser Ile>
_____IL-1RAcP_____>

1900            1910            1920           1930
         *       *       *       *       *       *       *       *
        AAG AAA GTT ACC TCT GAG GAT CTC AAG CGC AGC TAT GTC TGT
        TTC TTT CAA TGG AGA CTC CTA GAG TTC GCG TCG ATA CAG ACA
        Lys Lys Val Thr Ser Glu Asp Leu Lys Arg Ser Tyr Val Cys>
        _____IL-1RAcP_____>
```

Figure 39G

```
            1940           1950           1960           1970
     *        *       *      *       *      *       *      *
    CAT GCT AGA AGT GCC AAA GGC GAA GTT GCC AAA GCA GCC AAG
    GTA CGA TCT TCA CGG TTT CCG CTT CAA CGG TTT CGT CGG TTC
    His Ala Arg Ser Ala Lys Gly Glu Val Ala Lys Ala Ala Lys>
    _____IL-1RAcP_____>

1980           1990           2000           2010
     *        *       *      *       *      *       *      *       *
    GTG AAG CAG AAA GTG CCA GCT CCA AGA TAC ACA GTG GAA TCC
    CAC TTC GTC TTT CAC GGT CGA GGT TCT ATG TGT CAC CTT AGG
    Val Lys Gln Lys Val Pro Ala Pro Arg Tyr Thr Val Glu>
    _____IL-1RAcP_____>
                                                          Ser>
                                                          ___>

2020           2030           2040           2050
     *        *       *      *       *      *       *      *
    GGA GAG TCC AAA TAC GGT CCG CCA TGC CCA TCA TGC CCA GCA
    CCT CTC AGG TTT ATG CCA GGC GGT ACG GGT AGT ACG GGT CGT
        Glu Ser Lys Tyr Gly Pro Pro Cys Pro Ser Cys Pro Ala>
    _____FC-IgG4_____>
    Gly>
    ___>

2060           2070           2080           2090           2100
     *      *       *      *       *      *       *      *       *
    CCT GAG TTC CTG GGG GGA CCA TCA GTC TTC CTG TTC CCC CCA
    GGA CTC AAG GAC CCC CCT GGT AGT CAG AAG GAC AAG GGG GGT
    Pro Glu Phe Leu Gly Gly Pro Ser Val Phe Leu Phe Pro Pro>
    _____FC-IgG4_____>

2110           2120           2130           2140
         *        *       *      *       *      *       *      *
    AAA CCC AAG GAC ACT CTC ATG ATC TCC CGG ACC CCT GAG GTC
    TTT GGG TTC CTG TGA GAG TAC TAG AGG GCC TGG GGA CTC CAG
    Lys Pro Lys Asp Thr Leu Met Ile Ser Arg Thr Pro Glu Val>
    _____FC-IgG4_____>

2150           2160           2170       2180
         *        *       *      *       *      *       *      *
    ACG TGC GTG GTG GTG GAC GTG AGC CAG GAA GAC CCC GAG GTC
    TGC ACG CAC CAC CAC CTG CAC TCG GTC CTT CTG GGG CTC CAG
    Thr Cys Val Val Val Asp Val Ser Gln Glu Asp Pro Glu Val>
    _____FC-IgG4_____>

2190           2200           2210           2220
     *        *       *      *       *      *       *      *       *
    CAG TTC AAC TGG TAC GTG GAT GGC GTG GAG GTG CAT AAT GCC
    GTC AAG TTG ACC ATG CAC CTA CCG CAC CTC CAC GTA TTA CGG
    Gln Phe Asn Trp Tyr Val Asp Gly Val Glu Val His Asn Ala>
    _____FC-IgG4_____>
```

Figure 39H

```
      2230            2240            2250            2260
       *        *       *       *       *       *       *       *
    AAG ACA AAG CCG CGG GAG GAG CAG TTC AAC AGC ACG TAC CGT
    TTC TGT TTC GGC GCC CTC CTC GTC AAG TTG TCG TGC ATG GCA
    Lys Thr Lys Pro Arg Glu Glu Gln Phe Asn Ser Thr Tyr Arg>
    _____FC-IgG4_____>

2270            2280            2290            2300            2310
    *       *       *       *       *       *       *       *       *
    GTG GTC AGC GTC CTC ACC GTC CTG CAC CAG GAC TGG CTG AAC
    CAC CAG TCG CAG GAG TGG CAG GAC GTG GTC CTG ACC GAC TTG
    Val Val Ser Val Leu Thr Val Leu His Gln Asp Trp Leu Asn>
    _____FC-IgG4_____>

2320            2330            2340            2350
           *       *       *       *       *       *       *       *
    GGC AAG GAG TAC AAG TGC AAG GTC TCC AAC AAA GGC CTC CCG
    CCG TTC CTC ATG TTC ACG TTC CAG AGG TTG TTT CCG GAG GGC
    Gly Lys Glu Tyr Lys Cys Lys Val Ser Asn Lys Gly Leu Pro>
    _____FC-IgG4_____>

2360            2370            2380            2390
           *       *       *       *       *       *       *       *
    TCC TCC ATC GAG AAA ACC ATC TCC AAA GCC AAA GGG CAG CCC
    AGG AGG TAG CTC TTT TGG TAG AGG TTT CGG TTT CCC GTC GGG
    Ser Ser Ile Glu Lys Thr Ile Ser Lys Ala Lys Gly Gln Pro>
    _____FC-IgG4_____>

2400            2410            2420            2430
         *       *       *       *       *       *       *       *       *
    CGA GAG CCA CAG GTG TAC ACC CTG CCC CCA TCC CAG GAG GAG
    GCT CTC GGT GTC CAC ATG TGG GAC GGG GGT AGG GTC CTC CTC
    Arg Glu Pro Gln Val Tyr Thr Leu Pro Pro Ser Gln Glu Glu>
    _____FC-IgG4_____>

2440            2450            2460            2470
       *       *       *       *       *       *       *       *
    ATG ACC AAG AAC CAG GTC AGC CTG ACC TGC CTG GTC AAA GGC
    TAC TGG TTC TTG GTC CAG TCG GAC TGG ACG GAC CAG TTT CCG
    Met Thr Lys Asn Gln Val Ser Leu Thr Cys Leu Val Lys Gly>
    _____FC-IgG4_____>

2480            2490            2500            2510            2520
    *       *       *       *       *       *       *       *       *
    TTC TAC CCC AGC GAC ATC GCC GTG GAG TGG GAG AGC AAT GGG
    AAG ATG GGG TCG CTG TAG CGG CAC CTC ACC CTC TCG TTA CCC
    Phe Tyr Pro Ser Asp Ile Ala Val Glu Trp Glu Ser Asn Gly>
    _____FC-IgG4_____>

2530            2540            2550            2560
           *       *       *       *       *       *       *       *
    CAG CCG GAG AAC AAC TAC AAG ACC ACG CCT CCC GTG CTG GAC
    GTC GGC CTC TTG TTG ATG TTC TGG TGC GGA GGG CAC GAC CTG
    Gln Pro Glu Asn Asn Tyr Lys Thr Thr Pro Pro Val Leu Asp>
    _____FC-IgG4_____>
```

Figure 39I

```
        2570            2580            2590            2600
    *     *       *      *       *       *       *       *
   TCC  GAC  GGC  TCC  TTC  TTC  CTC  TAC  AGC  AGG  CTA  ACC  GTG  GAC
   AGG  CTG  CCG  AGG  AAG  AAG  GAG  ATG  TCG  TCC  GAT  TGG  CAC  CTG
   Ser  Asp  Gly  Ser  Phe  Phe  Leu  Tyr  Ser  Arg  Leu  Thr  Val  Asp>
   _____FC-IgG4_____>

2610            2620            2630            2640
    *     *       *      *       *       *       *       *       *
   AAG  AGC  AGG  TGG  CAG  GAG  GGG  AAT  GTC  TTC  TCA  TGC  TCC  GTG
   TTC  TCG  TCC  ACC  GTC  CTC  CCC  TTA  CAG  AAG  AGT  ACG  AGG  CAC
   Lys  Ser  Arg  Trp  Gln  Glu  Gly  Asn  Val  Phe  Ser  Cys  Ser  Val>
   _____FC-IgG4_____>

2650            2660            2670            2680
    *     *       *      *       *       *       *       *
   ATG  CAT  GAG  GCT  CTG  CAC  AAC  CAC  TAC  ACA  CAG  AAG  AGC  CTC
   TAC  GTA  CTC  CGA  GAC  GTG  TTG  GTG  ATG  TGT  GTC  TTC  TCG  GAG
   Met  His  Glu  Ala  Leu  His  Asn  His  Tyr  Thr  Gln  Lys  Ser  Leu>
   _____FC-IgG4_____>

2690           2700
    *     *       *      *
   TCC  CTG  TCT  CTG  GGT  AAA  TGA
   AGG  GAC  AGA  GAC  CCA  TTT  ACT
   Ser  Leu  Ser  Leu  Gly  Lys  ***>
           _FC-IgG4_____>
```

Figure 40A

```
            10          20          30          40
         *   *       *   *       *   *       *   *
ATG GTG TTA CTC AGA CTT ATT TGT TTC ATA GCT CTA CTG ATT
TAC CAC AAT GAG TCT GAA TAA ACA AAG TAT CGA GAT GAC TAA
Met Val Leu Leu Arg Leu Ile Cys Phe Ile Ala Leu Leu Ile>
                  _SIGNAL PEPTIDE_____>
                  _IL-1RI_____>

50          60          70          80
         *   *       *   *       *   *       *   *
TCT TCT CTG GAG GCT GAT AAA TGC AAG GAA CGT GAA GAA AAA
AGA AGA GAC CTC CGA CTA TTT ACG TTC CTT GCA CTT CTT TTT
Ser Ser Leu Glu Ala Asp>
___SIGNAL PEPTIDE_____>
                        Lys Cys Lys Glu Arg Glu Glu Lys>
                        _IL-1RI_____>

90         100         110         120
         *   *       *   *       *   *       *   *
ATA ATT TTA GTG TCA TCT GCA AAT GAA ATT GAT GTT CGT CCC
TAT TAA AAT CAC AGT AGA CGT TTA CTT TAA CTA CAA GCA GGG
Ile Ile Leu Val Ser Ser Ala Asn Glu Ile Asp Val Arg Pro>
                        _IL-1RI_____>

130         140         150         160
         *   *       *   *       *   *       *   *
TGT CCT CTT AAC CCA AAT GAA CAC AAA GGC ACT ATA ACT TGG
ACA GGA GAA TTG GGT TTA CTT GTG TTT CCG TGA TAT TGA ACC
Cys Pro Leu Asn Pro Asn Glu His Lys Gly Thr Ile Thr Trp>
                        _IL-1RI_____>

170         180         190         200         210
  *        *   *       *   *       *   *       *   *
TAT AAG GAT GAC AGC AAG ACA CCT GTA TCT ACA GAA CAA GCC
ATA TTC CTA CTG TCG TTC TGT GGA CAT AGA TGT CTT GTT CGG
Tyr Lys Asp Asp Ser Lys Thr Pro Val Ser Thr Glu Gln Ala>
                        _IL-1RI_____>

220         230         240         250
         *   *       *   *       *   *       *   *
TCC AGG ATT CAT CAA CAC AAA GAG AAA CTT TGG TTT GTT CCT
AGG TCC TAA GTA GTT GTG TTT CTC TTT GAA ACC AAA CAA GGA
Ser Arg Ile His Gln His Lys Glu Lys Leu Trp Phe Val Pro>
                        _IL-1RI_____>

260         270         280         290
         *   *       *   *       *   *       *   *
GCT AAG GTG GAG GAT TCA GGA CAT TAC TAT TGC GTG GTA AGA
CGA TTC CAC CTC CTA AGT CCT GTA ATG ATA ACG CAC CAT TCT
Ala Lys Val Glu Asp Ser Gly His Tyr Tyr Cys Val Val Arg>
                        _IL-1RI_____>
```

Figure 40B

```
         300           310           320           330
    *      *      *      *      *      *      *      *      *
   AAT    TCA    TCT    TAC    TGC    CTC    AGA    ATT    AAA    ATA    AGT    GCA    AAA    TTT
   TTA    AGT    AGA    ATG    ACG    GAG    TCT    TAA    TTT    TAT    TCA    CGT    TTT    AAA
   Asn    Ser    Ser    Tyr    Cys    Leu    Arg    Ile    Lys    Ile    Ser    Ala    Lys    Phe>
   _____IL-1RI_____>

340           350           360           370
    *      *      *      *      *      *      *      *
   GTG    GAG    AAT    GAG    CCT    AAC    TTA    TGT    TAT    AAT    GCA    CAA    GCC    ATA
   CAC    CTC    TTA    CTC    GGA    TTG    AAT    ACA    ATA    TTA    CGT    GTT    CGG    TAT
   Val    Glu    Asn    Glu    Pro    Asn    Leu    Cys    Tyr    Asn    Ala    Gln    Ala    Ile>
   _____IL-1RI_____>

380           390           400           410           420
    *      *      *      *      *      *      *      *      *
   TTT    AAG    CAG    AAA    CTA    CCC    GTT    GCA    GGA    GAC    GGA    GGA    CTT    GTG
   AAA    TTC    GTC    TTT    GAT    GGG    CAA    CGT    CCT    CTG    CCT    CCT    GAA    CAC
   Phe    Lys    Gln    Lys    Leu    Pro    Val    Ala    Gly    Asp    Gly    Gly    Leu    Val>
   _____IL-1RI_____>

430           440           450           460
    *      *      *      *      *      *      *      *
   TGC    CCT    TAT    ATG    GAG    TTT    TTT    AAA    AAT    GAA    AAT    AAT    GAG    TTA
   ACG    GGA    ATA    TAC    CTC    AAA    AAA    TTT    TTA    CTT    TTA    TTA    CTC    AAT
   Cys    Pro    Tyr    Met    Glu    Phe    Phe    Lys    Asn    Glu    Asn    Asn    Glu    Leu>
   _____IL-1RI_____>

470           480           490           500
    *      *      *      *      *      *      *      *
   CCT    AAA    TTA    CAG    TGG    TAT    AAG    GAT    TGC    AAA    CCT    CTA    CTT    CTT
   GGA    TTT    AAT    GTC    ACC    ATA    TTC    CTA    ACG    TTT    GGA    GAT    GAA    GAA
   Pro    Lys    Leu    Gln    Trp    Tyr    Lys    Asp    Cys    Lys    Pro    Leu    Leu    Leu>
   _____IL-1RI_____>

510           520           530           540
    *      *      *      *      *      *      *      *      *
   GAC    AAT    ATA    CAC    TTT    AGT    GGA    GTC    AAA    GAT    AGG    CTC    ATC    GTG
   CTG    TTA    TAT    GTG    AAA    TCA    CCT    CAG    TTT    CTA    TCC    GAG    TAG    CAC
   Asp    Asn    Ile    His    Phe    Ser    Gly    Val    Lys    Asp    Arg    Leu    Ile    Val>
   _____IL-1RI_____>

550           560           570           580
    *      *      *      *      *      *      *      *
   ATG    AAT    GTG    GCT    GAA    AAG    CAT    AGA    GGG    AAC    TAT    ACT    TGT    CAT
   TAC    TTA    CAC    CGA    CTT    TTC    GTA    TCT    CCC    TTG    ATA    TGA    ACA    GTA
   Met    Asn    Val    Ala    Glu    Lys    His    Arg    Gly    Asn    Tyr    Thr    Cys    His>
   _____IL-1RI_____>

590           600           610           620           630
    *      *      *      *      *      *      *      *      *
   GCA    TCC    TAC    ACA    TAC    TTG    GGC    AAG    CAA    TAT    CCT    ATT    ACC    CGG
   CGT    AGG    ATG    TGT    ATG    AAC    CCG    TTC    GTT    ATA    GGA    TAA    TGG    GCC
   Ala    Ser    Tyr    Thr    Tyr    Leu    Gly    Lys    Gln    Tyr    Pro    Ile    Thr    Arg>
   _____IL-1RI_____>
```

Figure 40C

```
              640            650            660            670
        *      *      *      *      *      *      *      *
      GTA    ATA    GAA    TTT    ATT    ACT    CTA    GAG    GAA    AAC    AAA    CCC    ACA    AGG
      CAT    TAT    CTT    AAA    TAA    TGA    GAT    CTC    CTT    TTG    TTT    GGG    TGT    TCC
      Val    Ile    Glu    Phe    Ile    Thr    Leu    Glu    Glu    Asn    Lys    Pro    Thr    Arg>
      _____IL-1RI_____>

680            690            700            710
        *      *      *      *      *      *      *      *
      CCT    GTG    ATT    GTG    AGC    CCA    GCT    AAT    GAG    ACA    ATG    GAA    GTA    GAC
      GGA    CAC    TAA    CAC    TCG    GGT    CGA    TTA    CTC    TGT    TAC    CTT    CAT    CTG
      Pro    Val    Ile    Val    Ser    Pro    Ala    Asn    Glu    Thr    Met    Glu    Val    Asp>
      _____IL-1RI_____>

720            730            740            750
        *      *      *      *      *      *      *      *      *
      TTG    GGA    TCC    CAG    ATA    CAA    TTG    ATC    TGT    AAT    GTC    ACC    GGC    CAG
      AAC    CCT    AGG    GTC    TAT    GTT    AAC    TAG    ACA    TTA    CAG    TGG    CCG    GTC
      Leu    Gly    Ser    Gln    Ile    Gln    Leu    Ile    Cys    Asn    Val    Thr    Gly    Gln>
      _____IL-1RI_____>

760            770            780            790
        *      *      *      *      *      *      *      *
      TTG    AGT    GAC    ATT    GCT    TAC    TGG    AAG    TGG    AAT    GGG    TCA    GTA    ATT
      AAC    TCA    CTG    TAA    CGA    ATG    ACC    TTC    ACC    TTA    CCC    AGT    CAT    TAA
      Leu    Ser    Asp    Ile    Ala    Tyr    Trp    Lys    Trp    Asn    Gly    Ser    Val    Ile>
      _____IL-1RI_____>

800            810            820            830            840
        *      *      *      *      *      *      *      *      *
      GAT    GAA    GAT    GAC    CCA    GTG    CTA    GGG    GAA    GAC    TAT    TAC    AGT    GTG
      CTA    CTT    CTA    CTG    GGT    CAC    GAT    CCC    CTT    CTG    ATA    ATG    TCA    CAC
      Asp    Glu    Asp    Asp    Pro    Val    Leu    Gly    Glu    Asp    Tyr    Tyr    Ser    Val>
      _____IL-1RI_____>

850            860            870            880
        *      *      *      *      *      *      *      *
      GAA    AAT    CCT    GCA    AAC    AAA    AGA    AGG    AGT    ACC    CTC    ATC    ACA    GTG
      CTT    TTA    GGA    CGT    TTG    TTT    TCT    TCC    TCA    TGG    GAG    TAG    TGT    CAC
      Glu    Asn    Pro    Ala    Asn    Lys    Arg    Arg    Ser    Thr    Leu    Ile    Thr    Val>
      _____IL-1RI_____>

890            900            910            920
        *      *      *      *      *      *      *      *
      CTT    AAT    ATA    TCG    GAA    ATT    GAG    AGT    AGA    TTT    TAT    AAA    CAT    CCA
      GAA    TTA    TAT    AGC    CTT    TAA    CTC    TCA    TCT    AAA    ATA    TTT    GTA    GGT
      Leu    Asn    Ile    Ser    Glu    Ile    Glu    Ser    Arg    Phe    Tyr    Lys    His    Pro>
      _____IL-1RI_____>

930            940            950            960
        *      *      *      *      *      *      *      *      *
      TTT    ACC    TGT    TTT    GCC    AAG    AAT    ACA    CAT    GGT    ATA    GAT    GCA    GCA
      AAA    TGG    ACA    AAA    CGG    TTC    TTA    TGT    GTA    CCA    TAT    CTA    CGT    CGT
      Phe    Thr    Cys    Phe    Ala    Lys    Asn    Thr    His    Gly    Ile    Asp    Ala    Ala>
      _____IL-1RI_____>
```

Figure 40D

```
         970         980         990        1000
          *     *     *     *     *     *     *     *
        TAT   ATC   CAG   TTA   ATA   TAT   CCA   GTC   ACT   AAT   TCA   GAA   CGC   TGC
        ATA   TAG   GTC   AAT   TAT   ATA   GGT   CAG   TGA   TTA   AGT   CTT   GCG   ACG
        Tyr   Ile   Gln   Leu   Ile   Tyr   Pro   Val   Thr   Asn>
        _____IL-1RI_____>
                                                      Ser   Glu   Arg   Cys>
                                                      ___IL-1RAcP____>

1010         1020         1030        1040         1050
   *     *     *     *     *     *     *     *     *
  GAT   GAC   TGG   GGA   CTA   GAC   ACC   ATG   AGG   CAA   ATC   CAA   GTG   TTT
  CTA   CTG   ACC   CCT   GAT   CTG   TGG   TAC   TCC   GTT   TAG   GTT   CAC   AAA
  Asp   Asp   Trp   Gly   Leu   Asp   Thr   Met   Arg   Gln   Ile   Gln   Val   Phe>
  _____IL-1RAcP_____>

1060        1070        1080        1090
          *     *     *     *     *     *     *     *
        GAA   GAT   GAG   CCA   GCT   CGC   ATC   AAG   TGC   CCA   CTC   TTT   GAA   CAC
        CTT   CTA   CTC   GGT   CGA   GCG   TAG   TTC   ACG   GGT   GAG   AAA   CTT   GTG
        Glu   Asp   Glu   Pro   Ala   Arg   Ile   Lys   Cys   Pro   Leu   Phe   Glu   His>
        _____IL-1RAcP_____>

1100        1110        1120        1130
          *     *     *     *     *     *     *     *
        TTC   TTG   AAA   TTC   AAC   TAC   AGC   ACA   GCC   CAT   TCA   GCT   GGC   CTT
        AAG   AAC   TTT   AAG   TTG   ATG   TCG   TGT   CGG   GTA   AGT   CGA   CCG   GAA
        Phe   Leu   Lys   Phe   Asn   Tyr   Ser   Thr   Ala   His   Ser   Ala   Gly   Leu>
        _____IL-1RAcP_____>

1140        1150        1160        1170
          *     *     *     *     *     *     *     *
        ACT   CTG   ATC   TGG   TAT   TGG   ACT   AGG   CAG   GAC   CGG   GAC   CTT   GAG
        TGA   GAC   TAG   ACC   ATA   ACC   TGA   TCC   GTC   CTG   GCC   CTG   GAA   CTC
        Thr   Leu   Ile   Trp   Tyr   Trp   Thr   Arg   Gln   Asp   Arg   Asp   Leu   Glu>
        _____IL-1RAcP_____>

1180        1190        1200        1210
          *     *     *     *     *     *     *     *
        GAG   CCA   ATT   AAC   TTC   CGC   CTC   CCC   GAG   AAC   CGC   ATT   AGT   AAG
        CTC   GGT   TAA   TTG   AAG   GCG   GAG   GGG   CTC   TTG   GCG   TAA   TCA   TTC
        Glu   Pro   Ile   Asn   Phe   Arg   Leu   Pro   Glu   Asn   Arg   Ile   Ser   Lys>
        _____IL-1RAcP_____>

1220         1230         1240        1250         1260
   *     *     *     *     *     *     *     *     *
  GAG   AAA   GAT   GTG   CTG   TGG   TTC   CGG   CCC   ACT   CTC   CTC   AAT   GAC
  CTC   TTT   CTA   CAC   GAC   ACC   AAG   GCC   GGG   TGA   GAG   GAG   TTA   CTG
  Glu   Lys   Asp   Val   Leu   Trp   Phe   Arg   Pro   Thr   Leu   Leu   Asn   Asp>
  _____IL-1RAcP_____>
```

Figure 40E

```
            1270          1280          1290          1300
         *     *     *     *     *     *     *     *
ACT GGC AAC TAT ACC TGC ATG TTA AGG AAC ACT ACA TAT TGC
TGA CCG TTG ATA TGG ACG TAC AAT TCC TTG TGA TGT ATA ACG
Thr Gly Asn Tyr Thr Cys Met Leu Arg Asn Thr Thr Tyr Cys>
                            IL-1RAcP                    >

1310          1320          1330          1340
         *     *     *     *     *     *     *     *
AGC AAA GTT GCA TTT CCC TTG GAA GTT GTT CAA AAA GAC AGC
TCG TTT CAA CGT AAA GGG AAC CTT CAA CAA GTT TTT CTG TCG
Ser Lys Val Ala Phe Pro Leu Glu Val Val Gln Lys Asp Ser>
                            IL-1RAcP                    >

1350          1360          1370          1380
      *     *     *     *     *     *     *     *     *
TGT TTC AAT TCC CCC ATG AAA CTC CCA GTG CAT AAA CTG TAT
ACA AAG TTA AGG GGG TAC TTT GAG GGT CAC GTA TTT GAC ATA
Cys Phe Asn Ser Pro Met Lys Leu Pro Val His Lys Leu Tyr>
                            IL-1RAcP                    >

1390          1400          1410          1420
   *     *     *     *     *     *     *     *
ATA GAA TAT GGC ATT CAG AGG ATC ACT TGT CCA AAT GTA GAT
TAT CTT ATA CCG TAA GTC TCC TAG TGA ACA GGT TTA CAT CTA
Ile Glu Tyr Gly Ile Gln Arg Ile Thr Cys Pro Asn Val Asp>
                            IL-1RAcP                    >

1430          1440          1450          1460          1470
   *     *     *     *     *     *     *     *     *
GGA TAT TTT CCT TCC AGT GTC AAA CCG ACT ATC ACT TGG TAT
CCT ATA AAA GGA AGG TCA CAG TTT GGC TGA TAG TGA ACC ATA
Gly Tyr Phe Pro Ser Ser Val Lys Pro Thr Ile Thr Trp Tyr>
                            IL-1RAcP                    >

1480          1490          1500          1510
         *     *     *     *     *     *     *     *
ATG GGC TGT TAT AAA ATA CAG AAT TTT AAT AAT GTA ATA CCC
TAC CCG ACA ATA TTT TAT GTC TTA AAA TTA TTA CAT TAT GGG
Met Gly Cys Tyr Lys Ile Gln Asn Phe Asn Asn Val Ile Pro>
                            IL-1RAcP                    >

1520          1530          1540          1550
         *     *     *     *     *     *     *     *
GAA GGT ATG AAC TTG AGT TTC CTC ATT GCC TTA ATT TCA AAT
CTT CCA TAC TTG AAC TCA AAG GAG TAA CGG AAT TAA AGT TTA
Glu Gly Met Asn Leu Ser Phe Leu Ile Ala Leu Ile Ser Asn>
                            IL-1RAcP                    >

1560          1570          1580          1590
      *     *     *     *     *     *     *     *     *
AAT GGA AAT TAC ACA TGT GTT GTT ACA TAT CCA GAA AAT GGA
TTA CCT TTA ATG TGT ACA CAA CAA TGT ATA GGT CTT TTA CCT
Asn Gly Asn Tyr Thr Cys Val Val Thr Tyr Pro Glu Asn Gly>
                            IL-1RAcP                    >
```

Figure 40F

```
           1600              1610              1620              1630
             *        *        *        *        *        *        *        *
           CGT ACG  TTT CAT  CTC ACC  AGG ACT  CTG ACT  GTA AAG  GTA GTA
           GCA TGC  AAA GTA  GAG TGG  TCC TGA  GAC TGA  CAT TTC  CAT CAT
           Arg Thr  Phe His  Leu Thr  Arg Thr  Leu Thr  Val Lys  Val Val>
                                    ___IL-1RAcP_____>

1640              1650              1660              1670              1680
    *        *        *        *        *        *        *        *        *
  GGC TCT  CCA AAA  AAT GCA  GTG CCC  CCT GTG  ATC CAT  TCA CCT
  CCG AGA  GGT TTT  TTA CGT  CAC GGG  GGA CAC  TAG GTA  AGT GGA
  Gly Ser  Pro Lys  Asn Ala  Val Pro  Pro Val  Ile His  Ser Pro>
                           ___IL-1RAcP_____>

1690              1700              1710              1720
             *        *        *        *        *        *        *        *
           AAT GAT  CAT GTG  GTC TAT  GAG AAA  GAA CCA  GGA GAG  GAG CTA
           TTA CTA  GTA CAC  CAG ATA  CTC TTT  CTT GGT  CCT CTC  CTC GAT
           Asn Asp  His Val  Val Tyr  Glu Lys  Glu Pro  Gly Glu  Glu Leu>
                                    ___IL-1RAcP_____>

1730              1740              1750              1760
             *        *        *        *        *        *        *        *
           CTC ATT  CCC TGT  ACG GTC  TAT TTT  AGT TTT  CTG ATG  GAT TCT
           GAG TAA  GGG ACA  TGC CAG  ATA AAA  TCA AAA  GAC TAC  CTA AGA
           Leu Ile  Pro Cys  Thr Val  Tyr Phe  Ser Phe  Leu Met  Asp Ser>
                                    ___IL-1RAcP_____>

1770              1780              1790              1800
             *        *        *        *        *        *        *        *
           CGC AAT  GAG GTT  TGG TGG  ACC ATT  GAT GGA  AAA AAA  CCT GAT
           GCG TTA  CTC CAA  ACC ACC  TGG TAA  CTA CCT  TTT TTT  GGA CTA
           Arg Asn  Glu Val  Trp Trp  Thr Ile  Asp Gly  Lys Lys  Pro Asp>
                                    ___IL-1RAcP_____>

1810              1820              1830              1840
             *        *        *        *        *        *        *        *
           GAC ATC  ACT ATT  GAT GTC  ACC ATT  AAC GAA  AGT ATA  AGT CAT
           CTG TAG  TGA TAA  CTA CAG  TGG TAA  TTG CTT  TCA TAT  TCA GTA
           Asp Ile  Thr Ile  Asp Val  Thr Ile  Asn Glu  Ser Ile  Ser His>
                                    ___IL-1RAcP_____>

1850              1860              1870              1880              1890
    *        *        *        *        *        *        *        *        *
  AGT AGA  ACA GAA  GAT GAA  ACA AGA  ACT CAG  ATT TTG  AGC ATC
  TCA TCT  TGT CTT  CTA CTT  TGT TCT  TGA GTC  TAA AAC  TCG TAG
  Ser Arg  Thr Glu  Asp Glu  Thr Arg  Thr Gln  Ile Leu  Ser Ile>
                           ___IL-1RAcP_____>

1900              1910              1920              1930
             *        *        *        *        *        *        *        *
           AAG AAA  GTT ACC  TCT GAG  GAT CTC  AAG CGC  AGC TAT  GTC TGT
           TTC TTT  CAA TGG  AGA CTC  CTA GAG  TTC GCG  TCG ATA  CAG ACA
           Lys Lys  Val Thr  Ser Glu  Asp Leu  Lys Arg  Ser Tyr  Val Cys>
                                    ___IL-1RAcP_____>
```

Figure 40G

```
          1940             1950             1960             1970
    *       *       *       *       *       *       *       *
   CAT GCT AGA AGT GCC AAA GGC GAA GTT GCC AAA GCA GCC AAG
   GTA CGA TCT TCA CGG TTT CCG CTT CAA CGG TTT CGT CGG TTC
   His Ala Arg Ser Ala Lys Gly Glu Val Ala Lys Ala Ala Lys>
   _____IL-1RAcP_____>

1980             1990             2000             2010
    *       *       *       *       *       *       *       *
   GTG AAG CAG AAA GTG CCA GCT CCA AGA TAC ACA GTG GAA TCC
   CAC TTC GTC TTT CAC GGT CGA GGT TCT ATG TGT CAC CTT AGG
   Val Lys Gln Lys Val Pro Ala Pro Arg Tyr Thr Val Glu>
   _____IL-1RAcP_____>.
                                                          Ser>
                                                          ___>

>Mutation Serine to Proline
                                                       |
       2020             2030             2040          |2050
    *       *       *     ⟨ *       *       *       |  *       *
   GGA GAG TCC AAA TAC GGT CCG CCA TGC CCA CCA TGC CCA GCA
   CCT CTC AGG TTT ATG CCA GGC GGT ACG GGT GGT ACG GGT CGT
       Glu Ser Lys Tyr Gly Pro Pro Cys Pro Pro Cys Pro Ala>
   _____FC-IgG4_____>
   Gly>
   ___>

2060             2070             2080             2090             2100
    *       *       *       *       *       *       *       *       *
   CCT GAG TTC CTG GGG GGA CCA TCA GTC TTC CTG TTC CCC CCA
   GGA CTC AAG GAC CCC CCT GGT AGT CAG AAG GAC AAG GGG GGT
   Pro Glu Phe Leu Gly Gly Pro Ser Val Phe Leu Phe Pro Pro>
   _____FC-IgG4_____>

2110             2120             2130             2140
    *       *       *       *       *       *       *       *
   AAA CCC AAG GAC ACT CTC ATG ATC TCC CGG ACC CCT GAG GTC
   TTT GGG TTC CTG TGA GAG TAC TAG AGG GCC TGG GGA CTC CAG
   Lys Pro Lys Asp Thr Leu Met Ile Ser Arg Thr Pro Glu Val>
   _____FC-IgG4_____>

2150             2160             2170             2180
    *       *       *       *       *       *       *       *
   ACG TGC GTG GTG GTG GAC GTG AGC CAG GAA GAC CCC GAG GTC
   TGC ACG CAC CAC CAC CTG CAC TCG GTC CTT CTG GGG CTC CAG
   Thr Cys Val Val Val Asp Val Ser Gln Glu Asp Pro Glu Val>
   _____FC-IgG4_____>

2190             2200             2210             2220
    *       *       *       *       *       *       *       *       *
   CAG TTC AAC TGG TAC GTG GAT GGC GTG GAG GTG CAT AAT GCC
   GTC AAG TTG ACC ATG CAC CTA CCG CAC CTC CAC GTA TTA CGG
   Gln Phe Asn Trp Tyr Val Asp Gly Val Glu Val His Asn Ala>
   _____FC-IgG4_____>
```

Figure 40H

```
        2230            2240            2250              2260
         *       *       *       *       *       *       *       *
       AAG ACA AAG CCG CGG GAG GAG CAG TTC AAC AGC ACG TAC CGT
       TTC TGT TTC GGC GCC CTC CTC GTC AAG TTG TCG TGC ATG GCA
       Lys Thr Lys Pro Arg Glu Glu Gln Phe Asn Ser Thr Tyr Arg>
                           ___FC-IgG4_____>

2270            2280            2290            2300            2310
    *       *       *       *       *       *       *       *       *
  GTG GTC AGC GTC CTC ACC GTC CTG CAC CAG GAC TGG CTG AAC
  CAC CAG TCG CAG GAG TGG CAG GAC GTG GTC CTG ACC GAC TTG
  Val Val Ser Val Leu Thr Val Leu His Gln Asp Trp Leu Asn>
                           ___FC-IgG4_____>

2320            2330            2340            2350
           *       *       *       *       *       *       *
       GGC AAG GAG TAC AAG TGC AAG GTC TCC AAC AAA GGC CTC CCG
       CCG TTC CTC ATG TTC ACG TTC CAG AGG TTG TTT CCG GAG GGC
       Gly Lys Glu Tyr Lys Cys Lys Val Ser Asn Lys Gly Leu Pro>
                           ___FC-IgG4_____>

2360            2370            2380            2390
               *       *       *       *       *       *       *
           TCC TCC ATC GAG AAA ACC ATC TCC AAA GCC AAA GGG CAG CCC
           AGG AGG TAG CTC TTT TGG TAG AGG TTT CGG TTT CCC GTC GGG
           Ser Ser Ile Glu Lys Thr Ile Ser Lys Ala Lys Gly Gln Pro>
                           ___FC-IgG4_____>

2400            2410            2420            2430
           *       *       *       *       *       *       *       *.
       CGA GAG CCA CAG GTG TAC ACC CTG CCC CCA TCC CAG GAG GAG
       GCT CTC GGT GTC CAC ATG TGG GAC GGG GGT AGG GTC CTC CTC
       Arg Glu Pro Gln Val Tyr Thr Leu Pro Pro Ser Gln Glu Glu>
                           ___FC-IgG4_____>

2440            2450            2460            2470
       *       *       *       *       *       *       *       *
   ATG ACC AAG AAC CAG GTC AGC CTG ACC TGC CTG GTC AAA GGC
   TAC TGG TTC TTG GTC CAG TCG GAC TGG ACG GAC CAG TTT CCG
   Met Thr Lys Asn Gln Val Ser Leu Thr Cys Leu Val Lys Gly>
                           ___FC-IgG4_____>

2480            2490            2500            2510            2520
    *       *       *       *       *       *       *       *       *
  TTC TAC CCC AGC GAC ATC GCC GTG GAG TGG GAG AGC AAT GGG
  AAG ATG GGG TCG CTG TAG CGG CAC CTC ACC CTC TCG TTA CCC
  Phe Tyr Pro Ser Asp Ile Ala Val Glu Trp Glu Ser Asn Gly>
                           ___FC-IgG4_____>

2530            2540            2550            2560
           *       *       *       *       *       *       *       *
       CAG CCG GAG AAC AAC TAC AAG ACC ACG CCT CCC GTG CTG GAC
       GTC GGC CTC TTG TTG ATG TTC TGG TGC GGA GGG CAC GAC CTG
       Gln Pro Glu Asn Asn Tyr Lys Thr Thr Pro Pro Val Leu Asp>
                           ___FC-IgG4_____>
```

Figure 40I

```
              2570              2580              2590              2600
       *        *        *        *        *        *        *        *
      TCC      GAC      GGC      TCC      TTC      TTC      CTC      TAC      AGC      AGG      CTA      ACC      GTG      GAC
      AGG      CTG      CCG      AGG      AAG      AAG      GAG      ATG      TCG      TCC      GAT      TGG      CAC      CTG
      Ser      Asp      Gly      Ser      Phe      Phe      Leu      Tyr      Ser      Arg      Leu      Thr      Val      Asp>
      _____FC-IgG4_____>

2610              2620              2630              2640
       *        *        *        *        *        *        *        *        *
      AAG      AGC      AGG      TGG      CAG      GAG      GGG      AAT      GTC      TTC      TCA      TGC      TCC      GTG
      TTC      TCG      TCC      ACC      GTC      CTC      CCC      TTA      CAG      AAG      AGT      ACG      AGG      CAC
      Lys      Ser      Arg      Trp      Gln      Glu      Gly      Asn      Val      Phe      Ser      Cys      Ser      Val>
      _____FC-IgG4_____>

2650              2660              2670              2680
       *        *        *        *        *        *        *        *
      ATG      CAT      GAG      GCT      CTG      CAC      AAC      CAC      TAC      ACA      CAG      AAG      AGC      CTC
      TAC      GTA      CTC      CGA      GAC      GTG      TTG      GTG      ATG      TGT      GTC      TTC      TCG      GAG
      Met      His      Glu      Ala      Leu      His      Asn      His      Tyr      Thr      Gln      Lys      Ser      Leu>
      _____FC-IgG4_____>

2690              2700
   *        *        *        *
  TCC      CTG      TCT      CTG      GGT      AAA      TGA
  AGG      GAC      AGA      GAC      CCA      TTT      ACT
  Ser      Leu      Ser      Leu      Gly      Lys      ***>
          _____FC-IgG4_____>
```

Figure 41A

```
          10              20              30              40
       *     *     *     *     *     *     *     *
ATG GTG CTT CTG TGG TGT GTA GTG AGT CTC TAC TTT TAT GGA
TAC CAC GAA GAC ACC ACA CAT CAC TCA GAG ATG AAA ATA CCT
Met Val Leu Leu Trp Cys Val Val Ser Leu Tyr Phe Tyr Gly>
_____SIGNAL PEPTIDE_____>
_____IL-1RAcP_____>

50              60              70              80
       *     *     *     *     *     *     *     *
ATC CTG CAA AGT GAT GCC TCA GAA CGC TGC GAT GAC TGG GGA
TAG GAC GTT TCA CTA CGG AGT CTT GCG ACG CTA CTG ACC CCT
Ile Leu Gln Ser Asp Ala>
____SIGNAL PEPTIDE_____>
                      Ser Glu Arg Cys Asp Asp Trp Gly>
                     _____IL-1RAcP_____>

90             100             110             120
       *     *     *     *     *     *     *     *     *
CTA GAC ACC ATG AGG CAA ATC CAA GTG TTT GAA GAT GAG CCA
GAT CTG TGG TAC TCC GTT TAG GTT CAC AAA CTT CTA CTC GGT
Leu Asp Thr Met Arg Gln Ile Gln Val Phe Glu Asp Glu Pro>
_____IL-1RAcP_____>

130             140             150             160
    *     *     *     *     *     *     *     *
GCT CGC ATC AAG TGC CCA CTC TTT GAA CAC TTC TTG AAA TTC
CGA GCG TAG TTC ACG GGT GAG AAA CTT GTG AAG AAC TTT AAG
Ala Arg Ile Lys Cys Pro Leu Phe Glu His Phe Leu Lys Phe>
_____IL-1RAcP_____>

170         180             190             200         210
   *     *     *     *     *     *     *     *     *
AAC TAC AGC ACA GCC CAT TCA GCT GGC CTT ACT CTG ATC TGG
TTG ATG TCG TGT CGG GTA AGT CGA CCG GAA TGA GAC TAG ACC
Asn Tyr Ser Thr Ala His Ser Ala Gly Leu Thr Leu Ile Trp>
_____IL-1RAcP_____>

220             230             240             250
       *     *     *     *     *     *     *     *
TAT TGG ACT AGG CAG GAC CGG GAC CTT GAG GAG CCA ATT AAC
ATA ACC TGA TCC GTC CTG GCC CTG GAA CTC CTC GGT TAA TTG
Tyr Trp Thr Arg Gln Asp Arg Asp Leu Glu Glu Pro Ile Asn>
_____IL-1RAcP_____>

260             270             280             290
       *     *     *     *     *     *     *     *
TTC CGC CTC CCC GAG AAC CGC ATT AGT AAG GAG AAA GAT GTG
AAG GCG GAG GGG CTC TTG GCG TAA TCA TTC CTC TTT CTA CAC
Phe Arg Leu Pro Glu Asn Arg Ile Ser Lys Glu Lys Asp Val>
_____IL-1RAcP_____>

300             310             320             330
       *     *     *     *     *     *     *     *     *
CTG TGG TTC CGG CCC ACT CTC CTC AAT GAC ACT GGC AAC TAT
GAC ACC AAG GCC GGG TGA GAG GAG TTA CTG TGA CCG TTG ATA
Leu Trp Phe Arg Pro Thr Leu Leu Asn Asp Thr Gly Asn Tyr>
_____IL-1RAcP_____>
```

Figure 41B

```
       340           350           360           370
        *      *      *      *      *      *      *      *
   ACC TGC ATG TTA AGG AAC ACT ACA TAT TGC AGC AAA GTT GCA
   TGG ACG TAC AAT TCC TTG TGA TGT ATA ACG TCG TTT CAA CGT
   Thr Cys Met Leu Arg Asn Thr Thr Tyr Cys Ser Lys Val Ala>
   _____IL-1RAcP_____>

380           390           400           410           420
  *      *      *      *      *      *      *      *      *
 TTT CCC TTG GAA GTT GTT CAA AAA GAC AGC TGT TTC AAT TCC
 AAA GGG AAC CTT CAA CAA GTT TTT CTG TCG ACA AAG TTA AGG
 Phe Pro Leu Glu Val Val Gln Lys Asp Ser Cys Phe Asn Ser>
 _____IL-1RAcP_____>

430           440           450           460
        *      *      *      *      *      *      *      *
   CCC ATG AAA CTC CCA GTG CAT AAA CTG TAT ATA GAA TAT GGC
   GGG TAC TTT GAG GGT CAC GTA TTT GAC ATA TAT CTT ATA CCG
   Pro Met Lys Leu Pro Val His Lys Leu Tyr Ile Glu Tyr Gly>
   _____IL-1RAcP_____>

470           480           490           500
        *      *      *      *      *      *      *      *
   ATT CAG AGG ATC ACT TGT CCA AAT GTA GAT GGA TAT TTT CCT
   TAA GTC TCC TAG TGA ACA GGT TTA CAT CTA CCT ATA AAA GGA
   Ile Gln Arg Ile Thr Cys Pro Asn Val Asp Gly Tyr Phe Pro>
   _____IL-1RAcP_____>

510           520           530           540
  *      *      *      *      *      *      *      *      *
 TCC AGT GTC AAA CCG ACT ATC ACT TGG TAT ATG GGC TGT TAT
 AGG TCA CAG TTT GGC TGA TAG TGA ACC ATA TAC CCG ACA ATA
 Ser Ser Val Lys Pro Thr Ile Thr Trp Tyr Met Gly Cys Tyr>
 _____IL-1RAcP_____>

550           560           570           580
  *      *      *      *      *      *      *      *      *
 AAA ATA CAG AAT TTT AAT AAT GTA ATA CCC GAA GGT ATG AAC
 TTT TAT GTC TTA AAA TTA TTA CAT TAT GGG CTT CCA TAC TTG
 Lys Ile Gln Asn Phe Asn Asn Val Ile Pro Glu Gly Met Asn>
 _____IL-1RAcP_____>

590           600           610           620           630
  *      *      *      *      *      *      *      *      *
 TTG AGT TTC CTC ATT GCC TTA ATT TCA AAT AAT GGA AAT TAC
 AAC TCA AAG GAG TAA CGG AAT TAA AGT TTA TTA CCT TTA ATG
 Leu Ser Phe Leu Ile Ala Leu Ile Ser Asn Asn Gly Asn Tyr>
 _____IL-1RAcP_____>

640           650           660           670
        *      *      *      *      *      *      *      *
   ACA TGT GTT GTT ACA TAT CCA GAA AAT GGA CGT ACG TTT CAT
   TGT ACA CAA CAA TGT ATA GGT CTT TTA CCT GCA TGC AAA GTA
   Thr Cys Val Val Thr Tyr Pro Glu Asn Gly Arg Thr Phe His>
   _____IL-1RAcP_____>
```

Figure 41C

```
           680              690              700              710
      *         *       *         *      *         *      *         *
     CTC ACC AGG ACT CTG ACT GTA AAG GTA GTA GGC TCT CCA AAA
     GAG TGG TCC TGA GAC TGA CAT TTC CAT CAT CCG AGA GGT TTT
     Leu Thr Arg Thr Leu Thr Val Lys Val Val Gly Ser Pro Lys>
     _____IL-1RAcP_____>

720              730              740              750
      *         *       *         *      *         *      *         *
     AAT GCA GTG CCC CCT GTG ATC CAT TCA CCT AAT GAT CAT GTG
     TTA CGT CAC GGG GGA CAC TAG GTA AGT GGA TTA CTA GTA CAC
     Asn Ala Val Pro Pro Val Ile His Ser Pro Asn Asp His Val>
     _____IL-1RAcP_____>

760              770              780              790
      *         *       *         *      *         *      *         *
     GTC TAT GAG AAA GAA CCA GGA GAG GAG CTA CTC ATT CCC TGT
     CAG ATA CTC TTT CTT GGT CCT CTC CTC GAT GAG TAA GGG ACA
     Val Tyr Glu Lys Glu Pro Gly Glu Glu Leu Leu Ile Pro Cys>
     _____IL-1RAcP_____>

800          810              820              830          840
    *    *         *      *         *       *         *      *
     ACG GTC TAT TTT AGT TTT CTG ATG GAT TCT CGC AAT GAG GTT
     TGC CAG ATA AAA TCA AAA GAC TAC CTA AGA GCG TTA CTC CAA
     Thr Val Tyr Phe Ser Phe Leu Met Asp Ser Arg Asn Glu Val>
     _____IL-1RAcP_____>

850              860              870              880
          *         *      *         *      *         *      *         *
         TGG TGG ACC ATT GAT GGA AAA AAA CCT GAT GAC ATC ACT ATT
         ACC ACC TGG TAA CTA CCT TTT TTT GGA CTA CTG TAG TGA TAA
         Trp Trp Thr Ile Asp Gly Lys Lys Pro Asp Asp Ile Thr Ile>
         _____IL-1RAcP_____>

890              900              910              920
          *         *      *         *      *         *      *         *
         GAT GTC ACC ATT AAC GAA AGT ATA AGT CAT AGT AGA ACA GAA
         CTA CAG TGG TAA TTG CTT TCA TAT TCA GTA TCA TCT TGT CTT
         Asp Val Thr Ile Asn Glu Ser Ile Ser His Ser Arg Thr Glu>
         _____IL-1RAcP_____>

930              940              950              960
          *         *      *         *      *         *      *         *
         GAT GAA ACA AGA ACT CAG ATT TTG AGC ATC AAG AAA GTT ACC
         CTA CTT TGT TCT TGA GTC TAA AAC TCG TAG TTC TTT CAA TGG
         Asp Glu Thr Arg Thr Gln Ile Leu Ser Ile Lys Lys Val Thr>
         _____IL-1RAcP_____>

970              980              990             1000
          *         *      *         *      *         *      *         *
         TCT GAG GAT CTC AAG CGC AGC TAT GTC TGT CAT GCT AGA AGT
         AGA CTC CTA GAG TTC GCG TCG ATA CAG ACA GTA CGA TCT TCA
         Ser Glu Asp Leu Lys Arg Ser Tyr Val Cys His Ala Arg Ser>
         _____IL-1RAcP_____>
```

Figure 41D

```
           1010           1020           1030           1040           1050
            *        *     *        *     *        *     *        *     *
           GCC AAA GGC GAA GTT GCC AAA GCA GCC AAG GTG AAG CAG AAA
           CGG TTT CCG CTT CAA CGG TTT CGT CGG TTC CAC TTC GTC TTT
           Ala Lys Gly Glu Val Ala Lys Ala Ala Lys Val Lys Gln Lys>
           _____IL-1RAcP_____>

1060           1070           1080           1090
                  *     *        *     *        *     *        *     *
           GTG CCA GCT CCA AGA TAC ACA GTG GAA AAA TGC AAG GAA CGT
           CAC GGT CGA GGT TCT ATG TGT CAC CTT TTT ACG TTC CTT GCA
           Val Pro Ala Pro Arg Tyr Thr Val Glu>
           _____IL-1RAcP_____>
                                              Lys Cys Lys Glu Arg>
                                              _____IL-1RI_____>

1100           1110           1120           1130
                  *     *        *     *        *     *        *     *
           GAA GAA AAA ATA ATT TTA GTG AGC TCA GCA AAT GAA ATC GAT
           CTT CTT TTT TAT TAA AAT CAC TCG AGT CGT TTA CTT TAG CTA
           Glu Glu Lys Ile Ile Leu Val Ser Ser Ala Asn Glu Ile Asp>
           _____IL-1RI_____>

1140           1150           1160           1170
                  *     *        *     *        *     *        *     *
           GTT CGT CCC TGT CCT CTT AAC CCA AAT GAA CAC AAA GGC ACT
           CAA GCA GGG ACA GGA GAA TTG GGT TTA CTT GTG TTT CCG TGA
           Val Arg Pro Cys Pro Leu Asn Pro Asn Glu His Lys Gly Thr>
           _____IL-1RI_____>

1180           1190           1200           1210
            *     *        *     *        *     *        *     *
           ATA ACT TGG TAT AAG GAT GAC AGC AAG ACA CCT GTA TCT ACA
           TAT TGA ACC ATA TTC CTA CTG TCG TTC TGT GGA CAT AGA TGT
           Ile Thr Trp Tyr Lys Asp Asp Ser Lys Thr Pro Val Ser Thr>
           _____IL-1RI_____>

1220           1230           1240           1250           1260
            *        *     *        *     *        *     *        *     *
           GAA CAA GCC TCC AGG ATT CAT CAA CAC AAA GAG AAA CTT TGG
           CTT GTT CGG AGG TCC TAA GTA GTT GTG TTT CTC TTT GAA ACC
           Glu Gln Ala Ser Arg Ile His Gln His Lys Glu Lys Leu Trp>
           _____IL-1RI_____>

1270           1280           1290           1300
                  *     *        *     *        *     *        *     *
           TTT GTT CCT GCT AAG GTG GAG GAT TCA GGA CAT TAC TAT TGC
           AAA CAA GGA CGA TTC CAC CTC CTA AGT CCT GTA ATG ATA ACG
           Phe Val Pro Ala Lys Val Glu Asp Ser Gly His Tyr Tyr Cys>
           _____IL-1RI_____>

1310           1320           1330           1340
                  *     *        *     *        *     *        *     *
           GTG GTA AGA AAT TCA TCT TAC TGC CTC AGA ATT AAA ATA AGT
           CAC CAT TCT TTA AGT AGA ATG ACG GAG TCT TAA TTT TAT TCA
           Val Val Arg Asn Ser Ser Tyr Cys Leu Arg Ile Lys Ile Ser>
           _____IL-1RI_____>
```

Figure 41E

```
          1350           1360           1370           1380
     *      *      *      *      *      *      *      *      *
    GCA    AAA    TTT    GTG    GAG    AAT    GAG    CCT    AAC    TTA    TGT    TAT    AAT    GCA
    CGT    TTT    AAA    CAC    CTC    TTA    CTC    GGA    TTG    AAT    ACA    ATA    TTA    CGT
    Ala    Lys    Phe    Val    Glu    Asn    Glu    Pro    Asn    Leu    Cys    Tyr    Asn    Ala>
    _____IL-1RI_____>

1390           1400           1410           1420
          *      *      *      *      *      *      *      *
         CAA    GCC    ATA    TTT    AAG    CAG    AAA    CTA    CCC    GTT    GCA    GGA    GAC    GGA
         GTT    CGG    TAT    AAA    TTC    GTC    TTT    GAT    GGG    CAA    CGT    CCT    CTG    CCT
         Gln    Ala    Ile    Phe    Lys    Gln    Lys    Leu    Pro    Val    Ala    Gly    Asp    Gly>
         _____IL-1RI_____>

1430           1440           1450           1460           1470
    *      *      *      *      *      *      *      *      *
   GGA    CTT    GTG    TGC    CCT    TAT    ATG    GAG    TTT    TTT    AAA    AAT    GAA    AAT
   CCT    GAA    CAC    ACG    GGA    ATA    TAC    CTC    AAA    AAA    TTT    TTA    CTT    TTA
   Gly    Leu    Val    Cys    Pro    Tyr    Met    Glu    Phe    Phe    Lys    Asn    Glu    Asn>
   _____IL-1RI_____>

1480           1490           1500           1510
          *      *      *      *      *      *      *      *
         AAT    GAG    TTA    CCT    AAA    TTA    CAG    TGG    TAT    AAG    GAT    TGC    AAA    CCT
         TTA    CTC    AAT    GGA    TTT    AAT    GTC    ACC    ATA    TTC    CTA    ACG    TTT    GGA
         Asn    Glu    Leu    Pro    Lys    Leu    Gln    Trp    Tyr    Lys    Asp    Cys    Lys    Pro>
         _____IL-1RI_____>

1520           1530           1540           1550
          *      *      *      *      *      *      *      *
         CTA    CTT    CTT    GAC    AAT    ATA    CAC    TTT    AGT    GGA    GTC    AAA    GAT    AGG
         GAT    GAA    GAA    CTG    TTA    TAT    GTG    AAA    TCA    CCT    CAG    TTT    CTA    TCC
         Leu    Leu    Leu    Asp    Asn    Ile    His    Phe    Ser    Gly    Val    Lys    Asp    Arg>
         _____IL-1RI_____>

1560           1570           1580           1590
          *      *      *      *      *      *      *      *      *
         CTC    ATC    GTG    ATG    AAT    GTG    GCT    GAA    AAG    CAT    AGA    GGG    AAC    TAT
         GAG    TAG    CAC    TAC    TTA    CAC    CGA    CTT    TTC    GTA    TCT    CCC    TTG    ATA
         Leu    Ile    Val    Met    Asn    Val    Ala    Glu    Lys    His    Arg    Gly    Asn    Tyr>
         _____IL-1RI_____>

1600           1610           1620           1630
       *      *      *      *      *      *      *      *
      ACT    TGT    CAT    GCA    TCC    TAC    ACA    TAC    TTG    GGC    AAG    CAA    TAT    CCT
      TGA    ACA    GTA    CGT    AGG    ATG    TGT    ATG    AAC    CCG    TTC    GTT    ATA    GGA
      Thr    Cys    His    Ala    Ser    Tyr    Thr    Tyr    Leu    Gly    Lys    Gln    Tyr    Pro>
      _____IL-1RI_____>

1640           1650           1660           1670           1680
    *      *      *      *      *      *      *      *      *
   ATT    ACC    CGG    GTA    ATA    GAA    TTT    ATT    ACT    CTA    GAG    GAA    AAC    AAA
   TAA    TGG    GCC    CAT    TAT    CTT    AAA    TAA    TGA    GAT    CTC    CTT    TTG    TTT
   Ile    Thr    Arg    Val    Ile    Glu    Phe    Ile    Thr    Leu    Glu    Glu    Asn    Lys>
   _____IL-1RI_____>
```

Figure 41F

```
         1690           1700            1710            1720
          *       *      *       *       *       *       *       *
       CCC ACA AGG CCT GTG ATT GTG AGC CCA GCT AAT GAG ACA ATG
       GGG TGT TCC GGA CAC TAA CAC TCG GGT CGA TTA CTC TGT TAC
       Pro Thr Arg Pro Val Ile Val Ser Pro Ala Asn Glu Thr Met>
       _____IL-1RI_____>

1730            1740            1750           1760
             *       *       *       *       *       *       *       *
          GAA GTA GAC TTG GGA TCC CAG ATA CAA TTG ATC TGT AAT GTC
          CTT CAT CTG AAC CCT AGG GTC TAT GTT AAC TAG ACA TTA CAG
          Glu Val Asp Leu Gly Ser Gln Ile Gln Leu Ile Cys Asn Val>
          _____IL-1RI_____>

1770            1780            1790           1800
           *       *       *       *       *       *       *       *
        ACC GGC CAG TTG AGT GAC ATT GCT TAC TGG AAG TGG AAT GGG
        TGG CCG GTC AAC TCA CTG TAA CGA ATG ACC TTC ACC TTA CCC
        Thr Gly Gln Leu Ser Asp Ile Ala Tyr Trp Lys Trp Asn Gly>
        _____IL-1RI_____>

1810            1820            1830           1840
         *       *       *       *       *       *       *       *
      TCA GTA ATT GAT GAA GAT GAC CCA GTG CTA GGG GAA GAC TAT
      AGT CAT TAA CTA CTT CTA CTG GGT CAC GAT CCC CTT CTG ATA
      Ser Val Ile Asp Glu Asp Asp Pro Val Leu Gly Glu Asp Tyr>
      _____IL-1RI_____>

1850            1860            1870            1880           1890
 *       *       *       *       *       *       *       *       *
TAC AGT GTG GAA AAT CCT GCA AAC AAA AGA AGG AGT ACC CTC
ATG TCA CAC CTT TTA GGA CGT TTG TTT TCT TCC TCA TGG GAG
Tyr Ser Val Glu Asn Pro Ala Asn Lys Arg Arg Ser Thr Leu>
_____IL-1RI_____>

1900            1910            1920           1930
          *       *       *       *       *       *       *       *
       ATC ACA GTG CTT AAT ATA TCG GAA ATT GAG AGT AGA TTT TAT
       TAG TGT CAC GAA TTA TAT AGC CTT TAA CTC TCA TCT AAA ATA
       Ile Thr Val Leu Asn Ile Ser Glu Ile Glu Ser Arg Phe Tyr>
       _____IL-1RI_____>

1940            1950            1960           1970
          *       *       *       *       *       *       *       *
       AAA CAT CCA TTT ACC TGT TTT GCC AAG AAT ACA CAT GGT ATA
       TTT GTA GGT AAA TGG ACA AAA CGG TTC TTA TGT GTA CCA TAT
       Lys His Pro Phe Thr Cys Phe Ala Lys Asn Thr His Gly Ile>
       _____IL-1RI_____>

1980            1990            2000           2010
         *       *       *       *       *       *       *       *       *
      GAT GCA GCA TAT ATC CAG TTA ATA TAT CCA GTC ACT AAT TCC
      CTA CGT CGT ATA TAG GTC AAT TAT ATA GGT CAG TGA TTA AGG
                                                             Ser>
                                                             ___>

Asp Ala Ala Tyr Ile Gln Leu Ile Tyr Pro Val Thr Asn>
      _____IL-1RI_____>
```

Figure 41G

```
      2020           2030           2040           2050
        *        *    *       *    *       *    *    *
     GGA GAC AAA ACT CAC ACA TGC CCA CCG TGC CCA GCA CCT GAA
     CCT CTG TTT TGA GTG TGT ACG GGT GGC ACG GGT CGT GGA CTT
     Gly Asp Lys Thr His Thr Cys Pro Pro Cys Pro Ala Pro Glu>
     _____FC-IgG1_____>

2060           2070           2080           2090           2100
        *        *    *       *    *       *    *       *    *    *
     CTC CTG GGG GGA CCG TCA GTC TTC CTC TTC CCC CCA AAA CCC
     GAG GAC CCC CCT GGC AGT CAG AAG GAG AAG GGG GGT TTT GGG
     Leu Leu Gly Gly Pro Ser Val Phe Leu Phe Pro Pro Lys Pro>
     _____FC-IgG1_____>

2110           2120           2130           2140
        *    *       *    *       *    *       *    *    *
     AAG GAC ACC CTC ATG ATC TCC CGG ACC CCT GAG GTC ACA TGC
     TTC CTG TGG GAG TAC TAG AGG GCC TGG GGA CTC CAG TGT ACG
     Lys Asp Thr Leu Met Ile Ser Arg Thr Pro Glu Val Thr Cys>
     _____FC-IgG1_____>

2150           2160           2170           2180
        *    *       *    *       *    *       *    *    *
     GTG GTG GTG GAC GTG AGC CAC GAA GAC CCT GAG GTC AAG TTC
     CAC CAC CAC CTG CAC TCG GTG CTT CTG GGA CTC CAG TTC AAG
     Val Val Val Asp Val Ser His Glu Asp Pro Glu Val Lys Phe>
     _____FC-IgG1_____>

2190           2200           2210           2220
        *    *    *    *       *    *       *    *    *
     AAC TGG TAC GTG GAC GGC GTG GAG GTG CAT AAT GCC AAG ACA
     TTG ACC ATG CAC CTG CCG CAC CTC CAC GTA TTA CGG TTC TGT
     Asn Trp Tyr Val Asp Gly Val Glu Val His Asn Ala Lys Thr>
     _____FC-IgG1_____>

2230           2240           2250           2260
        *    *       *    *       *    *       *    *
     AAG CCG CGG GAG GAG CAG TAC AAC AGC ACG TAC CGT GTG GTC
     TTC GGC GCC CTC CTC GTC ATG TTG TCG TGC ATG GCA CAC CAG
     Lys Pro Arg Glu Glu Gln Tyr Asn Ser Thr Tyr Arg Val Val>
     _____FC-IgG1_____>

2270           2280           2290           2300           2310
        *        *    *       *    *       *    *       *    *    *
     AGC GTC CTC ACC GTC CTG CAC CAG GAC TGG CTG AAT GGC AAG
     TCG CAG GAG TGG CAG GAC GTG GTC CTG ACC GAC TTA CCG TTC
     Ser Val Leu Thr Val Leu His Gln Asp Trp Leu Asn Gly Lys>
     _____FC-IgG1_____>

2320           2330           2340           2350
        *    *       *    *    *       *    *    *       *
     GAG TAC AAG TGC AAG GTC TCC AAC AAA GCC CTC CCA GCC CCC
     CTC ATG TTC ACG TTC CAG AGG TTG TTT CGG GAG GGT CGG GGG
     Glu Tyr Lys Cys Lys Val Ser Asn Lys Ala Leu Pro Ala Pro>
     _____FC-IgG1_____>
```

Figure 41H

```
              2360              2370              2380              2390
               *                 *                 *                 *     *
         ATC GAG AAA ACC ATC TCC AAA GCC AAA GGG CAG CCC CGA GAA
         TAG CTC TTT TGG TAG AGG TTT CGG TTT CCC GTC GGG GCT CTT
         Ile Glu Lys Thr Ile Ser Lys Ala Lys Gly Gln Pro Arg Glu>
         _____FC-IgG1_____>

2400              2410              2420              2430
          *     *           *     *           *     *           *     *     *
         CCA CAG GTG TAC ACC CTG CCC CCA TCC CGG GAT GAG CTG ACC
         GGT GTC CAC ATG TGG GAC GGG GGT AGG GCC CTA CTC GAC TGG
         Pro Gln Val Tyr Thr Leu Pro Pro Ser Arg Asp Glu Leu Thr>
         _____FC-IgG1_____>

2440              2450              2460              2470
           *     *           *     *           *     *           *     *
         AAG AAC CAG GTC AGC CTG ACC TGC CTG GTC AAA GGC TTC TAT
         TTC TTG GTC CAG TCG GAC TGG ACG GAC CAG TTT CCG AAG ATA
         Lys Asn Gln Val Ser Leu Thr Cys Leu Val Lys Gly Phe Tyr>
         _____FC-IgG1_____>

2480              2490              2500              2510              2520
     *     *           *     *           *     *           *     *           *
    CCC AGC GAC ATC GCC GTG GAG TGG GAG AGC AAT GGG CAG CCG
    GGG TCG CTG TAG CGG CAC CTC ACC CTC TCG TTA CCC GTC GGC
    Pro Ser Asp Ile Ala Val Glu Trp Glu Ser Asn Gly Gln Pro>
    _____FC-IgG1_____>

2530              2540              2550              2560
               *                 *                 *                 *
         GAG AAC AAC TAC AAG ACC ACG CCT CCC GTG CTG GAC TCC GAC
         CTC TTG TTG ATG TTC TGG TGC GGA GGG CAC GAC CTG AGG CTG
         Glu Asn Asn Tyr Lys Thr Thr Pro Pro Val Leu Asp Ser Asp>
         _____FC-IgG1_____>

2570              2580              2590              2600
           *     *           *     *           *     *           *     *
         GGC TCC TTC TTC CTC TAC AGC AAG CTC ACC GTG GAC AAG AGC
         CCG AGG AAG AAG GAG ATG TCG TTC GAG TGG CAC CTG TTC TCG
         Gly Ser Phe Phe Leu Tyr Ser Lys Leu Thr Val Asp Lys Ser>
         _____FC-IgG1_____>

2610              2620              2630              2640
           *     *           *     *           *     *           *     *     *
         AGG TGG CAG CAG GGG AAC GTC TTC TCA TGC TCC GTG ATG CAT
         TCC ACC GTC GTC CCC TTG CAG AAG AGT ACG AGG CAC TAC GTA
         Arg Trp Gln Gln Gly Asn Val Phe Ser Cys Ser Val Met His>
         _____FC-IgG1_____>

2650              2660              2670              2680
           *     *           *     *           *     *           *     *
         GAG GCT CTG CAC AAC CAC TAC ACG CAG AAG AGC CTC TCC CTG
         CTC CGA GAC GTG TTG GTG ATG TGC GTC TTC TCG GAG AGG GAC
         Glu Ala Leu His Asn His Tyr Thr Gln Lys Ser Leu Ser Leu>
         _____FC-IgG1_____>
```

```
        2690               2700
          *         *         *
        TCT CCG GGT AAA TGA
        AGA GGC CCA TTT ACT
        Ser Pro Gly Lys ***>
        _____FC-IgG1_____>
```

```
              10              20              30              40
       *       *       *       *       *       *       *       *
      ATG GTG CTT CTG TGG TGT GTA GTG AGT CTC TAC TTT TAT GGA
      TAC CAC GAA GAC ACC ACA CAT CAC TCA GAG ATG AAA ATA CCT
      Met Val Leu Leu Trp Cys Val Val Ser Leu Tyr Phe Tyr Gly>
      _____SIGNAL PEPTIDE_____>
      _____IL-1RAcP_____>

50              60              70              80
       *       *       *       *       *       *       *       *
      ATC CTG CAA AGT GAT GCC TCA GAA CGC TGC GAT GAC TGG GGA
      TAG GAC GTT TCA CTA CGG AGT CTT GCG ACG CTA CTG ACC CCT
      Ile Leu Gln Ser Asp Ala>
      ___SIGNAL PEPTIDE  ____>
                              Ser Glu Arg Cys Asp Asp Trp Gly>
                              _____IL-1RAcP_____>

90             100             110             120
       *       *       *       *       *       *       *       *
      CTA GAC ACC ATG AGG CAA ATC CAA GTG TTT GAA GAT GAG CCA
      GAT CTG TGG TAC TCC GTT TAG GTT CAC AAA CTT CTA CTC GGT
      Leu Asp Thr Met Arg Gln Ile Gln Val Phe Glu Asp Glu Pro>
      _____IL-1RAcP_____>

130             140             150             160
       *       *       *       *       *       *       *       *
      GCT CGC ATC AAG TGC CCA CTC TTT GAA CAC TTC TTG AAA TTC
      CGA GCG TAG TTC ACG GGT GAG AAA CTT GTG AAG AAC TTT AAG
      Ala Arg Ile Lys Cys Pro Leu Phe Glu His Phe Leu Lys Phe>
      _____IL-1RAcP_____>

170             180             190             200             210
      *       *       *       *       *       *       *       *       *
     AAC TAC AGC ACA GCC CAT TCA GCT GGC CTT ACT CTG ATC TGG
     TTG ATG TCG TGT CGG GTA AGT CGA CCG GAA TGA GAC TAG ACC
     Asn Tyr Ser Thr Ala His Ser Ala Gly Leu Thr Leu Ile Trp>
     _____IL-1RAcP_____>

220             230             240             250
         *       *       *       *       *       *       *       *
        TAT TGG ACT AGG CAG GAC CGG GAC CTT GAG GAG CCA ATT AAC
        ATA ACC TGA TCC GTC CTG GCC CTG GAA CTC CTC GGT TAA TTG
        Tyr Trp Thr Arg Gln Asp Arg Asp Leu Glu Glu Pro Ile Asn>
        _____IL-1RAcP_____>

260             270             280             290
         *       *       *       *       *       *       *       *
        TTC CGC CTC CCC GAG AAC CGC ATT AGT AAG GAG AAA GAT GTG
        AAG GCG GAG GGG CTC TTG GCG TAA TCA TTC CTC TTT CTA CAC
        Phe Arg Leu Pro Glu Asn Arg Ile Ser Lys Glu Lys Asp Val>
        _____IL-1RAcP_____>

300             310             320             330
         *       *       *       *       *       *       *       *       *
        CTG TGG TTC CGG CCC ACT CTC CTC AAT GAC ACT GGC AAC TAT
        GAC ACC AAG GCC GGG TGA GAG GAG TTA CTG TGA CCG TTG ATA
        Leu Trp Phe Arg Pro Thr Leu Leu Asn Asp Thr Gly Asn Tyr>
        _____IL-1RAcP_____>
```

Figure 42B

```
          340         350         360         370
           *     *     *     *     *     *     *     *
          ACC TGC ATG TTA AGG AAC ACT ACA TAT TGC AGC AAA GTT GCA
          TGG ACG TAC AAT TCC TTG TGA TGT ATA ACG TCG TTT CAA CGT
          Thr Cys Met Leu Arg Asn Thr Thr Tyr Cys Ser Lys Val Ala>
          _____IL-1RAcP_____>

380         390         400         410         420
   *     *     *     *     *     *     *     *     *
  TTT CCC TTG GAA GTT GTT CAA AAA GAC AGC TGT TTC AAT TCC
  AAA GGG AAC CTT CAA CAA GTT TTT CTG TCG ACA AAG TTA AGG
  Phe Pro Leu Glu Val Val Gln Lys Asp Ser Cys Phe Asn Ser>
  _____IL-1RAcP_____>

430         440         450         460
         *     *     *     *     *     *     *     *
         CCC ATG AAA CTC CCA GTG CAT AAA CTG TAT ATA GAA TAT GGC
         GGG TAC TTT GAG GGT CAC GTA TTT GAC ATA TAT CTT ATA CCG
         Pro Met Lys Leu Pro Val His Lys Leu Tyr Ile Glu Tyr Gly>
         _____IL-1RAcP_____>

470         480         490         500
         *     *     *     *     *     *     *     *
         ATT CAG AGG ATC ACT TGT CCA AAT GTA GAT GGA TAT TTT CCT
         TAA GTC TCC TAG TGA ACA GGT TTA CAT CTA CCT ATA AAA GGA
         Ile Gln Arg Ile Thr Cys Pro Asn Val Asp Gly Tyr Phe Pro>
         _____IL-1RAcP_____>

510         520         530         540
         *     *     *     *     *     *     *     *     *
         TCC AGT GTC AAA CCG ACT ATC ACT TGG TAT ATG GGC TGT TAT
         AGG TCA CAG TTT GGC TGA TAG TGA ACC ATA TAC CCG ACA ATA
         Ser Ser Val Lys Pro Thr Ile Thr Trp Tyr Met Gly Cys Tyr>
         _____IL-1RAcP_____>

550         560         570         580
          *     *     *     *     *     *     *     *
         AAA ATA CAG AAT TTT AAT AAT GTA ATA CCC GAA GGT ATG AAC
         TTT TAT GTC TTA AAA TTA TTA CAT TAT GGG CTT CCA TAC TTG
         Lys Ile Gln Asn Phe Asn Asn Val Ile Pro Glu Gly Met Asn>
         _____IL-1RAcP_____>

590         600         610         620         630
   *     *     *     *     *     *     *     *     *
  TTG AGT TTC CTC ATT GCC TTA ATT TCA AAT AAT GGA AAT TAC
  AAC TCA AAG GAG TAA CGG AAT TAA AGT TTA TTA CCT TTA ATG
  Leu Ser Phe Leu Ile Ala Leu Ile Ser Asn Asn Gly Asn Tyr>
  _____IL-1RAcP_____>

640         650         660         670
         *     *     *     *     *     *     *     *
         ACA TGT GTT GTT ACA TAT CCA GAA AAT GGA CGT ACG TTT CAT
         TGT ACA CAA CAA TGT ATA GGT CTT TTA CCT GCA TGC AAA GTA
         Thr Cys Val Val Thr Tyr Pro Glu Asn Gly Arg Thr Phe His>
         _____IL-1RAcP_____>
```

Figure 42C

```
         680              690              700              710
  *       *       *       *       *       *       *       *
 CTC ACC AGG ACT CTG ACT GTA AAG GTA GTA GGC TCT CCA AAA
 GAG TGG TCC TGA GAC TGA CAT TTC CAT CAT CCG AGA GGT TTT
 Leu Thr Arg Thr Leu Thr Val Lys Val Val Gly Ser Pro Lys>
 _____IL-1RAcP_____>

720              730              740              750
  *       *       *       *       *       *       *       *       *
 AAT GCA GTG CCC CCT GTG ATC CAT TCA CCT AAT GAT CAT GTG
 TTA CGT CAC GGG GGA CAC TAG GTA AGT GGA TTA CTA GTA CAC
 Asn Ala Val Pro Pro Val Ile His Ser Pro Asn Asp His Val>
 _____IL-1RAcP_____>

760              770              780              790
  *       *       *       *       *       *       *       *
 GTC TAT GAG AAA GAA CCA GGA GAG GAG CTA CTC ATT CCC TGT
 CAG ATA CTC TTT CTT GGT CCT CTC CTC GAT GAG TAA GGG ACA
 Val Tyr Glu Lys Glu Pro Gly Glu Glu Leu Leu Ile Pro Cys>
 _____IL-1RAcP_____>

800         810              820              830              840
  *       *       *       *       *       *       *       *       *
 ACG GTC TAT TTT AGT TTT CTG ATG GAT TCT CGC AAT GAG GTT
 TGC CAG ATA AAA TCA AAA GAC TAC CTA AGA GCG TTA CTC CAA
 Thr Val Tyr Phe Ser Phe Leu Met Asp Ser Arg Asn Glu Val>
 _____IL-1RAcP_____>

850              860              870              880
  *       *       *       *       *       *       *       *
 TGG TGG ACC ATT GAT GGA AAA AAA CCT GAT GAC ATC ACT ATT
 ACC ACC TGG TAA CTA CCT TTT TTT GGA CTA CTG TAG TGA TAA
 Trp Trp Thr Ile Asp Gly Lys Lys Pro Asp Asp Ile Thr Ile>
 _____IL-1RAcP_____>

890              900              910              920
  *       *       *       *       *       *       *       *
 GAT GTC ACC ATT AAC GAA AGT ATA AGT CAT AGT AGA ACA GAA
 CTA CAG TGG TAA TTG CTT TCA TAT TCA GTA TCA TCT TGT CTT
 Asp Val Thr Ile Asn Glu Ser Ile Ser His Ser Arg Thr Glu>
 _____IL-1RAcP_____>

930              940              950              960
  *       *       *       *       *       *       *       *       *
 GAT GAA ACA AGA ACT CAG ATT TTG AGC ATC AAG AAA GTT ACC
 CTA CTT TGT TCT TGA GTC TAA AAC TCG TAG TTC TTT CAA TGG
 Asp Glu Thr Arg Thr Gln Ile Leu Ser Ile Lys Lys Val Thr>
 _____IL-1RAcP_____>

970              980              990              1000
  *       *       *       *       *       *       *       *
 TCT GAG GAT CTC AAG CGC AGC TAT GTC TGT CAT GCT AGA AGT
 AGA CTC CTA GAG TTC GCG TCG ATA CAG ACA GTA CGA TCT TCA
 Ser Glu Asp Leu Lys Arg Ser Tyr Val Cys His Ala Arg Ser>
 _____IL-1RAcP_____>
```

Figure 42D

```
         1010                1020              1030              1040               1050
           *         *         *         *         *         *         *         *         *
         GCC  AAA  GGC  GAA  GTT  GCC  AAA  GCA  GCC  AAG  GTG  AAG  CAG  AAA
         CGG  TTT  CCG  CTT  CAA  CGG  TTT  CGT  CGG  TTC  CAC  TTC  GTC  TTT
         Ala  Lys  Gly  Glu  Val  Ala  Lys  Ala  Ala  Lys  Val  Lys  Gln  Lys>
         _____IL-1RAcP_____>

1060              1070              1080              1090
                 *         *         *         *         *         *         *         *
              GTG  CCA  GCT  CCA  AGA  TAC  ACA  GTG  GAA  AAA  TGC  AAG  GAA  CGT
              CAC  GGT  CGA  GGT  TCT  ATG  TGT  CAC  CTT  TTT  ACG  TTC  CTT  GCA
              Val  Pro  Ala  Pro  Arg  Tyr  Thr  Val  Glu>
              _____IL-1RAcP_____>
                                                        Lys  Cys  Lys  Glu  Arg>
                                                        _____IL-1RI_____>

1100              1110              1120              1130
           *         *         *         *         *         *         *         *
         GAA  GAA  AAA  ATA  ATT  TTA  GTG  AGC  TCA  GCA  AAT  GAA  ATC  GAT
         CTT  CTT  TTT  TAT  TAA  AAT  CAC  TCG  AGT  CGT  TTA  CTT  TAG  CTA
         Glu  Glu  Lys  Ile  Ile  Leu  Val  Ser  Ser  Ala  Asn  Glu  Ile  Asp>
         _____IL-1RI_____>

1140              1150              1160              1170
           *         *         *         *         *         *         *         *         *
         GTT  CGT  CCC  TGT  CCT  CTT  AAC  CCA  AAT  GAA  CAC  AAA  GGC  ACT
         CAA  GCA  GGG  ACA  GGA  GAA  TTG  GGT  TTA  CTT  GTG  TTT  CCG  TGA
         Val  Arg  Pro  Cys  Pro  Leu  Asn  Pro  Asn  Glu  His  Lys  Gly  Thr>
         _____IL-1RI_____>

1180              1190              1200              1210
           *         *         *         *         *         *         *         *
         ATA  ACT  TGG  TAT  AAG  GAT  GAC  AGC  AAG  ACA  CCT  GTA  TCT  ACA
         TAT  TGA  ACC  ATA  TTC  CTA  CTG  TCG  TTC  TGT  GGA  CAT  AGA  TGT
         Ile  Thr  Trp  Tyr  Lys  Asp  Asp  Ser  Lys  Thr  Pro  Val  Ser  Thr>
         _____IL-1RI_____>

1220              1230              1240              1250              1260
           *         *         *         *         *         *         *         *         *
         GAA  CAA  GCC  TCC  AGG  ATT  CAT  CAA  CAC  AAA  GAG  AAA  CTT  TGG
         CTT  GTT  CGG  AGG  TCC  TAA  GTA  GTT  GTG  TTT  CTC  TTT  GAA  ACC
         Glu  Gln  Ala  Ser  Arg  Ile  His  Gln  His  Lys  Glu  Lys  Leu  Trp>
         _____IL-1RI_____>

1270              1280              1290              1300
                 *         *         *         *         *         *         *         *
              TTT  GTT  CCT  GCT  AAG  GTG  GAG  GAT  TCA  GGA  CAT  TAC  TAT  TGC
              AAA  CAA  GGA  CGA  TTC  CAC  CTC  CTA  AGT  CCT  GTA  ATG  ATA  ACG
              Phe  Val  Pro  Ala  Lys  Val  Glu  Asp  Ser  Gly  His  Tyr  Tyr  Cys>
              _____IL-1RI_____>

1310              1320              1330              1340
                 *         *         *         *         *         *         *         *
              GTG  GTA  AGA  AAT  TCA  TCT  TAC  TGC  CTC  AGA  ATT  AAA  ATA  AGT
              CAC  CAT  TCT  TTA  AGT  AGA  ATG  ACG  GAG  TCT  TAA  TTT  TAT  TCA
              Val  Val  Arg  Asn  Ser  Ser  Tyr  Cys  Leu  Arg  Ile  Lys  Ile  Ser>
              _____IL-1RI_____>
```

Figure 42E

```
         1350           1360            1370              1380
     *     *       *     *       *       *        *        *       *
   GCA AAA TTT GTG GAG AAT GAG CCT AAC TTA TGT TAT AAT GCA
   CGT TTT AAA CAC CTC TTA CTC GGA TTG AAT ACA ATA TTA CGT
   Ala Lys Phe Val Glu Asn Glu Pro Asn Leu Cys Tyr Asn Ala>
                                 ___IL-1RI_____>

1390           1400           1410           1420
       *     *       *     *       *      *       *      *       *
   CAA GCC ATA TTT AAG CAG AAA CTA CCC GTT GCA GGA GAC GGA
   GTT CGG TAT AAA TTC GTC TTT GAT GGG CAA CGT CCT CTG CCT
   Gln Ala Ile Phe Lys Gln Lys Leu Pro Val Ala Gly Asp Gly>
                                 ___IL-1RI_____>

1430            1440           1450           1460           1470
    *      *       *      *       *      *       *       *      *
   GGA CTT GTG TGC CCT TAT ATG GAG TTT TTT AAA AAT GAA AAT
   CCT GAA CAC ACG GGA ATA TAC CTC AAA AAA TTT TTA CTT TTA
   Gly Leu Val Cys Pro Tyr Met Glu Phe Phe Lys Asn Glu Asn>
                                 ___IL-1RI_____>

1480           1490           1500            1510
       *      *      *       *       *      *       *      *      *
   AAT GAG TTA CCT AAA TTA CAG TGG TAT AAG GAT TGC AAA CCT
   TTA CTC AAT GGA TTT AAT GTC ACC ATA TTC CTA ACG TTT GGA
   Asn Glu Leu Pro Lys Leu Gln Trp Tyr Lys Asp Cys Lys Pro>
                                 ___IL-1RI_____>

1520           1530           1540           1550
       *      *       *      *       *       *      *       *
   CTA CTT CTT GAC AAT ATA CAC TTT AGT GGA GTC AAA GAT AGG
   GAT GAA GAA CTG TTA TAT GTG AAA TCA CCT CAG TTT CTA TCC
   Leu Leu Leu Asp Asn Ile His Phe Ser Gly Val Lys Asp Arg>
                                 ___IL-1RI_____>

1560           1570           1580           1590
       *      *       *     *       *       *       *      *       *
   CTC ATC GTG ATG AAT GTG GCT GAA AAG CAT AGA GGG AAC TAT
   GAG TAG CAC TAC TTA CAC CGA CTT TTC GTA TCT CCC TTG ATA
   Leu Ile Val Met Asn Val Ala Glu Lys His Arg Gly Asn Tyr>
                                 ___IL-1RI_____>

1600           1610           1620           1630
       *     *       *      *      *       *      *       *      *
   ACT TGT CAT GCA TCC TAC ACA TAC TTG GGC AAG CAA TAT CCT
   TGA ACA GTA CGT AGG ATG TGT ATG AAC CCG TTC GTT ATA GGA
   Thr Cys His Ala Ser Tyr Thr Tyr Leu Gly Lys Gln Tyr Pro>
                                 ___IL-1RI_____>

1640            1650           1660           1670            1680
    *      *       *      *       *      *       *      *       *
   ATT ACC CGG GTA ATA GAA TTT ATT ACT CTA GAG GAA AAC AAA
   TAA TGG GCC CAT TAT CTT AAA TAA TGA GAT CTC CTT TTG TTT
   Ile Thr Arg Val Ile Glu Phe Ile Thr Leu Glu Glu Asn Lys>
                                 ___IL-1RI_____>
```

Figure 42F

```
           1690            1700            1710            1720
       *       *       *       *       *       *       *       *
     CCC ACA AGG CCT GTG ATT GTG AGC CCA GCT AAT GAG ACA ATG
     GGG TGT TCC GGA CAC TAA CAC TCG GGT CGA TTA CTC TGT TAC
     Pro Thr Arg Pro Val Ile Val Ser Pro Ala Asn Glu Thr Met>
     _____IL-1RI_____>

1730            1740            1750            1760
       *       *       *       *       *       *       *       *
     GAA GTA GAC TTG GGA TCC CAG ATA CAA TTG ATC TGT AAT GTC
     CTT CAT CTG AAC CCT AGG GTC TAT GTT AAC TAG ACA TTA CAG
     Glu Val Asp Leu Gly Ser Gln Ile Gln Leu Ile Cys Asn Val>
     _____IL-1RI_____>

1770            1780            1790            1800
       *       *       *       *       *       *       *       *
     ACC GGC CAG TTG AGT GAC ATT GCT TAC TGG AAG TGG AAT GGG
     TGG CCG GTC AAC TCA CTG TAA CGA ATG ACC TTC ACC TTA CCC
     Thr Gly Gln Leu Ser Asp Ile Ala Tyr Trp Lys Trp Asn Gly>
     _____IL-1RI_____>

1810            1820            1830            1840
       *       *       *       *       *       *       *       *
     TCA GTA ATT GAT GAA GAT GAC CCA GTG CTA GGG GAA GAC TAT
     AGT CAT TAA CTA CTT CTA CTG GGT CAC GAT CCC CTT CTG ATA
     Ser Val Ile Asp Glu Asp Asp Pro Val Leu Gly Glu Asp Tyr>
     _____IL-1RI_____>

1850            1860            1870            1880            1890
   *       *       *       *       *       *       *       *       *
 TAC AGT GTG GAA AAT CCT GCA AAC AAA AGA AGG AGT ACC CTC
 ATG TCA CAC CTT TTA GGA CGT TTG TTT TCT TCC TCA TGG GAG
 Tyr Ser Val Glu Asn Pro Ala Asn Lys Arg Arg Ser Thr Leu>
     _____IL-1RI_____>

1900            1910            1920            1930
       *       *       *       *       *       *       *       *
     ATC ACA GTG CTT AAT ATA TCG GAA ATT GAG AGT AGA TTT TAT
     TAG TGT CAC GAA TTA TAT AGC CTT TAA CTC TCA TCT AAA ATA
     Ile Thr Val Leu Asn Ile Ser Glu Ile Glu Ser Arg Phe Tyr>
     _____IL-1RI_____>

1940            1950            1960            1970
       *       *       *       *       *       *       *       *
     AAA CAT CCA TTT ACC TGT TTT GCC AAG AAT ACA CAT GGT ATA
     TTT GTA GGT AAA TGG ACA AAA CGG TTC TTA TGT GTA CCA TAT
     Lys His Pro Phe Thr Cys Phe Ala Lys Asn Thr His Gly Ile>
     _____IL-1RI_____>

1980            1990            2000            2010
       *       *       *       *       *       *       *       *       *
     GAT GCA GCA TAT ATC CAG TTA ATA TAT CCA GTC ACT AAT TCC
     CTA CGT CGT ATA TAG GTC AAT TAT ATA GGT CAG TGA TTA AGG
     Asp Ala Ala Tyr Ile Gln Leu Ile Tyr Pro Val Thr Asn>
     _____IL-1RI_____>
                                                     Ser>
                                                     ___>
```

Figure 42G

```
       2020          2030          2040          2050
         *             *     *       *     *       *     *
  GGA GAG TCC AAA TAC GGT CCG CCA TGC CCA TCA TGC CCA GCA
  CCT CTC AGG TTT ATG CCA GGC GGT ACG GGT AGT ACG GGT CGT
  Gly>
  ___>
       Glu Ser Lys Tyr Gly Pro Pro Cys Pro Ser Cys Pro Ala>
                              _FC-IgG4_____>

2060          2070          2080          2090          2100
      *     *       *     *       *     *       *     *       *
  CCT GAG TTC CTG GGG GGA CCA TCA GTC TTC CTG TTC CCC CCA
  GGA CTC AAG GAC CCC CCT GGT AGT CAG AAG GAC AAG GGG GGT
  Pro Glu Phe Leu Gly Gly Pro Ser Val Phe Leu Phe Pro Pro>
                      _FC-IgG4_____>

2110          2120          2130          2140
                *             *     *       *     *       *
  AAA CCC AAG GAC ACT CTC ATG ATC TCC CGG ACC CCT GAG GTC
  TTT GGG TTC CTG TGA GAG TAC TAG AGG GCC TGG GGA CTC CAG
  Lys Pro Lys Asp Thr Leu Met Ile Ser Arg Thr Pro Glu Val>
                      _FC-IgG4_____>

2150          2160          2170          2180
                *             *     *       *     *       *
  ACG TGC GTG GTG GTG GAC GTG AGC CAG GAA GAC CCC GAG GTC
  TGC ACG CAC CAC CAC CTG CAC TCG GTC CTT CTG GGG CTC CAG
  Thr Cys Val Val Val Asp Val Ser Gln Glu Asp Pro Glu Val>
                      _FC-IgG4_____>

2190          2200          2210          2220
                *             *     *       *     *       *     *
  CAG TTC AAC TGG TAC GTG GAT GGC GTG GAG GTG CAT AAT GCC
  GTC AAG TTG ACC ATG CAC CTA CCG CAC CTC CAC GTA TTA CGG
  Gln Phe Asn Trp Tyr Val Asp Gly Val Glu Val His Asn Ala>
                      _FC-IgG4_____>

2230          2240          2250          2260
                *     *       *     *       *     *       *
  AAG ACA AAG CCG CGG GAG GAG CAG TTC AAC AGC ACG TAC CGT
  TTC TGT TTC GGC GCC CTC CTC GTC AAG TTG TCG TGC ATG GCA
  Lys Thr Lys Pro Arg Glu Glu Gln Phe Asn Ser Thr Tyr Arg>
                      _FC-IgG4_____>

2270          2280          2290          2300          2310
      *     *       *     *       *     *       *     *       *
  GTG GTC AGC GTC CTC ACC GTC CTG CAC CAG GAC TGG CTG AAC
  CAC CAG TCG CAG GAG TGG CAG GAC GTG GTC CTG ACC GAC TTG
  Val Val Ser Val Leu Thr Val Leu His Gln Asp Trp Leu Asn>
                      _FC-IgG4_____>

2320          2330          2340          2350
                *     *       *     *       *     *       *
  GGC AAG GAG TAC AAG TGC AAG GTC TCC AAC AAA GGC CTC CCG
  CCG TTC CTC ATG TTC ACG TTC CAG AGG TTG TTT CCG GAG GGC
  Gly Lys Glu Tyr Lys Cys Lys Val Ser Asn Lys Gly Leu Pro>
                      _FC-IgG4_____>
```

Figure 42H

```
            2360           2370           2380           2390
             *       *       *       *       *       *       *       *
        TCC TCC ATC GAG AAA ACC ATC TCC AAA GCC AAA GGG CAG CCC
        AGG AGG TAG CTC TTT TGG TAG AGG TTT CGG TTT CCC GTC GGG
        Ser Ser Ile Glu Lys Thr Ile Ser Lys Ala Lys Gly Gln Pro>
        _____FC-IgG4_____>

2400           2410           2420           2430
             *       *       *       *       *       *       *       *
        CGA GAG CCA CAG GTG TAC ACC CTG CCC CCA TCC CAG GAG GAG
        GCT CTC GGT GTC CAC ATG TGG GAC GGG GGT AGG GTC CTC CTC
        Arg Glu Pro Gln Val Tyr Thr Leu Pro Pro Ser Gln Glu Glu>
        _____FC-IgG4_____>

2440           2450           2460           2470
             *       *       *       *       *       *       *       *
        ATG ACC AAG AAC CAG GTC AGC CTG ACC TGC CTG GTC AAA GGC
        TAC TGG TTC TTG GTC CAG TCG GAC TGG ACG GAC CAG TTT CCG
        Met Thr Lys Asn Gln Val Ser Leu Thr Cys Leu Val Lys Gly>
        _____FC-IgG4_____>

2480           2490           2500           2510           2520
     *       *       *       *       *       *       *       *       *
TTC TAC CCC AGC GAC ATC GCC GTG GAG TGG GAG AGC AAT GGG
AAG ATG GGG TCG CTG TAG CGG CAC CTC ACC CTC TCG TTA CCC
Phe Tyr Pro Ser Asp Ile Ala Val Glu Trp Glu Ser Asn Gly>
_____FC-IgG4_____>

2530           2540           2550           2560
             *       *       *       *       *       *       *       *
        CAG CCG GAG AAC AAC TAC AAG ACC ACG CCT CCC GTG CTG GAC
        GTC GGC CTC TTG TTG ATG TTC TGG TGC GGA GGG CAC GAC CTG
        Gln Pro Glu Asn Asn Tyr Lys Thr Thr Pro Pro Val Leu Asp>
        _____FC-IgG4_____>

2570           2580           2590           2600
             *       *       *       *       *       *       *       *
        TCC GAC GGC TCC TTC TTC CTC TAC AGC AGG CTA ACC GTG GAC
        AGG CTG CCG AGG AAG AAG GAG ATG TCG TCC GAT TGG CAC CTG
        Ser Asp Gly Ser Phe Phe Leu Tyr Ser Arg Leu Thr Val Asp>
        _____FC-IgG4_____>

2610           2620           2630           2640
             *       *       *       *       *       *       *       *
        AAG AGC AGG TGG CAG GAG GGG AAT GTC TTC TCA TGC TCC GTG
        TTC TCG TCC ACC GTC CTC CCC TTA CAG AAG AGT ACG AGG CAC
        Lys Ser Arg Trp Gln Glu Gly Asn Val Phe Ser Cys Ser Val>
        _____FC-IgG4_____>

2650           2660           2670           2680
             *       *       *       *       *       *       *       *
        ATG CAT GAG GCT CTG CAC AAC CAC TAC ACA CAG AAG AGC CTC
        TAC GTA CTC CGA GAC GTG TTG GTG ATG TGT GTC TTC TCG GAG
        Met His Glu Ala Leu His Asn His Tyr Thr Gln Lys Ser Leu>
        _____FC-IgG4_____>
```

Figure 42 I

```
         2690                2700
           *        *          *          *
         TCC      CTG        TCT        CTG      GGT      AAA      TGA
         AGG      GAC        AGA        GAC      CCA      TTT      ACT
         Ser      Leu        Ser        Leu      Gly      Lys      ***>
                         _____FC-IgG4_____>
```

Figure 43A

```
           10             20             30             40
            *              *              *              *
ATG GTG CTT CTG TGG TGT GTA GTG AGT CTC TAC TTT TAT GGA
TAC CAC GAA GAC ACC ACA CAT CAC TCA GAG ATG AAA ATA CCT
Met Val Leu Leu Trp Cys Val Val Ser Leu Tyr Phe Tyr Gly>
_____SIGNAL PEPTIDE_____>
_____IL-1RAcP_____>

50             60             70             80
            *              *              *              *
ATC CTG CAA AGT GAT GCC TCA GAA CGC TGC GAT GAC TGG GGA
TAG GAC GTT TCA CTA CGG AGT CTT GCG ACG CTA CTG ACC CCT
Ile Leu Gln Ser Asp Ala>
___SIGNAL PEPTIDE ____>
                        Ser Glu Arg Cys Asp Asp Trp Gly>
_____IL-1RAcP_____>

90            100            110            120
            *              *              *              *
CTA GAC ACC ATG AGG CAA ATC CAA GTG TTT GAA GAT GAG CCA
GAT CTG TGG TAC TCC GTT TAG GTT CAC AAA CTT CTA CTC GGT
Leu Asp Thr Met Arg Gln Ile Gln Val Phe Glu Asp Glu Pro>
_____IL-1RAcP_____>

130            140            150            160
            *              *              *              *
GCT CGC ATC AAG TGC CCA CTC TTT GAA CAC TTC TTG AAA TTC
CGA GCG TAG TTC ACG GGT GAG AAA CTT GTG AAG AAC TTT AAG
Ala Arg Ile Lys Cys Pro Leu Phe Glu His Phe Leu Lys Phe>
_____IL-1RAcP_____>

170           180            190            200           210
   *             *              *              *             *
AAC TAC AGC ACA GCC CAT TCA GCT GGC CTT ACT CTG ATC TGG
TTG ATG TCG TGT CGG GTA AGT CGA CCG GAA TGA GAC TAG ACC
Asn Tyr Ser Thr Ala His Ser Ala Gly Leu Thr Leu Ile Trp>
_____IL-1RAcP_____>

220            230            240            250
            *              *              *              *
TAT TGG ACT AGG CAG GAC CGG GAC CTT GAG GAG CCA ATT AAC
ATA ACC TGA TCC GTC CTG GCC CTG GAA CTC CTC GGT TAA TTG
Tyr Trp Thr Arg Gln Asp Arg Asp Leu Glu Glu Pro Ile Asn>
_____IL-1RAcP_____>

260            270            280            290
            *              *              *              *
TTC CGC CTC CCC GAG AAC CGC ATT AGT AAG GAG AAA GAT GTG
AAG GCG GAG GGG CTC TTG GCG TAA TCA TTC CTC TTT CTA CAC
Phe Arg Leu Pro Glu Asn Arg Ile Ser Lys Glu Lys Asp Val>
_____IL-1RAcP_____>

300            310            320            330
         *              *              *              *
CTG TGG TTC CGG CCC ACT CTC CTC AAT GAC ACT GGC AAC TAT
GAC ACC AAG GCC GGG TGA GAG GAG TTA CTG TGA CCG TTG ATA
Leu Trp Phe Arg Pro Thr Leu Leu Asn Asp Thr Gly Asn Tyr>
_____IL-1RAcP_____>
```

Figure 43B

```
       340            350            360              370
        *      *       *      *       *       *       *        *
       ACC    TGC    ATG    TTA    AGG    AAC    ACT    ACA    TAT    TGC    AGC    AAA    GTT    GCA
       TGG    ACG    TAC    AAT    TCC    TTG    TGA    TGT    ATA    ACG    TCG    TTT    CAA    CGT
       Thr    Cys    Met    Leu    Arg    Asn    Thr    Thr    Tyr    Cys    Ser    Lys    Val    Ala>
       _____IL-1RAcP_____>

380            390            400            410              420
        *      *       *      *       *       *       *      *       *
       TTT    CCC    TTG    GAA    GTT    GTT    CAA    AAA    GAC    AGC    TGT    TTC    AAT    TCC
       AAA    GGG    AAC    CTT    CAA    CAA    GTT    TTT    CTG    TCG    ACA    AAG    TTA    AGG
       Phe    Pro    Leu    Glu    Val    Val    Gln    Lys    Asp    Ser    Cys    Phe    Asn    Ser>
       _____IL-1RAcP_____>

430            440            450              460
        *      *      *       *      *       *       *      *
       CCC    ATG    AAA    CTC    CCA    GTG    CAT    AAA    CTG    TAT    ATA    GAA    TAT    GGC
       GGG    TAC    TTT    GAG    GGT    CAC    GTA    TTT    GAC    ATA    TAT    CTT    ATA    CCG
       Pro    Met    Lys    Leu    Pro    Val    His    Lys    Leu    Tyr    Ile    Glu    Tyr    Gly>
       _____IL-1RAcP_____>

470            480            490              500
        *      *      *       *      *       *       *      *
       ATT    CAG    AGG    ATC    ACT    TGT    CCA    AAT    GTA    GAT    GGA    TAT    TTT    CCT
       TAA    GTC    TCC    TAG    TGA    ACA    GGT    TTA    CAT    CTA    CCT    ATA    AAA    GGA
       Ile    Gln    Arg    Ile    Thr    Cys    Pro    Asn    Val    Asp    Gly    Tyr    Phe    Pro>
       _____IL-1RAcP_____>

510            520            530            540
        *      *      *       *      *       *      *       *      *
       TCC    AGT    GTC    AAA    CCG    ACT    ATC    ACT    TGG    TAT    ATG    GGC    TGT    TAT
       AGG    TCA    CAG    TTT    GGC    TGA    TAG    TGA    ACC    ATA    TAC    CCG    ACA    ATA
       Ser    Ser    Val    Lys    Pro    Thr    Ile    Thr    Trp    Tyr    Met    Gly    Cys    Tyr>
       _____IL-1RAcP_____>

550            560            570            580
        *      *       *      *       *      *       *      *
       AAA    ATA    CAG    AAT    TTT    AAT    AAT    GTA    ATA    CCC    GAA    GGT    ATG    AAC
       TTT    TAT    GTC    TTA    AAA    TTA    TTA    CAT    TAT    GGG    CTT    CCA    TAC    TTG
       Lys    Ile    Gln    Asn    Phe    Asn    Asn    Val    Ile    Pro    Glu    Gly    Met    Asn>
       _____IL-1RAcP_____>

590            600            610            620              630
        *      *       *      *       *       *       *      *       *
       TTG    AGT    TTC    CTC    ATT    GCC    TTA    ATT    TCA    AAT    AAT    GGA    AAT    TAC
       AAC    TCA    AAG    GAG    TAA    CGG    AAT    TAA    AGT    TTA    TTA    CCT    TTA    ATG
       Leu    Ser    Phe    Leu    Ile    Ala    Leu    Ile    Ser    Asn    Asn    Gly    Asn    Tyr>
       _____IL-1RAcP_____>

640            650            660              670
        *      *      *       *      *       *       *      *
       ACA    TGT    GTT    GTT    ACA    TAT    CCA    GAA    AAT    GGA    CGT    ACG    TTT    CAT
       TGT    ACA    CAA    CAA    TGT    ATA    GGT    CTT    TTA    CCT    GCA    TGC    AAA    GTA
       Thr    Cys    Val    Val    Thr    Tyr    Pro    Glu    Asn    Gly    Arg    Thr    Phe    His>
       _____IL-1RAcP_____>
```

Figure 43C

```
         680              690              700              710
  *        *        *        *        *        *        *        *
CTC ACC AGG ACT CTG ACT GTA AAG GTA GTA GGC TCT CCA AAA
GAG TGG TCC TGA GAC TGA CAT TTC CAT CAT CCG AGA GGT TTT
Leu Thr Arg Thr Leu Thr Val Lys Val Val Gly Ser Pro Lys>
                        ___IL-1RAcP_____>

720              730              740              750
  *        *        *        *        *        *        *        *        *
AAT GCA GTG CCC CCT GTG ATC CAT TCA CCT AAT GAT CAT GTG
TTA CGT CAC GGG GGA CAC TAG GTA AGT GGA TTA CTA GTA CAC
Asn Ala Val Pro Pro Val Ile His Ser Pro Asn Asp His Val>
                        ___IL-1RAcP_____>

760              770              780              790
  *   *    *    *    *    *    *    *    *    *    *    *
GTC TAT GAG AAA GAA CCA GGA GAG GAG CTA CTC ATT CCC TGT
CAG ATA CTC TTT CTT GGT CCT CTC CTC GAT GAG TAA GGG ACA
Val Tyr Glu Lys Glu Pro Gly Glu Glu Leu Leu Ile Pro Cys>
                        ___IL-1RAcP_____>

800            810            820            830            840
 *      *       *       *       *       *       *       *       *
ACG GTC TAT TTT AGT TTT CTG ATG GAT TCT CGC AAT GAG GTT
TGC CAG ATA AAA TCA AAA GAC TAC CTA AGA GCG TTA CTC CAA
Thr Val Tyr Phe Ser Phe Leu Met Asp Ser Arg Asn Glu Val>
                        ___IL-1RAcP_____>

850              860              870              880
  *        *        *        *        *        *        *        *
TGG TGG ACC ATT GAT GGA AAA AAA CCT GAT GAC ATC ACT ATT
ACC ACC TGG TAA CTA CCT TTT TTT GGA CTA CTG TAG TGA TAA
Trp Trp Thr Ile Asp Gly Lys Lys Pro Asp Asp Ile Thr Ile>
                        ___IL-1RAcP_____>

890              900              910              920
  *        *        *        *        *        *        *        *
GAT GTC ACC ATT AAC GAA AGT ATA AGT CAT AGT AGA ACA GAA
CTA CAG TGG TAA TTG CTT TCA TAT TCA GTA TCA TCT TGT CTT
Asp Val Thr Ile Asn Glu Ser Ile Ser His Ser Arg Thr Glu>
                        ___IL-1RAcP_____>

930              940              950              960
  *        *        *        *        *        *        *        *        *
GAT GAA ACA AGA ACT CAG ATT TTG AGC ATC AAG AAA GTT ACC
CTA CTT TGT TCT TGA GTC TAA AAC TCG TAG TTC TTT CAA TGG
Asp Glu Thr Arg Thr Gln Ile Leu Ser Ile Lys Lys Val Thr>
                        ___IL-1RAcP_____>

970            980            990           1000
  *   *    *    *    *    *    *    *    *    *
TCT GAG GAT CTC AAG CGC AGC TAT GTC TGT CAT GCT AGA AGT
AGA CTC CTA GAG TTC GCG TCG ATA CAG ACA GTA CGA TCT TCA
Ser Glu Asp Leu Lys Arg Ser Tyr Val Cys His Ala Arg Ser>
                        ___IL-1RAcP_____>
```

Figure 43D

```
      1010            1020            1030            1040            1050
        *       *       *       *       *       *       *       *       *
       GCC     AAA     GGC     GAA     GTT     GCC     AAA     GCA     GCC     AAG     GTG     AAG     CAG     AAA
       CGG     TTT     CCG     CTT     CAA     CGG     TTT     CGT     CGG     TTC     CAC     TTC     GTC     TTT
       Ala     Lys     Gly     Glu     Val     Ala     Lys     Ala     Ala     Lys     Val     Lys     Gln     Lys>
       _____IL-1RAcP_____>

1060            1070            1080            1090
              *       *       *       *       *       *       *       *
             GTG     CCA     GCT     CCA     AGA     TAC     ACA     GTG     GAA     AAA     TGC     AAG     GAA     CGT
             CAC     GGT     CGA     GGT     TCT     ATG     TGT     CAC     CTT     TTT     ACG     TTC     CTT     GCA
             Val     Pro     Ala     Pro     Arg     Tyr     Thr     Val     Glu>
             _____IL-1RAcP_____>
                                                              Lys     Cys     Lys     Glu     Arg>
                                                              _____IL-1RI_____>

1100            1110            1120            1130
        *       *       *       *       *       *       *       *
       GAA     GAA     AAA     ATA     ATT     TTA     GTG     AGC     TCA     GCA     AAT     GAA     ATC     GAT
       CTT     CTT     TTT     TAT     TAA     AAT     CAC     TCG     AGT     CGT     TTA     CTT     TAG     CTA
       Glu     Glu     Lys     Ile     Ile     Leu     Val     Ser     Ser     Ala     Asn     Glu     Ile     Asp>
       _____IL-1RI_____>

1140            1150            1160            1170
        *       *       *       *       *       *       *       *       *
       GTT     CGT     CCC     TGT     CCT     CTT     AAC     CCA     AAT     GAA     CAC     AAA     GGC     ACT
       CAA     GCA     GGG     ACA     GGA     GAA     TTG     GGT     TTA     CTT     GTG     TTT     CCG     TGA
       Val     Arg     Pro     Cys     Pro     Leu     Asn     Pro     Asn     Glu     His     Lys     Gly     Thr>
       _____IL-1RI_____>

1180            1190            1200            1210
        *       *       *       *       *       *       *       *
       ATA     ACT     TGG     TAT     AAG     GAT     GAC     AGC     AAG     ACA     CCT     GTA     TCT     ACA
       TAT     TGA     ACC     ATA     TTC     CTA     CTG     TCG     TTC     TGT     GGA     CAT     AGA     TGT
       Ile     Thr     Trp     Tyr     Lys     Asp     Asp     Ser     Lys     Thr     Pro     Val     Ser     Thr>
       _____IL-1RI_____>

1220            1230            1240            1250            1260
        *       *       *       *       *       *       *       *       *
       GAA     CAA     GCC     TCC     AGG     ATT     CAT     CAA     CAC     AAA     GAG     AAA     CTT     TGG
       CTT     GTT     CGG     AGG     TCC     TAA     GTA     GTT     GTG     TTT     CTC     TTT     GAA     ACC
       Glu     Gln     Ala     Ser     Arg     Ile     His     Gln     His     Lys     Glu     Lys     Leu     Trp>
       _____IL-1RI_____>

1270            1280            1290            1300
              *       *       *       *       *       *       *       *
             TTT     GTT     CCT     GCT     AAG     GTG     GAG     GAT     TCA     GGA     CAT     TAC     TAT     TGC
             AAA     CAA     GGA     CGA     TTC     CAC     CTC     CTA     AGT     CCT     GTA     ATG     ATA     ACG
             Phe     Val     Pro     Ala     Lys     Val     Glu     Asp     Ser     Gly     His     Tyr     Tyr     Cys>
             _____IL-1RI_____>

1310            1320            1330            1340
        *       *       *       *       *       *       *       *
       GTG     GTA     AGA     AAT     TCA     TCT     TAC     TGC     CTC     AGA     ATT     AAA     ATA     AGT
       CAC     CAT     TCT     TTA     AGT     AGA     ATG     ACG     GAG     TCT     TAA     TTT     TAT     TCA
       Val     Val     Arg     Asn     Ser     Ser     Tyr     Cys     Leu     Arg     Ile     Lys     Ile     Ser>
       _____IL-1RI_____>
```

Figure 43E

```
         1350           1360           1370           1380
     *      *       *      *       *      *       *      *       *
    GCA AAA TTT GTG GAG AAT GAG CCT AAC TTA TGT TAT AAT GCA
    CGT TTT AAA CAC CTC TTA CTC GGA TTG AAT ACA ATA TTA CGT
    Ala Lys Phe Val Glu Asn Glu Pro Asn Leu Cys Tyr Asn Ala>
                              IL-1RI                          >

1390           1400           1410           1420
     *      *       *      *       *      *       *      *
    CAA GCC ATA TTT AAG CAG AAA CTA CCC GTT GCA GGA GAC GGA
    GTT CGG TAT AAA TTC GTC TTT GAT GGG CAA CGT CCT CTG CCT
    Gln Ala Ile Phe Lys Gln Lys Leu Pro Val Ala Gly Asp Gly>
                              IL-1RI                          >

1430           1440           1450           1460           1470
  *      *       *      *       *      *       *      *       *
    GGA CTT GTG TGC CCT TAT ATG GAG TTT TTT AAA AAT GAA AAT
    CCT GAA CAC ACG GGA ATA TAC CTC AAA AAA TTT TTA CTT TTA
    Gly Leu Val Cys Pro Tyr Met Glu Phe Phe Lys Asn Glu Asn>
                              IL-1RI                          >

1480           1490           1500           1510
           *      *       *      *       *      *       *      *
    AAT GAG TTA CCT AAA TTA CAG TGG TAT AAG GAT TGC AAA CCT
    TTA CTC AAT GGA TTT AAT GTC ACC ATA TTC CTA ACG TTT GGA
    Asn Glu Leu Pro Lys Leu Gln Trp Tyr Lys Asp Cys Lys Pro>
                              IL-1RI                          >

1520           1530           1540           1550
       *      *       *      *       *      *       *      *
    CTA CTT CTT GAC AAT ATA CAC TTT AGT GGA GTC AAA GAT AGG
    GAT GAA GAA CTG TTA TAT GTG AAA TCA CCT CAG TTT CTA TCC
    Leu Leu Leu Asp Asn Ile His Phe Ser Gly Val Lys Asp Arg>
                              IL-1RI                          >

1560           1570           1580           1590
     *      *       *      *       *      *       *      *       *
    CTC ATC GTG ATG AAT GTG GCT GAA AAG CAT AGA GGG AAC TAT
    GAG TAG CAC TAC TTA CAC CGA CTT TTC GTA TCT CCC TTG ATA
    Leu Ile Val Met Asn Val Ala Glu Lys His Arg Gly Asn Tyr>
                              IL-1RI                          >

1600           1610           1620           1630
     *      *       *      *       *      *       *      *
    ACT TGT CAT GCA TCC TAC ACA TAC TTG GGC AAG CAA TAT CCT
    TGA ACA GTA CGT AGG ATG TGT ATG AAC CCG TTC GTT ATA GGA
    Thr Cys His Ala Ser Tyr Thr Tyr Leu Gly Lys Gln Tyr Pro>
                              IL-1RI                          >

1640           1650           1660           1670           1680
  *      *       *      *       *      *       *      *       *
    ATT ACC CGG GTA ATA GAA TTT ATT ACT CTA GAG GAA AAC AAA
    TAA TGG GCC CAT TAT CTT AAA TAA TGA GAT CTC CTT TTG TTT
    Ile Thr Arg Val Ile Glu Phe Ile Thr Leu Glu Glu Asn Lys>
                              IL-1RI                          >
```

Figure 43F

```
            1690            1700            1710            1720
          *       *       *       *       *       *       *       *
        CCC ACA AGG CCT GTG ATT GTG AGC CCA GCT AAT GAG ACA ATG
        GGG TGT TCC GGA CAC TAA CAC TCG GGT CGA TTA CTC TGT TAC
        Pro Thr Arg Pro Val Ile Val Ser Pro Ala Asn Glu Thr Met>
                              _____IL-1RI_____>

1730            1740            1750            1760
          *       *       *       *       *       *       *       *
        GAA GTA GAC TTG GGA TCC CAG ATA CAA TTG ATC TGT AAT GTC
        CTT CAT CTG AAC CCT AGG GTC TAT GTT AAC TAG ACA TTA CAG
        Glu Val Asp Leu Gly Ser Gln Ile Gln Leu Ile Cys Asn Val>
                              _____IL-1RI_____>

1770            1780            1790            1800
        *       *       *       *       *       *       *       *       *
        ACC GGC CAG TTG AGT GAC ATT GCT TAC TGG AAG TGG AAT GGG
        TGG CCG GTC AAC TCA CTG TAA CGA ATG ACC TTC ACC TTA CCC
        Thr Gly Gln Leu Ser Asp Ile Ala Tyr Trp Lys Trp Asn Gly>
                              _____IL-1RI_____>

1810            1820            1830            1840
     *       *       *       *       *       *       *       *
        TCA GTA ATT GAT GAA GAT GAC CCA GTG CTA GGG GAA GAC TAT
        AGT CAT TAA CTA CTT CTA CTG GGT CAC GAT CCC CTT CTG ATA
        Ser Val Ile Asp Glu Asp Asp Pro Val Leu Gly Glu Asp Tyr>
                              _____IL-1RI_____>

1850            1860            1870            1880            1890
  *       *       *       *       *       *       *       *       *       *
        TAC AGT GTG GAA AAT CCT GCA AAC AAA AGA AGG AGT ACC CTC
        ATG TCA CAC CTT TTA GGA CGT TTG TTT TCT TCC TCA TGG GAG
        Tyr Ser Val Glu Asn Pro Ala Asn Lys Arg Arg Ser Thr Leu>
                              _____IL-1RI_____>

1900            1910            1920            1930
          *       *       *       *       *       *       *       *
        ATC ACA GTG CTT AAT ATA TCG GAA ATT GAG AGT AGA TTT TAT
        TAG TGT CAC GAA TTA TAT AGC CTT TAA CTC TCA TCT AAA ATA
        Ile Thr Val Leu Asn Ile Ser Glu Ile Glu Ser Arg Phe Tyr>
                              _____IL-1RI_____>

1940            1950            1960            1970
          *       *       *       *       *       *       *       *
        AAA CAT CCA TTT ACC TGT TTT GCC AAG AAT ACA CAT GGT ATA
        TTT GTA GGT AAA TGG ACA AAA CGG TTC TTA TGT GTA CCA TAT
        Lys His Pro Phe Thr Cys Phe Ala Lys Asn Thr His Gly Ile>
                              _____IL-1RI_____>

1980            1990            2000            2010
          *       *       *       *       *       *       *       *       *
        GAT GCA GCA TAT ATC CAG TTA ATA TAT CCA GTC ACT AAT TCC
        CTA CGT CGT ATA TAG GTC AAT TAT ATA GGT CAG TGA TTA AGG
        Asp Ala Ala Tyr Ile Gln Leu Ile Tyr Pro Val Thr Asn>
                              _____IL-1RI_____>
                                                                Ser>
                                                                ___>
```

Figure 43G

```
         2020         2030          2040         2050
           *            *     *       *    *       *    *     *
      GGA GAG TCC AAA TAC GGT CCG CCA TGC CCA CCA TGC CCA GCA
      CCT CTC AGG TTT ATG CCA GGC GGT ACG GGT GGT ACG GGT CGT
      Gly>
      ___>
          Glu Ser Lys Tyr Gly Pro Pro Cys Pro Pro Cys Pro Ala>
                           ____FC-IgG4_____>

2060          2070          2080          2090          2100
    *      *      *     *       *     *      *     *       *
  CCT GAG TTC CTG GGG GGA CCA TCA GTC TTC CTG TTC CCC CCA
  GGA CTC AAG GAC CCC CCT GGT AGT CAG AAG GAC AAG GGG GGT
  Pro Glu Phe Leu Gly Gly Pro Ser Val Phe Leu Phe Pro Pro>
  _____FC-IgG4_____>

2110          2120          2130          2140
         *     *      *      *     *      *     *       *
      AAA CCC AAG GAC ACT CTC ATG ATC TCC CGG ACC CCT GAG GTC
      TTT GGG TTC CTG TGA GAG TAC TAG AGG GCC TGG GGA CTC CAG
      Lys Pro Lys Asp Thr Leu Met Ile Ser Arg Thr Pro Glu Val>
      _____FC-IgG4_____>

2150          2160          2170          2180
         *      *     *      *      *     *     *       *
      ACG TGC GTG GTG GTG GAC GTG AGC CAG GAA GAC CCC GAG GTC
      TGC ACG CAC CAC CAC CTG CAC TCG GTC CTT CTG GGG CTC CAG
      Thr Cys Val Val Val Asp Val Ser Gln Glu Asp Pro Glu Val>
      _____FC-IgG4_____>

2190          2200          2210          2220
         *     *      *      *     *      *     *       *
      CAG TTC AAC TGG TAC GTG GAT GGC GTG GAG GTG CAT AAT GCC
      GTC AAG TTG ACC ATG CAC CTA CCG CAC CTC CAC GTA TTA CGG
      Gln Phe Asn Trp Tyr Val Asp Gly Val Glu Val His Asn Ala>
      _____FC-IgG4_____>

2230          2240          2250          2260
        *      *      *     *       *     *      *     *
      AAG ACA AAG CCG CGG GAG GAG CAG TTC AAC AGC ACG TAC CGT
      TTC TGT TTC GGC GCC CTC CTC GTC AAG TTG TCG TGC ATG GCA
      Lys Thr Lys Pro Arg Glu Glu Gln Phe Asn Ser Thr Tyr Arg>
      _____FC-IgG4_____>

2270          2280          2290          2300          2310
    *      *      *     *       *     *      *     *       *
  GTG GTC AGC GTC CTC ACC GTC CTG CAC CAG GAC TGG CTG AAC
  CAC CAG TCG CAG GAG TGG CAG GAC GTG GTC CTG ACC GAC TTG
  Val Val Ser Val Leu Thr Val Leu His Gln Asp Trp Leu Asn>
  _____FC-IgG4_____>

2320          2330          2340          2350
         *      *      *     *      *      *     *       *
      GGC AAG GAG TAC AAG TGC AAG GTC TCC AAC AAA GGC CTC CCG
      CCG TTC CTC ATG TTC ACG TTC CAG AGG TTG TTT CCG GAG GGC
      Gly Lys Glu Tyr Lys Cys Lys Val Ser Asn Lys Gly Leu Pro>
      _____FC-IgG4_____>
```

Figure 43H

```
          2360           2370             2380             2390
    *       *       *       *       *       *       *       *
   TCC TCC ATC GAG AAA ACC ATC TCC AAA GCC AAA GGG CAG CCC
   AGG AGG TAG CTC TTT TGG TAG AGG TTT CGG TTT CCC GTC GGG
   Ser Ser Ile Glu Lys Thr Ile Ser Lys Ala Lys Gly Gln Pro>
                            _____FC-IgG4_____>

2400           2410             2420             2430
    *       *       *       *       *       *       *       *
   CGA GAG CCA CAG GTG TAC ACC CTG CCC CCA TCC CAG GAG GAG
   GCT CTC GGT GTC CAC ATG TGG GAC GGG GGT AGG GTC CTC CTC
   Arg Glu Pro Gln Val Tyr Thr Leu Pro Pro Ser Gln Glu Glu>
                            _____FC-IgG4_____>

2440           2450             2460             2470
    *       *       *       *       *       *       *       *
   ATG ACC AAG AAC CAG GTC AGC CTG ACC TGC CTG GTC AAA GGC
   TAC TGG TTC TTG GTC CAG TCG GAC TGG ACG GAC CAG TTT CCG
   Met Thr Lys Asn Gln Val Ser Leu Thr Cys Leu Val Lys Gly>
                            _____FC-IgG4_____>

2480           2490             2500             2510           2520
    *       *       *       *       *       *       *       *       *
   TTC TAC CCC AGC GAC ATC GCC GTG GAG TGG GAG AGC AAT GGG
   AAG ATG GGG TCG CTG TAG CGG CAC CTC ACC CTC TCG TTA CCC
   Phe Tyr Pro Ser Asp Ile Ala Val Glu Trp Glu Ser Asn Gly>
                            _____FC-IgG4_____>

2530           2540             2550             2560
    *       *       *       *       *       *       *       *
   CAG CCG GAG AAC AAC TAC AAG ACC ACG CCT CCC GTG CTG GAC
   GTC GGC CTC TTG TTG ATG TTC TGG TGC GGA GGG CAC GAC CTG
   Gln Pro Glu Asn Asn Tyr Lys Thr Thr Pro Pro Val Leu Asp>
                            _____FC-IgG4_____>

2570           2580             2590             2600
    *       *       *       *       *       *       *       *
   TCC GAC GGC TCC TTC TTC CTC TAC AGC AGG CTA ACC GTG GAC
   AGG CTG CCG AGG AAG AAG GAG ATG TCG TCC GAT TGG CAC CTG
   Ser Asp Gly Ser Phe Phe Leu Tyr Ser Arg Leu Thr Val Asp>
                            _____FC-IgG4_____>

2610           2620             2630             2640
    *       *       *       *       *       *       *       *
   AAG AGC AGG TGG CAG GAG GGG AAT GTC TTC TCA TGC TCC GTG
   TTC TCG TCC ACC GTC CTC CCC TTA CAG AAG AGT ACG AGG CAC
   Lys Ser Arg Trp Gln Glu Gly Asn Val Phe Ser Cys Ser Val>
                            _____FC-IgG4_____>

2650           2660             2670             2680
    *       *       *       *       *       *       *       *
   ATG CAT GAG GCT CTG CAC AAC CAC TAC ACA CAG AAG AGC CTC
   TAC GTA CTC CGA GAC GTG TTG GTG ATG TGT GTC TTC TCG GAG
   Met His Glu Ala Leu His Asn His Tyr Thr Gln Lys Ser Leu>
                            _____FC-IgG4_____>
```

Figure 43.I

```
       2690                2700
        *         *         *         *
       TCC CTG TCT CTG GGT AAA TGA
       AGG GAC AGA GAC CCA TTT ACT
       Ser Leu Ser Leu Gly Lys ***>
       _____FC-IgG4_____>
```

Figure 44A

```
                  10             20             30             40
         *         *    *         *    *         *    *         *
      ATG GTG CGC TTG TAC GTG TTG GTA ATG GGA GTT TCT GCC TTC
      TAC CAC GCG AAC ATG CAC AAC CAT TAC CCT CAA AGA CGG AAG
      Met Val Arg Leu Tyr Val Leu Val Met Gly Val Ser Ala Phe>
      _____SIGNAL PEPTIDE_____>
      _____IL-1RII_____>

50             60             70             80
         *         *    *         *    *         *    *         *
      ACC CTT CAG CCT GCG GCA CAC ACA GGG GCT GCC AGA AGC TGC
      TGG GAA GTC GGA CGC CGT GTG TGT CCC CGA CGG TCT TCG ACG
      Thr Leu Gln Pro Ala Ala>
      _____SIGNAL PEPTIDE____>
                              His Thr Gly Ala Ala Arg Ser Cys>
      _____IL-1RII_____>

90            100            110            120
         *         *    *         *    *         *    *         *
      CGG TTT CGT GGG AGG CAT TAC AAG CGG GAG TTC AGG CTG GAA
      GCC AAA GCA CCC TCC GTA ATG TTC GCC CTC AAG TCC GAC CTT
      Arg Phe Arg Gly Arg His Tyr Lys Arg Glu Phe Arg Leu Glu>
      _____IL-1RII_____>

130            140            150            160
         *    *         *    *         *    *         *    *
      GGG GAG CCT GTA GCC CTG AGG TGC CCC CAG GTG CCC TAC TGG
      CCC CTC GGA CAT CGG GAC TCC ACG GGG GTC CAC GGG ATG ACC
      Gly Glu Pro Val Ala Leu Arg Cys Pro Gln Val Pro Tyr Trp>
      _____IL-1RII_____>

170            180            190            200            210
      *         *    *         *    *    *         *    *         *
      TTG TGG GCC TCT GTC AGC CCC CGC ATC AAC CTG ACA TGG CAT
      AAC ACC CGG AGA CAG TCG GGG GCG TAG TTG GAC TGT ACC GTA
      Leu Trp Ala Ser Val Ser Pro Arg Ile Asn Leu Thr Trp His>
      _____IL-1RII_____>

220            230            240            250
         *         *    *         *    *    *         *    *
      AAA AAT GAC TCT GCT AGG ACG GTC CCA GGA GAA GAA GAG ACA
      TTT TTA CTG AGA CGA TCC TGC CAG GGT CCT CTT CTT CTC TGT
      Lys Asn Asp Ser Ala Arg Thr Val Pro Gly Glu Glu Glu Thr>
      _____IL-1RII_____>

260            270            280            290
         *         *    *         *    *         *    *         *
      CGG ATG TGG GCC CAG GAC GGT GCT CTG TGG CTT CTG CCA GCC
      GCC TAC ACC CGG GTC CTG CCA CGA GAC ACC GAA GAC GGT CGG
      Arg Met Trp Ala Gln Asp Gly Ala Leu Trp Leu Leu Pro Ala>
      _____IL-1RII_____>
```

Figure 44B

```
          300            310            320            330
    *      *      *      *      *      *      *      *      *
   TTG    CAG    GAG    GAC    TCT    GGC    ACC    TAC    GTC    TGC    ACT    ACT    AGA    AAT
   AAC    GTC    CTC    CTG    AGA    CCG    TGG    ATG    CAG    ACG    TGA    TGA    TCT    TTA
   Leu    Gln    Glu    Asp    Ser    Gly    Thr    Tyr    Val    Cys    Thr    Thr    Arg    Asn>
                                         __IL-1RII_____>

340            350            360            370
    *      *      *      *      *      *      *      *
   GCT    TCT    TAC    TGT    GAC    AAA    ATG    TCC    ATT    GAG    CTC    AGA    GTT    TTT
   CGA    AGA    ATG    ACA    CTG    TTT    TAC    AGG    TAA    CTC    GAG    TCT    CAA    AAA
   Ala    Ser    Tyr    Cys    Asp    Lys    Met    Ser    Ile    Glu    Leu    Arg    Val    Phe>
                                         __IL-1RII_____>

380            390            400            410            420
    *      *      *      *      *      *      *      *      *
   GAG    AAT    ACA    GAT    GCT    TTC    CTG    CCG    TTC    ATC    TCA    TAC    CCG    CAA
   CTC    TTA    TGT    CTA    CGA    AAG    GAC    GGC    AAG    TAG    AGT    ATG    GGC    GTT
   Glu    Asn    Thr    Asp    Ala    Phe    Leu    Pro    Phe    Ile    Ser    Tyr    Pro    Gln>
                                         __IL-1RII_____>

430            440            450            460
          *      *      *      *      *      *      *      *
   ATT    TTA    ACC    TTG    TCA    ACC    TCT    GGG    GTA    TTA    GTA    TGC    CCT    GAC
   TAA    AAT    TGG    AAC    AGT    TGG    AGA    CCC    CAT    AAT    CAT    ACG    GGA    CTG
   Ile    Leu    Thr    Leu    Ser    Thr    Ser    Gly    Val    Leu    Val    Cys    Pro    Asp>
                                         __IL-1RII_____>

470            480            490            500
    *      *      *      *      *      *      *      *
   CTG    AGT    GAA    TTC    ACC    CGT    GAC    AAA    ACT    GAC    GTG    AAG    ATT    CAA
   GAC    TCA    CTT    AAG    TGG    GCA    CTG    TTT    TGA    CTG    CAC    TTC    TAA    GTT
   Leu    Ser    Glu    Phe    Thr    Arg    Asp    Lys    Thr    Asp    Val    Lys    Ile    Gln>
                                         __IL-1RII_____>

510            520            530            540
    *      *      *      *      *      *      *      *      *
   TGG    TAC    AAG    GAT    TCT    CTT    CTT    TTG    GAT    AAA    GAC    AAT    GAG    AAA
   ACC    ATG    TTC    CTA    AGA    GAA    GAA    AAC    CTA    TTT    CTG    TTA    CTC    TTT
   Trp    Tyr    Lys    Asp    Ser    Leu    Leu    Leu    Asp    Lys    Asp    Asn    Glu    Lys>
                                         __IL-1RII_____>

550            560            570            580
    *      *      *      *      *      *      *      *      *
   TTT    CTA    AGT    GTG    AGG    GGG    ACC    ACT    CAC    TTA    CTC    GTA    CAC    GAT
   AAA    GAT    TCA    CAC    TCC    CCC    TGG    TGA    GTG    AAT    GAG    CAT    GTG    CTA
   Phe    Leu    Ser    Val    Arg    Gly    Thr    Thr    His    Leu    Leu    Val    His    Asp>
                                         __IL-1RII_____>
```

Figure 44C

```
      590            600            610            620            630
   *         *     *         *     *         *     *         *     *
   GTG GCC CTG GAA GAT GCT GGC TAT TAC CGC TGT GTC CTG ACA
   CAC CGG GAC CTT CTA CGA CCG ATA ATG GCG ACA CAG GAC TGT
   Val Ala Leu Glu Asp Ala Gly Tyr Tyr Arg Cys Val Leu Thr>
                              ___IL-1RII_____>

640            650            660            670
         *     *         *     *         *     *         *     *
   TTT GCC CAT GAA GGC CAG CAA TAC AAC ATC ACT AGG AGT ATT
   AAA CGG GTA CTT CCG GTC GTT ATG TTG TAG TGA TCC TCA TAA
   Phe Ala His Glu Gly Gln Gln Tyr Asn Ile Thr Arg Ser Ile>
                              ___IL-1RII_____>

680            690            700            710
         *     *         *     *         *     *     *     *
   GAG CTA CGC ATC AAG AAA AAA AAA GAA GAG ACC ATT CCT GTG
   CTC GAT GCG TAG TTC TTT TTT TTT CTT CTC TGG TAA GGA CAC
   Glu Leu Arg Ile Lys Lys Lys Lys Glu Glu Thr Ile Pro Val>
                              ___IL-1RII_____>

720            730            740            750
   *     *        *     *     *     *        *     *        *
   ATC ATT TCC CCC CTC AAG ACC ATA TCA GCT TCT CTG GGG TCA
   TAG TAA AGG GGG GAG TTC TGG TAT AGT CGA AGA GAC CCC AGT
   Ile Ile Ser Pro Leu Lys Thr Ile Ser Ala Ser Leu Gly Ser>
                              ___IL-1RII_____>

760            770            780            790
      *        *     *        *     *        *     *        *
   AGA CTG ACA ATC CCA TGT AAG GTG TTT CTG GGA ACC GGC ACA
   TCT GAC TGT TAG GGT ACA TTC CAC AAA GAC CCT TGG CCG TGT
   Arg Leu Thr Ile Pro Cys Lys Val Phe Leu Gly Thr Gly Thr>
                              ___IL-1RII_____>

800            810            820            830            840
      *        *     *        *     *        *     *        *
   CCC TTA ACC ACC ATG CTG TGG TGG ACG GCC AAT GAC ACC CAC
   GGG AAT TGG TGG TAC GAC ACC ACC TGC CGG TTA CTG TGG GTG
   Pro Leu Thr Thr Met Leu Trp Trp Thr Ala Asn Asp Thr His>
                              ___IL-1RII_____>

850            860            870            880
         *        *     *        *     *        *     *
   ATA GAG AGC GCC TAC CCG GGA GGC CGC GTG ACC GAG GGG CCA
   TAT CTC TCG CGG ATG GGC CCT CCG GCG CAC TGG CTC CCC GGT
   Ile Glu Ser Ala Tyr Pro Gly Gly Arg Val Thr Glu Gly Pro>
                              ___IL-1RII_____>

890            900            910            920
         *        *     *        *     *        *     *
   CGC CAG GAA TAT TCA GAA AAT AAT GAG AAC TAC ATT GAA GTG
   GCG GTC CTT ATA AGT CTT TTA TTA CTC TTG ATG TAA CTT CAC
   Arg Gln Glu Tyr Ser Glu Asn Asn Glu Asn Tyr Ile Glu Val>
                              ___IL-1RII_____>
```

Figure 44D

```
          930              940              950              960
     *      *       *      *       *      *       *      *       *
    CCA TTG ATT TTT GAT CCT GTC ACA AGA GAG GAT TTG CAC ATG
    GGT AAC TAA AAA CTA GGA CAG TGT TCT CTC CTA AAC GTG TAC
    Pro Leu Ile Phe Asp Pro Val Thr Arg Glu Asp Leu His Met>
                              IL-1RII                         >

970              980              990             1000
     *      *       *      *       *      *       *      *       *
    GAT TTT AAA TGT GTT GTC CAT AAT ACC CTG AGT TTT CAG ACA
    CTA AAA TTT ACA CAA CAG GTA TTA TGG GAC TCA AAA GTC TGT
    Asp Phe Lys Cys Val Val His Asn Thr Leu Ser Phe Gln Thr>
                              IL-1RII                         >

1010           1020             1030             1040             1050
   *    *       *      *       *      *       *      *       *
    CTA CGC ACC ACA GTC AAG GAA GCC TCC TCC ACG TTC TCA GAA
    GAT GCG TGG TGT CAG TTC CTT CGG AGG AGG TGC AAG AGT CTT
                                                    Ser Glu>
                                                         >

Leu Arg Thr Thr Val Lys Glu Ala Ser Ser Thr Phe>
                        IL-1RII                    >

1060             1070             1080             1090
     *      *       *      *       *      *       *      *
    CGC TGC GAT GAC TGG GGA CTA GAC ACC ATG AGG CAA ATC CAA
    GCG ACG CTA CTG ACC CCT GAT CTG TGG TAC TCC GTT TAG GTT
    Arg Cys Asp Asp Trp Gly Leu Asp Thr Met Arg Gln Ile Gln>
                              IL-1RAcP                        >

1100             1110             1120             1130
     *      *       *      *       *      *       *      *
    GTG TTT GAA GAT GAG CCA GCT CGC ATC AAG TGC CCA CTC TTT
    CAC AAA CTT CTA CTC GGT CGA GCG TAG TTC ACG GGT GAG AAA
    Val Phe Glu Asp Glu Pro Ala Arg Ile Lys Cys Pro Leu Phe>
                              IL-1RAcP                        >

1140             1150             1160             1170
     *      *       *      *       *      *       *      *       *
    GAA CAC TTC TTG AAA TTC AAC TAC AGC ACA GCC CAT TCA GCT
    CTT GTG AAG AAC TTT AAG TTG ATG TCG TGT CGG GTA AGT CGA
    Glu His Phe Leu Lys Phe Asn Tyr Ser Thr Ala His Ser Ala>
                              IL-1RAcP                        >

1180             1190             1200             1210
     *      *       *      *       *      *       *      *       *
    GGC TTA ACT CTG ATC TGG TAT TGG ACT AGG CAG GAC CGG GAC
    CCG AAT TGA GAC TAG ACC ATA ACC TGA TCC GTC CTG GCC CTG
    Gly Leu Thr Leu Ile Trp Tyr Trp Thr Arg Gln Asp Arg Asp>
                              IL-1RAcP                        >
```

Figure 44E

```
      1220          1230          1240          1250          1260
         *     *     *     *     *     *     *     *     *
       CTT GAG GAG CCA ATT AAC TTC CGC CTC CCC GAG AAC CGC ATT
       GAA CTC CTC GGT TAA TTG AAG GCG GAG GGG CTC TTG GCG TAA
       Leu Glu Glu Pro Ile Asn Phe Arg Leu Pro Glu Asn Arg Ile>
                                  _IL-1RAcP_____>

1270          1280          1290          1300
         *     *     *     *     *     *     *     *
       AGT AAG GAG AAA GAT GTG CTG TGG TTC CGG CCC ACT CTC CTC
       TCA TTC CTC TTT CTA CAC GAC ACC AAG GCC GGG TGA GAG GAG
       Ser Lys Glu Lys Asp Val Leu Trp Phe Arg Pro Thr Leu Leu>
       _____IL-1RAcP_____>

1310          1320          1330          1340
         *     *     *     *     *     *     *     *
       AAT GAC ACT GGC AAC TAT ACC TGC ATG TTA AGG AAC ACT ACA
       TTA CTG TGA CCG TTG ATA TGG ACG TAC AAT TCC TTG TGA TGT
       Asn Asp Thr Gly Asn Tyr Thr Cys Met Leu Arg Asn Thr Thr>
       _____IL-1RAcP_____>

1350          1360          1370          1380
         *     *     *     *     *     *     *     *     *
       TAT TGC AGC AAA GTT GCA TTT CCC TTG GAA GTT GTT CAA AAA
       ATA ACG TCG TTT CAA CGT AAA GGG AAC CTT CAA CAA GTT TTT
       Tyr Cys Ser Lys Val Ala Phe Pro Leu Glu Val Val Gln Lys>
                                  _IL-1RAcP_____>

1390          1400          1410          1420
         *     *     *     *     *     *     *     *
       GAC AGC TGT TTC AAT TCC CCC ATG AAA CTC CCA GTG CAT AAA
       CTG TCG ACA AAG TTA AGG GGG TAC TTT GAG GGT CAC GTA TTT
       Asp Ser Cys Phe Asn Ser Pro Met Lys Leu Pro Val His Lys>
                                  _IL-1RAcP_____>

1430          1440          1450          1460          1470
         *     *     *     *     *     *     *     *     *
       CTG TAT ATA GAA TAT GGC ATT CAG AGG ATC ACT TGT CCA AAT
       GAC ATA TAT CTT ATA CCG TAA GTC TCC TAG TGA ACA GGT TTA
       Leu Tyr Ile Glu Tyr Gly Ile Gln Arg Ile Thr Cys Pro Asn>
                                  _IL-1RAcP_____>

1480          1490          1500          1510
         *     *     *     *     *     *     *     *
       GTA GAT GGA TAT TTT CCT TCC AGT GTC AAA CCG ACT ATC ACT
       CAT CTA CCT ATA AAA GGA AGG TCA CAG TTT GGC TGA TAG TGA
       Val Asp Gly Tyr Phe Pro Ser Ser Val Lys Pro Thr Ile Thr>
                                  _IL-1RAcP_____>

1520          1530          1540          1550
         *     *     *     *     *     *     *     *
       TGG TAT ATG GGC TGT TAT AAA ATA CAG AAT TTT AAT AAT GTA
       ACC ATA TAC CCG ACA ATA TTT TAT GTC TTA AAA TTA TTA CAT
       Trp Tyr Met Gly Cys Tyr Lys Ile Gln Asn Phe Asn Asn Val>
                                  _IL-1RAcP_____>
```

Figure 44F

```
          1560                1570                1580                1590
      *         *         *         *         *         *         *         *         *
    ATA CCC GAA GGT ATG AAC TTG AGT TTC CTC ATT GCC TTA ATT
    TAT GGG CTT CCA TAC TTG AAC TCA AAG GAG TAA CGG AAT TAA
    Ile Pro Glu Gly Met Asn Leu Ser Phe Leu Ile Ala Leu Ile>
                                   IL-1RAcP                        >

1600                1610                1620                1630
      *         *         *         *         *         *         *         *
    TCA AAT AAT GGA AAT TAC ACA TGT GTT GTT ACA TAT CCA GAA
    AGT TTA TTA CCT TTA ATG TGT ACA CAA CAA TGT ATA GGT CTT
    Ser Asn Asn Gly Asn Tyr Thr Cys Val Val Thr Tyr Pro Glu>
                                   IL-1RAcP                        >

1640                1650                1660                1670                1680
    *         *         *         *         *         *         *         *         *
  AAT GGA CGT ACG TTT CAT CTC ACC AGG ACT CTG ACT GTA AAG
  TTA CCT GCA TGC AAA GTA GAG TGG TCC TGA GAC TGA CAT TTC
  Asn Gly Arg Thr Phe His Leu Thr Arg Thr Leu Thr Val Lys>
                                 IL-1RAcP                        >

1690                1700                1710                1720
          *         *         *         *         *         *         *         *
       GTA GTA GGC TCT CCA AAA AAT GCA GTG CCC CCT GTG ATC CAT
       CAT CAT CCG AGA GGT TTT TTA CGT CAC GGG GGA CAC TAG GTA
       Val Val Gly Ser Pro Lys Asn Ala Val Pro Pro Val Ile His>
                                      IL-1RAcP                        >

1730                1740                1750                1760
          *         *         *         *         *         *         *         *
       TCA CCT AAT GAT CAT GTG GTC TAT GAG AAA GAA CCA GGA GAG
       AGT GGA TTA CTA GTA CAC CAG ATA CTC TTT CTT GGT CCT CTC
       Ser Pro Asn Asp His Val Val Tyr Glu Lys Glu Pro Gly Glu>
                                      IL-1RAcP                        >

1770                1780                1790                1800
          *         *         *         *         *         *         *         *         *
       GAG CTA CTC ATT CCC TGT ACG GTC TAT TTT AGT TTT CTG ATG
       CTC GAT GAG TAA GGG ACA TGC CAG ATA AAA TCA AAA GAC TAC
       Glu Leu Leu Ile Pro Cys Thr Val Tyr Phe Ser Phe Leu Met>
                                      IL-1RAcP                        >

1810                1820                1830                1840
          *         *         *         *         *         *         *         *
       GAT TCT CGC AAT GAG GTT TGG TGG ACC ATT GAT GGA AAA AAA
       CTA AGA GCG TTA CTC CAA ACC ACC TGG TAA CTA CCT TTT TTT
       Asp Ser Arg Asn Glu Val Trp Trp Thr Ile Asp Gly Lys Lys>
                                      IL-1RAcP                        >

1850                1860                1870                1880                1890
    *         *         *         *         *         *         *         *         *
  CCT GAT GAC ATC ACT ATT GAT GTC ACC ATT AAC GAA AGT ATA
  GGA CTA CTG TAG TGA TAA CTA CAG TGG TAA TTG CTT TCA TAT
  Pro Asp Asp Ile Thr Ile Asp Val Thr Ile Asn Glu Ser Ile>
                                 IL-1RAcP                        >
```

Figure 44G

```
              1900            1910            1920            1930
          *       *       *       *       *       *       *       *
       AGT CAT AGT AGA ACA GAA GAT GAA ACA AGA ACT CAG ATT TTG
       TCA GTA TCA TCT TGT CTT CTA CTT TGT TCT TGA GTC TAA AAC
       Ser His Ser Arg Thr Glu Asp Glu Thr Arg Thr Gln Ile Leu>
       _____IL-1RAcP_____>

1940            1950            1960            1970
          *       *       *       *       *       *       *       *
       AGC ATC AAG AAA GTT ACC TCT GAG GAT CTC AAG CGC AGC TAT
       TCG TAG TTC TTT CAA TGG AGA CTC CTA GAG TTC GCG TCG ATA
       Ser Ile Lys Lys Val Thr Ser Glu Asp Leu Lys Arg Ser Tyr>
       _____IL-1RAcP_____>

1980            1990            2000            2010
         *       *       *       *       *       *       *       *
       GTC TGT CAT GCT AGA AGT GCC AAA GGC GAA GTT GCC AAA GCA
       CAG ACA GTA CGA TCT TCA CGG TTT CCG CTT CAA CGG TTT CGT
       Val Cys His Ala Arg Ser Ala Lys Gly Glu Val Ala Lys Ala>
       _____IL-1RAcP_____>

2020            2030            2040            2050
         *       *       *       *       *       *       *       *
       GCC AAG GTG AAG CAG AAA GTG CCA GCT CCA AGA TAC ACA GTG
       CGG TTC CAC TTC GTC TTT CAC GGT CGA GGT TCT ATG TGT CAC
       Ala Lys Val Lys Gln Lys Val Pro Ala Pro Arg Tyr Thr Val>
       _____IL-1RAcP_____>

2060            2070            2080            2090            2100
       *       *       *       *       *       *       *       *       *
     TCC GGA GAC AAA ACT CAC ACA TGC CCA CCG TGC CCA GCA CCT
     AGG CCT CTG TTT TGA GTG TGT ACG GGT GGC ACG GGT CGT GGA
     Ser Gly Asp Lys Thr His Thr Cys Pro Pro Cys Pro Ala Pro>
     _____FC-IgG1_____>

2110            2120            2130            2140
            *       *       *       *       *       *       *       *
         GAA CTC CTG GGG GGA CCG TCA GTC TTC CTC TTC CCC CCA AAA
         CTT GAG GAC CCC CCT GGC AGT CAG AAG GAG AAG GGG GGT TTT
         Glu Leu Leu Gly Gly Pro Ser Val Phe Leu Phe Pro Pro Lys>
         _____FC-IgG1_____>

2150            2160            2170            2180
           *       *       *       *       *       *       *       *
        CCC AAG GAC ACC CTC ATG ATC TCC CGG ACC CCT GAG GTC ACA
        GGG TTC CTG TGG GAG TAC TAG AGG GCC TGG GGA CTC CAG TGT
        Pro Lys Asp Thr Leu Met Ile Ser Arg Thr Pro Glu Val Thr>
        _____FC-IgG1_____>

2190            2200            2210            2220
          *       *       *       *       *       *       *       *
       TGC GTG GTG GTG GAC GTG AGC CAC GAA GAC CCT GAG GTC AAG
       ACG CAC CAC CAC CTG CAC TCG GTG CTT CTG GGA CTC CAG TTC
       Cys Val Val Val Asp Val Ser His Glu Asp Pro Glu Val Lys>
       _____FC-IgG1_____>
```

Figure 44H

```
        2230            2240            2250           2260
         *       *       *       *       *       *       *       *
        TTC     AAC     TGG     TAC     GTG     GAC     GGC     GTG     GAG     GTG     CAT     AAT     GCC     AAG
        AAG     TTG     ACC     ATG     CAC     CTG     CCG     CAC     CTC     CAC     GTA     TTA     CGG     TTC
        Phe     Asn     Trp     Tyr     Val     Asp     Gly     Val     Glu     Val     His     Asn     Ala     Lys>
                                                ___FC-IgG1_____>

2270            2280            2290            2300            2310
   *       *       *       *       *       *       *       *       *
  ACA     AAG     CCG     CGG     GAG     GAG     CAG     TAC     AAC     AGC     ACG     TAC     CGT     GTG
  TGT     TTC     GGC     GCC     CTC     CTC     GTC     ATG     TTG     TCG     TGC     ATG     GCA     CAC
  Thr     Lys     Pro     Arg     Glu     Glu     Gln     Tyr     Asn     Ser     Thr     Tyr     Arg     Val>
                                          ___FC-IgG1_____>

2320            2330            2340            2350
           *       *       *       *       *       *       *       *
          GTC     AGC     GTC     CTC     ACC     GTC     CTG     CAC     CAG     GAC     TGG     CTG     AAT     GGC
          CAG     TCG     CAG     GAG     TGG     CAG     GAC     GTG     GTC     CTG     ACC     GAC     TTA     CCG
          Val     Ser     Val     Leu     Thr     Val     Leu     His     Gln     Asp     Trp     Leu     Asn     Gly>
                                                  ___FC-IgG1_____>

2360            2370            2380            2390
           *       *       *       *       *       *       *       *
          AAG     GAG     TAC     AAG     TGC     AAG     GTC     TCC     AAC     AAA     GCC     CTC     CCA     GCC
          TTC     CTC     ATG     TTC     ACG     TTC     CAG     AGG     TTG     TTT     CGG     GAG     GGT     CGG
          Lys     Glu     Tyr     Lys     Cys     Lys     Val     Ser     Asn     Lys     Ala     Leu     Pro     Ala>
                                                  ___FC-IgG1_____>

2400            2410            2420            2430
   *       *       *       *       *       *       *       *       *
  CCC     ATC     GAG     AAA     ACC     ATC     TCC     AAA     GCC     AAA     GGG     CAG     CCC     CGA
  GGG     TAG     CTC     TTT     TGG     TAG     AGG     TTT     CGG     TTT     CCC     GTC     GGG     GCT
  Pro     Ile     Glu     Lys     Thr     Ile     Ser     Lys     Ala     Lys     Gly     Gln     Pro     Arg>
                                          ___FC-IgG1_____>

2440            2450            2460            2470
     *       *       *       *       *       *       *       *
    GAA     CCA     CAG     GTG     TAC     ACC     CTG     CCC     CCA     TCC     CGG     GAT     GAG     CTG
    CTT     GGT     GTC     CAC     ATG     TGG     GAC     GGG     GGT     AGG     GCC     CTA     CTC     GAC
    Glu     Pro     Gln     Val     Tyr     Thr     Leu     Pro     Pro     Ser     Arg     Asp     Glu     Leu>
                                            ___FC-IgG1_____>

2480            2490            2500            2510            2520
 *       *       *       *       *       *       *       *       *
ACC     AAG     AAC     CAG     GTC     AGC     CTG     ACC     TGC     CTG     GTC     AAA     GGC     TTC
TGG     TTC     TTG     GTC     CAG     TCG     GAC     TGG     ACG     GAC     CAG     TTT     CCG     AAG
Thr     Lys     Asn     Gln     Val     Ser     Leu     Thr     Cys     Leu     Val     Lys     Gly     Phe>
                                        ___FC-IgG1_____>

2530            2540            2550            2560
         *       *       *       *       *       *       *       *
        TAT     CCC     AGC     GAC     ATC     GCC     GTG     GAG     TGG     GAG     AGC     AAT     GGG     CAG
        ATA     GGG     TCG     CTG     TAG     CGG     CAC     CTC     ACC     CTC     TCG     TTA     CCC     GTC
        Tyr     Pro     Ser     Asp     Ile     Ala     Val     Glu     Trp     Glu     Ser     Asn     Gly     Gln>
                                                ___FC-IgG1_____>
```

Figure 44I

```
          2570            2580            2590            2600
       *       *       *       *       *       *       *       *
      CCG GAG AAC AAC TAC AAG ACC ACG CCT CCC GTG CTG GAC TCC
      GGC CTC TTG TTG ATG TTC TGG TGC GGA GGG CAC GAC CTG AGG
      Pro Glu Asn Asn Tyr Lys Thr Thr Pro Pro Val Leu Asp Ser>
      _____FC-IgG1_____>

2610            2620            2630            2640
       *       *       *       *       *       *       *       *
      GAC GGC TCC TTC TTC CTC TAT AGC AAG CTC ACC GTG GAC AAG
      CTG CCG AGG AAG AAG GAG ATA TCG TTC GAG TGG CAC CTG TTC
      Asp Gly Ser Phe Phe Leu Tyr Ser Lys Leu Thr Val Asp Lys>
      _____FC-IgG1_____>

2650            2660            2670            2680
       *       *       *       *       *       *       *       *
      AGC AGG TGG CAG CAG GGG AAC GTC TTC TCA TGC TCC GTG ATG
      TCG TCC ACC GTC GTC CCC TTG CAG AAG AGT ACG AGG CAC TAC
      Ser Arg Trp Gln Gln Gly Asn Val Phe Ser Cys Ser Val Met>
      _____FC-IgG1_____>

2690            2700            2710            2720            2730
    *       *       *       *       *       *       *       *       *
   CAT GAG GCT CTG CAC AAC CAC TAC ACG CAG AAG AGC CTC TCC
   GTA CTC CGA GAC GTG TTG GTG ATG TGC GTC TTC TCG GAG AGG
   His Glu Ala Leu His Asn His Tyr Thr Gln Lys Ser Leu Ser>
   _____FC-IgG1_____>

2740
       *       *       *
      CTG TCT CCG GGT AAA TGA
      GAC AGA GGC CCA TTT ACT
      Leu Ser Pro Gly Lys ***>
      _____FC-IgG1_____>
```

Figure 45A

```
              10             20             30             40
         *    *         *    *         *    *         *    *
ATG GTG CGC TTG TAC GTG TTG GTA ATG GGA GTT TCT GCC TTC
TAC CAC GCG AAC ATG CAC AAC CAT TAC CCT CAA AGA CGG AAG
Met Val Arg Leu Tyr Val Leu Val Met Gly Val Ser Ala Phe>
_____SIGNAL PEPTIDE_____>
_____IL-1RII_____>

50             60             70             80
         *    *         *    *         *    *    *    *
ACC CTT CAG CCT GCG GCA CAC ACA GGG GCT GCC AGA AGC TGC
TGG GAA GTC GGA CGC CGT GTG TGT CCC CGA CGG TCT TCG ACG
Thr Leu Gln Pro Ala Ala>
_____SIGNAL PEPTIDE____>
                        His Thr Gly Ala Ala Arg Ser Cys>
_____IL-1RII_____>

90            100            110            120
         *    *         *    *         *    *         *    *
CGG TTT CGT GGG AGG CAT TAC AAG CGG GAG TTC AGG CTG GAA
GCC AAA GCA CCC TCC GTA ATG TTC GCC CTC AAG TCC GAC CTT
Arg Phe Arg Gly Arg His Tyr Lys Arg Glu Phe Arg Leu Glu>
_____IL-1RII_____>

130            140            150            160
    *    *         *    *    *    *         *    *    *
GGG GAG CCT GTA GCC CTG AGG TGC CCC CAG GTG CCC TAC TGG
CCC CTC GGA CAT CGG GAC TCC ACG GGG GTC CAC GGG ATG ACC
Gly Glu Pro Val Ala Leu Arg Cys Pro Gln Val Pro Tyr Trp>
_____IL-1RII_____>

170            180            190            200            210
*    *    *    *    *    *         *         *    *    *    *
TTG TGG GCC TCT GTC AGC CCC CGC ATC AAC CTG ACA TGG CAT
AAC ACC CGG AGA CAG TCG GGG GCG TAG TTG GAC TGT ACC GTA
Leu Trp Ala Ser Val Ser Pro Arg Ile Asn Leu Thr Trp His>
_____IL-1RII_____>

220            230            240            250
         *    *         *    *         *    *         *    *
AAA AAT GAC TCT GCT AGG ACG GTC CCA GGA GAA GAA GAG ACA
TTT TTA CTG AGA CGA TCC TGC CAG GGT CCT CTT CTT CTC TGT
Lys Asn Asp Ser Ala Arg Thr Val Pro Gly Glu Glu Glu Thr>
_____IL-1RII_____>

260            270            280            290
         *    *         *    *         *    *    *    *
CGG ATG TGG GCC CAG GAC GGT GCT CTG TGG CTT CTG CCA GCC
GCC TAC ACC CGG GTC CTG CCA CGA GAC ACC GAA GAC GGT CGG
Arg Met Trp Ala Gln Asp Gly Ala Leu Trp Leu Leu Pro Ala>
_____IL-1RII_____>
```

Figure 45B

```
           300           310           320           330
            *             *             *             *         *         *         *         *
      TTG CAG GAG GAC TCT GGC ACC TAC GTC TGC ACT ACT AGA AAT
      AAC GTC CTC CTG AGA CCG TGG ATG CAG ACG TGA TGA TCT TTA
      Leu Gln Glu Asp Ser Gly Thr Tyr Val Cys Thr Thr Arg Asn>
      _____IL-1RII_____>

340           350           360           370
                 *             *             *             *         *         *         *         *
      GCT TCT TAC TGT GAC AAA ATG TCC ATT GAG CTC AGA GTT TTT
      CGA AGA ATG ACA CTG TTT TAC AGG TAA CTC GAG TCT CAA AAA
      Ala Ser Tyr Cys Asp Lys Met Ser Ile Glu Leu Arg Val Phe>
      _____IL-1RII_____>

380           390           400           410           420
     *         *         *         *         *         *         *         *         *
      GAG AAT ACA GAT GCT TTC CTG CCG TTC ATC TCA TAC CCG CAA
      CTC TTA TGT CTA CGA AAG GAC GGC AAG TAG AGT ATG GGC GTT
      Glu Asn Thr Asp Ala Phe Leu Pro Phe Ile Ser Tyr Pro Gln>
      _____IL-1RII_____>

430           440           450           460
                      *             *             *             *         *         *         *         *
      ATT TTA ACC TTG TCA ACC TCT GGG GTA TTA GTA TGC CCT GAC
      TAA AAT TGG AAC AGT TGG AGA CCC CAT AAT CAT ACG GGA CTG
      Ile Leu Thr Leu Ser Thr Ser Gly Val Leu Val Cys Pro Asp>
      _____IL-1RII_____>

470           480           490           500
                      *             *             *             *         *         *         *         *
      CTG AGT GAA TTC ACC CGT GAC AAA ACT GAC GTG AAG ATT CAA
      GAC TCA CTT AAG TGG GCA CTG TTT TGA CTG CAC TTC TAA GTT
      Leu Ser Glu Phe Thr Arg Asp Lys Thr Asp Val Lys Ile Gln>
      _____IL-1RII_____>

510           520           530           540
            *             *             *             *         *         *         *         *         *
      TGG TAC AAG GAT TCT CTT CTT TTG GAT AAA GAC AAT GAG AAA
      ACC ATG TTC CTA AGA GAA GAA AAC CTA TTT CTG TTA CTC TTT
      Trp Tyr Lys Asp Ser Leu Leu Leu Asp Lys Asp Asn Glu Lys>
      _____IL-1RII_____>

550           560           570           580
            *             *             *             *         *         *         *         *
      TTT CTA AGT GTG AGG GGG ACC ACT CAC TTA CTC GTA CAC GAT
      AAA GAT TCA CAC TCC CCC TGG TGA GTG AAT GAG CAT GTG CTA
      Phe Leu Ser Val Arg Gly Thr Thr His Leu Leu Val His Asp>
      _____IL-1RII_____>

590           600           610           620           630
     *         *         *         *         *         *         *         *         *
      GTG GCC CTG GAA GAT GCT GGC TAT TAC CGC TGT GTC CTG ACA
      CAC CGG GAC CTT CTA CGA CCG ATA ATG GCG ACA CAG GAC TGT
      Val Ala Leu Glu Asp Ala Gly Tyr Tyr Arg Cys Val Leu Thr>
      _____IL-1RII_____>
```

Figure 45C

```
             640         650         660         670
              *     *     *     *     *     *     *     *
         TTT GCC CAT GAA GGC CAG CAA TAC AAC ATC ACT AGG AGT ATT
         AAA CGG GTA CTT CCG GTC GTT ATG TTG TAG TGA TCC TCA TAA
         Phe Ala His Glu Gly Gln Gln Tyr Asn Ile Thr Arg Ser Ile>
         _____IL-1RII_____>

680         690         700         710
              *     *     *     *     *     *     *     *
         GAG CTA CGC ATC AAG AAA AAA AAA GAA GAG ACC ATT CCT GTG
         CTC GAT GCG TAG TTC TTT TTT TTT CTT CTC TGG TAA GGA CAC
         Glu Leu Arg Ile Lys Lys Lys Lys Glu Glu Thr Ile Pro Val>
         _____IL-1RII_____>

720         730         740         750
              *     *     *     *     *     *     *     *     *
         ATC ATT TCC CCC CTC AAG ACC ATA TCA GCT TCT CTG GGG TCA
         TAG TAA AGG GGG GAG TTC TGG TAT AGT CGA AGA GAC CCC AGT
         Ile Ile Ser Pro Leu Lys Thr Ile Ser Ala Ser Leu Gly Ser>
         _____IL-1RII_____>

760         770         780         790
              *     *     *     *     *     *     *     *
         AGA CTG ACA ATC CCA TGT AAG GTG TTT CTG GGA ACC GGC ACA
         TCT GAC TGT TAG GGT ACA TTC CAC AAA GAC CCT TGG CCG TGT
         Arg Leu Thr Ile Pro Cys Lys Val Phe Leu Gly Thr Gly Thr>
         _____IL-1RII_____>

800         810         820         830         840
          *     *     *     *     *     *     *     *     *
         CCC TTA ACC ACC ATG CTG TGG TGG ACG GCC AAT GAC ACC CAC
         GGG AAT TGG TGG TAC GAC ACC ACC TGC CGG TTA CTG TGG GTG
         Pro Leu Thr Thr Met Leu Trp Trp Thr Ala Asn Asp Thr His>
         _____IL-1RII_____>

850         860         870         880
              *     *     *     *     *     *     *     *
         ATA GAG AGC GCC TAC CCG GGA GGC CGC GTG ACC GAG GGG CCA
         TAT CTC TCG CGG ATG GGC CCT CCG GCG CAC TGG CTC CCC GGT
         Ile Glu Ser Ala Tyr Pro Gly Gly Arg Val Thr Glu Gly Pro>
         _____IL-1RII_____>

890         900         910         920
              *     *     *     *     *     *     *     *
         CGC CAG GAA TAT TCA GAA AAT AAT GAG AAC TAC ATT GAA GTG
         GCG GTC CTT ATA AGT CTT TTA TTA CTC TTG ATG TAA CTT CAC
         Arg Gln Glu Tyr Ser Glu Asn Asn Glu Asn Tyr Ile Glu Val>
         _____IL-1RII_____>

930         940         950         960
              *     *     *     *     *     *     *     *     *
         CCA TTG ATT TTT GAT CCT GTC ACA AGA GAG GAT TTG CAC ATG
         GGT AAC TAA AAA CTA GGA CAG TGT TCT CTC CTA AAC GTG TAC
         Pro Leu Ile Phe Asp Pro Val Thr Arg Glu Asp Leu His Met>
         _____IL-1RII_____>
```

Figure 45D

```
         970         980         990        1000
          *     *     *     *     *     *     *     *
         GAT   TTT   AAA   TGT   GTT   GTC   CAT   AAT   ACC   CTG   AGT   TTT   CAG   ACA
         CTA   AAA   TTT   ACA   CAA   CAG   GTA   TTA   TGG   GAC   TCA   AAA   GTC   TGT
         Asp   Phe   Lys   Cys   Val   Val   His   Asn   Thr   Leu   Ser   Phe   Gln   Thr>
                                       _____IL-1RII_____>

1010         1020         1030         1040         1050
    *     *     *     *     *     *     *     *     *     *
   CTA   CGC   ACC   ACA   GTC   AAG   GAA   GCC   TCC   TCC   ACG   TTC   TCA   GAA
   GAT   GCG   TGG   TGT   CAG   TTC   CTT   CGG   AGG   AGG   TGC   AAG   AGT   CTT
                                                                       Ser   Glu>
                                                                       _____>
   Leu   Arg   Thr   Thr   Val   Lys   Glu   Ala   Ser   Ser   Thr   Phe>
         _____IL-1RII_____>

1060         1070         1080         1090
          *     *     *     *     *     *     *     *
         CGC   TGC   GAT   GAC   TGG   GGA   CTA   GAC   ACC   ATG   AGG   CAA   ATC   CAA
         GCG   ACG   CTA   CTG   ACC   CCT   GAT   CTG   TGG   TAC   TCC   GTT   TAG   GTT
         Arg   Cys   Asp   Asp   Trp   Gly   Leu   Asp   Thr   Met   Arg   Gln   Ile   Gln>
                                       _____IL-1RAcP_____>

1100         1110         1120         1130
          *     *     *     *     *     *     *     *
         GTG   TTT   GAA   GAT   GAG   CCA   GCT   CGC   ATC   AAG   TGC   CCA   CTC   TTT
         CAC   AAA   CTT   CTA   CTC   GGT   CGA   GCG   TAG   TTC   ACG   GGT   GAG   AAA
         Val   Phe   Glu   Asp   Glu   Pro   Ala   Arg   Ile   Lys   Cys   Pro   Leu   Phe>
                                       _____IL-1RAcP_____>

1140         1150         1160         1170
          *     *     *     *     *     *     *     *     *
         GAA   CAC   TTC   TTG   AAA   TTC   AAC   TAC   AGC   ACA   GCC   CAT   TCA   GCT
         CTT   GTG   AAG   AAC   TTT   AAG   TTG   ATG   TCG   TGT   CGG   GTA   AGT   CGA
         Glu   His   Phe   Leu   Lys   Phe   Asn   Tyr   Ser   Thr   Ala   His   Ser   Ala>
                                       _____IL-1RAcP_____>

1180         1190         1200         1210
          *     *     *     *     *     *     *     *
         GGC   CTT   ACT   CTG   ATC   TGG   TAT   TGG   ACT   AGG   CAG   GAC   CGG   GAC
         CCG   GAA   TGA   GAC   TAG   ACC   ATA   ACC   TGA   TCC   GTC   CTG   GCC   CTG
         Gly   Leu   Thr   Leu   Ile   Trp   Tyr   Trp   Thr   Arg   Gln   Asp   Arg   Asp>
                                       _____IL-1RAcP_____>

1220         1230         1240         1250         1260
    *     *     *     *     *     *     *     *     *     *
   CTT   GAG   GAG   CCA   ATT   AAC   TTC   CGC   CTC   CCC   GAG   AAC   CGC   ATT
   GAA   CTC   CTC   GGT   TAA   TTG   AAG   GCG   GAG   GGG   CTC   TTG   GCG   TAA
   Leu   Glu   Glu   Pro   Ile   Asn   Phe   Arg   Leu   Pro   Glu   Asn   Arg   Ile>
         _____IL-1RAcP_____>
```

Figure 45E

```
            1270            1280            1290            1300
             *       *       *       *       *       *       *       *
      AGT AAG GAG AAA GAT GTG CTG TGG TTC CGG CCC ACT CTC CTC
      TCA TTC CTC TTT CTA CAC GAC ACC AAG GCC GGG TGA GAG GAG
      Ser Lys Glu Lys Asp Val Leu Trp Phe Arg Pro Thr Leu Leu>
      _____IL-1RAcP_____>

1310            1320            1330            1340
             *       *       *       *       *       *       *       *
      AAT GAC ACT GGC AAC TAT ACC TGC ATG TTA AGG AAC ACT ACA
      TTA CTG TGA CCG TTG ATA TGG ACG TAC AAT TCC TTG TGA TGT
      Asn Asp Thr Gly Asn Tyr Thr Cys Met Leu Arg Asn Thr Thr>
      _____IL-1RAcP_____>

1350            1360            1370            1380
         *       *       *       *       *       *       *       *       *
      TAT TGC AGC AAA GTT GCA TTT CCC TTG GAA GTT GTT CAA AAA
      ATA ACG TCG TTT CAA CGT AAA GGG AAC CTT CAA CAA GTT TTT
      Tyr Cys Ser Lys Val Ala Phe Pro Leu Glu Val Val Gln Lys>
      _____IL-1RAcP_____>

1390            1400            1410            1420
          *       *       *       *       *       *       *       *
      GAC AGC TGT TTC AAT TCC CCC ATG AAA CTC CCA GTG CAT AAA
      CTG TCG ACA AAG TTA AGG GGG TAC TTT GAG GGT CAC GTA TTT
      Asp Ser Cys Phe Asn Ser Pro Met Lys Leu Pro Val His Lys>
      _____IL-1RAcP_____>

1430            1440            1450            1460            1470
    *       *       *       *       *       *       *       *       *
      CTG TAT ATA GAA TAT GGC ATT CAG AGG ATC ACT TGT CCA AAT
      GAC ATA TAT CTT ATA CCG TAA GTC TCC TAG TGA ACA GGT TTA
      Leu Tyr Ile Glu Tyr Gly Ile Gln Arg Ile Thr Cys Pro Asn>
      _____IL-1RAcP_____>

1480            1490            1500            1510
             *       *       *       *       *       *       *       *
      GTA GAT GGA TAT TTT CCT TCC AGT GTC AAA CCG ACT ATC ACT
      CAT CTA CCT ATA AAA GGA AGG TCA CAG TTT GGC TGA TAG TGA
      Val Asp Gly Tyr Phe Pro Ser Ser Val Lys Pro Thr Ile Thr>
      _____IL-1RAcP_____>

1520            1530            1540            1550
             *       *       *       *       *       *      *       *
      TGG TAT ATG GGC TGT TAT AAA ATA CAG AAT TTT AAT AAT GTA
      ACC ATA TAC CCG ACA ATA TTT TAT GTC TTA AAA TTA TTA CAT
      Trp Tyr Met Gly Cys Tyr Lys Ile Gln Asn Phe Asn Asn Val>
      _____IL-1RAcP_____>

1560            1570            1580            1590
             *       *       *       *       *       *       *       *       *
      ATA CCC GAA GGT ATG AAC TTG AGT TTC CTC ATT GCC TTA ATT
      TAT GGG CTT CCA TAC TTG AAC TCA AAG GAG TAA CGG AAT TAA
      Ile Pro Glu Gly Met Asn Leu Ser Phe Leu Ile Ala Leu Ile>
      _____IL-1RAcP_____>
```

Figure 45F

```
        1600           1610           1620           1630
          *       *      *       *      *       *      *       *
        TCA AAT AAT GGA AAT TAC ACA TGT GTT GTT ACA TAT CCA GAA
        AGT TTA TTA CCT TTA ATG TGT ACA CAA CAA TGT ATA GGT CTT
        Ser Asn Asn Gly Asn Tyr Thr Cys Val Val Thr Tyr Pro Glu>
        _____IL-1RAcP_____>

1640           1650           1660           1670           1680
     *       *      *       *      *       *      *       *       *
   AAT GGA CGT ACG TTT CAT CTC ACC AGG ACT CTG ACT GTA AAG
   TTA CCT GCA TGC AAA GTA GAG TGG TCC TGA GAC TGA CAT TTC
   Asn Gly Arg Thr Phe His Leu Thr Arg Thr Leu Thr Val Lys>
   _____IL-1RAcP_____>

1690           1700           1710           1720
               *       *      *       *      *       *      *
             GTA GTA GGC TCT CCA AAA AAT GCA GTG CCC CCT GTG ATC CAT
             CAT CAT CCG AGA GGT TTT TTA CGT CAC GGG GGA CAC TAG GTA
             Val Val Gly Ser Pro Lys Asn Ala Val Pro Pro Val Ile His>
             _____IL-1RAcP_____>

1730           1740           1750           1760
               *       *      *       *      *       *      *
             TCA CCT AAT GAT CAT GTG GTC TAT GAG AAA GAA CCA GGA GAG
             AGT GGA TTA CTA GTA CAC CAG ATA CTC TTT CTT GGT CCT CTC
             Ser Pro Asn Asp His Val Val Tyr Glu Lys Glu Pro Gly Glu>
             _____IL-1RAcP_____>

1770           1780           1790           1800
          *       *      *       *      *       *      *       *
        GAG CTA CTC ATT CCC TGT ACG GTC TAT TTT AGT TTT CTG ATG
        CTC GAT GAG TAA GGG ACA TGC CAG ATA AAA TCA AAA GAC TAC
        Glu Leu Leu Ile Pro Cys Thr Val Tyr Phe Ser Phe Leu Met>
        _____IL-1RAcP_____>

1810           1820           1830           1840
     *       *      *       *      *       *      *
   GAT TCT CGC AAT GAG GTT TGG TGG ACC ATT GAT GGA AAA AAA
   CTA AGA GCG TTA CTC CAA ACC ACC TGG TAA CTA CCT TTT TTT
   Asp Ser Arg Asn Glu Val Trp Trp Thr Ile Asp Gly Lys Lys>
   _____IL-1RAcP_____>

1850           1860           1870           1880           1890
  *       *      *       *      *       *      *       *       *
CCT GAT GAC ATC ACT ATT GAT GTC ACC ATT AAC GAA AGT ATA
GGA CTA CTG TAG TGA TAA CTA CAG TGG TAA TTG CTT TCA TAT
Pro Asp Asp Ile Thr Ile Asp Val Thr Ile Asn Glu Ser Ile>
_____IL-1RAcP_____>

1900           1910           1920           1930
          *       *      *       *      *       *      *
        AGT CAT AGT AGA ACA GAA GAT GAA ACA AGA ACT CAG ATT TTG
        TCA GTA TCA TCT TGT CTT CTA CTT TGT TCT TGA GTC TAA AAC
        Ser His Ser Arg Thr Glu Asp Glu Thr Arg Thr Gln Ile Leu>
        _____IL-1RAcP_____>
```

Figure 45G

```
         1940          1950           1960           1970
          *    *    *    *    *    *    *    *
         AGC  ATC  AAG  AAA  GTT  ACC  TCT  GAG  GAT  CTC  AAG  CGC  AGC  TAT
         TCG  TAG  TTC  TTT  CAA  TGG  AGA  CTC  CTA  GAG  TTC  GCG  TCG  ATA
         Ser  Ile  Lys  Lys  Val  Thr  Ser  Glu  Asp  Leu  Lys  Arg  Ser  Tyr>
         _____IL-1RAcP_____>

1980          1990           2000           2010
          *    *    *    *    *    *    *    *    *
         GTC  TGT  CAT  GCT  AGA  AGT  GCC  AAA  GGC  GAA  GTT  GCC  AAA  GCA
         CAG  ACA  GTA  CGA  TCT  TCA  CGG  TTT  CCG  CTT  CAA  CGG  TTT  CGT
         Val  Cys  His  Ala  Arg  Ser  Ala  Lys  Gly  Glu  Val  Ala  Lys  Ala>
         _____IL-1RAcP_____>

2020          2030           2040           2050
          *    *    *    *    *    *    *    *
         GCC  AAG  GTG  AAG  CAG  AAA  GTG  CCA  GCT  CCA  AGA  TAC  ACA  GTG
         CGG  TTC  CAC  TTC  GTC  TTT  CAC  GGT  CGA  GGT  TCT  ATG  TGT  CAC
         Ala  Lys  Val  Lys  Gln  Lys  Val  Pro  Ala  Pro  Arg  Tyr  Thr  Val>
         _____IL-1RAcP_____>

2060           2070            2080           2090          2100
    *    *    *    *    *    *    *    *    *    *
   TCC  GGA  GAG  TCC  AAA  TAC  GGT  CCG  CCA  TGC  CCA  TCA  TGC  CCA
   AGG  CCT  CTC  AGG  TTT  ATG  CCA  GGC  GGT  ACG  GGT  AGT  ACG  GGT
   Ser  Gly>
   _____>
             Glu  Ser  Lys  Tyr  Gly  Pro  Pro  Cys  Pro  Ser  Cys  Pro>
             _____FC-IgG4_____>

2110           2120           2130           2140
             *    *    *    *    *    *    *    *
            GCA  CCT  GAG  TTC  CTG  GGG  GGA  CCA  TCA  GTC  TTC  CTG  TTC  CCC
            CGT  GGA  CTC  AAG  GAC  CCC  CCT  GGT  AGT  CAG  AAG  GAC  AAG  GGG
            Ala  Pro  Glu  Phe  Leu  Gly  Gly  Pro  Ser  Val  Phe  Leu  Phe  Pro>
            _____FC-IgG4_____>

2150           2160           2170           2180
             *    *    *    *    *    *    *    *
            CCA  AAA  CCC  AAG  GAC  ACT  CTC  ATG  ATC  TCC  CGG  ACC  CCT  GAG
            GGT  TTT  GGG  TTC  CTG  TGA  GAG  TAC  TAG  AGG  GCC  TGG  GGA  CTC
            Pro  Lys  Pro  Lys  Asp  Thr  Leu  Met  Ile  Ser  Arg  Thr  Pro  Glu>
            _____FC-IgG4_____>

2190           2200           2210           2220
             *    *    *    *    *    *    *    *    *
            GTC  ACG  TGC  GTG  GTG  GTG  GAC  GTG  AGC  CAG  GAA  GAC  CCC  GAG
            CAG  TGC  ACG  CAC  CAC  CAC  CTG  CAC  TCG  GTC  CTT  CTG  GGG  CTC
            Val  Thr  Cys  Val  Val  Val  Asp  Val  Ser  Gln  Glu  Asp  Pro  Glu>
            _____FC-IgG4_____>
```

Figure 45H

```
         2230           2240            2250             2260
           *       *      *       *       *        *       *       *
         GTC     CAG    TTC     AAC     TGG      TAC     GTG     GAT     GGC     GTG     GAG     GTG     CAT     AAT
         CAG     GTC    AAG     TTG     ACC      ATG     CAC     CTA     CCG     CAC     CTC     CAC     GTA     TTA
         Val     Gln    Phe     Asn     Trp      Tyr     Val     Asp     Gly     Val     Glu     Val     His     Asn>
                                                 __FC-IgG4_____>

2270            2280           2290             2300             2310
           *       *      *       *       *        *       *       *       *       *
         GCC     AAG    ACA     AAG     CCG      CGG     GAG     GAG     CAG     TTC     AAC     AGC     ACG     TAC
         CGG     TTC    TGT     TTC     GGC      GCC     CTC     CTC     GTC     AAG     TTG     TCG     TGC     ATG
         Ala     Lys    Thr     Lys     Pro      Arg     Glu     Glu     Gln     Phe     Asn     Ser     Thr     Tyr>
                                                 __FC-IgG4_____>

2320            2330             2340             2350
           *       *      *       *       *        *       *       *
         CGT     GTG    GTC     AGC     GTC      CTC     ACC     GTC     CTG     CAC     CAG     GAC     TGG     CTG
         GCA     CAC    CAG     TCG     CAG      GAG     TGG     CAG     GAC     GTG     GTC     CTG     ACC     GAC
         Arg     Val    Val     Ser     Val      Leu     Thr     Val     Leu     His     Gln     Asp     Trp     Leu>
                                                 __FC-IgG4_____>

2360            2370             2380             2390
           *       *      *       *       *        *       *       *
         AAC     GGC    AAG     GAG     TAC      AAG     TGC     AAG     GTC     TCC     AAC     AAA     GGC     CTC
         TTG     CCG    TTC     CTC     ATG      TTC     ACG     TTC     CAG     AGG     TTG     TTT     CCG     GAG
         Asn     Gly    Lys     Glu     Tyr      Lys     Cys     Lys     Val     Ser     Asn     Lys     Gly     Leu>
                                                 __FC-IgG4_____>

2400            2410             2420             2430
           *       *      *       *       *        *       *       *
         CCG     TCC    TCC     ATC     GAG      AAA     ACC     ATC     TCC     AAA     GCC     AAA     GGG     CAG
         GGC     AGG    AGG     TAG     CTC      TTT     TGG     TAG     AGG     TTT     CGG     TTT     CCC     GTC
         Pro     Ser    Ser     Ile     Glu      Lys     Thr     Ile     Ser     Lys     Ala     Lys     Gly     Gln>
                                                 __FC-IgG4_____>

2440            2450             2460             2470
           *       *      *       *       *        *       *       *
         CCC     CGA    GAG     CCA     CAG      GTG     TAC     ACC     CTG     CCC     CCA     TCC     CAG     GAG
         GGG     GCT    CTC     GGT     GTC      CAC     ATG     TGG     GAC     GGG     GGT     AGG     GTC     CTC
         Pro     Arg    Glu     Pro     Gln      Val     Tyr     Thr     Leu     Pro     Pro     Ser     Gln     Glu>
                                                 __FC-IgG4_____>

2480            2490            2500             2510            2520
           *       *      *       *       *        *       *       *       *       *
         GAG     ATG    ACC     AAG     AAC      CAG     GTC     AGC     CTG     ACC     TGC     CTG     GTC     AAA
         CTC     TAC    TGG     TTC     TTG      GTC     CAG     TCG     GAC     TGG     ACG     GAC     CAG     TTT
         Glu     Met    Thr     Lys     Asn      Gln     Val     Ser     Leu     Thr     Cys     Leu     Val     Lys>
                                                 __FC-IgG4_____>

2530            2540             2550             2560
           *       *      *       *       *        *       *       *
         GGC     TTC    TAC     CCC     AGC      GAC     ATC     GCC     GTG     GAG     TGG     GAG     AGC     AAT
         CCG     AAG    ATG     GGG     TCG      CTG     TAG     CGG     CAC     CTC     ACC     CTC     TCG     TTA
         Gly     Phe    Tyr     Pro     Ser      Asp     Ile     Ala     Val     Glu     Trp     Glu     Ser     Asn>
                                                 __FC-IgG4_____>
```

Figure 45I

```
        2570            2580            2590            2600
          *       *       *       *       *       *       *       *
GGG CAG CCG GAG AAC AAC TAC AAG ACC ACG CCT CCC GTG CTG
CCC GTC GGC CTC TTG TTG ATG TTC TGG TGC GGA GGG CAC GAC
Gly Gln Pro Glu Asn Asn Tyr Lys Thr Thr Pro Pro Val Leu>
                     ____FC-IgG4_____>

2610            2620            2630            2640
          *       *       *       *       *       *       *       *
GAC TCC GAC GGC TCC TTC TTC CTC TAC AGC AGG CTA ACC GTG
CTG AGG CTG CCG AGG AAG AAG GAG ATG TCG TCC GAT TGG CAC
Asp Ser Asp Gly Ser Phe Phe Leu Tyr Ser Arg Leu Thr Val>
                     ____FC-IgG4_____>

2650            2660            2670            2680
          *       *       *       *       *       *       *       *
GAC AAG AGC AGG TGG CAG GAG GGG AAT GTC TTC TCA TGC TCC
CTG TTC TCG TCC ACC GTC CTC CCC TTA CAG AAG AGT ACG AGG
Asp Lys Ser Arg Trp Gln Glu Gly Asn Val Phe Ser Cys Ser>
                     ____FC-IgG4_____>

2690            2700            2710            2720            2730
   *       *       *       *       *       *       *       *       *
GTG ATG CAT GAG GCT CTG CAC AAC CAC TAC ACA CAG AAG AGC
CAC TAC GTA CTC CGA GAC GTG TTG GTG ATG TGT GTC TTC TCG
Val Met His Glu Ala Leu His Asn His Tyr Thr Gln Lys Ser>
                     ____FC-IgG4_____>

2740            2750
          *       *       *       *
CTC TCC CTG TCT CTG GGT AAA TGA
GAG AGG GAC AGA GAC CCA TTT ACT
Leu Ser Leu Ser Leu Gly Lys ***>
                 ____FC-IgG4____>
```

Figure 46A

```
            10          20          30          40
            *           *           *           *
ATG GTG CGC TTG TAC GTG TTG GTA ATG GGA GTT TCT GCC TTC
TAC CAC GCG AAC ATG CAC AAC CAT TAC CCT CAA AGA CGG AAG
Met Val Arg Leu Tyr Val Leu Val Met Gly Val Ser Ala Phe>
_____SIGNAL PEPTIDE_____>
_____IL-1RII_____>

50          60          70          80
        *           *           *           *
ACC CTT CAG CCT GCG GCA CAC ACA GGG GCT GCC AGA AGC TGC
TGG GAA GTC GGA CGC CGT GTG TGT CCC CGA CGG TCT TCG ACG
Thr Leu Gln Pro Ala Ala>
_____SIGNAL PEPTIDE_____>
                        His Thr Gly Ala Ala Arg Ser Cys>
_____IL-1RII_____>

90         100         110         120
        *           *           *           *
CGG TTT CGT GGG AGG CAT TAC AAG CGG GAG TTC AGG CTG GAA
GCC AAA GCA CCC TCC GTA ATG TTC GCC CTC AAG TCC GAC CTT
Arg Phe Arg Gly Arg His Tyr Lys Arg Glu Phe Arg Leu Glu>
_____IL-1RII_____>

130         140         150         160
        *           *           *           *
GGG GAG CCT GTA GCC CTG AGG TGC CCC CAG GTG CCC TAC TGG
CCC CTC GGA CAT CGG GAC TCC ACG GGG GTC CAC GGG ATG ACC
Gly Glu Pro Val Ala Leu Arg Cys Pro Gln Val Pro Tyr Trp>
_____IL-1RII_____>

170         180         190         200         210
  *           *           *           *           *
TTG TGG GCC TCT GTC AGC CCC CGC ATC AAC CTG ACA TGG CAT
AAC ACC CGG AGA CAG TCG GGG GCG TAG TTG GAC TGT ACC GTA
Leu Trp Ala Ser Val Ser Pro Arg Ile Asn Leu Thr Trp His>
_____IL-1RII_____>

220         230         240         250
        *           *           *           *
AAA AAT GAC TCT GCT AGG ACG GTC CCA GGA GAA GAA GAG ACA
TTT TTA CTG AGA CGA TCC TGC CAG GGT CCT CTT CTT CTC TGT
Lys Asn Asp Ser Ala Arg Thr Val Pro Gly Glu Glu Glu Thr>
_____IL-1RII_____>

260         270         280         290
        *           *           *           *
CGG ATG TGG GCC CAG GAC GGT GCT CTG TGG CTT CTG CCA GCC
GCC TAC ACC CGG GTC CTG CCA CGA GAC ACC GAA GAC GGT CGG
Arg Met Trp Ala Gln Asp Gly Ala Leu Trp Leu Leu Pro Ala>
_____IL-1RII_____>
```

Figure 46B

```
         300           310           320           330
          *     *       *     *       *     *       *     *       *
         TTG   CAG   GAG   GAC   TCT   GGC   ACC   TAC   GTC   TGC   ACT   ACT   AGA   AAT
         AAC   GTC   CTC   CTG   AGA   CCG   TGG   ATG   CAG   ACG   TGA   TGA   TCT   TTA
         Leu   Gln   Glu   Asp   Ser   Gly   Thr   Tyr   Val   Cys   Thr   Thr   Arg   Asn>
         _____IL-1RII_____>

340           350           360           370
          *     *       *     *       *     *       *     *
         GCT   TCT   TAC   TGT   GAC   AAA   ATG   TCC   ATT   GAG   CTC   AGA   GTT   TTT
         CGA   AGA   ATG   ACA   CTG   TTT   TAC   AGG   TAA   CTC   GAG   TCT   CAA   AAA
         Ala   Ser   Tyr   Cys   Asp   Lys   Met   Ser   Ile   Glu   Leu   Arg   Val   Phe>
         _____IL-1RII_____>

380           390           400           410           420
    *     *       *     *       *     *       *     *       *
   GAG   AAT   ACA   GAT   GCT   TTC   CTG   CCG   TTC   ATC   TCA   TAC   CCG   CAA
   CTC   TTA   TGT   CTA   CGA   AAG   GAC   GGC   AAG   TAG   AGT   ATG   GGC   GTT
   Glu   Asn   Thr   Asp   Ala   Phe   Leu   Pro   Phe   Ile   Ser   Tyr   Pro   Gln>
   _____IL-1RII_____>

430           440           450           460
                *     *       *     *       *     *       *     *
               ATT   TTA   ACC   TTG   TCA   ACC   TCT   GGG   GTA   TTA   GTA   TGC   CCT   GAC
               TAA   AAT   TGG   AAC   AGT   TGG   AGA   CCC   CAT   AAT   CAT   ACG   GGA   CTG
               Ile   Leu   Thr   Leu   Ser   Thr   Ser   Gly   Val   Leu   Val   Cys   Pro   Asp>
               _____IL-1RII_____>

470           480           490           500
                *     *       *     *       *     *       *     *
               CTG   AGT   GAA   TTC   ACC   CGT   GAC   AAA   ACT   GAC   GTG   AAG   ATT   CAA
               GAC   TCA   CTT   AAG   TGG   GCA   CTG   TTT   TGA   CTG   CAC   TTC   TAA   GTT
               Leu   Ser   Glu   Phe   Thr   Arg   Asp   Lys   Thr   Asp   Val   Lys   Ile   Gln>
               _____IL-1RII_____>

510           520           530           540
          *     *       *     *       *     *       *     *       *
         TGG   TAC   AAG   GAT   TCT   CTT   CTT   TTG   GAT   AAA   GAC   AAT   GAG   AAA
         ACC   ATG   TTC   CTA   AGA   GAA   GAA   AAC   CTA   TTT   CTG   TTA   CTC   TTT
         Trp   Tyr   Lys   Asp   Ser   Leu   Leu   Leu   Asp   Lys   Asp   Asn   Glu   Lys>
         _____IL-1RII_____>

550           560           570           580
                *     *       *     *       *     *       *     *       *
               TTT   CTA   AGT   GTG   AGG   GGG   ACC   ACT   CAC   TTA   CTC   GTA   CAC   GAT
               AAA   GAT   TCA   CAC   TCC   CCC   TGG   TGA   GTG   AAT   GAG   CAT   GTG   CTA
               Phe   Leu   Ser   Val   Arg   Gly   Thr   Thr   His   Leu   Leu   Val   His   Asp>
               _____IL-1RII_____>

590           600           610           620           630
    *     *       *     *       *     *       *     *       *
   GTG   GCC   CTG   GAA   GAT   GCT   GGC   TAT   TAC   CGC   TGT   GTC   CTG   ACA
   CAC   CGG   GAC   CTT   CTA   CGA   CCG   ATA   ATG   GCG   ACA   CAG   GAC   TGT
   Val   Ala   Leu   Glu   Asp   Ala   Gly   Tyr   Tyr   Arg   Cys   Val   Leu   Thr>
   _____IL-1RII_____>
```

Figure 46C

```
              640             650             660             670
               *       *       *       *       *       *       *
          TTT GCC CAT GAA GGC CAG CAA TAC AAC ATC ACT AGG AGT ATT
          AAA CGG GTA CTT CCG GTC GTT ATG TTG TAG TGA TCC TCA TAA
          Phe Ala His Glu Gly Gln Gln Tyr Asn Ile Thr Arg Ser Ile>
          _____IL-1RII_____>

680             690             700             710
                   *       *       *       *       *       *       *
              GAG CTA CGC ATC AAG AAA AAA AAA GAA GAG ACC ATT CCT GTG
              CTC GAT GCG TAG TTC TTT TTT TTT CTT CTC TGG TAA GGA CAC
              Glu Leu Arg Ile Lys Lys Lys Lys Glu Glu Thr Ile Pro Val>
              _____IL-1RII_____>

720             730             740             750
               *       *       *       *       *       *       *       *
          ATC ATT TCC CCC CTC AAG ACC ATA TCA GCT TCT CTG GGG TCA
          TAG TAA AGG GGG GAG TTC TGG TAT AGT CGA AGA GAC CCC AGT
          Ile Ile Ser Pro Leu Lys Thr Ile Ser Ala Ser Leu Gly Ser>
          _____IL-1RII_____>

760             770             780             790
              *       *       *       *       *       *       *
         AGA CTG ACA ATC CCA TGT AAG GTG TTT CTG GGA ACC GGC ACA
         TCT GAC TGT TAG GGT ACA TTC CAC AAA GAC CCT TGG CCG TGT
         Arg Leu Thr Ile Pro Cys Lys Val Phe Leu Gly Thr Gly Thr>
         _____IL-1RII_____>

800             810             820             830             840
       *       *       *       *       *       *       *       *       *
      CCC TTA ACC ACC ATG CTG TGG TGG ACG GCC AAT GAC ACC CAC
      GGG AAT TGG TGG TAC GAC ACC ACC TGC CGG TTA CTG TGG GTG
      Pro Leu Thr Thr Met Leu Trp Trp Thr Ala Asn Asp Thr His>
      _____IL-1RII_____>

850             860             870             880
                  *       *       *       *       *       *       *       *
             ATA GAG AGC GCC TAC CCG GGA GGC CGC GTG ACC GAG GGG CCA
             TAT CTC TCG CGG ATG GGC CCT CCG GCG CAC TGG CTC CCC GGT
             Ile Glu Ser Ala Tyr Pro Gly Gly Arg Val Thr Glu Gly Pro>
             _____IL-1RII_____>

890             900             910             920
                  *       *       *       *       *       *       *       *
             CGC CAG GAA TAT TCA GAA AAT AAT GAG AAC TAC ATT GAA GTG
             GCG GTC CTT ATA AGT CTT TTA TTA CTC TTG ATG TAA CTT CAC
             Arg Gln Glu Tyr Ser Glu Asn Asn Glu Asn Tyr Ile Glu Val>
             _____IL-1RII_____>

930             940             950             960
               *       *       *       *       *       *       *       *       *
          CCA TTG ATT TTT GAT CCT GTC ACA AGA GAG GAT TTG CAC ATG
          GGT AAC TAA AAA CTA GGA CAG TGT TCT CTC CTA AAC GTG TAC
          Pro Leu Ile Phe Asp Pro Val Thr Arg Glu Asp Leu His Met>
          _____IL-1RII_____>
```

Figure 46D

```
        970              980              990             1000
         *         *      *          *     *         *      *         *
        GAT TTT AAA TGT GTT GTC CAT AAT ACC CTG AGT TTT CAG ACA
        CTA AAA TTT ACA CAA CAG GTA TTA TGG GAC TCA AAA GTC TGT
        Asp Phe Lys Cys Val Val His Asn Thr Leu Ser Phe Gln Thr>
        _____IL-1RII_____>

1010            1020             1030             1040             1050
  *       *      *         *      *        *      *         *      *        *
 CTA CGC ACC ACA GTC AAG GAA GCC TCC TCC ACG TTC TCA GAA
 GAT GCG TGG TGT CAG TTC CTT CGG AGG AGG TGC AAG AGT CTT
                                                     Ser Glu>
                                                     _____>

Leu Arg Thr Thr Val Lys Glu Ala Ser Ser Thr Phe>
 _____IL-1RII_____>

1060             1070             1080             1090
      *       *      *         *     *         *      *         *      *
     CGC TGC GAT GAC TGG GGA CTA GAC ACC ATG AGG CAA ATC CAA
     GCG ACG CTA CTG ACC CCT GAT CTG TGG TAC TCC GTT TAG GTT
     Arg Cys Asp Asp Trp Gly Leu Asp Thr Met Arg Gln Ile Gln>
     _____IL-1RAcP_____>

1100             1110             1120             1130
     *       *         *     *         *      *         *      *
    GTG TTT GAA GAT GAG CCA GCT CGC ATC AAG TGC CCA CTC TTT
    CAC AAA CTT CTA CTC GGT CGA GCG TAG TTC ACG GGT GAG AAA
    Val Phe Glu Asp Glu Pro Ala Arg Ile Lys Cys Pro Leu Phe>
    _____IL-1RAcP_____>

1140             1150             1160             1170
  *       *      *         *      *         *      *        *      *
 GAA CAC TTC TTG AAA TTC AAC TAC AGC ACA GCC CAT TCA GCT
 CTT GTG AAG AAC TTT AAG TTG ATG TCG TGT CGG GTA AGT CGA
 Glu His Phe Leu Lys Phe Asn Tyr Ser Thr Ala His Ser Ala>
 _____IL-1RAcP_____>

1180             1190             1200             1210
     *       *      *         *      *         *      *         *      *
    GGC CTT ACT CTG ATC TGG TAT TGG ACT AGG CAG GAC CGG GAC
    CCG GAA TGA GAC TAG ACC ATA ACC TGA TCC GTC CTG GCC CTG
    Gly Leu Thr Leu Ile Trp Tyr Trp Thr Arg Gln Asp Arg Asp>
    _____IL-1RAcP_____>

1220             1230             1240             1250             1260
     *       *        *       *        *       *        *       *        *
    CTT GAG GAG CCA ATT AAC TTC CGC CTC CCC GAG AAC CGC ATT
    GAA CTC CTC GGT TAA TTG AAG GCG GAG GGG CTC TTG GCG TAA
    Leu Glu Glu Pro Ile Asn Phe Arg Leu Pro Glu Asn Arg Ile>
    _____IL-1RAcP_____>
```

Figure 46E

```
               1270           1280           1290           1300
           *       *       *       *       *       *       *       *
       AGT AAG GAG AAA GAT GTG CTG TGG TTC CGG CCC ACT CTC CTC
       TCA TTC CTC TTT CTA CAC GAC ACC AAG GCC GGG TGA GAG GAG
       Ser Lys Glu Lys Asp Val Leu Trp Phe Arg Pro Thr Leu Leu>
                                   _IL-1RAcP_____>

1310           1320           1330           1340
           *       *       *       *       *       *       *
       AAT GAC ACT GGC AAC TAT ACC TGC ATG TTA AGG AAC ACT ACA
       TTA CTG TGA CCG TTG ATA TGG ACG TAC AAT TCC TTG TGA TGT
       Asn Asp Thr Gly Asn Tyr Thr Cys Met Leu Arg Asn Thr Thr>
                                   _IL-1RAcP_____>

1350           1360           1370           1380
       *       *       *       *       *       *       *       *       *
       TAT TGC AGC AAA GTT GCA TTT CCC TTG GAA GTT GTT CAA AAA
       ATA ACG TCG TTT CAA CGT AAA GGG AAC CTT CAA CAA GTT TTT
       Tyr Cys Ser Lys Val Ala Phe Pro Leu Glu Val Val Gln Lys>
                                   _IL-1RAcP_____>

1390           1400           1410           1420
           *       *       *       *       *       *       *       *
       GAC AGC TGT TTC AAT TCC CCC ATG AAA CTC CCA GTG CAT AAA
       CTG TCG ACA AAG TTA AGG GGG TAC TTT GAG GGT CAC GTA TTT
       Asp Ser Cys Phe Asn Ser Pro Met Lys Leu Pro Val His Lys>
                                   _IL-1RAcP_____>

1430           1440           1450           1460           1470
       *       *       *       *       *       *       *       *       *
       CTG TAT ATA GAA TAT GGC ATT CAG AGG ATC ACT TGT CCA AAT
       GAC ATA TAT CTT ATA CCG TAA GTC TCC TAG TGA ACA GGT TTA
       Leu Tyr Ile Glu Tyr Gly Ile Gln Arg Ile Thr Cys Pro Asn>
                                   _IL-1RAcP_____>

1480           1490           1500           1510
               *       *       *       *       *       *       *       *
           GTA GAT GGA TAT TTT CCT TCC AGT GTC AAA CCG ACT ATC ACT
           CAT CTA CCT ATA AAA GGA AGG TCA CAG TTT GGC TGA TAG TGA
           Val Asp Gly Tyr Phe Pro Ser Ser Val Lys Pro Thr Ile Thr>
                                       _IL-1RAcP_____>

1520           1530           1540           1550
               *       *       *       *       *       *       *
           TGG TAT ATG GGC TGT TAT AAA ATA CAG AAT TTT AAT AAT GTA
           ACC ATA TAC CCG ACA ATA TTT TAT GTC TTA AAA TTA TTA CAT
           Trp Tyr Met Gly Cys Tyr Lys Ile Gln Asn Phe Asn Asn Val>
                                       _IL-1RAcP_____>

1560           1570           1580           1590
               *       *       *       *       *       *       *       *       *
           ATA CCC GAA GGT ATG AAC TTG AGT TTC CTC ATT GCC TTA ATT
           TAT GGG CTT CCA TAC TTG AAC TCA AAG GAG TAA CGG AAT TAA
           Ile Pro Glu Gly Met Asn Leu Ser Phe Leu Ile Ala Leu Ile>
                                       _IL-1RAcP_____>
```

Figure 46F

```
        1600           1610           1620           1630
         *      *       *      *       *      *       *      *
        TCA AAT AAT GGA AAT TAC ACA TGT GTT GTT ACA TAT CCA GAA
        AGT TTA TTA CCT TTA ATG TGT ACA CAA CAA TGT ATA GGT CTT
        Ser Asn Asn Gly Asn Tyr Thr Cys Val Val Thr Tyr Pro Glu>
                                  ___IL-1RAcP_____>

1640           1650           1660           1670           1680
   *      *       *      *       *      *       *      *       *
  AAT GGA CGT ACG TTT CAT CTC ACC AGG ACT CTG ACT GTA AAG
  TTA CCT GCA TGC AAA GTA GAG TGG TCC TGA GAC TGA CAT TTC
  Asn Gly Arg Thr Phe His Leu Thr Arg Thr Leu Thr Val Lys>
  _____IL-1RAcP_____>

1690           1700           1710           1720
            *      *       *      *       *      *       *      *
           GTA GTA GGC TCT CCA AAA AAT GCA GTG CCC CCT GTG ATC CAT
           CAT CAT CCG AGA GGT TTT TTA CGT CAC GGG GGA CAC TAG GTA
           Val Val Gly Ser Pro Lys Asn Ala Val Pro Pro Val Ile His>
           _____IL-1RAcP_____>

1730           1740           1750           1760
            *      *       *      *       *      *       *      *
           TCA CCT AAT GAT CAT GTG GTC TAT GAG AAA GAA CCA GGA GAG
           AGT GGA TTA CTA GTA CAC CAG ATA CTC TTT CTT GGT CCT CTC
           Ser Pro Asn Asp His Val Val Tyr Glu Lys Glu Pro Gly Glu>
           _____IL-1RAcP_____>

1770           1780           1790           1800
        *      *       *      *       *      *       *      *
       GAG CTA CTC ATT CCC TGT ACG GTC TAT TTT AGT TTT CTG ATG
       CTC GAT GAG TAA GGG ACA TGC CAG ATA AAA TCA AAA GAC TAC
       Glu Leu Leu Ile Pro Cys Thr Val Tyr Phe Ser Phe Leu Met>
       _____IL-1RAcP_____>

1810           1820           1830           1840
      *      *       *      *       *      *       *      *
     GAT TCT CGC AAT GAG GTT TGG TGG ACC ATT GAT GGA AAA AAA
     CTA AGA GCG TTA CTC CAA ACC ACC TGG TAA CTA CCT TTT TTT
     Asp Ser Arg Asn Glu Val Trp Trp Thr Ile Asp Gly Lys Lys>
     _____IL-1RAcP_____>

1850           1860           1870           1880           1890
   *      *       *      *       *      *       *      *       *
   CCT GAT GAC ATC ACT ATT GAT GTC ACC ATT AAC GAA AGT ATA
   GGA CTA CTG TAG TGA TAA CTA CAG TGG TAA TTG CTT TCA TAT
   Pro Asp Asp Ile Thr Ile Asp Val Thr Ile Asn Glu Ser Ile>
   _____IL-1RAcP_____>

1900           1910           1920           1930
          *      *       *      *       *      *       *      *
         AGT CAT AGT AGA ACA GAA GAT GAA ACA AGA ACT CAG ATT TTG
         TCA GTA TCA TCT TGT CTT CTA CTT TGT TCT TGA GTC TAA AAC
         Ser His Ser Arg Thr Glu Asp Glu Thr Arg Thr Gln Ile Leu>
         _____IL-1RAcP_____>
```

Figure 46G

```
        1940              1950              1960              1970
   *       *       *       *       *       *       *       *
 AGC ATC AAG AAA GTT ACC TCT GAG GAT CTC AAG CGC AGC TAT
 TCG TAG TTC TTT CAA TGG AGA CTC CTA GAG TTC GCG TCG ATA
 Ser Ile Lys Lys Val Thr Ser Glu Asp Leu Lys Arg Ser Tyr>
 _____IL-1RAcP_____>

1980              1990              2000              2010
   *       *       *       *       *       *       *       *       *
 GTC TGT CAT GCT AGA AGT GCC AAA GGC GAA GTT GCC AAA GCA
 CAG ACA GTA CGA TCT TCA CGG TTT CCG CTT CAA CGG TTT CGT
 Val Cys His Ala Arg Ser Ala Lys Gly Glu Val Ala Lys Ala>
 _____IL-1RAcP_____>

2020              2030              2040              2050
   *       *       *       *       *       *       *       *
 GCC AAG GTG AAG CAG AAA GTG CCA GCT CCA AGA TAC ACA GTG
 CGG TTC CAC TTC GTC TTT CAC GGT CGA GGT TCT ATG TGT CAC
 Ala Lys Val Lys Gln Lys Val Pro Ala Pro Arg Tyr Thr Val>
 _____IL-1RAcP_____>

>Mutation Serine to Proline 2060              2070              2080              2090              2100
   *       *       *       *       *       *       *       *       *
 TCC GGA GAG TCC AAA TAC GGT CCG CCA TGC CCA CCA TGC CCA
 AGG CCT CTC AGG TTT ATG CCA GGC GGT ACG GGT GGT ACG GGT
 Ser Gly>
 _____>
         Glu Ser Lys Tyr Gly Pro Pro Cys Pro Pro Cys Pro>
         _____FC-IgG4_____>

2110              2120              2130              2140
   *       *       *       *       *       *       *       *
 GCA CCT GAG TTC CTG GGG GGA CCA TCA GTC TTC CTG TTC CCC
 CGT GGA CTC AAG GAC CCC CCT GGT AGT CAG AAG GAC AAG GGG
 Ala Pro Glu Phe Leu Gly Gly Pro Ser Val Phe Leu Phe Pro>
 _____FC-IgG4_____>

2150              2160              2170              2180
   *       *       *       *       *       *       *       *
 CCA AAA CCC AAG GAC ACT CTC ATG ATC TCC CGG ACC CCT GAG
 GGT TTT GGG TTC CTG TGA GAG TAC TAG AGG GCC TGG GGA CTC
 Pro Lys Pro Lys Asp Thr Leu Met Ile Ser Arg Thr Pro Glu>
 _____FC-IgG4_____>

2190              2200              2210              2220
   *       *       *       *       *       *       *       *       *
 GTC ACG TGC GTG GTG GTG GAC GTG AGC CAG GAA GAC CCC GAG
 CAG TGC ACG CAC CAC CAC CTG CAC TCG GTC CTT CTG GGG CTC
 Val Thr Cys Val Val Val Asp Val Ser Gln Glu Asp Pro Glu>
 _____FC-IgG4_____>
```

Figure 46H

```
         2230            2240            2250            2260
          *       *       *       *       *       *       *       *
         GTC CAG TTC AAC TGG TAC GTG GAT GGC GTG GAG GTG CAT AAT
         CAG GTC AAG TTG ACC ATG CAC CTA CCG CAC CTC CAC GTA TTA
         Val Gln Phe Asn Trp Tyr Val Asp Gly Val Glu Val His Asn>
                                 __FC-IgG4_____>

2270            2280            2290            2300            2310
   *       *       *       *       *       *       *       *       *
  GCC AAG ACA AAG CCG CGG GAG GAG CAG TTC AAC AGC ACG TAC
  CGG TTC TGT TTC GGC GCC CTC CTC GTC AAG TTG TCG TGC ATG
  Ala Lys Thr Lys Pro Arg Glu Glu Gln Phe Asn Ser Thr Tyr>
                         __FC-IgG4_____>

2320            2330            2340            2350
          *       *       *       *       *       *       *       *
         CGT GTG GTC AGC GTC CTC ACC GTC CTG CAC CAG GAC TGG CTG
         GCA CAC CAG TCG CAG GAG TGG CAG GAC GTG GTC CTG ACC GAC
         Arg Val Val Ser Val Leu Thr Val Leu His Gln Asp Trp Leu>
                                 __FC-IgG4_____>

2360            2370            2380            2390
            *       *       *       *       *       *       *       *
           AAC GGC AAG GAG TAC AAG TGC AAG GTC TCC AAC AAA GGC CTC
           TTG CCG TTC CTC ATG TTC ACG TTC CAG AGG TTG TTT CCG GAG
           Asn Gly Lys Glu Tyr Lys Cys Lys Val Ser Asn Lys Gly Leu>
                                 __FC-IgG4_____>

2400            2410            2420            2430
          *       *       *       *       *       *       *       *
         CCG TCC TCC ATC GAG AAA ACC ATC TCC AAA GCC AAA GGG CAG
         GGC AGG AGG TAG CTC TTT TGG TAG AGG TTT CGG TTT CCC GTC
         Pro Ser Ser Ile Glu Lys Thr Ile Ser Lys Ala Lys Gly Gln>
                                 __FC-IgG4_____>

2440            2450            2460            2470
            *       *       *       *       *       *       *       *
           CCC CGA GAG CCA CAG GTG TAC ACC CTG CCC CCA TCC CAG GAG
           GGG GCT CTC GGT GTC CAC ATG TGG GAC GGG GGT AGG GTC CTC
           Pro Arg Glu Pro Gln Val Tyr Thr Leu Pro Pro Ser Gln Glu>
                                 __FC-IgG4_____>

2480            2490            2500            2510            2520
   *       *       *       *       *       *       *       *       *
  GAG ATG ACC AAG AAC CAG GTC AGC CTG ACC TGC CTG GTC AAA
  CTC TAC TGG TTC TTG GTC CAG TCG GAC TGG ACG GAC CAG TTT
  Glu Met Thr Lys Asn Gln Val Ser Leu Thr Cys Leu Val Lys>
                         __FC-IgG4_____>

2530            2540            2550            2560
            *       *       *       *       *       *       *       *
           GGC TTC TAC CCC AGC GAC ATC GCC GTG GAG TGG GAG AGC AAT
           CCG AAG ATG GGG TCG CTG TAG CGG CAC CTC ACC CTC TCG TTA
           Gly Phe Tyr Pro Ser Asp Ile Ala Val Glu Trp Glu Ser Asn>
                                 __FC-IgG4_____>
```

Figure 46I

```
              2570            2580            2590            2600
         *       *       *       *       *       *       *       *
        GGG     CAG     CCG     GAG     AAC     AAC     TAC     AAG     ACC     ACG     CCT     CCC     GTG     CTG
        CCC     GTC     GGC     CTC     TTG     TTG     ATG     TTC     TGG     TGC     GGA     GGG     CAC     GAC
        Gly     Gln     Pro     Glu     Asn     Asn     Tyr     Lys     Thr     Thr     Pro     Pro     Val     Leu>
                                              _FC-IgG4_____>

2610            2620            2630            2640
         *       *       *       *       *       *       *       *       *
        GAC     TCC     GAC     GGC     TCC     TTC     TTC     CTC     TAC     AGC     AGG     CTA     ACC     GTG
        CTG     AGG     CTG     CCG     AGG     AAG     AAG     GAG     ATG     TCG     TCC     GAT     TGG     CAC
        Asp     Ser     Asp     Gly     Ser     Phe     Phe     Leu     Tyr     Ser     Arg     Leu     Thr     Val>
                                              _FC-IgG4_____>

2650            2660            2670            2680
         *       *       *       *       *       *       *       *
        GAC     AAG     AGC     AGG     TGG     CAG     GAG     GGG     AAT     GTC     TTC     TCA     TGC     TCC
        CTG     TTC     TCG     TCC     ACC     GTC     CTC     CCC     TTA     CAG     AAG     AGT     ACG     AGG
        Asp     Lys     Ser     Arg     Trp     Gln     Glu     Gly     Asn     Val     Phe     Ser     Cys     Ser>
                                              _FC-IgG4_____>

2690            2700            2710            2720            2730
         *       *       *       *       *       *       *       *       *       *
        GTG     ATG     CAT     GAG     GCT     CTG     CAC     AAC     CAC     TAC     ACA     CAG     AAG     AGC
        CAC     TAC     GTA     CTC     CGA     GAC     GTG     TTG     GTG     ATG     TGT     GTC     TTC     TCG
        Val     Met     His     Glu     Ala     Leu     His     Asn     His     Tyr     Thr     Gln     Lys     Ser>
                                              _FC-IgG4_____>

2740            2750
                 *       *       *       *
                CTC     TCC     CTG     TCT     CTG     GGT     AAA     TGA
                GAG     AGG     GAC     AGA     GAC     CCA     TTT     ACT
                Leu     Ser     Leu     Ser     Leu     Gly     Lys     ***>
                        _FC-IgG4_____>
```

Figure 47A

```
              10              20              30              40
         *         *         *         *         *         *         *    *
ATG GTG CTT CTG TGG TGT GTA GTG AGT CTC TAC TTT TAT GGA
TAC CAC GAA GAC ACC ACA CAT CAC TCA GAG ATG AAA ATA CCT
Met Val Leu Leu Trp Cys Val Val Ser Leu Tyr Phe Tyr Gly>
_____SIGNAL PEPTIDE_____>
_____IL-1RAcP_____>

50              60              70              80
         *         *         *         *         *         *    *    *
ATC CTG CAA AGT GAT GCC TCA GAA CGC TGC GAT GAC TGG GGA
TAG GAC GTT TCA CTA CGG AGT CTT GCG ACG CTA CTG ACC CCT
Ile Leu Gln Ser Asp Ala>
____ SIGNAL PEPTIDE_____>
                        Ser Glu Arg Cys Asp Asp Trp Gly>
                        _____IL-1RAcP_____>

90             100             110             120
         *         *    *    *    *    *    *    *    *
CTA GAC ACC ATG AGG CAA ATC CAA GTG TTT GAA GAT GAG CCA
GAT CTG TGG TAC TCC GTT TAG GTT CAC AAA CTT CTA CTC GGT
Leu Asp Thr Met Arg Gln Ile Gln Val Phe Glu Asp Glu Pro>
_____IL-1RAcP_____>

130             140             150             160
    *         *    *    *    *    *    *    *    *
GCT CGC ATC AAG TGC CCA CTC TTT GAA CAC TTC TTG AAA TTC
CGA GCG TAG TTC ACG GGT GAG AAA CTT GTG AAG AAC TTT AAG
Ala Arg Ile Lys Cys Pro Leu Phe Glu His Phe Leu Lys Phe>
_____IL-1RAcP_____>

170            180             190             200             210
    *    *    *    *    *    *    *    *    *
AAC TAC AGC ACA GCC CAT TCA GCT GGC CTT ACT CTG ATC TGG
TTG ATG TCG TGT CGG GTA AGT CGA CCG GAA TGA GAC TAG ACC
Asn Tyr Ser Thr Ala His Ser Ala Gly Leu Thr Leu Ile Trp>
_____IL-1RAcP_____>

220             230             240             250
         *    *    *    *    *    *    *    *    *
TAT TGG ACT AGG CAG GAC CGG GAC CTT GAG GAG CCA ATT AAC
ATA ACC TGA TCC GTC CTG GCC CTG GAA CTC CTC GGT TAA TTG
Tyr Trp Thr Arg Gln Asp Arg Asp Leu Glu Glu Pro Ile Asn>
_____IL-1RAcP_____>

260             270             280             290
         *    *    *    *    *    *    *    *
TTC CGC CTC CCC GAG AAC CGC ATT AGT AAG GAG AAA GAT GTG
AAG GCG GAG GGG CTC TTG GCG TAA TCA TTC CTC TTT CTA CAC
Phe Arg Leu Pro Glu Asn Arg Ile Ser Lys Glu Lys Asp Val>
_____IL-1RAcP_____>

300             310             320             330
         *    *    *    *    *    *    *    *    *
CTG TGG TTC CGG CCC ACT CTC CTC AAT GAC ACT GGC AAC TAT
GAC ACC AAG GCC GGG TGA GAG GAG TTA CTG TGA CCG TTG ATA
Leu Trp Phe Arg Pro Thr Leu Leu Asn Asp Thr Gly Asn Tyr>
_____IL-1RAcP_____>
```

Figure 47B

```
          340            350              360              370
           *       *      *         *       *         *      *       *
         ACC     TGC    ATG       TTA     AGG       AAC    ACT     ACA    TAT    TGC    AGC    AAA    GTT    GCA
         TGG     ACG    TAC       AAT     TCC       TTG    TGA     TGT    ATA    ACG    TCG    TTT    CAA    CGT
         Thr     Cys    Met       Leu     Arg       Asn    Thr     Thr    Tyr    Cys    Ser    Lys    Val    Ala>
         _____IL-1RAcP_____>

380              390              400              410              420
    *       *        *       *        *       *        *       *        *
   TTT     CCC      TTG     GAA      GTT     GTT      CAA     AAA      GAC    AGC    TGT    TTC    AAT    TCC
   AAA     GGG      AAC     CTT      CAA     CAA      GTT     TTT      CTG    TCG    ACA    AAG    TTA    AGG
   Phe     Pro      Leu     Glu      Val     Val      Gln     Lys      Asp    Ser    Cys    Phe    Asn    Ser>
   _____IL-1RAcP_____>

430              440              450              460
       *       *        *       *        *       *        *       *
      CCC     ATG      AAA     CTC      CCA     GTG      CAT     AAA      CTG    TAT    ATA    GAA    TAT    GGC
      GGG     TAC      TTT     GAG      GGT     CAC      GTA     TTT      GAC    ATA    TAT    CTT    ATA    CCG
      Pro     Met      Lys     Leu      Pro     Val      His     Lys      Leu    Tyr    Ile    Glu    Tyr    Gly>
      _____IL-1RAcP_____>

470              480              490              500
     *        *        *       *        *       *        *       *
    ATT     CAG      AGG     ATC      ACT     TGT      CCA     AAT      GTA    GAT    GGA    TAT    TTT    CCT
    TAA     GTC      TCC     TAG      TGA     ACA      GGT     TTA      CAT    CTA    CCT    ATA    AAA    GGA
    Ile     Gln      Arg     Ile      Thr     Cys      Pro     Asn      Val    Asp    Gly    Tyr    Phe    Pro>
    _____IL-1RAcP_____>

510              520              530              540
      *       *        *       *        *       *        *       *        *
     TCC     AGT      GTC     AAA      CCG     ACT      ATC     ACT      TGG    TAT    ATG    GGC    TGT    TAT
     AGG     TCA      CAG     TTT      GGC     TGA      TAG     TGA      ACC    ATA    TAC    CCG    ACA    ATA
     Ser     Ser      Val     Lys      Pro     Thr      Ile     Thr      Trp    Tyr    Met    Gly    Cys    Tyr>
     _____IL-1RAcP_____>

550              560              570              580
      *       *        *       *        *       *        *       *
     AAA     ATA      CAG     AAT      TTT     AAT      AAT     GTA      ATA    CCC    GAA    GGT    ATG    AAC
     TTT     TAT      GTC     TTA      AAA     TTA      TTA     CAT      TAT    GGG    CTT    CCA    TAC    TTG
     Lys     Ile      Gln     Asn      Phe     Asn      Asn     Val      Ile    Pro    Glu    Gly    Met    Asn>
     _____IL-1RAcP_____>

590              600              610              620              630
    *       *        *       *        *       *        *       *        *
   TTG     AGT      TTC     CTC      ATT     GCC      TTA     ATT      TCA    AAT    AAT    GGA    AAT    TAC
   AAC     TCA      AAG     GAG      TAA     CGG      AAT     TAA      AGT    TTA    TTA    CCT    TTA    ATG
   Leu     Ser      Phe     Leu      Ile     Ala      Leu     Ile      Ser    Asn    Asn    Gly    Asn    Tyr>
   _____IL-1RAcP_____>

640              650              660              670
       *       *        *       *        *       *        *       *
      ACA     TGT      GTT     GTT      ACA     TAT      CCA     GAA      AAT    GGA    CGT    ACG    TTT    CAT
      TGT     ACA      CAA     CAA      TGT     ATA      GGT     CTT      TTA    CCT    GCA    TGC    AAA    GTA
      Thr     Cys      Val     Val      Thr     Tyr      Pro     Glu      Asn    Gly    Arg    Thr    Phe    His>
      _____IL-1RAcP_____>
```

Figure 47C

```
           680          690           700          710
       *     *     *     *     *     *     *     *
     CTC   ACC   AGG   ACT   CTG   ACT   GTA   AAG   GTA   GTA   GGC   TCT   CCA   AAA
     GAG   TGG   TCC   TGA   GAC   TGA   CAT   TTC   CAT   CAT   CCG   AGA   GGT   TTT
     Leu   Thr   Arg   Thr   Leu   Thr   Val   Lys   Val   Val   Gly   Ser   Pro   Lys>
     _____IL-1RAcP_____>

720          730           740          750
       *     *     *     *     *     *     *     *     *
     AAT   GCA   GTG   CCC   CCT   GTG   ATC   CAT   TCA   CCT   AAT   GAT   CAT   GTG
     TTA   CGT   CAC   GGG   GGA   CAC   TAG   GTA   AGT   GGA   TTA   CTA   GTA   CAC
     Asn   Ala   Val   Pro   Pro   Val   Ile   His   Ser   Pro   Asn   Asp   His   Val>
     _____IL-1RAcP_____>

760          770           780          790
       *     *     *     *     *     *     *     *
     GTC   TAT   GAG   AAA   GAA   CCA   GGA   GAG   GAG   CTA   CTC   ATT   CCC   TGT
     CAG   ATA   CTC   TTT   CTT   GGT   CCT   CTC   CTC   GAT   GAG   TAA   GGG   ACA
     Val   Tyr   Glu   Lys   Glu   Pro   Gly   Glu   Glu   Leu   Leu   Ile   Pro   Cys>
     _____IL-1RAcP_____>

800          810          820          830          840
       *     *     *     *     *     *     *     *     *
     ACG   GTC   TAT   TTT   AGT   TTT   CTG   ATG   GAT   TCT   CGC   AAT   GAG   GTT
     TGC   CAG   ATA   AAA   TCA   AAA   GAC   TAC   CTA   AGA   GCG   TTA   CTC   CAA
     Thr   Val   Tyr   Phe   Ser   Phe   Leu   Met   Asp   Ser   Arg   Asn   Glu   Val>
     _____IL-1RAcP_____>

850          860           870          880
       *     *     *     *     *     *     *     *
     TGG   TGG   ACC   ATT   GAT   GGA   AAA   AAA   CCT   GAT   GAC   ATC   ACT   ATT
     ACC   ACC   TGG   TAA   CTA   CCT   TTT   TTT   GGA   CTA   CTG   TAG   TGA   TAA
     Trp   Trp   Thr   Ile   Asp   Gly   Lys   Lys   Pro   Asp   Asp   Ile   Thr   Ile>
     _____IL-1RAcP_____>

890          900           910          920
       *     *     *     *     *     *     *     *
     GAT   GTC   ACC   ATT   AAC   GAA   AGT   ATA   AGT   CAT   AGT   AGA   ACA   GAA
     CTA   CAG   TGG   TAA   TTG   CTT   TCA   TAT   TCA   GTA   TCA   TCT   TGT   CTT
     Asp   Val   Thr   Ile   Asn   Glu   Ser   Ile   Ser   His   Ser   Arg   Thr   Glu>
     _____IL-1RAcP_____>

930          940           950          960
       *     *     *     *     *     *     *     *     *
     GAT   GAA   ACA   AGA   ACT   CAG   ATT   TTG   AGC   ATC   AAG   AAA   GTT   ACC
     CTA   CTT   TGT   TCT   TGA   GTC   TAA   AAC   TCG   TAG   TTC   TTT   CAA   TGG
     Asp   Glu   Thr   Arg   Thr   Gln   Ile   Leu   Ser   Ile   Lys   Lys   Val   Thr>
     _____IL-1RAcP_____>

970          980           990         1000
       *     *     *     *     *     *     *     *
     TCT   GAG   GAT   CTC   AAG   CGC   AGC   TAT   GTC   TGT   CAT   GCT   AGA   AGT
     AGA   CTC   CTA   GAG   TTC   GCG   TCG   ATA   CAG   ACA   GTA   CGA   TCT   TCA
     Ser   Glu   Asp   Leu   Lys   Arg   Ser   Tyr   Val   Cys   His   Ala   Arg   Ser>
     _____IL-1RAcP_____>
```

Figure 47D

```
      1010           1020           1030           1040          1050
       *       *      *       *      *      *       *      *      *
      GCC     AAA    GGC     GAA    GTT    GCC     AAA    GCA    GCC    AAG    GTG    AAG    CAG    AAA
      CGG     TTT    CCG     CTT    CAA    CGG     TTT    CGT    CGG    TTC    CAC    TTC    GTC    TTT
      Ala     Lys    Gly     Glu    Val    Ala     Lys    Ala    Ala    Lys    Val    Lys    Gln    Lys>
                                          _____IL-1RAcP_____>

1060           1070           1080          1090
              *      *       *      *      *       *      *      *
             GTG    CCA     GCT    CCA    AGA     TAC    ACA    GTG    CAC    ACA    GGG    GCT    GCC    AGA
             CAC    GGT     CGA    GGT    TCT     ATG    TGT    CAC    GTG    TGT    CCC    CGA    CGG    TCT
             Val    Pro     Ala    Pro    Arg     Tyr    Thr    Val>
             _____IL-1RAcP_____>
                                                          His    Thr    Gly    Ala    Ala    Arg>
                                                          _____IL-1RII_____>

1100           1110           1120          1130
              *      *       *      *      *       *      *      *
             AGC    TGC     CGG    TTT    CGT     GGG    AGG    CAT    TAC    AAG    CGG    GAG    TTC    AGG
             TCG    ACG     GCC    AAA    GCA     CCC    TCC    GTA    ATG    TTC    GCC    CTC    AAG    TCC
             Ser    Cys     Arg    Phe    Arg     Gly    Arg    His    Tyr    Lys    Arg    Glu    Phe    Arg>
             _____IL-1RII_____>

1140           1150           1160          1170
              *      *       *      *      *       *      *      *      *
             CTG    GAA     GGG    GAG    CCT     GTA    GCC    CTG    AGG    TGC    CCC    CAG    GTG    CCC
             GAC    CTT     CCC    CTC    GGA     CAT    CGG    GAC    TCC    ACG    GGG    GTC    CAC    GGG
             Leu    Glu     Gly    Glu    Pro     Val    Ala    Leu    Arg    Cys    Pro    Gln    Val    Pro>
             _____IL-1RII_____>

1180           1190           1200          1210
              *      *       *      *      *       *      *      *
             TAC    TGG     TTG    TGG    GCC     TCT    GTC    AGC    CCC    CGC    ATC    AAC    CTG    ACA
             ATG    ACC     AAC    ACC    CGG     AGA    CAG    TCG    GGG    GCG    TAG    TTG    GAC    TGT
             Tyr    Trp     Leu    Trp    Ala     Ser    Val    Ser    Pro    Arg    Ile    Asn    Leu    Thr>
             _____IL-1RII_____>

1220           1230           1240           1250          1260
       *       *      *       *      *      *       *      *      *
      TGG     CAT    AAA     AAT    GAC    TCT     GCT    AGG    ACG    GTC    CCA    GGA    GAA    GAA
      ACC     GTA    TTT     TTA    CTG    AGA     CGA    TCC    TGC    CAG    GGT    CCT    CTT    CTT
      Trp     His    Lys     Asn    Asp    Ser     Ala    Arg    Thr    Val    Pro    Gly    Glu    Glu>
                                          _____IL-1RII_____>

1270           1280           1290          1300
              *      *       *      *      *       *      *      *
             GAG    ACA     CGG    ATG    TGG     GCC    CAG    GAC    GGT    GCT    CTG    TGG    CTT    CTG
             CTC    TGT     GCC    TAC    ACC     CGG    GTC    CTG    CCA    CGA    GAC    ACC    GAA    GAC
             Glu    Thr     Arg    Met    Trp     Ala    Gln    Asp    Gly    Ala    Leu    Trp    Leu    Leu>
             _____IL-1RII_____>

1310           1320           1330          1340
              *      *       *      *      *       *      *      *
             CCA    GCC     TTG    CAG    GAG     GAC    TCT    GGC    ACC    TAC    GTC    TGC    ACT    ACT
             GGT    CGG     AAC    GTC    CTC     CTG    AGA    CCG    TGG    ATG    CAG    ACG    TGA    TGA
             Pro    Ala     Leu    Gln    Glu     Asp    Ser    Gly    Thr    Tyr    Val    Cys    Thr    Thr>
             _____IL-1RII_____>
```

Figure 47E

```
          1350            1360            1370            1380
            *       *       *       *       *       *       *       *
         AGA AAT GCT TCT TAC TGT GAC AAA ATG TCC ATT GAG CTC AGA
         TCT TTA CGA AGA ATG ACA CTG TTT TAC AGG TAA CTC GAG TCT
         Arg Asn Ala Ser Tyr Cys Asp Lys Met Ser Ile Glu Leu Arg>
         _____IL-1RII_____>

1390            1400            1410            1420
               *       *       *       *       *       *       *       *
         GTT TTT GAG AAT ACA GAT GCT TTC CTG CCG TTC ATC TCA TAC
         CAA AAA CTC TTA TGT CTA CGA AAG GAC GGC AAG TAG AGT ATG
         Val Phe Glu Asn Thr Asp Ala Phe Leu Pro Phe Ile Ser Tyr>
         _____IL-1RII_____>

1430            1440            1450            1460            1470
    *       *       *       *       *       *       *       *       *
 CCG CAA ATT TTA ACC TTG TCA ACC TCT GGG GTA TTA GTA TGC
 GGC GTT TAA AAT TGG AAC AGT TGG AGA CCC CAT AAT CAT ACG
 Pro Gln Ile Leu Thr Leu Ser Thr Ser Gly Val Leu Val Cys>
 _____IL-1RII_____>

1480            1490            1500            1510
               *       *       *       *       *       *       *       *
         CCT GAC CTG AGT GAA TTC ACC CGT GAC AAA ACT GAC GTG AAG
         GGA CTG GAC TCA CTT AAG TGG GCA CTG TTT TGA CTG CAC TTC
         Pro Asp Leu Ser Glu Phe Thr Arg Asp Lys Thr Asp Val Lys>
         _____IL-1RII_____>

1520            1530            1540            1550
             *       *       *       *       *       *       *       *
       ATT CAA TGG TAC AAG GAT TCT CTT CTT TTG GAT AAA GAC AAT
       TAA GTT ACC ATG TTC CTA AGA GAA GAA AAC CTA TTT CTG TTA
       Ile Gln Trp Tyr Lys Asp Ser Leu Leu Leu Asp Lys Asp Asn>
       _____IL-1RII_____>

1560            1570            1580            1590
               *       *       *       *       *       *       *       *
         GAG AAA TTT CTA AGT GTG AGG GGG ACC ACT CAC TTA CTC GTA
         CTC TTT AAA GAT TCA CAC TCC CCC TGG TGA GTG AAT GAG CAT
         Glu Lys Phe Leu Ser Val Arg Gly Thr Thr His Leu Leu Val>
         _____IL-1RII_____>

1600            1610            1620            1630
               *       *       *       *       *       *       *       *
         CAC GAT GTG GCC CTG GAA GAT GCT GGC TAT TAC CGC TGT GTC
         GTG CTA CAC CGG GAC CTT CTA CGA CCG ATA ATG GCG ACA CAG
         His Asp Val Ala Leu Glu Asp Ala Gly Tyr Tyr Arg Cys Val>
         _____IL-1RII_____>

1640            1650            1660            1670            1680
    *       *       *       *       *       *       *       *       *
 CTG ACA TTT GCC CAT GAA GGC CAG CAA TAC AAC ATC ACT AGG
 GAC TGT AAA CGG GTA CTT CCG GTC GTT ATG TTG TAG TGA TCC
 Leu Thr Phe Ala His Glu Gly Gln Gln Tyr Asn Ile Thr Arg>
 _____IL-1RII_____>
```

Figure 47F

```
              1690           1700           1710           1720
                *      *       *       *      *      *      *      *
            AGT ATT GAG CTA CGC ATC AAG AAA AAA AAA GAA GAG ACC ATT
            TCA TAA CTC GAT GCG TAG TTC TTT TTT TTT CTT CTC TGG TAA
            Ser Ile Glu Leu Arg Ile Lys Lys Lys Lys Glu Glu Thr Ile>
                                    ____IL-1RII_____>

1730           1740           1750           1760
                *      *       *       *      *      *      *      *
            CCT GTG ATC ATT TCC CCC CTC AAG ACC ATA TCA GCT TCT CTG
            GGA CAC TAG TAA AGG GGG GAG TTC TGG TAT AGT CGA AGA GAC
            Pro Val Ile Ile Ser Pro Leu Lys Thr Ile Ser Ala Ser Leu>
                                    ____IL-1RII_____>

1770           1780           1790           1800
              *       *       *      *       *      *      *      *      *
            GGG TCA AGA CTG ACA ATC CCA TGT AAG GTG TTT CTG GGA ACC
            CCC AGT TCT GAC TGT TAG GGT ACA TTC CAC AAA GAC CCT TGG
            Gly Ser Arg Leu Thr Ile Pro Cys Lys Val Phe Leu Gly Thr>
                                    ____IL-1RII_____>

1810           1820           1830           1840
             *      *       *       *      *       *      *      *
            GGC ACA CCC TTA ACC ACC ATG CTG TGG TGG ACG GCC AAT GAC
            CCG TGT GGG AAT TGG TGG TAC GAC ACC ACC TGC CGG TTA CTG
            Gly Thr Pro Leu Thr Thr Met Leu Trp Trp Thr Ala Asn Asp>
                                    ____IL-1RII_____>

1850           1860           1870           1880           1890
           *      *       *       *      *       *      *      *      *
            ACC CAC ATA GAG AGC GCC TAC CCG GGA GGC CGC GTG ACC GAG
            TGG GTG TAT CTC TCG CGG ATG GGC CCT CCG GCG CAC TGG CTC
            Thr His Ile Glu Ser Ala Tyr Pro Gly Gly Arg Val Thr Glu>
                                    ____IL-1RII_____>

1900           1910           1920           1930
                *      *       *       *      *      *      *      *
            GGG CCA CGC CAG GAA TAT TCA GAA AAT AAT GAG AAC TAC ATT
            CCC GGT GCG GTC CTT ATA AGT CTT TTA TTA CTC TTG ATG TAA
            Gly Pro Arg Gln Glu Tyr Ser Glu Asn Asn Glu Asn Tyr Ile>
                                    ____IL-1RII_____>

1940           1950           1960           1970
                *      *       *       *      *      *      *      *
            GAA GTG CCA TTG ATT TTT GAT CCT GTC ACA AGA GAG GAT TTG
            CTT CAC GGT AAC TAA AAA CTA GGA CAG TGT TCT CTC CTA AAC
            Glu Val Pro Leu Ile Phe Asp Pro Val Thr Arg Glu Asp Leu>
                                    ____IL-1RII_____>

1980           1990           2000           2010
                *      *       *       *      *      *      *      *
            CAC ATG GAT TTT AAA TGT GTT GTC CAT AAT ACC CTG AGT TTT
            GTG TAC CTA AAA TTT ACA CAA CAG GTA TTA TGG GAC TCA AAA
            His Met Asp Phe Lys Cys Val Val His Asn Thr Leu Ser Phe>
                                    ____IL-1RII_____>
```

Figure 47G

```
         2020           2030           2040            2050
           *              *      *       *        *      *      *
     CAG ACA CTA CGC ACC ACA GTC AAG GAA GCC TCC TCC ACG TTC
     GTC TGT GAT GCG TGG TGT CAG TTC CTT CGG AGG AGG TGC AAG
     Gln Thr Leu Arg Thr Thr Val Lys Glu Ala Ser Ser Thr Phe>
     _____IL-1RII_____>

2060           2070           2080           2090           2100
     *      *      *      *        *      *      *      *      *
     TCC GGA GAC AAA ACT CAC ACA TGC CCA CCG TGC CCA GCA CCT
     AGG CCT CTG TTT TGA GTG TGT ACG GGT GGC ACG GGT CGT GGA
     Ser Gly Asp Lys Thr His Thr Cys Pro Pro Cys Pro Ala Pro>
     _____FC-IgG1_____>

2110           2120           2130            2140
          *      *      *      *      *      *      *        *
     GAA CTC CTG GGG GGA CCG TCA GTC TTC CTC TTC CCC CCA AAA
     CTT GAG GAC CCC CCT GGC AGT CAG AAG GAG AAG GGG GGT TTT
     Glu Leu Leu Gly Gly Pro Ser Val Phe Leu Phe Pro Pro Lys>
     _____FC-IgG1_____>

2150           2160           2170           2180
          *      *      *      *      *      *      *      *
     CCC AAG GAC ACC CTC ATG ATC TCC CGG ACC CCT GAG GTC ACA
     GGG TTC CTG TGG GAG TAC TAG AGG GCC TGG GGA CTC CAG TGT
     Pro Lys Asp Thr Leu Met Ile Ser Arg Thr Pro Glu Val Thr>
     _____FC-IgG1_____>

2190           2200           2210            2220
       *      *      *      *      *      *      *      *     *
     TGC GTG GTG GTG GAC GTG AGC CAC GAA GAC CCT GAG GTC AAG
     ACG CAC CAC CAC CTG CAC TCG GTG CTT CTG GGA CTC CAG TTC
     Cys Val Val Val Asp Val Ser His Glu Asp Pro Glu Val Lys>
     _____FC-IgG1_____>

2230           2240           2250            2260
       *      *      *      *      *      *      *      *
     TTC AAC TGG TAC GTG GAC GGC GTG GAG GTG CAT AAT GCC AAG
     AAG TTG ACC ATG CAC CTG CCG CAC CTC CAC GTA TTA CGG TTC
     Phe Asn Trp Tyr Val Asp Gly Val Glu Val His Asn Ala Lys>
     _____FC-IgG1_____>

2270           2280           2290           2300           2310
     *      *      *      *      *      *      *      *      *
     ACA AAG CCG CGG GAG GAG CAG TAC AAC AGC ACG TAC CGT GTG
     TGT TTC GGC GCC CTC CTC GTC ATG TTG TCG TGC ATG GCA CAC
     Thr Lys Pro Arg Glu Glu Gln Tyr Asn Ser Thr Tyr Arg Val>
     _____FC-IgG1_____>

2320           2330           2340           2350
          *      *      *      *      *      *      *      *
     GTC AGC GTC CTC ACC GTC CTG CAC CAG GAC TGG CTG AAT GGC
     CAG TCG CAG GAG TGG CAG GAC GTG GTC CTG ACC GAC TTA CCG
     Val Ser Val Leu Thr Val Leu His Gln Asp Trp Leu Asn Gly>
     _____FC-IgG1_____>
```

Figure 47H

```
            2360            2370            2380            2390
       *       *       *       *       *       *       *       *
      AAG GAG TAC AAG TGC AAG GTC TCC AAC AAA GCC CTC CCA GCC
      TTC CTC ATG TTC ACG TTC CAG AGG TTG TTT CGG GAG GGT CGG
      Lys Glu Tyr Lys Cys Lys Val Ser Asn Lys Ala Leu Pro Ala>
      _____FC-IgG1_____>

2400            2410            2420            2430
       *       *       *       *       *       *       *       *
      CCC ATC GAG AAA ACC ATC TCC AAA GCC AAA GGG CAG CCC CGA
      GGG TAG CTC TTT TGG TAG AGG TTT CGG TTT CCC GTC GGG GCT
      Pro Ile Glu Lys Thr Ile Ser Lys Ala Lys Gly Gln Pro Arg>
      _____FC-IgG1_____>

2440            2450            2460            2470
       *       *       *       *       *       *       *       *
      GAA CCA CAG GTG TAC ACC CTG CCC CCA TCC CGG GAT GAG CTG
      CTT GGT GTC CAC ATG TGG GAC GGG GGT AGG GCC CTA CTC GAC
      Glu Pro Gln Val Tyr Thr Leu Pro Pro Ser Arg Asp Glu Leu>
      _____FC-IgG1_____>

2480            2490            2500            2510            2520
    *       *       *       *       *       *       *       *       *
   ACC AAG AAC CAG GTC AGC CTG ACC TGC CTG GTC AAA GGC TTC
   TGG TTC TTG GTC CAG TCG GAC TGG ACG GAC CAG TTT CCG AAG
   Thr Lys Asn Gln Val Ser Leu Thr Cys Leu Val Lys Gly Phe>
   _____FC-IgG1_____>

2530            2540            2550            2560
       *       *       *       *       *       *       *       *
      TAT CCC AGC GAC ATC GCC GTG GAG TGG GAG AGC AAT GGG CAG
      ATA GGG TCG CTG TAG CGG CAC CTC ACC CTC TCG TTA CCC GTC
      Tyr Pro Ser Asp Ile Ala Val Glu Trp Glu Ser Asn Gly Gln>
      _____FC-IgG1_____>

2570            2580            2590            2600
       *       *       *       *       *       *       *       *
      CCG GAG AAC AAC TAC AAG ACC ACG CCT CCC GTG CTG GAC TCC
      GGC CTC TTG TTG ATG TTC TGG TGC GGA GGG CAC GAC CTG AGG
      Pro Glu Asn Asn Tyr Lys Thr Thr Pro Pro Val Leu Asp Ser>
      _____FC-IgG1_____>

2610            2620            2630            2640
       *       *       *       *       *       *       *       *
      GAC GGC TCC TTC TTC CTC TAT AGC AAG CTC ACC GTG GAC AAG
      CTG CCG AGG AAG AAG GAG ATA TCG TTC GAG TGG CAC CTG TTC
      Asp Gly Ser Phe Phe Leu Tyr Ser Lys Leu Thr Val Asp Lys>
      _____FC-IgG1_____>

2650            2660            2670            2680
       *       *       *       *       *       *       *       *
      AGC AGG TGG CAG CAG GGG AAC GTC TTC TCA TGC TCC GTG ATG
      TCG TCC ACC GTC GTC CCC TTG CAG AAG AGT ACG AGG CAC TAC
      Ser Arg Trp Gln Gln Gly Asn Val Phe Ser Cys Ser Val Met>
      _____FC-IgG1_____>
```

Figure 47 I

```
    2690         2700         2710         2720         2730
      *       *     *       *     *       *     *       *     *
    CAT  GAG  GCT  CTG  CAC  AAC  CAC  TAC  ACG  CAG  AAG  AGC  CTC  TCC
    GTA  CTC  CGA  GAC  GTG  TTG  GTG  ATG  TGC  GTC  TTC  TCG  GAG  AGG
    His  Glu  Ala  Leu  His  Asn  His  Tyr  Thr  Gln  Lys  Ser  Leu  Ser>
    _____FC-IgG1_____>

2740
            *     *     *
    CTG  TCT  CCG  GGT  AAA  TGA
    GAC  AGA  GGC  CCA  TTT  ACT
    Leu  Ser  Pro  Gly  Lys  ***>
          _____FC-IgG1_____>
```

Figure 48A

```
               10             20             30             40
         *      *      *      *      *      *      *      *
    ATG GTG CTT CTG TGG TGT GTA GTG AGT CTC TAC TTT TAT GGA
    TAC CAC GAA GAC ACC ACA CAT CAC TCA GAG ATG AAA ATA CCT
    Met Val Leu Leu Trp Cys Val Val Ser Leu Tyr Phe Tyr Gly>
    _____SIGNAL PEPTIDE_____>
    _____IL-1RAcP_____>

50             60             70             80
       *      *      *      *      *      *      *      *
    ATC CTG CAA AGT GAT GCC TCA GAA CGC TGC GAT GAC TGG GGA
    TAG GAC GTT TCA CTA CGG AGT CTT GCG ACG CTA CTG ACC CCT
    Ile Leu Gln Ser Asp Ala>
    _____SIGNAL PEPTIDE_____>
                            Ser Glu Arg Cys Asp Asp Trp Gly>
                            _____IL-1RAcP_____>

90            100            110            120
      *     *      *      *      *      *      *      *      *
    CTA GAC ACC ATG AGG CAA ATC CAA GTG TTT GAA GAT GAG CCA
    GAT CTG TGG TAC TCC GTT TAG GTT CAC AAA CTT CTA CTC GGT
    Leu Asp Thr Met Arg Gln Ile Gln Val Phe Glu Asp Glu Pro>
    _____IL-1RAcP_____>

130            140            150            160
      *      *      *      *      *      *      *      *
    GCT CGC ATC AAG TGC CCA CTC TTT GAA CAC TTC TTG AAA TTC
    CGA GCG TAG TTC ACG GGT GAG AAA CTT GTG AAG AAC TTT AAG
    Ala Arg Ile Lys Cys Pro Leu Phe Glu His Phe Leu Lys Phe>
    _____IL-1RAcP_____>

170           180            190            200           210
      *     *      *      *      *      *      *      *      *
    AAC TAC AGC ACA GCC CAT TCA GCT GGC CTT ACT CTG ATC TGG
    TTG ATG TCG TGT CGG GTA AGT CGA CCG GAA TGA GAC TAG ACC
    Asn Tyr Ser Thr Ala His Ser Ala Gly Leu Thr Leu Ile Trp>
    _____IL-1RAcP_____>

220            230            240            250
       *      *      *      *      *      *      *      *
    TAT TGG ACT AGG CAG GAC CGG GAC CTT GAG GAG CCA ATT AAC
    ATA ACC TGA TCC GTC CTG GCC CTG GAA CTC CTC GGT TAA TTG
    Tyr Trp Thr Arg Gln Asp Arg Asp Leu Glu Glu Pro Ile Asn>
    _____IL-1RAcP_____>

260            270            280            290
       *      *      *      *      *      *      *      *
    TTC CGC CTC CCC GAG AAC CGC ATT AGT AAG GAG AAA GAT GTG
    AAG GCG GAG GGG CTC TTG GCG TAA TCA TTC CTC TTT CTA CAC
    Phe Arg Leu Pro Glu Asn Arg Ile Ser Lys Glu Lys Asp Val>
    _____IL-1RAcP_____>

300            310            320            330
       *      *      *      *      *      *      *      *      *
    CTG TGG TTC CGG CCC ACT CTC CTC AAT GAC ACT GGC AAC TAT
    GAC ACC AAG GCC GGG TGA GAG GAG TTA CTG TGA CCG TTG ATA
    Leu Trp Phe Arg Pro Thr Leu Leu Asn Asp Thr Gly Asn Tyr>
    _____IL-1RAcP_____>
```

Figure 48B

```
         340           350           360           370
          *    *    *    *    *    *    *    *
        ACC  TGC  ATG  TTA  AGG  AAC  ACT  ACA  TAT  TGC  AGC  AAA  GTT  GCA
        TGG  ACG  TAC  AAT  TCC  TTG  TGA  TGT  ATA  ACG  TCG  TTT  CAA  CGT
        Thr  Cys  Met  Leu  Arg  Asn  Thr  Thr  Tyr  Cys  Ser  Lys  Val  Ala>
        _____IL-1RAcP_____>

380           390           400           410           420
          *    *    *    *    *    *    *    *    *    *
        TTT  CCC  TTG  GAA  GTT  GTT  CAA  AAA  GAC  AGC  TGT  TTC  AAT  TCC
        AAA  GGG  AAC  CTT  CAA  CAA  GTT  TTT  CTG  TCG  ACA  AAG  TTA  AGG
        Phe  Pro  Leu  Glu  Val  Val  Gln  Lys  Asp  Ser  Cys  Phe  Asn  Ser>
        _____IL-1RAcP_____>

430           440           450           460
           *    *    *    *    *    *    *    *
         CCC  ATG  AAA  CTC  CCA  GTG  CAT  AAA  CTG  TAT  ATA  GAA  TAT  GGC
         GGG  TAC  TTT  GAG  GGT  CAC  GTA  TTT  GAC  ATA  TAT  CTT  ATA  CCG
         Pro  Met  Lys  Leu  Pro  Val  His  Lys  Leu  Tyr  Ile  Glu  Tyr  Gly>
         _____IL-1RAcP_____>

470           480           490           500
           *    *    *    *    *    *    *    *
         ATT  CAG  AGG  ATC  ACT  TGT  CCA  AAT  GTA  GAT  GGA  TAT  TTT  CCT
         TAA  GTC  TCC  TAG  TGA  ACA  GGT  TTA  CAT  CTA  CCT  ATA  AAA  GGA
         Ile  Gln  Arg  Ile  Thr  Cys  Pro  Asn  Val  Asp  Gly  Tyr  Phe  Pro>
         _____IL-1RAcP_____>

510           520           530           540
           *    *    *    *    *    *    *    *    *
         TCC  AGT  GTC  AAA  CCG  ACT  ATC  ACT  TGG  TAT  ATG  GGC  TGT  TAT
         AGG  TCA  CAG  TTT  GGC  TGA  TAG  TGA  ACC  ATA  TAC  CCG  ACA  ATA
         Ser  Ser  Val  Lys  Pro  Thr  Ile  Thr  Trp  Tyr  Met  Gly  Cys  Tyr>
         _____IL-1RAcP_____>

550           560           570           580
           *    *    *    *    *    *    *    *
         AAA  ATA  CAG  AAT  TTT  AAT  AAT  GTA  ATA  CCC  GAA  GGT  ATG  AAC
         TTT  TAT  GTC  TTA  AAA  TTA  TTA  CAT  TAT  GGG  CTT  CCA  TAC  TTG
         Lys  Ile  Gln  Asn  Phe  Asn  Asn  Val  Ile  Pro  Glu  Gly  Met  Asn>
         _____IL-1RAcP_____>

590           600           610           620           630
          *    *    *    *    *    *    *    *    *
        TTG  AGT  TTC  CTC  ATT  GCC  TTA  ATT  TCA  AAT  AAT  GGA  AAT  TAC
        AAC  TCA  AAG  GAG  TAA  CGG  AAT  TAA  AGT  TTA  TTA  CCT  TTA  ATG
        Leu  Ser  Phe  Leu  Ile  Ala  Leu  Ile  Ser  Asn  Asn  Gly  Asn  Tyr>
        _____IL-1RAcP_____>

640           650           660           670
            *    *    *    *    *    *    *    *
          ACA  TGT  GTT  GTT  ACA  TAT  CCA  GAA  AAT  GGA  CGT  ACG  TTT  CAT
          TGT  ACA  CAA  CAA  TGT  ATA  GGT  CTT  TTA  CCT  GCA  TGC  AAA  GTA
          Thr  Cys  Val  Val  Thr  Tyr  Pro  Glu  Asn  Gly  Arg  Thr  Phe  His>
          _____IL-1RAcP_____>
```

Figure 48C

```
              680           690            700           710
       *       *      *      *       *      *      *       *
      CTC ACC AGG ACT CTG ACT GTA AAG GTA GTA GGC TCT CCA AAA
      GAG TGG TCC TGA GAC TGA CAT TTC CAT CAT CCG AGA GGT TTT
      Leu Thr Arg Thr Leu Thr Val Lys Val Val Gly Ser Pro Lys>
      _____IL-1RAcP_____>

720           730            740           750
       *       *      *      *       *      *      *       *      *
      AAT GCA GTG CCC CCT GTG ATC CAT TCA CCT AAT GAT CAT GTG
      TTA CGT CAC GGG GGA CAC TAG GTA AGT GGA TTA CTA GTA CAC
      Asn Ala Val Pro Pro Val Ile His Ser Pro Asn Asp His Val>
      _____IL-1RAcP_____>

760           770            780           790
       *       *      *      *       *      *      *       *
      GTC TAT GAG AAA GAA CCA GGA GAG GAG CTA CTC ATT CCC TGT
      CAG ATA CTC TTT CTT GGT CCT CTC CTC GAT GAG TAA GGG ACA
      Val Tyr Glu Lys Glu Pro Gly Glu Glu Leu Leu Ile Pro Cys>
      _____IL-1RAcP_____>

800           810           820            830           840
       *      *      *      *      *       *      *      *       *
      ACG GTC TAT TTT AGT TTT CTG ATG GAT TCT CGC AAT GAG GTT
      TGC CAG ATA AAA TCA AAA GAC TAC CTA AGA GCG TTA CTC CAA
      Thr Val Tyr Phe Ser Phe Leu Met Asp Ser Arg Asn Glu Val>
      _____IL-1RAcP_____>

850           860            870           880
       *       *      *      *       *      *      *       *
      TGG TGG ACC ATT GAT GGA AAA AAA CCT GAT GAC ATC ACT ATT
      ACC ACC TGG TAA CTA CCT TTT TTT GGA CTA CTG TAG TGA TAA
      Trp Trp Thr Ile Asp Gly Lys Lys Pro Asp Asp Ile Thr Ile>
      _____IL-1RAcP_____>

890           900            910           920
       *       *      *      *       *      *      *       *
      GAT GTC ACC ATT AAC GAA AGT ATA AGT CAT AGT AGA ACA GAA
      CTA CAG TGG TAA TTG CTT TCA TAT TCA GTA TCA TCT TGT CTT
      Asp Val Thr Ile Asn Glu Ser Ile Ser His Ser Arg Thr Glu>
      _____IL-1RAcP_____>

930           940            950           960
       *       *      *      *       *      *      *       *
      GAT GAA ACA AGA ACT CAG ATT TTG AGC ATC AAG AAA GTT ACC
      CTA CTT TGT TCT TGA GTC TAA AAC TCG TAG TTC TTT CAA TGG
      Asp Glu Thr Arg Thr Gln Ile Leu Ser Ile Lys Lys Val Thr>
      _____IL-1RAcP_____>

970           980            990          1000
       *      *       *      *       *      *      *       *
      TCT GAG GAT CTC AAG CGC AGC TAT GTC TGT CAT GCT AGA AGT
      AGA CTC CTA GAG TTC GCG TCG ATA CAG ACA GTA CGA TCT TCA
      Ser Glu Asp Leu Lys Arg Ser Tyr Val Cys His Ala Arg Ser>
      _____IL-1RAcP_____>
```

Figure 48D

```
      1010           1020          1030          1040          1050
       *       *      *      *      *      *      *      *      *
      GCC    AAA    GGC    GAA    GTT    GCC    AAA    GCA    GCC    AAG    GTG    AAG    CAG    AAA
      CGG    TTT    CCG    CTT    CAA    CGG    TTT    CGT    CGG    TTC    CAC    TTC    GTC    TTT
      Ala    Lys    Gly    Glu    Val    Ala    Lys    Ala    Ala    Lys    Val    Lys    Gln    Lys>
      _____IL-1RAcP_____>

1060          1070          1080          1090
            *       *      *      *      *      *      *      *
           GTG    CCA    GCT    CCA    AGA    TAC    ACA    GTG    CAC    ACA    GGG    GCT    GCC    AGA
           CAC    GGT    CGA    GGT    TCT    ATG    TGT    CAC    GTG    TGT    CCC    CGA    CGG    TCT
           Val    Pro    Ala    Pro    Arg    Tyr    Thr    Val>
           _____IL-1RAcP_____>
                                                           His    Thr    Gly    Ala    Ala    Arg>
                                                           _____IL-1RII_____>

1100          1110          1120          1130
         *       *      *      *      *      *      *      *
        AGC    TGC    CGG    TTT    CGT    GGG    AGG    CAT    TAC    AAG    CGG    GAG    TTC    AGG
        TCG    ACG    GCC    AAA    GCA    CCC    TCC    GTA    ATG    TTC    GCC    CTC    AAG    TCC
        Ser    Cys    Arg    Phe    Arg    Gly    Arg    His    Tyr    Lys    Arg    Glu    Phe    Arg>
        _____IL-1RII_____>

1140          1150          1160          1170
        *       *      *      *      *      *      *      *      *
       CTG    GAA    GGG    GAG    CCT    GTA    GCC    CTG    AGG    TGC    CCC    CAG    GTG    CCC
       GAC    CTT    CCC    CTC    GGA    CAT    CGG    GAC    TCC    ACG    GGG    GTC    CAC    GGG
       Leu    Glu    Gly    Glu    Pro    Val    Ala    Leu    Arg    Cys    Pro    Gln    Val    Pro>
       _____IL-1RII_____>

1180          1190          1200          1210
        *       *      *      *      *      *      *      *
       TAC    TGG    TTG    TGG    GCC    TCT    GTC    AGC    CCC    CGC    ATC    AAC    CTG    ACA
       ATG    ACC    AAC    ACC    CGG    AGA    CAG    TCG    GGG    GCG    TAG    TTG    GAC    TGT
       Tyr    Trp    Leu    Trp    Ala    Ser    Val    Ser    Pro    Arg    Ile    Asn    Leu    Thr>
       _____IL-1RII_____>

1220          1230          1240          1250          1260
      *       *      *      *      *      *      *      *      *
     TGG    CAT    AAA    AAT    GAC    TCT    GCT    AGG    ACG    GTC    CCA    GGA    GAA    GAA
     ACC    GTA    TTT    TTA    CTG    AGA    CGA    TCC    TGC    CAG    GGT    CCT    CTT    CTT
     Trp    His    Lys    Asn    Asp    Ser    Ala    Arg    Thr    Val    Pro    Gly    Glu    Glu>
     _____IL-1RII_____>

1270          1280          1290          1300
         *       *      *      *      *      *      *      *
        GAG    ACA    CGG    ATG    TGG    GCC    CAG    GAC    GGT    GCT    CTG    TGG    CTT    CTG
        CTC    TGT    GCC    TAC    ACC    CGG    GTC    CTG    CCA    CGA    GAC    ACC    GAA    GAC
        Glu    Thr    Arg    Met    Trp    Ala    Gln    Asp    Gly    Ala    Leu    Trp    Leu    Leu>
        _____IL-1RII_____>

1310          1320          1330          1340
         *       *      *      *      *      *      *      *
        CCA    GCC    TTG    CAG    GAG    GAC    TCT    GGC    ACC    TAC    GTC    TGC    ACT    ACT
        GGT    CGG    AAC    GTC    CTC    CTG    AGA    CCG    TGG    ATG    CAG    ACG    TGA    TGA
        Pro    Ala    Leu    Gln    Glu    Asp    Ser    Gly    Thr    Tyr    Val    Cys    Thr    Thr>
        _____IL-1RII_____>
```

Figure 48E

```
         1350              1360             1370             1380
           *       *         *       *        *       *        *       *        *
         AGA AAT GCT TCT TAC TGT GAC AAA ATG TCC ATT GAG CTC AGA
         TCT TTA CGA AGA ATG ACA CTG TTT TAC AGG TAA CTC GAG TCT
         Arg Asn Ala Ser Tyr Cys Asp Lys Met Ser Ile Glu Leu Arg>
         _____IL-1RII_____>

1390              1400              1410              1420
              *       *         *         *       *         *       *       *
            GTT TTT GAG AAT ACA GAT GCT TTC CTG CCG TTC ATC TCA TAC
            CAA AAA CTC TTA TGT CTA CGA AAG GAC GGC AAG TAG AGT ATG
            Val Phe Glu Asn Thr Asp Ala Phe Leu Pro Phe Ile Ser Tyr>
            _____IL-1RII_____>

1430              1440              1450              1460              1470
        *         *       *         *       *         *        *        *        *
      CCG CAA ATT TTA ACC TTG TCA ACC TCT GGG GTA TTA GTA TGC
      GGC GTT TAA AAT TGG AAC AGT TGG AGA CCC CAT AAT CAT ACG
      Pro Gln Ile Leu Thr Leu Ser Thr Ser Gly Val Leu Val Cys>
      _____IL-1RII_____>

1480              1490              1500              1510
              *         *       *         *         *         *        *        *
            CCT GAC CTG AGT GAA TTC ACC CGT GAC AAA ACT GAC GTG AAG
            GGA CTG GAC TCA CTT AAG TGG GCA CTG TTT TGA CTG CAC TTC
            Pro Asp Leu Ser Glu Phe Thr Arg Asp Lys Thr Asp Val Lys>
            _____IL-1RII_____>

1520              1530              1540              1550
           *         *        *        *        *         *        *        *
         ATT CAA TGG TAC AAG GAT TCT CTT CTT TTG GAT AAA GAC AAT
         TAA GTT ACC ATG TTC CTA AGA GAA GAA AAC CTA TTT CTG TTA
         Ile Gln Trp Tyr Lys Asp Ser Leu Leu Leu Asp Lys Asp Asn>
         _____IL-1RII_____>

1560              1570              1580              1590
          *         *        *         *        *         *       *        *        *
         GAG AAA TTT CTA AGT GTG AGG GGG ACC ACT CAC TTA CTC GTA
         CTC TTT AAA GAT TCA CAC TCC CCC TGG TGA GTG AAT GAG CAT
         Glu Lys Phe Leu Ser Val Arg Gly Thr Thr His Leu Leu Val>
         _____IL-1RII_____>

1600              1610              1620              1630
           *        *         *        *         *        *        *        *
         CAC GAT GTG GCC CTG GAA GAT GCT GGC TAT TAC CGC TGT GTC
         GTG CTA CAC CGG GAC CTT CTA CGA CCG ATA ATG GCG ACA CAG
         His Asp Val Ala Leu Glu Asp Ala Gly Tyr Tyr Arg Cys Val>
         _____IL-1RII_____>

1640              1650              1660              1670              1680
        *         *        *         *        *         *        *         *        *
      CTG ACA TTT GCC CAT GAA GGC CAG CAA TAC AAC ATC ACT AGG
      GAC TGT AAA CGG GTA CTT CCG GTC GTT ATG TTG TAG TGA TCC
      Leu Thr Phe Ala His Glu Gly Gln Gln Tyr Asn Ile Thr Arg>
      _____IL-1RII_____>
```

Figure 48F

```
          1690           1700           1710          1720
      *      *      *      *      *      *      *      *
AGT  ATT  GAG  CTA  CGC  ATC  AAG  AAA  AAA  AAA  GAA  GAG  ACC  ATT
TCA  TAA  CTC  GAT  GCG  TAG  TTC  TTT  TTT  TTT  CTT  CTC  TGG  TAA
Ser  Ile  Glu  Leu  Arg  Ile  Lys  Lys  Lys  Lys  Glu  Glu  Thr  Ile>
_____IL-1RII_____>

1730           1740           1750          1760
      *      *      *      *      *      *      *      *
CCT  GTG  ATC  ATT  TCC  CCC  CTC  AAG  ACC  ATA  TCA  GCT  TCT  CTG
GGA  CAC  TAG  TAA  AGG  GGG  GAG  TTC  TGG  TAT  AGT  CGA  AGA  GAC
Pro  Val  Ile  Ile  Ser  Pro  Leu  Lys  Thr  Ile  Ser  Ala  Ser  Leu>
_____IL-1RII_____>

1770           1780           1790          1800
      *      *      *      *      *      *      *      *      *
GGG  TCA  AGA  CTG  ACA  ATC  CCA  TGT  AAG  GTG  TTT  CTG  GGA  ACC
CCC  AGT  TCT  GAC  TGT  TAG  GGT  ACA  TTC  CAC  AAA  GAC  CCT  TGG
Gly  Ser  Arg  Leu  Thr  Ile  Pro  Cys  Lys  Val  Phe  Leu  Gly  Thr>
_____IL-1RII_____>

1810           1820           1830          1840
      *      *      *      *      *      *      *      *
GGC  ACA  CCC  TTA  ACC  ACC  ATG  CTG  TGG  TGG  ACG  GCC  AAT  GAC
CCG  TGT  GGG  AAT  TGG  TGG  TAC  GAC  ACC  ACC  TGC  CGG  TTA  CTG
Gly  Thr  Pro  Leu  Thr  Thr  Met  Leu  Trp  Trp  Thr  Ala  Asn  Asp>
_____IL-1RII_____>

1850           1860           1870          1880           1890
  *      *      *      *      *      *      *      *      *
ACC  CAC  ATA  GAG  AGC  GCC  TAC  CCG  GGA  GGC  CGC  GTG  ACC  GAG
TGG  GTG  TAT  CTC  TCG  CGG  ATG  GGC  CCT  CCG  GCG  CAC  TGG  CTC
Thr  His  Ile  Glu  Ser  Ala  Tyr  Pro  Gly  Gly  Arg  Val  Thr  Glu>
_____IL-1RII_____>

1900           1910          1920           1930
      *      *      *      *      *      *      *      *
GGG  CCA  CGC  CAG  GAA  TAT  TCA  GAA  AAT  AAT  GAG  AAC  TAC  ATT
CCC  GGT  GCG  GTC  CTT  ATA  AGT  CTT  TTA  TTA  CTC  TTG  ATG  TAA
Gly  Pro  Arg  Gln  Glu  Tyr  Ser  Glu  Asn  Asn  Glu  Asn  Tyr  Ile>
_____IL-1RII_____>

1940           1950          1960           1970
      *      *      *      *      *      *      *      *
GAA  GTG  CCA  TTG  ATT  TTT  GAT  CCT  GTC  ACA  AGA  GAG  GAT  TTG
CTT  CAC  GGT  AAC  TAA  AAA  CTA  GGA  CAG  TGT  TCT  CTC  CTA  AAC
Glu  Val  Pro  Leu  Ile  Phe  Asp  Pro  Val  Thr  Arg  Glu  Asp  Leu>
_____IL-1RII_____>

1980           1990          2000           2010
      *      *      *      *      *      *      *      *      *
CAC  ATG  GAT  TTT  AAA  TGT  GTT  GTC  CAT  AAT  ACC  CTG  AGT  TTT
GTG  TAC  CTA  AAA  TTT  ACA  CAA  CAG  GTA  TTA  TGG  GAC  TCA  AAA
His  Met  Asp  Phe  Lys  Cys  Val  Val  His  Asn  Thr  Leu  Ser  Phe>
_____IL-1RII_____>
```

Figure 48G

```
        2020          2030          2040          2050
          *             *     *       *     *       *     *
        CAG ACA CTA CGC ACC ACA GTC AAG GAA GCC TCC TCC ACG TTC
        GTC TGT GAT GCG TGG TGT CAG TTC CTT CGG AGG AGG TGC AAG
        Gln Thr Leu Arg Thr Thr Val Lys Glu Ala Ser Ser Thr Phe>
        _____IL-1RII_____>

2060          2070          2080          2090          2100
    *     *       *     *       *     *       *     *       *
  TCC GGA GAG TCC AAA TAC GGT CCG CCA TGC CCA TCA TGC CCA
  AGG CCT CTC AGG TTT ATG CCA GGC GGT ACG GGT AGT ACG GGT
  Ser Gly>
  _____>
              Glu Ser Lys Tyr Gly Pro Pro Cys Pro Ser Cys Pro>
                          _____FC-IgG4_____>

2110          2120          2130          2140
                *     *       *     *       *     *       *     *
            GCA CCT GAG TTC CTG GGG GGA CCA TCA GTC TTC CTG TTC CCC
            CGT GGA CTC AAG GAC CCC CCT GGT AGT CAG AAG GAC AAG GGG
            Ala Pro Glu Phe Leu Gly Gly Pro Ser Val Phe Leu Phe Pro>
            _____FC-IgG4_____>

2150          2160          2170          2180
              *     *       *     *       *     *       *     *
            CCA AAA CCC AAG GAC ACT CTC ATG ATC TCC CGG ACC CCT GAG
            GGT TTT GGG TTC CTG TGA GAG TAC TAG AGG GCC TGG GGA CTC
            Pro Lys Pro Lys Asp Thr Leu Met Ile Ser Arg Thr Pro Glu>
            _____FC-IgG4_____>

2190          2200          2210          2220
              *     *       *     *       *.    *       *     *
            GTC ACG TGC GTG GTG GTG GAC GTG AGC CAG GAA GAC CCC GAG
            CAG TGC ACG CAC CAC CAC CTG CAC TCG GTC CTT CTG GGG CTC
            Val Thr Cys Val Val Val Asp Val Ser Gln Glu Asp Pro Glu>
            _____FC-IgG4_____>

2230          2240          2250          2260
          *     *       *     *       *     *       *     *
        GTC CAG TTC AAC TGG TAC GTG GAT GGC GTG GAG GTG CAT AAT
        CAG GTC AAG TTG ACC ATG CAC CTA CCG CAC CTC CAC GTA TTA
        Val Gln Phe Asn Trp Tyr Val Asp Gly Val Glu Val His Asn>
        _____FC-IgG4_____>

2270          2280          2290          2300          2310
    *     *       *     *       *     *       *     *       *
  GCC AAG ACA AAG CCG CGG GAG GAG CAG TTC AAC AGC ACG TAC
  CGG TTC TGT TTC GGC GCC CTC CTC GTC AAG TTG TCG TGC ATG
  Ala Lys Thr Lys Pro Arg Glu Glu Gln Phe Asn Ser Thr Tyr>
  _____FC-IgG4_____>

2320          2330          2340          2350
                *     *       *     *       *     *       *     *
            CGT GTG GTC AGC GTC CTC ACC GTC CTG CAC CAG GAC TGG CTG
            GCA CAC CAG TCG CAG GAG TGG CAG GAC GTG GTC CTG ACC GAC
            Arg Val Val Ser Val Leu Thr Val Leu His Gln Asp Trp Leu>
            _____FC-IgG4_____>
```

Figure 48H

```
           2360           2370           2380           2390
    *       *       *       *       *       *       *       *
   AAC     GGC     AAG     GAG     TAC     AAG     TGC     AAG     GTC     TCC     AAC     AAA     GGC     CTC
   TTG     CCG     TTC     CTC     ATG     TTC     ACG     TTC     CAG     AGG     TTG     TTT     CCG     GAG
   Asn     Gly     Lys     Glu     Tyr     Lys     Cys     Lys     Val     Ser     Asn     Lys     Gly     Leu>
                                            FC-IgG4                                                         >

2400           2410           2420           2430
    *       *       *       *       *       *       *       *       *
   CCG     TCC     TCC     ATC     GAG     AAA     ACC     ATC     TCC     AAA     GCC     AAA     GGG     CAG
   GGC     AGG     AGG     TAG     CTC     TTT     TGG     TAG     AGG     TTT     CGG     TTT     CCC     GTC
   Pro     Ser     Ser     Ile     Glu     Lys     Thr     Ile     Ser     Lys     Ala     Lys     Gly     Gln>
                                            FC-IgG4                                                         >

2440           2450           2460           2470
    *       *       *       *       *       *       *       *
   CCC     CGA     GAG     CCA     CAG     GTG     TAC     ACC     CTG     CCC     CCA     TCC     CAG     GAG
   GGG     GCT     CTC     GGT     GTC     CAC     ATG     TGG     GAC     GGG     GGT     AGG     GTC     CTC
   Pro     Arg     Glu     Pro     Gln     Val     Tyr     Thr     Leu     Pro     Pro     Ser     Gln     Glu>
                                            FC-IgG4                                                         >

2480           2490           2500           2510           2520
    *       *       *       *       *       *       *       *       *       *
   GAG     ATG     ACC     AAG     AAC     CAG     GTC     AGC     CTG     ACC     TGC     CTG     GTC     AAA
   CTC     TAC     TGG     TTC     TTG     GTC     CAG     TCG     GAC     TGG     ACG     GAC     CAG     TTT
   Glu     Met     Thr     Lys     Asn     Gln     Val     Ser     Leu     Thr     Cys     Leu     Val     Lys>
                                            FC-IgG4                                                         >

2530           2540           2550           2560
    *       *       *       *       *       *       *       *
   GGC     TTC     TAC     CCC     AGC     GAC     ATC     GCC     GTG     GAG     TGG     GAG     AGC     AAT
   CCG     AAG     ATG     GGG     TCG     CTG     TAG     CGG     CAC     CTC     ACC     CTC     TCG     TTA
   Gly     Phe     Tyr     Pro     Ser     Asp     Ile     Ala     Val     Glu     Trp     Glu     Ser     Asn>
                                            FC-IgG4                                                         >

2570           2580           2590           2600
    *       *       *       *       *       *       *       *
   GGG     CAG     CCG     GAG     AAC     AAC     TAC     AAG     ACC     ACG     CCT     CCC     GTG     CTG
   CCC     GTC     GGC     CTC     TTG     TTG     ATG     TTC     TGG     TGC     GGA     GGG     CAC     GAC
   Gly     Gln     Pro     Glu     Asn     Asn     Tyr     Lys     Thr     Thr     Pro     Pro     Val     Leu>
                                            FC-IgG4                                                         >

2610           2620           2630           2640
    *       *       *       *       *       *       *       *       *
   GAC     TCC     GAC     GGC     TCC     TTC     TTC     CTC     TAC     AGC     AGG     CTA     ACC     GTG
   CTG     AGG     CTG     CCG     AGG     AAG     AAG     GAG     ATG     TCG     TCC     GAT     TGG     CAC
   Asp     Ser     Asp     Gly     Ser     Phe     Phe     Leu     Tyr     Ser     Arg     Leu     Thr     Val>
                                            FC-IgG4                                                         >

2650           2660           2670           2680
    *       *       *       *       *       *       *       *
   GAC     AAG     AGC     AGG     TGG     CAG     GAG     GGG     AAT     GTC     TTC     TCA     TGC     TCC
   CTG     TTC     TCG     TCC     ACC     GTC     CTC     CCC     TTA     CAG     AAG     AGT     ACG     AGG
   Asp     Lys     Ser     Arg     Trp     Gln     Glu     Gly     Asn     Val     Phe     Ser     Cys     Ser>
                                            FC-IgG4                                                         >
```

Figure 48 I

```
2690           2700           2710           2720           2730
  *          *      *       *      *       *      *       *      *
GTG ATG CAT GAG GCT CTG CAC AAC CAC TAC ACA CAG AAG AGC
CAC TAC GTA CTC CGA GAC GTG TTG GTG ATG TGT GTC TTC TCG
Val Met His Glu Ala Leu His Asn His Tyr Thr Gln Lys Ser>
_____FC-IgG4_____>

2740           2750
         *      *      *      *
CTC TCC CTG TCT CTG GGT AAA TGA
GAG AGG GAC AGA GAC CCA TTT ACT
Leu Ser Leu Ser Leu Gly Lys ***>
_____FC-IgG4_____>
```

Figure 49A

```
           10              20              30              40
   *        *     *        *     *        *     *        *
ATG GTG CTT CTG TGG TGT GTA GTG AGT CTC TAC TTT TAT GGA
TAC CAC GAA GAC ACC ACA CAT CAC TCA GAG ATG AAA ATA CCT
Met Val Leu Leu Trp Cys Val Val Ser Leu Tyr Phe Tyr Gly>
_____SIGNAL PEPTIDE_____>
_____IL-1RAcP_____>

50              60              70              80
   *        *     *        *     *        *     *        *
ATC CTG CAA AGT GAT GCC TCA GAA CGC TGC GAT GAC TGG GGA
TAG GAC GTT TCA CTA CGG AGT CTT GCG ACG CTA CTG ACC CCT
Ile Leu Gln Ser Asp Ala>
____ SIGNAL PEPTIDE_____>
                        Ser Glu Arg Cys Asp Asp Trp Gly>
                        _____IL-1RAcP_____>

90             100             110             120
   *        *     *        *     *        *     *        *
CTA GAC ACC ATG AGG CAA ATC CAA GTG TTT GAA GAT GAG CCA
GAT CTG TGG TAC TCC GTT TAG GTT CAC AAA CTT CTA CTC GGT
Leu Asp Thr Met Arg Gln Ile Gln Val Phe Glu Asp Glu Pro>
_____IL-1RAcP_____>

130             140             150             160
     *     *        *     *        *     *        *     *
GCT CGC ATC AAG TGC CCA CTC TTT GAA CAC TTC TTG AAA TTC
CGA GCG TAG TTC ACG GGT GAG AAA CTT GTG AAG AAC TTT AAG
Ala Arg Ile Lys Cys Pro Leu Phe Glu His Phe Leu Lys Phe>
_____IL-1RAcP_____>

170             180             190             200             210
  *     *        *     *        *     *        *     *        *
AAC TAC AGC ACA GCC CAT TCA GCT GGC CTT ACT CTG ATC TGG
TTG ATG TCG TGT CGG GTA AGT CGA CCG GAA TGA GAC TAG ACC
Asn Tyr Ser Thr Ala His Ser Ala Gly Leu Thr Leu Ile Trp>
_____IL-1RAcP_____>

220             230             240             250
   *        *     *        *     *        *     *        *
TAT TGG ACT AGG CAG GAC CGG GAC CTT GAG GAG CCA ATT AAC
ATA ACC TGA TCC GTC CTG GCC CTG GAA CTC CTC GGT TAA TTG
Tyr Trp Thr Arg Gln Asp Arg Asp Leu Glu Glu Pro Ile Asn>
_____IL-1RAcP_____>

260             270             280             290
   *        *     *        *     *        *     *        *
TTC CGC CTC CCC GAG AAC CGC ATT AGT AAG GAG AAA GAT GTG
AAG GCG GAG GGG CTC TTG GCG TAA TCA TTC CTC TTT CTA CAC
Phe Arg Leu Pro Glu Asn Arg Ile Ser Lys Glu Lys Asp Val>
_____IL-1RAcP_____>

300             310             320             330
   *        *     *        *     *        *     *        *
CTG TGG TTC CGG CCC ACT CTC CTC AAT GAC ACT GGC AAC TAT
GAC ACC AAG GCC GGG TGA GAG GAG TTA CTG TGA CCG TTG ATA
Leu Trp Phe Arg Pro Thr Leu Leu Asn Asp Thr Gly Asn Tyr>
_____IL-1RAcP_____>
```

Figure 49B

```
        340         350         360         370
         *           *           *           *           *
ACC TGC ATG TTA AGG AAC ACT ACA TAT TGC AGC AAA GTT GCA
TGG ACG TAC AAT TCC TTG TGA TGT ATA ACG TCG TTT CAA CGT
Thr Cys Met Leu Arg Asn Thr Thr Tyr Cys Ser Lys Val Ala>
_____IL-1RAcP_____>

380         390         400         410         420
   *           *           *           *           *
TTT CCC TTG GAA GTT GTT CAA AAA GAC AGC TGT TTC AAT TCC
AAA GGG AAC CTT CAA CAA GTT TTT CTG TCG ACA AAG TTA AGG
Phe Pro Leu Glu Val Val Gln Lys Asp Ser Cys Phe Asn Ser>
_____IL-1RAcP_____>

430         440         450         460
   *         *           *           *           *           *
CCC ATG AAA CTC CCA GTG CAT AAA CTG TAT ATA GAA TAT GGC
GGG TAC TTT GAG GGT CAC GTA TTT GAC ATA TAT CTT ATA CCG
Pro Met Lys Leu Pro Val His Lys Leu Tyr Ile Glu Tyr Gly>
_____IL-1RAcP_____>

470         480         490         500
         *           *           *           *           *
ATT CAG AGG ATC ACT TGT CCA AAT GTA GAT GGA TAT TTT CCT
TAA GTC TCC TAG TGA ACA GGT TTA CAT CTA CCT ATA AAA GGA
Ile Gln Arg Ile Thr Cys Pro Asn Val Asp Gly Tyr Phe Pro>
_____IL-1RAcP_____>

510         520         530         540
   *     *           *           *           *           *
TCC AGT GTC AAA CCG ACT ATC ACT TGG TAT ATG GGC TGT TAT
AGG TCA CAG TTT GGC TGA TAG TGA ACC ATA TAC CCG ACA ATA
Ser Ser Val Lys Pro Thr Ile Thr Trp Tyr Met Gly Cys Tyr>
_____IL-1RAcP_____>

550         560         570         580
         *           *           *           *           *
AAA ATA CAG AAT TTT AAT AAT GTA ATA CCC GAA GGT ATG AAC
TTT TAT GTC TTA AAA TTA TTA CAT TAT GGG CTT CCA TAC TTG
Lys Ile Gln Asn Phe Asn Asn Val Ile Pro Glu Gly Met Asn>
_____IL-1RAcP_____>

590         600         610         620         630
   *           *           *           *           *
TTG AGT TTC CTC ATT GCC TTA ATT TCA AAT AAT GGA AAT TAC
AAC TCA AAG GAG TAA CGG AAT TAA AGT TTA TTA CCT TTA ATG
Leu Ser Phe Leu Ile Ala Leu Ile Ser Asn Asn Gly Asn Tyr>
_____IL-1RAcP_____>

640         650         660         670
   *         *           *           *           *           *
ACA TGT GTT GTT ACA TAT CCA GAA AAT GGA CGT ACG TTT CAT
TGT ACA CAA CAA TGT ATA GGT CTT TTA CCT GCA TGC AAA GTA
Thr Cys Val Val Thr Tyr Pro Glu Asn Gly Arg Thr Phe His>
_____IL-1RAcP_____>
```

Figure 49C

```
          680              690              700              710
     *         *       *         *       *         *       *         *
    CTC  ACC  AGG  ACT  CTG  ACT  GTA  AAG  GTA  GTA  GGC  TCT  CCA  AAA
    GAG  TGG  TCC  TGA  GAC  TGA  CAT  TTC  CAT  CAT  CCG  AGA  GGT  TTT
    Leu  Thr  Arg  Thr  Leu  Thr  Val  Lys  Val  Val  Gly  Ser  Pro  Lys>
    _____IL-1RAcP_____>

720              730              740              750
     *         *       *         *       *         *       *         *
    AAT  GCA  GTG  CCC  CCT  GTG  ATC  CAT  TCA  CCT  AAT  GAT  CAT  GTG
    TTA  CGT  CAC  GGG  GGA  CAC  TAG  GTA  AGT  GGA  TTA  CTA  GTA  CAC
    Asn  Ala  Val  Pro  Pro  Val  Ile  His  Ser  Pro  Asn  Asp  His  Val>
    _____IL-1RAcP_____>

760              770              780              790
     *         *       *         *       *         *       *         *
    GTC  TAT  GAG  AAA  GAA  CCA  GGA  GAG  GAG  CTA  CTC  ATT  CCC  TGT
    CAG  ATA  CTC  TTT  CTT  GGT  CCT  CTC  CTC  GAT  GAG  TAA  GGG  ACA
    Val  Tyr  Glu  Lys  Glu  Pro  Gly  Glu  Glu  Leu  Leu  Ile  Pro  Cys>
    _____IL-1RAcP_____>

800          810              820              830              840
     *       *         *       *         *       *         *       *
    ACG  GTC  TAT  TTT  AGT  TTT  CTG  ATG  GAT  TCT  CGC  AAT  GAG  GTT
    TGC  CAG  ATA  AAA  TCA  AAA  GAC  TAC  CTA  AGA  GCG  TTA  CTC  CAA
    Thr  Val  Tyr  Phe  Ser  Phe  Leu  Met  Asp  Ser  Arg  Asn  Glu  Val>
    _____IL-1RAcP_____>

850              860              870              880
         *         *       *         *       *         *       *         *
        TGG  TGG  ACC  ATT  GAT  GGA  AAA  AAA  CCT  GAT  GAC  ATC  ACT  ATT
        ACC  ACC  TGG  TAA  CTA  CCT  TTT  TTT  GGA  CTA  CTG  TAG  TGA  TAA
        Trp  Trp  Thr  Ile  Asp  Gly  Lys  Lys  Pro  Asp  Asp  Ile  Thr  Ile>
        _____IL-1RAcP_____>

890              900              910              920
         *         *       *         *       *         *       *         *
        GAT  GTC  ACC  ATT  AAC  GAA  AGT  ATA  AGT  CAT  AGT  AGA  ACA  GAA
        CTA  CAG  TGG  TAA  TTG  CTT  TCA  TAT  TCA  GTA  TCA  TCT  TGT  CTT
        Asp  Val  Thr  Ile  Asn  Glu  Ser  Ile  Ser  His  Ser  Arg  Thr  Glu>
        _____IL-1RAcP_____>

930              940              950              960
         *         *       *         *       *         *       *         *
        GAT  GAA  ACA  AGA  ACT  CAG  ATT  TTG  AGC  ATC  AAG  AAA  GTT  ACC
        CTA  CTT  TGT  TCT  TGA  GTC  TAA  AAC  TCG  TAG  TTC  TTT  CAA  TGG
        Asp  Glu  Thr  Arg  Thr  Gln  Ile  Leu  Ser  Ile  Lys  Lys  Val  Thr>
        _____IL-1RAcP_____>

970              980              990              1000
     *         *       *         *       *         *       *         *
    TCT  GAG  GAT  CTC  AAG  CGC  AGC  TAT  GTC  TGT  CAT  GCT  AGA  AGT
    AGA  CTC  CTA  GAG  TTC  GCG  TCG  ATA  CAG  ACA  GTA  CGA  TCT  TCA
    Ser  Glu  Asp  Leu  Lys  Arg  Ser  Tyr  Val  Cys  His  Ala  Arg  Ser>
    _____IL-1RAcP_____>
```

Figure 49D

```
      1010          1020          1030          1040          1050
        *    *        *    *        *    *        *    *        *
      GCC  AAA  GGC  GAA  GTT  GCC  AAA  GCA  GCC  AAG  GTG  AAG  CAG  AAA
      CGG  TTT  CCG  CTT  CAA  CGG  TTT  CGT  CGG  TTC  CAC  TTC  GTC  TTT
      Ala  Lys  Gly  Glu  Val  Ala  Lys  Ala  Ala  Lys  Val  Lys  Gln  Lys>
                                    IL-1RAcP                                 >

1060          1070          1080          1090
               *    *        *    *        *    *        *
             GTG  CCA  GCT  CCA  AGA  TAC  ACA  GTG  CAC  ACA  GGG  GCT  GCC  AGA
             CAC  GGT  CGA  GGT  TCT  ATG  TGT  CAC  GTG  TGT  CCC  CGA  CGG  TCT
             Val  Pro  Ala  Pro  Arg  Tyr  Thr  Val>
                        IL-1RAcP                    >
                                                     His  Thr  Gly  Ala  Ala  Arg>
                                                          IL-1RII                 >

1100          1110          1120          1130
                      *    *        *    *        *    *        *
                    AGC  TGC  CGG  TTT  CGT  GGG  AGG  CAT  TAC  AAG  CGG  GAG  TTC  AGG
                    TCG  ACG  GCC  AAA  GCA  CCC  TCC  GTA  ATG  TTC  GCC  CTC  AAG  TCC
                    Ser  Cys  Arg  Phe  Arg  Gly  Arg  His  Tyr  Lys  Arg  Glu  Phe  Arg>
                                              IL-1RII                                    >

1140          1150          1160          1170
            *    *        *    *        *    *        *    *        *
          CTG  GAA  GGG  GAG  CCT  GTA  GCC  CTG  AGG  TGC  CCC  CAG  GTG  CCC
          GAC  CTT  CCC  CTC  GGA  CAT  CGG  GAC  TCC  ACG  GGG  GTC  CAC  GGG
          Leu  Glu  Gly  Glu  Pro  Val  Ala  Leu  Arg  Cys  Pro  Gln  Val  Pro>
                                    IL-1RII                                    >

1180          1190          1200          1210
               *    *        *    *        *    *        *    *
             TAC  TGG  TTG  TGG  GCC  TCT  GTC  AGC  CCC  CGC  ATC  AAC  CTG  ACA
             ATG  ACC  AAC  ACC  CGG  AGA  CAG  TCG  GGG  GCG  TAG  TTG  GAC  TGT
             Tyr  Trp  Leu  Trp  Ala  Ser  Val  Ser  Pro  Arg  Ile  Asn  Leu  Thr>
                                        IL-1RII                                    >

1220          1230          1240          1250          1260
        *    *        *    *        *    *        *    *        *
      TGG  CAT  AAA  AAT  GAC  TCT  GCT  AGG  ACG  GTC  CCA  GGA  GAA  GAA
      ACC  GTA  TTT  TTA  CTG  AGA  CGA  TCC  TGC  CAG  GGT  CCT  CTT  CTT
      Trp  His  Lys  Asn  Asp  Ser  Ala  Arg  Thr  Val  Pro  Gly  Glu  Glu>
                                    IL-1RII                                 >

1270          1280          1290          1300
                  *    *        *    *        *    *        *
                GAG  ACA  CGG  ATG  TGG  GCC  CAG  GAC  GGT  GCT  CTG  TGG  CTT  CTG
                CTC  TGT  GCC  TAC  ACC  CGG  GTC  CTG  CCA  CGA  GAC  ACC  GAA  GAC
                Glu  Thr  Arg  Met  Trp  Ala  Gln  Asp  Gly  Ala  Leu  Trp  Leu  Leu>
                                          IL-1RII                                     >

1310          1320          1330          1340
                     *    *        *    *        *    *        *
                   CCA  GCC  TTG  CAG  GAG  GAC  TCT  GGC  ACC  TAC  GTC  TGC  ACT  ACT
                   GGT  CGG  AAC  GTC  CTC  CTG  AGA  CCG  TGG  ATG  CAG  ACG  TGA  TGA
                   Pro  Ala  Leu  Gln  Glu  Asp  Ser  Gly  Thr  Tyr  Val  Cys  Thr  Thr>
                                              IL-1RII                                    >
```

Figure 49E

```
            1350          1360          1370          1380
    *        *        *        *        *        *        *        *        *
  AGA  AAT  GCT  TCT  TAC  TGT  GAC  AAA  ATG  TCC  ATT  GAG  CTC  AGA
  TCT  TTA  CGA  AGA  ATG  ACA  CTG  TTT  TAC  AGG  TAA  CTC  GAG  TCT
  Arg  Asn  Ala  Ser  Tyr  Cys  Asp  Lys  Met  Ser  Ile  Glu  Leu  Arg>
                              _____IL-1RII_____>

1390          1400          1410          1420
    *        *        *        *        *        *        *        *
  GTT  TTT  GAG  AAT  ACA  GAT  GCT  TTC  CTG  CCG  TTC  ATC  TCA  TAC
  CAA  AAA  CTC  TTA  TGT  CTA  CGA  AAG  GAC  GGC  AAG  TAG  AGT  ATG
  Val  Phe  Glu  Asn  Thr  Asp  Ala  Phe  Leu  Pro  Phe  Ile  Ser  Tyr>
                              _____IL-1RII_____>

1430          1440          1450          1460          1470
    *        *        *        *        *        *        *        *        *
  CCG  CAA  ATT  TTA  ACC  TTG  TCA  ACC  TCT  GGG  GTA  TTA  GTA  TGC
  GGC  GTT  TAA  AAT  TGG  AAC  AGT  TGG  AGA  CCC  CAT  AAT  CAT  ACG
  Pro  Gln  Ile  Leu  Thr  Leu  Ser  Thr  Ser  Gly  Val  Leu  Val  Cys>
                              _____IL-1RII_____>

1480          1490          1500          1510
    *        *        *        *        *        *        *        *
  CCT  GAC  CTG  AGT  GAA  TTC  ACC  CGT  GAC  AAA  ACT  GAC  GTG  AAG
  GGA  CTG  GAC  TCA  CTT  AAG  TGG  GCA  CTG  TTT  TGA  CTG  CAC  TTC
  Pro  Asp  Leu  Ser  Glu  Phe  Thr  Arg  Asp  Lys  Thr  Asp  Val  Lys>
                              _____IL-1RII_____>

1520          1530          1540          1550
    *        *        *        *        *        *        *        *
  ATT  CAA  TGG  TAC  AAG  GAT  TCT  CTT  CTT  TTG  GAT  AAA  GAC  AAT
  TAA  GTT  ACC  ATG  TTC  CTA  AGA  GAA  GAA  AAC  CTA  TTT  CTG  TTA
  Ile  Gln  Trp  Tyr  Lys  Asp  Ser  Leu  Leu  Leu  Asp  Lys  Asp  Asn>
                              _____IL-1RII_____>

1560          1570          1580          1590
    *        *        *        *        *        *        *        *        *
  GAG  AAA  TTT  CTA  AGT  GTG  AGG  GGG  ACC  ACT  CAC  TTA  CTC  GTA
  CTC  TTT  AAA  GAT  TCA  CAC  TCC  CCC  TGG  TGA  GTG  AAT  GAG  CAT
  Glu  Lys  Phe  Leu  Ser  Val  Arg  Gly  Thr  Thr  His  Leu  Leu  Val>
                              _____IL-1RII_____>

1600          1610          1620          1630
    *        *        *        *        *        *        *        *
  CAC  GAT  GTG  GCC  CTG  GAA  GAT  GCT  GGC  TAT  TAC  CGC  TGT  GTC
  GTG  CTA  CAC  CGG  GAC  CTT  CTA  CGA  CCG  ATA  ATG  GCG  ACA  CAG
  His  Asp  Val  Ala  Leu  Glu  Asp  Ala  Gly  Tyr  Tyr  Arg  Cys  Val>
                              _____IL-1RII_____>

1640          1650          1660          1670          1680
    *        *        *        *        *        *        *        *        *
  CTG  ACA  TTT  GCC  CAT  GAA  GGC  CAG  CAA  TAC  AAC  ATC  ACT  AGG
  GAC  TGT  AAA  CGG  GTA  CTT  CCG  GTC  GTT  ATG  TTG  TAG  TGA  TCC
  Leu  Thr  Phe  Ala  His  Glu  Gly  Gln  Gln  Tyr  Asn  Ile  Thr  Arg>
                              _____IL-1RII_____>
```

Figure 49F

```
              1690           1700           1710           1720
               *      *       *      *       *      *       *      *
         AGT ATT GAG CTA CGC ATC AAG AAA AAA AAA GAA GAG ACC ATT
         TCA TAA CTC GAT GCG TAG TTC TTT TTT TTT CTT CTC TGG TAA
         Ser Ile Glu Leu Arg Ile Lys Lys Lys Lys Glu Glu Thr Ile>
                             ____IL-1RII_____>

1730           1740           1750           1760
               *      *       *      *       *      *       *.
         CCT GTG ATC ATT TCC CCC CTC AAG ACC ATA TCA GCT TCT CTG
         GGA CAC TAG TAA AGG GGG GAG TTC TGG TAT AGT CGA AGA GAC
         Pro Val Ile Ile Ser Pro Leu Lys Thr Ile Ser Ala Ser Leu>
                             ____IL-1RII_____>

1770           1780           1790           1800
          *      *       *      *       *      *       *      *
         GGG TCA AGA CTG ACA ATC CCA TGT AAG GTG TTT CTG GGA ACC
         CCC AGT TCT GAC TGT TAG GGT ACA TTC CAC AAA GAC CCT TGG
         Gly Ser Arg Leu Thr Ile Pro Cys Lys Val Phe Leu Gly Thr>
                             ____IL-1RII_____>

1810           1820           1830           1840
          *      *       *      *       *      *       *      *
         GGC ACA CCC TTA ACC ACC ATG CTG TGG TGG ACG GCC AAT GAC
         CCG TGT GGG AAT TGG TGG TAC GAC ACC ACC TGC CGG TTA CTG
         Gly Thr Pro Leu Thr Thr Met Leu Trp Trp Thr Ala Asn Asp>
                             ____IL-1RII_____>

1850           1860           1870           1880           1890
     *      *      *      *       *      *       *      *       *
         ACC CAC ATA GAG AGC GCC TAC CCG GGA GGC CGC GTG ACC GAG
         TGG GTG TAT CTC TCG CGG ATG GGC CCT CCG GCG CAC TGG CTC
         Thr His Ile Glu Ser Ala Tyr Pro Gly Gly Arg Val Thr Glu>
                             ____IL-1RII_____>

1900           1910           1920           1930
               *      *       *      *       *      *       *      *
         GGG CCA CGC CAG GAA TAT TCA GAA AAT AAT GAG AAC TAC ATT
         CCC GGT GCG GTC CTT ATA AGT CTT TTA TTA CTC TTG ATG TAA
         Gly Pro Arg Gln Glu Tyr Ser Glu Asn Asn Glu Asn Tyr Ile>
                             ____IL-1RII_____>

1940           1950           1960           1970
               *      *       *      *       *      *       *      *
         GAA GTG CCA TTG ATT TTT GAT CCT GTC ACA AGA GAG GAT TTG
         CTT CAC GGT AAC TAA AAA CTA GGA CAG TGT TCT CTC CTA AAC
         Glu Val Pro Leu Ile Phe Asp Pro Val Thr Arg Glu Asp Leu>
                             ____IL-1RII_____>

1980           1990           2000           2010
               *      *       *      *       *      *       *      *
         CAC ATG GAT TTT AAA TGT GTT GTC CAT AAT ACC CTG AGT TTT
         GTG TAC CTA AAA TTT ACA CAA CAG GTA TTA TGG GAC TCA AAA
         His Met Asp Phe Lys Cys Val Val His Asn Thr Leu Ser Phe>
                             ____IL-1RII_____>
```

Figure 49G

```
       2020            2030            2040            2050
        *               *       *       *               *       *
    CAG ACA CTA CGC ACC ACA GTC AAG GAA GCC TCC TCC ACG TTC
    GTC TGT GAT GCG TGG TGT CAG TTC CTT CGG AGG AGG TGC AAG
    Gln Thr Leu Arg Thr Thr Val Lys Glu Ala Ser Ser Thr Phe>
    _____IL-1RII_____>

2060            2070            2080            2090            2100
    *       *       *       *       *       *       *       *       *
    TCC GGA GAG TCC AAA TAC GGT CCG CCA TGC CCA CCA TGC CCA
    AGG CCT CTC AGG TTT ATG CCA GGC GGT ACG GGT GGT ACG GGT
    Ser Gly>
    _____>
                    Glu Ser Lys Tyr Gly Pro Pro Cys Pro Pro Cys Pro>
                                        ____FC-IgG4_____>

2110            2120            2130            2140
                *       *       *       *       *       *       *       *
            GCA CCT GAG TTC CTG GGG GGA CCA TCA GTC TTC CTG TTC CCC
            CGT GGA CTC AAG GAC CCC CCT GGT AGT CAG AAG GAC AAG GGG
            Ala Pro Glu Phe Leu Gly Gly Pro Ser Val Phe Leu Phe Pro>
            _____FC-IgG4_____>

2150            2160            2170            2180
                *       *       *       *       *       *       *       *
            CCA AAA CCC AAG GAC ACT CTC ATG ATC TCC CGG ACC CCT GAG
            GGT TTT GGG TTC CTG TGA GAG TAC TAG AGG GCC TGG GGA CTC
            Pro Lys Pro Lys Asp Thr Leu Met Ile Ser Arg Thr Pro Glu>
            _____FC-IgG4_____>

2190            2200            2210            2220
                *       *       *       *       *       *       *       *
            GTC ACG TGC GTG GTG GTG GAC GTG AGC CAG GAA GAC CCC GAG
            CAG TGC ACG CAC CAC CAC CTG CAC TCG GTC CTT CTG GGG CTC
            Val Thr Cys Val Val Val Asp Val Ser Gln Glu Asp Pro Glu>
            _____FC-IgG4_____>

2230            2240            2250            2260
         *       *       *       *       *       *       *       *
        GTC CAG TTC AAC TGG TAC GTG GAT GGC GTG GAG GTG CAT AAT
        CAG GTC AAG TTG ACC ATG CAC CTA CCG CAC CTC CAC GTA TTA
        Val Gln Phe Asn Trp Tyr Val Asp Gly Val Glu Val His Asn>
        _____FC-IgG4_____>

2270            2280            2290            2300            2310
    *       *       *       *       *       *       *       *       *
    GCC AAG ACA AAG CCG CGG GAG GAG CAG TTC AAC AGC ACG TAC
    CGG TTC TGT TTC GGC GCC CTC CTC GTC AAG TTG TCG TGC ATG
    Ala Lys Thr Lys Pro Arg Glu Glu Gln Phe Asn Ser Thr Tyr>
    _____FC-IgG4_____>

2320            2330            2340            2350
                *       *       *       *       *       *       *       *
            CGT GTG GTC AGC GTC CTC ACC GTC CTG CAC CAG GAC TGG CTG
            GCA CAC CAG TCG CAG GAG TGG CAG GAC GTG GTC CTG ACC GAC
            Arg Val Val Ser Val Leu Thr Val Leu His Gln Asp Trp Leu>
            _____FC-IgG4_____>
```

Figure 49H

```
           2360              2370              2380              2390
       *     *     *     *     *     *     *     *
     AAC   GGC   AAG   GAG   TAC   AAG   TGC   AAG   GTC   TCC   AAC   AAA   GGC   CTC
     TTG   CCG   TTC   CTC   ATG   TTC   ACG   TTC   CAG   AGG   TTG   TTT   CCG   GAG
     Asn   Gly   Lys   Glu   Tyr   Lys   Cys   Lys   Val   Ser   Asn   Lys   Gly   Leu>
     _____FC-IgG4_____>

2400              2410              2420              2430
       *     *     *     *     *     *     *     *     *
     CCG   TCC   TCC   ATC   GAG   AAA   ACC   ATC   TCC   AAA   GCC   AAA   GGG   CAG
     GGC   AGG   AGG   TAG   CTC   TTT   TGG   TAG   AGG   TTT   CGG   TTT   CCC   GTC
     Pro   Ser   Ser   Ile   Glu   Lys   Thr   Ile   Ser   Lys   Ala   Lys   Gly   Gln>
     _____FC-IgG4_____>

2440           2450           2460              2470
       *     *     *     *     *     *     *     *
     CCC   CGA   GAG   CCA   CAG   GTG   TAC   ACC   CTG   CCC   CCA   TCC   CAG   GAG
     GGG   GCT   CTC   GGT   GTC   CAC   ATG   TGG   GAC   GGG   GGT   AGG   GTC   CTC
     Pro   Arg   Glu   Pro   Gln   Val   Tyr   Thr   Leu   Pro   Pro   Ser   Gln   Glu>
     _____FC-IgG4_____>

2480             2490              2500              2510              2520
       *     *     *     *     *     *     *     *     *
     GAG   ATG   ACC   AAG   AAC   CAG   GTC   AGC   CTG   ACC   TGC   CTG   GTC   AAA
     CTC   TAC   TGG   TTC   TTG   GTC   CAG   TCG   GAC   TGG   ACG   GAC   CAG   TTT
     Glu   Met   Thr   Lys   Asn   Gln   Val   Ser   Leu   Thr   Cys   Leu   Val   Lys>
     _____FC-IgG4_____>

2530           2540           2550              2560
       *     *     *     *     *     *     *     *
     GGC   TTC   TAC   CCC   AGC   GAC   ATC   GCC   GTG   GAG   TGG   GAG   AGC   AAT
     CCG   AAG   ATG   GGG   TCG   CTG   TAG   CGG   CAC   CTC   ACC   CTC   TCG   TTA
     Gly   Phe   Tyr   Pro   Ser   Asp   Ile   Ala   Val   Glu   Trp   Glu   Ser   Asn>
     _____FC-IgG4_____>

2570              2580              2590              2600
       *     *     *     *     *     *     *     *
     GGG   CAG   CCG   GAG   AAC   AAC   TAC   AAG   ACC   ACG   CCT   CCC   GTG   CTG
     CCC   GTC   GGC   CTC   TTG   TTG   ATG   TTC   TGG   TGC   GGA   GGG   CAC   GAC
     Gly   Gln   Pro   Glu   Asn   Asn   Tyr   Lys   Thr   Thr   Pro   Pro   Val   Leu>
     _____FC-IgG4_____>

2610              2620              2630              2640
       *     *     *     *     *     *     *     *     *
     GAC   TCC   GAC   GGC   TCC   TTC   TTC   CTC   TAC   AGC   AGG   CTA   ACC   GTG
     CTG   AGG   CTG   CCG   AGG   AAG   AAG   GAG   ATG   TCG   TCC   GAT   TGG   CAC
     Asp   Ser   Asp   Gly   Ser   Phe   Phe   Leu   Tyr   Ser   Arg   Leu   Thr   Val>
     _____FC-IgG4_____>

2650              2660              2670              2680
       *     *     *     *     *     *     *     *
     GAC   AAG   AGC   AGG   TGG   CAG   GAG   GGG   AAT   GTC   TTC   TCA   TGC   TCC
     CTG   TTC   TCG   TCC   ACC   GTC   CTC   CCC   TTA   CAG   AAG   AGT   ACG   AGG
     Asp   Lys   Ser   Arg   Trp   Gln   Glu   Gly   Asn   Val   Phe   Ser   Cys   Ser>
     _____FC-IgG4_____>
```

Figure 49 I

```
     2690          2700          2710          2720          2730
       *        *    *        *    *        *    *        *    *
     GTG ATG CAT GAG GCT CTG CAC AAC CAC TAC ACA CAG AAG AGC
     CAC TAC GTA CTC CGA GAC GTG TTG GTG ATG TGT GTC TTC TCG
     Val Met His Glu Ala Leu His Asn His Tyr Thr Gln Lys Ser>
     _____FC-IgG4_____>

2740          2750
             *      *    *        *
     CTC TCC CTG TCT CTG GGT AAA TGA
     GAG AGG GAC AGA GAC CCA TTT ACT
     Leu Ser Leu Ser Leu Gly Lys ***>
     _____FC-IgG4_____>
```

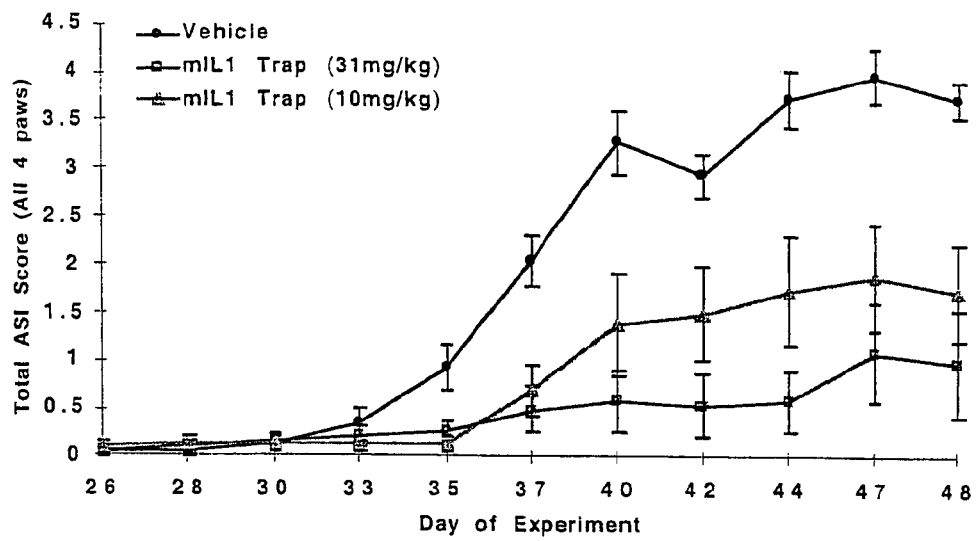
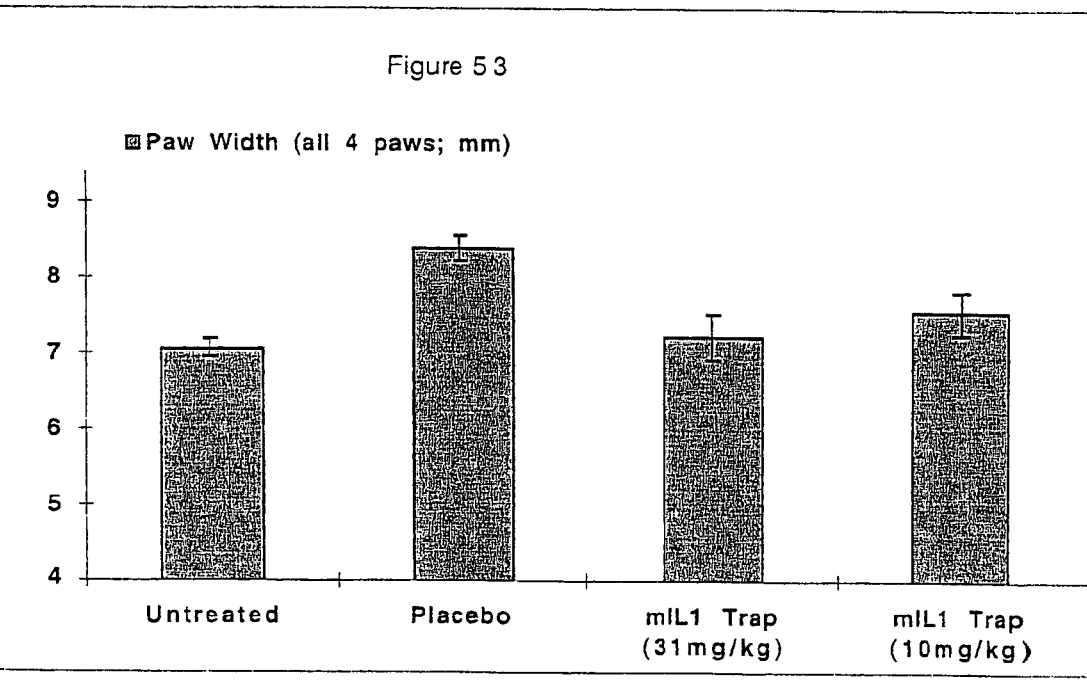

IL-1 RECEPTOR BASED CYTOKINE TRAPS AND METHOD OF USING

CROSS-REFERENCE TO RELATED APPLICATIONS

This application is a continuation of U.S. Ser. No. 10/282,162 filed 28 Oct. 2002, now U.S. Pat. No. 6,927,044, which is a continuation-in-part of U.S. Ser. No. 09/787,835, filed 22 Mar. 2001, now abandoned, which is a U.S. National Stage Application of International Application No. PCT/US99/22045, filed 22 Sep. 1999, which is a continuation of U.S. Ser. No. 09/313,942, filed 19 May 1999, now U.S. Pat. No. 6,472,179, which claims the benefit under 35 U.S.C. § 119(e) of U.S. Provisional Application No. 60/101,858 filed Sep. 25, 1998. The disclosures of these publications are hereby incorporated by reference into this application in their entireties.

FIELD OF THE INVENTION

The invention relates to receptor-based fusion proteins capable of binding and inhibiting the biological activity of a cytokine. More specifically, the invention relates to interleukin-1 (IL-1) fusion proteins capable of trapping and inhibiting the action of IL-1, and therapeutic uses thereof.

DESCRIPTION OF RELATED ART

Although discovered for varying biological activities, ciliary neurotrophic factor (CNTF), leukemia inhibitory factor (LIF), oncostatin M (OSM) and interleukin-6 (IL-6) comprise a defined family of cytokines (referred to herein as the "CNTF family" of cytokines). These cytokines are grouped together because of their distant structural similarities (Bazan et al. 1991 J. Neuron 7:197-208), and, perhaps more importantly, because they share "β" signal-transducing receptor components (Baumann et al. 1993 J. Biol. Chem. 265:19853-19862); Davis et al. 1993 Science 260:1805-1808; Gearing et al. 1992 Science 255:1434-1437; Ip et al. 1992 Cell 69: 1121-1132; Stahl et al. 1993 J. Biol. Chem. 268: 7628-7631; Stahl et al. 1993 Cell 74:587-590). Receptor activation by this family of cytokines results from either homo- or hetero-dimerization of these β components.

In addition to the β components, some of these cytokines also require specificity-determining "α" components that are more limited in their tissue distribution than the β components, and thus determine the cellular targets of the particular cytokines. Thus, LIF and OSM are broadly acting factors that may only require the presence of gp130 and LIFRβ on responding cells, while CNTF requires CNTFRα. Both CNTFRα and IL-6Rα (Hibi et al. Cell 63:1149-1157) can function as soluble proteins, consistent with the notion that they do not interact with intracellular signaling molecules but that they serve to help their ligands interact with the appropriate signal transducing β subunits.

Additional evidence from other cytokine systems also supports the notion that dimerization provides a common mechanism by which all cytokine receptors initiate signal transduction. Studies with the erythropoietin (EPO) receptor are also consistent with the importance of dimerization in receptor activation, as EPO receptors can be constitutively activated by a single amino acid change that introduces a cysteine residue and results in disulfide-linked homodimers (Watowich et al. 1992 Proc. Natl. Acad. Sci. USA 89:2140-2144).

In addition to homo- or hetero-dimerization of β subunits as the critical step for receptor activation, a second important feature is that formation of the final receptor complex by the CNTF family of cytokines occurs through a mechanism whereby the ligand successively binds to receptor components in an ordered manner (Davis et al. 1993 supra). Thus CNTF first binds to CNTFRα, forming a complex which then binds gp130 to form an intermediate (called here the αβ1 intermediate) that is not signaling competent because it has only a single β component, before finally recruiting LIFRβ to form a heterodimer of β components which then initiates signal transduction. Altogether, these findings led to a proposal for the structure of a generic cytokine receptor complex in which each cytokine can have up to 3 receptor binding sites: a site that binds to an optional a specificity-determining component (a site), a site that binds to the first β signal-transducing component (β1 site), and a site that binds to the second β signal-transducing component (β2 site). These 3 sites are used in sequential fashion, with the last step in complex formation—resulting in β component dimerization—critical for initiating signal transduction (Davis et al. 1993 supra). Knowledge of the details of receptor activation and the existence of the non-functional β1 intermediate for CNTF has led to the finding that CNTF is a high affinity antagonist for IL-6 under certain circumstances, and provides the strategic basis for designing ligand or receptor-based antagonists for the CNTF family of cytokines as detailed below.

BRIEF SUMMARY OF THE INVENTION

An object of the invention is the construction of several specific interleukin-1 (IL-1) cytokine antagonists, termed "IL-1 Traps", each having different sequences but all being capable of blocking the binding of IL-1 to its receptor, thus functioning as IL-1 antagonists.

BRIEF DESCRIPTION OF THE FIGURES

FIGS. 4A-4B. The amino acid sequence of human gp130-Fc-His$_6$ (SEQ ID NO: 7). Amino acids 1 to 619 are from human gp130 (Hibi et al., Cell 63:1149-1157 (1990). Note that amino acid number 2 has been changed from a Leu to a Val in order to accommodate a Kozak sequence in the coding DNA sequence. The signal peptide of gp130-Fc-His$_6$ has been italicized (amino acids 1 to 22). The Ser-Gly bridge is shown in bold type (amino acids 620, 621). Amino acids 662 to 853 are from the Fc domain of human IgG1 (Lewis, et al., J. Immunol. 151:2829-2838 (1993). (†) mark the two cysteines (amino acids number 632 and 635) of the IgG hinge preceding the Fc that form the inter-chain disulfide bridges that link two Fc domains. The hexahistine tag is shown in bold/italic type (amino acids 854 to 859). (•) shows the position of the STOP codon.

FIG. 5: The amino acid sequence of human IL-6Ra-Fc (SEQ ID NO: 8). Key: Amino acids 1 to 358 are from human IL-6Ra (Yamasaki et al. 1088 Science 241:825-828). Note that amino acid number 2 has been changed from a Leu to a Val in order to accommodate a Kozak sequence in the coding DNA sequence. The signal peptide of IL-6Ra-Fc has been italicized (amino acids 1 to 19). The Ala-Gly bridge is shown in bold type (amino acids 359, 360). Amino acids 361 to 592 are from the Fc domain of human IgG1 (Lewis et al., J. Immunol. 151:2829-2838 (1993). (†) mark the two cysteines (amino acids number 371 and 374) of the IgG hinge preceding the Fc that form the inter-chain disulfide bridges that link two Fc domains. (•) shows the position of the STOP codon.

FIG. 6: The CNTF/IL-6/IL-11 receptor system. The ordered formation of the hexameric signal transducing receptor complex is depicted schematically. The cytokine associates with the Ra component to form an obligatory cytokine•Ra complex (Kd is about 5 nM). This low affinity complex next associates with the first signal transducing component, marked b1, to form a high affinity cytokine•Ra•b1 complex (Kd is about 10 pM). In the case of IL-6Ra, this component is gp130. This trimeric high affinity complex subsequently associates with another such complex. Formation of this complex results in signal transduction as it involves dimerization of two signal transducing components, marked b1 and b2 respectively (adapted from (Ward et al., J. Bio. Chem. 269:23286-23289 (1994); Stahl and Yancopoulos, J. Neurobiology 25:1454-1466 (1994); Stahl and Yancopoulos, Cell 74:587-590 (1993).

FIG. 7: Design of heterodimeric receptor-based ligand Traps for IL-6. The heterodimeric ligand Trap is comprised of two interdisulfide linked proteins, gp130-Fc and IL-6Ra-Fc. The gp130-Fc•IL-6Ra-Fc complex (upper panel) is shown to mimic the high affinity cytokine•Ra•b1 complex (lower panel). The ligand Trap functions as an antagonist by sequestering IL-6 and thus rendering unavailable to interact with the native receptors on IL-6-responsive cells.

FIGS. 9A-9B. Amino acid sequence of gp130-Cg1 (SEQ ID NO: 9). Key: Amino acids 1 to 619 are from human gp130 (Hibi, et al., Cell 63:1149-1157 (1990). Ser-Gly bridge is shown in bold type. Amino acids 662 to 651 are from the constant region of human IgG1 (Lewis et al., J. Immunol. 151:2829-2838 (1993). (*) shows the position of the STOP codon.

FIG. 10: Amino acid sequence of gp130D3fibro (SEQ ID NO: 10). Key: Amino acids 1 to 330 are from human gp130 (Hibi et al. Cell 63:1149-1157 (1990). Other symbols as described in FIG. 9.

FIG. 11: Amino acid sequence of J-CH1 (SEQ ID NO: 11). Key: The Ser-Gly bridge is shown in bold, the J-peptide is shown in italics, the C$_H$1 domain is underlined.

FIG. 12: Amino acid sequence of Cg4 (SEQ ID NO: 12). Key: The Ser-Gly bridge is shown in bold type. Amino acids 2 to 239 comprise the Cg4 sequence.

FIG. 13: Amino acid sequence of k-domain (SEQ ID NO: 13). Key: The Ser-Gly bridge is shown in bold type. Amino acids 2 to 108 comprise the k domain. The C-terminal cysteine (amino acid 108) is that involved in the disulfide bond of the k domain with the C$_H$1 domain of Cg.

FIG. 14: Amino acid sequence of l-domain (SEQ ID NO: 14). Key: The Ser-Gly bridge is shown in bold type. Amino acids 2 to 106 comprise the l domain (Cheung, et al., J. Virol. 66: 6714-6720 (1992). The C-terminal cysteine (amino acid 106) is that involved in the disulfide bond of the l domain with the C$_H$1 domain of Cg.

FIG. 15: Amino acid sequence of the soluble IL-6Ra domain (SEQ ID NO: 15). Key: Amino acids 1 to 358 comprise the soluble IL-6Ra domain (Yamasaki, et al., Science 241:825-828 (1988). The Ala-Gly bridge is shown in bold type.

FIG. 16: Amino acid sequence of the soluble IL-6Rα313 domain (SEQ ID NO: 16): Key: Amino acids 1 to 313 comprise the truncated IL-6Ra domain (IL-6Ra313). The Thr-Gly bridge is shown in bold type.

FIGS. 19A-19B: IL-6 can induce multimerization of the ligand Trap. (FIG. 19A) Two different ligand Traps are depicted schematically and listed according to their ability to bind protein A. gp130-Fc•IL-6Ra-Fc (GF6F) binds protein A via its Fc-domains, whereas gp130—C$_H$1•IL-6Ra-k (G16K) does not bind to protein A. (FIG. 19B) Anti-kappa western blotting of proteins precipitated with Protein A-Sepharose from mixtures of GF6F±IL-6, G16K±IL-6, or GF6F plus G16K±IL-6, as marked.

FIG. 20: Inhibition of IL-6-dependent XG-1 cell proliferation. XG-1 cells [Zhang, et al., Blood 83:3654-3663 (1994)] were prepared for a proliferation assay by starving the cells from IL-6 for 5 hours. Assays were set up in 96-well tissue culture dishes in RPMI+10% fetal calf serum+penicillin/streptomycin+0.050 nM 2-mercaptoethanol+glutamine. 0.1 ml of that media was used per well. Cells were suspended at a density of 250,000 per ml at the start of the assay. 72 hours post addition of IL-6±ligands Traps or antibodies, an MTT assay was performed as described (Panayotatos et al. Biochemistry 33:5813-5818 (1994). The different ligand Traps utilized are listed.

FIGS. 21A-21D: Nucleotide sequence (SEQ ID NO: 17) encoding and deduced amino acid sequence (SEQ ID NO: 18) of fusion polypeptide designated 424 which is capable of binding the cytokine IL-4 to form a nonfunctional complex.

FIGS. 22A-22D: Nucleotide sequence (SEQ ID NO: 19) encoding and deduced amino acid sequence (SEQ ID NO: 20) of fusion polypeptide designated 603 which is capable of binding the cytokine IL-4 to form a nonfunctional complex.

FIGS. 23A-23D: Nucleotide sequence (SEQ ID NO: 21) encoding and deduced amino acid sequence (SEQ ID NO: 22) of fusion polypeptide designated 622 which is capable of binding the cytokine IL-4 to form a nonfunctional complex.

FIGS. 24A-24F: Nucleotide sequence (SEQ ID NO: 23) encoding and deduced amino acid sequence (SEQ ID NO: 24) of fusion polypeptide designated 412 which is capable of binding the cytokine IL-6 to form a nonfunctional complex.

FIGS. 25A-25F: Nucleotide sequence (SEQ ID NO: 25) encoding and deduced amino acid sequence (SEQ ID NO: 26) of fusion polypeptide designated 616 which is capable of binding the cytokine IL-6 to form a nonfunctional complex.

FIGS. 26A-26E: Nucleotide sequence (SEQ ID NO: 27) encoding and deduced amino acid sequence (SEQ ID NO: 28) of fusion polypeptide designated 569 which is capable of binding the cytokine IL-1 to form a nonfunctional complex.

FIGS. 31A-31G: The nucleotide (SEQ ID NO: 29) and encoded amino acid (SEQ ID NO: 30) sequence of the IL-4Ra.IL-13Ra1.Fc single chain Trap construct is set forth.

FIGS. 32A-32G: The nucleotide (SEQ ID NO: 31) and encoded amino acid (SEQ ID NO: 32) sequence of the IL-13Ra1.IL-4Ra.Fc single chain Trap construct is set forth.

FIG. 33: Blocking of IL-13 by IL-4Ra.IL-13Ra1.Fc and IL-13Ra1.IL-4Ra.Fc. Addition of either IL-4Ra.IL-13Ra1.Fc or IL-13Ra1.IL-4Ra.Fc Trap at a concentration of 10 nM blocks IL-13-induced growth up to ~2 nM. At an IL-13 concentration of ~4-5 nM the growth of TF1 cells is inhibited by 50%.

FIG. 36A: Cynomologus monkeys were treated in three parts as indicated. Human IL-4 (25 μg/kg) was injected subcutaneously twice daily for 4 days and human IL-4 Trap (8 mg/ml) and vehicle were given intravenously daily for 5 days, beginning 1 day prior to human IL-4 administration. Plasma was collected daily and assayed for MCP-1 levels. Results were expressed as mean +/–SEM; n=4. (ANOVA p<0.0007; Tukey-Kramer: Part 2 vs. Part 1, p, 0.05; Part 2 vs. Part 3, p, 0.05; Part 1 vs. Part 3, not significant.) FIG. 36B: Cynomologus monkeys were treated in three parts as indicated. Human IL-4 (25 μg/kg) was injected subcutaneously twice daily for 4 days and human IL-4 Trap (8 mg/ml) and vehicle were given intravenously daily for 5 days, beginning 1 day prior to human IL-4 administration. Whole blood was collected daily for flow cytometry analysis for CD16. Results were expressed as mean +/–SEM; n=4. (ANOVA p<0.042; Tukey-Kramer: Part 2 vs. Part 1, p<0.05; Part 2 vs. Part 3 and Part 1 vs. Part 3, not significant.)

FIGS. 38A-38I: Nucleotide (SEQ ID NO: 33) and deduced amino acid (SEQ ID NO: 34) sequence of Human IL-1 Trap 570-FE.

FIG. 39A-39I: Nucleotide (SEQ ID NO: 35) and deduced amino acid (SEQ ID NO: 36) sequence of Human IL-1 Trap 570-FE.B.

FIGS. 40A-40I: Nucleotide (SEQ ID NO: 37) and deduced amino acid (SEQ ID NO: 38) sequence of Human IL-1 Trap 570-FE.C.

FIGS. 41A-41I: Nucleotide (SEQ ID NO: 39) and deduced amino acid (SEQ ID NO: 40) sequence of Human IL-1 Trap 823.

FIGS. 42A-42I: Nucleotide (SEQ ID NO: 41) and deduced amino acid (SEQ ID NO: 42) sequence of Human IL-1 Trap 823-1198.B.

FIGS. 43A-43I: Nucleotide (SEQ ID NO: 43) and deduced amino acid (SEQ ID NO: 44) sequence of Human IL-1 Trap 823-1267.C.

FIGS. 44A-44I: Nucleotide (SEQ ID NO: 45) and deduced amino acid (SEQ ID NO: 46) sequence of Human IL-1 Trap 1647-CtF.

FIGS. 45A-45I: Nucleotide (SEQ ID NO: 47) and deduced amino acid (SEQ ID NO: 48) sequence of Human IL-1 Trap 1647-CtF.B.

FIGS. 46A-46I: Nucleotide (SEQ ID NO: 49) and deduced amino acid (SEQ ID NO: 50) sequence of Human IL-1 Trap 1647-CtF.C.

FIGS. 47A-47I: Nucleotide (SEQ ID NO: 51) and deduced amino acid (SEQ ID NO: 52) sequence of Human IL-1 Trap 1649.

FIGS. 48A-48I: Nucleotide (SEQ ID NO: 53) and deduced amino acid (SEQ ID NO: 54) sequence of Human IL-1 Trap 1649-B.

FIGS. 49A-49I: Nucleotide (SEQ ID NO: 55) and deduced amino acid (SEQ ID NO: 56) sequence of Human IL-1 Trap 1646-C.

FIGS. 52-53: Murine IL-1 Trap Reduces the Severity of Arthritis Symptoms in a Zymosan-Accelerated Collagen-Induced Arthritis (CIA) model. Male DBA-1 mice were immunized intradermally at the base of the tail with 100 μg/50 μl bovine Type II collagen (CII) emulsified with complete and incomplete Freund's adjuvant (2:1:1 ratio) and boosted intradermally with CII (100 μg/50 μl) emulsified with incomplete Freund's adjuvant on day 21. Since CIA in DBA-1 mice occurs gradually over a long time period with a low incidence, we synchronized the onset of arthritis symptoms by injecting the animals intraperitoneally on day 30 with 3 mg zymosan. Two hours prior to zymosan injection, the mice were randomly distributed into treatment groups and were injected with either vehicle or mIL-1 Trap (31 or 10 mg/kg, 3×/week, 8 injections, s.c.). Arthritis symptoms (ASI scores) in the paws were evaluated 3×/week by individuals who were blinded to the treatment group. Animals were sacrificed 24 h after the 8th injection at which time paw width along with ASI scores were measured. Within 5 days after i.p injection of zymosan, vehicle treated animals had an significant increase in ASI score relative to those receiving mIL-1 Trap with symptoms reaching a maximum 10 to 14 days after zymosan injection. Murine IL-1 Trap acted in a dose-dependent fashion such that animals receiving 10 mg/kg Trap had more arthritis symptoms (greater ASI score) than those receiving 31 mg/kg. However, both mIL-1 Trap treated groups had a significantly lower degree of arthritis symptoms than vehicle. This difference in ASI score is also reflected in the paw width at the time of sacrifice (FIG. 67). Animals receiving mIL-1 Trap had paw widths that were similar to those of naive, non-collagen immunized animals

DETAILED DESCRIPTION OF THE INVENTION

Figure 1:
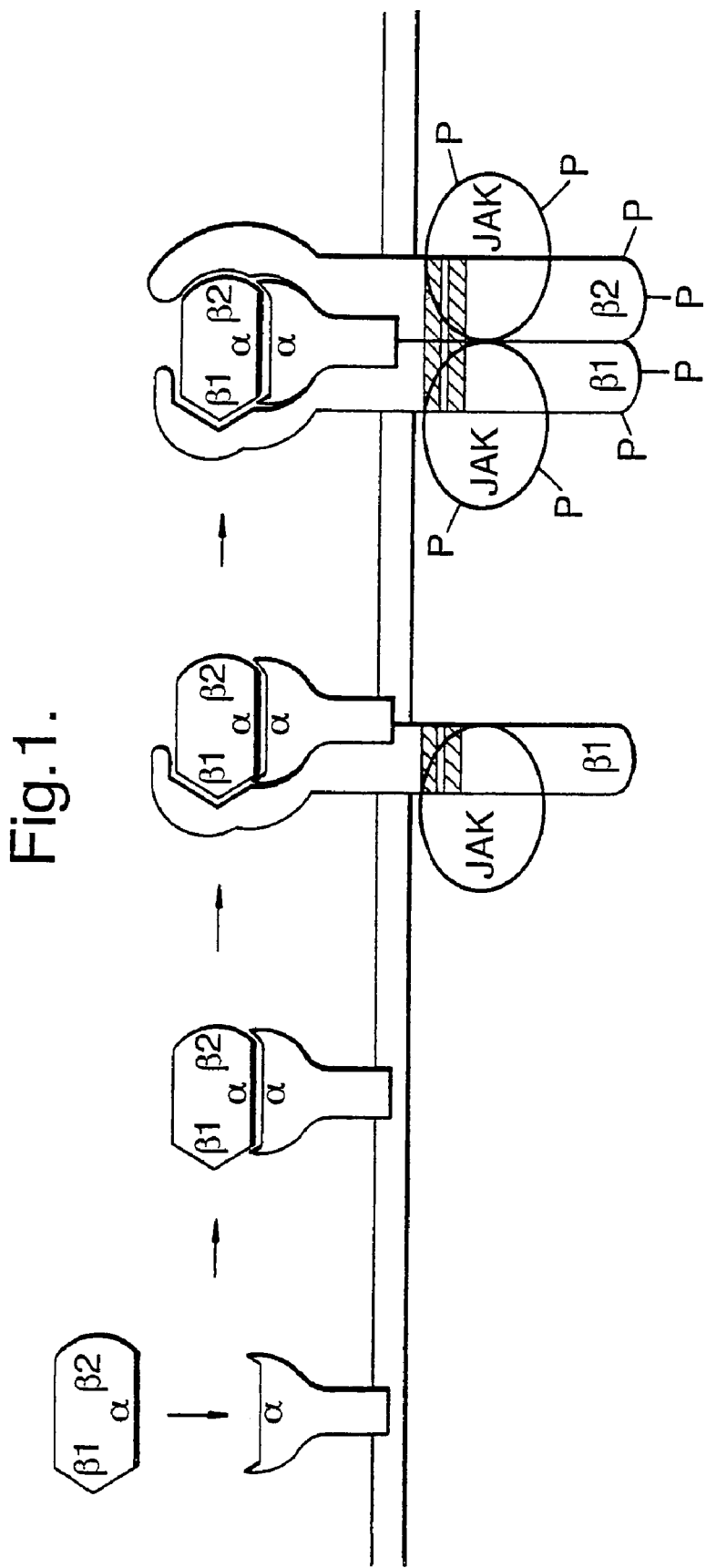
FIG. 1: Ordered binding of receptor components in a model of a generic cytokine receptor. The model indicates that cytokines contain up to 3 receptor binding sites and interact with their receptor components by binding first the optional a component, followed by binding to b1, and then b2. The b components for many cytokine receptors interact through membrane proximal regions (shaded boxes) with the Jak/Tyk family of cytoplasmic protein tyrosine kinases. Only upon dimerization of b components is signal transduction initiated, as schematized by the tyrosine phosphorylations (P) of the b components and the Jak/Tyk kinases.

The present invention provides an isolated nucleic acid molecule encoding a fusion polypeptide capable of binding a cytokine to form a nonfunctional complex comprising: (a) a nucleotide sequence encoding a first fusion polypeptide component comprising the amino acid sequence of the cytokine binding portion of the extracellular domain of the specificity determining component of a cytokine's receptor; (b) a nucleotide sequence encoding a second fusion polypeptide component comprising the amino acid sequence of the cytokine binding portion of the extracellular domain of the signal transducing component of a cytokine's receptor; and (c) a nucleotide sequence encoding a third fusion polypeptide component comprising the amino acid sequence of a multimerizing component.

By "cytokine binding portion" what is meant is the minimal portion of the extracellular domain necessary to bind the cytokine. It is accepted by those of skill in the art that a defining characteristic of a cytokine receptor is the presence of the two fibronectin-like domains that contain canonical cysteines and of the WSXWS box (Bazan 1990 supra). Sequences encoding the extracellular domains of the binding component of the cytokine's receptor and of the signal transducing component of the cytokine's receptor may also be used to create the fusion polypeptide of the invention. Similarly, longer sequences encoding larger portions of the components of the cytokine's receptor may be used. However, it is contemplated that fragments smaller than the extracellular domain will function to bind the cytokine and therefore, the invention contemplates fusion polypeptides comprising the minimal portion of the extracellular domain necessary to bind the cytokine as the cytokine binding portion.

The invention comprises a "specificity determining component" of a cytokine receptor and a "signal transducing component" of the cytokine receptor. Regardless of the nomenclature used to designate a particular component or subunit of a cytokine receptor, one skilled in the art would recognize which component or subunit of a receptor is responsible for determining the cellular target of the cytokine, and thus would know which component constitutes the "specificity determining component."

Similarly, regardless of the nomenclature used, one of skill in the art would know which component or subunit of a receptor would constitute the "signal transducing component." As used herein, the "signal transducing component" is a component of the native receptor which is not the specificity determining component and which does not bind or weakly binds the cytokine in the absence of the specificity determining component. In the native receptor, the "signal transducing component" may participate in signaling.

For example, while some cytokine receptors have components designated α and β, the IL-4 receptor has a signal transducing component referred to as IL-2Rγ. However, regardless of what name is associated with that component, one skilled in the art would know which component of the IL-4 receptor is the signal transducing component. Thus to practice the present invention and create a high affinity Trap for IL-4, one of skill in the art would create an isolated nucleic acid comprising a nucleotide sequence encoding a first fusion polypeptide component comprising the amino acid sequence of the cytokine binding portion of the extracellular domain of the specificity determining component of the IL-4 receptor (IL-4Rα); a nucleotide sequence encoding a second fusion polypeptide component comprising the amino acid sequence of the cytokine binding portion of the extracellular domain of the signal transducing component of the IL-4 receptor (IL-2Rγ); and a nucleotide sequence encoding a third fusion polypeptide component comprising the amino acid sequence of a multimerizing component (for example, an Fc domain of IgG) to create a high affinity Trap for IL-4.

In preparing the nucleic acid sequence encoding the fusion polypeptide of the invention, the first, second, and third components of the fusion polypeptide are encoded in a single strand of nucleotides which, when expressed by a host vector system, produces a monomeric species of the fusion polypeptide. The monomers thus expressed then multimerize due to the interactions between the multimerizing components (the third fusion polypeptide components). Producing the fusion polypeptides in this manner avoids the need for purification of heterodimeric mixtures that would result if the first and second components were produced as separate molecules and then multimerized. For example, U.S. Pat. No. 5,470,952 describes the production of heterodimeric proteins that function as CNTF or IL-6 antagonists. The heterodimers are purified from cell lines co-transfected with the appropriate alpha (α) and beta (β) components. Heterodimers are then separated from homodimers using methods such as passive elution from preparative, nondenaturing polyacrylamide gels or by using high pressure cation exchange chromatography. The need for this purification step is avoided by the methods of the present invention.

In addition, WO 96/11213 states that the applicant has prepared homodimers in which two IL-4 receptors are bound by a polymeric spacer and has prepared heterodimers in which an IL-4 receptor is linked by a polymeric spacer to an IL-2 receptor gamma chain. The polymeric spacer described is polyethylene glycol (PEG). The two receptor components, IL-4R and IL-2Rγ are separately expressed and purified. Pegylated homodimers and heterodimers are then produced by joining the components together using bi-functional PEG reagents. It is an advantage of the present invention that it avoids the need for such time consuming and costly purification and pegylation steps.

In one embodiment of the invention, the nucleotide sequence encoding the first component is upstream of the nucleotide sequence encoding the second component. In another embodiment of the invention, the nucleotide sequence encoding the first component is downstream of the nucleotide sequence encoding the second component. Further embodiments of the invention may be prepared in which the order of the first, second and third fusion polypeptide components are rearranged. For example, if the nucleotide sequence encoding the first component is designated 1, the nucleotide sequence encoding the second component is designated 2, and the nucleotide sequence of the third component is designated 3, then the order of the components in the isolated nucleic acid of the invention as read from 5' to 3' may be any of the following six combinations: 1,2,3; 1,3,2; 2,1,3; 2,3,1; 3,1,2; or 3,2,1.

In further embodiments of the invention, the cytokine bound by the fusion polypeptide may be a member of the hematopoietin family of cytokines selected from the group consisting of interleukin-2, interleukin-3, interleukin-4, interleukin-5, interleukin-6, interleukin-7, interleukin-9, interleukin-11, interleukin-13, interleukin-15, granulocyte macrophage colony stimulating factor, oncostatin M, leukemia inhibitory factor, and cardiotrophin-1.

In additional embodiments of the invention, the cytokine bound by the fusion polypeptide may be a member of the interferon family of cytokines selected from the group consisting of IFN-γ, IFN-α, and IFN-β.

In additional embodiments of the invention, the cytokine bound by the fusion polypeptide may be a member of the immunoglobulin superfamily of cytokines selected from the group consisting of B7.1 (CD80) and B7.2 (B70).

In still further embodiments of the invention, the cytokine bound by the fusion polypeptide may be a member of the TNF family of cytokines selected from the group consisting of TNF-α, TNF-βbeta, LT-β, CD40 ligand, Fas ligand, CD 27 ligand, CD 30 ligand, and 4-1BBL.

In additional embodiments of the invention, the cytokine bound by the fusion polypeptide may be a cytokine selected from the group consisting of interleukin-1 (IL-1), IL-10, IL-12, IL-14, IL-18, and MIF.

Because specificity determination and signal transduction occurs by a similar mechanism in the TGF-β/BMP family of cytokines (see, for example, Kingsley 1994 Genes & Development 8:133-146) the present invention may be used to produce high affinity antagonists for cytokines that are members of the TGF-β/BMP family.

Therefore, in additional embodiments of the invention, the cytokine bound by the fusion polypeptide may be a member of the TGF-β/BMP family selected from the group consisting of TGF-β1, TGF-β2, TGF-β3, BMP-2, BMP-3a, BMP-3b, BMP-4, BMP-5, BMP-6, BMP-7, BMP-8a, BMP-8b, BMP-9, BMP-10, BMP-11, BMP-15, BMP-16, endometrial bleeding associated factor (EBAF), growth differentiation factor-1 (GDF-1), GDF-2, GDF-3, GDF-5, GDF-6, GDF-7, GDF-8, GDF-9, GDF-12, GDF-14, mullerian inhibiting substance (MIS), activin-1, activin-2, activin-3, activin-4, and activin-5.

In alternative embodiments of the invention, the specificity determining component, the signal transducing component, or both, may be substituted for by a single chain Fv. A single chain Fv (scFv) is a truncated Fab having only the V region of a heavy chain linked by a stretch of synthetic peptide to a V region of a light chain. (See, for example, U.S. Pat. Nos. 5,565,332; 5,733,743; 5,837,242; 5,858,657; and 5,871,907 incorporated by reference herein). Thus the present invention contemplates, for example, an isolated nucleic acid molecule encoding a fusion polypeptide capable of binding a cytokine to form a nonfunctional complex comprising a nucleotide sequence encoding a first fusion polypeptide component comprising the amino acid sequence of the cytokine binding portion of the extracellular domain of the specificity determining component of the cytokine receptor; a nucleotide sequence encoding a second fusion polypeptide component comprising the amino acid sequence of an scFv capable of binding the cytokine at a site different from the site at which the cytokine binding portion of the extracellular domain of the specificity determining component of the cytokine receptor binds; and a nucleotide sequence encoding a third fusion polypeptide component comprising the amino acid sequence of a multimerizing component. Alternatively, the specificity determining component may be substituted for by a scFv that binds to a site on the cytokine different from the site at which the signal transducing component binds. Thus the invention contemplates an isolated nucleic acid molecule encoding a fusion polypeptide capable of binding a cytokine to form a nonfunctional complex comprising a nucleotide sequence encoding a first fusion polypeptide component comprising the amino acid sequence of a scFv that binds to a site on the cytokine different from the site at which the cytokine binding portion of the extracellular domain of the signal transducing component of the cytokine receptor binds; a nucleotide sequence encoding a second fusion polypeptide component comprising the amino acid sequence of the cytokine binding portion of the extracellular domain of the signal transducing component of the cytokine's receptor; and a nucleotide sequence encoding a third fusion polypeptide component comprising the amino acid sequence of a multimerizing component.

In another embodiment, the invention contemplates an isolated nucleic acid molecule encoding a fusion polypeptide capable of binding a cytokine to form a nonfunctional complex comprising a nucleotide sequence encoding a first fusion polypeptide component comprising the amino acid sequence of a first scFv that binds to a site on the cytokine; a nucleotide sequence encoding a second fusion polypeptide component comprising the amino acid sequence a second scFv that binds to a site on the cytokine different from the site at which the first scFv binds; and a nucleotide sequence encoding a third fusion polypeptide component comprising the amino acid sequence of a multimerizing component.

In all of the above described embodiments comprising scFvs, the invention also contemplates embodiments in which the nucleotide sequence encoding the first component is upstream of the nucleotide sequence encoding the second component; embodiments in which the nucleotide sequence encoding the first component is downstream of the nucleotide sequence encoding the second component; and further embodiments of the invention in which the order of the first, second and third fusion polypeptide components is rearranged. For example, if the nucleotide sequence encoding the first component is designated 1, the nucleotide sequence encoding the second component is designated 2, and the nucleotide sequence of the third component is designated 3, then the order of the components in the isolated nucleic acid of the invention as read from 5' to 3' may be any of the following six combinations: 1,2,3; 1,3,2; 2,1,3; 2,3,1; 3,1,2; or 3,2,1.

In preferred embodiments of the invention, the multimerizing component comprises an immunoglobulin derived domain. More specifically, the immunoglobulin derived domain may be selected from the group consisting of the Fc domain or the heavy chain of IgG. Even more specifically, immunoglobulin domain may be selected from the group consisting of the Fc domain or the heavy chain of $IgG_1$ or $IgG_4$. In another embodiment, the multimerizing component may be an Fc domain from which the first five amino acids (including a cysteine) have been removed to produce a multimerizing component referred to as Fc(DCI). Alternatively, the multimerizing component may be an Fc domain in which a cysteine within the first five amino acids has been substituted for by another amino acid such as, for example, serine or alanine.

The present invention also provides for fusion polypeptides encoded by the isolated nucleic acid molecules of the invention. Preferably, the fusion polypeptides are in multimeric form, due to the function of the third component, the multimerizing component. In a preferred embodiment, the multimer is a dimer. Suitable multimerizing components are sequences encoding an immunoglobulin heavy chain hinge region (Takahashi et al. 1982 supra); immunoglobulin gene sequences, and portions thereof. In a preferred embodiment of the invention, immunoglobulin gene sequences, especially one encoding the Fc domain, are used to encode the multimerizing component.

The present invention also contemplates a vector which comprises the nucleic acid molecule of the invention as described herein.

A preferred embodiment of the invention is an isolated nucleic acid molecule having the sequence set forth in SEQ ID NO:33 encoding a fusion polypeptide having the sequence set forth in SEQ ID NO:34, wherein the fusion polypeptide forms a multimer that is capable of binding a cytokine to form a nonfunctional complex; an isolated nucleic acid molecule having the sequence set forth in SEQ ID NO:35 encoding a fusion polypeptide having the sequence set forth in SEQ ID NO:36, wherein the fusion polypeptide forms a multimer that is capable of binding a cytokine to form a nonfunctional complex; and an isolated nucleic acid molecule having the sequence set forth in SEQ ID NO:37 encoding a fusion polypeptide having the sequence set forth in SEQ ID NO:38, wherein the fusion polypeptide forms a multimer that is capable of binding a cytokine to form a nonfunctional complex; as well as fusion polypeptides encoded by the above-described nucleic acid molecules.

Other preferred embodiments of the invention are isolated nucleic acid molecules having the sequences set forth in SEQ ID NO: 39, 41, 43, 45, 47, 49, 51, 53, 55, 57, 59, 61, 63, 65, 67, 69, 71, 73, 75, 77, 79, 81, or 83 encoding fusion polypeptides having the sequences set forth in SEQ ID NO: 40, 42, 44, 46, 48, 50, 52, 54, 56, 58, 60, 62, 64, 66, 68, 70, 72, 74, 76, 78, 80, 82, or 84, respectively, wherein each fusion polypeptide forms a multimer that is capable of binding IL-1 to form a non-functional complex.

Also provided is an expression vector comprising a nucleic acid molecule of the invention as described herein, wherein the nucleic acid molecule is operatively linked to an expression control sequence. Also provided is a host-vector system for the production of a fusion polypeptide comprising the expression vector of the invention which has been introduced into a host cell suitable for expression of the fusion polypeptide. The suitable host cell may be a bacterial cell such as *E. coli*, a yeast cell, such as *Pichia pastoris*, an insect cell, such as *Spodoptera frugiperda*, or a mammalian cell, such as a COS, CHO, 293, BHK or NS0 cell.

The present invention also provides for methods of producing the fusion polypeptides of the invention by growing cells of the host-vector systems described herein, under conditions permitting production of the fusion polypeptide and recovering the fusion polypeptide so produced.

The present invention provides novel antagonists which are based on receptor components that are shared by cytokines such as the CNTF family of cytokines.

The invention described herein contemplates the production of antagonists to any cytokine that utilizes an α specificity determining component which, when combined with the cytokine, binds to a first β signal transducing component to form a nonfunctional intermediate which then binds to a second β signal transducing component causing β-receptor dimerization and consequent signal transduction. According to the invention, the soluble α specificity determining component of the receptor (sRα) and the extracellular domain of the first β signal transducing component of the cytokine receptor (β1) are combined to form heterodimers (sRα:β1) that act as antagonists to the cytokine by binding the cytokine to form a nonfunctional complex.

The invention described herein also contemplates the production of antagonists to any cytokine that utilizes an a specificity determining component which, when combined with the cytokine, binds to a β signal transducing component to form a receptor complex which then initiates signal transduction. According to the invention, the soluble a specificity determining component of the receptor (sRα) and the extracellular domain of the β signal transducing component of the cytokine receptor (b) are combined to form heterodimers (sRα:β) that act as antagonists to the cytokine by binding the cytokine to form a nonfunctional complex.

As described in Example 1, CNTF and IL-6 share the β1 receptor component gp130. The fact that CNTF forms an intermediate with CNTFRα and gp130 can be demonstrated (Example 1) in cells lacking LIFRβ, where the complex of CNTF and CNTFRα binds gp130, and prevents homodimerization of gp130 by IL-6 and IL-6Rα, thereby blocking signal transduction. These studies provide the basis for the development of the IL-6 antagonists described herein, as they show that if, in the presence of a ligand, a nonfunctional intermediate complex, consisting of the ligand, its a receptor component and its b1 receptor component, can be formed, it will effectively block the action of the ligand. Other cytokines may use other β1 receptor components, such as LIFRβ, which may also be used to produce antagonists according to the present invention.

Thus for example, in one embodiment of the invention, effective antagonists of IL-6 or CNTF consist of heterodimers of the extracellular domains of the a specificity determining components of their receptors (sIL-6Rα and sCNTFRα, respectively) and the extracellular domain of gp130. The resultant heterodimers, which are referred to hereinafter as sIL-6Rα:β1 and sCNTFRα:β1, respectively, function as high-affinity Traps for IL-6 or CNTF, respectively, thus rendering the cytokine inaccessible to form a signal transducing complex with the native membrane-bound forms of their receptors.

Although soluble ligand binding domains from the extracellular portion of receptors have proven to be somewhat effective as Traps for their ligands and thus act as antagonists (Bargetzi et al. 1993 Cancer Res 53:4010-4013; and 1992 Proc. Natl. Acad. Sci. USA 89:8616-8620; Mohler et al. 1993 J. Immunol. 151: 1548-1561; Narazaki et al. 1993 Blood 82:1120-1126), the IL-6 and CNTF receptors are unusual in that the α receptor components constitute ligand binding domains that, in concert with their ligands, function effectively in soluble form as receptor agonists (Davis et al. 1993 supra; Taga et al. 1989 Cell 58: 573-581). The sRα:β1 heterodimers prepared according to the present invention provide effective Traps for their ligands, binding these ligands with affinities in the picomolar range (based on binding studies for CNTF to PC12D cells) without creating functional intermediates. The technology described herein may be applied to develop a cytokine Trap for any cytokine that utilizes an α-component that confers specificity, as well as a β component which, when bound to the α-specificity component, has a higher affinity for the cytokine than either component alone. Accordingly, antagonists according to the invention include antagonists of IL-1 through IL-5 (IL-1: Greenfeder, et al. 1995 J Biol Chem 270:13757-13765; Guo et al. 1995 J Biol Chem 270:27562-27568), IL-2 (Taniguchi et al. EP 0386289-A and 0386304-A; Takeshita et al. 1992 Science 257:379-382); IL-3 (Kitamura et al. 1991 Cell 66:1165-1174), IL-4 (Idzerda et al. 1990 J Exp Med 171:861-873), IL-5 (Taverneir et al. 1991 Cell 66:1175-1184), IL-11 (Cherel et al. EMBL/GenBank/DDBJ databases Accession No. Z38102), IL-15 (Hemar et al. 1995 J Cell Biol 1295:55-64); Taniguchi et al. EP 0386289-A and 0386304-A); Takeshita et al. 1992 Science 257:379-382), granulocyte-macrophage colony stimulating factor (GM-CSF) Hayashida et al. 1990 Proc. Natl. Acad. Sci. U.S.A. 97:9655-9659), LIF, γ-interferon (Aguet 1988 et al. Cell 55:273-280; Soh et al. 1994 Cell 76:793-802), and transforming growth factor beta (TGFβ) (Inagaki et al. 1993 Proc. Natl. Acad. Sci. USA 90:5359-5363).

The α and β receptor extracellular domains may be prepared using methods known to those skilled in the art. The CNTFRa receptor has been cloned, sequenced and expressed (Davis et al. 1991 Science 253:59-63 which is incorporated by reference in its entirety herein). The cloning of LIFRβ and gp130 are described in Gearing et al. 1991 EMBO J. 10:2839-2848, Hibi et al. 1990 supra and WO 93/10151, all of which are incorporated by reference in their entirety herein.

The receptor molecules useful for practicing the present invention may be prepared by cloning and expression in a prokaryotic or eukaryotic expression system. The recombinant receptor gene may be expressed and purified utilizing any number of methods. The gene encoding the factor may be subcloned into a bacterial expression vector, such as for example, but not by way of limitation, pCP110.

The recombinant factors may be purified by any technique which allows for the subsequent formation of a stable, biologically active protein. For example, and not by way of limitation, the factors may be recovered from cells either as soluble proteins or as inclusion bodies, from which they may be extracted quantitatively by 8M guanidinium hydrochloride and dialysis. In order to further purify the factors, conventional ion exchange chromatography, hydrophobic interaction chromatography, reverse phase chromatography or gel filtration may be used.

The sRα:β heterodimeric receptors may be engineered using known fusion regions, as described in WO 93/10151 which describes production of β receptor heterodimers, or they may be prepared by crosslinking of extracellular domains by chemical means. The domains utilized may consist of the entire extracellular domain of the a and b components, or they may consist of mutants or fragments thereof that maintain the ability to form a complex with its ligand and other components in the sRα:β1 complex. For example, as described below in Example 4, IL-6 antagonists have been prepared using gp130 that is lacking its three fibronectin-like domains.

In one embodiment of the invention, the extracellular domains are engineered using leucine zippers. The leucine zipper domains of the human transcription factors c-jun and c-fos have been shown to form stable heterodimers (Busch et al. 1990 Trends Genetics 6:36-40; Gentz et al. 1989 Science 243:1695-1699) with a 1:1 stoichiometry. Although jun-jun homodimers have also been shown to form, they are about 1000-fold less stable than jun-fos heterodimers. Fos-fos homodimers have not been detected.

The leucine zipper domain of either c-jun or c-fos are fused in frame at the C-terminus of the soluble or extracellular domains of the above mentioned receptor components by genetically engineering chimeric genes. The fusions may be direct or they may employ a flexible linker domain, such as the hinge region of human IgG, or polypeptide linkers consisting of small amino acids such as glycine, serine, threonine or alanine, at various lengths and combinations. Additionally, the chimeric proteins may be tagged by His-His-His-His-His- His (His6) (SEQ. ID NO. 1) to allow rapid purification by metal-chelate chromatography, and/or by epitopes to which antibodies are available, to allow for detection on western blots, immunoprecipitation, or activity depletion/blocking in bioassays.

In another embodiment, as described below in Example 3, the sRα:β1 heterodimer is prepared using a similar method, but using the Fc-domain of human IgG1 (Aruffo et al. 1991 Cell 67:35-44). In contrast to the latter, formation of heterodimers must be biochemically achieved, as chimeric molecules carrying the Fc-domain will be expressed as disulfide-linked homodimers. Thus, homodimers may be reduced under conditions that favor the disruption of inter-chain disulfides but do not effect intra-chain disulfides. Then monomers with different extracellular portions are mixed in equimolar amounts and oxidized to form a mixture of homo- and heterodimers. The components of this mixture are separated by chromatographic techniques. Alternatively, the formation of this type of heterodimers may be biased by genetically engineering and expressing molecules that consist of the soluble or extracellular portion of the receptor components followed by the Fc-domain of hIgG, followed by either the c-jun or the c-fos leucine zippers described above (Kostelny et al. 1992 J Immunol 148:1547-1553). Since these leucine zippers form predominately heterodimers, they may be used to drive formation of the heterodimers where desired. As for the chimeric proteins described using leucine zippers, these may also be tagged with metal chelates or an epitope. This tagged domain can be used for rapid purification by metal-chelate chromatography, and/or by antibodies, to allow for detection on western blots, immunoprecipitation, or activity depletion/blocking in bioassays.

In additional embodiments, heterodimers may be prepared using other immunoglobulin derived domains that drive the formation of dimers. Such domains include, for example, the heavy chains of IgG (Cg1 and Cg4), as well as the constant regions of kappa (κ) and lambda (λ) light chains of human immunoglobulins. The heterodimerization of Cγ with the light chain occurs between the CH1 domain of Cγ and the constant region of the light chain ($C_L$), and is stabilized by covalent linking of the two domains via a single disulfide bridge. Accordingly, as described in Example 4, constructs may be prepared using these immunoglobulin domains. Alternatively, the immunoglobulin domains include domains that may be derived from T cell receptor components which drive dimerization.

In another embodiment of the invention, the sRα:β1 heterodimers are prepared by expression as chimeric molecules utilizing flexible linker loops. A DNA construct encoding the chimeric protein is designed such that it expresses two soluble or extracellular domains fused together in tandem ("head to head") by a flexible loop. This loop may be entirely artificial (e.g. polyglycine repeats interrupted by serine or threonine at a certain interval) or "borrowed" from naturally occurring proteins (e.g. the hinge region of hIgG). Molecules may be engineered in which the order of the soluble or extracellular domains fused is switched (e.g. sIL6Rα/loop/sgp130 or sgp130/loop/sIL-6Rα) and/or in which the length and composition of the loop is varied, to allow for selection of molecules with desired characteristics.

Alternatively, the heterodimers made according to the present invention may be purified from cell lines cotransfected with the appropriate α and β components. Heterodimers may be separated from homodimers using methods available to those skilled in the art. For example, limited quantities of heterodimers may be recovered by passive elution from preparative, nondenaturing polyacrylamide gels. Alternatively, heterodimers may be purified using high pressure cation exchange chromatography. Excellent purification has been obtained using a Mono S cation exchange column.

In addition to sRα:β1 heterodimers that act as antagonists by binding free CNTF or IL-6, the present invention also contemplates the use of engineered, mutated versions of IL-6 with novel properties that allow it to bind to IL-6Rα and a single gp130 molecule, but fail to engage the second gp130 to complete β component homodimerization, and thus act as an effective IL-6 antagonist on any IL-6 responsive cell. Our model for the structure of the IL-6 and CNTF receptor complexes indicates that these cytokines have distinct sites for binding the α, β1, and β2 receptor components (Stahl et al. 1993 supra). Mutations of critical amino acid residues comprising each of these sites gives rise to novel molecules which have the desired antagonistic properties. Ablation of the b1 site would give a molecule which could still bind to the a receptor component but not the β1 component, and thereby comprise an antagonist with nanomolar affinity. Mutations of critical amino acid residues comprising the β2 site of IL-6 (IL-6β2$^-$) would give a molecule that would bind to IL-6Rα and the first gp130 monomer, but fail to engage the second gp130 and thus be functionally inactive. Similarly, mutations of the CNTF β2 site would give a molecule (CNTFβ2$^-$) that would bind CNTFRα and gp130, but fail to engage LIFRβ, thereby antagonizing CNTF action by forming the non-functional β1 intermediate. Based on the binding results described above where CNTF forms the β1 intermediate with high affinity, both CNTFβ2$^-$ and IL-β2$^-$ would constitute antagonists with affinity in the range of 10 pM.

A variety of means are used to generate and identify mutations of IL-6 or CNTF that have the desired properties. Random mutagenesis by standard methods of the DNA encoding IL-6 or CNTF may be used, followed by analysis of the collection of products to identify mutated cytokines having the desired novel properties as outlined below. Mutagenesis by genetic engineering has been used extensively in order to elucidate the structural organization of functional domains of recombinant proteins. Several different approaches have been described in the literature for carrying out deletion or substitution mutagenesis. The most successful appear to be alanine scanning mutagenesis (Cunningham et al. 1989 Science 244: 1081-1085) and homolog-scanning mutagenesis (Cunningham et al. 1989 Science 243:1330-1336).

Targeted mutagenesis of the IL-6 or CNTF nucleic acid sequences using such methods can be used to generate CNTFβ2- or IL-6β2-candidates. The choice of regions appropriate for targeted mutagenesis is done systematically, or determined from studies whereby panels of monoclonal antibodies against each factor are used to map regions of the cytokine that might be exposed after binding of the cytokine to the a receptor component alone, or to the ab1 heterodimeric soluble receptors described above. Similarly, chemical modification or limited proteolysis of the cytokine alone or in a complex bound to the a receptor component or the ab1 heterodimeric soluble receptors described above, followed by analysis of the protected and exposed regions could reveal potential β2 binding sites.

Assays for identifying CNTF or IL-6 mutants with the desired properties involve the ability to block with high affinity the action of IL-6 or CNTF on appropriately responsive cell lines (Davis et al. 1993 supra; Murakami et al. 1991 Proc Natl Acad Sci USA 88:11349-11353). Such assays include cell proliferation, survival, or DNA synthesis driven by CNTF or IL-6, or the construction of cell lines where binding of factor induces production of reporters such as CAT or β-galactosidase (Savino et al. 1993 Proc Natl Acad Sci USA 90:4067-4071).

Alternatively, the properties of various mutants may be assessed with a receptor-based assay. One such assay consists of screening mutants for their ability to bind the sRα:β1 receptor heterodimers described above using epitope-tagged (Davis et al. 1991 supra) sRα:β1 reagents. Furthermore, one can probe for the presence or absence of the β2 site by assessing whether an epitope-tagged soluble β2 reagent will bind to the cytokine in the presence of the β1 heterodimer. For example, CNTF only binds to LIFRβ (the β2 component) in the presence of both CNTFRα and gp130 (Davis et al. 1993 supra; Stahl et al. 1993 supra). Thus a soluble LIFRβ reagent would only bind to CNTF in the presence of the soluble sRα:β1 dimer sCNTFRα:β1. For IL-6, the sRα:β1 reagent would be IL-6Rα:β1, and the probe for the β2 site would be epitope-tagged sgp130. Thus β2-mutants of CNTF would be identified as those that bound the sRα:β1 reagent, demonstrating that the α and β1 site of the cytokine were intact, yet failed to bind the β2 reagent.

In addition, the present invention provides for methods of detecting or measuring the activity of potential β2⁻ mutants by measuring the phosphorylation of a β-receptor component or a signal transduction component selected from the group consisting of Jak1, Jak2 and Tyk2 or any other signal transduction component, such as the CLIPs, that are determined to be phosphorylated in response to a member of the CNTF family of cytokines.

A cell that expresses the signal transduction component(s) described herein may either do so naturally or be genetically engineered to do so. For example, Jak1 and Tyk-2-encoding nucleic acid sequences obtained as described in Velazquez et al. 1992 Cell 70:313-322, may be introduced into a cell by transduction, transfection, microinjection, electroporation, via a transgenic animal, etc., using any known method known in the art.

According to the invention, cells are exposed to a potential antagonist and the tyrosine phosphorylation of either the β-component(s) or the signal transduction component(s) are compared to the tyrosine phosphorylation of the same component(s) in the absence of the potential antagonist.

In another embodiment of the invention, the tyrosine phosphorylation that results from contacting the above cells with the potential antagonist is compared to the tyrosine phosphorylation of the same cells exposed to the parental CNTF family member. In such assays, the cell must either express the extracellular receptor (α-component) or the cells may be exposed to the test agent in the presence of the soluble receptor component. Thus, for example, in an assay system designed to identify agonists or antagonists of CNTF, the cell may express the α-component CNTFRα, the β-components gp130 and LIFRβ and a signal transducing component such as Jak1. The cell is exposed to test agents, and the tyrosine phosphorylation of either the β-components or the signal transducing component is compared to the phosphorylation pattern produced in the presence of CNTF. Alternatively, the tyrosine phosphorylation which results from exposure to a test agent is compared to the phosphorylation which occurs in the absence of the test agent. Alternatively, an assay system, for example, for IL-6 may involve exposing a cell that expresses the β-component gp130 and a signal transducing protein such as Jak1, Jak2 or Tyk2 to a test agent in conjunction with the soluble IL-6 receptor.

In another embodiment of the invention the above approaches are used to develop a method for screening for small molecule antagonists that act at various steps in the process of ligand binding, receptor complex formation, and subsequent signal transduction. Molecules that potentially interfere with ligand-receptor interactions are screened by assessing interference of complex formation between the soluble receptors and ligand as described above. Alternatively, cell-based assays in which IL-6 or CNTF induce response of a reporter gene are screened against libraries of small molecules or natural products to identify potential antagonists. Those molecules showing antagonist activity are rescreened on cell-based assays responding to other factors (such as GM-CSF or factors like Neurotrophin-3 that activate receptor tyrosine kinases) to evaluate their specificity against the CNTF/IL-6/OSM/LIF family of factors. Such cell-based screens are used to identify antagonists that inhibit any of numerous targets in the signal transduction process.

In one such assay system, the specific target for antagonists is the interaction of the Jak/Tyk family of kinases (Firmbach-Kraft 1990 Oncogene 5:1329-1336; Wilks et al. 1991 Mol Cell Biol 11:2057-2065) with the receptor β subunits. As described above, LIFRβ and gp130 preassociate with members of the Jak/Tyk family of cytoplasmic protein tyrosine kinases, which become activated in response to ligand-induced β component dimerization (Stahl et al. 1993 supra). Thus small molecules that could enter the cell cytoplasm and disrupt the interaction between the β component and the Jak/Tyk kinase could potentially block all subsequent intracellular signaling. Such activity could be screened with an in vitro scheme that assessed the ability of small molecules to block the interaction between the relevant binding domains of purified β component and Jak/Tyk kinase. Alternatively, one could easily screen for molecules that could inhibit a yeast-based assay of b component binding to Jak/Tyk kinases using the two-hybrid interaction system (Chien et al. 1991 Proc. Natl. Acad. Sci. 88: 9578-9582). In such a system, the interaction between two proteins (β component and Jak/Tyk kinase or relevant domains thereof in this example) induces production of a convenient marker such as β-galactosidase. Collections of small molecules are tested for their ability to disrupt the desired interaction without inhibiting the interaction between two control proteins. The advantage of this screen would be the requirement that the test compounds enter the cell before inhibiting the interaction between the b component and the Jak/Tyk kinase.

The CNTF family antagonists described herein either bind to, or compete with the cytokines CNTF and IL-6. Accordingly, they are useful for treating diseases or disorders mediated by CNTF or IL-6. For example, therapeutic uses of IL-6 antagonists would include the following: (1) In osteoporosis, which can be exacerbated by lowering of estrogen levels in post-menopausal women or through ovariectomy, IL-6 appears to be a critical mediator of osteoclastogenesis, leading to bone resorption (Horowitz 1993 Science 260:626-627; Jilka et al. 1992 Science 257:88-91). Importantly, IL-6 only appears to play a major role in the estrogen-depleted state, and apparently is minimally involved in normal bone maintenance. Consistent with this, experimental evidence indicates that function-blocking antibodies to IL-6 can reduce the number of osteoclasts (Jilka et al. 1992 Science 257:88-91). While estrogen replacement therapy is also used, there appear to be side effects that may include increased risk of endometrial and breast cancer. Thus, IL-6 antagonists as described herein would be more specific to reduce osteoclastogenesis to normal levels; (2) IL-6 appears to be directly involved in multiple myeloma by acting in either an autocrine or paracrine fashion to promote tumor formation (van Oers et al. 1993 Ann Hematol 66:219-223). Furthermore, the elevated IL-6 levels create undesirable secondary effects such as bone resorption, hypercalcemia, and cachexia; in limited studies function-blocking antibodies to IL-6 or IL-6Rα have some efficacy (Klein et al. 1991 Blood 78:1198-1204; Suzuki et al. 1992 Eur J Immunol 22:1989-1993). Therefore, IL-6 antagonists as described herein would be beneficial for both the secondary effects as well as for inhibiting tumor growth; (3) IL-6 may be a mediator of tumor necrosis factor (TNF) that leads to cachexia associated with AIDS and cancer (Strassmann et al. 1992 J Clin Invest 89:1681-1684), perhaps by reducing lipoprotein lipase activity in adipose tissue (Greenberg et al. 1992 Cancer Research 52:4113-4116). Accordingly, antagonists described herein would be useful in alleviating or reducing cachexia in such patients.

Effective doses useful for treating these or other CNTF family related diseases or disorders may be determined using methods known to one skilled in the art [see, for example, Fingl et al. 1975 The Pharmacological Basis of Therapeutics, Goodman and Gilman, eds. Macmillan Publishing Co., New York, pp. 1-46). Pharmaceutical compositions for use according to the invention include the antagonists described above in a pharmacologically acceptable liquid, solid or semi-solid carrier, linked to a carrier or targeting molecule (e.g., antibody, hormone, growth factor, etc.) and/or incorporated into liposomes, microcapsules, and controlled release preparation (including antagonist expressing cells) prior to administration in vivo. For example, the pharmaceutical composition may comprise one or more of the antagonists in an aqueous solution, such as sterile water, saline, phosphate buffer or dextrose solution. Alternatively, the active agents may be comprised in a solid (e.g. wax) or semi-solid (e.g. gelatinous) formulation that may be implanted into a patient in need of such treatment. The administration route may be any mode of administration known in the art, including but not limited to intravenously, intrathecally, subcutaneously, by injection into involved tissue, intraarterially, intranasally, orally, or via an implanted device.

Administration may result in the distribution of the active agent of the invention throughout the body or in a localized area. For example, in some conditions which involve distant regions of the nervous system, intravenous or intrathecal administration of agent may be desirable. In some situations, an implant containing active agent may be placed in or near the lesioned area. Suitable implants include, but are not limited to, gelfoam, wax, or microparticle-based implants.

EXAMPLES

Example 1

CNTF Competes with IL-6 for Binding to gp130

Materials and methods. A clone of PC12 cells that respond to IL-6 (PC12D) was obtained from DNAX. Rat CNTF was prepared as described (Masiakowski et al. 1991 J Neurochem 57:1003-10012). IL-6 and sIL-6Ra were purchased from R & D Systems. Antisera was raised in rabbits against a peptide derived from a region near the C-terminus of gp130 (CGTEGQVERFETVGME) (SEQ ID NO:2) by the method of Stahl et al. 1993 J Biol Chem 268:7628-7631. Anti-phosphotyrosine monoclonal 4G10 was purchased from UBI, and reagents for ECL from Amersham.

Signal Transduction Assays. Plates (10 cm) of PC12D were starved in serum-free medium (RPMI 1640+glutamine) for 1 hour, then incubated with IL-6 (50 ng/mL)+sIL-6R (1 mg/mL) in the presence or absence of added rat CNTF at the indicated concentrations for 5 minutes at 37° C. Samples were then subjected to anti-gp130 immunoprecipitation, SDS PAGE, and anti-phosphotyrosine immunoblotting.

Figure 2:
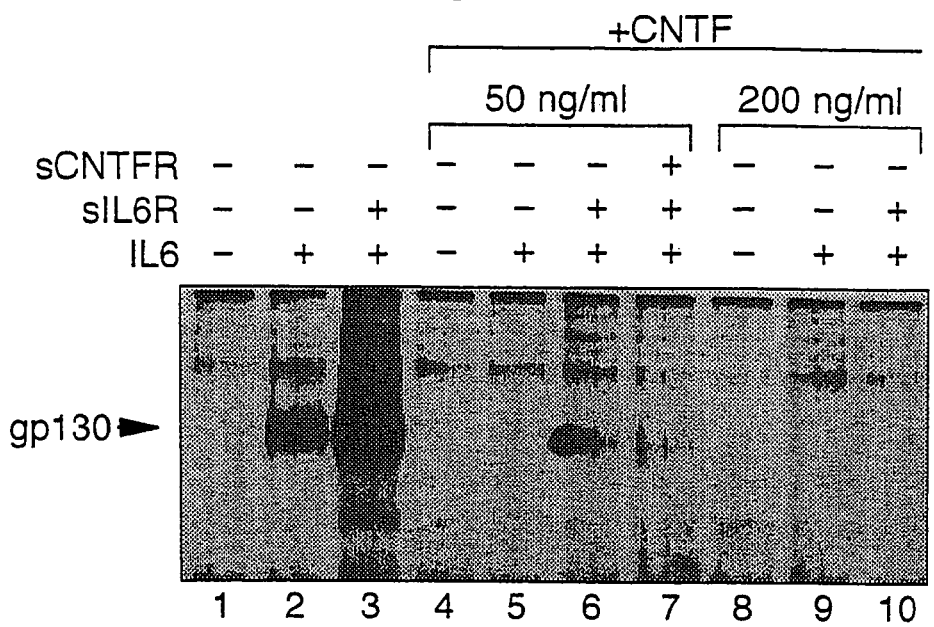
FIG. 2: CNTF inhibits IL-6 responses in a PC12 cell line (called PC12D) that expresses IL6Ra, gp130, CNTFRa, but not LIFRb. Serum-deprived PC12D cells were incubated +IL-6 (50 ng/mL) in the presence or absence of CNTF as indicated. Some plates also received soluble IL6Ra (1 mg/mL) or soluble CNTFRa (1 mg/mL) as indicated. Cell lysates were subjected to immunoprecipitation with anti-gp130 and immunoblotted with anti-phosphotyrosine. Tyrosine phosphorylation of gp130 is indicative of IL-6 induced activation of the IL-6 receptor system, which is blocked upon coaddition of CNTF.

Results. The ability of CNTF to block IL-6 responses was measured using a PC12 cell line (called PC12D) that expresses IL-6Rα, gp130, and CNTFRα, but not LIFRb. As one would predict, these cells respond to IL-6, but not to CNTF (FIG. 2) since LIFRβ is a required component for CNTF signal transduction (Davis et al. 1993 supra). In accordance with results on other cell lines (Ip et al. 1992 supra), PC12D cells give tyrosine phosphorylation of gp130 (as well as a variety of other proteins called CLIPs) in response to 2 nM IL-6 (FIG. 2). Addition of recombinant soluble IL-6Ra (sIL-6Ra) enhances the level of gp130 tyrosine phosphorylation, as has been reported in some other systems (Taga et al. 1989 supra). However, addition of 2 nM CNTF simultaneously with IL-6 severely diminishes the tyrosine phosphorylation of gp130. Although a slight gp130 phosphorylation response remains in the presence of CNTF, IL-6, and sIL-6Rα, it is eliminated if the CNTF concentration is increased fourfold to 8 nM. Thus, in IL-6 responsive cells that contain CNTFRa but no LIFRb, CNTF is a rather potent antagonist of IL-6 action.

Example 2

Binding of CNTF to the CNTFRα:β

Scatchard Analysis of CNTF Binding. $^{125}$I-CNTF was prepared and purified as described [Stahl et al. 1993 supra). Saturation binding studies were carried out in PC12 cells, using concentrations of $^{125}$I-CNTF ranging from 20 pM to 10 nM. Binding was performed directly on a monolayer of cells. Medium was removed from wells and cells were washed once with assay buffer consisting of phosphate buffered saline (PBS; pH 7.4), 0.1 mM bacitracin, 1 mM PMSF, 1 mg/ml leupeptin, and 1 mg/ml BSA. Cells were incubated in $^{125}$I-CNTF for 2 hours at room temperature, followed by 2 quick washes with assay buffer. Cells were lysed with PBS containing 1% SDS and counted in a Packard Gamma Counter at 90-95% efficiency. Non-specific binding was defined by the presence of 100-fold excess of unlabelled CNTF. Specific binding ranged from 70% to 95%.

Figure 3:
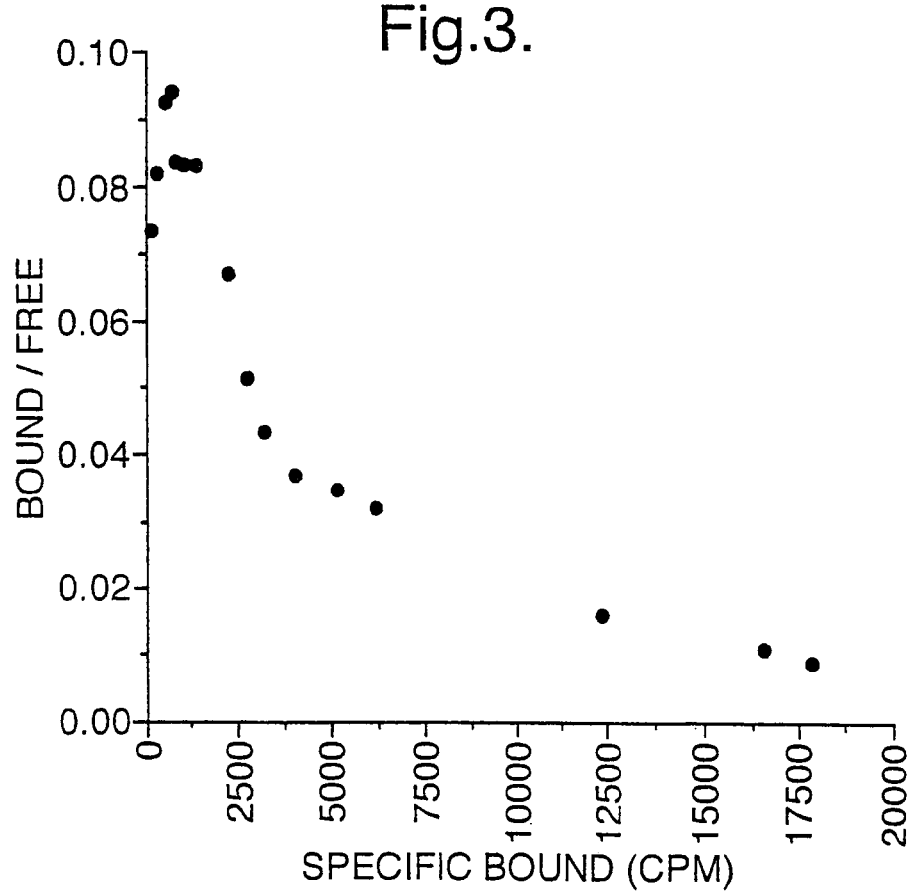
FIG. 3: Scatchard analysis of iodinated CNTF binding on PC12D cells. PC12D cells were incubated with various concentrations of iodinated CNTF in the presence or absence of excess non-radioactive competitor to determine the specific binding. The figure shows a Scatchard plot of the amount of iodinated CNTF specifically bound, and gives data consistent with two binding sites with dissociation constants of 9 pM and 3.4 nM.

Results. The equilibrium constant for binding of CNTF to CNTFRα:β1 was estimated from Scatchard analysis of iodinated CNTF binding on PC12D cells (FIG. 3). The data is consistent with a 2 site fit having dissociation constants of 9 pM and 3.4 nM. The low affinity site corresponds to interaction of CNTF with CNTFRα, which has a Kd near 3 nM (Panayotatos et al. 1993 J Biol Chem 268: 19000-19003). We interpret the high affinity complex as the intermediate containing CNTF, CNTFRa, and gp130. A Ewing sarcoma cell line (EW-1) which does contain CNTFRα, gp130, and LIFRβ, and therefore gives robust tyrosine phosphorylation in response to CNTF, displays a very similar two site fit with dissociation constants of 1 nM and 10. Thus it is apparent that CNTF binds with equally high affinity to a complex containing only CNTFR and gp130, as it does to a complex which additionally contains LIFRβ, thus demonstrating the feasibility of creating the sRα:β antagonists described herein.

Example 3

Methods of Producing Cytokine Ligand Traps

Virus Stock Production. SF21 insect cells obtained from *Spodoptera frugiperda* were grown at 27° C. in Gibco SF900 II medium to a density of 1×10⁶ cells/mL. The individual virus stock for either GP130-Fc-His$_6$ (FIGS. 4A-4B, SEQ ID NO:7) or IL6Rα-Fc (FIG. 5, SEQ ID NO:8) was added to the bioreactor to a low multiplicity 0.01-0.1 PFU/cell to begin the infection. The infection process was allowed to continue for 5-7 days allowing maximum virus replication without incurring substantial cell lysis. The cell suspension was aseptically aliquoted into sterile centrifuge bottles and the cells removed by centrifugation. The cell-free supernatant was collected in sterile bottles and stored at 4° C. until further use.

The virus titer was determined by plaque assay and is carried out in 60 mm tissue-culture dishes which are seeded with 2×10$^6$ cells. Serial dilutions of the virus stock are added to the attached cells and the mixture incubated with rocking to allow the virus to adsorb to individual cells. An agar overlay is added and plates incubated for 5-7 days at 27° C. Staining of viable cells with neutral red revealed circular plaques resulting which were counted to give the virus titer.

Coinfection of Cells for Protein Production. Uninfected SF21 Cells were grown in a 60 L ABEC bioreactor containing 40 L of SF900 II medium. Temperature was controlled at 27° C. and the dissolved oxygen level was maintained at 50% of saturation by controlling the flow rate of oxygen in the inlet gas stream. When a density of 2×10$^6$ cells/mL was reached, the cells were concentrated within the bioreactor to a volume of 20L using a low shear steam sterilizable pump with a tangential flow filtration device with Millipore Prostak 0.65 micron membranes. After concentration fresh sterile growth medium is slowly added to the bioreactor while the filtration system continues to remove the spent growth medium by diafiltration. After two volume exchanges (40L) have been carried out an additional 20L of fresh medium was added to the bioreactor to resuspend the cells to the original volume of 40L. The cell density was determined once again by counting viable cells using a hemacytometer.

The required amount of each virus stock was calculated based on the cell density, virus titer and the desired multiplicity of infection (MOI). Virus stock ratios of 5:1, 5:2, 10:2 and 10:4, IL6Ra-Fc to GP130-Fc-His$_6$ all resulted in production of significant amounts of heterodimer. The ideal virus stock ratio is highly dependent on the ease of purification of the heterodimer from each of the two homodimers. The IL6Rα-Fc homodimer is relatively easy to remove downstream by immobilized metal affinity chromatography. Virus infection ratios have been chosen to minimize the formation of the GP130-Fc-His$_6$ homodimer which is more difficult to clear downstream. The relative amount of GP130-Fc-His$_6$ virus stock chosen for infection has increased with successive batches as the purification method for clearing the resultant homodimer has improved.

The virus stocks were aseptically mixed in a single vessel then transferred to the bioreactor. This results in synchronous infection of the SF21 cells. The infection is allowed to proceed for three to four days, allowing sufficient time for maximal production of the heterodimer protein.

Recovery and Protein A Chromatographic Purification. At the conclusion of the infection phase of the bioreactor process the cells were concentrated in the bioreactor using a 10 ft$^2$ Millipore Prostak filter (0.65 micron) pore size. The cell-free permeate passing through the filter was collected in a clean process vessel. At the conclusion of the filtration operation the pH of permeate stream, containing the protein product, was adjusted to 8.0 with 10N NaOH. The resultant precipitate was removed by forcing the extract through a 0.8 micron depth filter (Sartorious), followed by a 0.2 micron filter. Sufficient 0.5M EDTA stock was added to give a final concentration of 5 mM. The filtered protein solution was loaded onto a 10 cm diameter column containing 100-200 mL of Pharmacia Protein A Sepharose 4 Fast Flow, equilibrated with PBS. Protein A has a very high affinity for the Fc-Fc domain of each of the 3 recombinant protein products, allowing them to bind while other proteins in the cell-free extract flow through the column. After loading the column was washed to baseline with PBS containing an additional 350 mM NaCl. The IgG-Fc tagged proteins were eluted at low pH, either with 0.5M acetic acid or with a decreasing pH gradient of 0.1M citric acid and 0.2M disodium phosphate buffers. Tris base or disodium phosphate was added to the eluted protein to avoid prolonged exposure to low pH conditions.

The pooled protein was diafiltered into PBS or HEPES buffer and derivitized with 1 mM iodoacetamide to protect the exposed sulfhydryl group on the free cysteine near the hinge region of each Fc domain. This prevents disulfide mediated aggregation of proteins. A 6 ft$^2$ Millipore spiral wound ultrafiltration membrane with nominal 30 kDa cutoff was used to perform the buffer exchange. The total protein was determined by UV absorbance at 280 nm using the diafiltration buffer as a blank. The relative amounts of heterodimer and two homodimer proteins were determined by SDS PAGE gel electrophoresis using a 6% Tris-Glycine gel (Novex). Gels were Coomassie-stained then transferred into destain solution overnight. A Shimadzu scanning densitometer was used to determine the relative intensity of the individual protein bands on the SDS PAGE gel. The peak area ratios are used to compute the fraction of heterodimer and each of the homodimers in the column pool fractions.

Immobilized Metal Affinity Chromatographic Purification. The six histidine residues on the C-terminus of the GP130-Fc-His$_6$ fusion protein provides an excellent molecular handle for separation of the heterodimeric IL6 antagonist from the two homodimers. The imidazole group on each of the C-terminal histidines of the GP130-Fc-His$_6$ moiety has a strong binding constant with several divalent metals, including copper, nickel, zinc, cobalt, iron and calcium. Since the IL6Rα-Fc homodimer has no C-terminal histidine residues, it clearly has the lowest affinity. The IL6Rα-Fc-GP130-Fc-His$_6$ heterodimer has a single stand set six histidines giving it greater affinity for the metal, while the GP130-Fc-His$_6$ homodimer has two sets of six histidines each giving it the highest affinity of the three IgG tagged proteins to the metal affinity column. Selective elution of the three proteins with increasing amounts of imidazole in the elution buffer therefore elutes the proteins in the following order: 1. IL6Rα-Fc homodimers, 2. IL6Rα-Fc-GP130-Fc-His heterodimer, 3. GP130-Fc-His homodimers.

A 26 mm diameter column containing 100 mL of Pharmacia Chelating Sepharose Fast Flow was saturated with a solution of nickel sulfate until a significant green color is observed in the column eluate. The column is then washed with several column volumes of deionized water, then equilibrated with 50 mM HEPES, 40 mM imidazole, pH 8.0. The binding of imidazole to the immobilized nickel results in a green to blue color change. Imidazole was added to the protein load to a final concentration of 40 mM. Addition of imidazole to the protein load reduces the binding of IL6Rα-Fc homodimer, increasing the surface area available for the remaining two species. After loading, the column was washed with several column volumes of 50 mM HEPES, 80 mM imidazole, pH 8.0 until a steady baseline was reestablished. The heterodimer was selectively eluted with 50 mM HEPES, 150 mM imidazole, pH 8.0 over several column volumes. The protein fractions were pooled and diafiltered into PBS as described in the section above.

Example 4

Alternative Methods of Constructing Ligand Traps

As described above, receptor activation by CNTF, and analogously by IL-6 and IL-11, follows an ordered sequence of binding events (FIG. 6). The cytokine initially binds to its cognate Rα with low affinity (Kd=3 to 10 nM); this is a required step—cells which do not express the cognate Rα do not respond to the cognate cytokine. The cytokine•Rα complex associates with the first signal transducing component, gp130, to form a high affinity complex (Kd in the order of 10 pM for the CNTF•CNTFRa•gp130 complex). This complex does not transduce signal, as it is the dimerization of the signal transducing components that brings about signaling (Stahl et al. 1994 J Neurobiology 25:1454-1466; Stahl et al. 1995 Science 267:1349-1353; Davis et al. 1993 supra; Stahl et al. 1994 Science 263:92-95; Murakami et al. 1993 Science 260:1808-1810). At least in the case of IL-6, the cytokine•Rα•signal transducer heterotrimeric complex subsequently associates with another like complex, to form a hexameric complex (FIG. 6) (Ward et al. 1994 J Biol Chem 269:23286-23289). The resulting dimerization of the signal transducers—gp130 in the case of IL-6 (Murakami et al. 1993 supra) and IL-11, gp130 and LIFR in the case of CNTF (Davis et al. 1993 supra)—brings about signal transduction.

The initial heterodimeric molecules made comprised a soluble Rα-component linked to the extracellular domain of gp130. These molecules were shown to mimic the high affinity cytokine•Rα•gp130 complex and behave as a high affinity antagonist of their cognate cytokine (FIG. 7). To make these molecules, the extracellular domain of gp130 was paired with the extracellular domain of the a-receptor components for IL-6 and CNTF, IL-6Rα and CNTFRα respectively. To link the Rα with the extracellular domain of gp130, the soluble Rα-components and gp130 were fused to the Fc portion of human IgG1 to produce Rα-Fc and gp130-Fc respectively. The Fc domain was chosen primarily but not solely because it naturally forms disulfide-linked dimers. Heterodimeric molecules comprising Rα-Fc•gp130-Fc were expressed, purified and shown to behave as highly potent antagonists of their cognate ligand. Furthermore, these molecules were found to be highly specific for their cognate cytokine since it is the choice of the α-receptor component which specifies which cytokine is bound and trapped (there is no measurable binding of the cytokine to gp130 in the absence of the appropriate Rα).

Here we describe an extension of this technology which allows the engineering of different heteromeric soluble receptor ligand Traps which by virtue of their design may have additional beneficial characteristics such as stability, Fc-receptor-mediated clearance, or reduced effector functions (such as complement fixation). Furthermore, the technology described should prove suitable for the engineering of any heteromeric protein in mammalian or other suitable protein expression systems, including but not limited to heteromeric molecules which employ receptors, ligands, and catalytic components such as enzymes or catalytic antibodies.

Figure 8:
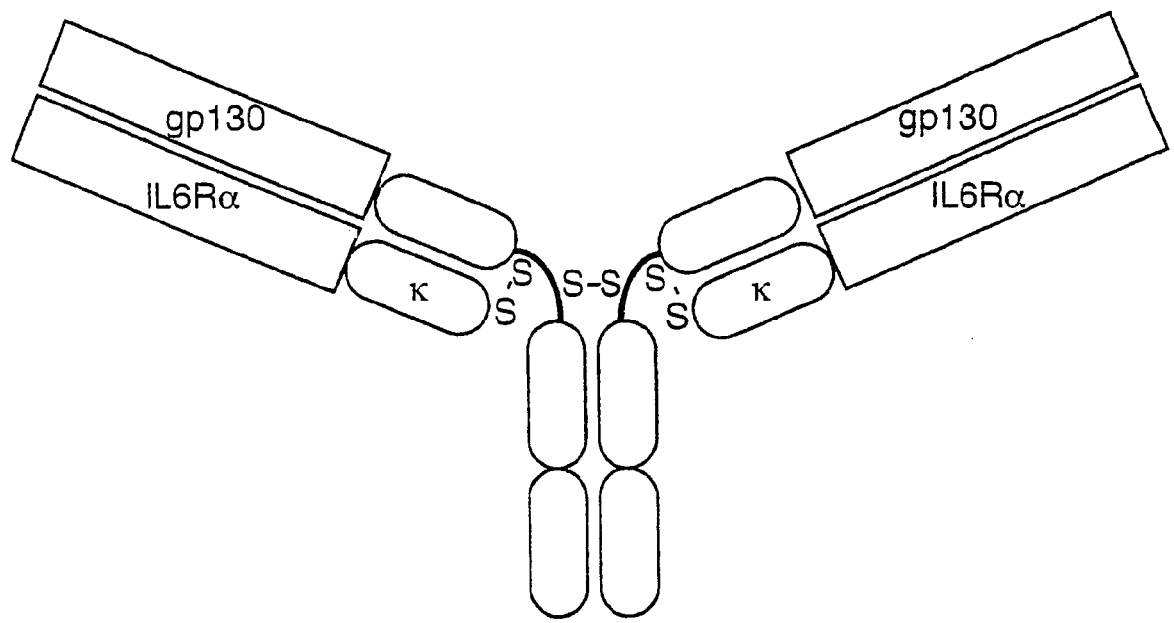
FIG. 8. Heteromeric immunoglobulin Heavy/Light Chain Receptor Fusions. An example of a heavy/light chain receptor fusion molecule is schematically depicted. The extracellular domain of gp130 is fused to Cg, whereas the extracellular domain of IL-6Ra is fused to the constant region of the kappa chain (k). The inter-chain disulfide bridges are also depicted (S-S).

Genetic engineering of heteromeric immunoglobulin heavy/light chain soluble receptor-based ligand Traps for IL-6. The IL-6 Traps described here were engineered using human gp130, human IL-6 α-receptor (IL-6Ra), the constant region of the heavy chains (Cγ) of human IgG1 (Cγ1) (Lewis et al. 1993 J Immunology 151:2829-2838) or IgG4 (Cγ4) with or without a join-region (J), and the constant regions of kappa (κ) and lambda (λ) (Cheung et al. 1992 J Virology 66:6714-6720) light chains of human immunoglobulin (Ig), also with or without a different j-peptide (j). This design takes advantage of the natural ability of the Cg domain to heterodimerize with κ or λ light chains. The heterodimerization of Cg with the light chain occurs between the CH1 domain of Cg and the constant region of the light chain ($C_L$), and is stabilized by covalent linking of the two domains via a single disulfide bridge. We reasoned that, like the Fc domain of human IgG1, the combination of Cg with $C_L$ could be used to produce disulfide linked heteromeric proteins comprised of the extracellular domain of gp130 on one chain and the extracellular domain of IL-6Rα on the other chain. Like their Fc-based counterparts, such proteins were postulated to be high affinity ligand Traps for IL-6 and as a result to inhibit the interaction of IL-6 with the native receptor on IL-6-responsive cells, thus functioning as IL-6 antagonists. Furthermore, constructs employing the full length Cg region would, much like antibodies, form homodimers of the Cg chain, giving rise to antibody-like molecules comprising of two "light chains" and two "heavy chains" (FIG. 8). The potential advantage of this design is that it may more closely mimic the IL-6IL•-6Rα•gp130 complex and may display a higher affinity for the ligand than comparable single heterodimers. An additional design is incorporated by using truncated versions of Cγ, comprised only of the $C_H1$ domain. These will form heterodimeric molecules with receptor-k fusion proteins, and will thus resemble the Fab fragment of antibodies.

All the soluble receptor-Ig chimeric genes may be engineered in plasmid vectors including, but not limited to, vectors suitable for mammalian expression (COS monkey kidney cells, Chinese Hamster Ovary cells (CHO), and ras-transformed fibroblasts (MG-ras) and include a Kozak sequence (CGC CGC CAC CAT GGT G) (SEQ ID NO: 3) at the beginning of each chimeric gene for efficient translation. Engineering was performed using standard genetic engineering methodology. Each construct was verified by DNA sequencing, mammalian expression followed by western blotting with suitable antibodies, biophysical assays that determine ligand binding and dissociation, and by growth inhibition assays (XG-1, as described later). Since the domains utilized to engineer these chimeric proteins are flanked by appropriate restriction sites, it is possible to use these domains to engineer other chimeric proteins, including chimeras employing the extracellular domains of the receptors for factors such as IL-1, IL-2, IL-3, IL-4, IL-5, GM-CSF, LIF, IL-11, IL-15, IFNg, TGFb, and others. The amino acid coordinates for each component utilized in making the IL-6 Traps are listed below (Note: numbering starts with the initiating methionine as 1; long sequences are listed using the single letter code for the twenty amino acids):

(a) Constructs employing human gp130: (i) gp130-Cγ1 was engineered by fusing in frame the extracellular domain of gp130 (amino acids 1 to 619) to a Ser-Gly bridge, followed by the 330 amino acids which comprise Cγ1 and a termination codon (SEQ ID NO: 9).

(ii) gp130-J-Cγ1 was engineered in the same manner as gp130-Cγ1 except that a J-peptide (amino acid sequence: GQGTLVTVSS) (SEQ ID NO: 4) was inserted between the Ser-Gly bridge and the sequence of Cγ1 (SEQ ID NO: 9).

(iii) gp130D3fibro-Cγ1 was engineered by fusing in frame the extracellular domain of gp130 without its three fibronectin-like domains (SEQ ID NO: 10). The remaining part of this chimeric protein is identical to gp130-Cγ1.

(iv) gp130-J-$C_H1$ was engineered in a manner identical for that described for gp130-Cγ1, except that in place of the Cγ1 region only the $C_H1$ part of Cγ1 has been used (SEQ ID NO: 11). The C-terminal domain of this construct includes the part of the hinge that contains the cysteine residue responsible for heterodimerization of the heavy chain of IgG with a light chain. The part of the hinge that contains the two cysteines involved in Cγ1 homodimerization has been deleted along with the $C_H2$ and $C_H3$ domains.

(v) gp130-Cγ4 was engineered in a manner identical to that described for gp130-Cγ1, except that Cγ4 was used in place of Cγ1 (SEQ ID NO: 12). In addition, an RsrII DNA restriction site was engineered at the hinge region of the Cg4 domain by introducing two silent base mutations. The RsrsII site allows for other desired genetic engineering manipulations, such as the construction of the $C_H1$ equivalent of gp130-Cγ4.

(vi) gp130-κ was engineered in a manner identical to that described for gp130-Cg1, except that the constant region of the κ light chain of human Ig was used in place of Cγ1 (SEQ ID NO: 13).

(vi) gp130-J-k was engineered in a manner identical to that described for gp130-J-κ, except that a j-peptide (SEQ ID NO: 5) was inserted between the Ser-Gly bridge and the κ-region.

(viii) gp130-l was engineered in a manner identical to that described for gp130-Cγ1, except that the constant region of the λ light chain (Cheung et al. 1992 supra) of human Ig was used in place of Cγ1 (SEQ ID NO: 14).

(b) Constructs employing human IL-6Rα: (i) IL6Rα-Cγ1 was engineered by fusing in frame amino acids 1 to 358 of IL-6Ra (Yamasaki et al. 1988 Science 241:825-828), which comprise the extracellular domain of IL-6Rα (SEQ ID NO: 15), to an Ala-Gly bridge, followed by the 330 amino acids which comprise Cγ1 and a termination codon.

(ii) IL6Rα-κ was engineered as described for IL6Rα-Cγ1, except that the κ-domain (SEQ ID NO: 13) utilized for gp130-κ was used in place of Cγ1.

(iii) IL6Rα-j-k was engineered as described for IL6Rα-κ except that the j-peptide described for gp130-j-κ was placed between the Ala-Gly bridge and the κ-domain.

(iv) Three additional constructs, IL6Rα313-Cγ1, IL6Rα313-κ, and IL6Rα313-j-κ, were engineered as using a truncated form of IL-6Rα comprised of amino acids 1 to 313 (SEQ ID NO:16). Each of these constructs were made by fusing in frame IL6Rα313 with a Thr-Gly bridge followed by the Cγ1, κ-, and j-κ-domains described above. These constructs were engineered in order to complement the gp130D3fibro-derived constructs.

Expression and purification of ligand Traps. To produce covalently linked heterodimers of soluble gp130 and soluble IL-6Rα, gp130-Ig chimeric proteins were co-expressed with appropriate IL-6Rα-Ig chimeric proteins in complementing pairs. Co-expression was achieved by co-transfecting the corresponding expression vectors into suitable mammalian cell lines, either stably or transiently. The resulting disulfide-linked heterodimers were purified from conditioned media by several different methods, including but not limited to affinity chromatography on immobilized Protein A or Protein G, ligand-based affinity chromatography, ion exchange, and gel filtration.

Figure 17:
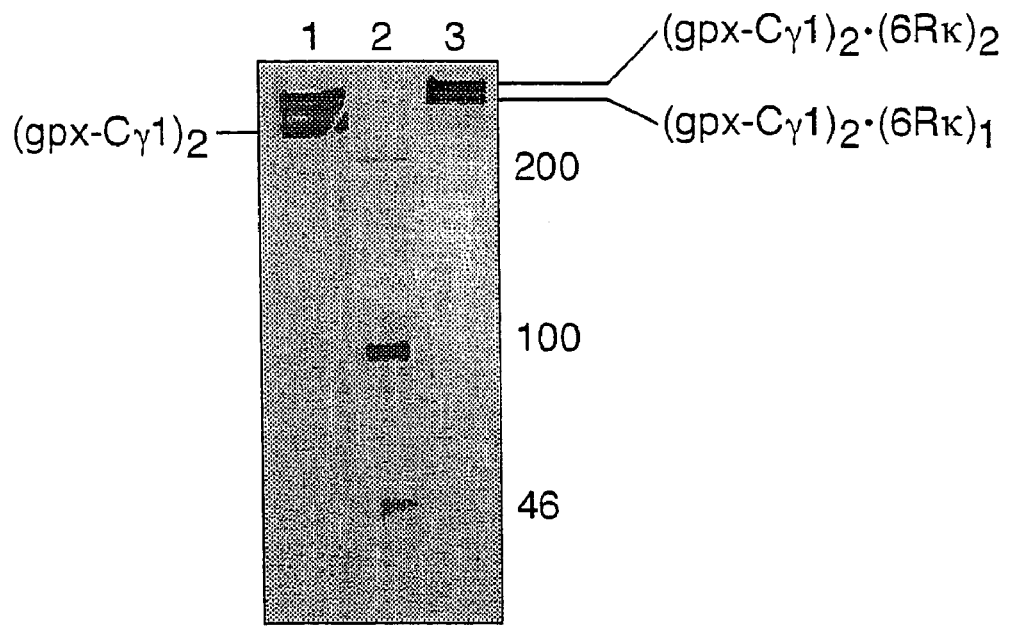
FIG. 17: Purification of gp130-Cg1•IL-6Ra-k. 4% to 12% SDS-PAGE gradient gel run under non-reducing conditions. Proteins were visualized by staining with silver. Lane 1: approximately 100 ng of material purified over Protein A Sepharose (Pharmacia). Lane 2: Molecular size standards (Amersham). Lane 3: The Protein A-purified material shown here after further purification over an IL-6 affinity chromatography step. The positions of the gp130-Cg1 dimer [(gp130-Cg1)$_2$], the gp130-Cg1 dimer associated with one IL-6Ra-k [(gp130-Cg1)$_2$•(IL-6Ra-k)$_1$], and the gp130-Cg1 dimer associated with two IL-6Ra-k [(gp130-Cg1)$_2$•(IL-6Ra-k)$_2$] are shown, as well as the sizes for the molecular size standards in kilodaltons (200, 100, and 46).

An example of the type of methods used for purification of a heavy/light receptor fusion protein is as follows: gp130-Cγ1•IL-6Rα-k was expressed in COS cells by co-transfecting two different vectors, encoding gp130-Cγ1 and IL-6Rα-κ respectively. Serum-free conditioned media (400 ml) were collected two days post-transfection and Cγ1-bearing proteins were purified by affinity chromatography over a 1 ml Protein A Sepharose (Pharmacia). The material generated in this step was further purified by a second affinity chromatography step over a 1 ml NHS-activated Sepharose (Pharmacia) which was derivatized with recombinant human IL-6, in order to remove gp130-Cγ1 dimer from gp130-Cγ1•IL-6Rα-k complexes (the gp130-Cγ1 dimer does not bind IL-6). Proteins generated by this method were more than 90% pure, as evidenced by SDS-PAGE followed by silver-staining (FIG. 17). Similar protocols have been employed successfully towards the purification of other heavy/light receptor heterodimers.

Figure 18:
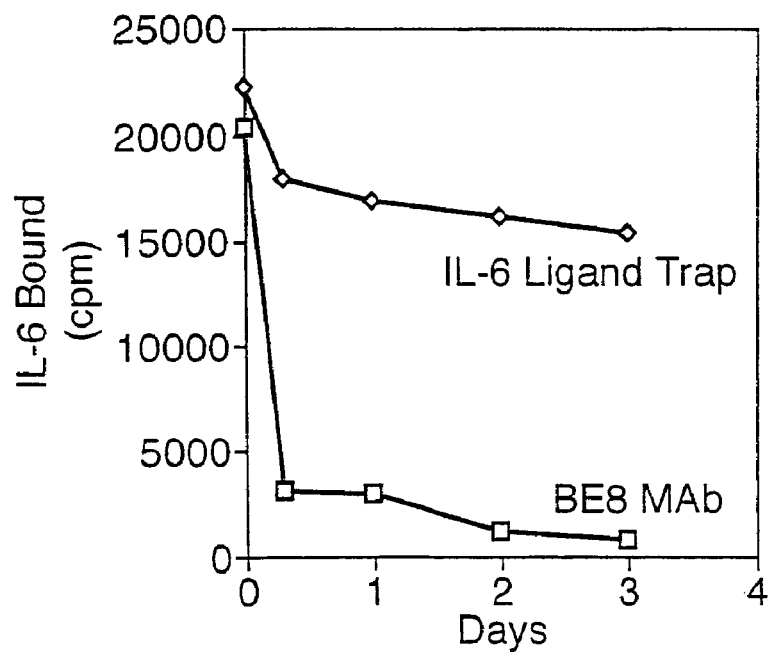
FIG. 18: IL-6 dissociates slowly from the ligand Trap. The dissociation rate of IL-6 from a heavy/light chain receptor-based ligand Trap (gp130-Cg1•IL-6Ra-k) was compared to that obtained with the neutralizing monoclonal antibody B-E8 (BE8 MAb).

Biological activity of immunoglobulin heavy/light chain receptor fusion antagonists. The purified ligand Traps were tested for their ability to bind IL-6 in a variety of different assays. For example, the dissociation rate of IL-6 bound to the ligand Trap was measured in parallel with the dissociation rate of IL-6 from the anti-IL-6 monoclonal neutralizing antibody B-E8 (Brochier et al. 1995 Int J Immunopharmacology 17:41-48). An example of this type of experiment is shown in FIG. 18. In this experiment 20 pM $^{125}$I-IL-6 (1000 μCi/mmol; Amersham) was preincubated with 500 pM of either gp130-Cg1•IL-6Rα-κ or mAb B-E8 for 20 hours. At this point a 1000-fold excess (20 nM) of "cold" IL-6 was added. Periodically, aliquots of the reaction were removed, the ligand Trap or B-E8 were precipitated with Protein G-Sepharose, and the number of cpm of $^{125}$I-IL-6 that remained bound was determined. Clearly, the dissociation rate of human $^{125}$I-IL6 from the ligand Trap was very slow—after three days, approximately 75% of the initial counts were still bound to the ligand Trap. In contrast, less than 5% of the counts remained associated with the antibody after three days. This result demonstrates that the dissociation rate of the ligand from these ligand Traps is very slow.

In a different set of experiments the ability of the ligand Traps to multimerize in the presence of ligand was tested. An example of this is shown in FIGS. 19A-19B. IL-6-induced association of gp130-Fc•IL-6Rα-Fc with gp130-$C_H$1•IL-6Rα-κ was determined by testing whether gp130-$C_H$1•IL-6Rα-κ, which does not by itself bind Protein A, could be precipitated by Protein A-Sepharose in the presence of gp130-Fc•IL-6Rα-Fc in an IL-6-depended manner (SEQ ID NO: 9). Precipitation of gp130-$C_H$1•IL-6Rα-κ by Protein A-Sepharose was determined by western blotting with an anti-kappa specific HRP conjugate, which does not detect gp130-Fc•IL-6Rα-Fc. gp130-$C_H$1•IL-6Rα-κ could be precipitated by Protein A-Sepharose only when both gp130-Fc•IL-6Rα-Fc and IL-6 were present. This result conclusively indicates that IL-6 can induce ligand Trap multimerization, and further indicate that the ligand Trap can mimic the hexameric cytokine•Rα•signal transducer complex (FIG. 1). Ligand-induced multimerization may play a significant role in the clearance of cytokine•ligand Trap complexes in vivo.

The biological activity of the different ligand Traps may be further tested in assays which measure ligand-depended cell proliferation. Several cell proliferation assays exist for IL-6 and they employ cell lines such as B9, CESS, or XG-1. An example of this type of assay using the XG-1 cell line is presented below: XG-1 is a cell line derived from a human multiple myeloma (Zhang et al. 1994 Blood 83:3654-3663). XG-1 depends on exogenously supplied human IL-6 for survival and proliferation. The $EC_{50}$ of IL-6 for the XG-1 line is approximately 50 pmoles/ml. The ability of several different IL-6 Traps to block IL-6-depended proliferation of XG-1 cells was tested by incubating increasing amounts of purified ligand Traps with 50 pg/ml IL-6 in XG-1 cultures. The ligand Traps which were tested had been expressed and purified by methods similar to those described above. All of the ligand Traps tested were found to inhibit IL-6-dependent proliferation of XG-1 in a dose dependent manner (FIG. 20). Of the five different Traps tested gp130-Cg1•IL-6Rα-κ was the most active and essentially display the same neutralizing activity towards IL-6 as the antibody B-E8. As little as a 10-fold molar excess of either gp130-Cg1•IL-6Rα-κ or B-E8 completely blocked the activity of IL-6 (a reading of A570-650=0.3 AU corresponds to no proliferation of the XG-1 cells). At a 100-fold molar excess all of the ligand Traps tested completely blocked the activity of IL-6. This observed inhibition is highly selective as neither a gp130-Fc•CNTFRα-Fc ligand Trap which blocks CNTF activity, nor gp130-Fc homodimer exhibit any blocking activity towards IL-6 even when used at a 1000-fold molar excess over IL-6 (data not shown). This data demonstrates that the heteromeric immunoglobulin heavy/light chain receptor-based ligand Traps function as selective high affinity antagonists of their cognate ligand.

Example 5

Cloning of Fusion Polypeptide Components

The extracellular domains of the human cytokine receptors were obtained by standard PCR techniques using tissue cDNAs (CLONTECH), cloned into the expression vector, pMT21 (Genetics Institute, Inc.), and the sequences were sequenced by standard techniques using an ABI 373A DNA sequencer and Taq Dideoxy Terminator Cycle Sequencing Kit (Applied Biosystems, Inc., Foster City, Calif.). For the IL-4Rα nucleotides 241 through 868 (corresponding to the amino acids 24-231) from the Genbank sequence, X52425, were cloned. For the IL-2Rg, nucleotides 15 through 776 (corresponding to amino acids 1-233) from the Genbank sequence, D11086, were cloned. For the IL-6Rα, nucleotides 52 through 1044 (corresponding to the amino acids 1-331) from the Genbank sequence, X52425, were cloned. For gp130, nucleotides 322 through 2112 (corresponding to the amino acids 30-619) from the Genbank sequence, M57230, were cloned. For the IL-1RAcP, nucleotides 1 through 1074 (corresponding to the amino acids 1-358) from the Genbank sequence, AB006357, were cloned. For the IL-1RI, nucleotides 55 through 999 (corresponding to the amino acids 19-333) from the Genbank sequence, X16896, were cloned.

Example 6

Production of Fusion Polypeptides (Cytokine Traps)

The nucleotide sequences encoding the cytokine Traps were constructed from the individual cloned DNAs (described supra) by standard cloning and PCR techniques. In each case, the sequences were constructed in frame such that the sequence encoding the first fusion polypeptide component was fused to the sequence encoding the second fusion polypeptide component followed by an Fc domain (hinge, CH2 and CH3 region of human IgG1) as the multimerizing component. In some cases extra nucleotides were inserted in frame between sequences encoding the first and second fusion polypeptide components to add a linker region between the two components: Trap 424 (SEQ ID NO: 17); Trap 412 (SEQ ID NO:23); and Trap 569 (SEQ ID NO:27).

For the IL-4 Traps, 424 (SEQ ID NO: 17), 603 (SEQ ID NO: 19) and 622 (SEQ ID NO:21), the IL-2Rγ component is 5', followed by the IL4Rα component and then the Fc component. For the IL-6 Traps, 412 (SEQ ID NO: 23) and 616 (SEQ ID NO:25), the IL-6Rα component is 5' followed by the gp130 component and then the Fc domain. For the IL-1 Trap 569 (SEQ ID NO: 27), the IL-1RAcP component is 5' followed by the IL1RI component and then the Fc domain. The final constructs were cloned into the mammalian expression vector pcDNA3.1 (STRATAGENE).

In the 569 sequence (SEQ ID NO: 27), nucleotides 1-1074 encode the IL1RAcP component, nucleotides 1075-1098 encode a linker region, nucleotides 1099-2043 encode the IL1RI component and nucleotides 2044-2730 encode the Fc domain.

In the 412 sequence (SEQ ID NO: 23), nucleotides 1-993 encode the IL6Rα component, nucleotides 994-1023 encode a linker region, nucleotides 1024-2814 encode the gp130 component and nucleotides 2815-3504 encode the Fc domain.

In the 616 sequence (SEQ ID NO: 25), nucleotides 1-993 encode the IL6Rα component, nucleotides 994-2784 encode the gp130 component and nucleotides 2785-3474 encode the Fc domain.

In the 424 (SEQ ID NO: 17) and 622 (SEQ ID NO: 21) sequences, nucleotides 1-762 encode the IL2Rγ component, nucleotides 763-771 encode a linker region, nucleotides 772-1395 encode the IL4Rα component and nucleotides 1396-2082 encode the Fc domain.

Finally, in the 603 sequence (SEQ ID NO: 19), nucleotides 1-762 encode the IL2Rg component, nucleotides 763-1386 encode the IL4Rα component and nucleotides 1387-2073 encode the Fc domain.

DNA constructs were either transiently transfected into COS cells or stably transfected into CHO cells by standard techniques well known to one of skill in the art. Supernatants were collected and purified by Protein A affinity chromatography and size exclusion chromatography by standard techniques. (See Harlow &Lane, Antibodies—A Laboratory Manual, Cold Spring Harbor Laboratory, 1988).

Example 7

IL-4 Bioassay Protocol Using TF-1 (ATCC) Cells

MTT Dye Solution: MTT(3-[4,5-Dimethylthiazole-2-yl]) (Sigma catalog# M2128) Working concentration: Dissolve 5 mg of anhydrous MTT in 200 ml PBS without $Ca^{+2}$, $Mg^{+2}$. Sterile filter and store aliquoted at −20° C.

Solubilization Solution: For 1000 ml, combine 100 g SDS, 950 ml $dH_2O$, 50 ml Dimethyl Formamide, and 850 μl concentrated HCl. Filter sterilize with a 0.45 μm filter unit. Store at room temperature.

TF-1 cell Growth Medium: RPMI 1640, 10% FBS, Pen/Strep, 2 mM L-glutamine

Other: 0.4% Trypan Blue Stain, sterile tubes for dilutions, sterile 96 well cell culture plates (Falcon #3072), hemacytometer, centrifuge, ELISA plate reader, multichannel pipet for 15, 25, 50 and 100 μl volume, sterile reagent reservoirs, sterile pipet tips, gloves.

Assay Protocol A. Preparation of Assay plates. 1. Prepare sterile 96 well tissue culture plates to contain 50 μl of growth medium per well with various concentrations of IL-4 and 10 nM IL-4 antagonist. This can be done by preparing a working dilution of IL-4 that is 4 times the highest concentration to be assayed. In separate tubes, do a two-fold serial dilution of the IL-4. Add 25 μl of each dilution to one row across the plate (i.e. row A gets highest concentration, row G gets lowest concentration). Add 25 μl of growth medium without IL-4 to row H. Prepare the antagonists to be tested by making a stock that is 4 times the final concentration. Add 25 μl to a triplicate set of IL-4 containing wells (columns 1,2,3, A through H). Be sure to include antagonist in row H. 2. As a positive control, leave one set with no antagonist. These wells will contain IL-4 and media only. 3. Incubate the plate for 1-2 hours at 37° C. in a humidified 5% $CO_2$ incubator before preparing cells to be used for assay.

B. Preparation of Cells. 4. Wash cells twice by centrifugation in assay medium free of growth factor. 5. Determine cell number and trypan blue viability and suspend cells to a final concentration of $8\times10^5$/ml in assay medium. 6. Dispense 50 µl of the cell suspension (40,000 cells) into all wells of the plates. Total volume should now be 100 µl/well. 7. Incubate the plate at 37° C. for 68 hours in a humidified 5% $CO_2$ incubator.

C. Color Development. 8. After incubating for 68 hours, add 15 µl of the MTT dye solution to each well. 9. Incubate the plate at 37° C. for 4 hours in a humidified 5% $CO_2$ incubator. 10. After 4 hours, add 100 µl of the solubilization solution to each well. Allow the plate to stand overnight in a sealed container to completely solubilize the formazan crystals. 11. Record the absorbance at 570/650 nm.

Figure 27:
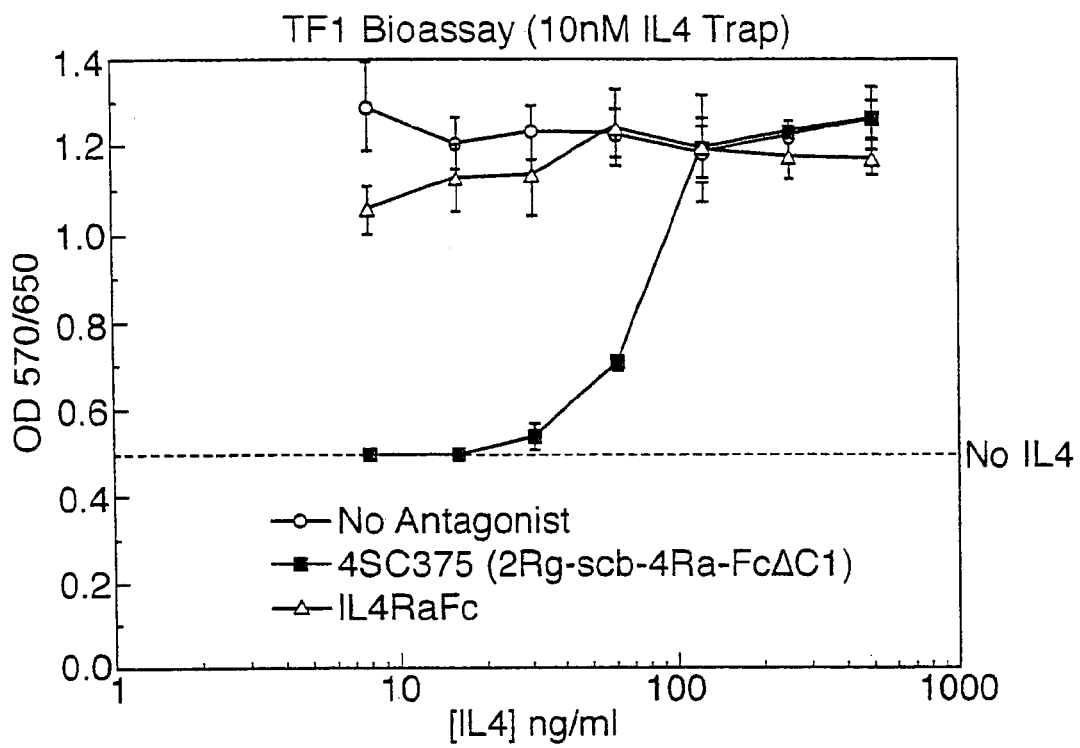
FIG. 27: Shows that an IL-4 Trap designated 4SC375, which is a fusion polypeptide of IL-2Rg-scb-IL4Ra-FcΔC1, is several orders of magnitude better as an IL-4 antagonist than IL4RaFcΔC1 alone in the TF1 cell bioassay.
Figure 28:
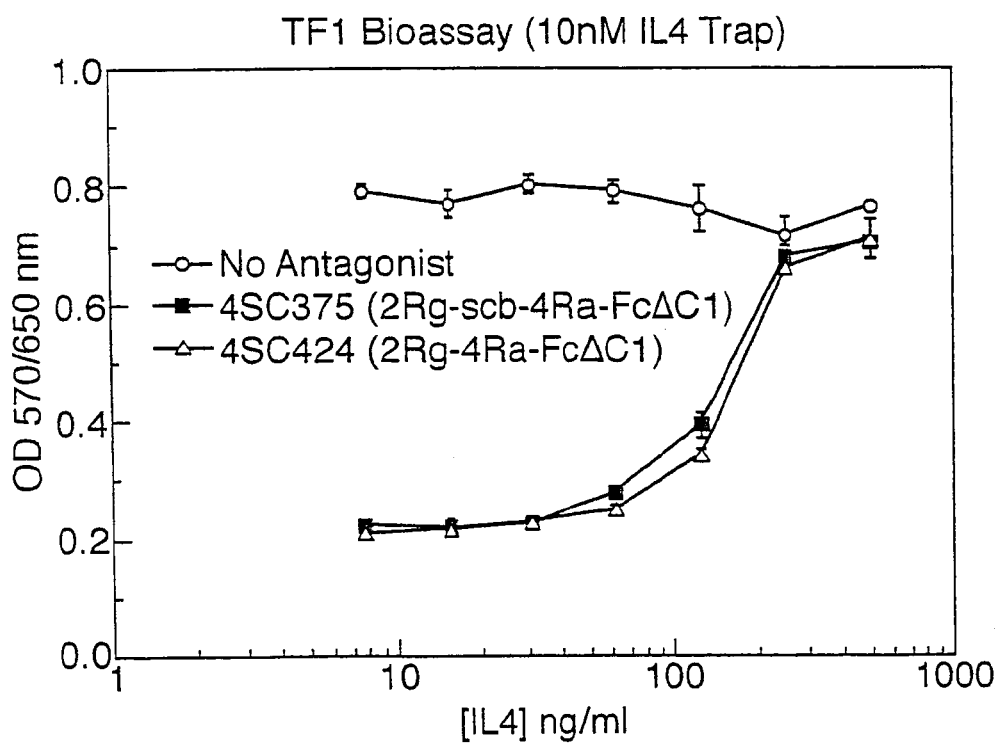
FIG. 28: Shows that an IL-4 Trap designated 4SC375 displays antagonistic activity in the TF1 cell bioassay equivalent to an IL-4 Trap designated 4SC424 (described in FIGS. 21A-21D) which is a fusion polypeptide of IL-2Rg-IL4Ra-FcΔC1 having the IL-2Rg component flush with the IL-4Ra component.

Results. FIG. 27 shows that an IL-4 Trap designated 4SC375, which is a fusion polypeptide of IL-2Rg-scb-IL4Ra-FcΔC1, is several orders of magnitude better as an IL-4 antagonist than IL4RαFcΔC1 alone in the TF1 cell bioassay. FIG. 28 shows that the IL-4 Trap designated 4SC375 shows antagonistic activity in the TF1 cell bioassay equivalent to an IL-4 Trap designated 4SC424 which is a fusion polypeptide of IL-2Rγ-IL4Rα-FcΔC1 having the IL-2Rγ component flush with the IL-4Rα component.

Example 8

IL-6 Bioassay Protocol Using XG-1 Cells

MTT dye solution and solubilization solution, assay protocol, cell preparation and color development were as described above with IL-6 used instead of IL-4. Assay Medium: RPMI 1640, 10% FBS, Pen/Strep, 2 mM L-glutamine, 50 µM mercapto-ethanol.

Figure 29:
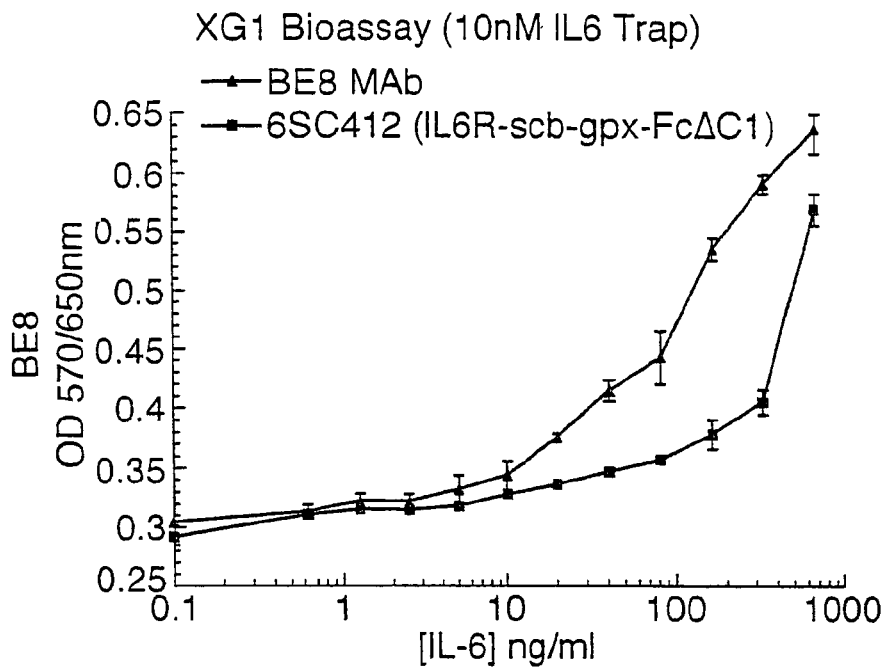
FIG. 29: Shows that the IL6 Trap (6SC412 IL6R-scb-gpx-FcΔC1) described in FIGS. 24A-24F is a better antagonist of IL-6 in the XG1 bioassay than the neutralizing monoclonal antibody to human IL-6-BE8.

Results. FIG. 29 shows that the IL6 Trap (6SC412 IL6R-scb-gpx-FcΔC1) (SEQ ID NO: 23 and 24) is a better antagonist of IL-6 in the XG1 bioassay than the neutralizing monoclonal antibody to human IL-6-BE8.

Example 9

MRC5 Bioassay for IL-1 Traps

MRC5 human lung fibroblast cells respond to IL-1 by secreting IL-6 and thus were utilized to assay the ability of IL-1 Traps to block the IL-1-dependent production of IL-6. IL1 Trap 1SC569 was tested against IL-1-RI.Fc which is the extracellular domain of the IL-1 Type I receptor fused to an Fc domain.

MRC5 cells are suspended at $1\times10^5$ cells per ml in medium and 0.1 ml of cells are plated (10,000 cells per well) into the wells of a 96 well tissue culture plate. Plates are incubated for 24 hours at 37° C. in a humidified 5% $CO_2$ incubator.

IL-1 Trap and recombinant human IL-1 at varying doses are pre-incubated in a 96 well tissue culture dish and incubated for 2 hours at 37° C. 0.1 ml of this mixture is then added to the 96 well plate containing the MRC5 cells such that the final concentration of IL-1 Trap is 10 nM and the final concentrations of the IL-1 ranges from 2.4 pM to 5 nM. Control wells contain Trap alone or nothing.

Plates are then incubated at 37° C. for 24 hours in a humidified 5% $CO_2$ incubator. Supernatant is collected and assayed for levels of IL-6 using R&D Systems Quantikine Immunoassay Kit according to the manufacturer's instructions.

Figure 30:
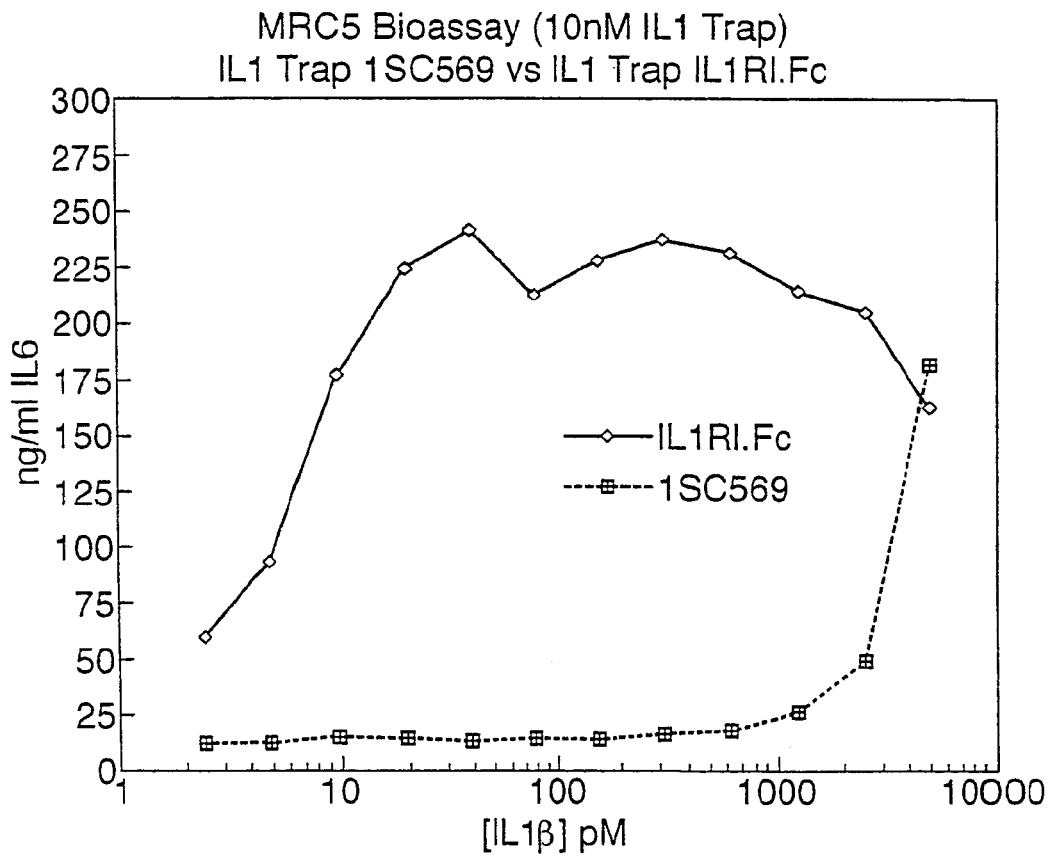
FIG. 30: Shows that the Trap 1SC569 (described in FIGS. 26A-26E) is able to antagonize the effects of IL-1 and block the IL-6 production from MRC 5 cells upon treatment with IL-1.

Results. FIG. 30 shows that the Trap 569 (SEQ ID NO:28) is able to antagonize the effects of IL-1 and block the IL-6 production from MRC 5 cells upon treatment with IL-1. At a concentration of 10 nM, the Trap 569 is able to block the production of IL-6 up to an IL-1 concentration of 3 nM. In contrast, the IL-1RI.Fc is a much poorer antagonist of IL-1. It is only able to block the effects of IL-1 up to about 10-20 pM. Thus, the Trap 569 is approximately 100× better at blocking IL-1 than IL1RI.Fc.

Example 10

Construction of IL-13/IL-4 Single Chain Traps

1. To create the IL-13/IL-4 dual Trap designated IL-4Rα.IL-13Rα1.Fc, the human IL-4Rα extracellular domain (corresponding to nucleotides 1-693 of SEQ ID NO: 29) and the human IL-13Ra1 extracellular domain (corresponding to nucleotides 700-1665 of SEQ ID NO: 29) were amplified by standard PCR techniques and ligated into an expression vector pMT21 which contained the human Fc sequence (corresponding to nucleotides 1671-2355 of SEQ ID NO: 29), thus creating a fusion protein consisting of the IL-4Rα, IL-13Rα1, and the hinge, CH2 and CH3 region of human IgG1 from the N to C terminus. In addition, a two amino acid linker (corresponding to nucleotides 694-699 of SEQ ID NO: 30) with the amino acid sequence SerGly was constructed in frame between the IL-4Rα and the IL-13Rα1 and a two amino acid linker (corresponding to nucleotides 1666-1671 of SEQ ID NO: 30) with the amino acid sequence ThrGly was constructed in frame between the IL-13Rα1 and the Fc portion. All sequences were sequence-verified by standard techniques. The IL-4Rα.IL-13Rα1.Fc coding sequence was then subcloned into the expression vector pcDNA3.1 (Stratagene) using standard molecular biology techniques.

2. To create the IL-13/IL-4 dual Trap designated IL-13Rα1.IL-4Rα.Fc, the IL-13Rα1 extracellular domain (corresponding to nucleotides 1-1029 of SEQ ID NO: 31) and the human IL-4Rα (corresponding to nucleotides 1060-1692 of SEQ ID NO: 31) were amplified by standard PCR techniques and ligated into the expression vector pJFE14, which contains the human Fc sequence (corresponding to nucleotides 1699-2382 of SEQ ID NO: 31) to create a fusion protein consisting of the IL-13Rα1, IL-4Rα, and the hinge, CH2 and CH3 region of human IgG1 from the N to C terminus. In addition, a ten amino acid linker with the amino acid sequence GlyAlaProSerGly-GlyGlyGlyArgPro (SEQ ID NO: 6) (corresponding to nucleotide 1030-1059 of SEQ ID NO: 31) was constructed in frame between the IL-13Rα1 and the IL-4Rα and a two amino acid linker (corresponding to nucleotides 1693-1698 of SEQ ID NO: 31) with the amino acid sequence SerGly was constructed in frame between IL-4Rα and the Fc portion. All sequences were sequence-verified using standard techniques. The coding sequence of IL-13Rα1.IL-4Rα.Fc was then subcloned into the expression vector pcDNA3.1 (Stratagene) using standard molecular biology techniques.

Example 11

Expression of IL-4Rα.IL-13Rα1.Fc and IL-13Rα1.IL-4Rα.Fc.IL-4Rα.

Large scale (1 L) cultures of the pCAE801 (the DNA vector construct encoding IL-4Rα.IL-13Rα1.Fc) and pCAE802 (the DNA plasmid construct encoding IL-13Rα1.IL-4Rα.Fc) in DH10B cells were grown overnight in LB+ampicillin and the plasmid DNA was extracted using a Qiagen Endofree Mega Kit following the manufacturer's protocol. The concentration of the purified plasmid DNA was determined in a UV spectrophotometer and fluorometer. The plasmid DNA was also verified by digestion of aliquots with BbsI, XmnI and NcoI restriction enzymes. All restriction enzyme digest fragments corresponded to the predicted sizes in a 1% agarose gel.

Forty 15 cm petri plates were seeded with CHO-K1/E1A cells at a density of $4 \times 10^6$ cells/plate. Plating media was Gibco Ham's F-12 w/10% Hyclone Fetal Bovine Serum (FBS)+penicillin/streptomycin and supplemented with glutamine. The following day each plate was transfected with 6 µg of pCAE801, or pCAE802, using Gibco Optimem and Gibco Lipofectamine in 12 ml volume, following the manufacturer's protocol. Four hours after adding the transfection mix to the cells 12 ml/plate of Optimem w/ 10% FBS was added. Plates were incubated at 37° C. in a 5% $CO_2$ incubator overnight. The following day the media was removed from each plate and 25 ml expression media (Gibco CHO-S-SFM II w/ glutamine+1 mM sodium butyrate) was added. The plates were incubated at 37° C. for 3 days.

After 3 days of incubation the media was removed from each plate and centrifuged at 400 rpm in a swinging bucket rotor to pellet cells. The supernatant was decanted into sterile 1 L bottles and expressed protein was purified as described infra.

Example 12

Purification of IL-4Rα.IL-13Rα1.Fc and IL-13Rα1.IL-4Rα.Fc Protein

1. Purification of IL-4Ra.IL-13Ra1.Fc. Human IL-4Ra.IL-13Ra1.Fc was transiently expressed in CHO cells and supernatants were harvested from plate transfections as described supra. Expression of the secreted protein was determined by a sandwich ELISA using goat anti-hIgG (γ chain specific; Sigma 1-3382) and goat anti-hIgG (Fc specific)-FITC conjugate (Sigma F9512) capture and report antibodies, respectively. The yield ranged from 5.8 to 9.2 mg (average of 7.5 mg) per liter of conditioned media. Complete™ protease inhibitor tablets (Roche Diagnostics Corp.) were dissolved into the media (1 tablet/L). The conditioned media was sterile filtered (0.22 µm pore size) prior to loading onto a pre-equilibrated, 5 mL HiTrap® Protein A affinity column (Amersham Pharmacia Biotech) in Dulbecco's PBS buffer (Life Technologies), pH 7.4 at 4° C. The flow rate was ~1-2 mL/min. The column was extensively washed with PBS buffer to remove nonspecifically bound proteins from the column. IL-4Rα.IL-13Rα1.Fc was eluted using 20 mM sodium citrate, 150 mM NaCl, pH 3.5. The eluate was immediately neutralized by titrating with 1 M Tris-OH. The fractions containing protein were pooled and immediately dialyzed in PBS buffer, pH 7.4 at 4° C. The recovery from Protein A purification was 6.8 mg (73%). IL-4Rα.IL-13Rα1.Fc was further purified by size exclusion chromatography using a superose 6 column (25 mL bed volume; Amersham Pharmacia Biotech) pre-equilibrated in PBS, 5% v/v glycerol, pH 7.4 at ambient temperature. The flow rate was 0.5 mL/min. Protein fractions were assessed from a Coomassie stained non-reduced and reduced SDS-PAGE (Novex NuPAGE 4-12% Bis-Tris gels). Fractions were conservatively pooled to reduce the amount of aggregated protein. The overall yield was 51% (4.4 mg) with a purity of 97% as judged by SDS-PAGE. Purified IL-4Rα.IL-13Rα1.Fc was analyzed by non-reduced and reduced SDS-PAGE (4-12% Bis-Tris), analytical size exclusion chromatography (Tosohaas TSKG4000SWXL), N-terminal sequencing, and immunoblotting with goat anti-hIgG-HRP conjugate (Promega W403B), and also mouse monoclonal anti-hIL-4R(R&D MAB230) followed by anti-mIgG-HRP conjugate (Promega W402B) as the secondary antibody.

2. Purification of IL-13Rα1.IL-4Rα.Fc. Human IL-13Rα1.IL-4Rα.Fc was transiently expressed in CHO cells and supernatants were harvested from plate transfections as described supra. Expression of the secreted protein was determined by a sandwich ELISA using goat anti-hIgG (γ chain specific; Sigma 1-3382) and goat anti-hIgG (Fc specific)-FITC conjugate (Sigma F9512) capture and report antibodies, respectively. The yield was 8.8 mg per liter of conditioned media. Complete™ protease inhibitor tablets (Roche Diagnostics Corp.) were dissolved into the media (1 tablet/L). The conditioned media was sterile filtered (0.22 µm pore size) prior to loading onto a pre-equilibrated, 5 mL HiTrap® Protein A affinity column (Amersham Pharmacia Biotech) in Dulbecco's PBS buffer (Life Technologies), pH 7.4 at 4° C. The flow rate was ~1-2 mL/min. The column was extensively washed with PBS buffer to remove nonspecifically bound proteins from the column. IL-13Ra1.IL-4Ra.Fc was eluted using 20 mM sodium citrate, 150 mM NaCl, pH 3.5. The eluate was immediately neutralized by titrating with 1 M Tris-OH. The fractions containing protein were pooled and immediately dialyzed in PBS buffer, pH 7.4 at 4° C. The recovery from Protein A purification was 3.8 mg (43%). IL-13Rα1.IL-4Rα.Fc was further purified by size exclusion chromatography using a superose 6 column (25 mL bed volume; Amersham Pharmacia Biotech) pre-equilibrated in PBS, 5% v/v glycerol, pH 7.4 at ambient temperature. The flow rate was 0.5 mL/min. Protein fractions were assessed from a Coomassie stained non-reduced and reduced SDS-PAGE (Novex NuPAGE 4-12% Bis-Tris gels). Fractions were conservatively pooled to reduce the amount of aggregated protein. The overall yield was 17% (1.5 mg) with a purity of 95% as judged by SDS-PAGE. Purified IL-13Rα1.IL-4Rα.Fc was analyzed by non-reduced and reduced SDS-PAGE (4-12% Bis-Tris), analytical size exclusion chromatography (Tosohaas TSKG4000SWXL), N-terminal sequencing, and immunoblotting with goat anti-hIgG-HRP conjugate (Promega W403B), and also mouse monoclonal anti-hIL-4Rα (R&D MAB230) followed by anti-mIgG-HRP conjugate (Promega W402B) as the secondary antibody.

Example 13

Blocking of IL-4Rα.IL-13Rα1.Fc and IL-13Rα1.IL-4Rα.Fc

TF1 Bioassay. TF1 cells were maintained in growth media (10 ng/ml GM-CSF, RPMI 1640, 10% FBS, L-glutamine, Penicillin, Streptomycin). For the bioassay, cells were washed 2 times in assay media (as above but without GM-CSF) and then plated at $2 \times 10^5$ cells in 50 µl of assay media. The purified IL-4Ra.IL-13Rα1.Fc and IL-13Rα1.IL-4Rα.Fc proteins were diluted into assay media at a concentration of 40 nM. 25ul of each of the Traps was added to the cells. Either IL-13 or IL-4 were diluted to 40 nM in assay media and then 2-fold dilution series in assay media were made. 25 µl of either IL-13 or IL-4 was then added to the wells containing the cells and the Traps. Cells were then incubated at 37° C., 5% $CO_2$ for ~70 hrs. The extent of TF1 cell proliferation was measured by the MTS assay according to the manufacturer's protocol (Promega, Inc.).

Figures 32G, 33:
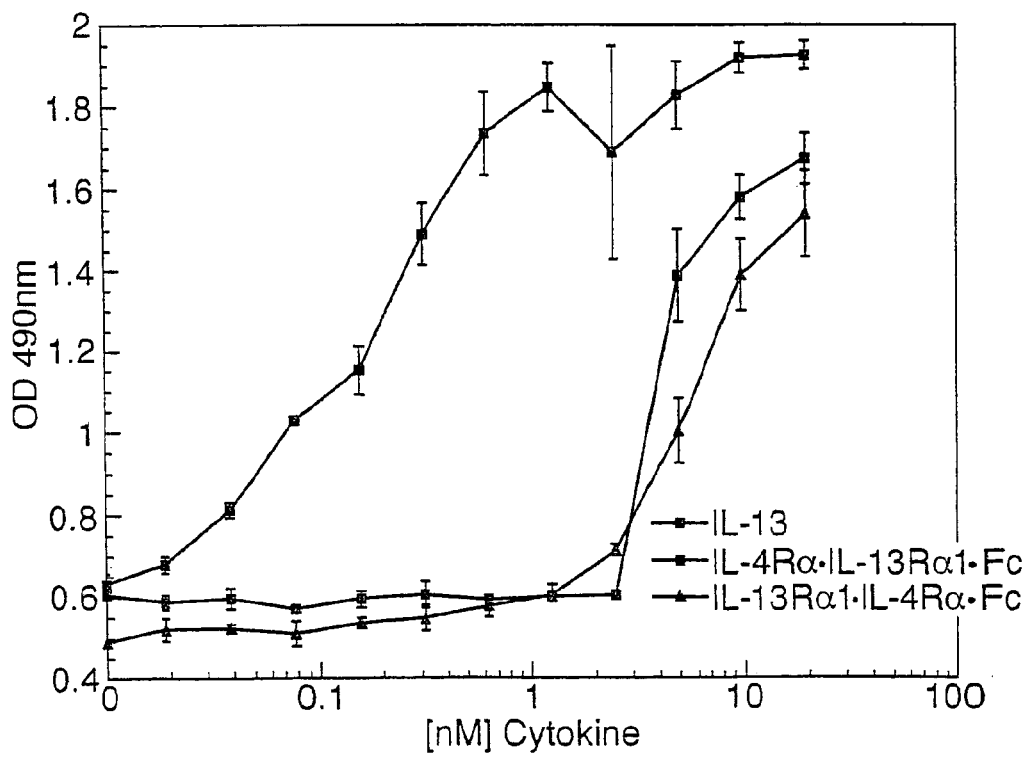
Figure 34:
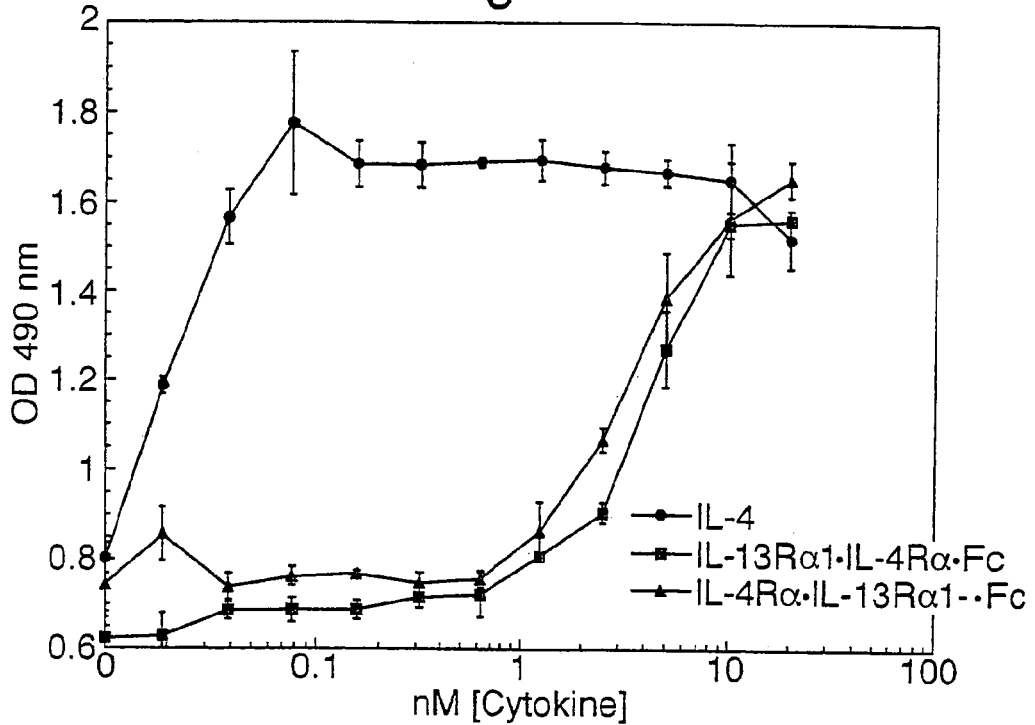
FIG. 34: Blocking of IL-4 by IL-4Ra.IL-13Ra1.Fc and IL-13Ra1.IL-4Ra.Fc. Addition of either IL-4Ra.IL-13Ra1.Fc or IL-13Ra1.IL-4Ra.Fc at a concentration of 10 nM blocks IL-4-induced growth up to ~1 nM. At an IL-4 concentration of ~3-4 nM the growth of TF1 cells is inhibited by 50%.

Results. The ability of the IL-4Rα.IL-13Rα1.Fc and IL-13Rα1.IL-4Rα.Fc Traps to block both human IL-13 and human IL-4 activity was measured in the TF1 bioassay described supra. IL-13 stimulates proliferation of TF1 cells, with half-maximal growth at a concentration of 0.2 nM. Addition of either IL-4Rα.IL-13Rα1.Fc or IL-13Rα1.IL-4Rα.Fc Trap at a concentration of 10 nM blocks IL-13-induced growth up to ~2 nM (FIG. 33). At an IL-13 concentration of ~4-5 nM the growth of TF1 cells is inhibited by 50%. TF1 cells are more sensitive to IL-4, which stimulates their proliferation with half-maximal growth at ~0.02 nM. Addition of either IL-4Rα.IL-13Rα1.Fc or IL-13Rα1.IL-4Rα.Fc at a concentration of 10 nM blocks IL-4-induced growth up to ~1 nM (FIG. 34). At an IL-4 concentration of ~3-4 nM the growth of TF1 cells is inhibited by 50%. These results show that both IL-4Rα.IL-13Rα1.Fc and IL-13Rα1.IL-4Rα.Fc can block the ability of both IL-13 and IL-4 to stimulate cellular responses.

Example 14

Blocking of Injected IL-1 by IL-1 Trap In Vivo

IL-1 is a pro-inflammatory cytokine. Systemic administration of IL-1 has been shown to elicit acute responses in animals, including transient hyperglycemia, hypoinsulinemia, fever, anorexia, and increased serum levels of interleukin-6 (IL-6). Since mice are responsive to both murine and human IL-1, human IL-1 can be used and in vivo binding effects of human specific IL-1 antagonists can be evaluated. This acute mouse model was used to determine the ability of a human IL-1 Trap to antagonize the in vivo effects of exogenously administered human IL-1. This provides a rapid indication of in vivo efficacy of the human IL-1 Trap and can be used as an assay to help molecule selection.

Experimental Design: Mice were given subcutaneous injections of human IL-1 (0.3 μg/kg). Twenty-four hours prior to human IL-1 injection, the animals were pre-treated with either vehicle or 150-fold molar excess of human IL-1 Trap (0.54 mg/kg). Two hours prior to sacrifice (26 hrs), the mice were given a second injection of human IL-1 (0.3 μg/kg). Blood samples were collected at various time points and sera were assayed for IL-6 levels.

Figure 35:
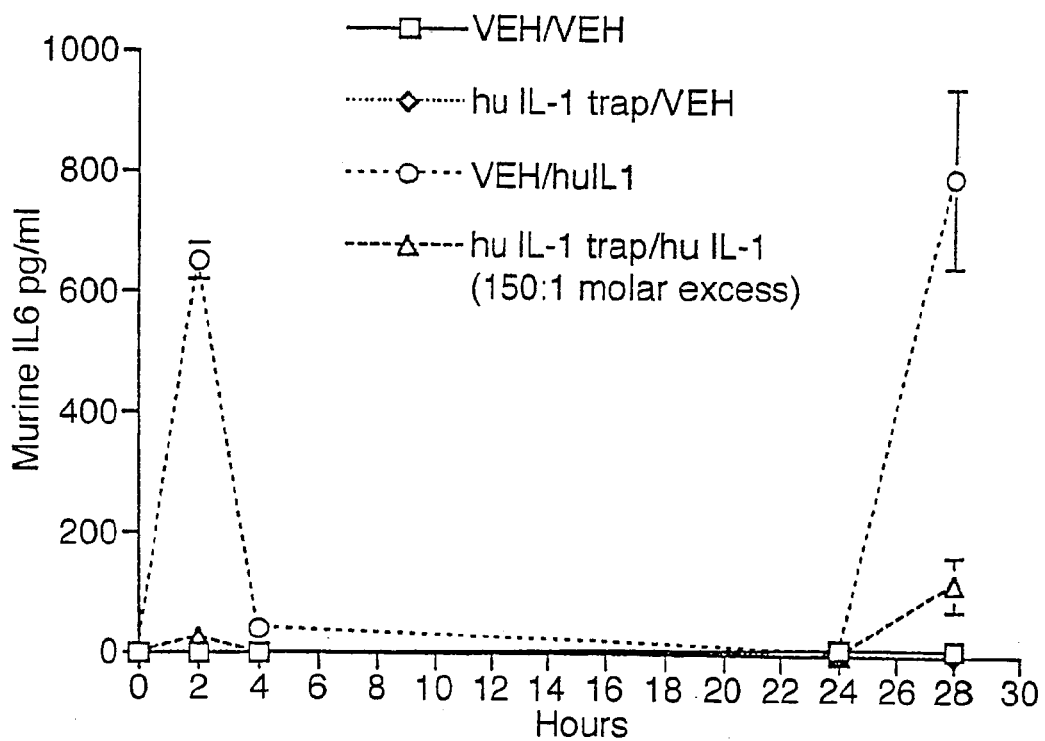
FIG. 35: Human IL-1 Trap blocks the in vivo effects of exogenously administered huIL-1. BALB/c mice were given subcutaneous injection of huIL-1 (0.3 μg/kg) at time 0. Twenty-four hours prior to huIL-1 injection, the animals were pre-treated with either vehicle or 150-fold molar excess of huIL-1 Trap. Two hours prior to sacrifice (26 hrs), the mice were re-challenged with a second injection of huIL-1 (0.3 μg/kg, s.c.). Blood samples were collected at various time points and sera were assayed for IL-1 levels (expressed as mean+/–SEM; n=5 per group).

Results. Exogenous administration of human IL-1 resulted a dramatic induction of serum IL-6 levels. At 150-fold molar excess, the human IL-1 Trap completely blocked the IL-6 increase (FIG. 35). Furthermore, the effects of the human IL-1 Trap persisted for at least another 24 hours, preventing an IL-6 increase even when IL-1 was re-administered (FIG. 35). Such long-lasting efficacy suggests that daily injection of an IL-1 Trap may not be necessary for chronic applications.

Figure 50:
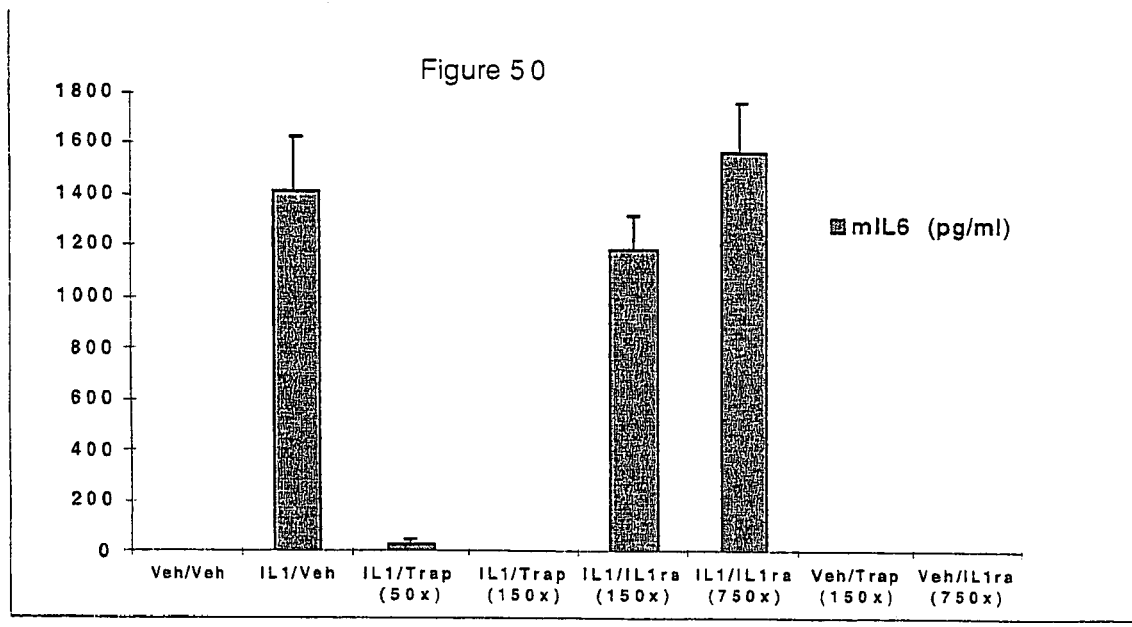
FIG. 50: Human IL-1 Trap blocks the in vivo effects of exogenously administered human IL-1. Male C57BL/6 mice were given a subcutaneous injection of recombinant human IL-1β (rhIL-1β; 0.3 mg/kg). Twenty four hours prior to rhIL-1β administration, animals were treated with either vehicle, human IL-1 Trap 569 (50 or 150-fold molar excess; 0.18 or 0.54 mg/kg, respectively), or recombinant murine IL-1 receptor antagonist (rmIL-1ra; 150 or 750-fold molar excess; 45.8 or 229 μg/kg, respectively). Blood samples were taken 2 h after administration of rhIL-1β and the sera were assayed for IL-6 levels using a mouse IL-6 ELISA. Exogenous administration of rhIL-1β significantly increased serum IL-6 levels. Pretreatment with either a 50 or 150-fold molar excess of hIL-1 Trap blocked the rhIL-1β-induction of IL-6. In contrast, injection of rmIL-1ra at either a 150 or 750-fold molar excess did not block IL-6 induction.

In a separate experiment, IL-1ra at 150-fold or 750-fold molar excess did not significantly block IL6 induction. Therefore, in this paradigm. IL-1 Trap appears to be a better blocker of IL-1 activity (see FIG. 50).

Example 15

Evaluating the Ability of an IL-4 Trap to Block the Physiological Responses to Human IL-4 in Cynomologus Monkeys Systemic administration of human IL-4 elicits systemic responses in Cynomolgus monkeys (Gundel et al., 1996). Thus, the effectiveness of the IL-4 Trap in blocking human IL-4 can be demonstrated by measuring these responses.

Experimental Design: The experiment consisted of 3 parts: human IL-4+vehicle (part 1), human IL-4+IL-4 Trap (part 2), and human IL-4+vehicle (part 3). Human IL-4 (25 μg/kg) was injected subcutaneously twice daily for 4 days and IL-4 Trap (8 mg/kg) and vehicle were given intravenously daily for 5 days, beginning 1 day prior to human IL-4 administration. Whole blood was collected daily for flow cytometry analysis for CD16 and plasma was obtained to assay for the cytokine monocyte chemotactic protein 1 (MCP-1). CD16 and MCP-1 are markers of IL-4-mediated inflammation in both humans and monkeys.

Figure 36A:
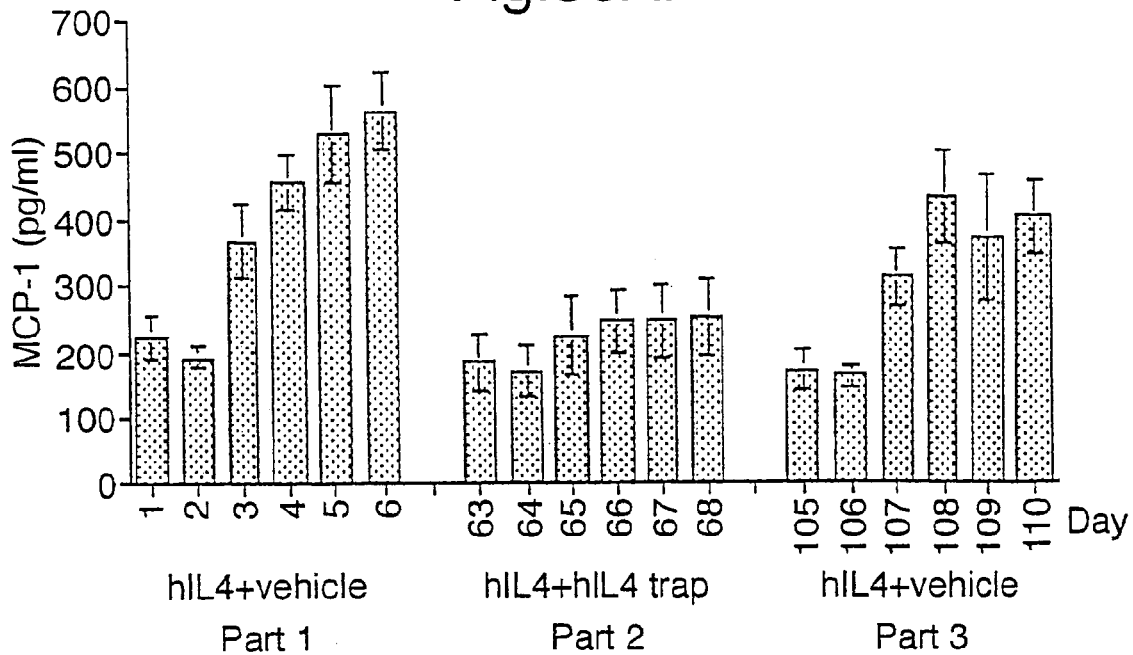
FIGS. 36A & 36B: Human IL-4 Trap antagonizes the effects of human IL-4 in monkeys.
Figure 36B:
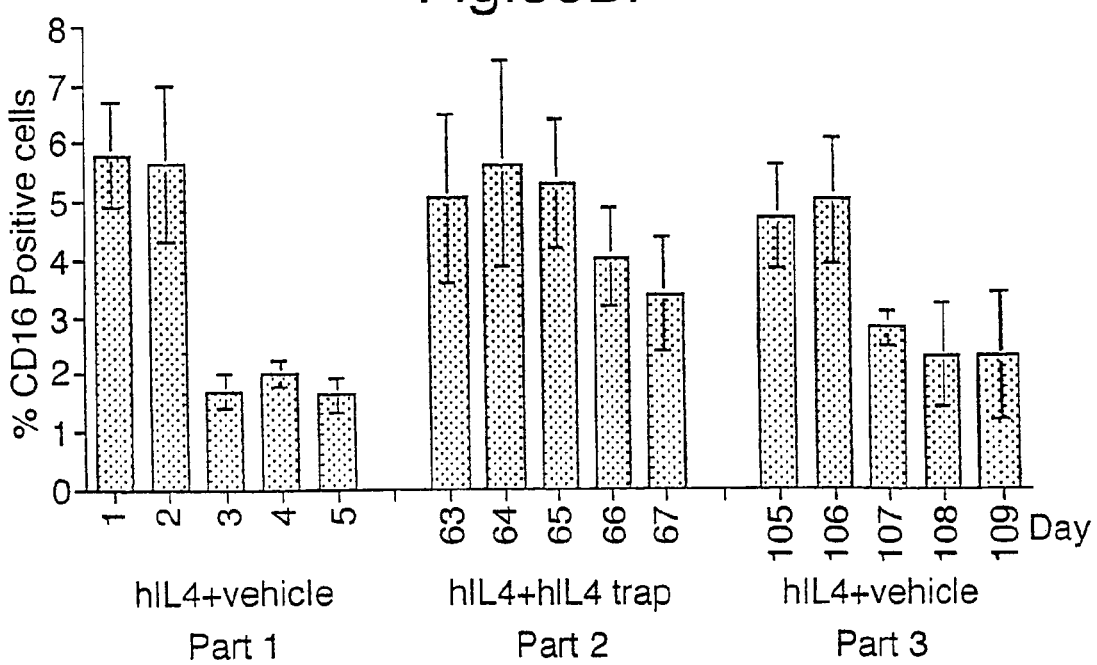

Results. In the presence of human IL-4, MCP-1 increased 2.5-fold and was significantly blocked by the IL-4 Trap (FIG. 36A). Similarly, the decrease in the percent of CD16 positive lymphocytes in peripheral blood was attenuated by the IL-4 Trap (FIG. 36B). After a rest period, the monkeys were re-injected with human IL-4 and the responsiveness of the animals to human IL-4 was re-confirmed (FIGS. 36A and 36B), suggesting that inhibition of the MCP-1 and CD 16 responses is specifically mediated by the IL-4 Trap.

Example 16

The Effects of IL-4 Trap on IL-4-Induced IgE Secretion

It has been shown that injection of anti-mouse IgD antibody stimulates an IL-4-mediated IgE increase in normal mice. This model has been widely used to evaluate IL-4 antagonists, such as soluble IL-4 receptor and anti-IL-4 monoclonal antibodies (Sato et al., 1993). We decided to use this model to evaluate the ability if the IL-4 Trap to block IL-4-mediated increases of IgE.

Experimental design: BALB/C mice injected with anti-mouse IgD (100 μl/mouse, s.c.) were randomly divided into 3 groups. Each received (on days 3-5) either vehicle, murine IL-4 Trap (1 mg/kg, s.c.), or a monoclonal antibody to mouse IL-4 (1 mg/kg, s.c.). Serum was collected at various time points and assayed for IgE levels.

Figure 37:
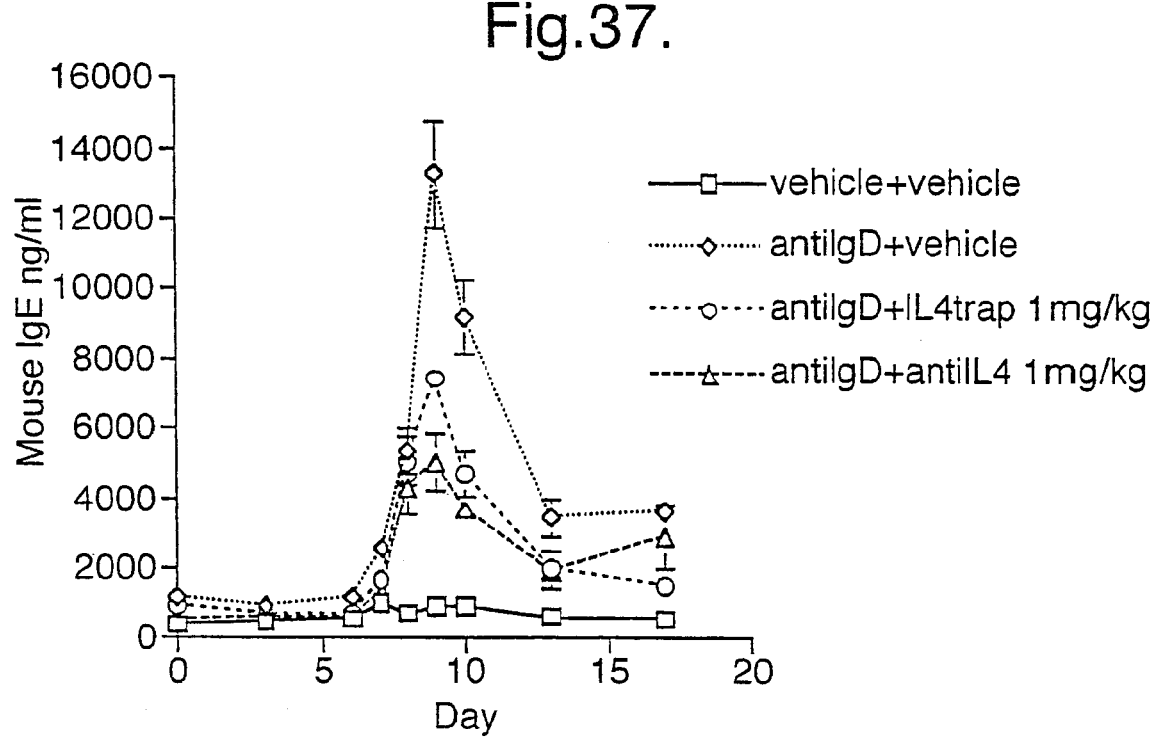
FIG. 37: Murine IL-4 Trap partially prevented IL-4-mediated IgE increase in mice. BALB/C mice injected with anti-mouse IgD (100 μl/mouse, s.c.) were randomly divided into 3 groups, each received (on days 3-5) either vehicle, murine IL-4 Trap (1 mg/kg, s.c.), or a monoclonal antibody to mouse IL-4 (1 mg/kg, s.c.). Sera were collected at various time points and assayed for IgE levels. Results were expressed as mean +/–SEM (n=5 per group). (ANOVA p=0.0002; Tukey-Kramer: vehicle vs. IL-4 Trap, p<0.01; vehicle vs. IL-4 antibody, p<0.001; IL-4 Trap vs. IL-4 antibody, not significant).

Results. Treatment with the murine IL-4 Trap or the mouse IL-4 antibody both significantly antagonized the IL-4-mediated IgE increase in this mouse model (FIG. 37). This suggests that the murine IL-4 Trap binds murine IL-4 and antagonizes physiological responses elicited by endogenous IL-4 in vivo.

Example 17

Construction of Additional Single Chain IL-1 Traps

The techniques used to construct the DNA vectors described herein are standard molecular biology techniques well known to the skilled artisan (see e.g., Sambrook et al. 1989 Molecular Cloning: A Laboratory Manual, Second Edition, Vols 1, 2, and 3, 1989; Current Protocols in Molecular Biology, Eds. Ausubel et al., Greene Publ. Assoc., Wiley Interscience, N.Y.). All DNA sequencing is done by standard techniques using an ABI 373A DNA sequencer and Taq Dideoxy Terminator Cycle Sequencing Kit (Applied Biosystems, Inc., Foster City, Calif.).

a) IL-1 Trap 823 Sequence—The IL-1 Trap 823 sequence consists of the extracellular domain of human IL-1RAcP (corresponding to nucleotides 1-1077 of SEQ ID NO: 39) followed by the extracellular domain of human IL-1RI (corresponding to nucleotides 1078-2013 of SEQ ID NO: 39) followed by a part of the hinge region, the CH2 and CH3 domains of human IgG1 (corresponding to nucleotides 2014-2703 of SEQ ID NO: 39) containing a mutation at nucleotides 2017-2019 (TGT->GGA) to change a cysteine to a glycine. The nucleic acid sequence encodes the fusion polypeptide sequence as set forth in SEQ ID NO: 40.

b) IL-1 Trap 823-1198-B Sequence—The IL-1 Trap 823-1198-B sequence consists of the extracellular domain of human IL-1RAcP (corresponding to nucleotides 1-1077 of SEQ ID NO: 41), followed by the extracellular domain of human IL-1RI (corresponding to nucleotides 1078-2013 of SEQ ID NO: 41), followed by a stretch of amino acids (corresponding to nucleotides 2014-2019 of SEQ ID NO: 41), followed by the hinge region, the CH2 and CH3 domains of human IgG4 (corresponding to nucleotides 2020-2709 of SEQ ID NO: 41). The nucleic acid sequence encodes the fusion polypeptide sequence as set forth in SEQ ID NO: 42.

c) IL-1 Trap 823-1267-C Sequence—The IL-1 Trap 823-1267-C sequence consists of the extracellular domain of human IL-1RAcP (corresponding to nucleotides 1-1077 of SEQ ID NO: 43), followed by the extracellular domain of human IL-1RI (corresponding to nucleotides 1078-2013 of SEQ ID NO: 43), followed by a stretch of amino acids (corresponding to nucleotides 2014-2019 of SEQ ID NO: 43), followed by the hinge region, the CH2 and CH3 domains of human IgG4 (corresponding to nucleotides 2020-2709 of SEQ ID NO: 43) containing a mutation at nucleotide 2047 (T>C) to change a serine to a proline. The nucleic acid sequence encodes the fusion polypeptide sequence as set forth in SEQ ID NO: 44.

d) IL-1 Trap 570-FE Sequence—The IL-1 Trap 570-FE sequence consists of the extracellular domain of human IL-1RI (corresponding to nucleotides 1 to 996 of SEQ ID NO: 33), followed by the extracellular domain of human IL-1RAcP (corresponding to nucleotides 997-2013 of SEQ ID NO: 33) followed by part of the hinge region, the CH2 and CH3 domains of human IgG1 (corresponding to nucleotides 2014-2703 of SEQ ID NO: 33) containing a mutation at nucleotides 2017-2019 (TGT->GGA) to change a cysteine to a glycine. The nucleic acid sequence encodes the fusion polypeptide sequence as set forth in SEQ ID NO: 34.

e) IL-1 Trap 570-FE-B Sequence—The IL-1 Trap 570-FE-B sequence consists of the extracellular domain of human IL-1RI (corresponding to nucleotides 1 to 996 of SEQ ID NO: 35), followed by the extracellular domain of human IL-1RAcP (corresponding to nucleotides 997-2013 of SEQ ID NO: 35) followed by a stretch of amino acids (corresponding to nucleotides 2014-2019 of SEQ ID NO: 35) followed by the hinge region, the CH2 and CH3 domains of human IgG4 (corresponding to nucleotides 2020-2709 of SEQ ID NO: 35). The nucleic acid sequence encodes the fusion polypeptide sequence as set forth in SEQ ID NO: 36.

f) IL-1 Trap 570-FE-C Sequence—The IL-1 Trap 570-FE-C sequence consists of the extracellular domain of human IL-1RI (corresponding to nucleotides 1 to 996 of SEQ ID NO: 37), followed by the extracellular domain of human IL-1RAcP (corresponding to nucleotides 997-2013 of SEQ ID NO: 37) followed by a stretch of amino acids (corresponding to nucleotides 2014-2019 of SEQ ID NO: 37) followed by the hinge region, the CH2 and CH3 domains of human IgG4 (corresponding to nucleotides 2020-2709 of SEQ ID NO: 37) containing a mutation at nucleotide 2047 (T>C) to change a serine to a proline. The nucleic acid sequence encodes the fusion polypeptide sequence as set forth in SEQ ID NO: 38.

g) IL-1 Trap 1647-CtF Sequence—The IL-1 Trap 1647-CtF sequence consists of the extracellular domain of human IL-1RII (corresponding to nucleotides 1-1044 of SEQ ID NO: 45) followed by the extracellular domain of human IL-1RAcP (corresponding to nucleotides 1045-2058 of SEQ ID NO: 45) followed by a part of the hinge region, the CH2 and CH3 domains of human IgG1 (corresponding to nucleotides 2059-2748 of SEQ ID NO: 45) containing a mutation at nucleotides 2062-2064 (TGT->GGA) to change a cysteine to a glycine. The nucleic acid sequence encodes the fusion polypeptide sequence as set forth in SEQ ID NO: 46.

h) IL-1 Trap 1647-CtF-B Sequence—The IL-1 Trap 1647-CtF-B sequence consists of the extracellular domain of human IL-1RII (corresponding to nucleotides 1-1044 of SEQ ID NO: 47) followed by the extracellular domain of human IL-1RAcP (corresponding to nucleotides 1045-2058 of SEQ ID NO: 47) followed by a stretch of amino acids (corresponding to nucleotides 2059-2064 of SEQ ID NO: 47) followed by the hinge region, the CH2 and CH3 domains of human IgG4 (corresponding to nucleotides 2065-2754 of SEQ ID NO: 47). The nucleic acid sequence encodes the fusion polypeptide sequence as set forth in SEQ ID NO: 48.

i) IL-1 Trap 1647-CtF-C Sequence—The IL-1 Trap 1647-CtF-C sequence consists of the extracellular domain of human IL-1RII (corresponding to nucleotides 1-1044 of SEQ ID NO: 49) followed by the extracellular domain of human IL-1RAcP (corresponding to nucleotides 1045-2058 of SEQ ID NO: 49) followed by a stretch of amino acids (corresponding to nucleotides 2059-2064 of SEQ ID NO: 49) followed by the hinge region, the CH2 and CH3 domains of human IgG4 (corresponding to nucleotides 2065-2754 of SEQ ID NO: 49) containing a mutation at nucleotide 2092 (T>C) to change a serine to a proline. The nucleic acid sequence encodes the fusion polypeptide sequence as set forth in SEQ ID NO: 50.

j) IL-1 Trap 1649 Sequence—The IL-1 Trap 1649 sequence consists of the extracellular domain of human IL-1RAcP (corresponding to nucleotides 1-1074 of SEQ ID NO: 51) followed by the extracellular domain of human IL-1RII (corresponding to nucleotides 1075-2058 of SEQ ID NO: 51) followed by a part of the hinge region, the CH2 and CH3 domains of human IgG1 (corresponding to nucleotides 2059-2748 of SEQ ID NO: 51) containing a mutation at nucleotides 2062-2064 (TGT->GGA) to change a cysteine to a glycine. The nucleic acid sequence encodes the fusion polypeptide sequence as set forth in SEQ ID NO: 52.

k) IL-1 Trap 1649-B Sequence—The IL-1 Trap 1649-B sequence consists of the extracellular domain of human IL-1RAcP (corresponding to nucleotides 1-1074 of SEQ ID NO:53) followed by the extracellular domain of human IL-1RII (corresponding to nucleotides 1075-2058 of SEQ ID NO:53) followed by a stretch of amino acids (corresponding to nucleotides 2059-2064) followed by the hinge region, the CH2 and CH3 domains of human IgG4 (corresponding to nucleotides 2065-2754 of SEQ ID NO:53). The nucleic acid sequence encodes the fusion polypeptide sequence as set forth in SEQ ID NO:54.

l) IL-1 Trap 1649-C Sequence—The IL-1 Trap 1649-C sequence consists of the extracellular domain of human IL-1RAcP (corresponding to nucleotides 1-1074 of SEQ ID NO: 55) followed by the extracellular domain of human IL-1RII (corresponding to nucleotides 1075-2058 of SEQ ID NO: 55) followed by a stretch of amino acids (corresponding to nucleotides 2059-2064) followed by the hinge region, the CH2 and CH3 domains of human IgG4 (corresponding to nucleotides 2065-2754 of SEQ ID NO: 55) containing a mutation at nucleotide 2092(T>C) to change a serine to a proline. The nucleic acid sequence encodes the fusion polypeptide sequence as set forth in SEQ ID NO: 56.

In addition to the sequences described supra and in the associated figures, the following modifications to those sequences are also contemplated by the subject invention. For IL1 Traps 823, 823-1198.B, and 823-1267.C:AcP alternative: A change at nucleotide 1043 from A to C to change the amino acid from Lys to Thr. SG insertion: Between nucleotides 1077 and 1078 an insertion of the nucleotides TCC GGA would add a Ser Gly stretch of amino acids between the two receptor domains of the Trap. For IL1 Traps 570-FE, 570-FE.B, and 570-FE.C: AcP alternative: A change at nucleotide 1979 from A to C to change the amino acid from Lys to Thr. SG insertion: Between nucleotides 996 and 977 an insertion of the nucleotides TCC GGA would add a Ser Gly stretch of amino acids between the two receptor domains of the Trap. For IL1 Traps1647-CtF, 1647-CtF.B, and 1647-CtF.C: AcP alternative: A change at nucleotide 2027 from A to C to change the amino acid from Lys to Thr. SG insertion: Between nucleotides 1044 and 1045 an insertion of the nucleotides TCC GGA would add a Ser Gly stretch of amino acids between the two receptor domains of the Trap. For IL1 Traps 1649, 1649-B, and 1649-C: AcP alternative: A change at nucleotide 1043 from A to C to change the amino acid from Lys to Thr. SG insertion: Between nucleotides 1074 and 1075 an insertion of the nucleotides TCC GGA would add a Ser Gly stretch of amino acids between the two receptor domains of the Trap.

In addition, one of skill in the art will recognize that it may be desirable to construct IL1 Traps in which the Fc domain is derived from immunoglobulins with different allotypes. None of the modifications described supra will alter the Trap's ability to bind IL1.

Example 18

Human IL-1 Trap Blocks the Effects of IL-1 in Inflamed Joints

Background: Zymosan is a yeast cell wall extract that when injected into the knee causes acute inflammation and upregulation of IL-1β in the joint (Joosten et al. 1994 Clin Exp Immunol 97:204-211). Chondrocytes will respond to the inflammation and local IL-1β by down regulating proteoglycan synthesis, a feature of human arthritis that contributes to the gradual destruction of cartilage in the joint (van den Berg et al. 1982 Rheum Intl 1:165-169). Antagonists to IL-1β can be used to evaluate their ability to block the effects of zymosan-induced elevations in IL-1β.

Materials and Methods: Anesthetized male C57BL/6 mice (Taconic) were given an intra-articular (i.a.) injection of Zymosan A (Sigma; 300 µg in 10 µl) into the right knee joint through the patellar ligament. Sterile PBS was injected i.a. (10 µl) into the left knee joint through the patellar ligament. Twenty four hours prior to i.a. injections, animals were treated with either vehicle or hIL-1 Trap 569 (19 mg/kg, s.c.). The patellae were removed 24h after injection of zymosan in order to measure proteoglycan synthesis as described by van den Berg et al. 1982 supra. Briefly, each patella and associated ligament were incubated for 3 h at 37° C., 5% $CO_2$ in media (RPMI with HEPES, $HCO_3$, glutamine & penicillin/streptomycin) containing 10 µCi/ml $^{35}$S-sulfate (NEN DuPont). Following incubation, tissue was washed and fixed overnight in 10% formalin (VWR). The tissue was then placed in Decalcifing Solution (J. T. Baker) for 4 h prior to dissection of the patella from surrounding tissue. Each patella was then incubated overnight in Solvable (Packard) at 50° C. Ultima Gold liquid scintillation fluid (Packard) was added and the samples were counted in a liquid scintillation counter. Values were reported as the ratio of cpm of zymosan patella/cpm of vehicle patella for each animal.

Figure 51:
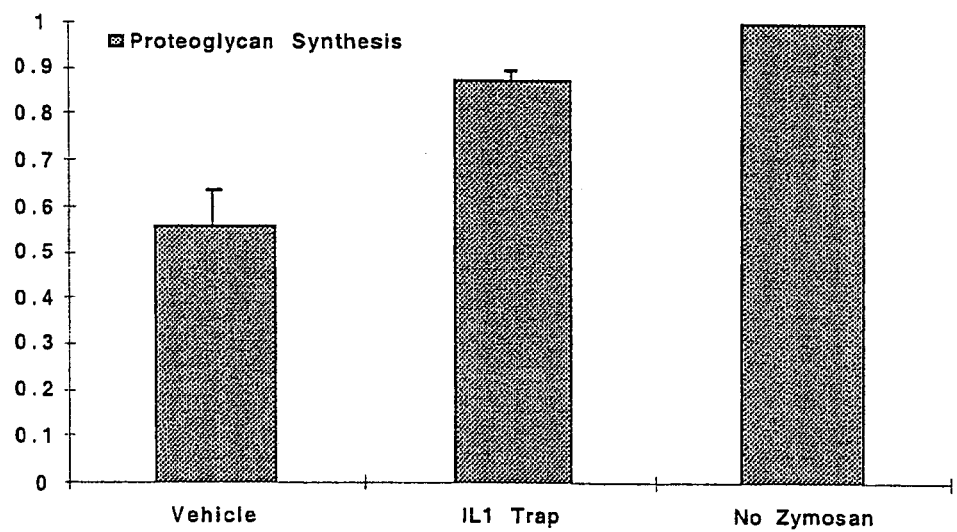
FIG. 51: Human IL-1 Trap blocks the effects of IL-1 in Inflamed Joints. Anesthetized male C57BL/6 mice were given an intra-articular (i.a.) injection of Zymosan A (300 μg in 10 μl) into the right knee joint through the patellar ligament. Sterile PBS was injected i.a. (10 μl) into the left knee joint through the patellar ligament. Twenty four hours prior to i.a. injections, animals were treated with either vehicle or hIL-1 Trap 569 (19 mg/kg, s.c.). The patellae were removed 24 h after injection of zymosan in order to measure proteoglycan synthesis, each patella and associated ligament were incubated for 3 h at 37° C., 5% $CO_2$ in media (RPMI with HEPES, $HCO_3$, glutamine & penicillin/streptomycin) containing 10 uCi/ml $^{35}$S-sulfate. Following incubation, tissue was washed and fixed overnight in 10% formalin. The tissue was then placed in Decalcifing Solution for 4 h prior to dissection of the patella from surrounding tissue. Each patella was then incubated overnight in Solvable at 50° C. Ultima Gold liquid scintillation fluid was added and the samples were counted in a liquid scintillation counter. Values were reported as the ratio of cpm of zymosan patella/cpm of vehicle patella for each animal. Intra-articular injection of zymosan reduces proteoglycan synthesis by approximately 50% relative to vehicle injection. Administration of hIL-1 Trap prior to zymosan injection blocked the local action of IL-1β and proteoglycan synthesis returned to approximately 90% of control.

Results: Intra-articular injection of zymosan reduces proteoglycan synthesis by approximately 50% relative to vehicle injection (FIG. 51). Administration of hIL-1 Trap prior to zymosan injection blocked the local action of IL-1β and proteoglycan synthesis returned to approximately 90% of control. These data demonstrate that hIL-1 Trap 569 can penetrate the joints after subcutaneous injection to effectively neutralize the biological effect of IL-1 within these joints.

Example 19

Murine IL-1 Trap Reduces the Severity of Arthritis Symptoms in Zymosan-Accelerated Collagen-Induced Arthritis (CIA) Model Background. IL-1 has been implicated in the development of inflammation and cartilage destruction in rheumatoid arthritis (Dinarello 1996 Blood 87(6):2095-2147; Wooley et al. 1993 Arthritis & Rheumatism 36(9): 1305-1314). Collagen-induced arthritis (CIA) is a widely studied animal model of inflammatory polyarthritis with similarities to rheumatoid arthritis; common histopathological features include joint inflammation and erosion, synovial hyperplasia and inflammatory cell infiltration (Joe et al. 1999 Mol Med Today 5:367-369). Since previous studies have shown that various anti-IL-1 treatments have a positive effect on reducing arthritis symptoms in CIA animals (van den Berg et al. 1994 Clin Exp Immunol 95:237-243; Joosten et al. 1999 J Immunol 163:5049-5055.; van de Loo 1992 J Rheumatol 19:348-356), Applicants examined the effect of a murine version of the IL-1 Trap (mIL-1 Trap) on the progression of arthritis symptoms in this animal model. The human version of the IL-1 Trap is poorly cross-reactive with rodent IL-1. The mIL-1 Trap consists of the extracellular domain of murine IL-1RAcP, followed by the extracellular domain of murine IL-1RI, followed by the hinge, CH2 and CH3 domain of murine IgG2a.

Male DBA-1 mice (Jackson Laboratories) were immunized intradermally at the base of the tail with 100 µg/50 µl bovine Type II collagen (CII; Chondrex) emulsified with complete and incomplete Freund's adjuvant (2:1:1 ratio; Chondrex) and boosted intradermally with CII (100 µg/50 µl) emulsified with incomplete Freund's adjuvant on day 21. Since CIA in DBA-1 mice occurs gradually over a long time period with a low incidence (Joosten et al. 1994 supra), Applicants synchronized the onset of arthritis symptoms by injecting the animals intraperitoneally on day 30 with 3 mg zymosan (Sigma). Two hours prior to zymosan injection, the mice were randomly distributed into treatment groups and were injected with either vehicle or mIL-1 Trap (31 or 10 mg/kg, 3x/week, 8 injections, s.c.). Arthritis symptoms (ASI scores, as described by Wooley et al. 1993 supra) in the paws were evaluated 3x/week by individuals who were blinded to the treatment groups. Animals were sacrificed 24 h after the 8th injection at which time paw width along with ASI scores were measured.

Results. Within 5 days after i.p injection of zymosan, vehicle treated animals had an significant increase in ASI score relative to those receiving mIL-1 Trap (FIG. 52) with symptoms reaching a maximum 10 to 14 days after zymosan injection. Murine IL-1 Trap acted in a dose-dependent fashion such that animals receiving 10 mg/kg Trap had more arthritis symptoms (greater ASI score) than those receiving 31 mg/kg. However, both mIL-1 Trap-treated groups had a significantly lower degree of arthritis symptoms than vehicle. This difference in ASI score is also reflected in the paw width at the time of sacrifice (FIG. 53). Animals receiving mIL-1 Trap had paw widths that were similar to those of naive, non-collagen immunized animals. These data indicate that mIL-1 Trap can effectively neutralize IL-1 and block the development of arthritic joints.

Example 20

IL-1 Trap 1649 Can Block the Activity of IL-1β

Figure 54:
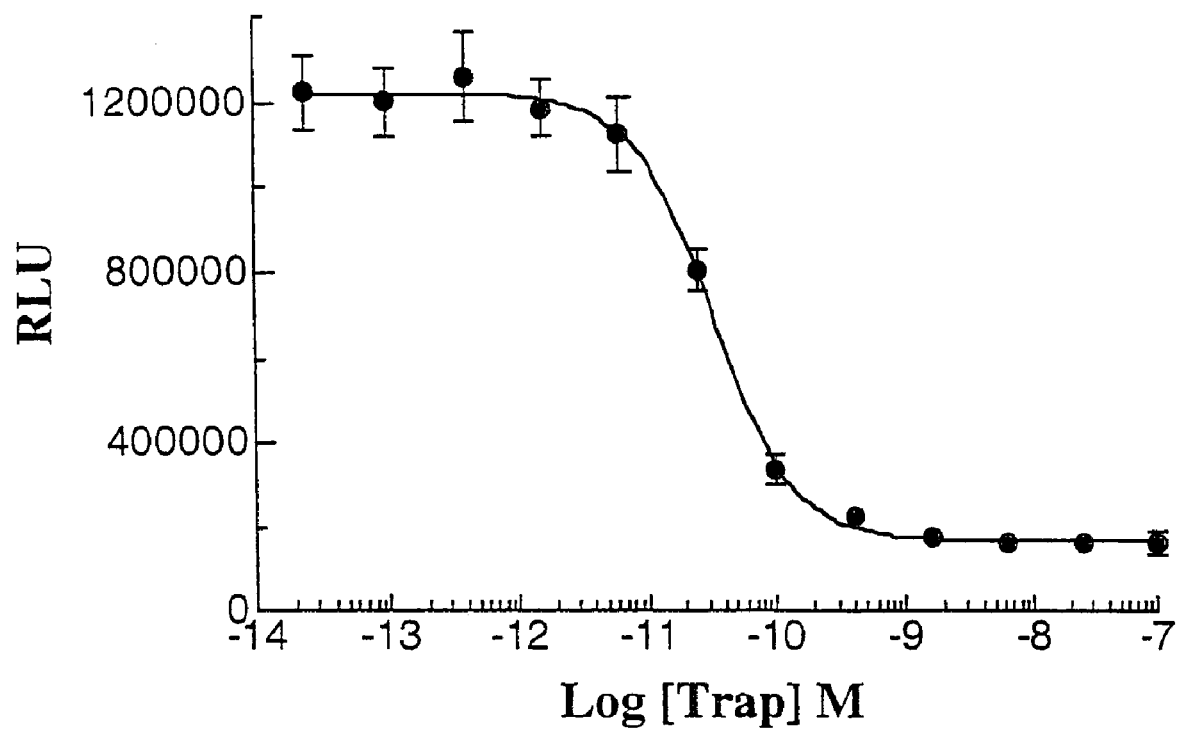
FIG. 54: Various concentrations of IL-1 Trap 1649 were incubated in the presence of 5 pM human IL-1b overnight at room temperature. The mixtures were then added to duplicate wells of 293-NFkB cells (20,000 cells/well) for 5 hrs at 37° C., 5% $CO_2$. Steady-Glo Reagent (Promega) was added to the cells for 15 min at room temperature and luciferase gene expression was quantitated as relative light units (RLU) by luminometry. IL-1 Trap 1649 displays an $IC_{50}$ of 32 pM.

Various concentrations of IL-1 Trap 1649 were incubated in the presence of 5 pM human IL-1b overnight at room temperature. The mixtures were then added to duplicate wells of 293-NFkB cells (20,000 cells/well) for 5 hrs at 37° C., 5% $CO_2$. 293-NFkB cells contain a stably integrated reporter plasmid possessing a luciferase gene driven by a promoter containing 5 NFkB sites. Addition of IL-1b results in increased luciferase gene expression. Steady-Glo Reagent (Promega) was added to the cells for 15 min at room temperature and luciferase gene expression was quantitated as relative light units (RLU) by luminometry. IL-1 Trap 1649 displays an $IC_{50}$ of 32 pM which indicates a Kd of ~30 pM (see FIG. 54). These data indicate that IL-1 Trap 1649 potently blocks IL-1.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

---

SEQUENCE LISTING

```
<160> NUMBER OF SEQ ID NOS: 56

<210> SEQ ID NO 1
<211> LENGTH: 6
<212> TYPE: PRT
<213> ORGANISM: Artificial Sequence
<220> FEATURE:
<223> OTHER INFORMATION: Tag sequence

<400> SEQUENCE: 1

His His His His His His
1               5

<210> SEQ ID NO 2
<211> LENGTH: 16
<212> TYPE: PRT
<213> ORGANISM: Artificial Sequence
<220> FEATURE:
<223> OTHER INFORMATION: peptide derived from region near C-terminus of
      gp130

<400> SEQUENCE: 2

Cys Gly Thr Glu Gly Gln Val Glu Arg Phe Glu Thr Val Gly Met Glu
1               5                   10                  15

<210> SEQ ID NO 3
<211> LENGTH: 16
<212> TYPE: DNA
<213> ORGANISM: Artificial Sequence
<220> FEATURE:
<223> OTHER INFORMATION: Kozak sequence

<400> SEQUENCE: 3
cgccgccacc atggtg                                                          16

<210> SEQ ID NO 4
<211> LENGTH: 10
<212> TYPE: PRT
<213> ORGANISM: Artificial Sequence
<220> FEATURE:
<223> OTHER INFORMATION: J peptide

<400> SEQUENCE: 4

Gly Gln Gly Thr Leu Val Thr Val Ser Ser
1               5                   10

<210> SEQ ID NO 5
<211> LENGTH: 11
<212> TYPE: PRT
<213> ORGANISM: Artificial Sequence
<220> FEATURE:
```

-continued

```
<223> OTHER INFORMATION: J peptide

<400> SEQUENCE: 5

Thr Phe Gly Gln Gly Thr Lys Val Glu Ile Lys
1               5                   10

<210> SEQ ID NO 6
<211> LENGTH: 10
<212> TYPE: PRT
<213> ORGANISM: Artificial Sequence
<220> FEATURE:
<223> OTHER INFORMATION: linker sequence

<400> SEQUENCE: 6

Gly Ala Pro Ser Gly Gly Gly Arg Pro
1               5                   10

<210> SEQ ID NO 7
<211> LENGTH: 859
<212> TYPE: PRT
<213> ORGANISM: Homo sapiens

<400> SEQUENCE: 7

Met Val Thr Leu Gln Thr Trp Val Val Gln Ala Leu Phe Ile Phe Leu
1               5                   10                  15

Thr Thr Glu Ser Thr Gly Glu Leu Leu Asp Pro Cys Gly Tyr Ile Ser
            20                  25                  30

Pro Glu Ser Pro Val Val Gln Leu His Ser Asn Phe Thr Ala Val Cys
        35                  40                  45

Val Leu Lys Glu Lys Cys Met Asp Tyr Phe His Val Asn Ala Asn Tyr
    50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
    130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
        195                 200                 205

Ser Asp His Ile Asn Phe Asp Pro Val Tyr Lys Val Lys Pro Asn Pro
    210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                245                 250                 255

Tyr Asn Ile Gln Tyr Arg Thr Lys Asp Ala Ser Thr Trp Ser Gln Ile
            260                 265                 270
```

```
Pro Pro Glu Asp Thr Ala Ser Thr Arg Ser Ser Phe Thr Val Gln Asp
        275                 280                 285

Leu Lys Pro Phe Thr Glu Tyr Val Phe Arg Ile Arg Cys Met Lys Glu
    290                 295                 300

Asp Gly Lys Gly Tyr Trp Ser Asp Trp Ser Glu Glu Ala Ser Gly Ile
305                 310                 315                 320

Thr Tyr Glu Asp Arg Pro Ser Lys Ala Pro Ser Phe Trp Tyr Lys Ile
                325                 330                 335

Asp Pro Ser His Thr Gln Gly Tyr Arg Thr Val Gln Leu Val Trp Lys
            340                 345                 350

Thr Leu Pro Pro Phe Glu Ala Asn Gly Lys Ile Leu Asp Tyr Glu Val
        355                 360                 365

Thr Leu Thr Arg Trp Lys Ser His Leu Gln Asn Tyr Thr Val Asn Ala
    370                 375                 380

Thr Lys Leu Thr Val Asn Leu Thr Asn Asp Arg Tyr Leu Ala Thr Leu
385                 390                 395                 400

Thr Val Arg Asn Leu Val Gly Lys Ser Asp Ala Ala Val Leu Thr Ile
                405                 410                 415

Pro Ala Cys Asp Phe Gln Ala Thr His Pro Val Met Asp Leu Lys Ala
            420                 425                 430

Phe Pro Lys Asp Asn Met Leu Trp Val Glu Trp Thr Thr Pro Arg Glu
        435                 440                 445

Ser Val Lys Lys Tyr Ile Leu Glu Trp Cys Val Leu Ser Asp Lys Ala
    450                 455                 460

Pro Cys Ile Thr Asp Trp Gln Gln Glu Asp Gly Thr Val His Arg Thr
465                 470                 475                 480

Tyr Leu Arg Gly Asn Leu Ala Glu Ser Lys Cys Tyr Leu Ile Thr Val
                485                 490                 495

Thr Pro Val Tyr Ala Asp Gly Pro Gly Ser Pro Glu Ser Ile Lys Ala
            500                 505                 510

Tyr Leu Lys Gln Ala Pro Pro Ser Lys Gly Pro Thr Val Arg Thr Lys
        515                 520                 525

Lys Val Gly Lys Asn Glu Ala Val Leu Glu Trp Asp Gln Leu Pro Val
    530                 535                 540

Asp Val Gln Asn Gly Phe Ile Arg Asn Tyr Thr Ile Phe Tyr Arg Thr
545                 550                 555                 560

Ile Ile Gly Asn Glu Thr Ala Val Asn Val Asp Ser Ser His Thr Glu
                565                 570                 575

Tyr Thr Leu Ser Ser Leu Thr Ser Asp Thr Leu Tyr Met Val Arg Met
            580                 585                 590

Ala Ala Tyr Thr Asp Glu Gly Gly Lys Asp Gly Pro Glu Phe Thr Phe
        595                 600                 605

Thr Thr Pro Lys Phe Ala Gln Gly Glu Ile Glu Ser Gly Glu Pro Lys
    610                 615                 620

Ser Cys Asp Lys Thr His Thr Cys Pro Pro Cys Pro Ala Pro Glu Leu
625                 630                 635                 640

Leu Gly Gly Pro Ser Val Phe Leu Phe Pro Pro Lys Pro Lys Asp Thr
                645                 650                 655

Leu Met Ile Ser Arg Thr Pro Glu Val Thr Cys Val Val Val Asp Val
            660                 665                 670

Ser His Glu Asp Pro Glu Val Lys Phe Asn Trp Tyr Val Asp Gly Val
        675                 680                 685

Glu Val His Asn Ala Lys Thr Lys Pro Arg Glu Glu Gln Tyr Asn Ser
```

```
                    690                 695                 700
Thr Tyr Arg Val Val Ser Val Leu Thr Val Leu His Gln Asp Trp Leu
705                 710                 715                 720

Asn Gly Lys Glu Tyr Lys Cys Lys Val Ser Asn Lys Ala Leu Pro Ala
                    725                 730                 735

Pro Ile Glu Lys Thr Ile Ser Lys Ala Lys Gly Gln Pro Arg Glu Pro
                740                 745                 750

Gln Val Tyr Thr Leu Pro Pro Ser Arg Asp Glu Leu Thr Lys Asn Gln
                755                 760                 765

Val Ser Leu Thr Cys Leu Val Lys Gly Phe Tyr Pro Ser Asp Ile Ala
770                 775                 780

Val Glu Trp Glu Ser Asn Gly Gln Pro Glu Asn Asn Tyr Lys Thr Thr
785                 790                 795                 800

Pro Pro Val Leu Asp Ser Asp Gly Ser Phe Phe Leu Tyr Ser Lys Leu
                    805                 810                 815

Thr Val Asp Lys Ser Arg Trp Gln Gln Gly Asn Val Phe Ser Cys Ser
                820                 825                 830

Val Met His Glu Ala Leu His Asn His Tyr Thr Gln Lys Ser Leu Ser
                835                 840                 845

Leu Ser Pro Gly Lys His His His His His His
    850                 855

<210> SEQ ID NO 8
<211> LENGTH: 592
<212> TYPE: PRT
<213> ORGANISM: Homo sapiens

<400> SEQUENCE: 8

Met Val Ala Val Gly Cys Ala Leu Leu Ala Ala Leu Leu Ala Ala Pro
1               5                   10                  15

Gly Ala Ala Leu Ala Pro Arg Arg Cys Pro Ala Gln Glu Val Ala Arg
                20                  25                  30

Gly Val Leu Thr Ser Leu Pro Gly Asp Ser Val Thr Leu Thr Cys Pro
            35                  40                  45

Gly Val Glu Pro Glu Asp Asn Ala Thr Val His Trp Val Leu Arg Lys
50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
                100                 105                 110

Pro Pro Glu Glu Pro Gln Leu Ser Cys Phe Arg Lys Ser Pro Leu Ser
            115                 120                 125

Asn Val Val Cys Glu Trp Gly Pro Arg Ser Thr Pro Ser Leu Thr Thr
        130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
                180                 185                 190

Cys Val Ala Ser Ser Val Gly Ser Lys Phe Ser Lys Thr Gln Thr Phe
            195                 200                 205
```

Gln Gly Cys Gly Ile Leu Gln Pro Asp Pro Ala Asn Ile Thr Val
    210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
        275                 280                 285

Val Val Gln Leu Arg Ala Gln Glu Glu Phe Gly Gln Gly Glu Trp Ser
290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Gln Ala Leu Thr Thr
                325                 330                 335

Asn Lys Asp Asp Asp Asn Ile Leu Phe Arg Asp Ser Ala Asn Ala Thr
            340                 345                 350

Ser Leu Pro Val Gln Asp Ala Gly Glu Pro Lys Ser Cys Asp Lys Thr
        355                 360                 365

His Thr Cys Pro Pro Cys Pro Ala Pro Glu Leu Leu Gly Gly Pro Ser
    370                 375                 380

Val Phe Leu Phe Pro Pro Lys Pro Lys Asp Thr Leu Met Ile Ser Arg
385                 390                 395                 400

Thr Pro Glu Val Thr Cys Val Val Val Asp Val Ser His Glu Asp Pro
                405                 410                 415

Glu Val Lys Phe Asn Trp Tyr Val Asp Gly Val Glu Val His Asn Ala
            420                 425                 430

Lys Thr Lys Pro Arg Glu Glu Gln Tyr Asn Ser Thr Tyr Arg Val Val
        435                 440                 445

Ser Val Leu Thr Val Leu His Gln Asp Trp Leu Asn Gly Lys Glu Tyr
    450                 455                 460

Lys Cys Lys Val Ser Asn Lys Ala Leu Pro Ala Pro Ile Glu Lys Thr
465                 470                 475                 480

Ile Ser Lys Ala Lys Gly Gln Pro Arg Glu Pro Gln Val Tyr Thr Leu
                485                 490                 495

Pro Pro Ser Arg Asp Glu Leu Thr Lys Asn Gln Val Ser Leu Thr Cys
            500                 505                 510

Leu Val Lys Gly Phe Tyr Pro Ser Asp Ile Ala Val Glu Trp Glu Ser
        515                 520                 525

Asn Gly Gln Pro Glu Asn Asn Tyr Lys Thr Thr Pro Pro Val Leu Asp
    530                 535                 540

Ser Asp Gly Ser Phe Phe Leu Tyr Ser Lys Leu Thr Val Asp Lys Ser
545                 550                 555                 560

Arg Trp Gln Gln Gly Asn Val Phe Ser Cys Ser Val Met His Glu Ala
                565                 570                 575

Leu His Asn His Tyr Thr Gln Lys Ser Leu Ser Leu Ser Pro Gly Lys
            580                 585                 590

<210> SEQ ID NO 9
<211> LENGTH: 951
<212> TYPE: PRT
<213> ORGANISM: Homo sapiens

<400> SEQUENCE: 9

```
Met Val Thr Leu Gln Thr Trp Val Gln Ala Leu Phe Ile Phe Leu
 1               5                  10                  15

Thr Thr Glu Ser Thr Gly Glu Leu Leu Asp Pro Cys Gly Tyr Ile Ser
            20                  25                  30

Pro Glu Ser Pro Val Val Gln Leu His Ser Asn Phe Thr Ala Val Cys
        35                  40                  45

Val Leu Lys Glu Lys Cys Met Asp Tyr Phe His Val Asn Ala Asn Tyr
 50                  55                  60

Ile Val Trp Lys Thr Asn His Phe Thr Ile Pro Lys Glu Gln Tyr Thr
 65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
        195                 200                 205

Ser Asp His Ile Asn Phe Asp Pro Val Tyr Lys Val Lys Pro Asn Pro
210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                245                 250                 255

Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
        275                 280                 285

Leu Lys Pro Phe Thr Glu Tyr Val Phe Arg Ile Arg Cys Met Lys Glu
290                 295                 300

Asp Gly Lys Gly Tyr Trp Ser Asp Trp Ser Glu Glu Ala Ser Gly Ile
305                 310                 315                 320

Thr Tyr Glu Asp Arg Pro Ser Lys Ala Pro Ser Phe Trp Tyr Lys Ile
                325                 330                 335

Asp Pro Ser His Thr Gln Gly Tyr Arg Thr Val Gln Leu Val Trp Lys
            340                 345                 350

Thr Leu Pro Pro Phe Glu Ala Asn Gly Lys Ile Leu Asp Tyr Glu Val
        355                 360                 365

Thr Leu Thr Arg Trp Lys Ser His Leu Gln Asn Tyr Thr Val Asn Ala
370                 375                 380

Thr Lys Leu Thr Val Asn Leu Thr Asn Asp Arg Tyr Leu Ala Thr Leu
385                 390                 395                 400

Thr Val Arg Asn Leu Val Gly Lys Ser Asp Ala Ala Val Leu Thr Ile
                405                 410                 415
```

-continued

```
Pro Ala Cys Asp Phe Gln Ala Thr His Pro Val Met Asp Leu Lys Ala
            420                 425                 430

Phe Pro Lys Asp Asn Met Leu Trp Val Glu Trp Thr Pro Arg Glu
        435                 440                 445

Ser Val Lys Lys Tyr Ile Leu Glu Trp Cys Val Leu Ser Asp Lys Ala
        450                 455                 460

Pro Cys Ile Thr Asp Trp Gln Gln Glu Asp Gly Thr Val His Arg Thr
465                 470                 475                 480

Tyr Leu Arg Gly Asn Leu Ala Glu Ser Lys Cys Tyr Leu Ile Thr Val
                485                 490                 495

Thr Pro Val Tyr Ala Asp Gly Pro Gly Ser Pro Glu Ser Ile Lys Ala
            500                 505                 510

Tyr Leu Lys Gln Ala Pro Pro Ser Lys Gly Pro Thr Val Arg Thr Lys
        515                 520                 525

Lys Val Gly Lys Asn Glu Ala Val Leu Glu Trp Asp Gln Leu Pro Val
    530                 535                 540

Asp Val Gln Asn Gly Phe Ile Arg Asn Tyr Thr Ile Phe Tyr Arg Thr
545                 550                 555                 560

Ile Ile Gly Asn Glu Thr Ala Val Asn Val Asp Ser Ser His Thr Glu
                565                 570                 575

Tyr Thr Leu Ser Ser Leu Thr Ser Asp Thr Leu Tyr Met Val Arg Met
            580                 585                 590

Ala Ala Tyr Thr Asp Glu Gly Gly Lys Asp Gly Pro Glu Phe Thr Phe
        595                 600                 605

Thr Thr Pro Lys Phe Ala Gln Gly Glu Ile Glu Ser Gly Ala Ser Thr
    610                 615                 620

Lys Gly Pro Ser Val Phe Pro Leu Ala Pro Ser Ser Lys Ser Thr Ser
625                 630                 635                 640

Gly Gly Thr Ala Ala Leu Gly Cys Leu Val Lys Asp Tyr Phe Pro Glu
                645                 650                 655

Pro Val Thr Val Ser Trp Asn Ser Gly Ala Leu Thr Ser Gly Val His
            660                 665                 670

Thr Phe Pro Ala Val Leu Gln Ser Ser Gly Leu Tyr Ser Leu Ser Ser
        675                 680                 685

Val Val Thr Val Pro Ser Ser Ser Leu Gly Thr Gln Thr Tyr Ile Cys
    690                 695                 700

Asn Val Asn His Lys Pro Ser Asn Thr Lys Val Asp Lys Lys Val Glu
705                 710                 715                 720

Pro Lys Ser Cys Asp Lys Thr His Thr Cys Pro Pro Cys Pro Ala Pro
                725                 730                 735

Glu Leu Leu Gly Gly Pro Ser Val Phe Leu Phe Pro Pro Lys Pro Lys
            740                 745                 750

Asp Thr Leu Met Ile Ser Arg Thr Pro Glu Val Thr Cys Val Val Val
        755                 760                 765

Asp Val Ser His Glu Asp Pro Glu Val Lys Phe Asn Trp Tyr Val Asp
    770                 775                 780

Gly Val Glu Val His Asn Ala Lys Thr Lys Pro Arg Glu Glu Gln Tyr
785                 790                 795                 800

Asn Ser Thr Tyr Arg Val Val Ser Val Leu Thr Val Leu His Gln Asp
                805                 810                 815

Trp Leu Asn Gly Lys Glu Tyr Lys Cys Lys Val Ser Asn Lys Ala Leu
            820                 825                 830

Pro Ala Pro Ile Glu Lys Thr Ile Ser Lys Ala Lys Gly Gln Pro Arg
```

```
                835                 840                 845
Glu Pro Gln Val Tyr Thr Leu Pro Pro Ser Arg Asp Glu Leu Thr Lys
    850                 855                 860

Asn Gln Val Ser Leu Thr Cys Leu Val Lys Gly Phe Tyr Pro Ser Asp
865                 870                 875                 880

Ile Ala Val Glu Trp Glu Ser Asn Gly Gln Pro Glu Asn Asn Tyr Lys
                885                 890                 895

Thr Thr Pro Pro Val Leu Asp Ser Asp Gly Ser Phe Phe Leu Tyr Ser
            900                 905                 910

Lys Leu Thr Val Asp Lys Ser Arg Trp Gln Gln Gly Asn Val Phe Ser
        915                 920                 925

Cys Ser Val Met His Glu Ala Leu His Asn His Tyr Thr Gln Lys Ser
    930                 935                 940

Leu Ser Leu Ser Pro Gly Lys
945                 950

<210> SEQ ID NO 10
<211> LENGTH: 332
<212> TYPE: PRT
<213> ORGANISM: Homo sapiens

<400> SEQUENCE: 10

Met Val Thr Leu Gln Thr Trp Val Val Gln Ala Leu Phe Ile Phe Leu
1               5                   10                  15

Thr Thr Glu Ser Thr Gly Glu Leu Leu Asp Pro Cys Gly Tyr Ile Ser
            20                  25                  30

Pro Glu Ser Pro Val Val Gln Leu His Ser Asn Phe Thr Ala Val Cys
        35                  40                  45

Val Leu Lys Glu Lys Cys Met Asp Tyr Phe His Val Asn Ala Asn Tyr
    50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
    130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
        195                 200                 205

Ser Asp His Ile Asn Phe Asp Pro Val Tyr Lys Val Lys Pro Asn Pro
    210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                245                 250                 255
```

```
Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
            275                 280                 285

Leu Lys Pro Phe Thr Glu Tyr Val Phe Arg Ile Arg Cys Met Lys Glu
            290                 295                 300

Asp Gly Lys Gly Tyr Trp Ser Asp Trp Ser Glu Glu Ala Ser Gly Ile
305                 310                 315                 320

Thr Tyr Glu Asp Arg Pro Ser Lys Ala Pro Ser Gly
            325                 330

<210> SEQ ID NO 11
<211> LENGTH: 120
<212> TYPE: PRT
<213> ORGANISM: Homo sapiens

<400> SEQUENCE: 11

Ser Gly Gly Gln Gly Thr Leu Val Thr Val Ser Ser Ala Ser Thr Lys
1               5                   10                  15

Gly Pro Ser Val Phe Pro Leu Ala Pro Ser Ser Lys Ser Thr Ser Gly
            20                  25                  30

Gly Thr Ala Ala Leu Gly Cys Leu Val Lys Asp Tyr Phe Pro Glu Pro
        35                  40                  45

Val Thr Val Ser Trp Asn Ser Gly Ala Leu Thr Ser Gly Val His Thr
    50                  55                  60

Phe Pro Ala Val Leu Gln Ser Ser Gly Leu Tyr Ser Leu Ser Ser Val
65                  70                  75                  80

Val Thr Val Pro Ser Ser Ser Leu Gly Thr Gln Thr Tyr Ile Cys Asn
                85                  90                  95

Val Asn His Lys Pro Ser Asn Thr Lys Val Asp Lys Lys Val Glu Pro
            100                 105                 110

Lys Ser Cys Asp Lys Thr His Thr
            115                 120

<210> SEQ ID NO 12
<211> LENGTH: 329
<212> TYPE: PRT
<213> ORGANISM: Homo sapiens

<400> SEQUENCE: 12

Ser Gly Ala Ser Thr Lys Gly Pro Ser Val Phe Pro Leu Ala Pro Cys
1               5                   10                  15

Ser Arg Ser Thr Ser Glu Ser Thr Ala Ala Leu Gly Cys Leu Val Lys
            20                  25                  30

Asp Tyr Phe Pro Glu Pro Val Thr Val Ser Trp Asn Ser Gly Ala Leu
        35                  40                  45

Thr Ser Gly Val His Thr Phe Pro Ala Val Leu Gln Ser Ser Gly Leu
    50                  55                  60

Tyr Ser Leu Ser Ser Val Val Thr Val Pro Ser Ser Ser Leu Gly Thr
65                  70                  75                  80

Lys Thr Tyr Thr Cys Asn Val Asp His Lys Pro Ser Asn Thr Lys Val
                85                  90                  95

Asp Lys Arg Val Glu Ser Lys Tyr Gly Pro Pro Cys Pro Ser Cys Pro
            100                 105                 110

Ala Pro Glu Phe Leu Gly Gly Pro Ser Val Phe Leu Phe Pro Pro Lys
            115                 120                 125
```

```
Pro Lys Asp Thr Leu Met Ile Ser Arg Thr Pro Glu Val Thr Cys Val
        130                 135                 140

Val Val Asp Val Ser Gln Glu Asp Pro Glu Val Gln Phe Asn Trp Tyr
145                 150                 155                 160

Val Asp Gly Val Glu Val His Asn Ala Lys Thr Lys Pro Arg Glu Glu
                165                 170                 175

Gln Phe Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Gly Leu Pro Ser Ser Ile Glu Lys Thr Ile Ser Lys Ala Lys Gly Gln
210                 215                 220

Pro Arg Glu Pro Gln Val Tyr Thr Leu Pro Pro Ser Gln Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Arg Leu Thr Val Asp Lys Ser Arg Trp Gln Glu Gly Asn Val
290                 295                 300

Phe Ser Cys Ser Val Met His Glu Ala Leu His Asn His Tyr Thr Gln
305                 310                 315                 320

Lys Ser Leu Ser Leu Ser Leu Gly Lys
                325

<210> SEQ ID NO 13
<211> LENGTH: 108
<212> TYPE: PRT
<213> ORGANISM: Homo sapiens

<400> SEQUENCE: 13

Ser Gly Thr Val Ala Ala Pro Ser Val Phe Ile Phe Pro Pro Ser Asp
1               5                   10                  15

Glu Gln Leu Lys Ser Gly Thr Ala Ser Val Val Cys Leu Leu Asn Asn
            20                  25                  30

Phe Tyr Pro Arg Glu Ala Lys Val Gln Trp Lys Val Asp Asn Ala Leu
        35                  40                  45

Gln Ser Gly Asn Ser Gln Glu Ser Val Thr Glu Gln Asp Ser Lys Asp
    50                  55                  60

Ser Thr Tyr Ser Leu Ser Ser Thr Leu Thr Leu Ser Lys Ala Asp Tyr
65                  70                  75                  80

Glu Lys His Lys Val Tyr Ala Cys Glu Val Thr His Gln Gly Leu Ser
                85                  90                  95

Ser Pro Val Thr Lys Ser Phe Asn Arg Gly Glu Cys
            100                 105

<210> SEQ ID NO 14
<211> LENGTH: 106
<212> TYPE: PRT
<213> ORGANISM: Homo sapiens

<400> SEQUENCE: 14

Ser Gly Pro Lys Ala Ala Pro Ser Val Thr Leu Phe Pro Pro Ser Ser
1               5                   10                  15
```

```
Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

<210> SEQ ID NO 15
<211> LENGTH: 360
<212> TYPE: PRT
<213> ORGANISM: Homo sapiens

<400> SEQUENCE: 15

```
Met Val Ala Val Gly Cys Ala Leu Leu Ala Ala Leu Leu Ala Ala Pro
 1               5                  10                  15

Gly Ala Ala Leu Ala Pro Arg Arg Cys Pro Ala Gln Glu Val Ala Arg
            20                  25                  30

Gly Val Leu Thr Ser Leu Pro Gly Asp Ser Val Thr Leu Thr Cys Pro
        35                  40                  45

Gly Val Glu Pro Glu Asp Asn Ala Thr Val His Trp Val Leu Arg Lys
 50                  55                  60

Pro Ala Ala Gly Ser His Pro Ser Arg Trp Ala Gly Met Gly Arg Arg
 65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
            100                 105                 110

Pro Pro Glu Glu Pro Gln Leu Ser Cys Phe Arg Lys Ser Pro Leu Ser
        115                 120                 125

Asn Val Val Cys Glu Trp Gly Pro Arg Ser Thr Pro Ser Leu Thr Thr
130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
        195                 200                 205

Gln Gly Cys Gly Ile Leu Gln Pro Asp Pro Ala Asn Ile Thr Val
210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
        275                 280                 285
```

```
Val Val Gln Leu Arg Ala Gln Glu Glu Phe Gly Gln Gly Glu Trp Ser
    290                 295                 300
Glu Trp Ser Pro Glu Ala Met Gly Thr Pro Trp Thr Glu Ser Arg Ser
305                 310                 315                 320
Pro Pro Ala Glu Asn Glu Val Ser Thr Pro Met Gln Ala Leu Thr Thr
                325                 330                 335
Asn Lys Asp Asp Asp Asn Ile Leu Phe Arg Asp Ser Ala Asn Ala Thr
                340                 345                 350
Ser Leu Pro Val Gln Asp Ala Gly
            355                 360

<210> SEQ ID NO 16
<211> LENGTH: 315
<212> TYPE: PRT
<213> ORGANISM: Homo sapiens

<400> SEQUENCE: 16

Met Val Ala Val Gly Cys Ala Leu Leu Ala Ala Leu Leu Ala Ala Pro
1               5                   10                  15
Gly Ala Ala Leu Ala Pro Arg Arg Cys Pro Ala Gln Glu Val Ala Arg
            20                  25                  30
Gly Val Leu Thr Ser Leu Pro Gly Asp Ser Val Thr Leu Thr Cys Pro
        35                  40                  45
Gly Val Glu Pro Glu Asp Asn Ala Thr Val His Trp Val Leu Arg Lys
    50                  55                  60
Pro Ala Ala Gly Ser His Pro Ser Arg Trp Ala Gly Met Gly Arg Arg
65                  70                  75                  80
Leu Leu Leu Arg Ser Val Gln Leu His Asp Ser Gly Asn Tyr Ser Cys
                85                  90                  95
Tyr Arg Ala Gly Arg Pro Ala Gly Thr Val His Leu Leu Val Asp Val
            100                 105                 110
Pro Pro Glu Glu Pro Gln Leu Ser Cys Phe Arg Lys Ser Pro Leu Ser
        115                 120                 125
Asn Val Val Cys Glu Trp Gly Pro Arg Ser Thr Pro Ser Leu Thr Thr
    130                 135                 140
Lys Ala Val Leu Leu Val Arg Lys Phe Gln Asn Ser Pro Ala Glu Asp
145                 150                 155                 160
Phe Gln Glu Pro Cys Gln Tyr Ser Gln Glu Ser Gln Lys Phe Ser Cys
                165                 170                 175
Gln Leu Ala Val Pro Glu Gly Asp Ser Ser Phe Tyr Ile Val Ser Met
            180                 185                 190
Cys Val Ala Ser Ser Val Gly Ser Lys Phe Ser Lys Thr Gln Thr Phe
        195                 200                 205
Gln Gly Cys Gly Ile Leu Gln Pro Asp Pro Pro Ala Asn Ile Thr Val
    210                 215                 220
Thr Ala Val Ala Arg Asn Pro Arg Trp Leu Ser Val Thr Trp Gln Asp
225                 230                 235                 240
Pro His Ser Trp Asn Ser Ser Phe Tyr Arg Leu Arg Phe Glu Leu Arg
                245                 250                 255
Tyr Arg Ala Glu Arg Ser Lys Thr Phe Thr Thr Trp Met Val Lys Asp
            260                 265                 270
Leu Gln His His Cys Val Ile His Asp Ala Trp Ser Gly Leu Arg His
        275                 280                 285
Val Val Gln Leu Arg Ala Gln Glu Glu Phe Gly Gln Gly Glu Trp Ser
```

-continued

```
            290                 295                 300
Glu Trp Ser Pro Glu Ala Met Gly Thr Thr Gly
305                 310                 315

<210> SEQ ID NO 17
<211> LENGTH: 2085
<212> TYPE: DNA
<213> ORGANISM: Homo sapiens
<220> FEATURE:
<221> NAME/KEY: CDS
<222> LOCATION: (1)...(2082)

<400> SEQUENCE: 17 atg gtg aag cca tca tta cca ttc aca tcc ctc tta ttc ctg cag ctg      48
Met Val Lys Pro Ser Leu Pro Phe Thr Ser Leu Leu Phe Leu Gln Leu
1               5                   10                  15 ccc ctg ctg gga gtg ggg ctg aac acg aca att ctg acg ccc aat ggg      96
Pro Leu Leu Gly Val Gly Leu Asn Thr Thr Ile Leu Thr Pro Asn Gly
                20                  25                  30 aat gaa gac acc aca gct gat ttc ttc ctg acc act atg ccc act gac     144
Asn Glu Asp Thr Thr Ala Asp Phe Phe Leu Thr Thr Met Pro Thr Asp
            35                  40                  45 tcc ctc agt gtt tcc act ctg ccc ctc cca gag gtt cag tgt ttt gtg     192
Ser Leu Ser Val Ser Thr Leu Pro Leu Pro Glu Val Gln Cys Phe Val
        50                  55                  60 ttc aat gtc gag tac atg aat tgc act tgg aac agc agc tct gag ccc     240
Phe Asn Val Glu Tyr Met Asn Cys Thr Trp Asn Ser Ser Ser Glu Pro
65                  70                  75                  80 cag cct acc aac ctc act ctg cat tat tgg tac aag aac tcg gat aat     288
Gln Pro Thr Asn Leu Thr Leu His Tyr Trp Tyr Lys Asn Ser Asp Asn
                85                  90                  95 gat aaa gtc cag aag tgc agc cac tat cta ttc tct gaa gaa atc act     336
Asp Lys Val Gln Lys Cys Ser His Tyr Leu Phe Ser Glu Glu Ile Thr
            100                 105                 110 tct ggc tgt cag ttg caa aaa aag gag atc cac ctc tac caa aca ttt     384
Ser Gly Cys Gln Leu Gln Lys Lys Glu Ile His Leu Tyr Gln Thr Phe
        115                 120                 125 gtt gtt cag ctc cag gac cca cgg gaa ccc agg aga cag gcc aca cag     432
Val Val Gln Leu Gln Asp Pro Arg Glu Pro Arg Arg Gln Ala Thr Gln
    130                 135                 140 atg cta aaa ctg cag aat ctg gtg atc ccc tgg gct cca gag aac cta     480
Met Leu Lys Leu Gln Asn Leu Val Ile Pro Trp Ala Pro Glu Asn Leu
145                 150                 155                 160 aca ctt cac aaa ctg agt gaa tcc cag cta gaa ctg aac tgg aac aac     528
Thr Leu His Lys Leu Ser Glu Ser Gln Leu Glu Leu Asn Trp Asn Asn
                165                 170                 175 aga ttc ttg aac cac tgt ttg gag cac ttg gtg cag tac cgg act gac     576
Arg Phe Leu Asn His Cys Leu Glu His Leu Val Gln Tyr Arg Thr Asp
            180                 185                 190 tgg gac cac agc tgg act gaa caa tca gtg gat tat aga cat aag ttc     624
Trp Asp His Ser Trp Thr Glu Gln Ser Val Asp Tyr Arg His Lys Phe
        195                 200                 205 tcc ttg cct agt gtg gat ggg cag aaa cgc tac acg ttt cgt gtt cgg     672
Ser Leu Pro Ser Val Asp Gly Gln Lys Arg Tyr Thr Phe Arg Val Arg
    210                 215                 220 agc cgc ttt aac cca ctc tgt gga agt gct cag cat tgg agt gaa tgg     720
Ser Arg Phe Asn Pro Leu Cys Gly Ser Ala Gln His Trp Ser Glu Trp
225                 230                 235                 240 agc cac cca atc cac tgg ggg agc aat act tca aaa gag aac gcg tcg     768
Ser His Pro Ile His Trp Gly Ser Asn Thr Ser Lys Glu Asn Ala Ser
                245                 250                 255
```

```
tct ggg aac atg aag gtc ctg cag gag ccc acc tgc gtc tcc gac tac        816
Ser Gly Asn Met Lys Val Leu Gln Glu Pro Thr Cys Val Ser Asp Tyr
        260                 265                 270 atg agc atc tct act tgc gag tgg aag atg aat ggt ccc acc aat tgc        864
Met Ser Ile Ser Thr Cys Glu Trp Lys Met Asn Gly Pro Thr Asn Cys
            275                 280                 285 agc acc gag ctc cgc ctg ttg tac cag ctg gtt ttt ctg ctc tcc gaa        912
Ser Thr Glu Leu Arg Leu Leu Tyr Gln Leu Val Phe Leu Leu Ser Glu
        290                 295                 300 gcc cac acg tgt atc cct gag aac aac gga ggc gcg ggg tgc gtg tgc        960
Ala His Thr Cys Ile Pro Glu Asn Asn Gly Gly Ala Gly Cys Val Cys
305                 310                 315                 320 cac ctg ctc atg gat gac gtg gtc agt gcg gat aac tat aca ctg gac       1008
His Leu Leu Met Asp Asp Val Val Ser Ala Asp Asn Tyr Thr Leu Asp
                325                 330                 335 ctg tgg gct ggg cag cag ctg ctg tgg aag ggc tcc ttc aag ccc agc       1056
Leu Trp Ala Gly Gln Gln Leu Leu Trp Lys Gly Ser Phe Lys Pro Ser
            340                 345                 350 gag cat gtg aaa ccc agg gcc cca gga aac ctg aca gtt cac acc aat       1104
Glu His Val Lys Pro Arg Ala Pro Gly Asn Leu Thr Val His Thr Asn
        355                 360                 365 gtc tcc gac act ctg ctg ctg acc tgg agc aac ccg tat ccc cct gac       1152
Val Ser Asp Thr Leu Leu Leu Thr Trp Ser Asn Pro Tyr Pro Pro Asp
370                 375                 380 aat tac ctg tat aat cat ctc acc tat gca gtc aac att tgg agt gaa       1200
Asn Tyr Leu Tyr Asn His Leu Thr Tyr Ala Val Asn Ile Trp Ser Glu
                385                 390                 395                 400 aac gac ccg gca gat ttc aga atc tat aac gtg acc tac cta gaa ccc       1248
Asn Asp Pro Ala Asp Phe Arg Ile Tyr Asn Val Thr Tyr Leu Glu Pro
                    405                 410                 415 tcc ctc cgc atc gca gcc agc acc ctg aag tct ggg att tcc tac agg       1296
Ser Leu Arg Ile Ala Ala Ser Thr Leu Lys Ser Gly Ile Ser Tyr Arg
                420                 425                 430 gca cgg gtg agg gcc tgg gct cag tgc tat aac acc acc tgg agt gag       1344
Ala Arg Val Arg Ala Trp Ala Gln Cys Tyr Asn Thr Thr Trp Ser Glu
            435                 440                 445 tgg agc ccc agc acc aag tgg cac aac tcc tac agg gag ccc ttc gag       1392
Trp Ser Pro Ser Thr Lys Trp His Asn Ser Tyr Arg Glu Pro Phe Glu
450                 455                 460 cag tcc gga gac aaa act cac aca tgc cca ccg tgc cca gca cct gaa       1440
Gln Ser Gly Asp Lys Thr His Thr Cys Pro Pro Cys Pro Ala Pro Glu
465                 470                 475                 480 ctc ctg ggg gga ccg tca gtc ttc ctc ttc ccc cca aaa ccc aag gac       1488
Leu Leu Gly Gly Pro Ser Val Phe Leu Phe Pro Pro Lys Pro Lys Asp
                485                 490                 495 acc ctc atg atc tcc cgg acc cct gag gtc aca tgc gtg gtg gtg gac       1536
Thr Leu Met Ile Ser Arg Thr Pro Glu Val Thr Cys Val Val Val Asp
            500                 505                 510 gtg agc cac gaa gac cct gag gtc aag ttc aac tgg tac gtg gac ggc       1584
Val Ser His Glu Asp Pro Glu Val Lys Phe Asn Trp Tyr Val Asp Gly
        515                 520                 525 gtg gag gtg cat aat gcc aag aca aag ccg cgg gag gag cag tac aac       1632
Val Glu Val His Asn Ala Lys Thr Lys Pro Arg Glu Glu Gln Tyr Asn
        530                 535                 540 agc acg tac cgt gtg gtc agc gtc ctc acc gtc ctg cac cag gac tgg       1680
Ser Thr Tyr Arg Val Val Ser Val Leu Thr Val Leu His Gln Asp Trp
545                 550                 555                 560 ctg aat ggc aag gag tac aag tgc aag gtc tcc aac aaa gcc ctc cca       1728
Leu Asn Gly Lys Glu Tyr Lys Cys Lys Val Ser Asn Lys Ala Leu Pro
```

-continued

```
                565                 570                 575
gcc ccc atc gag aaa acc atc tcc aaa gcc aaa ggg cag ccc cga gaa      1776
Ala Pro Ile Glu Lys Thr Ile Ser Lys Ala Lys Gly Gln Pro Arg Glu
            580                 585                 590 cca cag gtg tac acc ctg ccc cca tcc cgg gag gag atg acc aag aac      1824
Pro Gln Val Tyr Thr Leu Pro Pro Ser Arg Glu Glu Met Thr Lys Asn
        595                 600                 605 cag gtc agc ctg acc tgc ctg gtc aaa ggc ttc tat ccc agc gac atc      1872
Gln Val Ser Leu Thr Cys Leu Val Lys Gly Phe Tyr Pro Ser Asp Ile
    610                 615                 620 gcc gtg gag tgg gag agc aat ggg cag ccg gag aac aac tac aag acc      1920
Ala Val Glu Trp Glu Ser Asn Gly Gln Pro Glu Asn Asn Tyr Lys Thr
625                 630                 635                 640 acg cct ccc gtg ctg gac tcc gac ggc tcc ttc ttc ctc tat agc aag      1968
Thr Pro Pro Val Leu Asp Ser Asp Gly Ser Phe Phe Leu Tyr Ser Lys
            645                 650                 655 ctc acc gtg gac aag agc agg tgg cag cag ggg aac gtc ttc tca tgc      2016
Leu Thr Val Asp Lys Ser Arg Trp Gln Gln Gly Asn Val Phe Ser Cys
        660                 665                 670 tcc gtg atg cat gag gct ctg cac aac cac tac acg cag aag agc ctc      2064
Ser Val Met His Glu Ala Leu His Asn His Tyr Thr Gln Lys Ser Leu
    675                 680                 685 tcc ctg tct ccg ggt aaa tga                                          2085
Ser Leu Ser Pro Gly Lys
        690

<210> SEQ ID NO 18
<211> LENGTH: 694
<212> TYPE: PRT
<213> ORGANISM: Homo sapiens

<400> SEQUENCE: 18

Met Val Lys Pro Ser Leu Pro Phe Thr Ser Leu Leu Phe Leu Gln Leu
1               5                   10                  15

Pro Leu Leu Gly Val Gly Leu Asn Thr Thr Ile Leu Thr Pro Asn Gly
            20                  25                  30

Asn Glu Asp Thr Thr Ala Asp Phe Phe Leu Thr Thr Met Pro Thr Asp
        35                  40                  45

Ser Leu Ser Val Ser Thr Leu Pro Leu Pro Glu Val Gln Cys Phe Val
    50                  55                  60

Phe Asn Val Glu Tyr Met Asn Cys Thr Trp Asn Ser Ser Ser Glu Pro
65                  70                  75                  80

Gln Pro Thr Asn Leu Thr Leu His Tyr Trp Tyr Lys Asn Ser Asp Asn
            85                  90                  95

Asp Lys Val Gln Lys Cys Ser His Tyr Leu Phe Ser Glu Glu Ile Thr
        100                 105                 110

Ser Gly Cys Gln Leu Gln Lys Lys Glu Ile His Leu Tyr Gln Thr Phe
    115                 120                 125

Val Val Gln Leu Gln Asp Pro Arg Glu Pro Arg Arg Gln Ala Thr Gln
130                 135                 140

Met Leu Lys Leu Gln Asn Leu Val Ile Pro Trp Ala Pro Glu Asn Leu
145                 150                 155                 160

Thr Leu His Lys Leu Ser Glu Ser Gln Leu Glu Leu Asn Trp Asn Asn
            165                 170                 175

Arg Phe Leu Asn His Cys Leu Glu His Leu Val Gln Tyr Arg Thr Asp
        180                 185                 190

Trp Asp His Ser Trp Thr Glu Gln Ser Val Asp Tyr Arg His Lys Phe
```

-continued

```
            195                 200                 205
Ser Leu Pro Ser Val Asp Gly Gln Lys Arg Tyr Thr Phe Arg Val Arg
    210                 215                 220

Ser Arg Phe Asn Pro Leu Cys Gly Ser Ala Gln His Trp Ser Glu Trp
225                 230                 235                 240

Ser His Pro Ile His Trp Gly Ser Asn Thr Ser Lys Glu Asn Ala Ser
            245                 250                 255

Ser Gly Asn Met Lys Val Leu Gln Glu Pro Thr Cys Val Ser Asp Tyr
            260                 265                 270

Met Ser Ile Ser Thr Cys Glu Trp Lys Met Asn Gly Pro Thr Asn Cys
            275                 280                 285

Ser Thr Glu Leu Arg Leu Leu Tyr Gln Leu Val Phe Leu Leu Ser Glu
            290                 295                 300

Ala His Thr Cys Ile Pro Glu Asn Asn Gly Gly Ala Gly Cys Val Cys
305                 310                 315                 320

His Leu Leu Met Asp Asp Val Val Ser Ala Asp Asn Tyr Thr Leu Asp
            325                 330                 335

Leu Trp Ala Gly Gln Gln Leu Leu Trp Lys Gly Ser Phe Lys Pro Ser
            340                 345                 350

Glu His Val Lys Pro Arg Ala Pro Gly Asn Leu Thr Val His Thr Asn
            355                 360                 365

Val Ser Asp Thr Leu Leu Thr Trp Ser Asn Pro Tyr Pro Pro Asp
    370                 375                 380

Asn Tyr Leu Tyr Asn His Leu Thr Tyr Ala Val Asn Ile Trp Ser Glu
385                 390                 395                 400

Asn Asp Pro Ala Asp Phe Arg Ile Tyr Asn Val Thr Tyr Leu Glu Pro
                405                 410                 415

Ser Leu Arg Ile Ala Ala Ser Thr Leu Lys Ser Gly Ile Ser Tyr Arg
            420                 425                 430

Ala Arg Val Arg Ala Trp Ala Gln Cys Tyr Asn Thr Thr Trp Ser Glu
            435                 440                 445

Trp Ser Pro Ser Thr Lys Trp His Asn Ser Tyr Arg Glu Pro Phe Glu
450                 455                 460

Gln Ser Gly Asp Lys Thr His Thr Cys Pro Pro Cys Pro Ala Pro Glu
465                 470                 475                 480

Leu Leu Gly Gly Pro Ser Val Phe Leu Phe Pro Pro Lys Pro Lys Asp
                485                 490                 495

Thr Leu Met Ile Ser Arg Thr Pro Glu Val Thr Cys Val Val Val Asp
            500                 505                 510

Val Ser His Glu Asp Pro Glu Val Lys Phe Asn Trp Tyr Val Asp Gly
            515                 520                 525

Val Glu Val His Asn Ala Lys Thr Lys Pro Arg Glu Glu Gln Tyr Asn
    530                 535                 540

Ser Thr Tyr Arg Val Val Ser Val Leu Thr Val Leu His Gln Asp Trp
545                 550                 555                 560

Leu Asn Gly Lys Glu Tyr Lys Cys Lys Val Ser Asn Lys Ala Leu Pro
                565                 570                 575

Ala Pro Ile Glu Lys Thr Ile Ser Lys Ala Lys Gly Gln Pro Arg Glu
            580                 585                 590

Pro Gln Val Tyr Thr Leu Pro Pro Ser Arg Glu Glu Met Thr Lys Asn
            595                 600                 605

Gln Val Ser Leu Thr Cys Leu Val Lys Gly Phe Tyr Pro Ser Asp Ile
            610                 615                 620
```

```
Ala Val Glu Trp Glu Ser Asn Gly Gln Pro Glu Asn Asn Tyr Lys Thr
625                 630                 635                 640

Thr Pro Pro Val Leu Asp Ser Asp Gly Ser Phe Phe Leu Tyr Ser Lys
                645                 650                 655

Leu Thr Val Asp Lys Ser Arg Trp Gln Gln Gly Asn Val Phe Ser Cys
                660                 665                 670

Ser Val Met His Glu Ala Leu His Asn His Tyr Thr Gln Lys Ser Leu
            675                 680                 685

Ser Leu Ser Pro Gly Lys
        690

<210> SEQ ID NO 19
<211> LENGTH: 2076
<212> TYPE: DNA
<213> ORGANISM: Homo sapiens
<220> FEATURE:
<221> NAME/KEY: CDS
<222> LOCATION: (1)...(2073)

<400> SEQUENCE: 19 atg gtg aag cca tca tta cca ttc aca tcc ctc tta ttc ctg cag ctg      48
Met Val Lys Pro Ser Leu Pro Phe Thr Ser Leu Leu Phe Leu Gln Leu
1               5                   10                  15 ccc ctg ctg gga gtg ggg ctg aac acg aca att ctg acg ccc aat ggg      96
Pro Leu Leu Gly Val Gly Leu Asn Thr Thr Ile Leu Thr Pro Asn Gly
            20                  25                  30 aat gaa gac acc aca gct gat ttc ttc ctg acc act atg ccc act gac     144
Asn Glu Asp Thr Thr Ala Asp Phe Phe Leu Thr Thr Met Pro Thr Asp
        35                  40                  45 tcc ctc agt gtt tcc act ctg ccc ctc cca gag gtt cag tgt ttt gtg     192
Ser Leu Ser Val Ser Thr Leu Pro Leu Pro Glu Val Gln Cys Phe Val
    50                  55                  60 ttc aat gtc gag tac atg aat tgc act tgg aac agc agc tct gag ccc     240
Phe Asn Val Glu Tyr Met Asn Cys Thr Trp Asn Ser Ser Ser Glu Pro
65                  70                  75                  80 cag cct acc aac ctc act ctg cat tat tgg tac aag aac tcg gat aat     288
Gln Pro Thr Asn Leu Thr Leu His Tyr Trp Tyr Lys Asn Ser Asp Asn
                85                  90                  95 gat aaa gtc cag aag tgc agc cac tat cta ttc tct gaa gaa atc act     336
Asp Lys Val Gln Lys Cys Ser His Tyr Leu Phe Ser Glu Glu Ile Thr
            100                 105                 110 tct ggc tgt cag ttg caa aaa aag gag atc cac ctc tac caa aca ttt     384
Ser Gly Cys Gln Leu Gln Lys Lys Glu Ile His Leu Tyr Gln Thr Phe
        115                 120                 125 gtt gtt cag ctc cag gac cca cgg gaa ccc agg aga cag gcc aca cag     432
Val Val Gln Leu Gln Asp Pro Arg Glu Pro Arg Arg Gln Ala Thr Gln
    130                 135                 140 atg cta aaa ctg cag aat ctg gtg atc ccc tgg gct cca gag aac cta     480
Met Leu Lys Leu Gln Asn Leu Val Ile Pro Trp Ala Pro Glu Asn Leu
145                 150                 155                 160 aca ctt cac aaa ctg agt gaa tcc cag cta gaa ctg aac tgg aac aac     528
Thr Leu His Lys Leu Ser Glu Ser Gln Leu Glu Leu Asn Trp Asn Asn
                165                 170                 175 aga ttc ttg aac cac tgt ttg gag cac ttg gtg cag tac cgg act gac     576
Arg Phe Leu Asn His Cys Leu Glu His Leu Val Gln Tyr Arg Thr Asp
            180                 185                 190 tgg gac cac agc tgg act gaa caa tca gtg gat tat aga cat aag ttc     624
Trp Asp His Ser Trp Thr Glu Gln Ser Val Asp Tyr Arg His Lys Phe
        195                 200                 205
```

-continued

| | | |
|---|---|---|
| tcc ttg cct agt gtg gat ggg cag aaa cgc tac acg ttt cgt gtt cgg<br>Ser Leu Pro Ser Val Asp Gly Gln Lys Arg Tyr Thr Phe Arg Val Arg<br>210                                215                              220 | 672 |
| agc cgc ttt aac cca ctc tgt gga agt gct cag cat tgg agt gaa tgg<br>Ser Arg Phe Asn Pro Leu Cys Gly Ser Ala Gln His Trp Ser Glu Trp<br>225                                230                              235                         240 | 720 |
| agc cac cca atc cac tgg ggg agc aat act tca aaa gag aac ggg aac<br>Ser His Pro Ile His Trp Gly Ser Asn Thr Ser Lys Glu Asn Gly Asn<br>                         245                                250                              255 | 768 |
| atg aag gtc ctg cag gag ccc acc tgc gtc tcc gac tac atg agc atc<br>Met Lys Val Leu Gln Glu Pro Thr Cys Val Ser Asp Tyr Met Ser Ile<br>                             260                                265                            270 | 816 |
| tct act tgc gag tgg aag atg aat ggt ccc acc aat tgc agc acc gag<br>Ser Thr Cys Glu Trp Lys Met Asn Gly Pro Thr Asn Cys Ser Thr Glu<br>275                                280                              285 | 864 |
| ctc cgc ctg ttg tac cag ctg gtt ttt ctg ctc tcc gaa gcc cac acg<br>Leu Arg Leu Leu Tyr Gln Leu Val Phe Leu Leu Ser Glu Ala His Thr<br>                         290                                295                            300 | 912 |
| tgt atc cct gag aac aac gga ggc gcg ggg tgc gtg tgc cac ctg ctc<br>Cys Ile Pro Glu Asn Asn Gly Gly Ala Gly Cys Val Cys His Leu Leu<br>305                                310                              315                            320 | 960 |
| atg gat gac gtg gtc agt gcg gat aac tat aca ctg gac ctg tgg gct<br>Met Asp Asp Val Val Ser Ala Asp Asn Tyr Thr Leu Asp Leu Trp Ala<br>                         325                                330                            335 | 1008 |
| ggg cag cag ctg ctg tgg aag ggc tcc ttc aag ccc agc gag cat gtg<br>Gly Gln Gln Leu Leu Trp Lys Gly Ser Phe Lys Pro Ser Glu His Val<br>                             340                                345                            350 | 1056 |
| aaa ccc agg gcc cca gga aac ctg aca gtt cac acc aat gtc tcc gac<br>Lys Pro Arg Ala Pro Gly Asn Leu Thr Val His Thr Asn Val Ser Asp<br>                         355                                360                            365 | 1104 |
| act ctg ctg ctg acc tgg agc aac ccg tat ccc cct gac aat tac ctg<br>Thr Leu Leu Leu Thr Trp Ser Asn Pro Tyr Pro Pro Asp Asn Tyr Leu<br>370                                375                              380 | 1152 |
| tat aat cat ctc acc tat gca gtc aac att tgg agt gaa aac gac ccg<br>Tyr Asn His Leu Thr Tyr Ala Val Asn Ile Trp Ser Glu Asn Asp Pro<br>385                                390                              395                            400 | 1200 |
| gca gat ttc aga atc tat aac gtg acc tac cta gaa ccc tcc ctc cgc<br>Ala Asp Phe Arg Ile Tyr Asn Val Thr Tyr Leu Glu Pro Ser Leu Arg<br>                         405                                410                            415 | 1248 |
| atc gca gcc agc acc ctg aag tct ggg att tcc tac agg gca cgg gtg<br>Ile Ala Ala Ser Thr Leu Lys Ser Gly Ile Ser Tyr Arg Ala Arg Val<br>                         420                                425                            430 | 1296 |
| agg gcc tgg gct cag agc tat aac acc acc tgg agt gag tgg agc ccc<br>Arg Ala Trp Ala Gln Ser Tyr Asn Thr Thr Trp Ser Glu Trp Ser Pro<br>                         435                                440                            445 | 1344 |
| agc acc aag tgg cac aac tcc tac agg gag ccc ttc gag cag tcc gga<br>Ser Thr Lys Trp His Asn Ser Tyr Arg Glu Pro Phe Glu Gln Ser Gly<br>450                                455                              460 | 1392 |
| gac aaa act cac aca tgc cca ccg tgc cca gca cct gaa ctc ctg ggg<br>Asp Lys Thr His Thr Cys Pro Pro Cys Pro Ala Pro Glu Leu Leu Gly<br>465                                470                              475                            480 | 1440 |
| gga ccg tca gtc ttc ctc ttc ccc cca aaa ccc aag gac acc ctc atg<br>Gly Pro Ser Val Phe Leu Phe Pro Pro Lys Pro Lys Asp Thr Leu Met<br>                         485                                490                            495 | 1488 |
| atc tcc cgg acc cct gag gtc aca tgc gtg gtg gtg gac gtg agc cac<br>Ile Ser Arg Thr Pro Glu Val Thr Cys Val Val Val Asp Val Ser His<br>                         500                                505                            510 | 1536 |
| gaa gac cct gag gtc aag ttc aac tgg tac gtg gac ggc gtg gag gtg<br>Glu Asp Pro Glu Val Lys Phe Asn Trp Tyr Val Asp Gly Val Glu Val<br>                         515                                520                            525 | 1584 |

```
cat aat gcc aag aca aag ccg cgg gag gag cag tac aac agc acg tac    1632
His Asn Ala Lys Thr Lys Pro Arg Glu Glu Gln Tyr Asn Ser Thr Tyr
    530                 535                 540 cgt gtg gtc agc gtc ctc acc gtc ctg cac cag gac tgg ctg aat ggc    1680
Arg Val Ser Val Leu Thr Val Leu His Gln Asp Trp Leu Asn Gly
545                 550                 555                 560 aag gag tac aag tgc aag gtc tcc aac aaa gcc ctc cca gcc ccc atc    1728
Lys Glu Tyr Lys Cys Lys Val Ser Asn Lys Ala Leu Pro Ala Pro Ile
                565                 570                 575 gag aaa acc atc tcc aaa gcc aaa ggg cag ccc cga gaa cca cag gtg    1776
Glu Lys Thr Ile Ser Lys Ala Lys Gly Gln Pro Arg Glu Pro Gln Val
            580                 585                 590 tac acc ctg ccc cca tcc cgg gat gag ctg acc aag aac cag gtc agc    1824
Tyr Thr Leu Pro Pro Ser Arg Asp Glu Leu Thr Lys Asn Gln Val Ser
        595                 600                 605 ctg acc tgc ctg gtc aaa ggc ttc tat ccc agc gac atc gcc gtg gag    1872
Leu Thr Cys Leu Val Lys Gly Phe Tyr Pro Ser Asp Ile Ala Val Glu
    610                 615                 620 tgg gag agc aat ggg cag ccg gag aac aac tac aag acc acg cct ccc    1920
Trp Glu Ser Asn Gly Gln Pro Glu Asn Asn Tyr Lys Thr Thr Pro Pro
625                 630                 635                 640 gtg ctg gac tcc gac ggc tcc ttc ttc ctc tat agc aag ctc acc gtg    1968
Val Leu Asp Ser Asp Gly Ser Phe Phe Leu Tyr Ser Lys Leu Thr Val
                645                 650                 655 gac aag agc agg tgg cag cag ggg aac gtc ttc tca tgc tcc gtg atg    2016
Asp Lys Ser Arg Trp Gln Gln Gly Asn Val Phe Ser Cys Ser Val Met
            660                 665                 670 cat gag gct ctg cac aac cac tac acg cag aag agc ctc tcc ctg tct    2064
His Glu Ala Leu His Asn His Tyr Thr Gln Lys Ser Leu Ser Leu Ser
        675                 680                 685 ccg ggt aaa tga                                                    2076
Pro Gly Lys
    690

<210> SEQ ID NO 20
<211> LENGTH: 691
<212> TYPE: PRT
<213> ORGANISM: Homo sapiens

<400> SEQUENCE: 20

Met Val Lys Pro Ser Leu Pro Phe Thr Ser Leu Leu Phe Leu Gln Leu
1               5                   10                  15

Pro Leu Leu Gly Val Gly Leu Asn Thr Thr Ile Leu Thr Pro Asn Gly
            20                  25                  30

Asn Glu Asp Thr Thr Ala Asp Phe Phe Leu Thr Thr Met Pro Thr Asp
        35                  40                  45

Ser Leu Ser Val Ser Thr Leu Pro Leu Pro Glu Val Gln Cys Phe Val
    50                  55                  60

Phe Asn Val Glu Tyr Met Asn Cys Thr Trp Asn Ser Ser Ser Glu Pro
65                  70                  75                  80

Gln Pro Thr Asn Leu Thr Leu His Tyr Trp Tyr Lys Asn Ser Asp Asn
                85                  90                  95

Asp Lys Val Gln Lys Cys Ser His Tyr Leu Phe Ser Glu Glu Ile Thr
            100                 105                 110

Ser Gly Cys Gln Leu Gln Lys Lys Glu Ile His Leu Tyr Gln Thr Phe
        115                 120                 125

Val Val Gln Leu Gln Asp Pro Arg Glu Pro Arg Arg Gln Ala Thr Gln
    130                 135                 140
```

-continued

```
Met Leu Lys Leu Gln Asn Leu Val Ile Pro Trp Ala Pro Glu Asn Leu
145                 150                 155                 160

Thr Leu His Lys Leu Ser Glu Ser Gln Leu Glu Leu Asn Trp Asn Asn
            165                 170                 175

Arg Phe Leu Asn His Cys Leu Glu His Leu Val Gln Tyr Arg Thr Asp
                180                 185                 190

Trp Asp His Ser Trp Thr Glu Gln Ser Val Asp Tyr Arg His Lys Phe
            195                 200                 205

Ser Leu Pro Ser Val Asp Gly Gln Lys Arg Tyr Thr Phe Arg Val Arg
        210                 215                 220

Ser Arg Phe Asn Pro Leu Cys Gly Ser Ala Gln His Trp Ser Glu Trp
225                 230                 235                 240

Ser His Pro Ile His Trp Gly Ser Asn Thr Ser Lys Glu Asn Gly Asn
                245                 250                 255

Met Lys Val Leu Gln Glu Pro Thr Cys Val Ser Asp Tyr Met Ser Ile
            260                 265                 270

Ser Thr Cys Glu Trp Lys Met Asn Gly Pro Thr Asn Cys Ser Thr Glu
        275                 280                 285

Leu Arg Leu Leu Tyr Gln Leu Val Phe Leu Leu Ser Glu Ala His Thr
        290                 295                 300

Cys Ile Pro Glu Asn Asn Gly Gly Ala Gly Cys Val Cys His Leu Leu
305                 310                 315                 320

Met Asp Asp Val Val Ser Ala Asp Asn Tyr Thr Leu Asp Leu Trp Ala
                325                 330                 335

Gly Gln Gln Leu Leu Trp Lys Gly Ser Phe Lys Pro Ser Glu His Val
            340                 345                 350

Lys Pro Arg Ala Pro Gly Asn Leu Thr Val His Thr Asn Val Ser Asp
        355                 360                 365

Thr Leu Leu Leu Thr Trp Ser Asn Pro Tyr Pro Pro Asp Asn Tyr Leu
        370                 375                 380

Tyr Asn His Leu Thr Tyr Ala Val Asn Ile Trp Ser Glu Asn Asp Pro
385                 390                 395                 400

Ala Asp Phe Arg Ile Tyr Asn Val Thr Tyr Leu Glu Pro Ser Leu Arg
                405                 410                 415

Ile Ala Ala Ser Thr Leu Lys Ser Gly Ile Ser Tyr Arg Ala Arg Val
            420                 425                 430

Arg Ala Trp Ala Gln Ser Tyr Asn Thr Thr Trp Ser Glu Trp Ser Pro
        435                 440                 445

Ser Thr Lys Trp His Asn Ser Tyr Arg Glu Pro Phe Glu Gln Ser Gly
    450                 455                 460

Asp Lys Thr His Thr Cys Pro Pro Cys Pro Ala Pro Glu Leu Leu Gly
465                 470                 475                 480

Gly Pro Ser Val Phe Leu Phe Pro Pro Lys Pro Lys Asp Thr Leu Met
                485                 490                 495

Ile Ser Arg Thr Pro Glu Val Thr Cys Val Val Val Asp Val Ser His
            500                 505                 510

Glu Asp Pro Glu Val Lys Phe Asn Trp Tyr Val Asp Gly Val Glu Val
        515                 520                 525

His Asn Ala Lys Thr Lys Pro Arg Glu Glu Gln Tyr Asn Ser Thr Tyr
    530                 535                 540

Arg Val Val Ser Val Leu Thr Val Leu His Gln Asp Trp Leu Asn Gly
545                 550                 555                 560
```

-continued

```
Lys Glu Tyr Lys Cys Lys Val Ser Asn Lys Ala Leu Pro Ala Pro Ile
            565                 570                 575

Glu Lys Thr Ile Ser Lys Ala Lys Gly Gln Pro Arg Glu Pro Gln Val
        580                 585                 590

Tyr Thr Leu Pro Pro Ser Arg Asp Glu Leu Thr Lys Asn Gln Val Ser
        595                 600                 605

Leu Thr Cys Leu Val Lys Gly Phe Tyr Pro Ser Asp Ile Ala Val Glu
    610                 615                 620

Trp Glu Ser Asn Gly Gln Pro Glu Asn Asn Tyr Lys Thr Thr Pro Pro
625                 630                 635                 640

Val Leu Asp Ser Asp Gly Ser Phe Phe Leu Tyr Ser Lys Leu Thr Val
                645                 650                 655

Asp Lys Ser Arg Trp Gln Gln Gly Asn Val Phe Ser Cys Ser Val Met
            660                 665                 670

His Glu Ala Leu His Asn His Tyr Thr Gln Lys Ser Leu Ser Leu Ser
        675                 680                 685

Pro Gly Lys
    690
```

```
<210> SEQ ID NO 21
<211> LENGTH: 2085
<212> TYPE: DNA
<213> ORGANISM: Homo sapiens
<220> FEATURE:
<221> NAME/KEY: CDS
<222> LOCATION: (1)...(2082)

<400> SEQUENCE: 21
```

| | | | | | | | | | | | | | | | | |
|---|---|---|---|---|---|---|---|---|---|---|---|---|---|---|---|---|
| atg | gtg | aag | cca | tca | tta | cca | ttc | aca | tcc | ctc | tta | ttc | ctg | cag | ctg | 48 |
| Met | Val | Lys | Pro | Ser | Leu | Pro | Phe | Thr | Ser | Leu | Leu | Phe | Leu | Gln | Leu | |
| 1 | | | | 5 | | | | | 10 | | | | | 15 | | |
| ccc | ctg | ctg | gga | gtg | ggg | ctg | aac | acg | aca | att | ctg | acg | ccc | aat | ggg | 96 |
| Pro | Leu | Leu | Gly | Val | Gly | Leu | Asn | Thr | Thr | Ile | Leu | Thr | Pro | Asn | Gly | |
| | | | 20 | | | | | 25 | | | | | 30 | | | |
| aat | gaa | gac | acc | aca | gct | gat | ttc | ttc | ctg | acc | act | atg | ccc | act | gac | 144 |
| Asn | Glu | Asp | Thr | Thr | Ala | Asp | Phe | Phe | Leu | Thr | Thr | Met | Pro | Thr | Asp | |
| | | 35 | | | | | 40 | | | | | 45 | | | | |
| tcc | ctc | agt | gtt | tcc | act | ctg | ccc | ctc | cca | gag | gtt | cag | tgt | ttt | gtg | 192 |
| Ser | Leu | Ser | Val | Ser | Thr | Leu | Pro | Leu | Pro | Glu | Val | Gln | Cys | Phe | Val | |
| | 50 | | | | | 55 | | | | | 60 | | | | | |
| ttc | aat | gtc | gag | tac | atg | aat | tgc | act | tgg | aac | agc | agc | tct | gag | ccc | 240 |
| Phe | Asn | Val | Glu | Tyr | Met | Asn | Cys | Thr | Trp | Asn | Ser | Ser | Ser | Glu | Pro | |
| 65 | | | | 70 | | | | | 75 | | | | | 80 | | |
| cag | cct | acc | aac | ctc | act | ctg | cat | tat | tgg | tac | aag | aac | tcg | gat | aat | 288 |
| Gln | Pro | Thr | Asn | Leu | Thr | Leu | His | Tyr | Trp | Tyr | Lys | Asn | Ser | Asp | Asn | |
| | | | | 85 | | | | | 90 | | | | | 95 | | |
| gat | aaa | gtc | cag | aag | tgc | agc | cac | tat | cta | ttc | tct | gaa | gaa | atc | act | 336 |
| Asp | Lys | Val | Gln | Lys | Cys | Ser | His | Tyr | Leu | Phe | Ser | Glu | Glu | Ile | Thr | |
| | | | 100 | | | | | 105 | | | | | 110 | | | |
| tct | ggc | tgt | cag | ttg | caa | aaa | aag | gag | atc | cac | ctc | tac | caa | aca | ttt | 384 |
| Ser | Gly | Cys | Gln | Leu | Gln | Lys | Lys | Glu | Ile | His | Leu | Tyr | Gln | Thr | Phe | |
| | | 115 | | | | | 120 | | | | | 125 | | | | |
| gtt | gtt | cag | ctc | cag | gac | cca | cgg | gaa | ccc | agg | aga | cag | gcc | aca | cag | 432 |
| Val | Val | Gln | Leu | Gln | Asp | Pro | Arg | Glu | Pro | Arg | Arg | Gln | Ala | Thr | Gln | |
| | 130 | | | | | 135 | | | | | 140 | | | | | |
| atg | cta | aaa | ctg | cag | aat | ctg | gtg | atc | ccc | tgg | gct | cca | gag | aac | cta | 480 |
| Met | Leu | Lys | Leu | Gln | Asn | Leu | Val | Ile | Pro | Trp | Ala | Pro | Glu | Asn | Leu | |
| 145 | | | | 150 | | | | | 155 | | | | | 160 | | |
| aca | ctt | cac | aaa | ctg | agt | gaa | tcc | cag | cta | gaa | ctg | aac | tgg | aac | aac | 528 |

```
                Thr Leu His Lys Leu Ser Glu Ser Gln Leu Glu Leu Asn Trp Asn Asn
                                165                 170                 175 aga ttc ttg aac cac tgt ttg gag cac ttg gtg cag tac cgg act gac            576
Arg Phe Leu Asn His Cys Leu Glu His Leu Val Gln Tyr Arg Thr Asp
            180                 185                 190 tgg gac cac agc tgg act gaa caa tca gtg gat tat aga cat aag ttc            624
Trp Asp His Ser Trp Thr Glu Gln Ser Val Asp Tyr Arg His Lys Phe
                195                 200                 205 tcc ttg cct agt gtg gat ggg cag aaa cgc tac acg ttt cgt gtt cgg            672
Ser Leu Pro Ser Val Asp Gly Gln Lys Arg Tyr Thr Phe Arg Val Arg
    210                 215                 220 agc cgc ttt aac cca ctc tgt gga agt gct cag cat tgg agt gaa tgg            720
Ser Arg Phe Asn Pro Leu Cys Gly Ser Ala Gln His Trp Ser Glu Trp
225                 230                 235                 240 agc cac cca atc cac tgg ggg agc aat act tca aaa gag aac gcg tcg            768
Ser His Pro Ile His Trp Gly Ser Asn Thr Ser Lys Glu Asn Ala Ser
                245                 250                 255 tct ggg aac atg aag gtc ctg cag gag ccc acc tgc gtc tcc gac tac            816
Ser Gly Asn Met Lys Val Leu Gln Glu Pro Thr Cys Val Ser Asp Tyr
                260                 265                 270 atg agc atc tct act tgc gag tgg aag atg aat ggt ccc acc aat tgc            864
Met Ser Ile Ser Thr Cys Glu Trp Lys Met Asn Gly Pro Thr Asn Cys
            275                 280                 285 agc acc gag ctc cgc ctg ttg tac cag ctg gtt ttt ctg ctc tcc gaa            912
Ser Thr Glu Leu Arg Leu Leu Tyr Gln Leu Val Phe Leu Leu Ser Glu
        290                 295                 300 gcc cac acg tgt atc cct gag aac aac gga ggc gcg ggg tgc gtg tgc            960
Ala His Thr Cys Ile Pro Glu Asn Asn Gly Gly Ala Gly Cys Val Cys
305                 310                 315                 320 cac ctg ctc atg gat gac gtg gtc agt gcg gat aac tat aca ctg gac           1008
His Leu Leu Met Asp Asp Val Val Ser Ala Asp Asn Tyr Thr Leu Asp
                325                 330                 335 ctg tgg gct ggg cag cag ctg ctg tgg aag ggc tcc ttc aag ccc agc           1056
Leu Trp Ala Gly Gln Gln Leu Leu Trp Lys Gly Ser Phe Lys Pro Ser
            340                 345                 350 gag cat gtg aaa ccc agg gcc cca gga aac ctg aca gtt cac acc aat           1104
Glu His Val Lys Pro Arg Ala Pro Gly Asn Leu Thr Val His Thr Asn
        355                 360                 365 gtc tcc gac act ctg ctg ctg acc tgg agc aac ccg tat ccc cct gac           1152
Val Ser Asp Thr Leu Leu Leu Thr Trp Ser Asn Pro Tyr Pro Pro Asp
    370                 375                 380 aat tac ctg tat aat cat ctc acc tat gca gtc aac att tgg agt gaa           1200
Asn Tyr Leu Tyr Asn His Leu Thr Tyr Ala Val Asn Ile Trp Ser Glu
385                 390                 395                 400 aac gac ccg gca gat ttc aga atc tat aac gtg acc tac cta gaa ccc           1248
Asn Asp Pro Ala Asp Phe Arg Ile Tyr Asn Val Thr Tyr Leu Glu Pro
                405                 410                 415 tcc ctc cgc atc gca gcc agc acc ctg aag tct ggg att tcc tac agg           1296
Ser Leu Arg Ile Ala Ala Ser Thr Leu Lys Ser Gly Ile Ser Tyr Arg
            420                 425                 430 gca cgg gtg agg gcc tgg gct cag agc tat aac acc acc tgg agt gag           1344
Ala Arg Val Arg Ala Trp Ala Gln Ser Tyr Asn Thr Thr Trp Ser Glu
        435                 440                 445 tgg agc ccc agc acc aag tgg cac aac tcc tac agg gag ccc ttc gag           1392
Trp Ser Pro Ser Thr Lys Trp His Asn Ser Tyr Arg Glu Pro Phe Glu
    450                 455                 460 cag tcc gga gac aaa act cac aca tgc cca ccg tgc cca gca cct gaa           1440
Gln Ser Gly Asp Lys Thr His Thr Cys Pro Pro Cys Pro Ala Pro Glu
465                 470                 475                 480
```

```
ctc ctg ggg gga ccg tca gtc ttc ctc ttc ccc cca aaa ccc aag gac    1488
Leu Leu Gly Gly Pro Ser Val Phe Leu Phe Pro Pro Lys Pro Lys Asp
            485                 490                 495 acc ctc atg atc tcc cgg acc cct gag gtc aca tgc gtg gtg gtg gac    1536
Thr Leu Met Ile Ser Arg Thr Pro Glu Val Thr Cys Val Val Val Asp
        500                 505                 510 gtg agc cac gaa gac cct gag gtc aag ttc aac tgg tac gtg gac ggc    1584
Val Ser His Glu Asp Pro Glu Val Lys Phe Asn Trp Tyr Val Asp Gly
    515                 520                 525 gtg gag gtg cat aat gcc aag aca aag ccg cgg gag gag cag tac aac    1632
Val Glu Val His Asn Ala Lys Thr Lys Pro Arg Glu Glu Gln Tyr Asn
530                 535                 540 agc acg tac cgt gtg gtc agc gtc ctc acc gtc ctg cac cag gac tgg    1680
Ser Thr Tyr Arg Val Val Ser Val Leu Thr Val Leu His Gln Asp Trp
545                 550                 555                 560 ctg aat ggc aag gag tac aag tgc aag gtc tcc aac aaa gcc ctc cca    1728
Leu Asn Gly Lys Glu Tyr Lys Cys Lys Val Ser Asn Lys Ala Leu Pro
                565                 570                 575 gcc ccc atc gag aaa acc atc tcc aaa gcc aaa ggg cag ccc cga gaa    1776
Ala Pro Ile Glu Lys Thr Ile Ser Lys Ala Lys Gly Gln Pro Arg Glu
            580                 585                 590 cca cag gtg tac acc ctg ccc cca tcc cgg gat gag ctg acc aag aac    1824
Pro Gln Val Tyr Thr Leu Pro Pro Ser Arg Asp Glu Leu Thr Lys Asn
        595                 600                 605 cag gtc agc ctg acc tgc ctg gtc aaa ggc ttc tat ccc agc gac atc    1872
Gln Val Ser Leu Thr Cys Leu Val Lys Gly Phe Tyr Pro Ser Asp Ile
    610                 615                 620 gcc gtg gag tgg gag agc aat ggg cag ccg gag aac aac tac aag acc    1920
Ala Val Glu Trp Glu Ser Asn Gly Gln Pro Glu Asn Asn Tyr Lys Thr
625                 630                 635                 640 acg cct ccc gtg ctg gac tcc gac ggc tcc ttc ttc ctc tat agc aag    1968
Thr Pro Pro Val Leu Asp Ser Asp Gly Ser Phe Phe Leu Tyr Ser Lys
                645                 650                 655 ctc acc gtg gac aag agc agg tgg cag cag ggg aac gtc ttc tca tgc    2016
Leu Thr Val Asp Lys Ser Arg Trp Gln Gln Gly Asn Val Phe Ser Cys
            660                 665                 670 tcc gtg atg cat gag gct ctg cac aac cac tac acg cag aag agc ctc    2064
Ser Val Met His Glu Ala Leu His Asn His Tyr Thr Gln Lys Ser Leu
        675                 680                 685 tcc ctg tct ccg ggt aaa tga                                        2085
Ser Leu Ser Pro Gly Lys
    690
```

<210> SEQ ID NO 22
<211> LENGTH: 694
<212> TYPE: PRT
<213> ORGANISM: Homo sapiens

<400> SEQUENCE: 22

```
Met Val Lys Pro Ser Leu Pro Phe Thr Ser Leu Leu Phe Leu Gln Leu
 1               5                  10                  15

Pro Leu Leu Gly Val Gly Leu Asn Thr Thr Ile Leu Thr Pro Asn Gly
                20                  25                  30

Asn Glu Asp Thr Thr Ala Asp Phe Phe Leu Thr Thr Met Pro Thr Asp
            35                  40                  45

Ser Leu Ser Val Ser Thr Leu Pro Leu Pro Glu Val Gln Cys Phe Val
        50                  55                  60

Phe Asn Val Glu Tyr Met Asn Cys Thr Trp Asn Ser Ser Ser Glu Pro
65                  70                  75                  80
```

-continued

```
Gln Pro Thr Asn Leu Thr Leu His Tyr Trp Tyr Lys Asn Ser Asp Asn
                 85                  90                  95

Asp Lys Val Gln Lys Cys Ser His Tyr Leu Phe Ser Glu Glu Ile Thr
                100                 105                 110

Ser Gly Cys Gln Leu Gln Lys Lys Glu Ile His Leu Tyr Gln Thr Phe
            115                 120                 125

Val Val Gln Leu Gln Asp Pro Arg Glu Pro Arg Arg Gln Ala Thr Gln
130                 135                 140

Met Leu Lys Leu Gln Asn Leu Val Ile Pro Trp Ala Pro Glu Asn Leu
145                 150                 155                 160

Thr Leu His Lys Leu Ser Glu Ser Gln Leu Glu Leu Asn Trp Asn Asn
                165                 170                 175

Arg Phe Leu Asn His Cys Leu Glu His Leu Val Gln Tyr Arg Thr Asp
                180                 185                 190

Trp Asp His Ser Trp Thr Glu Gln Ser Val Asp Tyr Arg His Lys Phe
            195                 200                 205

Ser Leu Pro Ser Val Asp Gly Gln Lys Arg Tyr Thr Phe Arg Val Arg
        210                 215                 220

Ser Arg Phe Asn Pro Leu Cys Gly Ser Ala Gln His Trp Ser Glu Trp
225                 230                 235                 240

Ser His Pro Ile His Trp Gly Ser Asn Thr Ser Lys Glu Asn Ala Ser
                245                 250                 255

Ser Gly Asn Met Lys Val Leu Gln Glu Pro Thr Cys Val Ser Asp Tyr
                260                 265                 270

Met Ser Ile Ser Thr Cys Glu Trp Lys Met Asn Gly Pro Thr Asn Cys
            275                 280                 285

Ser Thr Glu Leu Arg Leu Leu Tyr Gln Leu Val Phe Leu Leu Ser Glu
        290                 295                 300

Ala His Thr Cys Ile Pro Glu Asn Asn Gly Gly Ala Gly Cys Val Cys
305                 310                 315                 320

His Leu Leu Met Asp Asp Val Val Ser Ala Asp Asn Tyr Thr Leu Asp
                325                 330                 335

Leu Trp Ala Gly Gln Gln Leu Leu Trp Lys Gly Ser Phe Lys Pro Ser
            340                 345                 350

Glu His Val Lys Pro Arg Ala Pro Gly Asn Leu Thr Val His Thr Asn
        355                 360                 365

Val Ser Asp Thr Leu Leu Leu Thr Trp Ser Asn Pro Tyr Pro Pro Asp
370                 375                 380

Asn Tyr Leu Tyr Asn His Leu Thr Tyr Ala Val Asn Ile Trp Ser Glu
385                 390                 395                 400

Asn Asp Pro Ala Asp Phe Arg Ile Tyr Asn Val Thr Tyr Leu Glu Pro
                405                 410                 415

Ser Leu Arg Ile Ala Ala Ser Thr Leu Lys Ser Gly Ile Ser Tyr Arg
                420                 425                 430

Ala Arg Val Arg Ala Trp Ala Gln Ser Tyr Asn Thr Thr Trp Ser Glu
            435                 440                 445

Trp Ser Pro Ser Thr Lys Trp His Asn Ser Tyr Arg Glu Pro Phe Glu
        450                 455                 460

Gln Ser Gly Asp Lys Thr His Thr Cys Pro Pro Cys Pro Ala Pro Glu
465                 470                 475                 480

Leu Leu Gly Gly Pro Ser Val Phe Leu Phe Pro Pro Lys Pro Lys Asp
                485                 490                 495

Thr Leu Met Ile Ser Arg Thr Pro Glu Val Thr Cys Val Val Val Asp
```

```
                500                 505                 510
Val Ser His Glu Asp Pro Glu Val Lys Phe Asn Trp Tyr Val Asp Gly
    515                 520                 525

Val Glu Val His Asn Ala Lys Thr Lys Pro Arg Glu Glu Gln Tyr Asn
530                 535                 540

Ser Thr Tyr Arg Val Val Ser Val Leu Thr Val Leu His Gln Asp Trp
545                 550                 555                 560

Leu Asn Gly Lys Glu Tyr Lys Cys Lys Val Ser Asn Lys Ala Leu Pro
                565                 570                 575

Ala Pro Ile Glu Lys Thr Ile Ser Lys Ala Lys Gly Gln Pro Arg Glu
            580                 585                 590

Pro Gln Val Tyr Thr Leu Pro Pro Ser Arg Asp Glu Leu Thr Lys Asn
        595                 600                 605

Gln Val Ser Leu Thr Cys Leu Val Lys Gly Phe Tyr Pro Ser Asp Ile
    610                 615                 620

Ala Val Glu Trp Glu Ser Asn Gly Gln Pro Glu Asn Asn Tyr Lys Thr
625                 630                 635                 640

Thr Pro Pro Val Leu Asp Ser Asp Gly Ser Phe Phe Leu Tyr Ser Lys
                645                 650                 655

Leu Thr Val Asp Lys Ser Arg Trp Gln Gln Gly Asn Val Phe Ser Cys
            660                 665                 670

Ser Val Met His Glu Ala Leu His Asn His Tyr Thr Gln Lys Ser Leu
        675                 680                 685

Ser Leu Ser Pro Gly Lys
    690

<210> SEQ ID NO 23
<211> LENGTH: 3507
<212> TYPE: DNA
<213> ORGANISM: Homo sapiens
<220> FEATURE:
<221> NAME/KEY: CDS
<222> LOCATION: (1)...(3504)

<400> SEQUENCE: 23 atg gtg gcc gtc ggc tgc gcg ctg ctg gct gcc ctg ctg gcc gcg ccg     48
Met Val Ala Val Gly Cys Ala Leu Leu Ala Ala Leu Leu Ala Ala Pro
1               5                   10                  15 gga gcg gcg ctg gcc cca agg cgc tgc cct gcg cag gag gtg gca aga     96
Gly Ala Ala Leu Ala Pro Arg Arg Cys Pro Ala Gln Glu Val Ala Arg
            20                  25                  30 ggc gtg ctg acc agt ctg cca gga gac agc gtg act ctg acc tgc ccg    144
Gly Val Leu Thr Ser Leu Pro Gly Asp Ser Val Thr Leu Thr Cys Pro
        35                  40                  45 ggg gta gag ccg gaa gac aat gcc act gtt cac tgg gtg ctc agg aag    192
Gly Val Glu Pro Glu Asp Asn Ala Thr Val His Trp Val Leu Arg Lys
    50                  55                  60 ccg gct gca ggc tcc cac ccc agc aga tgg gct ggc atg gga agg agg    240
Pro Ala Ala Gly Ser His Pro Ser Arg Trp Ala Gly Met Gly Arg Arg
65                  70                  75                  80 ctg ctg ctg agg tcg gtg cag ctc cac gac tct gga aac tat tca tgc    288
Leu Leu Leu Arg Ser Val Gln Leu His Asp Ser Gly Asn Tyr Ser Cys
                85                  90                  95 tac cgg gcc ggc cgc cca gct ggg act gtg cac ttg ctg gtg gat gtt    336
Tyr Arg Ala Gly Arg Pro Ala Gly Thr Val His Leu Leu Val Asp Val
            100                 105                 110 ccc ccc gag gag ccc cag ctc tcc tgc ttc cgg aag agc ccc ctc agc    384
Pro Pro Glu Glu Pro Gln Leu Ser Cys Phe Arg Lys Ser Pro Leu Ser
```

-continued

```
              115                 120                 125
aat gtt gtt tgt gag tgg ggt cct cgg agc acc cca tcc ctg acg aca      432
Asn Val Val Cys Glu Trp Gly Pro Arg Ser Thr Pro Ser Leu Thr Thr
130                 135                 140 aag gct gtg ctc ttg gtg agg aag ttt cag aac agt ccg gcc gaa gac      480
Lys Ala Val Leu Leu Val Arg Lys Phe Gln Asn Ser Pro Ala Glu Asp
145                 150                 155                 160 ttc cag gag ccg tgc cag tat tcc cag gag tcc cag aag ttc tcc tgc      528
Phe Gln Glu Pro Cys Gln Tyr Ser Gln Glu Ser Gln Lys Phe Ser Cys
                165                 170                 175 cag tta gca gtc ccg gag gga gac agc tct ttc tac ata gtg tcc atg      576
Gln Leu Ala Val Pro Glu Gly Asp Ser Ser Phe Tyr Ile Val Ser Met
            180                 185                 190 tgc gtc gcc agt agt gtc ggg agc aag ttc agc aaa act caa acc ttt      624
Cys Val Ala Ser Ser Val Gly Ser Lys Phe Ser Lys Thr Gln Thr Phe
        195                 200                 205 cag ggt tgt gga atc ttg cag cct gat ccg cct gcc aac atc aca gtc      672
Gln Gly Cys Gly Ile Leu Gln Pro Asp Pro Pro Ala Asn Ile Thr Val
    210                 215                 220 act gcc gtg gcc aga aac ccc cgc tgg ctc agt gtc acc tgg caa gac      720
Thr Ala Val Ala Arg Asn Pro Arg Trp Leu Ser Val Thr Trp Gln Asp
225                 230                 235                 240 ccc cac tcc tgg aac tca tct ttc tac aga cta cgg ttt gag ctc aga      768
Pro His Ser Trp Asn Ser Ser Phe Tyr Arg Leu Arg Phe Glu Leu Arg
                245                 250                 255 tat cgg gct gaa cgg tca aag aca ttc aca aca tgg atg gtc aag gac      816
Tyr Arg Ala Glu Arg Ser Lys Thr Phe Thr Thr Trp Met Val Lys Asp
            260                 265                 270 ctc cag cat cac tgt gtc atc cac gac gcc tgg agc ggc ctg agg cac      864
Leu Gln His His Cys Val Ile His Asp Ala Trp Ser Gly Leu Arg His
        275                 280                 285 gtg gtg cag ctt cgt gcc cag gag gag ttc ggg caa ggc gag tgg agc      912
Val Val Gln Leu Arg Ala Gln Glu Glu Phe Gly Gln Gly Glu Trp Ser
    290                 295                 300 gag tgg agc ccg gag gcc atg ggc acg cct tgg aca gaa tcc agg agt      960
Glu Trp Ser Pro Glu Ala Met Gly Thr Pro Trp Thr Glu Ser Arg Ser
305                 310                 315                 320 cct cca gct gag aac gag gtg tcc acc ccc atg acc ggt ggc gcg cct     1008
Pro Pro Ala Glu Asn Glu Val Ser Thr Pro Met Thr Gly Gly Ala Pro
                325                 330                 335 tca ggt gct cag ctg gaa ctt cta gac cca tgt ggt tat atc agt cct     1056
Ser Gly Ala Gln Leu Glu Leu Leu Asp Pro Cys Gly Tyr Ile Ser Pro
            340                 345                 350 gaa tct cca gtt gta caa ctt cat tct aat ttc act gca gtt tgt gtg     1104
Glu Ser Pro Val Val Gln Leu His Ser Asn Phe Thr Ala Val Cys Val
        355                 360                 365 cta aag gaa aaa tgt atg gat tat ttt cat gta aat gct aat tac att     1152
Leu Lys Glu Lys Cys Met Asp Tyr Phe His Val Asn Ala Asn Tyr Ile
    370                 375                 380 gtc tgg aaa aca aac cat ttt act att cct aag gag caa tat act atc     1200
Val Trp Lys Thr Asn His Phe Thr Ile Pro Lys Glu Gln Tyr Thr Ile
385                 390                 395                 400 ata aac aga aca gca tcc agt gtc acc ttt aca gat ata gct tca tta     1248
Ile Asn Arg Thr Ala Ser Ser Val Thr Phe Thr Asp Ile Ala Ser Leu
                405                 410                 415 aat att cag ctc act tgc aac att ctt aca ttc gga cag ctt gaa cag     1296
Asn Ile Gln Leu Thr Cys Asn Ile Leu Thr Phe Gly Gln Leu Glu Gln
            420                 425                 430 aat gtt tat gga atc aca ata att tca ggc ttg cct cca gaa aaa cct     1344
```

```
                Asn Val Tyr Gly Ile Thr Ile Ile Ser Gly Leu Pro Pro Glu Lys Pro
                        435                 440                 445 aaa aat ttg agt tgc att gtg aac gag ggg aag aaa atg agg tgt gag      1392
Lys Asn Leu Ser Cys Ile Val Asn Glu Gly Lys Lys Met Arg Cys Glu
        450                 455                 460 tgg gat ggt gga agg gaa aca cac ttg gag aca aac ttc act tta aaa      1440
Trp Asp Gly Gly Arg Glu Thr His Leu Glu Thr Asn Phe Thr Leu Lys
465                 470                 475                 480 tct gaa tgg gca aca cac aag ttt gct gat tgc aaa gca aaa cgt gac      1488
Ser Glu Trp Ala Thr His Lys Phe Ala Asp Cys Lys Ala Lys Arg Asp
                    485                 490                 495 acc ccc acc tca tgc act gtt gat tat tct act gtg tat ttt gtc aac      1536
Thr Pro Thr Ser Cys Thr Val Asp Tyr Ser Thr Val Tyr Phe Val Asn
                500                 505                 510 att gaa gtc tgg gta gaa gca gag aat gcc ctt ggg aag gtt aca tca      1584
Ile Glu Val Trp Val Glu Ala Glu Asn Ala Leu Gly Lys Val Thr Ser
            515                 520                 525 gat cat atc aat ttt gat cct gta tat aaa gtg aag ccc aat ccg cca      1632
Asp His Ile Asn Phe Asp Pro Val Tyr Lys Val Lys Pro Asn Pro Pro
        530                 535                 540 cat aat tta tca gtg atc aac tca gag gaa ctg tct agt atc tta aaa      1680
His Asn Leu Ser Val Ile Asn Ser Glu Glu Leu Ser Ser Ile Leu Lys
545                 550                 555                 560 ttg aca tgg acc aac cca agt att aag agt gtt ata ata cta aaa tat      1728
Leu Thr Trp Thr Asn Pro Ser Ile Lys Ser Val Ile Ile Leu Lys Tyr
                    565                 570                 575 aac att caa tat agg acc aaa gat gcc tca act tgg agc cag att cct      1776
Asn Ile Gln Tyr Arg Thr Lys Asp Ala Ser Thr Trp Ser Gln Ile Pro
                580                 585                 590 cct gaa gac aca gca tcc acc cga tct tca ttc act gtc caa gac ctt      1824
Pro Glu Asp Thr Ala Ser Thr Arg Ser Ser Phe Thr Val Gln Asp Leu
            595                 600                 605 aaa cct ttt aca gaa tat gtg ttt agg att cgc tgt atg aag gaa gat      1872
Lys Pro Phe Thr Glu Tyr Val Phe Arg Ile Arg Cys Met Lys Glu Asp
610                 615                 620 ggt aag gga tac tgg agt gac tgg agt gaa gaa gca agt ggg atc acc      1920
Gly Lys Gly Tyr Trp Ser Asp Trp Ser Glu Glu Ala Ser Gly Ile Thr
625                 630                 635                 640 tat gaa gat aga cca tct aaa gca cca agt ttc tgg tat aaa ata gat      1968
Tyr Glu Asp Arg Pro Ser Lys Ala Pro Ser Phe Trp Tyr Lys Ile Asp
                    645                 650                 655 cca tcc cat act caa ggc tac aga act gta caa ctc gtg tgg aag aca      2016
Pro Ser His Thr Gln Gly Tyr Arg Thr Val Gln Leu Val Trp Lys Thr
                660                 665                 670 ttg cct cct ttt gaa gcc aat gga aaa atc ttg gat tat gaa gtg act      2064
Leu Pro Pro Phe Glu Ala Asn Gly Lys Ile Leu Asp Tyr Glu Val Thr
            675                 680                 685 ctc aca aga tgg aaa tca cat tta caa aat tac aca gtt aat gcc aca      2112
Leu Thr Arg Trp Lys Ser His Leu Gln Asn Tyr Thr Val Asn Ala Thr
        690                 695                 700 aaa ctg aca gta aat ctc aca aat gat cgc tat cta gca acc cta aca      2160
Lys Leu Thr Val Asn Leu Thr Asn Asp Arg Tyr Leu Ala Thr Leu Thr
705                 710                 715                 720 gta aga aat ctt gtt ggc aaa tca gat gca gct gtt tta act atc cct      2208
Val Arg Asn Leu Val Gly Lys Ser Asp Ala Ala Val Leu Thr Ile Pro
                    725                 730                 735 gcc tgt gac ttt caa gct act cac cct gta atg gat ctt aaa gca ttc      2256
Ala Cys Asp Phe Gln Ala Thr His Pro Val Met Asp Leu Lys Ala Phe
                740                 745                 750
```

```
ccc aaa gat aac atg ctt tgg gtg gaa tgg act act cca agg gaa tct      2304
Pro Lys Asp Asn Met Leu Trp Val Glu Trp Thr Thr Pro Arg Glu Ser
        755                 760                 765 gta aag aaa tat ata ctt gag tgg tgt gtg tta tca gat aaa gca ccc      2352
Val Lys Lys Tyr Ile Leu Glu Trp Cys Val Leu Ser Asp Lys Ala Pro
    770                 775                 780 tgt atc aca gac tgg caa caa gaa gat ggt acc gtg cat cgc acc tat      2400
Cys Ile Thr Asp Trp Gln Gln Glu Asp Gly Thr Val His Arg Thr Tyr
785                 790                 795                 800 tta aga ggg aac tta gca gag agc aaa tgc tat ttg ata aca gtt act      2448
Leu Arg Gly Asn Leu Ala Glu Ser Lys Cys Tyr Leu Ile Thr Val Thr
                805                 810                 815 cca gta tat gct gat gga cca gga agc cct gaa tcc ata aag gca tac      2496
Pro Val Tyr Ala Asp Gly Pro Gly Ser Pro Glu Ser Ile Lys Ala Tyr
            820                 825                 830 ctt aaa caa gct cca cct tcc aaa gga cct act gtt cgg aca aaa aaa      2544
Leu Lys Gln Ala Pro Pro Ser Lys Gly Pro Thr Val Arg Thr Lys Lys
        835                 840                 845 gta ggg aaa aac gaa gct gtc tta gag tgg gac caa ctt cct gtt gat      2592
Val Gly Lys Asn Glu Ala Val Leu Glu Trp Asp Gln Leu Pro Val Asp
850                 855                 860 gtt cag aat gga ttt atc aga aat tat act ata ttt tat aga acc atc      2640
Val Gln Asn Gly Phe Ile Arg Asn Tyr Thr Ile Phe Tyr Arg Thr Ile
865                 870                 875                 880 att gga aat gaa act gct gtg aat gtg gat tct tcc cac aca gaa tat      2688
Ile Gly Asn Glu Thr Ala Val Asn Val Asp Ser Ser His Thr Glu Tyr
                885                 890                 895 aca ttg tcc tct ttg act agt gac aca ttg tac atg gta cga atg gca      2736
Thr Leu Ser Ser Leu Thr Ser Asp Thr Leu Tyr Met Val Arg Met Ala
            900                 905                 910 gca tac aca gat gaa ggt ggg aag gat ggt cca gaa ttc act ttt act      2784
Ala Tyr Thr Asp Glu Gly Gly Lys Asp Gly Pro Glu Phe Thr Phe Thr
        915                 920                 925 acc cca aag ttt gct caa gga gaa att gaa tcc ggg ggc gac aaa act      2832
Thr Pro Lys Phe Ala Gln Gly Glu Ile Glu Ser Gly Gly Asp Lys Thr
    930                 935                 940 cac aca tgc cca ccg tgc cca gca cct gaa ctc ctg ggg gga ccg tca      2880
His Thr Cys Pro Pro Cys Pro Ala Pro Glu Leu Leu Gly Gly Pro Ser
945                 950                 955                 960 gtc ttc ctc ttc ccc cca aaa ccc aag gac acc ctc atg atc tcc cgg      2928
Val Phe Leu Phe Pro Pro Lys Pro Lys Asp Thr Leu Met Ile Ser Arg
                965                 970                 975 acc cct gag gtc aca tgc gtg gtg gtg gac gtg agc cac gaa gac cct      2976
Thr Pro Glu Val Thr Cys Val Val Val Asp Val Ser His Glu Asp Pro
            980                 985                 990 gag gtc aag ttc aac tgg tac gtg gac ggc gtg gag gtg cat aat gcc      3024
Glu Val Lys Phe Asn Trp Tyr Val Asp Gly Val Glu Val His Asn Ala
        995                 1000                1005 aag aca aag ccg cgg gag gag cag tac aac agc acg tac cgt gtg gtc      3072
Lys Thr Lys Pro Arg Glu Glu Gln Tyr Asn Ser Thr Tyr Arg Val Val
    1010                1015                1020 agc gtc ctc acc gtc ctg cac cag gac tgg ctg aat ggc aag gag tac      3120
Ser Val Leu Thr Val Leu His Gln Asp Trp Leu Asn Gly Lys Glu Tyr
1025                1030                1035                1040 aag tgc aag gtc tcc aac aaa gcc ctc cca gcc ccc atc gag aaa acc      3168
Lys Cys Lys Val Ser Asn Lys Ala Leu Pro Ala Pro Ile Glu Lys Thr
                1045                1050                1055 atc tcc aaa gcc aaa ggg cag ccc cga gaa cca cag gtg tac acc ctg      3216
Ile Ser Lys Ala Lys Gly Gln Pro Arg Glu Pro Gln Val Tyr Thr Leu
            1060                1065                1070
```

```
ccc cca tcc cgg gat gag ctg acc aag aac cag gtc agc ctg acc tgc    3264
Pro Pro Ser Arg Asp Glu Leu Thr Lys Asn Gln Val Ser Leu Thr Cys
        1075                1080                1085 ctg gtc aaa ggc ttc tat ccc agc gac atc gcc gtg gag tgg gag agc    3312
Leu Val Lys Gly Phe Tyr Pro Ser Asp Ile Ala Val Glu Trp Glu Ser
        1090                1095                1100 aat ggg cag ccg gag aac aac tac aag acc acg cct ccc gtg ctg gac    3360
Asn Gly Gln Pro Glu Asn Asn Tyr Lys Thr Thr Pro Pro Val Leu Asp
1105                1110                1115                1120 tcc gac ggc tcc ttc ttc ctc tac agc aag ctc acc gtg gac aag agc    3408
Ser Asp Gly Ser Phe Phe Leu Tyr Ser Lys Leu Thr Val Asp Lys Ser
                1125                1130                1135 agg tgg cag cag ggg aac gtc ttc tca tgc tcc gtg atg cat gag gct    3456
Arg Trp Gln Gln Gly Asn Val Phe Ser Cys Ser Val Met His Glu Ala
        1140                1145                1150 ctg cac aac cac tac acg cag aag agc ctc tcc ctg tct ccg ggt aaa    3504
Leu His Asn His Tyr Thr Gln Lys Ser Leu Ser Leu Ser Pro Gly Lys
        1155                1160                1165 tga                                                                 3507
```

<210> SEQ ID NO 24
<211> LENGTH: 1168
<212> TYPE: PRT
<213> ORGANISM: Homo sapiens

<400> SEQUENCE: 24

```
Met Val Ala Val Gly Cys Ala Leu Leu Ala Ala Leu Leu Ala Ala Pro
 1               5                   10                  15

Gly Ala Ala Leu Ala Pro Arg Arg Cys Pro Ala Gln Glu Val Ala Arg
                20                  25                  30

Gly Val Leu Thr Ser Leu Pro Gly Asp Ser Val Thr Leu Thr Cys Pro
            35                  40                  45

Gly Val Glu Pro Glu Asp Asn Ala Thr Val His Trp Val Leu Arg Lys
        50                  55                  60

Pro Ala Ala Gly Ser His Pro Ser Arg Trp Ala Gly Met Gly Arg Arg
 65                  70                  75                  80

Leu Leu Leu Arg Ser Val Gln Leu His Asp Ser Gly Asn Tyr Ser Cys
                 85                  90                  95

Tyr Arg Ala Gly Arg Pro Ala Gly Thr Val His Leu Leu Val Asp Val
                100                 105                 110

Pro Pro Glu Glu Pro Gln Leu Ser Cys Phe Arg Lys Ser Pro Leu Ser
            115                 120                 125

Asn Val Val Cys Glu Trp Gly Pro Arg Ser Thr Pro Ser Leu Thr Thr
        130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
        195                 200                 205

Gln Gly Cys Gly Ile Leu Gln Pro Asp Pro Pro Ala Asn Ile Thr Val
    210                 215                 220

Thr Ala Val Ala Arg Asn Pro Arg Trp Leu Ser Val Thr Trp Gln Asp
225                 230                 235                 240
```

```
Pro His Ser Trp Asn Ser Ser Phe Tyr Arg Leu Arg Phe Glu Leu Arg
            245                 250                 255

Tyr Arg Ala Glu Arg Ser Lys Thr Phe Thr Thr Trp Met Val Lys Asp
        260                 265                 270

Leu Gln His His Cys Val Ile His Asp Ala Trp Ser Gly Leu Arg His
    275                 280                 285

Val Val Gln Leu Arg Ala Gln Glu Glu Phe Gly Gln Gly Glu Trp Ser
290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Thr Gly Gly Ala Pro
            325                 330                 335

Ser Gly Ala Gln Leu Glu Leu Leu Asp Pro Cys Gly Tyr Ile Ser Pro
        340                 345                 350

Glu Ser Pro Val Val Gln Leu His Ser Asn Phe Thr Ala Val Cys Val
    355                 360                 365

Leu Lys Glu Lys Cys Met Asp Tyr Phe His Val Asn Ala Asn Tyr Ile
    370                 375                 380

Val Trp Lys Thr Asn His Phe Thr Ile Pro Lys Glu Gln Tyr Thr Ile
385                 390                 395                 400

Ile Asn Arg Thr Ala Ser Ser Val Thr Phe Thr Asp Ile Ala Ser Leu
            405                 410                 415

Asn Ile Gln Leu Thr Cys Asn Ile Leu Thr Phe Gly Gln Leu Glu Gln
        420                 425                 430

Asn Val Tyr Gly Ile Thr Ile Ile Ser Gly Leu Pro Pro Glu Lys Pro
    435                 440                 445

Lys Asn Leu Ser Cys Ile Val Asn Glu Gly Lys Lys Met Arg Cys Glu
    450                 455                 460

Trp Asp Gly Gly Arg Glu Thr His Leu Glu Thr Asn Phe Thr Leu Lys
465                 470                 475                 480

Ser Glu Trp Ala Thr His Lys Phe Ala Asp Cys Lys Ala Lys Arg Asp
            485                 490                 495

Thr Pro Thr Ser Cys Thr Val Asp Tyr Ser Thr Val Tyr Phe Val Asn
        500                 505                 510

Ile Glu Val Trp Val Glu Ala Glu Asn Ala Leu Gly Lys Val Thr Ser
    515                 520                 525

Asp His Ile Asn Phe Asp Pro Val Tyr Lys Val Lys Pro Asn Pro Pro
    530                 535                 540

His Asn Leu Ser Val Ile Asn Ser Glu Glu Leu Ser Ser Ile Leu Lys
545                 550                 555                 560

Leu Thr Trp Thr Asn Pro Ser Ile Lys Ser Val Ile Ile Leu Lys Tyr
            565                 570                 575

Asn Ile Gln Tyr Arg Thr Lys Asp Ala Ser Thr Trp Ser Gln Ile Pro
        580                 585                 590

Pro Glu Asp Thr Ala Ser Thr Arg Ser Ser Phe Thr Val Gln Asp Leu
    595                 600                 605

Lys Pro Phe Thr Glu Tyr Val Phe Arg Ile Arg Cys Met Lys Glu Asp
    610                 615                 620

Gly Lys Gly Tyr Trp Ser Asp Trp Ser Glu Ala Ser Gly Ile Thr
625                 630                 635                 640

Tyr Glu Asp Arg Pro Ser Lys Ala Pro Ser Phe Trp Tyr Lys Ile Asp
            645                 650                 655
```

```
Pro Ser His Thr Gln Gly Tyr Arg Thr Val Gln Leu Val Trp Lys Thr
            660                 665                 670
Leu Pro Pro Phe Glu Ala Asn Gly Lys Ile Leu Asp Tyr Glu Val Thr
        675                 680                 685
Leu Thr Arg Trp Lys Ser His Leu Gln Asn Tyr Thr Val Asn Ala Thr
    690                 695                 700
Lys Leu Thr Val Asn Leu Thr Asn Asp Arg Tyr Leu Ala Thr Leu Thr
705                 710                 715                 720
Val Arg Asn Leu Val Gly Lys Ser Asp Ala Ala Val Leu Thr Ile Pro
                725                 730                 735
Ala Cys Asp Phe Gln Ala Thr His Pro Val Met Asp Leu Lys Ala Phe
            740                 745                 750
Pro Lys Asp Asn Met Leu Trp Val Glu Trp Thr Thr Pro Arg Glu Ser
        755                 760                 765
Val Lys Lys Tyr Ile Leu Glu Trp Cys Val Leu Ser Asp Lys Ala Pro
    770                 775                 780
Cys Ile Thr Asp Trp Gln Gln Glu Asp Gly Thr Val His Arg Thr Tyr
785                 790                 795                 800
Leu Arg Gly Asn Leu Ala Glu Ser Lys Cys Tyr Leu Ile Thr Val Thr
                805                 810                 815
Pro Val Tyr Ala Asp Gly Pro Gly Ser Pro Glu Ser Ile Lys Ala Tyr
            820                 825                 830
Leu Lys Gln Ala Pro Pro Ser Lys Gly Pro Thr Val Arg Thr Lys Lys
        835                 840                 845
Val Gly Lys Asn Glu Ala Val Leu Glu Trp Asp Gln Leu Pro Val Asp
    850                 855                 860
Val Gln Asn Gly Phe Ile Arg Asn Tyr Thr Ile Phe Tyr Arg Thr Ile
865                 870                 875                 880
Ile Gly Asn Glu Thr Ala Val Asn Val Asp Ser Ser His Thr Glu Tyr
                885                 890                 895
Thr Leu Ser Ser Leu Thr Ser Asp Thr Leu Tyr Met Val Arg Met Ala
            900                 905                 910
Ala Tyr Thr Asp Glu Gly Gly Lys Asp Gly Pro Glu Phe Thr Phe Thr
        915                 920                 925
Thr Pro Lys Phe Ala Gln Gly Glu Ile Glu Ser Gly Gly Asp Lys Thr
    930                 935                 940
His Thr Cys Pro Pro Cys Pro Ala Pro Glu Leu Leu Gly Gly Pro Ser
945                 950                 955                 960
Val Phe Leu Phe Pro Pro Lys Pro Lys Asp Thr Leu Met Ile Ser Arg
                965                 970                 975
Thr Pro Glu Val Thr Cys Val Val Val Asp Val Ser His Glu Asp Pro
            980                 985                 990
Glu Val Lys Phe Asn Trp Tyr Val Asp Gly Val Glu Val His Asn Ala
        995                 1000                1005
Lys Thr Lys Pro Arg Glu Glu Gln Tyr Asn Ser Thr Tyr Arg Val Val
    1010                1015                1020
Ser Val Leu Thr Val Leu His Gln Asp Trp Leu Asn Gly Lys Glu Tyr
1025                1030                1035                1040
Lys Cys Lys Val Ser Asn Lys Ala Leu Pro Ala Pro Ile Glu Lys Thr
                1045                1050                1055
Ile Ser Lys Ala Lys Gly Gln Pro Arg Glu Pro Gln Val Tyr Thr Leu
            1060                1065                1070
Pro Pro Ser Arg Asp Glu Leu Thr Lys Asn Gln Val Ser Leu Thr Cys
```

```
                    1075                1080                1085
Leu Val Lys Gly Phe Tyr Pro Ser Asp Ile Ala Val Glu Trp Glu Ser
    1090                1095                1100

Asn Gly Gln Pro Glu Asn Asn Tyr Lys Thr Thr Pro Val Leu Asp
1105                1110                1115                1120

Ser Asp Gly Ser Phe Phe Leu Tyr Ser Lys Leu Thr Val Asp Lys Ser
            1125                1130                1135

Arg Trp Gln Gln Gly Asn Val Phe Ser Cys Ser Val Met His Glu Ala
                1140                1145                1150

Leu His Asn His Tyr Thr Gln Lys Ser Leu Ser Leu Ser Pro Gly Lys
            1155                1160                1165

<210> SEQ ID NO 25
<211> LENGTH: 3477
<212> TYPE: DNA
<213> ORGANISM: Homo sapiens
<220> FEATURE:
<221> NAME/KEY: CDS
<222> LOCATION: (1)...(3474)

<400> SEQUENCE: 25 atg gtg gcc gtc ggc tgc gcg ctg ctg gct gcc ctg ctg gcc gcg ccg       48
Met Val Ala Val Gly Cys Ala Leu Leu Ala Ala Leu Leu Ala Ala Pro
1               5                   10                  15 gga gcg gcg ctg gcc cca agg cgc tgc cct gcg cag gag gtg gca aga       96
Gly Ala Ala Leu Ala Pro Arg Arg Cys Pro Ala Gln Glu Val Ala Arg
                20                  25                  30 ggc gtg ctg acc agt ctg cca gga gac agc gtg act ctg acc tgc ccg      144
Gly Val Leu Thr Ser Leu Pro Gly Asp Ser Val Thr Leu Thr Cys Pro
            35                  40                  45 ggg gta gag ccg gaa gac aat gcc act gtt cac tgg gtg ctc agg aag      192
Gly Val Glu Pro Glu Asp Asn Ala Thr Val His Trp Val Leu Arg Lys
        50                  55                  60 ccg gct gca ggc tcc cac ccc agc aga tgg gct ggc atg gga agg agg      240
Pro Ala Ala Gly Ser His Pro Ser Arg Trp Ala Gly Met Gly Arg Arg
65                  70                  75                  80 ctg ctg ctg agg tcg gtg cag ctc cac gac tct gga aac tat tca tgc      288
Leu Leu Leu Arg Ser Val Gln Leu His Asp Ser Gly Asn Tyr Ser Cys
                85                  90                  95 tac cgg gcc ggc cgc cca gct ggg act gtg cac ttg ctg gtg gat gtt      336
Tyr Arg Ala Gly Arg Pro Ala Gly Thr Val His Leu Leu Val Asp Val
                100                 105                 110 ccc ccc gag gag ccc cag ctc tcc tgc ttc cgg aag agc ccc ctc agc      384
Pro Pro Glu Glu Pro Gln Leu Ser Cys Phe Arg Lys Ser Pro Leu Ser
            115                 120                 125 aat gtt gtt tgt gag tgg ggt cct cgg agc acc cca tcc ctg acg aca      432
Asn Val Val Cys Glu Trp Gly Pro Arg Ser Thr Pro Ser Leu Thr Thr
        130                 135                 140 aag gct gtg ctc ttg gtg agg aag ttt cag aac agt ccg gcc gaa gac      480
Lys Ala Val Leu Leu Val Arg Lys Phe Gln Asn Ser Pro Ala Glu Asp
145                 150                 155                 160 ttc cag gag ccg tgc cag tat tcc cag gag tcc cag aag ttc tcc tgc      528
Phe Gln Glu Pro Cys Gln Tyr Ser Gln Glu Ser Gln Lys Phe Ser Cys
                165                 170                 175 cag tta gca gtc ccg gag gga gac agc tct ttc tac ata gtg tcc atg      576
Gln Leu Ala Val Pro Glu Gly Asp Ser Ser Phe Tyr Ile Val Ser Met
                180                 185                 190 tgc gtc gcc agt agt gtc ggg agc aag ttc agc aaa act caa acc ttt      624
Cys Val Ala Ser Ser Val Gly Ser Lys Phe Ser Lys Thr Gln Thr Phe
            195                 200                 205
```

-continued

| | |
|---|---|
| cag ggt tgt gga atc ttg cag cct gat ccg cct gcc aac atc aca gtc<br>Gln Gly Cys Gly Ile Leu Gln Pro Asp Pro Pro Ala Asn Ile Thr Val<br>210                215                    220 | 672 |
| act gcc gtg gcc aga aac ccc cgc tgg ctc agt gtc acc tgg caa gac<br>Thr Ala Val Ala Arg Asn Pro Arg Trp Leu Ser Val Thr Trp Gln Asp<br>225                230                  235                  240 | 720 |
| ccc cac tcc tgg aac tca tct ttc tac aga cta cgg ttt gag ctc aga<br>Pro His Ser Trp Asn Ser Ser Phe Tyr Arg Leu Arg Phe Glu Leu Arg<br>                  245                  250                  255 | 768 |
| tat cgg gct gaa cgg tca aag aca ttc aca aca tgg atg gtc aag gac<br>Tyr Arg Ala Glu Arg Ser Lys Thr Phe Thr Thr Trp Met Val Lys Asp<br>260                265                  270 | 816 |
| ctc cag cat cac tgt gtc atc cac gac gcc tgg agc ggc ctg agg cac<br>Leu Gln His His Cys Val Ile His Asp Ala Trp Ser Gly Leu Arg His<br>        275                  280                  285 | 864 |
| gtg gtg cag ctt cgt gcc cag gag gag ttc ggg caa ggc gag tgg agc<br>Val Val Gln Leu Arg Ala Gln Glu Glu Phe Gly Gln Gly Glu Trp Ser<br>290                295                  300 | 912 |
| gag tgg agc ccg gag gcc atg ggc acg cct tgg aca gaa tcg cga tcg<br>Glu Trp Ser Pro Glu Ala Met Gly Thr Pro Trp Thr Glu Ser Arg Ser<br>305                310                  315                  320 | 960 |
| cct cca gct gag aac gag gtg tcc acc ccc atg gaa ctt cta gac cca<br>Pro Pro Ala Glu Asn Glu Val Ser Thr Pro Met Glu Leu Leu Asp Pro<br>                  325                  330                  335 | 1008 |
| tgt ggt tat atc agt cct gaa tct cca gtt gta caa ctt cat tct aat<br>Cys Gly Tyr Ile Ser Pro Glu Ser Pro Val Val Gln Leu His Ser Asn<br>                340                  345                  350 | 1056 |
| ttc act gca gtt tgt gtg cta aag gaa aaa tgt atg gat tat ttt cat<br>Phe Thr Ala Val Cys Val Leu Lys Glu Lys Cys Met Asp Tyr Phe His<br>355                360                  365 | 1104 |
| gta aat gct aat tac att gtc tgg aaa aca aac cat ttt act att cct<br>Val Asn Ala Asn Tyr Ile Val Trp Lys Thr Asn His Phe Thr Ile Pro<br>370                375                  380 | 1152 |
| aag gag caa tat act atc ata aac aga aca gca tcc agt gtc acc ttt<br>Lys Glu Gln Tyr Thr Ile Ile Asn Arg Thr Ala Ser Ser Val Thr Phe<br>385                390                  395                  400 | 1200 |
| aca gat ata gct tca tta aat att cag ctc act tgc aac att ctt aca<br>Thr Asp Ile Ala Ser Leu Asn Ile Gln Leu Thr Cys Asn Ile Leu Thr<br>                  405                  410                  415 | 1248 |
| ttc gga cag ctt gaa cag aat gtt tat gga atc aca ata att tca ggc<br>Phe Gly Gln Leu Glu Gln Asn Val Tyr Gly Ile Thr Ile Ile Ser Gly<br>                  420                  425                  430 | 1296 |
| ttg cct cca gaa aaa cct aaa aat ttg agt tgc att gtg aac gag ggg<br>Leu Pro Pro Glu Lys Pro Lys Asn Leu Ser Cys Ile Val Asn Glu Gly<br>435                440                  445 | 1344 |
| aag aaa atg agg tgt gag tgg gat ggt gga agg gaa aca cac ttg gag<br>Lys Lys Met Arg Cys Glu Trp Asp Gly Gly Arg Glu Thr His Leu Glu<br>450                455                  460 | 1392 |
| aca aac ttc act tta aaa tct gaa tgg gca aca cac aag ttt gct gat<br>Thr Asn Phe Thr Leu Lys Ser Glu Trp Ala Thr His Lys Phe Ala Asp<br>465                470                  475                  480 | 1440 |
| tgc aaa gca aaa cgt gac acc ccc acc tca tgc act gtt gat tat tct<br>Cys Lys Ala Lys Arg Asp Thr Pro Thr Ser Cys Thr Val Asp Tyr Ser<br>                  485                  490                  495 | 1488 |
| act gtg tat ttt gtc aac att gaa gtc tgg gta gaa gca gag aat gcc<br>Thr Val Tyr Phe Val Asn Ile Glu Val Trp Val Glu Ala Glu Asn Ala<br>                  500                  505                  510 | 1536 |
| ctt ggg aag gtt aca tca gat cat atc aat ttt gat cct gta tat aaa<br>Leu Gly Lys Val Thr Ser Asp His Ile Asn Phe Asp Pro Val Tyr Lys | 1584 |

```
              515                 520                 525
gtg aag ccc aat ccg cca cat aat tta tca gtg atc aac tca gag gaa    1632
Val Lys Pro Asn Pro Pro His Asn Leu Ser Val Ile Asn Ser Glu Glu
    530                 535                 540 ctg tct agt atc tta aaa ttg aca tgg acc aac cca agt att aag agt    1680
Leu Ser Ser Ile Leu Lys Leu Thr Trp Thr Asn Pro Ser Ile Lys Ser
545                 550                 555                 560 gtt ata ata cta aaa tat aac att caa tat agg acc aaa gat gcc tca    1728
Val Ile Ile Leu Lys Tyr Asn Ile Gln Tyr Arg Thr Lys Asp Ala Ser
                565                 570                 575 act tgg agc cag att cct cct gaa gac aca gca tcc acc cga tct tca    1776
Thr Trp Ser Gln Ile Pro Pro Glu Asp Thr Ala Ser Thr Arg Ser Ser
            580                 585                 590 ttc act gtc caa gac ctt aaa cct ttt aca gaa tat gtg ttt agg att    1824
Phe Thr Val Gln Asp Leu Lys Pro Phe Thr Glu Tyr Val Phe Arg Ile
        595                 600                 605 cgc tgt atg aag gaa gat ggt aag gga tac tgg agt gac tgg agt gaa    1872
Arg Cys Met Lys Glu Asp Gly Lys Gly Tyr Trp Ser Asp Trp Ser Glu
    610                 615                 620 gaa gca agt ggg atc acc tat gaa gat aga cca tct aaa gca cca agt    1920
Glu Ala Ser Gly Ile Thr Tyr Glu Asp Arg Pro Ser Lys Ala Pro Ser
625                 630                 635                 640 ttc tgg tat aaa ata gat cca tcc cat act caa ggc tac aga act gta    1968
Phe Trp Tyr Lys Ile Asp Pro Ser His Thr Gln Gly Tyr Arg Thr Val
                645                 650                 655 caa ctc gtg tgg aag aca ttg cct cct ttt gaa gcc aat gga aaa atc    2016
Gln Leu Val Trp Lys Thr Leu Pro Pro Phe Glu Ala Asn Gly Lys Ile
            660                 665                 670 ttg gat tat gaa gtg act ctc aca aga tgg aaa tca cat tta caa aat    2064
Leu Asp Tyr Glu Val Thr Leu Thr Arg Trp Lys Ser His Leu Gln Asn
        675                 680                 685 tac aca gtt aat gcc aca aaa ctg aca gta aat ctc aca aat gat cgc    2112
Tyr Thr Val Asn Ala Thr Lys Leu Thr Val Asn Leu Thr Asn Asp Arg
    690                 695                 700 tat cta gca acc cta aca gta aga aat ctt gtt ggc aaa tca gat gca    2160
Tyr Leu Ala Thr Leu Thr Val Arg Asn Leu Val Gly Lys Ser Asp Ala
705                 710                 715                 720 gct gtt tta act atc cct gcc tgt gac ttt caa gct act cac cct gta    2208
Ala Val Leu Thr Ile Pro Ala Cys Asp Phe Gln Ala Thr His Pro Val
                725                 730                 735 atg gat ctt aaa gca ttc ccc aaa gat aac atg ctt tgg gtg gaa tgg    2256
Met Asp Leu Lys Ala Phe Pro Lys Asp Asn Met Leu Trp Val Glu Trp
            740                 745                 750 act act cca agg gaa tct gta aag aaa tat ata ctt gag tgg tgt gtg    2304
Thr Thr Pro Arg Glu Ser Val Lys Lys Tyr Ile Leu Glu Trp Cys Val
        755                 760                 765 tta tca gat aaa gca ccc tgt atc aca gac tgg caa caa gaa gat ggt    2352
Leu Ser Asp Lys Ala Pro Cys Ile Thr Asp Trp Gln Gln Glu Asp Gly
    770                 775                 780 acc gtg cat cgc acc tat tta aga ggg aac tta gca gag agc aaa tgc    2400
Thr Val His Arg Thr Tyr Leu Arg Gly Asn Leu Ala Glu Ser Lys Cys
785                 790                 795                 800 tat ttg ata aca gtt act cca gta tat gct gat gga cca gga agc cct    2448
Tyr Leu Ile Thr Val Thr Pro Val Tyr Ala Asp Gly Pro Gly Ser Pro
                805                 810                 815 gaa tcc ata aag gca tac ctt aaa caa gct cca cct tcc aaa gga cct    2496
Glu Ser Ile Lys Ala Tyr Leu Lys Gln Ala Pro Pro Ser Lys Gly Pro
            820                 825                 830 act gtt cgg aca aaa aaa gta ggg aaa aac gaa gct gtc tta gag tgg    2544
```

-continued

| | | | | | | | | | | | | | | |
|---|---|---|---|---|---|---|---|---|---|---|---|---|---|---|
|Thr|Val|Arg|Thr|Lys|Lys|Val|Gly|Lys|Asn|Glu|Ala|Val|Leu|Glu|Trp|
| | |835| | | |840| | | |845| | | | |

```
gac caa ctt cct gtt gat gtt cag aat gga ttt atc aga aat tat act    2592
Asp Gln Leu Pro Val Asp Val Gln Asn Gly Phe Ile Arg Asn Tyr Thr
    850                 855                 860 ata ttt tat aga acc atc att gga aat gaa act gct gtg aat gtg gat    2640
Ile Phe Tyr Arg Thr Ile Ile Gly Asn Glu Thr Ala Val Asn Val Asp
865                 870                 875                 880 tct tcc cac aca gaa tat aca ttg tcc tct ttg act agt gac aca ttg    2688
Ser Ser His Thr Glu Tyr Thr Leu Ser Ser Leu Thr Ser Asp Thr Leu
                885                 890                 895 tac atg gta cga atg gca gca tac aca gat gaa ggt ggg aag gat ggt    2736
Tyr Met Val Arg Met Ala Ala Tyr Thr Asp Glu Gly Gly Lys Asp Gly
            900                 905                 910 cca gaa ttc act ttt act acc cca aag ttt gct caa gga gaa att gaa    2784
Pro Glu Phe Thr Phe Thr Thr Pro Lys Phe Ala Gln Gly Glu Ile Glu
        915                 920                 925 tcc ggg ggc gac aaa act cac aca tgc cca ccg tgc cca gca cct gaa    2832
Ser Gly Gly Asp Lys Thr His Thr Cys Pro Pro Cys Pro Ala Pro Glu
    930                 935                 940 ctc ctg ggg gga ccg tca gtc ttc ctc ttc ccc cca aaa ccc aag gac    2880
Leu Leu Gly Gly Pro Ser Val Phe Leu Phe Pro Pro Lys Pro Lys Asp
945                 950                 955                 960 acc ctc atg atc tcc cgg acc cct gag gtc aca tgc gtg gtg gtg gac    2928
Thr Leu Met Ile Ser Arg Thr Pro Glu Val Thr Cys Val Val Val Asp
                965                 970                 975 gtg agc cac gaa gac cct gag gtc aag ttc aac tgg tac gtg gac ggc    2976
Val Ser His Glu Asp Pro Glu Val Lys Phe Asn Trp Tyr Val Asp Gly
            980                 985                 990 gtg gag gtg cat aat gcc aag aca aag ccg cgg gag gag cag tac aac    3024
Val Glu Val His Asn Ala Lys Thr Lys Pro Arg Glu Glu Gln Tyr Asn
        995                 1000                1005 agc acg tac cgt gtg gtc agc gtc ctc acc gtc ctg cac cag gac tgg    3072
Ser Thr Tyr Arg Val Val Ser Val Leu Thr Val Leu His Gln Asp Trp
    1010                1015                1020 ctg aat ggc aag gag tac aag tgc aag gtc tcc aac aaa gcc ctc cca    3120
Leu Asn Gly Lys Glu Tyr Lys Cys Lys Val Ser Asn Lys Ala Leu Pro
1025                1030                1035                1040 gcc ccc atc gag aaa acc atc tcc aaa gcc aaa ggg cag ccc cga gaa    3168
Ala Pro Ile Glu Lys Thr Ile Ser Lys Ala Lys Gly Gln Pro Arg Glu
                1045                1050                1055 cca cag gtg tac acc ctg ccc cca tcc cgg gat gag ctg acc aag aac    3216
Pro Gln Val Tyr Thr Leu Pro Pro Ser Arg Asp Glu Leu Thr Lys Asn
            1060                1065                1070 cag gtc agc ctg acc tgc ctg gtc aaa ggc ttc tat ccc agc gac atc    3264
Gln Val Ser Leu Thr Cys Leu Val Lys Gly Phe Tyr Pro Ser Asp Ile
        1075                1080                1085 gcc gtg gag tgg gag agc aat ggg cag ccg gag aac aac tac aag acc    3312
Ala Val Glu Trp Glu Ser Asn Gly Gln Pro Glu Asn Asn Tyr Lys Thr
    1090                1095                1100 acg cct ccc gtg ctg gac tcc gac ggc tcc ttc ttc ctc tac agc aag    3360
Thr Pro Pro Val Leu Asp Ser Asp Gly Ser Phe Phe Leu Tyr Ser Lys
1105                1110                1115                1120 ctc acc gtg gac aag agc agg tgg cag cag ggg aac gtc ttc tca tgc    3408
Leu Thr Val Asp Lys Ser Arg Trp Gln Gln Gly Asn Val Phe Ser Cys
                1125                1130                1135 tcc gtg atg cat gag gct ctg cac aac cac tac acg cag aag agc ctc    3456
Ser Val Met His Glu Ala Leu His Asn His Tyr Thr Gln Lys Ser Leu
            1140                1145                1150
```

```
tcc ctg tct ccg ggt aaa tga                                              3477
Ser Leu Ser Pro Gly Lys
        1155
```

<210> SEQ ID NO 26
<211> LENGTH: 1158
<212> TYPE: PRT
<213> ORGANISM: Homo sapiens

<400> SEQUENCE: 26

```
Met Val Ala Val Gly Cys Ala Leu Leu Ala Leu Leu Ala Ala Pro
 1               5                  10                  15

Gly Ala Ala Leu Ala Pro Arg Arg Cys Pro Ala Gln Glu Val Ala Arg
                20                  25                  30

Gly Val Leu Thr Ser Leu Pro Gly Asp Ser Val Thr Leu Thr Cys Pro
                35                  40                  45

Gly Val Glu Pro Glu Asp Asn Ala Thr Val His Trp Val Leu Arg Lys
        50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
            100                 105                 110

Pro Pro Glu Glu Pro Gln Leu Ser Cys Phe Arg Lys Ser Pro Leu Ser
            115                 120                 125

Asn Val Val Cys Glu Trp Gly Pro Arg Ser Thr Pro Ser Leu Thr Thr
        130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
            195                 200                 205

Gln Gly Cys Gly Ile Leu Gln Pro Asp Pro Pro Ala Asn Ile Thr Val
        210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
            275                 280                 285

Val Val Gln Leu Arg Ala Gln Glu Glu Phe Gly Gln Gly Glu Trp Ser
        290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Glu Leu Leu Asp Pro
                325                 330                 335

Cys Gly Tyr Ile Ser Pro Glu Ser Pro Val Val Gln Leu His Ser Asn
            340                 345                 350

Phe Thr Ala Val Cys Val Leu Lys Glu Lys Cys Met Asp Tyr Phe His
```

```
                355                 360                 365
Val Asn Ala Asn Tyr Ile Val Trp Lys Thr Asn His Phe Thr Ile Pro
370                 375                 380

Lys Glu Gln Tyr Thr Ile Ile Asn Arg Thr Ala Ser Ser Val Thr Phe
385                 390                 395                 400

Thr Asp Ile Ala Ser Leu Asn Ile Gln Leu Thr Cys Asn Ile Leu Thr
                405                 410                 415

Phe Gly Gln Leu Glu Gln Asn Val Tyr Gly Ile Thr Ile Ile Ser Gly
                420                 425                 430

Leu Pro Pro Glu Lys Pro Lys Asn Leu Ser Cys Ile Val Asn Glu Gly
                435                 440                 445

Lys Lys Met Arg Cys Glu Trp Asp Gly Gly Arg Glu Thr His Leu Glu
450                 455                 460

Thr Asn Phe Thr Leu Lys Ser Glu Trp Ala Thr His Lys Phe Ala Asp
465                 470                 475                 480

Cys Lys Ala Lys Arg Asp Thr Pro Thr Ser Cys Thr Val Asp Tyr Ser
                485                 490                 495

Thr Val Tyr Phe Val Asn Ile Glu Val Trp Val Glu Ala Glu Asn Ala
                500                 505                 510

Leu Gly Lys Val Thr Ser Asp His Ile Asn Phe Asp Pro Val Tyr Lys
                515                 520                 525

Val Lys Pro Asn Pro Pro His Asn Leu Ser Val Ile Asn Ser Glu Glu
                530                 535                 540

Leu Ser Ser Ile Leu Lys Leu Thr Trp Thr Asn Pro Ser Ile Lys Ser
545                 550                 555                 560

Val Ile Ile Leu Lys Tyr Asn Ile Gln Tyr Arg Thr Lys Asp Ala Ser
                565                 570                 575

Thr Trp Ser Gln Ile Pro Pro Glu Asp Thr Ala Ser Thr Arg Ser Ser
                580                 585                 590

Phe Thr Val Gln Asp Leu Lys Pro Phe Thr Glu Tyr Val Phe Arg Ile
                595                 600                 605

Arg Cys Met Lys Glu Asp Gly Lys Gly Tyr Trp Ser Asp Trp Ser Glu
610                 615                 620

Glu Ala Ser Gly Ile Thr Tyr Glu Asp Arg Pro Ser Lys Ala Pro Ser
625                 630                 635                 640

Phe Trp Tyr Lys Ile Asp Pro Ser His Thr Gln Gly Tyr Arg Thr Val
                645                 650                 655

Gln Leu Val Trp Lys Thr Leu Pro Pro Phe Glu Ala Asn Gly Lys Ile
                660                 665                 670

Leu Asp Tyr Glu Val Thr Leu Thr Arg Trp Lys Ser His Leu Gln Asn
                675                 680                 685

Tyr Thr Val Asn Ala Thr Lys Leu Thr Val Asn Leu Thr Asn Asp Arg
690                 695                 700

Tyr Leu Ala Thr Leu Thr Val Arg Asn Leu Val Gly Lys Ser Asp Ala
705                 710                 715                 720

Ala Val Leu Thr Ile Pro Ala Cys Asp Phe Gln Ala Thr His Pro Val
                725                 730                 735

Met Asp Leu Lys Ala Phe Pro Lys Asp Asn Met Leu Trp Val Glu Trp
                740                 745                 750

Thr Thr Pro Arg Glu Ser Val Lys Lys Tyr Ile Leu Glu Trp Cys Val
                755                 760                 765

Leu Ser Asp Lys Ala Pro Cys Ile Thr Asp Trp Gln Gln Glu Asp Gly
770                 775                 780
```

```
Thr Val His Arg Thr Tyr Leu Arg Gly Asn Leu Ala Glu Ser Lys Cys
785                 790                 795                 800

Tyr Leu Ile Thr Val Thr Pro Val Tyr Ala Asp Gly Pro Gly Ser Pro
            805                 810                 815

Glu Ser Ile Lys Ala Tyr Leu Lys Gln Ala Pro Ser Lys Gly Pro
        820                 825                 830

Thr Val Arg Thr Lys Lys Val Gly Lys Asn Glu Ala Val Leu Glu Trp
        835                 840                 845

Asp Gln Leu Pro Val Asp Val Gln Asn Gly Phe Ile Arg Asn Tyr Thr
        850                 855                 860

Ile Phe Tyr Arg Thr Ile Ile Gly Asn Glu Thr Ala Val Asn Val Asp
865                 870                 875                 880

Ser Ser His Thr Glu Tyr Thr Leu Ser Ser Leu Thr Ser Asp Thr Leu
            885                 890                 895

Tyr Met Val Arg Met Ala Ala Tyr Thr Asp Glu Gly Gly Lys Asp Gly
            900                 905                 910

Pro Glu Phe Thr Phe Thr Thr Pro Lys Phe Ala Gln Gly Glu Ile Glu
        915                 920                 925

Ser Gly Gly Asp Lys Thr His Thr Cys Pro Pro Cys Pro Ala Pro Glu
930                 935                 940

Leu Leu Gly Gly Pro Ser Val Phe Leu Phe Pro Pro Lys Pro Lys Asp
945                 950                 955                 960

Thr Leu Met Ile Ser Arg Thr Pro Glu Val Thr Cys Val Val Val Asp
            965                 970                 975

Val Ser His Glu Asp Pro Glu Val Lys Phe Asn Trp Tyr Val Asp Gly
            980                 985                 990

Val Glu Val His Asn Ala Lys Thr Lys Pro Arg Glu Glu Gln Tyr Asn
        995                 1000                1005

Ser Thr Tyr Arg Val Val Ser Val Leu Thr Val Leu His Gln Asp Trp
        1010                1015                1020

Leu Asn Gly Lys Glu Tyr Lys Cys Lys Val Ser Asn Lys Ala Leu Pro
1025                1030                1035                1040

Ala Pro Ile Glu Lys Thr Ile Ser Lys Ala Lys Gly Gln Pro Arg Glu
            1045                1050                1055

Pro Gln Val Tyr Thr Leu Pro Pro Ser Arg Asp Glu Leu Thr Lys Asn
        1060                1065                1070

Gln Val Ser Leu Thr Cys Leu Val Lys Gly Phe Tyr Pro Ser Asp Ile
        1075                1080                1085

Ala Val Glu Trp Glu Ser Asn Gly Gln Pro Glu Asn Asn Tyr Lys Thr
        1090                1095                1100

Thr Pro Pro Val Leu Asp Ser Asp Gly Ser Phe Phe Leu Tyr Ser Lys
1105                1110                1115                1120

Leu Thr Val Asp Lys Ser Arg Trp Gln Gln Gly Asn Val Phe Ser Cys
            1125                1130                1135

Ser Val Met His Glu Ala Leu His Asn His Tyr Thr Gln Lys Ser Leu
            1140                1145                1150

Ser Leu Ser Pro Gly Lys
        1155

<210> SEQ ID NO 27
<211> LENGTH: 2733
<212> TYPE: DNA
<213> ORGANISM: Homo sapiens
<220> FEATURE:
```

```
<221> NAME/KEY: CDS
<222> LOCATION: (1)...(2730)

<400> SEQUENCE: 27
```

| | | | | | | | | | | | | | | | | |
|---|---|---|---|---|---|---|---|---|---|---|---|---|---|---|---|---|
| atg | gtg | ctt | ctg | tgg | tgt | gta | gtg | agt | ctc | tac | ttt | tat | gga | atc | ctg | 48 |
| Met | Val | Leu | Leu | Trp | Cys | Val | Val | Ser | Leu | Tyr | Phe | Tyr | Gly | Ile | Leu | |
| 1 | | | | 5 | | | | | 10 | | | | | 15 | | |
| caa | agt | gat | gcc | tca | gaa | cgc | tgc | gat | gac | tgg | gga | cta | gac | acc | atg | 96 |
| Gln | Ser | Asp | Ala | Ser | Glu | Arg | Cys | Asp | Asp | Trp | Gly | Leu | Asp | Thr | Met | |
| | | | 20 | | | | | 25 | | | | | 30 | | | |
| agg | caa | atc | caa | gtg | ttt | gaa | gat | gag | cca | gct | cgc | atc | aag | tgc | cca | 144 |
| Arg | Gln | Ile | Gln | Val | Phe | Glu | Asp | Glu | Pro | Ala | Arg | Ile | Lys | Cys | Pro | |
| | | 35 | | | | | 40 | | | | | 45 | | | | |
| ctc | ttt | gaa | cac | ttc | ttg | aaa | ttc | aac | tac | agc | aca | gcc | cat | tca | gct | 192 |
| Leu | Phe | Glu | His | Phe | Leu | Lys | Phe | Asn | Tyr | Ser | Thr | Ala | His | Ser | Ala | |
| 50 | | | | | 55 | | | | | 60 | | | | | | |
| ggc | ctt | act | ctg | atc | tgg | tat | tgg | act | agg | cag | gac | cgg | gac | ctt | gag | 240 |
| Gly | Leu | Thr | Leu | Ile | Trp | Tyr | Trp | Thr | Arg | Gln | Asp | Arg | Asp | Leu | Glu | |
| 65 | | | | 70 | | | | | 75 | | | | | 80 | | |
| gag | cca | att | aac | ttc | cgc | ctc | ccc | gag | aac | cgc | att | agt | aag | gag | aaa | 288 |
| Glu | Pro | Ile | Asn | Phe | Arg | Leu | Pro | Glu | Asn | Arg | Ile | Ser | Lys | Glu | Lys | |
| | | | | 85 | | | | | 90 | | | | | 95 | | |
| gat | gtg | ctg | tgg | ttc | cgg | ccc | act | ctc | ctc | aat | gac | act | ggc | aac | tat | 336 |
| Asp | Val | Leu | Trp | Phe | Arg | Pro | Thr | Leu | Leu | Asn | Asp | Thr | Gly | Asn | Tyr | |
| | | | 100 | | | | | 105 | | | | | 110 | | | |
| acc | tgc | atg | tta | agg | aac | act | aca | tat | tgc | agc | aaa | gtt | gca | ttt | ccc | 384 |
| Thr | Cys | Met | Leu | Arg | Asn | Thr | Thr | Tyr | Cys | Ser | Lys | Val | Ala | Phe | Pro | |
| | | 115 | | | | | 120 | | | | | 125 | | | | |
| ttg | gaa | gtt | gtt | caa | aaa | gac | agc | tgt | ttc | aat | tcc | ccc | atg | aaa | ctc | 432 |
| Leu | Glu | Val | Val | Gln | Lys | Asp | Ser | Cys | Phe | Asn | Ser | Pro | Met | Lys | Leu | |
| 130 | | | | | 135 | | | | | 140 | | | | | | |
| cca | gtg | cat | aaa | ctg | tat | ata | gaa | tat | ggc | att | cag | agg | atc | act | tgt | 480 |
| Pro | Val | His | Lys | Leu | Tyr | Ile | Glu | Tyr | Gly | Ile | Gln | Arg | Ile | Thr | Cys | |
| 145 | | | | | 150 | | | | | 155 | | | | | 160 | |
| cca | aat | gta | gat | gga | tat | ttt | cct | tcc | agt | gtc | aaa | ccg | act | atc | act | 528 |
| Pro | Asn | Val | Asp | Gly | Tyr | Phe | Pro | Ser | Ser | Val | Lys | Pro | Thr | Ile | Thr | |
| | | | | 165 | | | | | 170 | | | | | 175 | | |
| tgg | tat | atg | ggc | tgt | tat | aaa | ata | cag | aat | ttt | aat | aat | gta | ata | ccc | 576 |
| Trp | Tyr | Met | Gly | Cys | Tyr | Lys | Ile | Gln | Asn | Phe | Asn | Asn | Val | Ile | Pro | |
| | | | 180 | | | | | 185 | | | | | 190 | | | |
| gaa | ggt | atg | aac | ttg | agt | ttc | ctc | att | gcc | tta | att | tca | aat | aat | gga | 624 |
| Glu | Gly | Met | Asn | Leu | Ser | Phe | Leu | Ile | Ala | Leu | Ile | Ser | Asn | Asn | Gly | |
| | | | | 195 | | | | | 200 | | | | | 205 | | |
| aat | tac | aca | tgt | gtt | gtt | aca | tat | cca | gaa | aat | gga | cgt | acg | ttt | cat | 672 |
| Asn | Tyr | Thr | Cys | Val | Val | Thr | Tyr | Pro | Glu | Asn | Gly | Arg | Thr | Phe | His | |
| | | 210 | | | | | 215 | | | | | 220 | | | | |
| ctc | acc | agg | act | ctg | act | gta | aag | gta | gta | ggc | tct | cca | aaa | aat | gca | 720 |
| Leu | Thr | Arg | Thr | Leu | Thr | Val | Lys | Val | Val | Gly | Ser | Pro | Lys | Asn | Ala | |
| 225 | | | | | 230 | | | | | 235 | | | | | 240 | |
| gtg | ccc | cct | gtg | atc | cat | tca | cct | aat | gat | cat | gtg | gtc | tat | gag | aaa | 768 |
| Val | Pro | Pro | Val | Ile | His | Ser | Pro | Asn | Asp | His | Val | Val | Tyr | Glu | Lys | |
| | | | | 245 | | | | | 250 | | | | | 255 | | |
| gaa | cca | gga | gag | gag | cta | ctc | att | ccc | tgt | acg | gtc | tat | ttt | agt | ttt | 816 |
| Glu | Pro | Gly | Glu | Glu | Leu | Leu | Ile | Pro | Cys | Thr | Val | Tyr | Phe | Ser | Phe | |
| | | | 260 | | | | | 265 | | | | | 270 | | | |
| ctg | atg | gat | tct | cgc | aat | gag | gtt | tgg | tgg | acc | att | gat | gga | aaa | aaa | 864 |
| Leu | Met | Asp | Ser | Arg | Asn | Glu | Val | Trp | Trp | Thr | Ile | Asp | Gly | Lys | Lys | |
| | | 275 | | | | | 280 | | | | | 285 | | | | |
| cct | gat | gac | atc | act | att | gat | gtc | acc | att | aac | gaa | agt | ata | agt | cat | 912 |
| Pro | Asp | Asp | Ile | Thr | Ile | Asp | Val | Thr | Ile | Asn | Glu | Ser | Ile | Ser | His | |

-continued

```
              290                 295                 300
agt aga aca gaa gat gaa aca aga act cag att ttg agc atc aag aaa      960
Ser Arg Thr Glu Asp Glu Thr Arg Thr Gln Ile Leu Ser Ile Lys Lys
305                 310                 315                 320 gtt acc tct gag gat ctc aag cgc agc tat gtc tgt cat gct aga agt     1008
Val Thr Ser Glu Asp Leu Lys Arg Ser Tyr Val Cys His Ala Arg Ser
                325                 330                 335 gcc aaa ggc gaa gtt gcc aaa gca gcc aag gtg aag cag aaa gtg cca     1056
Ala Lys Gly Glu Val Ala Lys Ala Ala Lys Val Lys Gln Lys Val Pro
        340                 345                 350 gct cca aga tac aca gtg tcc ggt ggc gcg cct atg ctg agc gag gct     1104
Ala Pro Arg Tyr Thr Val Ser Gly Gly Ala Pro Met Leu Ser Glu Ala
    355                 360                 365 gat aaa tgc aag gaa cgt gaa gaa aaa ata att tta gtg tca tct gca     1152
Asp Lys Cys Lys Glu Arg Glu Glu Lys Ile Ile Leu Val Ser Ser Ala
370                 375                 380 aat gaa att gat gtt cgt ccc tgt cct ctt aac cca aat gaa cac aaa     1200
Asn Glu Ile Asp Val Arg Pro Cys Pro Leu Asn Pro Asn Glu His Lys
385                 390                 395                 400 ggc act ata act tgg tat aag gat gac agc aag aca cct gta tct aca     1248
Gly Thr Ile Thr Trp Tyr Lys Asp Asp Ser Lys Thr Pro Val Ser Thr
                405                 410                 415 gaa caa gcc tcc agg att cat caa cac aaa gag aaa ctt tgg ttt gtt     1296
Glu Gln Ala Ser Arg Ile His Gln His Lys Glu Lys Leu Trp Phe Val
        420                 425                 430 cct gct aag gtg gag gat tca gga cat tac tat tgc gtg gta aga aat     1344
Pro Ala Lys Val Glu Asp Ser Gly His Tyr Tyr Cys Val Val Arg Asn
    435                 440                 445 tca tct tac tgc ctc aga att aaa ata agt gca aaa ttt gtg gag aat     1392
Ser Ser Tyr Cys Leu Arg Ile Lys Ile Ser Ala Lys Phe Val Glu Asn
450                 455                 460 gag cct aac tta tgt tat aat gca caa gcc ata ttt aag cag aaa cta     1440
Glu Pro Asn Leu Cys Tyr Asn Ala Gln Ala Ile Phe Lys Gln Lys Leu
465                 470                 475                 480 ccc gtt gca gga gac gga gga ctt gtg tgc cct tat atg gag ttt ttt     1488
Pro Val Ala Gly Asp Gly Gly Leu Val Cys Pro Tyr Met Glu Phe Phe
                485                 490                 495 aaa aat gaa aat aat gag tta cct aaa tta cag tgg tat aag gat tgc     1536
Lys Asn Glu Asn Asn Glu Leu Pro Lys Leu Gln Trp Tyr Lys Asp Cys
        500                 505                 510 aaa cct cta ctt ctt gac aat ata cac ttt agt gga gtc aaa gat agg     1584
Lys Pro Leu Leu Leu Asp Asn Ile His Phe Ser Gly Val Lys Asp Arg
    515                 520                 525 ctc atc gtg atg aat gtg gct gaa aag cat aga ggg aac tat act tgt     1632
Leu Ile Val Met Asn Val Ala Glu Lys His Arg Gly Asn Tyr Thr Cys
    530                 535                 540 cat gca tcc tac aca tac ttg ggc aag caa tat cct att acc cgg gta     1680
His Ala Ser Tyr Thr Tyr Leu Gly Lys Gln Tyr Pro Ile Thr Arg Val
545                 550                 555                 560 ata gaa ttt att act cta gag gaa aac aaa ccc aca agg cct gtg att     1728
Ile Glu Phe Ile Thr Leu Glu Glu Asn Lys Pro Thr Arg Pro Val Ile
                565                 570                 575 gtg agc cca gct aat gag aca atg gaa gta gac ttg gga tcc cag ata     1776
Val Ser Pro Ala Asn Glu Thr Met Glu Val Asp Leu Gly Ser Gln Ile
        580                 585                 590 caa ttg atc tgt aat gtc acc ggc cag ttg agt gac att gct tac tgg     1824
Gln Leu Ile Cys Asn Val Thr Gly Gln Leu Ser Asp Ile Ala Tyr Trp
    595                 600                 605 aag tgg aat ggg tca gta att gat gaa gat gac cca gtg cta ggg gaa     1872
```

```
                Lys Trp Asn Gly Ser Val Ile Asp Glu Asp Pro Val Leu Gly Glu
                610                 615                 620 gac tat tac agt gtg gaa aat cct gca aac aaa aga agg agt acc ctc          1920
Asp Tyr Tyr Ser Val Glu Asn Pro Ala Asn Lys Arg Arg Ser Thr Leu
625                 630                 635                 640 atc aca gtg ctt aat ata tcg gaa att gag agt aga ttt tat aaa cat          1968
Ile Thr Val Leu Asn Ile Ser Glu Ile Glu Ser Arg Phe Tyr Lys His
                645                 650                 655 cca ttt acc tgt ttt gcc aag aat aca cat ggt ata gat gca gca tat          2016
Pro Phe Thr Cys Phe Ala Lys Asn Thr His Gly Ile Asp Ala Ala Tyr
            660                 665                 670 atc cag tta ata tat cca gtc act aat tcc gga gac aaa act cac aca          2064
Ile Gln Leu Ile Tyr Pro Val Thr Asn Ser Gly Asp Lys Thr His Thr
        675                 680                 685 tgc cca ccg tgc cca gca cct gaa ctc ctg ggg gga ccg tca gtc ttc          2112
Cys Pro Pro Cys Pro Ala Pro Glu Leu Leu Gly Gly Pro Ser Val Phe
    690                 695                 700 ctc ttc ccc cca aaa ccc aag gac acc ctc atg atc tcc cgg acc cct          2160
Leu Phe Pro Pro Lys Pro Lys Asp Thr Leu Met Ile Ser Arg Thr Pro
705                 710                 715                 720 gag gtc aca tgc gtg gtg gtg gac gtg agc cac gaa gac cct gag gtc          2208
Glu Val Thr Cys Val Val Val Asp Val Ser His Glu Asp Pro Glu Val
                725                 730                 735 aag ttc aac tgg tac gtg gac ggc gtg gag gtg cat aat gcc aag aca          2256
Lys Phe Asn Trp Tyr Val Asp Gly Val Glu Val His Asn Ala Lys Thr
                740                 745                 750 aag ccg cgg gag gag cag tac aac agc acg tac cgt gtg gtc agc gtc          2304
Lys Pro Arg Glu Glu Gln Tyr Asn Ser Thr Tyr Arg Val Val Ser Val
            755                 760                 765 ctc acc gtc ctg cac cag gac tgg ctg aat ggc aag gag tac aag tgc          2352
Leu Thr Val Leu His Gln Asp Trp Leu Asn Gly Lys Glu Tyr Lys Cys
        770                 775                 780 aag gtc tcc aac aaa gcc ctc cca gcc ccc atc gag aaa acc atc tcc          2400
Lys Val Ser Asn Lys Ala Leu Pro Ala Pro Ile Glu Lys Thr Ile Ser
785                 790                 795                 800 aaa gcc aaa ggg cag ccc cga gaa cca cag gtg tac acc ctg ccc cca          2448
Lys Ala Lys Gly Gln Pro Arg Glu Pro Gln Val Tyr Thr Leu Pro Pro
                805                 810                 815 tcc cgg gag gag atg acc aag aac cag gtc agc ctg acc tgc ctg gtc          2496
Ser Arg Glu Glu Met Thr Lys Asn Gln Val Ser Leu Thr Cys Leu Val
                820                 825                 830 aaa ggc ttc tat ccc agc gac atc gcc gtg gag tgg gag agc aat ggg          2544
Lys Gly Phe Tyr Pro Ser Asp Ile Ala Val Glu Trp Glu Ser Asn Gly
            835                 840                 845 cag ccg gag aac aac tac aag acc acg cct ccc gtg ctg gac tcc gac          2592
Gln Pro Glu Asn Asn Tyr Lys Thr Thr Pro Pro Val Leu Asp Ser Asp
        850                 855                 860 ggc tcc ttc ttc ctc tat agc aag ctc acc gtg gac aag agc agg tgg          2640
Gly Ser Phe Phe Leu Tyr Ser Lys Leu Thr Val Asp Lys Ser Arg Trp
865                 870                 875                 880 cag cag ggg aac gtc ttc tca tgc tcc gtg atg cat gag gct ctg cac          2688
Gln Gln Gly Asn Val Phe Ser Cys Ser Val Met His Glu Ala Leu His
                885                 890                 895 aac cac tac acg cag aag agc ctc tcc ctg tct ccg ggt aaa              2730
Asn His Tyr Thr Gln Lys Ser Leu Ser Leu Ser Pro Gly Lys
                900                 905                 910 tga                                                                       2733

<210> SEQ ID NO 28
```

```
<211> LENGTH: 910
<212> TYPE: PRT
<213> ORGANISM: Homo sapiens

<400> SEQUENCE: 28

Met Val Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
    290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350

Ala Pro Arg Tyr Thr Val Ser Gly Gly Ala Pro Met Leu Ser Glu Ala
        355                 360                 365

Asp Lys Cys Lys Glu Arg Glu Glu Lys Ile Ile Leu Val Ser Ser Ala
    370                 375                 380

Asn Glu Ile Asp Val Arg Pro Cys Pro Leu Asn Pro Asn Glu His Lys
```

-continued

```
            385                 390                 395                 400
Gly Thr Ile Thr Trp Tyr Lys Asp Asp Ser Lys Thr Pro Val Ser Thr
                    405                 410                 415
Glu Gln Ala Ser Arg Ile His Gln His Lys Glu Lys Leu Trp Phe Val
            420                 425                 430
Pro Ala Lys Val Glu Asp Ser Gly His Tyr Tyr Cys Val Val Arg Asn
                435                 440                 445
Ser Ser Tyr Cys Leu Arg Ile Lys Ile Ser Ala Lys Phe Val Glu Asn
        450                 455                 460
Glu Pro Asn Leu Cys Tyr Asn Ala Gln Ala Ile Phe Lys Gln Lys Leu
465                 470                 475                 480
Pro Val Ala Gly Asp Gly Gly Leu Val Cys Pro Tyr Met Glu Phe Phe
                    485                 490                 495
Lys Asn Glu Asn Asn Glu Leu Pro Lys Leu Gln Trp Tyr Lys Asp Cys
                500                 505                 510
Lys Pro Leu Leu Leu Asp Asn Ile His Phe Ser Gly Val Lys Asp Arg
            515                 520                 525
Leu Ile Val Met Asn Val Ala Glu Lys His Arg Gly Asn Tyr Thr Cys
        530                 535                 540
His Ala Ser Tyr Thr Tyr Leu Gly Lys Gln Tyr Pro Ile Thr Arg Val
545                 550                 555                 560
Ile Glu Phe Ile Thr Leu Glu Glu Asn Lys Pro Thr Arg Pro Val Ile
                    565                 570                 575
Val Ser Pro Ala Asn Glu Thr Met Glu Val Asp Leu Gly Ser Gln Ile
                580                 585                 590
Gln Leu Ile Cys Asn Val Thr Gly Gln Leu Ser Asp Ile Ala Tyr Trp
            595                 600                 605
Lys Trp Asn Gly Ser Val Ile Asp Glu Asp Asp Pro Val Leu Gly Glu
        610                 615                 620
Asp Tyr Tyr Ser Val Glu Asn Pro Ala Asn Lys Arg Arg Ser Thr Leu
625                 630                 635                 640
Ile Thr Val Leu Asn Ile Ser Glu Ile Glu Ser Arg Phe Tyr Lys His
                    645                 650                 655
Pro Phe Thr Cys Phe Ala Lys Asn Thr His Gly Ile Asp Ala Ala Tyr
                660                 665                 670
Ile Gln Leu Ile Tyr Pro Val Thr Asn Ser Gly Asp Lys Thr His Thr
            675                 680                 685
Cys Pro Pro Cys Pro Ala Pro Glu Leu Leu Gly Gly Pro Ser Val Phe
        690                 695                 700
Leu Phe Pro Pro Lys Pro Lys Asp Thr Leu Met Ile Ser Arg Thr Pro
705                 710                 715                 720
Glu Val Thr Cys Val Val Val Asp Val Ser His Glu Asp Pro Glu Val
                    725                 730                 735
Lys Phe Asn Trp Tyr Val Asp Gly Val Glu Val His Asn Ala Lys Thr
                740                 745                 750
Lys Pro Arg Glu Glu Gln Tyr Asn Ser Thr Tyr Arg Val Val Ser Val
            755                 760                 765
Leu Thr Val Leu His Gln Asp Trp Leu Asn Gly Lys Glu Tyr Lys Cys
        770                 775                 780
Lys Val Ser Asn Lys Ala Leu Pro Ala Pro Ile Glu Lys Thr Ile Ser
785                 790                 795                 800
Lys Ala Lys Gly Gln Pro Arg Glu Pro Gln Val Tyr Thr Leu Pro Pro
                    805                 810                 815
```

```
Ser Arg Glu Glu Met Thr Lys Asn Gln Val Ser Leu Thr Cys Leu Val
        820                 825                 830

Lys Gly Phe Tyr Pro Ser Asp Ile Ala Val Glu Trp Glu Ser Asn Gly
            835                 840                 845

Gln Pro Glu Asn Asn Tyr Lys Thr Thr Pro Pro Val Leu Asp Ser Asp
        850                 855                 860

Gly Ser Phe Phe Leu Tyr Ser Lys Leu Thr Val Asp Lys Ser Arg Trp
865                 870                 875                 880

Gln Gln Gly Asn Val Phe Ser Cys Ser Val Met His Glu Ala Leu His
                885                 890                 895

Asn His Tyr Thr Gln Lys Ser Leu Ser Leu Ser Pro Gly Lys
            900                 905                 910

<210> SEQ ID NO 29
<211> LENGTH: 2355
<212> TYPE: DNA
<213> ORGANISM: Homo sapiens
<220> FEATURE:
<221> NAME/KEY: CDS
<222> LOCATION: (1)...(2352)

<400> SEQUENCE: 29
```

| | | | | | | | | | | | | | | | | |
|---|---|---|---|---|---|---|---|---|---|---|---|---|---|---|---|---|
| atg | gtg | tgg | ctt | tgc | tct | ggg | ctc | ctg | ttc | cct | gtg | agc | tgc | ctg | gtc | 48 |
| Met | Val | Trp | Leu | Cys | Ser | Gly | Leu | Leu | Phe | Pro | Val | Ser | Cys | Leu | Val | |
| 1 | | | | 5 | | | | | 10 | | | | | 15 | | |
| ctg | ctg | cag | gtg | gca | agc | tct | ggg | aac | atg | aag | gtc | ttg | cag | gag | ccc | 96 |
| Leu | Leu | Gln | Val | Ala | Ser | Ser | Gly | Asn | Met | Lys | Val | Leu | Gln | Glu | Pro | |
| | | | | 20 | | | | | 25 | | | | | 30 | | |
| acc | tgc | gtc | tcc | gac | tac | atg | agc | atc | tct | act | tgc | gag | tgg | aag | atg | 144 |
| Thr | Cys | Val | Ser | Asp | Tyr | Met | Ser | Ile | Ser | Thr | Cys | Glu | Trp | Lys | Met | |
| | | | 35 | | | | | 40 | | | | | 45 | | | |
| aat | ggt | ccc | acc | aat | tgc | agc | acc | gag | ctc | cgc | ctg | ttg | tac | cag | ctg | 192 |
| Asn | Gly | Pro | Thr | Asn | Cys | Ser | Thr | Glu | Leu | Arg | Leu | Leu | Tyr | Gln | Leu | |
| | 50 | | | | | 55 | | | | | 60 | | | | | |
| gtt | ttt | ctg | ctc | tcc | gaa | gcc | cac | acg | tgt | atc | cct | gag | aac | aac | gga | 240 |
| Val | Phe | Leu | Leu | Ser | Glu | Ala | His | Thr | Cys | Ile | Pro | Glu | Asn | Asn | Gly | |
| 65 | | | | | 70 | | | | | 75 | | | | | 80 | |
| ggc | gcg | ggg | tgc | gtg | tgc | cac | ctg | ctc | atg | gat | gac | gtg | gtc | agt | gcg | 288 |
| Gly | Ala | Gly | Cys | Val | Cys | His | Leu | Leu | Met | Asp | Asp | Val | Val | Ser | Ala | |
| | | | | 85 | | | | | 90 | | | | | 95 | | |
| gat | aac | tat | aca | ctg | gac | ctg | tgg | gct | ggg | cag | cag | ctg | ctg | tgg | aag | 336 |
| Asp | Asn | Tyr | Thr | Leu | Asp | Leu | Trp | Ala | Gly | Gln | Gln | Leu | Leu | Trp | Lys | |
| | | | 100 | | | | | 105 | | | | | 110 | | | |
| ggc | tcc | ttc | aag | ccc | agc | gag | cat | gtg | aaa | ccc | agg | gcc | cca | gga | aac | 384 |
| Gly | Ser | Phe | Lys | Pro | Ser | Glu | His | Val | Lys | Pro | Arg | Ala | Pro | Gly | Asn | |
| | | 115 | | | | | 120 | | | | | 125 | | | | |
| ctg | aca | gtt | cac | acc | aat | gtc | tcc | gac | act | ctg | ctg | ctg | acc | tgg | agc | 432 |
| Leu | Thr | Val | His | Thr | Asn | Val | Ser | Asp | Thr | Leu | Leu | Leu | Thr | Trp | Ser | |
| | 130 | | | | | 135 | | | | | 140 | | | | | |
| aac | ccg | tat | ccc | cct | gac | aat | tac | ctg | tat | aat | cat | ctc | acc | tat | gca | 480 |
| Asn | Pro | Tyr | Pro | Pro | Asp | Asn | Tyr | Leu | Tyr | Asn | His | Leu | Thr | Tyr | Ala | |
| 145 | | | | | 150 | | | | | 155 | | | | | 160 | |
| gtc | aac | att | tgg | agt | gaa | aac | gac | ccg | gca | gat | ttc | aga | atc | tat | aac | 528 |
| Val | Asn | Ile | Trp | Ser | Glu | Asn | Asp | Pro | Ala | Asp | Phe | Arg | Ile | Tyr | Asn | |
| | | | | 165 | | | | | 170 | | | | | 175 | | |
| gtg | acc | tac | cta | gaa | ccc | tcc | ctc | cgc | atc | gca | gcc | agc | acc | ctg | aag | 576 |
| Val | Thr | Tyr | Leu | Glu | Pro | Ser | Leu | Arg | Ile | Ala | Ala | Ser | Thr | Leu | Lys | |
| | | | 180 | | | | | 185 | | | | | 190 | | | |
| tct | ggg | att | tcc | tac | agg | gca | cgg | gtg | agg | gcc | tgg | gct | cag | agc | tat | 624 |

-continued

```
Ser Gly Ile Ser Tyr Arg Ala Arg Val Arg Ala Trp Ala Gln Ser Tyr
        195                 200                 205 aac acc acc tgg agt gag tgg agc ccc agc acc aag tgg cac aac tcc      672
Asn Thr Thr Trp Ser Glu Trp Ser Pro Ser Thr Lys Trp His Asn Ser
        210                 215                 220 tac agg gag ccc ttc gag cag tcc ggt ggg ggc ggg ggc gcc gcg cct      720
Tyr Arg Glu Pro Phe Glu Gln Ser Gly Gly Gly Gly Gly Ala Ala Pro
225                 230                 235                 240 acg gaa act cag cca cct gtg aca aat ttg agt gtc tct gtt gaa aac      768
Thr Glu Thr Gln Pro Pro Val Thr Asn Leu Ser Val Ser Val Glu Asn
                245                 250                 255 ctc tgc aca gta ata tgg aca tgg aat cca ccc gag gga gcc agc tca      816
Leu Cys Thr Val Ile Trp Thr Trp Asn Pro Pro Glu Gly Ala Ser Ser
            260                 265                 270 aat tgt agt cta tgg tat ttt agt cat ttt ggc gac aaa caa gat aag      864
Asn Cys Ser Leu Trp Tyr Phe Ser His Phe Gly Asp Lys Gln Asp Lys
        275                 280                 285 aaa ata gct ccg gaa act cgt cgt tca ata gaa gta ccc ctg aat gag      912
Lys Ile Ala Pro Glu Thr Arg Arg Ser Ile Glu Val Pro Leu Asn Glu
290                 295                 300 agg att tgt ctg caa gtg ggg tcc cag tgt agc acc aat gag agt gag      960
Arg Ile Cys Leu Gln Val Gly Ser Gln Cys Ser Thr Asn Glu Ser Glu
305                 310                 315                 320 aag cct agc att ttg gtt gaa aaa tgc atc tca ccc cca gaa ggt gat     1008
Lys Pro Ser Ile Leu Val Glu Lys Cys Ile Ser Pro Pro Glu Gly Asp
                325                 330                 335 cct gag tct gct gtg act gag ctt caa tgc att tgg cac aac ctg agc     1056
Pro Glu Ser Ala Val Thr Glu Leu Gln Cys Ile Trp His Asn Leu Ser
            340                 345                 350 tac atg aag tgt tct tgg ctc cct gga agg aat acc agt ccc gac act     1104
Tyr Met Lys Cys Ser Trp Leu Pro Gly Arg Asn Thr Ser Pro Asp Thr
        355                 360                 365 aac tat act ctc tac tat tgg cac aga agc ctg gaa aaa att cat caa     1152
Asn Tyr Thr Leu Tyr Tyr Trp His Arg Ser Leu Glu Lys Ile His Gln
370                 375                 380 tgt gaa aac atc ttt aga gaa ggc caa tac ttt ggt tgt tcc ttt gat     1200
Cys Glu Asn Ile Phe Arg Glu Gly Gln Tyr Phe Gly Cys Ser Phe Asp
385                 390                 395                 400 ctg acc aaa gtg aag gat tcc agt ttt gaa caa cac agt gtc caa ata     1248
Leu Thr Lys Val Lys Asp Ser Ser Phe Glu Gln His Ser Val Gln Ile
                405                 410                 415 atg gtc aag gat aat gca gga aaa att aaa cca tcc ttc aat ata gtg     1296
Met Val Lys Asp Asn Ala Gly Lys Ile Lys Pro Ser Phe Asn Ile Val
            420                 425                 430 cct tta act tcc cgt gtg aaa cct gat cct cca cat att aaa aac ctc     1344
Pro Leu Thr Ser Arg Val Lys Pro Asp Pro Pro His Ile Lys Asn Leu
        435                 440                 445 tcc ttc cac aat gat gac cta tat gtg caa tgg gag aat cca cag aat     1392
Ser Phe His Asn Asp Asp Leu Tyr Val Gln Trp Glu Asn Pro Gln Asn
450                 455                 460 ttt att agc aga tgc cta ttt tat gaa gta gaa gtc aat aac agc caa     1440
Phe Ile Ser Arg Cys Leu Phe Tyr Glu Val Glu Val Asn Asn Ser Gln
465                 470                 475                 480 act gag aca cat aat gtt ttc tac gtc caa gag gct aaa tgt gag aat     1488
Thr Glu Thr His Asn Val Phe Tyr Val Gln Glu Ala Lys Cys Glu Asn
                485                 490                 495 cca gaa ttt gag aga aat gtg gag aat aca tct tgt ttc atg gtc cct     1536
Pro Glu Phe Glu Arg Asn Val Glu Asn Thr Ser Cys Phe Met Val Pro
            500                 505                 510
```

```
ggt gtt ctt cct gat act ttg aac aca gtc aga ata aga gtc aaa aca    1584
Gly Val Leu Pro Asp Thr Leu Asn Thr Val Arg Ile Arg Val Lys Thr
            515                 520                 525 aat aag tta tgc tat gag gat gac aaa ctc tgg agt aat tgg agc caa    1632
Asn Lys Leu Cys Tyr Glu Asp Asp Lys Leu Trp Ser Asn Trp Ser Gln
        530                 535                 540 gaa atg agt ata ggt aag aag cgc aat tcc aca acc gga gac aaa act    1680
Glu Met Ser Ile Gly Lys Lys Arg Asn Ser Thr Thr Gly Asp Lys Thr
545                 550                 555                 560 cac aca tgc cca ccg tgc cca gca cct gaa ctc ctg gga gga ccg tca    1728
His Thr Cys Pro Pro Cys Pro Ala Pro Glu Leu Leu Gly Gly Pro Ser
                565                 570                 575 gtc ttc ctc ttc ccc cca aaa ccc aag gac acc ctc atg atc tcc cgg    1776
Val Phe Leu Phe Pro Pro Lys Pro Lys Asp Thr Leu Met Ile Ser Arg
            580                 585                 590 acc cct gag gtc aca tgc gtg gtg gtg gac gtg agc cac gaa gac cct    1824
Thr Pro Glu Val Thr Cys Val Val Val Asp Val Ser His Glu Asp Pro
        595                 600                 605 gag gtc aag ttc aac tgg tac gtg gac ggc gtg gag gtg cat aat gcc    1872
Glu Val Lys Phe Asn Trp Tyr Val Asp Gly Val Glu Val His Asn Ala
610                 615                 620 aag aca aag ccg cgg gag gag cag tac aac agc acg tac cgt gtg gtc    1920
Lys Thr Lys Pro Arg Glu Glu Gln Tyr Asn Ser Thr Tyr Arg Val Val
625                 630                 635                 640 agc gtc ctc acc gtc ctg cac cag gac tgg ctg aat ggc aag gag tac    1968
Ser Val Leu Thr Val Leu His Gln Asp Trp Leu Asn Gly Lys Glu Tyr
                645                 650                 655 aag tgc aag gtc tcc aac aaa gcc ctc cca gcc ccc atc gag aaa acc    2016
Lys Cys Lys Val Ser Asn Lys Ala Leu Pro Ala Pro Ile Glu Lys Thr
            660                 665                 670 atc tcc aaa gcc aaa ggg cag ccc cga gaa cca cag gtg tac acc ctg    2064
Ile Ser Lys Ala Lys Gly Gln Pro Arg Glu Pro Gln Val Tyr Thr Leu
        675                 680                 685 ccc cca tcc cgg gag gag atg acc aag aac cag gtc agc ctg acc tgc    2112
Pro Pro Ser Arg Glu Glu Met Thr Lys Asn Gln Val Ser Leu Thr Cys
690                 695                 700 ctg gtc aaa ggc ttc tat ccc agc gac atc gcc gtg gag tgg gag agc    2160
Leu Val Lys Gly Phe Tyr Pro Ser Asp Ile Ala Val Glu Trp Glu Ser
705                 710                 715                 720 aat ggg cag ccg gag aac aac tac aag acc acg cct ccc gtg ctg gac    2208
Asn Gly Gln Pro Glu Asn Asn Tyr Lys Thr Thr Pro Pro Val Leu Asp
                725                 730                 735 tcc gac ggc tcc ttc ttc ctc tat agc aag ctc acc gtg gac aag agc    2256
Ser Asp Gly Ser Phe Phe Leu Tyr Ser Lys Leu Thr Val Asp Lys Ser
            740                 745                 750 agg tgg cag cag ggg aac gtc ttc tca tgc tcc gtg atg cat gag gct    2304
Arg Trp Gln Gln Gly Asn Val Phe Ser Cys Ser Val Met His Glu Ala
        755                 760                 765 ctg cac aac cac tac acg cag aag agc ctc tcc ctg tct ccg ggt aaa    2352
Leu His Asn His Tyr Thr Gln Lys Ser Leu Ser Leu Ser Pro Gly Lys
                775                 780 tga                                                                2355

<210> SEQ ID NO 30
<211> LENGTH: 784
<212> TYPE: PRT
<213> ORGANISM: Homo sapiens

<400> SEQUENCE: 30

Met Val Trp Leu Cys Ser Gly Leu Leu Phe Pro Val Ser Cys Leu Val
```

-continued

```
  1               5                  10                 15
Leu Leu Gln Val Ala Ser Ser Gly Asn Met Lys Val Leu Gln Glu Pro
             20                  25                  30

Thr Cys Val Ser Asp Tyr Met Ser Ile Ser Thr Cys Glu Trp Lys Met
             35                  40                  45

Asn Gly Pro Thr Asn Cys Ser Thr Glu Leu Arg Leu Leu Tyr Gln Leu
 50                  55                  60

Val Phe Leu Leu Ser Glu Ala His Thr Cys Ile Pro Glu Asn Asn Gly
 65                  70                  75                  80

Gly Ala Gly Cys Val Cys His Leu Leu Met Asp Asp Val Val Ser Ala
             85                  90                  95

Asp Asn Tyr Thr Leu Asp Leu Trp Ala Gly Gln Gln Leu Leu Trp Lys
            100                 105                 110

Gly Ser Phe Lys Pro Ser Glu His Val Lys Pro Arg Ala Pro Gly Asn
            115                 120                 125

Leu Thr Val His Thr Asn Val Ser Asp Thr Leu Leu Leu Thr Trp Ser
            130                 135                 140

Asn Pro Tyr Pro Pro Asp Asn Tyr Leu Tyr Asn His Leu Thr Tyr Ala
145                 150                 155                 160

Val Asn Ile Trp Ser Glu Asn Asp Pro Ala Asp Phe Arg Ile Tyr Asn
            165                 170                 175

Val Thr Tyr Leu Glu Pro Ser Leu Arg Ile Ala Ala Ser Thr Leu Lys
            180                 185                 190

Ser Gly Ile Ser Tyr Arg Ala Arg Val Arg Ala Trp Ala Gln Ser Tyr
            195                 200                 205

Asn Thr Thr Trp Ser Glu Trp Ser Pro Ser Thr Lys Trp His Asn Ser
            210                 215                 220

Tyr Arg Glu Pro Phe Glu Gln Ser Gly Gly Gly Gly Ala Ala Pro
225                 230                 235                 240

Thr Glu Thr Gln Pro Pro Val Thr Asn Leu Ser Val Ser Val Glu Asn
            245                 250                 255

Leu Cys Thr Val Ile Trp Thr Trp Asn Pro Pro Glu Gly Ala Ser Ser
            260                 265                 270

Asn Cys Ser Leu Trp Tyr Phe Ser His Phe Gly Asp Lys Gln Asp Lys
            275                 280                 285

Lys Ile Ala Pro Glu Thr Arg Arg Ser Ile Glu Val Pro Leu Asn Glu
            290                 295                 300

Arg Ile Cys Leu Gln Val Gly Ser Gln Cys Ser Thr Asn Glu Ser Glu
305                 310                 315                 320

Lys Pro Ser Ile Leu Val Glu Lys Cys Ile Ser Pro Pro Glu Gly Asp
            325                 330                 335

Pro Glu Ser Ala Val Thr Glu Leu Gln Cys Ile Trp His Asn Leu Ser
            340                 345                 350

Tyr Met Lys Cys Ser Trp Leu Pro Gly Arg Asn Thr Ser Pro Asp Thr
            355                 360                 365

Asn Tyr Thr Leu Tyr Tyr Trp His Arg Ser Leu Glu Lys Ile His Gln
            370                 375                 380

Cys Glu Asn Ile Phe Arg Glu Gly Gln Tyr Phe Gly Cys Ser Phe Asp
385                 390                 395                 400

Leu Thr Lys Val Lys Asp Ser Ser Phe Glu Gln His Ser Val Gln Ile
            405                 410                 415

Met Val Lys Asp Asn Ala Gly Lys Ile Lys Pro Ser Phe Asn Ile Val
            420                 425                 430
```

```
Pro Leu Thr Ser Arg Val Lys Pro Asp Pro His Ile Lys Asn Leu
        435                 440                 445
Ser Phe His Asn Asp Asp Leu Tyr Val Gln Trp Glu Asn Pro Gln Asn
450                 455                 460
Phe Ile Ser Arg Cys Leu Phe Tyr Glu Val Glu Val Asn Asn Ser Gln
465                 470                 475                 480
Thr Glu Thr His Asn Val Phe Tyr Val Gln Ala Lys Cys Glu Asn
            485                 490                 495
Pro Glu Phe Glu Arg Asn Val Glu Asn Thr Ser Cys Phe Met Val Pro
            500                 505                 510
Gly Val Leu Pro Asp Thr Leu Asn Thr Val Arg Ile Arg Val Lys Thr
            515                 520                 525
Asn Lys Leu Cys Tyr Glu Asp Asp Lys Leu Trp Ser Asn Trp Ser Gln
        530                 535                 540
Glu Met Ser Ile Gly Lys Lys Arg Asn Ser Thr Thr Gly Asp Lys Thr
545                 550                 555                 560
His Thr Cys Pro Pro Cys Pro Ala Pro Glu Leu Leu Gly Gly Pro Ser
                565                 570                 575
Val Phe Leu Phe Pro Pro Lys Pro Lys Asp Thr Leu Met Ile Ser Arg
            580                 585                 590
Thr Pro Glu Val Thr Cys Val Val Val Asp Val Ser His Glu Asp Pro
            595                 600                 605
Glu Val Lys Phe Asn Trp Tyr Val Asp Gly Val Glu Val His Asn Ala
            610                 615                 620
Lys Thr Lys Pro Arg Glu Glu Gln Tyr Asn Ser Thr Tyr Arg Val Val
625                 630                 635                 640
Ser Val Leu Thr Val Leu His Gln Asp Trp Leu Asn Gly Lys Glu Tyr
                645                 650                 655
Lys Cys Lys Val Ser Asn Lys Ala Leu Pro Ala Pro Ile Glu Lys Thr
                660                 665                 670
Ile Ser Lys Ala Lys Gly Gln Pro Arg Glu Pro Gln Val Tyr Thr Leu
            675                 680                 685
Pro Pro Ser Arg Glu Glu Met Thr Lys Asn Gln Val Ser Leu Thr Cys
            690                 695                 700
Leu Val Lys Gly Phe Tyr Pro Ser Asp Ile Ala Val Glu Trp Glu Ser
705                 710                 715                 720
Asn Gly Gln Pro Glu Asn Asn Tyr Lys Thr Thr Pro Pro Val Leu Asp
                725                 730                 735
Ser Asp Gly Ser Phe Phe Leu Tyr Ser Lys Leu Thr Val Asp Lys Ser
            740                 745                 750
Arg Trp Gln Gln Gly Asn Val Phe Ser Cys Ser Val Met His Glu Ala
            755                 760                 765
Leu His Asn His Tyr Thr Gln Lys Ser Leu Ser Leu Ser Pro Gly Lys
        770                 775                 780

<210> SEQ ID NO 31
<211> LENGTH: 2382
<212> TYPE: DNA
<213> ORGANISM: Homo sapiens
<220> FEATURE:
<221> NAME/KEY: CDS
<222> LOCATION: (1)...(2379)

<400> SEQUENCE: 31 atg gtg tgg ccg gcg cgg ctc tgc ggg ctg tgg gcg ctg ctg ctc tgc      48
```

```
                Met Val Trp Pro Ala Arg Leu Cys Gly Leu Trp Ala Leu Leu Leu Cys
                 1               5                  10                  15 gcc ggc ggc ggg ggg ggc ggg ggc gcc gcg cct acg gaa act cag                      96
Ala Gly Gly Gly Gly Gly Gly Gly Ala Ala Pro Thr Glu Thr Gln
                 20                  25                  30 cca cct gtg aca aat ttg agt gtc tct gtt gaa aac ctc tgc aca gta                 144
Pro Pro Val Thr Asn Leu Ser Val Ser Val Glu Asn Leu Cys Thr Val
             35                  40                  45 ata tgg aca tgg aat cca ccc gag gga gcc agc tca aat tgt agt cta                 192
Ile Trp Thr Trp Asn Pro Pro Glu Gly Ala Ser Ser Asn Cys Ser Leu
             50                  55                  60 tgg tat ttt agt cat ttt ggc gac aaa caa gat aag aaa ata gct ccg                 240
Trp Tyr Phe Ser His Phe Gly Asp Lys Gln Asp Lys Lys Ile Ala Pro
65                  70                  75                  80 gaa act cgt cgt tca ata gaa gta ccc ctg aat gag agg att tgt ctg                 288
Glu Thr Arg Arg Ser Ile Glu Val Pro Leu Asn Glu Arg Ile Cys Leu
                 85                  90                  95 caa gtg ggg tcc cag tgt agc acc aat gag agt gag aag cct agc att                 336
Gln Val Gly Ser Gln Cys Ser Thr Asn Glu Ser Glu Lys Pro Ser Ile
             100                 105                 110 ttg gtt gaa aaa tgc atc tca ccc cca gaa ggt gat cct gag tct gct                 384
Leu Val Glu Lys Cys Ile Ser Pro Pro Glu Gly Asp Pro Glu Ser Ala
             115                 120                 125 gtg act gag ctt caa tgc att tgg cac aac ctg agc tac atg aag tgt                 432
Val Thr Glu Leu Gln Cys Ile Trp His Asn Leu Ser Tyr Met Lys Cys
130                 135                 140 tct tgg ctc cct gga agg aat acc agt ccc gac act aac tat act ctc                 480
Ser Trp Leu Pro Gly Arg Asn Thr Ser Pro Asp Thr Asn Tyr Thr Leu
145                 150                 155                 160 tac tat tgg cac aga agc ctg gaa aaa att cat caa tgt gaa aac atc                 528
Tyr Tyr Trp His Arg Ser Leu Glu Lys Ile His Gln Cys Glu Asn Ile
                 165                 170                 175 ttt aga gaa ggc caa tac ttt ggt tgt tcc ttt gat ctg acc aaa gtg                 576
Phe Arg Glu Gly Gln Tyr Phe Gly Cys Ser Phe Asp Leu Thr Lys Val
             180                 185                 190 aag gat tcc agt ttt gaa caa cac agt gtc caa ata atg gtc aag gat                 624
Lys Asp Ser Ser Phe Glu Gln His Ser Val Gln Ile Met Val Lys Asp
             195                 200                 205 aat gca gga aaa att aaa cca tcc ttc aat ata gtg cct tta act tcc                 672
Asn Ala Gly Lys Ile Lys Pro Ser Phe Asn Ile Val Pro Leu Thr Ser
             210                 215                 220 cgt gtg aaa cct gat cct cca cat att aaa aac ctc tcc ttc cac aat                 720
Arg Val Lys Pro Asp Pro Pro His Ile Lys Asn Leu Ser Phe His Asn
225                 230                 235                 240 gat gac cta tat gtg caa tgg gag aat cca cag aat ttt att agc aga                 768
Asp Asp Leu Tyr Val Gln Trp Glu Asn Pro Gln Asn Phe Ile Ser Arg
                 245                 250                 255 tgc cta ttt tat gaa gta gaa gtc aat aac agc caa act gag aca cat                 816
Cys Leu Phe Tyr Glu Val Glu Val Asn Asn Ser Gln Thr Glu Thr His
             260                 265                 270 aat gtt ttc tac gtc caa gag gct aaa tgt gag aat cca gaa ttt gag                 864
Asn Val Phe Tyr Val Gln Glu Ala Lys Cys Glu Asn Pro Glu Phe Glu
             275                 280                 285 aga aat gtg gag aat aca tct tgt ttc atg gtc cct ggt gtt ctt cct                 912
Arg Asn Val Glu Asn Thr Ser Cys Phe Met Val Pro Gly Val Leu Pro
             290                 295                 300 gat act ttg aac aca gtc aga ata aga gtc aaa aca aat aag tta tgc                 960
Asp Thr Leu Asn Thr Val Arg Ile Arg Val Lys Thr Asn Lys Leu Cys
305                 310                 315                 320
```

```
tat gag gat gac aaa ctc tgg agt aat tgg agc caa gaa atg agt ata      1008
Tyr Glu Asp Asp Lys Leu Trp Ser Asn Trp Ser Gln Glu Met Ser Ile
            325                 330                 335 ggt aag aag cgc aat tcc aca ggc gcg cct agt ggt gga ggt ggc cgg      1056
Gly Lys Lys Arg Asn Ser Thr Gly Ala Pro Ser Gly Gly Gly Gly Arg
        340                 345                 350 ccc gca agc tct ggg aac atg aag gtc ttg cag gag ccc acc tgc gtc      1104
Pro Ala Ser Ser Gly Asn Met Lys Val Leu Gln Glu Pro Thr Cys Val
    355                 360                 365 tcc gac tac atg agc atc tct act tgc gag tgg aag atg aat ggt ccc      1152
Ser Asp Tyr Met Ser Ile Ser Thr Cys Glu Trp Lys Met Asn Gly Pro
370                 375                 380 acc aat tgc agc acc gag ctc cgc ctg ttg tac cag ctg gtt ttt ctg      1200
Thr Asn Cys Ser Thr Glu Leu Arg Leu Leu Tyr Gln Leu Val Phe Leu
385                 390                 395                 400 ctc tcc gaa gcc cac acg tgt atc cct gag aac aac gga ggc gcg ggg      1248
Leu Ser Glu Ala His Thr Cys Ile Pro Glu Asn Asn Gly Gly Ala Gly
                405                 410                 415 tgc gtg tgc cac ctg ctc atg gat gac gtg gtc agt gcg gat aac tat      1296
Cys Val Cys His Leu Leu Met Asp Asp Val Val Ser Ala Asp Asn Tyr
            420                 425                 430 aca ctg gac ctg tgg gct ggg cag cag ctg ctg tgg aag ggc tcc ttc      1344
Thr Leu Asp Leu Trp Ala Gly Gln Gln Leu Leu Trp Lys Gly Ser Phe
        435                 440                 445 aag ccc agc gag cat gtg aaa ccc agg gcc cca gga aac ctg aca gtt      1392
Lys Pro Ser Glu His Val Lys Pro Arg Ala Pro Gly Asn Leu Thr Val
    450                 455                 460 cac acc aat gtc tcc gac act ctg ctg ctg acc tgg agc aac ccg tat      1440
His Thr Asn Val Ser Asp Thr Leu Leu Leu Thr Trp Ser Asn Pro Tyr
465                 470                 475                 480 ccc cct gac aat tac ctg tat aat cat ctc acc tat gca gtc aac att      1488
Pro Pro Asp Asn Tyr Leu Tyr Asn His Leu Thr Tyr Ala Val Asn Ile
                485                 490                 495 tgg agt gaa aac gac ccg gca gat ttc aga atc tat aac gtg acc tac      1536
Trp Ser Glu Asn Asp Pro Ala Asp Phe Arg Ile Tyr Asn Val Thr Tyr
            500                 505                 510 cta gaa ccc tcc ctc cgc atc gca gcc agc acc ctg aag tct ggg att      1584
Leu Glu Pro Ser Leu Arg Ile Ala Ala Ser Thr Leu Lys Ser Gly Ile
        515                 520                 525 tcc tac agg gca cgg gtg agg gcc tgg gct cag tgc tat aac acc acc      1632
Ser Tyr Arg Ala Arg Val Arg Ala Trp Ala Gln Cys Tyr Asn Thr Thr
    530                 535                 540 tgg agt gag tgg agc ccc agc acc aag tgg cac aac tcc tac agg gag      1680
Trp Ser Glu Trp Ser Pro Ser Thr Lys Trp His Asn Ser Tyr Arg Glu
545                 550                 555                 560 ccc ttc gag cag tcc gga gac aaa act cac aca tgc cca ccg tgc cca      1728
Pro Phe Glu Gln Ser Gly Asp Lys Thr His Thr Cys Pro Pro Cys Pro
                565                 570                 575 gca cct gaa ctc ctg ggg gga ccg tca gtc ttc ctc ttc ccc cca aaa      1776
Ala Pro Glu Leu Leu Gly Gly Pro Ser Val Phe Leu Phe Pro Pro Lys
            580                 585                 590 ccc aag gac acc ctc atg atc tcc cgg acc cct gag gtc aca tgc gtg      1824
Pro Lys Asp Thr Leu Met Ile Ser Arg Thr Pro Glu Val Thr Cys Val
        595                 600                 605 gtg gtg gac gtg agc cac gaa gac cct gag gtc aag ttc aac tgg tac      1872
Val Val Asp Val Ser His Glu Asp Pro Glu Val Lys Phe Asn Trp Tyr
    610                 615                 620 gtg gac ggc gtg gag gtg cat aat gcc aag aca aag ccg cgg gag gag      1920
Val Asp Gly Val Glu Val His Asn Ala Lys Thr Lys Pro Arg Glu Glu
625                 630                 635                 640
```

| | | |
|---|---|---|
| cag tac aac agc acg tac cgt gtg gtc agc gtc ctc acc gtc ctg cac<br>Gln Tyr Asn Ser Thr Tyr Arg Val Val Ser Val Leu Thr Val Leu His<br>                                    645                            650                          655 | 1968 |
| cag gac tgg ctg aat ggc aag gag tac aag tgc aag gtc tcc aac aaa<br>Gln Asp Trp Leu Asn Gly Lys Glu Tyr Lys Cys Lys Val Ser Asn Lys<br>                660                          665                          670 | 2016 |
| gcc ctc cca gcc ccc atc gag aaa acc atc tcc aaa gcc aaa ggg cag<br>Ala Leu Pro Ala Pro Ile Glu Lys Thr Ile Ser Lys Ala Lys Gly Gln<br>                        675                          680                        685 | 2064 |
| ccc cga gaa cca cag gtg tac acc ctg ccc cca tcc cgg gag gag atg<br>Pro Arg Glu Pro Gln Val Tyr Thr Leu Pro Pro Ser Arg Glu Glu Met<br>690                                    695                          700 | 2112 |
| acc aag aac cag gtc agc ctg acc tgc ctg gtc aaa ggc ttc tat ccc<br>Thr Lys Asn Gln Val Ser Leu Thr Cys Leu Val Lys Gly Phe Tyr Pro<br>705                          710                          715                        720 | 2160 |
| agc gac atc gcc gtg gag tgg gag agc aat ggg cag ccg gag aac aac<br>Ser Asp Ile Ala Val Glu Trp Glu Ser Asn Gly Gln Pro Glu Asn Asn<br>                        725                          730                        735 | 2208 |
| tac aag acc acg cct ccc gtg ctg gac tcc gac ggc tcc ttc ttc ctc<br>Tyr Lys Thr Thr Pro Pro Val Leu Asp Ser Asp Gly Ser Phe Phe Leu<br>                740                          745                          750 | 2256 |
| tat agc aag ctc acc gtg gac aag agc agg tgg cag cag ggg aac gtc<br>Tyr Ser Lys Leu Thr Val Asp Lys Ser Arg Trp Gln Gln Gly Asn Val<br>                        755                          760                        765 | 2304 |
| ttc tca tgc tcc gtg atg cat gag gct ctg cac aac cac tac acg cag<br>Phe Ser Cys Ser Val Met His Glu Ala Leu His Asn His Tyr Thr Gln<br>770                                  775                          780 | 2352 |
| aag agc ctc tcc ctg tct ccg ggt aaa tga<br>Lys Ser Leu Ser Leu Ser Pro Gly Lys<br>785                                  790 | 2382 |

<210> SEQ ID NO 32
<211> LENGTH: 793
<212> TYPE: PRT
<213> ORGANISM: Homo sapiens

<400> SEQUENCE: 32

Met Val Trp Pro Ala Arg Leu Cys Gly Leu Trp Ala Leu Leu Leu Cys
 1               5                  10                  15

Ala Gly Gly Gly Gly Gly Gly Gly Ala Ala Pro Thr Glu Thr Gln
            20                  25                  30

Pro Pro Val Thr Asn Leu Ser Val Ser Val Glu Asn Leu Cys Thr Val
        35                  40                  45

Ile Trp Thr Trp Asn Pro Pro Glu Gly Ala Ser Ser Asn Cys Ser Leu
    50                  55                  60

Trp Tyr Phe Ser His Phe Gly Asp Lys Gln Asp Lys Lys Ile Ala Pro
65                  70                  75                  80

Glu Thr Arg Arg Ser Ile Glu Val Pro Leu Asn Glu Arg Ile Cys Leu
                85                  90                  95

Gln Val Gly Ser Gln Cys Ser Thr Asn Glu Ser Glu Lys Pro Ser Ile
            100                 105                 110

Leu Val Glu Lys Cys Ile Ser Pro Pro Glu Gly Asp Pro Glu Ser Ala
        115                 120                 125

Val Thr Glu Leu Gln Cys Ile Trp His Asn Leu Ser Tyr Met Lys Cys
    130                 135                 140

Ser Trp Leu Pro Gly Arg Asn Thr Ser Pro Asp Thr Asn Tyr Thr Leu
145                 150                 155                 160

```
Tyr Tyr Trp His Arg Ser Leu Glu Lys Ile His Gln Cys Glu Asn Ile
            165                 170                 175

Phe Arg Glu Gly Gln Tyr Phe Gly Cys Ser Phe Asp Leu Thr Lys Val
            180                 185                 190

Lys Asp Ser Ser Phe Glu Gln His Ser Val Gln Ile Met Val Lys Asp
            195                 200                 205

Asn Ala Gly Lys Ile Lys Pro Ser Phe Asn Ile Val Pro Leu Thr Ser
            210                 215                 220

Arg Val Lys Pro Asp Pro His Ile Lys Asn Leu Ser Phe His Asn
225                 230                 235                 240

Asp Asp Leu Tyr Val Gln Trp Glu Asn Pro Gln Asn Phe Ile Ser Arg
            245                 250                 255

Cys Leu Phe Tyr Glu Val Glu Val Asn Asn Ser Gln Thr Glu Thr His
            260                 265                 270

Asn Val Phe Tyr Val Gln Glu Ala Lys Cys Glu Asn Pro Glu Phe Glu
            275                 280                 285

Arg Asn Val Glu Asn Thr Ser Cys Phe Met Val Pro Gly Val Leu Pro
            290                 295                 300

Asp Thr Leu Asn Thr Val Arg Ile Arg Val Lys Thr Asn Lys Leu Cys
305                 310                 315                 320

Tyr Glu Asp Asp Lys Leu Trp Ser Asn Trp Ser Gln Glu Met Ser Ile
            325                 330                 335

Gly Lys Lys Arg Asn Ser Thr Gly Ala Pro Ser Gly Gly Gly Arg
            340                 345                 350

Pro Ala Ser Ser Gly Asn Met Lys Val Leu Gln Glu Pro Thr Cys Val
            355                 360                 365

Ser Asp Tyr Met Ser Ile Ser Thr Cys Glu Trp Lys Met Asn Gly Pro
            370                 375                 380

Thr Asn Cys Ser Thr Glu Leu Arg Leu Leu Tyr Gln Leu Val Phe Leu
385                 390                 395                 400

Leu Ser Glu Ala His Thr Cys Ile Pro Glu Asn Asn Gly Gly Ala Gly
            405                 410                 415

Cys Val Cys His Leu Leu Met Asp Asp Val Val Ser Ala Asp Asn Tyr
            420                 425                 430

Thr Leu Asp Leu Trp Ala Gly Gln Gln Leu Leu Trp Lys Gly Ser Phe
            435                 440                 445

Lys Pro Ser Glu His Val Lys Pro Arg Ala Pro Gly Asn Leu Thr Val
            450                 455                 460

His Thr Asn Val Ser Asp Thr Leu Leu Leu Thr Trp Ser Asn Pro Tyr
465                 470                 475                 480

Pro Pro Asp Asn Tyr Leu Tyr Asn His Leu Thr Tyr Ala Val Asn Ile
            485                 490                 495

Trp Ser Glu Asn Asp Pro Ala Asp Phe Arg Ile Tyr Asn Val Thr Tyr
            500                 505                 510

Leu Glu Pro Ser Leu Arg Ile Ala Ala Ser Thr Leu Lys Ser Gly Ile
            515                 520                 525

Ser Tyr Arg Ala Arg Val Arg Ala Trp Ala Gln Cys Tyr Asn Thr Thr
            530                 535                 540

Trp Ser Glu Trp Ser Pro Ser Thr Lys Trp His Asn Ser Tyr Arg Glu
545                 550                 555                 560

Pro Phe Glu Gln Ser Gly Asp Lys Thr His Thr Cys Pro Pro Cys Pro
            565                 570                 575

Ala Pro Glu Leu Leu Gly Gly Pro Ser Val Phe Leu Phe Pro Pro Lys
```

-continued

```
               580                 585                 590
Pro Lys Asp Thr Leu Met Ile Ser Arg Thr Pro Glu Val Thr Cys Val
        595                 600                 605
Val Val Asp Val Ser His Glu Asp Pro Glu Val Lys Phe Asn Trp Tyr
    610                 615                 620
Val Asp Gly Val Glu Val His Asn Ala Lys Thr Lys Pro Arg Glu Glu
625                 630                 635                 640
Gln Tyr Asn Ser Thr Tyr Arg Val Val Ser Val Leu Thr Val Leu His
                645                 650                 655
Gln Asp Trp Leu Asn Gly Lys Glu Tyr Lys Cys Lys Val Ser Asn Lys
            660                 665                 670
Ala Leu Pro Ala Pro Ile Glu Lys Thr Ile Ser Lys Ala Lys Gly Gln
        675                 680                 685
Pro Arg Glu Pro Gln Val Tyr Thr Leu Pro Pro Ser Arg Glu Glu Met
    690                 695                 700
Thr Lys Asn Gln Val Ser Leu Thr Cys Leu Val Lys Gly Phe Tyr Pro
705                 710                 715                 720
Ser Asp Ile Ala Val Glu Trp Glu Ser Asn Gly Gln Pro Glu Asn Asn
                725                 730                 735
Tyr Lys Thr Thr Pro Pro Val Leu Asp Ser Asp Gly Ser Phe Phe Leu
            740                 745                 750
Tyr Ser Lys Leu Thr Val Asp Lys Ser Arg Trp Gln Gln Gly Asn Val
        755                 760                 765
Phe Ser Cys Ser Val Met His Glu Ala Leu His Asn His Tyr Thr Gln
    770                 775                 780
Lys Ser Leu Ser Leu Ser Pro Gly Lys
785                 790
```

<210> SEQ ID NO 33
<211> LENGTH: 2703
<212> TYPE: DNA
<213> ORGANISM: Homo sapiens

<400> SEQUENCE: 33

```
atggtgttac tcagacttat ttgtttcata gctctactga tttcttctct ggaggctgat      60
aaatgcaagg aacgtgaaga aaaataatt ttagtgtcat ctgcaaatga aattgatgtt     120
cgtccctgtc ctcttaaccc aaatgaacac aaaggcacta aacttggta taaggatgac     180
agcaagacac ctgtatctac agaacaagcc tccaggattc atcaacacaa agagaaactt     240
tggtttgttc ctgctaaggt ggaggattca ggacattact attgcgtggt aagaaattca     300
tcttactgcc tcagaattaa aataagtgca aaatttgtgg agaatgagcc taacttatgt     360
tataatgcac aagccatatt taagcagaaa ctacccgttg caggagacgg aggacttgtg     420
tgcccttata tggagttttt taaaaatgaa aataatgagt acctaaaatt acagtggtat     480
aaggattgca aacctctact tcttgacaat atacacttta gtggagtcaa agataggctc     540
atcgtgatga atgtggctga aaagcataga gggaactata cttgtcatgc atcctacaca     600
tacttgggca agcaatatcc tattacccgg gtaatagaat ttattactct agaggaaaac     660
aaacccacaa ggcctgtgat tgtgagccca gctaatgaga caatggaagt agacttggga     720
tcccagatac aattgatctg taatgtcacc ggccagttga gtgacattgc ttactggaag     780
tggaatgggt cagtaattga tgaagatgac ccagtgctag ggaagactat tacagtgtg      840
gaaaatcctg caaacaaaag aaggagtacc ctcatcacag tgcttaatat atcggaaatt     900
```

-continued

```
gagagtagat tttataaaca tccatttacc tgttttgcca agaatacaca tggtatagat      960
gcagcatata tccagttaat atatccagtc actaattcag aacgctgcga tgactgggga     1020
ctagacacca tgaggcaaat ccaagtgttt gaagatgagc cagctcgcat caagtgccca     1080
ctctttgaac acttcttgaa attcaactac agcacagccc attcagctgg ccttactctg     1140
atctggtatt ggactaggca ggaccgggac cttgaggagc caattaactt ccgcctcccc     1200
gagaaccgca ttagtaagga gaaagatgtg ctgtggttcc ggcccactct cctcaatgac     1260
actggcaact ataccctgca gttaaggaac actacatatt gcagcaaagt tgcatttccc     1320
ttggaagttg ttcaaaaaga cagctgtttc aattccccca tgaaactccc agtgcataaa     1380
ctgtatatag aatatggcat tcagaggatc acttgtccaa atgtagatgg atattttcct     1440
tccagtgtca aaccgactat cacttggtat atgggctgtt ataaaataca gaattttaat     1500
aatgtaatac ccgaaggtat gaacttgagt ttcctcattg ccttaatttc aaataatgga     1560
aattacacat gtgttgttac atatccagaa aatggacgta cgtttcatct caccaggact     1620
ctgactgtaa aggtagtagg ctctccaaaa aatgcagtgc ccctgtgat ccattcacct      1680 aatgatcatg tggtctatga gaaagaacca ggagaggagc tactcattcc ctgtacggtc     1740
tattttagtt ttctgatgga ttctcgcaat gaggtttggt ggaccattga tggaaaaaaa     1800
cctgatgaca tcactattga tgtcaccatt aacgaaagta taagtcatag tagaacagaa     1860
gatgaaacaa gaactcagat tttgagcatc aagaaagtta cctctgagga tctcaagcgc     1920
agctatgtct gtcatgctag aagtgccaaa ggcgaagttg ccaaagcagc caaggtgaag     1980
cagaaagtgc cagctccaag atacacagtg gaatccggag acaaaactca cacatgccca     2040
ccgtgcccag cacctgaact cctgggggga ccgtcagtct tcctcttccc cccaaaaccc     2100
aaggacaccc tcatgatctc ccggacccct gaggtcacat gcgtggtggt ggacgtgagc     2160
cacgaagacc ctgaggtcaa gttcaactgg tacgtggacg gcgtggaggt gcataatgcc     2220
aagacaaagc cgcgggagga gcagtacaac agcacgtacc gtgtggtcag cgtcctcacc     2280
gtcctgcacc aggactggct gaatggcaag gagtacaagt gcaaggtctc caacaaagcc     2340
ctcccagccc ccatcgagaa aaccatctcc aaagccaaag ggcagccccg agaaccacag     2400
gtgtacaccc tgcccccatc ccgggaggag atgaccaaga accaggtcag cctgacctgc     2460
ctggtcaaag gcttctatcc cagcgacatc gccgtggagt gggagagcaa tgggcagccg     2520
gagaacaact acaagaccac gcctcccgtg ctggactccg acggctcctt cttcctctat     2580
agcaagctca ccgtggacaa gagcaggtgg cagcagggga acgtcttctc atgctccgtg     2640
atgcatgagg ctctgcacaa ccactacacg cagaagagcc tctccctgtc tccgggtaaa     2700
tga                                                                   2703
```

<210> SEQ ID NO 34
<211> LENGTH: 900
<212> TYPE: PRT
<213> ORGANISM: Homo sapiens

<400> SEQUENCE: 34

```
Met Val Leu Leu Arg Leu Ile Cys Phe Ile Ala Leu Leu Ile Ser Ser
  1               5                  10                  15

Leu Glu Ala Asp Lys Cys Lys Glu Arg Glu Glu Lys Ile Ile Leu Val
                 20                  25                  30

Ser Ser Ala Asn Glu Ile Asp Val Arg Pro Cys Pro Leu Asn Pro Asn
         35                  40                  45
```

-continued

```
Glu His Lys Gly Thr Ile Thr Trp Tyr Lys Asp Asp Ser Lys Thr Pro
 50                  55                  60

Val Ser Thr Glu Gln Ala Ser Arg Ile His Gln His Lys Glu Lys Leu
 65                  70                  75                  80

Trp Phe Val Pro Ala Lys Val Glu Asp Ser Gly His Tyr Tyr Cys Val
                 85                  90                  95

Val Arg Asn Ser Ser Tyr Cys Leu Arg Ile Lys Ile Ser Ala Lys Phe
                100                 105                 110

Val Glu Asn Glu Pro Asn Leu Cys Tyr Asn Ala Gln Ala Ile Phe Lys
                115                 120                 125

Gln Lys Leu Pro Val Ala Gly Asp Gly Leu Val Cys Pro Tyr Met
130                 135                 140

Glu Phe Phe Lys Asn Glu Asn Asn Glu Leu Pro Lys Leu Gln Trp Tyr
145                 150                 155                 160

Lys Asp Cys Lys Pro Leu Leu Leu Asp Asn Ile His Phe Ser Gly Val
                165                 170                 175

Lys Asp Arg Leu Ile Val Met Asn Val Ala Glu Lys His Arg Gly Asn
                180                 185                 190

Tyr Thr Cys His Ala Ser Tyr Thr Tyr Leu Gly Lys Gln Tyr Pro Ile
                195                 200                 205

Thr Arg Val Ile Glu Phe Ile Thr Leu Glu Glu Asn Lys Pro Thr Arg
210                 215                 220

Pro Val Ile Val Ser Pro Ala Asn Glu Thr Met Glu Val Asp Leu Gly
225                 230                 235                 240

Ser Gln Ile Gln Leu Ile Cys Asn Val Thr Gly Gln Leu Ser Asp Ile
                245                 250                 255

Ala Tyr Trp Lys Trp Asn Gly Ser Val Ile Asp Glu Asp Pro Val
                260                 265                 270

Leu Gly Glu Asp Tyr Tyr Ser Val Glu Asn Pro Ala Asn Lys Arg Arg
                275                 280                 285

Ser Thr Leu Ile Thr Val Leu Asn Ile Ser Glu Ile Glu Ser Arg Phe
290                 295                 300

Tyr Lys His Pro Phe Thr Cys Phe Ala Lys Asn Thr His Gly Ile Asp
305                 310                 315                 320

Ala Ala Tyr Ile Gln Leu Ile Tyr Pro Val Thr Asn Ser Glu Arg Cys
                325                 330                 335

Asp Asp Trp Gly Leu Asp Thr Met Arg Gln Ile Gln Val Phe Glu Asp
                340                 345                 350

Glu Pro Ala Arg Ile Lys Cys Pro Leu Phe Glu His Phe Leu Lys Phe
                355                 360                 365

Asn Tyr Ser Thr Ala His Ser Ala Gly Leu Thr Leu Ile Trp Tyr Trp
370                 375                 380

Thr Arg Gln Asp Arg Asp Leu Glu Glu Pro Ile Asn Phe Arg Leu Pro
385                 390                 395                 400

Glu Asn Arg Ile Ser Lys Glu Lys Asp Val Leu Trp Phe Arg Pro Thr
                405                 410                 415

Leu Leu Asn Asp Thr Gly Asn Tyr Thr Cys Met Leu Arg Asn Thr Thr
                420                 425                 430

Tyr Cys Ser Lys Val Ala Phe Pro Leu Glu Val Gln Lys Asp Ser
                435                 440                 445

Cys Phe Asn Ser Pro Met Lys Leu Pro Val His Lys Leu Tyr Ile Glu
450                 455                 460

Tyr Gly Ile Gln Arg Ile Thr Cys Pro Asn Val Asp Gly Tyr Phe Pro
```

```
                465                 470                 475                 480
Ser Ser Val Lys Pro Thr Ile Thr Trp Tyr Met Gly Cys Tyr Lys Ile
                    485                 490                 495

Gln Asn Phe Asn Asn Val Ile Pro Glu Gly Met Asn Leu Ser Phe Leu
                500                 505                 510

Ile Ala Leu Ile Ser Asn Asn Gly Asn Tyr Thr Cys Val Val Thr Tyr
                515                 520                 525

Pro Glu Asn Gly Arg Thr Phe His Leu Thr Arg Thr Leu Thr Val Lys
            530                 535                 540

Val Val Gly Ser Pro Lys Asn Ala Val Pro Pro Val Ile His Ser Pro
545                 550                 555                 560

Asn Asp His Val Val Tyr Glu Lys Glu Pro Gly Glu Glu Leu Leu Ile
                565                 570                 575

Pro Cys Thr Val Tyr Phe Ser Phe Leu Met Asp Ser Arg Asn Glu Val
                580                 585                 590

Trp Trp Thr Ile Asp Gly Lys Lys Pro Asp Asp Ile Thr Ile Asp Val
                595                 600                 605

Thr Ile Asn Glu Ser Ile Ser His Ser Arg Thr Glu Asp Glu Thr Arg
            610                 615                 620

Thr Gln Ile Leu Ser Ile Lys Lys Val Thr Ser Glu Asp Leu Lys Arg
625                 630                 635                 640

Ser Tyr Val Cys His Ala Arg Ser Ala Lys Gly Glu Val Ala Lys Ala
                    645                 650                 655

Ala Lys Val Lys Gln Lys Val Pro Ala Pro Arg Tyr Thr Val Glu Ser
                660                 665                 670

Gly Asp Lys Thr His Thr Cys Pro Pro Cys Pro Ala Pro Glu Leu Leu
            675                 680                 685

Gly Gly Pro Ser Val Phe Leu Phe Pro Pro Lys Pro Lys Asp Thr Leu
        690                 695                 700

Met Ile Ser Arg Thr Pro Glu Val Thr Cys Val Val Val Asp Val Ser
705                 710                 715                 720

His Glu Asp Pro Glu Val Lys Phe Asn Trp Tyr Val Asp Gly Val Glu
                725                 730                 735

Val His Asn Ala Lys Thr Lys Pro Arg Glu Glu Gln Tyr Asn Ser Thr
            740                 745                 750

Tyr Arg Val Val Ser Val Leu Thr Val Leu His Gln Asp Trp Leu Asn
        755                 760                 765

Gly Lys Glu Tyr Lys Cys Lys Val Ser Asn Lys Ala Leu Pro Ala Pro
    770                 775                 780

Ile Glu Lys Thr Ile Ser Lys Ala Lys Gly Gln Pro Arg Glu Pro Gln
785                 790                 795                 800

Val Tyr Thr Leu Pro Pro Ser Arg Glu Glu Met Thr Lys Asn Gln Val
                805                 810                 815

Ser Leu Thr Cys Leu Val Lys Gly Phe Tyr Pro Ser Asp Ile Ala Val
            820                 825                 830

Glu Trp Glu Ser Asn Gly Gln Pro Glu Asn Asn Tyr Lys Thr Thr Pro
        835                 840                 845

Pro Val Leu Asp Ser Asp Gly Ser Phe Phe Leu Tyr Ser Lys Leu Thr
    850                 855                 860

Val Asp Lys Ser Arg Trp Gln Gln Gly Asn Val Phe Ser Cys Ser Val
865                 870                 875                 880

Met His Glu Ala Leu His Asn His Tyr Thr Gln Lys Ser Leu Ser Leu
                885                 890                 895
```

Ser Pro Gly Lys
        900

<210> SEQ ID NO 35
<211> LENGTH: 2709
<212> TYPE: DNA
<213> ORGANISM: Homo sapiens

<400> SEQUENCE: 35

| | | | | | |
|---|---|---|---|---|---|
| atggtgttac | tcagacttat | ttgtttcata | gctctactga | tttcttctct | ggaggctgat | 60 |
| aaatgcaagg | aacgtgaaga | aaaaataatt | ttagtgtcat | ctgcaaatga | aattgatgtt | 120 |
| cgtccctgtc | ctcttaaccc | aaatgaacac | aaaggcacta | aacttggta | aaggatgac | 180 |
| agcaagacac | ctgtatctac | agaacaagcc | tccaggatta | tcaacacaa | agagaaactt | 240 |
| tggtttgttc | ctgctaaggt | ggaggattca | ggacattact | attgcgtggt | aagaaattca | 300 |
| tcttactgcc | tcagaattaa | aataagtgca | aaatttgtgg | agaatgagcc | taacttatgt | 360 |
| tataatgcac | aagccatatt | taagcagaaa | ctacccgttg | caggagacgg | aggacttgtg | 420 |
| tgcccttata | tggagttttt | taaaaatgaa | aataatgagt | tacctaaatt | acagtggtat | 480 |
| aaggattgca | aacctctact | tcttgacaat | atacacttta | gtggagtcaa | agataggctc | 540 |
| atcgtgatga | atgtggctga | aaagcataga | gggaactata | cttgtcatgc | atcctacaca | 600 |
| tacttgggca | agcaatatcc | tattacccgg | gtaatagaat | ttattactct | agaggaaaac | 660 |
| aaacccacaa | ggcctgtgat | tgtgagccca | gctaatgaga | caatggaagt | agacttggga | 720 |
| tcccagatac | aattgatctg | taatgtcacc | ggccagttga | gtgacattgc | ttactggaag | 780 |
| tggaatgggt | cagtaattga | tgaagatgac | ccagtgctag | ggaagactaa | ttacagtgtg | 840 |
| gaaaatcctg | caaacaaag | aaggagtacc | ctcatcacag | tgcttaatat | atcggaaatt | 900 |
| gagagtagat | tttataaaca | tccatttacc | tgttttgcca | agaatacaca | tggtatagat | 960 |
| gcagcatata | tccagttaat | atatccagtc | actaattcag | aacgctgcga | tgactgggga | 1020 |
| ctagacacca | tgaggcaaat | ccaagtgttt | gaagatgagc | cagctcgcat | caagtgccca | 1080 |
| ctctttgaac | acttcttgaa | attcaactac | agcacagccc | attcagctgg | ccttactctg | 1140 |
| atctggtatt | ggactaggca | ggaccgggac | cttgaggagc | caattaactt | ccgcctcccc | 1200 |
| gagaaccgca | ttagtaagga | aaagatgtg | ctgtggttcc | ggcccactct | cctcaatgac | 1260 |
| actggcaact | atacctgcat | gttaaggaac | actacatatt | gcagcaaagt | tgcatttccc | 1320 |
| ttggaagttg | ttcaaaaaga | cagctgtttc | aattcccca | tgaaactccc | agtgcataaa | 1380 |
| ctgtatatag | aatatggcat | tcagaggatc | acttgtccaa | atgtagatgg | atattttcct | 1440 |
| tccagtgtca | aaccgactat | cacttggtat | atgggctgtt | ataaaataca | gaattttaat | 1500 |
| aatgtaatac | ccgaaggtat | gaacttgagt | ttcctcattg | ccttaatttc | aaataatgga | 1560 |
| aattacacat | gtgttgttac | atatccagaa | aatggacgta | cgtttcatct | caccaggact | 1620 |
| ctgactgtaa | aggtagtagg | ctctccaaaa | aatgcagtgc | ccctgtgat | ccattcacct | 1680 |
| aatgatcatg | tggtctatga | aaagaaacca | ggagaggagc | tactcattcc | ctgtacggtc | 1740 |
| tattttagtt | ttctgatgga | ttctcgcaat | gaggtttggt | ggaccattga | tggaaaaaa | 1800 |
| cctgatgaca | tcactattga | tgtcaccatt | aacgaaagta | taagtcatag | tagaacgaaa | 1860 |
| gatgaaacaa | gaactcagat | tttgagcatc | aagaaagtta | cctctgagga | tctcaagcgc | 1920 |
| agctatgtct | gtcatgctag | aagtgccaaa | ggcgaagttc | caaagcagc | caaggtgaag | 1980 |
| cagaaagtgc | cagctccaag | atacacagtg | gaatccggag | agtccaaata | cggtccgcca | 2040 |

-continued

```
tgcccatcat gcccagcacc tgagttcctg gggggaccat cagtcttcct gttcccccca    2100
aaacccaagg acactctcat gatctcccgg acccctgagg tcacgtgcgt ggtggtggac    2160
gtgagccagg aagaccccga ggtccagttc aactggtacg tggatggcgt ggaggtgcat    2220
aatgccaaga caaagccgcg ggaggagcag ttcaacagca cgtaccgtgt ggtcagcgtc    2280
ctcaccgtcc tgcaccagga ctggctgaac ggcaaggagt acaagtgcaa ggtctccaac    2340
aaaggcctcc cgtcctccat cgagaaaacc atctccaaag ccaaagggca gccccgagag    2400
ccacaggtgt acaccctgcc cccatcccag gaggagatga ccaagaacca ggtcagcctg    2460
acctgcctgg tcaaaggctt ctaccccagc gacatcgccg tggagtggga gagcaatggg    2520
cagccggaga acaactacaa gaccacgcct cccgtgctgg actccgacgg ctccttcttc    2580
ctctacagca ggctaaccgt ggacaagagc aggtggcagg aggggaatgt cttctcatgc    2640
tccgtgatgc atgaggctct gcacaaccac tacacacaga gagcctctc cctgtctctg    2700 ggtaaatga                                                             2709
```

<210> SEQ ID NO 36
<211> LENGTH: 902
<212> TYPE: PRT
<213> ORGANISM: Homo sapiens

<400> SEQUENCE: 36

```
Met Val Leu Leu Arg Leu Ile Cys Phe Ile Ala Leu Leu Ile Ser Ser
 1               5                  10                  15

Leu Glu Ala Asp Lys Cys Lys Glu Arg Glu Glu Lys Ile Ile Leu Val
                20                  25                  30

Ser Ser Ala Asn Glu Ile Asp Val Arg Pro Cys Pro Leu Asn Pro Asn
            35                  40                  45

Glu His Lys Gly Thr Ile Thr Trp Tyr Lys Asp Asp Ser Lys Thr Pro
        50                  55                  60

Val Ser Thr Glu Gln Ala Ser Arg Ile His Gln His Lys Glu Lys Leu
65                  70                  75                  80

Trp Phe Val Pro Ala Lys Val Glu Asp Ser Gly His Tyr Tyr Cys Val
                85                  90                  95

Val Arg Asn Ser Ser Tyr Cys Leu Arg Ile Lys Ile Ser Ala Lys Phe
            100                 105                 110

Val Glu Asn Glu Pro Asn Leu Cys Tyr Asn Ala Gln Ala Ile Phe Lys
        115                 120                 125

Gln Lys Leu Pro Val Ala Gly Asp Gly Gly Leu Val Cys Pro Tyr Met
    130                 135                 140

Glu Phe Phe Lys Asn Glu Asn Asn Glu Leu Pro Lys Leu Gln Trp Tyr
145                 150                 155                 160

Lys Asp Cys Lys Pro Leu Leu Leu Asp Asn Ile His Phe Ser Gly Val
                165                 170                 175

Lys Asp Arg Leu Ile Val Met Asn Val Ala Glu Lys His Arg Gly Asn
            180                 185                 190

Tyr Thr Cys His Ala Ser Tyr Thr Tyr Leu Gly Lys Gln Tyr Pro Ile
        195                 200                 205

Thr Arg Val Ile Glu Phe Ile Thr Leu Glu Glu Asn Lys Pro Thr Arg
    210                 215                 220

Pro Val Ile Val Ser Pro Ala Asn Glu Thr Met Glu Val Asp Leu Gly
225                 230                 235                 240

Ser Gln Ile Gln Leu Ile Cys Asn Val Thr Gly Gln Leu Ser Asp Ile
```

-continued

```
                245                 250                 255
Ala Tyr Trp Lys Trp Asn Gly Ser Val Ile Asp Glu Asp Pro Val
            260                 265                 270

Leu Gly Glu Asp Tyr Tyr Ser Val Glu Asn Pro Ala Asn Lys Arg Arg
            275                 280                 285

Ser Thr Leu Ile Thr Val Leu Asn Ile Ser Glu Ile Glu Ser Arg Phe
            290                 295                 300

Tyr Lys His Pro Phe Thr Cys Phe Ala Lys Asn Thr His Gly Ile Asp
305                 310                 315                 320

Ala Ala Tyr Ile Gln Leu Ile Tyr Pro Val Thr Asn Ser Glu Arg Cys
                325                 330                 335

Asp Asp Trp Gly Leu Asp Thr Met Arg Gln Ile Gln Val Phe Glu Asp
            340                 345                 350

Glu Pro Ala Arg Ile Lys Cys Pro Leu Phe Glu His Phe Leu Lys Phe
            355                 360                 365

Asn Tyr Ser Thr Ala His Ser Ala Gly Leu Thr Leu Ile Trp Tyr Trp
            370                 375                 380

Thr Arg Gln Asp Arg Asp Leu Glu Glu Pro Ile Asn Phe Arg Leu Pro
385                 390                 395                 400

Glu Asn Arg Ile Ser Lys Glu Lys Asp Val Leu Trp Phe Arg Pro Thr
                405                 410                 415

Leu Leu Asn Asp Thr Gly Asn Tyr Thr Cys Met Leu Arg Asn Thr Thr
            420                 425                 430

Tyr Cys Ser Lys Val Ala Phe Pro Leu Glu Val Gln Lys Asp Ser
            435                 440                 445

Cys Phe Asn Ser Pro Met Lys Leu Pro Val His Lys Leu Tyr Ile Glu
450                 455                 460

Tyr Gly Ile Gln Arg Ile Thr Cys Pro Asn Val Asp Gly Tyr Phe Pro
465                 470                 475                 480

Ser Ser Val Lys Pro Thr Ile Thr Trp Tyr Met Gly Cys Tyr Lys Ile
                485                 490                 495

Gln Asn Phe Asn Asn Val Ile Pro Glu Gly Met Asn Leu Ser Phe Leu
            500                 505                 510

Ile Ala Leu Ile Ser Asn Asn Gly Asn Tyr Thr Cys Val Val Thr Tyr
            515                 520                 525

Pro Glu Asn Gly Arg Thr Phe His Leu Thr Arg Thr Leu Thr Val Lys
            530                 535                 540

Val Val Gly Ser Pro Lys Asn Ala Val Pro Pro Val Ile His Ser Pro
545                 550                 555                 560

Asn Asp His Val Val Tyr Glu Lys Glu Pro Gly Glu Glu Leu Leu Ile
                565                 570                 575

Pro Cys Thr Val Tyr Phe Ser Phe Leu Met Asp Ser Arg Asn Glu Val
            580                 585                 590

Trp Trp Thr Ile Asp Gly Lys Lys Pro Asp Asp Ile Thr Ile Asp Val
            595                 600                 605

Thr Ile Asn Glu Ser Ile Ser His Ser Arg Thr Glu Asp Glu Thr Arg
            610                 615                 620

Thr Gln Ile Leu Ser Ile Lys Lys Val Thr Ser Glu Asp Leu Lys Arg
625                 630                 635                 640

Ser Tyr Val Cys His Ala Arg Ser Ala Lys Gly Glu Val Ala Lys Ala
                645                 650                 655

Ala Lys Val Lys Gln Lys Val Pro Ala Pro Arg Tyr Thr Val Glu Ser
            660                 665                 670
```

Gly Glu Ser Lys Tyr Gly Pro Pro Cys Pro Ser Cys Pro Ala Pro Glu
        675                 680                 685

Phe Leu Gly Gly Pro Ser Val Phe Leu Phe Pro Pro Lys Pro Lys Asp
        690                 695                 700

Thr Leu Met Ile Ser Arg Thr Pro Glu Val Thr Cys Val Val Val Asp
705                 710                 715                 720

Val Ser Gln Glu Asp Pro Glu Val Gln Phe Asn Trp Tyr Val Asp Gly
                725                 730                 735

Val Glu Val His Asn Ala Lys Thr Lys Pro Arg Glu Glu Gln Phe Asn
            740                 745                 750

Ser Thr Tyr Arg Val Val Ser Val Leu Thr Val Leu His Gln Asp Trp
        755                 760                 765

Leu Asn Gly Lys Glu Tyr Lys Cys Lys Val Ser Asn Lys Gly Leu Pro
    770                 775                 780

Ser Ser Ile Glu Lys Thr Ile Ser Lys Ala Lys Gly Gln Pro Arg Glu
785                 790                 795                 800

Pro Gln Val Tyr Thr Leu Pro Pro Ser Gln Glu Glu Met Thr Lys Asn
                805                 810                 815

Gln Val Ser Leu Thr Cys Leu Val Lys Gly Phe Tyr Pro Ser Asp Ile
            820                 825                 830

Ala Val Glu Trp Glu Ser Asn Gly Gln Pro Glu Asn Asn Tyr Lys Thr
        835                 840                 845

Thr Pro Pro Val Leu Asp Ser Asp Gly Ser Phe Phe Leu Tyr Ser Arg
    850                 855                 860

Leu Thr Val Asp Lys Ser Arg Trp Gln Glu Gly Asn Val Phe Ser Cys
865                 870                 875                 880

Ser Val Met His Glu Ala Leu His Asn His Tyr Thr Gln Lys Ser Leu
                885                 890                 895

Ser Leu Ser Leu Gly Lys
            900

<210> SEQ ID NO 37
<211> LENGTH: 2709
<212> TYPE: DNA
<213> ORGANISM: Homo sapiens

<400> SEQUENCE: 37
atggtgttac tcagacttat ttgtttcata gctctactga tttcttctct ggaggctgat     60
aaatgcaagg aacgtgaaga aaaataatt ttagtgtcat ctgcaaatga aattgatgtt    120
cgtccctgtc ctcttaaccc aaatgaacac aaaggcacta aacttggta aaggatgac     180 agcaagacac ctgtatctac agaacaagcc tccaggattc atcaacacaa agagaaactt    240
tggtttgttc ctgctaaggt ggaggattca ggacattact attgcgtggt aagaaattca    300
tcttactgcc tcagaattaa aataagtgca aaatttgtgg agaatgagcc taacttatgt    360
tataatgcac aagccatatt taagcagaaa ctacccgttg caggagacgg aggacttgtg    420 tgccccttata tggagttttt taaaaatgaa ataatgagt acctaaaatt acagtggtat    480
aaggattgca aacctctact tcttgacaat atacacttta gtggagtcaa agataggctc    540
atcgtgatga atgtggctga aaagcataga gggaactata cttgtcatgc atcctacaca    600
tacttgggca agcaatatcc tattacccgg gtaatagaat ttattactct agaggaaaac    660
aaacccacaa ggcctgtgat tgtgagccca gctaatgaga caatggaagt agacttggga    720
tcccagatac aattgatctg taatgtcacc ggccagttga gtgacattgc ttactggaag    780

```
tggaatgggt cagtaattga tgaagatgac ccagtgctag gggaagacta ttacagtgtg      840
gaaaatcctg caaacaaaag aaggagtacc ctcatcacag tgcttaatat atcggaaatt      900
gagagtagat tttataaaca tccatttacc tgttttgcca agaatacaca tggtatagat      960
gcagcatata tccagttaat atatccagtc actaattcag aacgctgcga tgactgggga     1020
ctagacacca tgaggcaaat ccaagtgttt gaagatgagc cagctcgcat caagtgccca     1080
ctctttgaac acttcttgaa attcaactac agcacagccc attcagctgg ccttactctg     1140
atctggtatt ggactaggca ggaccgggac cttgaggagc caattaactt ccgcctcccc     1200
gagaaccgca ttagtaagga aaagatgtg  ctgtggttcc ggcccactct cctcaatgac     1260
actggcaact atacctgcat gttaaggaac actacatatt gcagcaaagt tgcatttccc     1320
ttggaagttg ttcaaaaaga cagctgtttc aattccccca tgaaactccc agtgcataaa     1380
ctgtatatag aatatggcat tcagaggatc acttgtccaa atgtagatgg atattttcct     1440
tccagtgtca aaccgactat cacttggtat atgggctgtt ataaaataca gaattttaat     1500
aatgtaatac ccgaaggtat gaacttgagt ttcctcattg ccttaatttc aaataatgga     1560
aattacacat gtgttgttac atatccagaa aatggacgta cgtttcatct caccaggact     1620
ctgactgtaa aggtagtagg ctctccaaaa aatgcagtgc cccctgtgat ccattcacct     1680
aatgatcatg tggtctatga gaaagaacca ggagaggagc tactcattcc ctgtacggtc     1740
tattttagtt ttctgatgga ttctcgcaat gaggtttggt ggaccattga tggaaaaaaa     1800
cctgatgaca tcactattga tgtcaccatt aacgaaagta taagtcatag tagaacagaa     1860
gatgaaacaa gaactcagat tttgagcatc aagaaagtta cctctgagga tctcaagcgc     1920
agctatgtct gtcatgctag aagtgccaaa ggcgaagttg ccaaagcagc caaggtgaag     1980
cagaaagtgc cagctccaag atacacagtg gaatccggag agtccaaata cggtccgcca     2040
tgcccaccat gcccagcacc tgagttcctg gggggaccat cagtcttcct gttcccccca     2100
aaacccaagg acactctcat gatctcccgg acccctgagg tcacgtgcgt ggtggtggac     2160
gtgagccagg aagaccccga ggtccagttc aactggtacg tggatggcgt ggaggtgcat     2220
aatgccaaga caaagccgcg ggaggagcag ttcaacagca cgtaccgtgt ggtcagcgtc     2280
ctcaccgtcc tgcaccagga ctggctgaac ggcaaggagt acaagtgcaa ggtctccaac     2340
aaaggcctcc cgtcctccat cgagaaaacc atctccaaag ccaaagggca gccccgagag     2400
ccacaggtgt acaccctgcc cccatcccag gaggagatga ccaagaacca ggtcagcctg     2460
acctgcctgg tcaaaggctt ctaccccagc gacatcgccg tggagtggga gagcaatggg     2520
cagccggaga acaactacaa gaccacgcct cccgtgctgg actccgacgg ctccttcttc     2580
ctctacagca ggctaaccgt ggacaagagc aggtggcagg aggggaatgt cttctcatgc     2640
tccgtgatgc atgaggctct gcacaaccac tacacacaga gagcctctcc ctgtctctg      2700 ggtaaatga                                                             2709
```

<210> SEQ ID NO 38
<211> LENGTH: 902
<212> TYPE: PRT
<213> ORGANISM: Homo sapiens

<400> SEQUENCE: 38

```
Met Val Leu Leu Arg Leu Ile Cys Phe Ile Ala Leu Leu Ile Ser Ser
 1               5                  10                  15

Leu Glu Ala Asp Lys Cys Lys Glu Arg Glu Glu Lys Ile Ile Leu Val
```

```
                  20                  25                  30
Ser Ser Ala Asn Glu Ile Asp Val Arg Pro Cys Pro Leu Asn Pro Asn
            35                  40                  45

Glu His Lys Gly Thr Ile Thr Trp Tyr Lys Asp Asp Ser Lys Thr Pro
        50                  55                  60

Val Ser Thr Glu Gln Ala Ser Arg Ile His Gln His Lys Glu Lys Leu
65                  70                  75                  80

Trp Phe Val Pro Ala Lys Val Glu Asp Ser Gly His Tyr Tyr Cys Val
                85                  90                  95

Val Arg Asn Ser Ser Tyr Cys Leu Arg Ile Lys Ile Ser Ala Lys Phe
            100                 105                 110

Val Glu Asn Glu Pro Asn Leu Cys Tyr Asn Ala Gln Ala Ile Phe Lys
        115                 120                 125

Gln Lys Leu Pro Val Ala Gly Asp Gly Gly Leu Val Cys Pro Tyr Met
        130                 135                 140

Glu Phe Phe Lys Asn Glu Asn Asn Glu Leu Pro Lys Leu Gln Trp Tyr
145                 150                 155                 160

Lys Asp Cys Lys Pro Leu Leu Leu Asp Asn Ile His Phe Ser Gly Val
                165                 170                 175

Lys Asp Arg Leu Ile Val Met Asn Val Ala Glu Lys His Arg Gly Asn
            180                 185                 190

Tyr Thr Cys His Ala Ser Tyr Thr Tyr Leu Gly Lys Gln Tyr Pro Ile
        195                 200                 205

Thr Arg Val Ile Glu Phe Ile Thr Leu Glu Glu Asn Lys Pro Thr Arg
210                 215                 220

Pro Val Ile Val Ser Pro Ala Asn Glu Thr Met Glu Val Asp Leu Gly
225                 230                 235                 240

Ser Gln Ile Gln Leu Ile Cys Asn Val Thr Gly Gln Leu Ser Asp Ile
                245                 250                 255

Ala Tyr Trp Lys Trp Asn Gly Ser Val Ile Asp Glu Asp Asp Pro Val
            260                 265                 270

Leu Gly Glu Asp Tyr Tyr Ser Val Glu Asn Pro Ala Asn Lys Arg Arg
        275                 280                 285

Ser Thr Leu Ile Thr Val Leu Asn Ile Ser Glu Ile Glu Ser Arg Phe
290                 295                 300

Tyr Lys His Pro Phe Thr Cys Phe Ala Lys Asn Thr His Gly Ile Asp
305                 310                 315                 320

Ala Ala Tyr Ile Gln Leu Ile Tyr Pro Val Thr Asn Ser Glu Arg Cys
                325                 330                 335

Asp Asp Trp Gly Leu Asp Thr Met Arg Gln Ile Gln Val Phe Glu Asp
            340                 345                 350

Glu Pro Ala Arg Ile Lys Cys Pro Leu Phe Glu His Phe Leu Lys Phe
        355                 360                 365

Asn Tyr Ser Thr Ala His Ser Ala Gly Leu Thr Leu Ile Trp Tyr Trp
        370                 375                 380

Thr Arg Gln Asp Arg Asp Leu Glu Glu Pro Ile Asn Phe Arg Leu Pro
385                 390                 395                 400

Glu Asn Arg Ile Ser Lys Glu Lys Asp Val Leu Trp Phe Arg Pro Thr
                405                 410                 415

Leu Leu Asn Asp Thr Gly Asn Tyr Thr Cys Met Leu Arg Asn Thr Thr
            420                 425                 430

Tyr Cys Ser Lys Val Ala Phe Pro Leu Glu Val Val Gln Lys Asp Ser
        435                 440                 445
```

```
Cys Phe Asn Ser Pro Met Lys Leu Pro Val His Lys Leu Tyr Ile Glu
    450                 455                 460
Tyr Gly Ile Gln Arg Ile Thr Cys Pro Asn Val Asp Gly Tyr Phe Pro
465                 470                 475                 480
Ser Ser Val Lys Pro Thr Ile Thr Trp Tyr Met Gly Cys Tyr Lys Ile
                485                 490                 495
Gln Asn Phe Asn Asn Val Ile Pro Glu Gly Met Asn Leu Ser Phe Leu
                500                 505                 510
Ile Ala Leu Ile Ser Asn Asn Gly Asn Tyr Thr Cys Val Val Thr Tyr
                515                 520                 525
Pro Glu Asn Gly Arg Thr Phe His Leu Thr Arg Thr Leu Thr Val Lys
    530                 535                 540
Val Val Gly Ser Pro Lys Asn Ala Val Pro Pro Val Ile His Ser Pro
545                 550                 555                 560
Asn Asp His Val Val Tyr Glu Lys Glu Pro Gly Glu Glu Leu Leu Ile
                565                 570                 575
Pro Cys Thr Val Tyr Phe Ser Phe Leu Met Asp Ser Arg Asn Glu Val
            580                 585                 590
Trp Trp Thr Ile Asp Gly Lys Lys Pro Asp Asp Ile Thr Ile Asp Val
            595                 600                 605
Thr Ile Asn Glu Ser Ile Ser His Ser Arg Thr Glu Asp Glu Thr Arg
    610                 615                 620
Thr Gln Ile Leu Ser Ile Lys Lys Val Thr Ser Glu Asp Leu Lys Arg
625                 630                 635                 640
Ser Tyr Val Cys His Ala Arg Ser Ala Lys Gly Glu Val Ala Lys Ala
                645                 650                 655
Ala Lys Val Lys Gln Lys Val Pro Ala Pro Arg Tyr Thr Val Glu Ser
                660                 665                 670
Gly Glu Ser Lys Tyr Gly Pro Pro Cys Pro Pro Cys Pro Ala Pro Glu
                675                 680                 685
Phe Leu Gly Gly Pro Ser Val Phe Leu Phe Pro Pro Lys Pro Lys Asp
    690                 695                 700
Thr Leu Met Ile Ser Arg Thr Pro Glu Val Thr Cys Val Val Val Asp
705                 710                 715                 720
Val Ser Gln Glu Asp Pro Glu Val Gln Phe Asn Trp Tyr Val Asp Gly
                725                 730                 735
Val Glu Val His Asn Ala Lys Thr Lys Pro Arg Glu Glu Gln Phe Asn
                740                 745                 750
Ser Thr Tyr Arg Val Val Ser Val Leu Thr Val Leu His Gln Asp Trp
                755                 760                 765
Leu Asn Gly Lys Glu Tyr Lys Cys Lys Val Ser Asn Lys Gly Leu Pro
    770                 775                 780
Ser Ser Ile Glu Lys Thr Ile Ser Lys Ala Lys Gly Gln Pro Arg Glu
785                 790                 795                 800
Pro Gln Val Tyr Thr Leu Pro Pro Ser Gln Glu Glu Met Thr Lys Asn
                805                 810                 815
Gln Val Ser Leu Thr Cys Leu Val Lys Gly Phe Tyr Pro Ser Asp Ile
                820                 825                 830
Ala Val Glu Trp Glu Ser Asn Gly Gln Pro Glu Asn Asn Tyr Lys Thr
                835                 840                 845
Thr Pro Pro Val Leu Asp Ser Asp Gly Ser Phe Phe Leu Tyr Ser Arg
    850                 855                 860
```

```
Leu Thr Val Asp Lys Ser Arg Trp Gln Glu Gly Asn Val Phe Ser Cys
865                 870                 875                 880

Ser Val Met His Glu Ala Leu His Asn His Tyr Thr Gln Lys Ser Leu
            885                 890                 895

Ser Leu Ser Leu Gly Lys
            900

<210> SEQ ID NO 39
<211> LENGTH: 2703
<212> TYPE: DNA
<213> ORGANISM: Homo sapiens

<400> SEQUENCE: 39
atggtgcttc tgtggtgtgt agtgagtctc tacttttatg gaatcctgca aagtgatgcc      60
tcagaacgct gcgatgactg gggactagac accatgaggc aaatccaagt gtttgaagat     120
gagccagctc gcatcaagtg cccactcttt gaacacttct tgaaattcaa ctacagcaca     180
gcccattcag ctggccttac tctgatctgg tattggacta ggcaggaccg ggaccttgag     240
gagccaatta acttccgcct ccccgagaac cgcattagta aggagaaaga tgtgctgtgg     300
ttccggccca ctctcctcaa tgacactggc aactataccc gcatgttaag gaacactaca     360
tattgcagca agttgcatt tcccttggaa gttgttcaaa aagacagctg tttcaattcc     420
cccatgaaac tcccagtgca taaactgtat atagaatatg gcattcagag gatcacttgt     480
ccaaatgtag atggatattt tccttccagt gtcaaaccga ctatcacttg gtatatgggc     540
tgttataaaa tacagaattt taataatgta atacccgaag gtatgaactt gagtttcctc     600
attgccttaa tttcaaataa tggaaattac acatgtgttg ttacatatcc agaaaatgga     660
cgtacgtttc atctcaccag gactctgact gtaaaggtag taggctctcc aaaaaatgca     720
gtgccccctg tgatccattc acctaatgat catgtggtct atgagaaaga accaggagag     780
gagctactca ttccctgtac ggtctatttt agttttctga tggattctcg caatgaggtt     840
tggtggacca ttgatggaaa aaaacctgat gacatcacta ttgatgtcac cattaacgaa     900
agtataagtc atagtagaac agaagatgaa acaagaactc agattttgag catcaagaaa     960
gttacctctg aggatctcaa gcgcagctat gtctgtcatg ctagaagtgc caaaggcgaa    1020
gttgccaaag cagccaaggt gaagcagaaa gtgccagctc aagatacac agtgaaaaa    1080 tgcaaggaac gtgaagaaaa aataattta gtgagctcag caaatgaaat cgatgttcgt    1140
ccctgtcctc ttaacccaaa tgaacacaaa ggcactataa cttggtataa ggatgacagc    1200
aagacacctg tatctacaga acaagcctcc aggattcatc aacacaaaga gaaactttgg    1260
tttgttcctg ctaaggtgga ggattcagga cattactatt gcgtggtaag aaattcatct    1320
tactgcctca gaattaaaat aagtgcaaaa tttgtggaga atgagcctaa cttatgttat    1380
aatgcacaag ccatatttaa gcagaaacta cccgttgcag agacggagg acttgtgtgc    1440 ccttatatgg agttttttaa aaatgaaaat aatgagttac taaattaca gtggtataag    1500 gattgcaaac ctctacttct tgacaatata cactttagtg gagtcaaaga taggctcatc    1560
gtgatgaatg tggctgaaaa gcatagaggg aactatactt gtcatgcatc ctacacatac    1620
ttgggcaagc aatatcctat tacccgggta atagaattta ttactctaga ggaaacaaaa    1680
cccacaaggc ctgtgattgt gagcccagct aatgagacaa tggaagtaga cttgggatcc    1740
cagatacaat tgatctgtaa tgtcaccggc cagttgagtg acattgctta ctggaagtgg    1800
aatgggtcag taattgatga agatgaccca gtgctagggg aagactatta cagtgtggaa    1860
```

-continued

```
aatcctgcaa acaaagaag gagtaccctc atcacagtgc ttaatatatc ggaaattgag    1920
agtagatttt ataaacatcc atttacctgt tttgccaaga atacacatgg tatagatgca    1980
gcatatatcc agttaatata tccagtcact aattccggag acaaaactca cacatgccca    2040
ccgtgcccag cacctgaact cctgggggga ccgtcagtct tcctcttccc cccaaaaccc    2100
aaggacaccc tcatgatctc ccggacccct gaggtcacat gcgtggtggt ggacgtgagc    2160
cacgaagacc ctgaggtcaa gttcaactgg tacgtggacg gcgtggaggt gcataatgcc    2220
aagacaaagc cgcgggagga gcagtacaac agcacgtacc gtgtggtcag cgtcctcacc    2280
gtcctgcacc aggactggct gaatggcaag gagtacaagt gcaaggtctc caacaaagcc    2340
ctcccagccc ccatcgagaa aaccatctcc aaagccaaag gcagccccg agaaccacag    2400 gtgtacaccc tgcccccatc ccgggatgag ctgaccaaga accaggtcag cctgacctgc    2460
ctggtcaaag gcttctatcc agcgacatc gccgtggagt gggagagcaa tgggcagccg    2520
gagaacaact acaagaccac gcctcccgtg ctggactccg acggctcctt cttcctctac    2580
agcaagctca ccgtggacaa gagcaggtgg cagcagggga acgtcttctc atgctccgtg    2640
atgcatgagg ctctgcacaa ccactacacg cagaagagcc tctccctgtc tccgggtaaa    2700
tga                                                                  2703
```

<210> SEQ ID NO 40
<211> LENGTH: 900
<212> TYPE: PRT
<213> ORGANISM: Homo sapiens

<400> SEQUENCE: 40

```
Met Val Leu Leu Trp Cys Val Val Ser Leu Tyr Phe Tyr Gly Ile Leu
 1               5                  10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220
```

```
Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
            245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
    290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350

Ala Pro Arg Tyr Thr Val Glu Lys Cys Lys Glu Arg Glu Glu Lys Ile
            355                 360                 365

Ile Leu Val Ser Ser Ala Asn Glu Ile Asp Val Arg Pro Cys Pro Leu
        370                 375                 380

Asn Pro Asn Glu His Lys Gly Thr Ile Thr Trp Tyr Lys Asp Asp Ser
385                 390                 395                 400

Lys Thr Pro Val Ser Thr Glu Gln Ala Ser Arg Ile His Gln His Lys
                405                 410                 415

Glu Lys Leu Trp Phe Val Pro Ala Lys Val Glu Asp Ser Gly His Tyr
            420                 425                 430

Tyr Cys Val Val Arg Asn Ser Ser Tyr Cys Leu Arg Ile Lys Ile Ser
        435                 440                 445

Ala Lys Phe Val Glu Asn Glu Pro Asn Leu Cys Tyr Asn Ala Gln Ala
    450                 455                 460

Ile Phe Lys Gln Lys Leu Pro Val Ala Gly Asp Gly Gly Leu Val Cys
465                 470                 475                 480

Pro Tyr Met Glu Phe Phe Lys Asn Glu Asn Asn Glu Leu Pro Lys Leu
                485                 490                 495

Gln Trp Tyr Lys Asp Cys Lys Pro Leu Leu Leu Asp Asn Ile His Phe
            500                 505                 510

Ser Gly Val Lys Asp Arg Leu Ile Val Met Asn Val Ala Glu Lys His
        515                 520                 525

Arg Gly Asn Tyr Thr Cys His Ala Ser Tyr Thr Tyr Leu Gly Lys Gln
    530                 535                 540

Tyr Pro Ile Thr Arg Val Ile Glu Phe Ile Thr Leu Glu Glu Asn Lys
545                 550                 555                 560

Pro Thr Arg Pro Val Ile Val Ser Pro Ala Asn Glu Thr Met Glu Val
                565                 570                 575

Asp Leu Gly Ser Gln Ile Gln Leu Ile Cys Asn Val Thr Gly Gln Leu
            580                 585                 590

Ser Asp Ile Ala Tyr Trp Lys Trp Asn Gly Ser Val Ile Asp Glu Asp
        595                 600                 605

Asp Pro Val Leu Gly Glu Asp Tyr Tyr Ser Val Glu Asn Pro Ala Asn
    610                 615                 620

Lys Arg Arg Ser Thr Leu Ile Thr Val Leu Asn Ile Ser Glu Ile Glu
625                 630                 635                 640
```

```
Ser Arg Phe Tyr Lys His Pro Phe Thr Cys Phe Ala Lys Asn Thr His
                645                 650                 655
Gly Ile Asp Ala Ala Tyr Ile Gln Leu Ile Tyr Pro Val Thr Asn Ser
            660                 665                 670
Gly Asp Lys Thr His Thr Cys Pro Pro Cys Pro Ala Pro Glu Leu Leu
        675                 680                 685
Gly Gly Pro Ser Val Phe Leu Phe Pro Pro Lys Pro Lys Asp Thr Leu
    690                 695                 700
Met Ile Ser Arg Thr Pro Glu Val Thr Cys Val Val Val Asp Val Ser
705                 710                 715                 720
His Glu Asp Pro Glu Val Lys Phe Asn Trp Tyr Val Asp Gly Val Glu
                725                 730                 735
Val His Asn Ala Lys Thr Lys Pro Arg Glu Glu Gln Tyr Asn Ser Thr
            740                 745                 750
Tyr Arg Val Val Ser Val Leu Thr Val Leu His Gln Asp Trp Leu Asn
        755                 760                 765
Gly Lys Glu Tyr Lys Cys Lys Val Ser Asn Lys Ala Leu Pro Ala Pro
    770                 775                 780
Ile Glu Lys Thr Ile Ser Lys Ala Lys Gly Gln Pro Arg Glu Pro Gln
785                 790                 795                 800
Val Tyr Thr Leu Pro Pro Ser Arg Asp Glu Leu Thr Lys Asn Gln Val
                805                 810                 815
Ser Leu Thr Cys Leu Val Lys Gly Phe Tyr Pro Ser Asp Ile Ala Val
            820                 825                 830
Glu Trp Glu Ser Asn Gly Gln Pro Glu Asn Asn Tyr Lys Thr Thr Pro
        835                 840                 845
Pro Val Leu Asp Ser Asp Gly Ser Phe Phe Leu Tyr Ser Lys Leu Thr
    850                 855                 860
Val Asp Lys Ser Arg Trp Gln Gln Gly Asn Val Phe Ser Cys Ser Val
865                 870                 875                 880
Met His Glu Ala Leu His Asn His Tyr Thr Gln Lys Ser Leu Ser Leu
                885                 890                 895
Ser Pro Gly Lys
            900

<210> SEQ ID NO 41
<211> LENGTH: 2709
<212> TYPE: DNA
<213> ORGANISM: Homo sapiens

<400> SEQUENCE: 41
atggtgcttc tgtggtgtgt agtgagtctc tactttatg gaatcctgca aagtgatgcc      60
tcagaacgct gcgatgactg gggactagac accatgaggc aaatccaagt gtttgaagat     120
gagccagctc gcatcaagtg cccactcttt gaacacttct tgaaattcaa ctacagcaca     180
gcccattcag ctggccttac tctgatctgg tattggacta ggcaggaccg ggaccttgag     240
gagccaatta acttccgcct ccccgagaac cgcattagta aggagaaaga tgtgctgtgg     300
ttccggccca ctctcctcaa tgacactggc aactatacct gcatgttaag gaacactaca     360
tattgcagca agttgcatt tcccttggaa gttgttcaaa aagacagctg tttcaattcc     420
cccatgaaac tcccagtgca taaactgtat atagaatatg gcattcagag gatcacttgt     480
ccaaatgtag atggatattt tccttccagt gtcaaaccga ctatcacttg gtatatgggc     540
tgttataaaa tacagaattt taataatgta atacccgaag gtatgaactt gagtttcctc     600
```

```
attgccttaa tttcaaataa tggaaattac acatgtgttg ttacatatcc agaaaatgga    660
cgtacgtttc atctcaccag gactctgact gtaaaggtag taggctctcc aaaaaatgca    720 gtgcccctg tgatccattc acctaatgat catgtggtct atgagaaaga accaggagag     780
gagctactca ttccctgtac ggtctatttt agttttctga tggattctcg caatgaggtt    840
tggtggacca ttgatggaaa aaaacctgat gacatcacta ttgatgtcac cattaacgaa    900
agtataagtc atagtagaac agaagatgaa acaagaactc agattttgag catcaagaaa    960
gttacctctg aggatctcaa gcgcagctat gtctgtcatg ctagaagtgc caaaggcgaa   1020
gttgccaaag cagccaaggt gaagcagaaa gtgccagctc aagatacac agtggaaaaa    1080 tgcaaggaac gtgaagaaaa ataattttta gtgagctcag caaatgaaat cgatgttcgt   1140
ccctgtcctc ttaacccaaa tgaacacaaa ggcactataa cttggtataa ggatgacagc   1200
aagacacctg tatctacaga acaagcctcc aggattcatc aacacaaaga gaaactttgg   1260
tttgttcctg ctaaggtgga ggattcagga cattactatt gcgtggtaag aaattcatct   1320
tactgcctca gaattaaaat aagtgcaaaa tttgtggaga atgagcctaa cttatgttat   1380
aatgcacaag ccatatttaa gcagaaacta cccgttgcag gagacggagg acttgtgtgc   1440
ccttatatgg agttttttaa aaatgaaaat aatgagttac ctaaattaca gtggtataag   1500
gattgcaaac ctctacttct tgacaatata cactttagtg gagtcaaaga taggctcatc   1560
gtgatgaatg tggctgaaaa gcatagaggg aactatactt gtcatgcatc ctacacatac   1620
ttgggcaagc aatatcctat tacccgggta atagaattta ttactctaga ggaaaacaaa   1680
cccacaaggc ctgtgattgt gagcccagct aatgagacaa tggaagtaga cttgggatcc   1740
cagatacaat tgatctgtaa tgtcaccggc cagttgagtg acattgctta ctggaagtgg   1800
aatgggtcag taattgatga agatgaccca gtgctagggg aagactatta cagtgtggaa   1860
aatcctgcaa acaaaagaag gagtaccctc atcacagtgc ttaatatatc ggaaattgag   1920
agtagatttt ataaacatcc atttacctgt tttgccaaga atacacatgg tatagatgca   1980
gcatatatcc agttaatata tccagtcact aattccggag agtccaaata cggtccgcca   2040
tgcccatcat gcccagcacc tgagttcctg gggggaccat cagtcttcct gttcccccca   2100
aaacccaagg acactctcat gatctcccgg acccctgagg tcacgtgcgt ggtggtggac   2160
gtgagccagg aagaccccga ggtccagttc aactggtacg tggatggcgt ggaggtgcat   2220
aatgccaaga caaagccgcg ggaggagcag ttcaacagca cgtaccgtgt ggtcagcgtc   2280
ctcaccgtcc tgcaccagga ctggctgaac ggcaaggagt acaagtgcaa ggtctccaac   2340
aaaggcctcc cgtcctccat cgagaaaacc atctccaaag ccaaagggca gccccgagag   2400
ccacaggtgt acaccctgcc cccatcccag gaggagatga ccaagaacca ggtcagcctg   2460
acctgcctgg tcaaaggctt ctaccccagc gacatcgccg tggagtggga gagcaatggg   2520
cagccggaga caactacaa gaccacgcct cccgtgctgg actccgacgg ctccttcttc    2580
ctctacagca ggctaaccgt ggacaagagc aggtggcagg aggggaatgt cttctcatgc   2640
tccgtgatgc atgaggctct gcacaaccac tacacacaga gagcctctc cctgtctctg    2700 ggtaaatga                                                          2709
```

<210> SEQ ID NO 42
<211> LENGTH: 902
<212> TYPE: PRT
<213> ORGANISM: Homo sapiens
<400> SEQUENCE: 42

```
Met Val Leu Leu Trp Cys Val Val Ser Leu Tyr Phe Tyr Gly Ile Leu
 1               5                  10                  15

Gln Ser Asp Ala Ser Glu Arg Cys Asp Asp Trp Gly Leu Asp Thr Met
             20                  25                  30

Arg Gln Ile Gln Val Phe Glu Asp Glu Pro Ala Arg Ile Lys Cys Pro
         35                  40                  45

Leu Phe Glu His Phe Leu Lys Phe Asn Tyr Ser Thr Ala His Ser Ala
     50                  55                  60

Gly Leu Thr Leu Ile Trp Tyr Trp Thr Arg Gln Asp Arg Asp Leu Glu
 65                  70                  75                  80

Glu Pro Ile Asn Phe Arg Leu Pro Glu Asn Arg Ile Ser Lys Glu Lys
             85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
    290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350

Ala Pro Arg Tyr Thr Val Glu Lys Cys Lys Glu Arg Glu Glu Lys Ile
        355                 360                 365

Ile Leu Val Ser Ser Ala Asn Glu Ile Asp Val Arg Pro Cys Pro Leu
    370                 375                 380

Asn Pro Asn Glu His Lys Gly Thr Ile Thr Trp Tyr Lys Asp Asp Ser
385                 390                 395                 400

Lys Thr Pro Val Ser Thr Glu Gln Ala Ser Arg Ile His Gln His Lys
                405                 410                 415
```

-continued

```
Glu Lys Leu Trp Phe Val Pro Ala Lys Val Glu Asp Ser Gly His Tyr
            420                 425                 430
Tyr Cys Val Val Arg Asn Ser Ser Tyr Cys Leu Arg Ile Lys Ile Ser
        435                 440                 445
Ala Lys Phe Val Glu Asn Glu Pro Asn Leu Cys Tyr Asn Ala Gln Ala
    450                 455                 460
Ile Phe Lys Gln Lys Leu Pro Val Ala Gly Asp Gly Gly Leu Val Cys
465                 470                 475                 480
Pro Tyr Met Glu Phe Phe Lys Asn Glu Asn Glu Leu Pro Lys Leu
                485                 490                 495
Gln Trp Tyr Lys Asp Cys Lys Pro Leu Leu Asp Asn Ile His Phe
            500                 505                 510
Ser Gly Val Lys Asp Arg Leu Ile Val Met Asn Val Ala Glu Lys His
        515                 520                 525
Arg Gly Asn Tyr Thr Cys His Ala Ser Tyr Thr Tyr Leu Gly Lys Gln
    530                 535                 540
Tyr Pro Ile Thr Arg Val Ile Glu Phe Ile Thr Leu Glu Glu Asn Lys
545                 550                 555                 560
Pro Thr Arg Pro Val Ile Val Ser Pro Ala Asn Glu Thr Met Glu Val
                565                 570                 575
Asp Leu Gly Ser Gln Ile Gln Leu Ile Cys Asn Val Thr Gly Gln Leu
            580                 585                 590
Ser Asp Ile Ala Tyr Trp Lys Trp Asn Gly Ser Val Ile Asp Glu Asp
        595                 600                 605
Asp Pro Val Leu Gly Glu Asp Tyr Tyr Ser Val Glu Asn Pro Ala Asn
    610                 615                 620
Lys Arg Arg Ser Thr Leu Ile Thr Val Leu Asn Ile Ser Glu Ile Glu
625                 630                 635                 640
Ser Arg Phe Tyr Lys His Pro Phe Thr Cys Phe Ala Lys Asn Thr His
                645                 650                 655
Gly Ile Asp Ala Ala Tyr Ile Gln Leu Ile Tyr Pro Val Thr Asn Ser
            660                 665                 670
Gly Glu Ser Lys Tyr Gly Pro Pro Cys Pro Ser Cys Pro Ala Pro Glu
        675                 680                 685
Phe Leu Gly Gly Pro Ser Val Phe Leu Phe Pro Pro Lys Pro Lys Asp
    690                 695                 700
Thr Leu Met Ile Ser Arg Thr Pro Glu Val Thr Cys Val Val Val Asp
705                 710                 715                 720
Val Ser Gln Glu Asp Pro Glu Val Gln Phe Asn Trp Tyr Val Asp Gly
                725                 730                 735
Val Glu Val His Asn Ala Lys Thr Lys Pro Arg Glu Glu Gln Phe Asn
            740                 745                 750
Ser Thr Tyr Arg Val Val Ser Val Leu Thr Val Leu His Gln Asp Trp
        755                 760                 765
Leu Asn Gly Lys Glu Tyr Lys Cys Lys Val Ser Asn Lys Gly Leu Pro
    770                 775                 780
Ser Ser Ile Glu Lys Thr Ile Ser Lys Ala Lys Gly Gln Pro Arg Glu
785                 790                 795                 800
Pro Gln Val Tyr Thr Leu Pro Pro Ser Gln Glu Glu Met Thr Lys Asn
                805                 810                 815
Gln Val Ser Leu Thr Cys Leu Val Lys Gly Phe Tyr Pro Ser Asp Ile
            820                 825                 830
Ala Val Glu Trp Glu Ser Asn Gly Gln Pro Glu Asn Asn Tyr Lys Thr
```

```
                835               840                845
Thr Pro Pro Val Leu Asp Ser Asp Gly Ser Phe Phe Leu Tyr Ser Arg
    850                 855                 860

Leu Thr Val Asp Lys Ser Arg Trp Gln Glu Gly Asn Val Phe Ser Cys
865                 870                 875                 880

Ser Val Met His Glu Ala Leu His Asn His Tyr Thr Gln Lys Ser Leu
                885                 890                 895

Ser Leu Ser Leu Gly Lys
            900

<210> SEQ ID NO 43
<211> LENGTH: 2709
<212> TYPE: DNA
<213> ORGANISM: Homo sapiens

<400> SEQUENCE: 43
```

| | | | | |
|---|---|---|---|---|
| atggtgcttc | tgtggtgtgt | agtgagtctc | tacttttatg | gaatcctgca | aagtgatgcc | 60 |
| tcagaacgct | gcgatgactg | gggactagac | accatgaggc | aaatccaagt | gtttgaagat | 120 |
| gagccagctc | gcatcaagtg | cccactcttt | gaacacttct | tgaaattcaa | ctacagcaca | 180 |
| gcccattcag | ctggccttac | tctgatctgg | tattggacta | ggcaggaccg | ggaccttgag | 240 |
| gagccaatta | acttccgcct | ccccgagaac | cgcattagta | aggagaaaga | tgtgctgtgg | 300 |
| ttccggccca | ctctcctcaa | tgacactggc | aactatacct | gcatgttaag | gaacactaca | 360 |
| tattgcagca | agttgcatt | tcccttggaa | gttgttcaaa | aagacagctg | tttcaattcc | 420 |
| cccatgaaac | tcccagtgca | taaactgtat | atagaatatg | gcattcagag | gatcacttgt | 480 |
| ccaaatgtag | atggatattt | tccttccagt | gtcaaaccga | ctatcacttg | gtatatgggc | 540 |
| tgttataaaa | tacagaattt | taataatgta | atacccgaag | gtatgaactt | gagtttcctc | 600 |
| attgccttaa | tttcaaataa | tggaaattac | acatgtgttg | ttacatatcc | agaaaatgga | 660 |
| cgtacgtttc | atctcaccag | gactctgact | gtaaaggtag | taggctctcc | aaaaaatgca | 720 |
| gtgccccctg | tgatccattc | acctaatgat | catgtggtct | atgagaaaga | accaggagag | 780 |
| gagctactca | ttccctgtac | ggtctatttt | agttttctga | tggattctcg | caatgaggtt | 840 |
| tggtggacca | ttgatggaaa | aaaacctgat | gacatcacta | ttgatgtcac | cattaacgaa | 900 |
| agtataagtc | atagtagaac | agaagatgaa | acaagaactc | agattttgag | catcaagaaa | 960 |
| gttacctctg | aggatctcaa | gcgcagctat | gtctgtcatg | ctagaagtgc | aaaggcgaa | 1020 |
| gttgccaaag | cagccaaggt | gaagcagaaa | gtgccagctc | caagatacac | agtggaaaaa | 1080 |
| tgcaaggaac | gtgaagaaaa | aataattta | gtgagctcag | caaatgaaat | cgatgttcgt | 1140 |
| ccctgtcctc | ttaacccaaa | tgaacacaaa | ggcactataa | cttggtataa | ggatgacagc | 1200 |
| aagacacctg | tatctacaga | acaagcctcc | aggattcatc | aacacaaaga | gaaactttgg | 1260 |
| tttgttcctg | ctaaggtgga | ggattcagga | cattactatt | gcgtggtaag | aaattcatct | 1320 |
| tactgcctca | gaattaaaat | aagtgcaaaa | tttgtggaga | atgagcctaa | cttatgttat | 1380 |
| aatgcacaag | ccatatttaa | gcagaaacta | cccgttgcag | agacggagg | acttgtgtgc | 1440 |
| ccttatatgg | agttttttaa | aaatgaaaat | aatgagttac | ctaaattaca | gtggtataag | 1500 |
| gattgcaaac | tctacttct | tgacaatata | cactttagtg | gagtcaaaga | taggctcatc | 1560 |
| gtgatgaatg | tggctgaaaa | gcatagaggg | aactatactt | gtcatgcatc | ctacacatac | 1620 |
| ttgggcaagc | aatatcctat | taccgggta | atagaattta | ttactctaga | ggaaaacaaa | 1680 |
| cccacaaggc | ctgtgattgt | gagcccagct | aatgagacaa | tggaagtaga | cttgggatcc | 1740 |

```
cagatacaat tgatctgtaa tgtcaccggc cagttgagtg acattgctta ctggaagtgg      1800
aatgggtcag taattgatga agatgaccca gtgctagggg aagactatta cagtgtggaa      1860
aatcctgcaa acaaaagaag gagtaccctc atcacagtgc ttaatatatc ggaaattgag      1920
agtagatttt ataaacatcc atttacctgt tttgccaaga atacacatgg tatagatgca      1980
gcatatatcc agttaatata tccagtcact aattccggag agtccaaata cggtccgcca      2040
tgcccaccat gcccagcacc tgagttcctg ggggaccat cagtcttcct gttccccca        2100 aaacccaagg acactctcat gatctcccgg acccctgagg tcacgtgcgt ggtggtggac      2160
gtgagccagg aagaccccga ggtccagttc aactggtacg tggatggcgt ggaggtgcat      2220
aatgccaaga caaagccgcg ggaggagcag ttcaacagca cgtaccgtgt ggtcagcgtc      2280
ctcaccgtcc tgcaccagga ctggctgaac ggcaaggagt acaagtgcaa ggtctccaac      2340
aaaggcctcc cgtcctccat cgagaaaacc atctccaaag ccaaagggca gccccgagag      2400
ccacaggtgt acaccctgcc cccatcccag gaggagatga ccaagaacca ggtcagcctg      2460
acctgcctgg tcaaaggctt ctaccccagc gacatcgccg tggagtggga gagcaatggg      2520
cagccggaga acaactacaa gaccacgcct cccgtgctgg actccgacgg ctccttcttc      2580
ctctacagca ggctaaccgt ggacaagagc aggtggcagg aggggaatgt cttctcatgc      2640
tccgtgatgc atgaggctct gcacaaccac tacacacaga gagcctctc cctgtctctg       2700 ggtaaatga                                                             2709

<210> SEQ ID NO 44
<211> LENGTH: 902
<212> TYPE: PRT
<213> ORGANISM: Homo sapiens

<400> SEQUENCE: 44

Met Val Leu Leu Trp Cys Val Val Ser Leu Tyr Phe Tyr Gly Ile Leu
  1               5                  10                  15

Gln Ser Asp Ala Ser Glu Arg Cys Asp Asp Trp Gly Leu Asp Thr Met
             20                  25                  30

Arg Gln Ile Gln Val Phe Glu Asp Glu Pro Ala Arg Ile Lys Cys Pro
         35                  40                  45

Leu Phe Glu His Phe Leu Lys Phe Asn Tyr Ser Thr Ala His Ser Ala
     50                  55                  60

Gly Leu Thr Leu Ile Trp Tyr Trp Thr Arg Gln Asp Arg Asp Leu Glu
 65                  70                  75                  80

Glu Pro Ile Asn Phe Arg Leu Pro Glu Asn Arg Ile Ser Lys Glu Lys
                 85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190
```

-continued

```
Glu Gly Met Asn Leu Ser Phe Leu Ile Ala Leu Ile Ser Asn Asn Gly
        195                 200                 205
Asn Tyr Thr Cys Val Val Thr Tyr Pro Glu Asn Gly Arg Thr Phe His
        210                 215                 220
Leu Thr Arg Thr Leu Thr Val Lys Val Val Gly Ser Pro Lys Asn Ala
225                 230                 235                 240
Val Pro Pro Val Ile His Ser Pro Asn Asp His Val Val Tyr Glu Lys
                245                 250                 255
Glu Pro Gly Glu Glu Leu Leu Ile Pro Cys Thr Val Tyr Phe Ser Phe
            260                 265                 270
Leu Met Asp Ser Arg Asn Glu Val Trp Trp Thr Ile Asp Gly Lys Lys
        275                 280                 285
Pro Asp Asp Ile Thr Ile Asp Val Thr Ile Asn Glu Ser Ile Ser His
        290                 295                 300
Ser Arg Thr Glu Asp Glu Thr Arg Thr Gln Ile Leu Ser Ile Lys Lys
305                 310                 315                 320
Val Thr Ser Glu Asp Leu Lys Arg Ser Tyr Val Cys His Ala Arg Ser
                325                 330                 335
Ala Lys Gly Glu Val Ala Lys Ala Lys Val Lys Gln Lys Val Pro
            340                 345                 350
Ala Pro Arg Tyr Thr Val Glu Lys Cys Lys Glu Arg Glu Glu Lys Ile
        355                 360                 365
Ile Leu Val Ser Ser Ala Asn Glu Ile Asp Val Arg Pro Cys Pro Leu
        370                 375                 380
Asn Pro Asn Glu His Lys Gly Thr Ile Thr Trp Tyr Lys Asp Asp Ser
385                 390                 395                 400
Lys Thr Pro Val Ser Thr Glu Gln Ala Ser Arg Ile His Gln His Lys
                405                 410                 415
Glu Lys Leu Trp Phe Val Pro Ala Lys Val Glu Asp Ser Gly His Tyr
            420                 425                 430
Tyr Cys Val Val Arg Asn Ser Ser Tyr Cys Leu Arg Ile Lys Ile Ser
        435                 440                 445
Ala Lys Phe Val Glu Asn Glu Pro Asn Leu Cys Tyr Asn Ala Gln Ala
        450                 455                 460
Ile Phe Lys Gln Lys Leu Pro Val Ala Gly Asp Gly Gly Leu Val Cys
465                 470                 475                 480
Pro Tyr Met Glu Phe Phe Lys Asn Glu Asn Asn Glu Leu Pro Lys Leu
                485                 490                 495
Gln Trp Tyr Lys Asp Cys Lys Pro Leu Leu Leu Asp Asn Ile His Phe
            500                 505                 510
Ser Gly Val Lys Asp Arg Leu Ile Val Met Asn Val Ala Glu Lys His
        515                 520                 525
Arg Gly Asn Tyr Thr Cys His Ala Ser Tyr Thr Tyr Leu Gly Lys Gln
        530                 535                 540
Tyr Pro Ile Thr Arg Val Ile Glu Phe Ile Thr Leu Glu Glu Asn Lys
545                 550                 555                 560
Pro Thr Arg Pro Val Ile Val Ser Pro Ala Asn Glu Thr Met Glu Val
                565                 570                 575
Asp Leu Gly Ser Gln Ile Gln Leu Ile Cys Asn Val Thr Gly Gln Leu
            580                 585                 590
Ser Asp Ile Ala Tyr Trp Lys Trp Asn Gly Ser Val Ile Asp Glu Asp
        595                 600                 605
Asp Pro Val Leu Gly Glu Asp Tyr Tyr Ser Val Glu Asn Pro Ala Asn
```

```
                610                 615                 620
Lys Arg Arg Ser Thr Leu Ile Thr Val Leu Asn Ile Ser Glu Ile Glu
625                 630                 635                 640

Ser Arg Phe Tyr Lys His Pro Phe Thr Cys Phe Ala Lys Asn Thr His
                645                 650                 655

Gly Ile Asp Ala Ala Tyr Ile Gln Leu Ile Tyr Pro Val Thr Asn Ser
            660                 665                 670

Gly Glu Ser Lys Tyr Gly Pro Pro Cys Pro Cys Pro Ala Pro Glu
        675                 680                 685

Phe Leu Gly Gly Pro Ser Val Phe Leu Phe Pro Pro Lys Pro Lys Asp
690                 695                 700

Thr Leu Met Ile Ser Arg Thr Pro Glu Val Thr Cys Val Val Val Asp
705                 710                 715                 720

Val Ser Gln Glu Asp Pro Glu Val Gln Phe Asn Trp Tyr Val Asp Gly
            725                 730                 735

Val Glu Val His Asn Ala Lys Thr Lys Pro Arg Glu Glu Gln Phe Asn
                740                 745                 750

Ser Thr Tyr Arg Val Val Ser Val Leu Thr Val Leu His Gln Asp Trp
            755                 760                 765

Leu Asn Gly Lys Glu Tyr Lys Cys Lys Val Ser Asn Lys Gly Leu Pro
770                 775                 780

Ser Ser Ile Glu Lys Thr Ile Ser Lys Ala Lys Gly Gln Pro Arg Glu
785                 790                 795                 800

Pro Gln Val Tyr Thr Leu Pro Pro Ser Gln Glu Glu Met Thr Lys Asn
                805                 810                 815

Gln Val Ser Leu Thr Cys Leu Val Lys Gly Phe Tyr Pro Ser Asp Ile
            820                 825                 830

Ala Val Glu Trp Glu Ser Asn Gly Gln Pro Glu Asn Asn Tyr Lys Thr
        835                 840                 845

Thr Pro Pro Val Leu Asp Ser Asp Gly Ser Phe Phe Leu Tyr Ser Arg
    850                 855                 860

Leu Thr Val Asp Lys Ser Arg Trp Gln Glu Gly Asn Val Phe Ser Cys
865                 870                 875                 880

Ser Val Met His Glu Ala Leu His Asn His Tyr Thr Gln Lys Ser Leu
                885                 890                 895

Ser Leu Ser Leu Gly Lys
            900

<210> SEQ ID NO 45
<211> LENGTH: 2748
<212> TYPE: DNA
<213> ORGANISM: Homo sapiens

<400> SEQUENCE: 45
atggtgcgct tgtacgtgtt ggtaatggga gtttctgcct tcacccttca gcctgcggca    60
cacacagggg ctgccagaag ctgccggttt cgtgggaggc attacaagcg ggagttcagg   120
ctggaagggg agcctgtagc cctgaggtgc ccccaggtgc cctactggtt gtgggcctct   180
gtcagccccc gcatcaacct gacatggcat aaaaatgact ctgctaggac ggtcccagga   240
gaagaagaga cacggatgtg gcccaggac ggtgctctgt ggcttctgcc agccttgcag   300
gaggactctg gcacctacgt ctgcactact agaaatgctt cttactgtga caaaatgtcc   360
attgagctca gagttttga gaatacagat gctttcctgc cgttcatctc ataccccgcaa   420 attttaacct tgtcaacctc tgggtatta gtatgccctg acctgagtga attcacccgt   480
```

```
gacaaaactg acgtgaagat tcaatggtac aaggattctc ttcttttgga taaagacaat      540
gagaaatttc taagtgtgag ggggaccact cacttactcg tacacgatgt ggccctggaa      600
gatgctggct attaccgctg tgtcctgaca tttgcccatg aaggccagca atacaacatc      660
actaggagta ttgagctacg catcaagaaa aaaaagaag agaccattcc tgtgatcatt       720
tccccctca agaccatatc agcttctctg gggtcaagac tgacaatccc atgtaaggtg       780
tttctgggaa ccggcacacc cttaaccacc atgctgtggt ggacggccaa tgacacccac      840
atagagagcg cctacccggg aggccgcgtg accgagggc cacgccagga atattcagaa       900
aataatgaga actacattga agtgccattg atttttgatc ctgtcacaag agaggatttg      960
cacatggatt ttaaatgtgt tgtccataat accctgagtt tcagacact acgcaccaca     1020
gtcaaggaag cctcctccac gttctcagaa cgctgcgatg actggggact agacaccatg    1080
aggcaaatcc aagtgtttga agatgagcca gctcgcatca agtgcccact ctttgaacac    1140
ttcttgaaat tcaactacag cacagcccat tcagctggcc ttactctgat ctggtattgg    1200
actaggcagg accgggacct tgaggagcca attaacttcc gcctcccga gaaccgcatt     1260
agtaaggaga aagatgtgct gtggttccgg cccactctcc tcaatgacac tggcaactat    1320
acctgcatgt taaggaacac tacatattgc agcaaagttg catttccctt ggaagttgtt    1380
caaaagaca gctgtttcaa ttcccccatg aaactcccag tgcataaact gtatatagaa     1440
tatggcattc agaggatcac ttgtccaaat gtagatggat attttccttc cagtgtcaaa    1500
ccgactatca cttggtatat gggctgttat aaaatacaga attttaataa tgtaataccc    1560
gaaggtatga acttgagttt cctcattgcc ttaatttcaa ataatggaaa ttacacatgt    1620
gttgttacat atccagaaaa tggacgtacg tttcatctca ccaggactct gactgtaaag    1680
gtagtaggct ctccaaaaaa tgcagtgccc cctgtgatcc attcacctaa tgatcatgtg    1740
gtctatgaga aagaaccagg agaggagcta ctcattccct gtacggtcta ttttagtttt    1800
ctgatggatt ctcgcaatga ggtttggtgg accattgatg aaaaaaacc tgatgacatc     1860
actattgatg tcaccattaa cgaaagtata agtcatagta gaacagaaga tgaaacaaga    1920
actcagattt tgagcatcaa gaaagttacc tctgaggatc tcaagcgcag ctatgtctgt    1980
catgctagaa gtgccaaagg cgaagttgcc aaagcagcca aggtgaagca gaaagtgcca    2040
gctccaagat acacagtgtc cggagacaaa actcacacat gcccaccgtg cccagcacct    2100
gaactcctgg ggggaccgtc agtcttcctc ttccccccaa aacccaagga caccctcatg    2160
atctcccgga cccctgaggt cacatgcgtg gtggtggacg tgagccacga agaccctgag    2220
gtcaagttca actggtacgt ggacggcgtg gaggtgcata atgccaagac aaagccgcgg    2280
gaggagcagt acaacagcac gtaccgtgtg gtcagcgtcc tcaccgtcct gcaccaggac    2340
tggctgaatg gcaaggagta caagtgcaag gtctccaaca aagccctccc agcccccatc    2400
gagaaaacca tctccaaagc caagggcag ccccgagaac cacaggtgta caccctgccc    2460
ccatcccggg atgagctgac caagaaccag gtcagcctga cctgcctggt caaaggcttc    2520
tatcccagcg acatcgccgt ggagtgggag agcaatgggc agccggagaa caactacaag    2580
accacgcctc ccgtgctgga ctccgacggc tccttcttcc tctatagcaa gctcaccgtg    2640
gacaagagca ggtggcagca ggggaacgtc ttctcatgct ccgtgatgca tgaggctctg    2700
cacaaccact acacgcagaa gagcctctcc ctgtctccgg gtaaatga                 2748
```

<210> SEQ ID NO 46

<211> LENGTH: 915
<212> TYPE: PRT
<213> ORGANISM: Homo sapiens

<400> SEQUENCE: 46

```
Met Val Arg Leu Tyr Val Leu Val Met Gly Val Ser Ala Phe Thr Leu
  1               5                  10                  15

Gln Pro Ala Ala His Thr Gly Ala Ala Arg Ser Cys Arg Phe Arg Gly
             20                  25                  30

Arg His Tyr Lys Arg Glu Phe Arg Leu Glu Gly Glu Pro Val Ala Leu
         35                  40                  45

Arg Cys Pro Gln Val Pro Tyr Trp Leu Trp Ala Ser Val Ser Pro Arg
     50                  55                  60

Ile Asn Leu Thr Trp His Lys Asn Asp Ser Ala Arg Thr Val Pro Gly
 65                  70                  75                  80

Glu Glu Glu Thr Arg Met Trp Ala Gln Asp Gly Ala Leu Trp Leu Leu
                 85                  90                  95

Pro Ala Leu Gln Glu Asp Ser Gly Thr Tyr Val Cys Thr Thr Arg Asn
            100                 105                 110

Ala Ser Tyr Cys Asp Lys Met Ser Ile Glu Leu Arg Val Phe Glu Asn
        115                 120                 125

Thr Asp Ala Phe Leu Pro Phe Ile Ser Tyr Pro Gln Ile Leu Thr Leu
    130                 135                 140

Ser Thr Ser Gly Val Leu Val Cys Pro Asp Leu Ser Glu Phe Thr Arg
145                 150                 155                 160

Asp Lys Thr Asp Val Lys Ile Gln Trp Tyr Lys Asp Ser Leu Leu Leu
                165                 170                 175

Asp Lys Asp Asn Glu Lys Phe Leu Ser Val Arg Gly Thr Thr His Leu
            180                 185                 190

Leu Val His Asp Val Ala Leu Glu Asp Ala Gly Tyr Tyr Arg Cys Val
        195                 200                 205

Leu Thr Phe Ala His Glu Gly Gln Gln Tyr Asn Ile Thr Arg Ser Ile
    210                 215                 220

Glu Leu Arg Ile Lys Lys Lys Glu Glu Thr Ile Pro Val Ile Ile
225                 230                 235                 240

Ser Pro Leu Lys Thr Ile Ser Ala Ser Leu Gly Ser Arg Leu Thr Ile
                245                 250                 255

Pro Cys Lys Val Phe Leu Gly Thr Gly Thr Pro Leu Thr Thr Met Leu
            260                 265                 270

Trp Trp Thr Ala Asn Asp Thr His Ile Glu Ser Ala Tyr Pro Gly Gly
        275                 280                 285

Arg Val Thr Glu Gly Pro Arg Gln Glu Tyr Ser Glu Asn Asn Glu Asn
    290                 295                 300

Tyr Ile Glu Val Pro Leu Ile Phe Asp Pro Val Thr Arg Glu Asp Leu
305                 310                 315                 320

His Met Asp Phe Lys Cys Val Val His Asn Thr Leu Ser Phe Gln Thr
                325                 330                 335

Leu Arg Thr Thr Val Lys Glu Ala Ser Ser Thr Phe Ser Glu Arg Cys
            340                 345                 350

Asp Asp Trp Gly Leu Asp Thr Met Arg Gln Ile Gln Val Phe Glu Asp
        355                 360                 365

Glu Pro Ala Arg Ile Lys Cys Pro Leu Phe Glu His Phe Leu Lys Phe
    370                 375                 380

Asn Tyr Ser Thr Ala His Ser Ala Gly Leu Thr Leu Ile Trp Tyr Trp
```

-continued

```
            385                 390                 395                 400
Thr Arg Gln Asp Arg Asp Leu Glu Glu Pro Ile Asn Phe Arg Leu Pro
                    405                 410                 415
Glu Asn Arg Ile Ser Lys Glu Lys Asp Val Leu Trp Phe Arg Pro Thr
                420                 425                 430
Leu Leu Asn Asp Thr Gly Asn Tyr Thr Cys Met Leu Arg Asn Thr Thr
            435                 440                 445
Tyr Cys Ser Lys Val Ala Phe Pro Leu Glu Val Val Gln Lys Asp Ser
        450                 455                 460
Cys Phe Asn Ser Pro Met Lys Leu Pro Val His Lys Leu Tyr Ile Glu
465                 470                 475                 480
Tyr Gly Ile Gln Arg Ile Thr Cys Pro Asn Val Asp Gly Tyr Phe Pro
                485                 490                 495
Ser Ser Val Lys Pro Thr Ile Thr Trp Tyr Met Gly Cys Tyr Lys Ile
                500                 505                 510
Gln Asn Phe Asn Asn Val Ile Pro Glu Gly Met Asn Leu Ser Phe Leu
            515                 520                 525
Ile Ala Leu Ile Ser Asn Asn Gly Asn Tyr Thr Cys Val Val Thr Tyr
        530                 535                 540
Pro Glu Asn Gly Arg Thr Phe His Leu Thr Arg Thr Leu Thr Val Lys
545                 550                 555                 560
Val Val Gly Ser Pro Lys Asn Ala Val Pro Pro Val Ile His Ser Pro
                565                 570                 575
Asn Asp His Val Val Tyr Glu Lys Glu Pro Gly Glu Glu Leu Leu Ile
            580                 585                 590
Pro Cys Thr Val Tyr Phe Ser Phe Leu Met Asp Ser Arg Asn Glu Val
        595                 600                 605
Trp Trp Thr Ile Asp Gly Lys Lys Pro Asp Asp Ile Thr Ile Asp Val
610                 615                 620
Thr Ile Asn Glu Ser Ile Ser His Ser Arg Thr Glu Asp Glu Thr Arg
625                 630                 635                 640
Thr Gln Ile Leu Ser Ile Lys Lys Val Thr Ser Glu Asp Leu Lys Arg
                645                 650                 655
Ser Tyr Val Cys His Ala Arg Ser Ala Lys Gly Glu Val Ala Lys Ala
            660                 665                 670
Ala Lys Val Lys Gln Lys Val Pro Ala Pro Arg Tyr Thr Val Ser Gly
        675                 680                 685
Asp Lys Thr His Thr Cys Pro Pro Cys Pro Ala Pro Glu Leu Leu Gly
        690                 695                 700
Gly Pro Ser Val Phe Leu Phe Pro Pro Lys Pro Lys Asp Thr Leu Met
705                 710                 715                 720
Ile Ser Arg Thr Pro Glu Val Thr Cys Val Val Val Asp Val Ser His
                725                 730                 735
Glu Asp Pro Glu Val Lys Phe Asn Trp Tyr Val Asp Gly Val Glu Val
                740                 745                 750
His Asn Ala Lys Thr Lys Pro Arg Glu Glu Gln Tyr Asn Ser Thr Tyr
            755                 760                 765
Arg Val Val Ser Val Leu Thr Val Leu His Gln Asp Trp Leu Asn Gly
        770                 775                 780
Lys Glu Tyr Lys Cys Lys Val Ser Asn Lys Ala Leu Pro Ala Pro Ile
785                 790                 795                 800
Glu Lys Thr Ile Ser Lys Ala Lys Gly Gln Pro Arg Glu Pro Gln Val
                805                 810                 815
```

```
Tyr Thr Leu Pro Pro Ser Arg Asp Glu Leu Thr Lys Asn Gln Val Ser
            820                 825                 830

Leu Thr Cys Leu Val Lys Gly Phe Tyr Pro Ser Asp Ile Ala Val Glu
        835                 840                 845

Trp Glu Ser Asn Gly Gln Pro Glu Asn Asn Tyr Lys Thr Thr Pro Pro
    850                 855                 860

Val Leu Asp Ser Asp Gly Ser Phe Phe Leu Tyr Ser Lys Leu Thr Val
865                 870                 875                 880

Asp Lys Ser Arg Trp Gln Gln Gly Asn Val Phe Ser Cys Ser Val Met
                885                 890                 895

His Glu Ala Leu His Asn His Tyr Thr Gln Lys Ser Leu Ser Leu Ser
            900                 905                 910

Pro Gly Lys
        915

<210> SEQ ID NO 47
<211> LENGTH: 2754
<212> TYPE: DNA
<213> ORGANISM: Homo sapiens

<400> SEQUENCE: 47
atggtgcgct tgtacgtgtt ggtaatggga gtttctgcct tcaccctcca gcctgcggca      60
cacacagggg ctgccagaag ctgccggttt cgtgggaggc attacaagcg ggagttcagg     120
ctggaagggg agcctgtagc cctgaggtgc ccccaggtgc cctactggtt gtgggcctct     180
gtcagccccc gcatcaacct gacatggcat aaaaatgact ctgctaggac ggtcccagga     240
gaagaagaga cacggatgtg ggcccaggac ggtgctctgt ggcttctgcc agccttgcag     300
gaggactctg gcacctacgt ctgcactact agaaatgctt cttactgtga caaaatgtcc     360
attgagctca gagtttttga gaatacagat gctttcctgc cgttcatctc ataccccgcaa    420 atttttaacct tgtcaacctc tggggtatta gtatgccctg acctgagtga attcacccgt    480
gacaaaactg acgtgaagat tcaatggtac aaggattctc ttcttttgga taaagacaat    540
gagaaatttc taagtgtgag ggggaccact cacttactcg tacacgatgt ggccctggaa     600
gatgctggct attaccgctg tgtcctgaca tttgcccatg aaggccagca atacaacatc     660
actaggagta ttgagctacg catcaagaaa aaaaagaag agaccattcc tgtgatcatt      720 tccccccctca agaccatatc agcttctctg gggtcaagac tgacaatccc atgtaaggtg   780
tttctgggaa ccggcacacc cttaaccacc atgctgtggt ggacggccaa tgacacccac    840
atagagagcg cctacccggg aggccgcgtg accgaggggc acgccagga atattcagaa      900 aataatgaga actacattga agtgccattg attttttgatc ctgtcacaag agaggatttg    960
cacatggatt ttaaatgtgt tgtccataat accctgagtt ttcagacact acgcaccaca   1020
gtcaaggaag cctcctccac gttctcagaa cgctgcgatg actggggact agacaccatg    1080
aggcaaatcc aagtgtttga agatgagcca gctcgcatca gtgcccact ctttgaacac    1140 ttcttgaaat tcaactacag cacagcccat tcagctggcc ttactctgat ctggtattgg    1200
actaggcagg accgggacct tgaggagcca attaacttcc gcctccccga gaaccgcatt    1260
agtaaggaga aagatgtgct gtggttccgg cccactctcc tcaatgacac tggcaactat    1320
acctgcatgt taggaacac tacatattgc agcaaagttg catttccctt ggaagttgtt    1380
caaaaagaca gctgtttcaa ttccccccatg aaactcccag tgcataaact gtatatagaa    1440
tatggcattc agaggatcac ttgtccaaat gtagatggat attttccttc agtgtcaaa     1500
```

-continued

```
ccgactatca cttggtatat gggctgttat aaaatacaga attttaataa tgtaataccc    1560
gaaggtatga acttgagttt cctcattgcc ttaatttcaa ataatggaaa ttacacatgt    1620
gttgttacat atccagaaaa tggacgtacg tttcatctca ccaggactct gactgtaaag    1680
gtagtaggct ctccaaaaaa tgcagtgccc cctgtgatcc attcacctaa tgatcatgtg    1740
gtctatgaga agaaccagg agaggagcta ctcattccct gtacggtcta ttttagtttt    1800
ctgatggatt ctcgcaatga ggtttggtgg accattgatg gaaaaaaacc tgatgacatc    1860
actattgatg tcaccattaa cgaaagtata agtcatagta gaacagaaga tgaaacaaga    1920
actcagattt tgagcatcaa gaaagttacc tctgaggatc tcaagcgcag ctatgtctgt    1980
catgctagaa gtgccaaagg cgaagttgcc aaagcagcca aggtgaagca gaaagtgcca    2040
gctccaagat acacagtgtc cggagagtcc aaatacggtc cgccatgccc atcatgccca    2100
gcacctgagt tcctgggggg accatcagtc ttcctgttcc ccccaaaacc caaggacact    2160
ctcatgatct cccggacccc tgaggtcacg tgcgtggtgg tggacgtgag ccaggaagac    2220
cccgaggtcc agttcaactg gtacgtggat ggcgtggagg tgcataatgc caagacaaag    2280
ccgcgggagg agcagttcaa cagcacgtac cgtgtggtca gcgtcctcac cgtcctgcac    2340
caggactggc tgaacggcaa ggagtacaag tgcaaggtct ccaacaaagg cctcccgtcc    2400
tccatcgaga aaaccatctc caaagccaaa gggcagcccc gagagccaca ggtgtacacc    2460
ctgcccccat cccaggagga tgaccaag aaccaggtca gcctgacctg cctggtcaaa    2520
ggcttctacc ccagcgacat cgccgtggag tgggagagca tgggcagcc ggagaacaac    2580 tacaagacca cgcctcccgt gctggactcc gacggctcct tcttcctcta cagcaggcta    2640
accgtggaca agagcaggtg gcaggagggg aatgtcttct catgctccgt gatgcatgag    2700
gctctgcaca accactacac acagaagagc ctctccctgt ctctgggtaa atga         2754
```

<210> SEQ ID NO 48
<211> LENGTH: 917
<212> TYPE: PRT
<213> ORGANISM: Homo sapiens

<400> SEQUENCE: 48

```
Met Val Arg Leu Tyr Val Leu Val Met Gly Val Ser Ala Phe Thr Leu
  1               5                  10                  15

Gln Pro Ala Ala His Thr Gly Ala Ala Arg Ser Cys Arg Phe Arg Gly
             20                  25                  30

Arg His Tyr Lys Arg Glu Phe Arg Leu Glu Gly Glu Pro Val Ala Leu
         35                  40                  45

Arg Cys Pro Gln Val Pro Tyr Trp Leu Trp Ala Ser Val Ser Pro Arg
     50                  55                  60

Ile Asn Leu Thr Trp His Lys Asn Asp Ser Ala Arg Thr Val Pro Gly
 65                  70                  75                  80

Glu Glu Glu Thr Arg Met Trp Ala Gln Asp Gly Ala Leu Trp Leu Leu
                 85                  90                  95

Pro Ala Leu Gln Glu Asp Ser Gly Thr Tyr Val Cys Thr Thr Arg Asn
            100                 105                 110

Ala Ser Tyr Cys Asp Lys Met Ser Ile Glu Leu Arg Val Phe Glu Asn
        115                 120                 125

Thr Asp Ala Phe Leu Pro Phe Ile Ser Tyr Pro Gln Ile Leu Thr Leu
    130                 135                 140

Ser Thr Ser Gly Val Leu Val Cys Pro Asp Leu Ser Glu Phe Thr Arg
```

```
                145                 150                 155                 160
           Asp Lys Thr Asp Val Lys Ile Gln Trp Tyr Lys Asp Ser Leu Leu Leu
                           165                 170                 175
           Asp Lys Asp Asn Glu Lys Phe Leu Ser Val Arg Gly Thr Thr His Leu
                       180                 185                 190
           Leu Val His Asp Val Ala Leu Glu Asp Ala Gly Tyr Tyr Arg Cys Val
                   195                 200                 205
           Leu Thr Phe Ala His Glu Gly Gln Gln Tyr Asn Ile Thr Arg Ser Ile
                   210                 215                 220
           Glu Leu Arg Ile Lys Lys Lys Glu Thr Ile Pro Val Ile Ile
           225                 230                 235                 240
           Ser Pro Leu Lys Thr Ile Ser Ala Ser Leu Gly Ser Arg Leu Thr Ile
                           245                 250                 255
           Pro Cys Lys Val Phe Leu Gly Thr Gly Thr Pro Leu Thr Thr Met Leu
                       260                 265                 270
           Trp Trp Thr Ala Asn Asp Thr His Ile Glu Ser Ala Tyr Pro Gly Gly
                       275                 280                 285
           Arg Val Thr Glu Gly Pro Arg Gln Glu Tyr Ser Glu Asn Asn Glu Asn
                   290                 295                 300
           Tyr Ile Glu Val Pro Leu Ile Phe Asp Pro Val Thr Arg Glu Asp Leu
           305                 310                 315                 320
           His Met Asp Phe Lys Cys Val Val His Asn Thr Leu Ser Phe Gln Thr
                           325                 330                 335
           Leu Arg Thr Thr Val Lys Glu Ala Ser Ser Thr Phe Ser Glu Arg Cys
                       340                 345                 350
           Asp Asp Trp Gly Leu Asp Thr Met Arg Gln Ile Gln Val Phe Glu Asp
                       355                 360                 365
           Glu Pro Ala Arg Ile Lys Cys Pro Leu Phe Glu His Phe Leu Lys Phe
                   370                 375                 380
           Asn Tyr Ser Thr Ala His Ser Ala Gly Leu Thr Leu Ile Trp Tyr Trp
           385                 390                 395                 400
           Thr Arg Gln Asp Arg Asp Leu Glu Glu Pro Ile Asn Phe Arg Leu Pro
                           405                 410                 415
           Glu Asn Arg Ile Ser Lys Glu Lys Asp Val Leu Trp Phe Arg Pro Thr
                       420                 425                 430
           Leu Leu Asn Asp Thr Gly Asn Tyr Thr Cys Met Leu Arg Asn Thr Thr
                       435                 440                 445
           Tyr Cys Ser Lys Val Ala Phe Pro Leu Glu Val Val Gln Lys Asp Ser
                   450                 455                 460
           Cys Phe Asn Ser Pro Met Lys Leu Pro Val His Lys Leu Tyr Ile Glu
           465                 470                 475                 480
           Tyr Gly Ile Gln Arg Ile Thr Cys Pro Asn Val Asp Gly Tyr Phe Pro
                           485                 490                 495
           Ser Ser Val Lys Pro Thr Ile Thr Trp Tyr Met Gly Cys Tyr Lys Ile
                       500                 505                 510
           Gln Asn Phe Asn Val Ile Pro Glu Gly Met Asn Leu Ser Phe Leu
                       515                 520                 525
           Ile Ala Leu Ile Ser Asn Asn Gly Asn Tyr Thr Cys Val Val Thr Tyr
                   530                 535                 540
           Pro Glu Asn Gly Arg Thr Phe His Leu Thr Arg Thr Leu Thr Val Lys
           545                 550                 555                 560
           Val Val Gly Ser Pro Lys Asn Ala Val Pro Pro Val Ile His Ser Pro
                           565                 570                 575
```

```
Asn Asp His Val Val Tyr Glu Lys Glu Pro Gly Glu Leu Leu Ile
        580                 585                 590

Pro Cys Thr Val Tyr Phe Ser Phe Leu Met Asp Ser Arg Asn Glu Val
            595                 600                 605

Trp Trp Thr Ile Asp Gly Lys Lys Pro Asp Asp Ile Thr Ile Asp Val
    610                 615                 620

Thr Ile Asn Glu Ser Ile Ser His Ser Arg Thr Glu Asp Glu Thr Arg
625                 630                 635                 640

Thr Gln Ile Leu Ser Ile Lys Lys Val Thr Ser Glu Asp Leu Lys Arg
                645                 650                 655

Ser Tyr Val Cys His Ala Arg Ser Ala Lys Gly Glu Val Ala Lys Ala
                    660                 665                 670

Ala Lys Val Lys Gln Lys Val Pro Ala Pro Arg Tyr Thr Val Ser Gly
            675                 680                 685

Glu Ser Lys Tyr Gly Pro Pro Cys Pro Ser Cys Pro Ala Pro Glu Phe
        690                 695                 700

Leu Gly Gly Pro Ser Val Phe Leu Phe Pro Pro Lys Pro Lys Asp Thr
705                 710                 715                 720

Leu Met Ile Ser Arg Thr Pro Glu Val Thr Cys Val Val Val Asp Val
                725                 730                 735

Ser Gln Glu Asp Pro Glu Val Gln Phe Asn Trp Tyr Val Asp Gly Val
                    740                 745                 750

Glu Val His Asn Ala Lys Thr Lys Pro Arg Glu Glu Gln Phe Asn Ser
            755                 760                 765

Thr Tyr Arg Val Val Ser Val Leu Thr Val Leu His Gln Asp Trp Leu
        770                 775                 780

Asn Gly Lys Glu Tyr Lys Cys Lys Val Ser Asn Lys Gly Leu Pro Ser
785                 790                 795                 800

Ser Ile Glu Lys Thr Ile Ser Lys Ala Lys Gly Gln Pro Arg Glu Pro
                805                 810                 815

Gln Val Tyr Thr Leu Pro Pro Ser Gln Glu Glu Met Thr Lys Asn Gln
                    820                 825                 830

Val Ser Leu Thr Cys Leu Val Lys Gly Phe Tyr Pro Ser Asp Ile Ala
            835                 840                 845

Val Glu Trp Glu Ser Asn Gly Gln Pro Glu Asn Asn Tyr Lys Thr Thr
        850                 855                 860

Pro Pro Val Leu Asp Ser Asp Gly Ser Phe Phe Leu Tyr Ser Arg Leu
865                 870                 875                 880

Thr Val Asp Lys Ser Arg Trp Gln Glu Gly Asn Val Phe Ser Cys Ser
                885                 890                 895

Val Met His Glu Ala Leu His Asn His Tyr Thr Gln Lys Ser Leu Ser
                    900                 905                 910

Leu Ser Leu Gly Lys
        915

<210> SEQ ID NO 49
<211> LENGTH: 2754
<212> TYPE: DNA
<213> ORGANISM: Homo sapiens

<400> SEQUENCE: 49
atggtgcgct tgtacgtgtt ggtaatggga gtttctgcct tcacccttca gcctgcggca      60
cacacagggg ctgccagaag ctgccggttt cgtgggaggc attacaagcg ggagttcagg     120
```

```
ctggaagggg agcctgtagc cctgaggtgc ccccaggtgc cctactggtt gtgggcctct      180
gtcagccccc gcatcaacct gacatggcat aaaaatgact ctgctaggac ggtcccagga      240
gaagaagaga cacggatgtg ggcccaggac ggtgctctgt ggcttctgcc agccttgcag      300
gaggactctg gcacctacgt ctgcactact agaaatgctt cttactgtga caaaatgtcc      360
attgagctca gagttttga gaatacagat gctttcctgc cgttcatctc atacccgcaa       420
attttaacct tgtcaacctc tggggtatta gtatgccctg acctgagtga attcacccgt      480
gacaaaactg acgtgaagat tcaatggtac aaggattctc ttcttttgga taaagacaat      540
gagaaatttc taagtgtgag ggggaccact cacttactcg tacacgatgt ggccctggaa      600
gatgctggct attaccgctg tgtcctgaca tttgcccatg aaggccagca atacaacatc      660
actaggagta ttgagctacg catcaagaaa aaaaagaag agaccattcc tgtgatcatt        720 tccccctca agaccatatc agcttctctg gggtcaagac tgacaatccc atgtaaggtg       780
tttctgggaa ccgcacacc cttaaccacc atgctgtggt ggacggccaa tgacacccac       840
atagagagcg cctacccggg aggccgcgtg accgaggggc cacgccagga atattcagaa      900
aataatgaga actacattga agtgccattg attttgatc ctgtcacaag agaggatttg         960
cacatggatt ttaaatgtgt tgtccataat accctgagtt ttcagacact acgcaccaca      1020
gtcaaggaag cctcctccac gttctcagaa cgctgcgatg actggggact agacaccatg      1080
aggcaaatcc aagtgtttga agatgagcca gctcgcatca agtgcccact ctttgaacac      1140
ttcttgaaat tcaactacag cacagcccat tcagctggcc ttactctgat ctggtattgg      1200
actaggcagg accgggacct tgaggagcca attaacttcc gcctccccga gaaccgcatt      1260
agtaaggaga aagatgtgct gtggttccgg cccactctcc tcaatgacac tggcaactat      1320
acctgcatgt taaggaacac tacatattgc agcaaagttg catttccctt ggaagttgtt      1380
caaaaagaca gctgtttcaa ttcccccatg aaactcccag tgcataaact gtatatagaa      1440
tatggcattc agaggatcac ttgtccaaat gtagatggat attttccttc cagtgtcaaa      1500
ccgactatca cttggtatat gggctgttat aaaaatacaga attttaataa tgtaataccc    1560
gaaggtatga acttgagttt cctcattgcc ttaatttcaa ataatggaaa ttacacatgt       1620
gttgttacat atccagaaaa tggacgtacg tttcatctca ccaggactct gactgtaaag      1680
gtagtaggct ctccaaaaaa tgcagtgccc cctgtgatcc attcacctaa tgatcatgtg      1740
gtctatgaga aagaaccagg agaggagcta ctcattccct gtacggtcta ttttagtttt      1800
ctgatggatt ctcgcaatga ggtttggtgg accattgatg gaaaaaaacc tgatgacatc      1860
actattgatg tcaccattaa cgaaagtata agtcatagta aaacagaaga tgaaacaaga      1920
actcagattt tgagcatcaa gaaagttacc tctgaggatc tcaagcgcag ctatgtctgt      1980
catgctagaa gtgccaaagg cgaagttgcc aaagcagcca aggtgaagca gaaagtgcca      2040
gctccaagat acacagtgtc cggagagtcc aaatacggtc cgcctatgcc accatgccca      2100
gcacctgagt tcctggggg accatcagtc ttcctgttcc ccccaaaacc caaggacact      2160
ctcatgatct cccggacccc tgaggtcacg tgcgtggtgg tggacgtgag ccaggaagac      2220
cccgaggtcc agttcaactg gtacgtggat ggcgtggagg tgcataatgc caagacaaag      2280
ccgcgggagg agcagttcaa cagcacgtac cgtgtggtca gcgtcctcac cgtcctgcac      2340
caggactggc tgaacggcaa ggagtacaag tgcaaggtct ccaacaaagg cctcccgtcc      2400
tccatcgaga aaaccatctc caaagccaaa gggcagcccc gagagccaca ggtgtacacc      2460
ctgcccccat cccaggagga gatgaccaag aaccaggtca gcctgacctg cctggtcaaa      2520
```

```
ggcttctacc ccagcgacat cgccgtggag tgggagagca atgggcagcc ggagaacaac   2580
tacaagacca cgcctcccgt gctggactcc gacggctcct tcttcctcta cagcaggcta   2640
accgtggaca agagcaggtg gcaggagggg aatgtcttct catgctccgt gatgcatgag   2700
gctctgcaca accactacac acagaagagc ctctccctgt ctctgggtaa atga         2754
```

<210> SEQ ID NO 50
<211> LENGTH: 917
<212> TYPE: PRT
<213> ORGANISM: Homo sapiens

<400> SEQUENCE: 50

```
Met Val Arg Leu Tyr Val Leu Val Met Gly Val Ser Ala Phe Thr Leu
 1               5                  10                  15

Gln Pro Ala Ala His Thr Gly Ala Ala Arg Ser Cys Arg Phe Arg Gly
             20                  25                  30

Arg His Tyr Lys Arg Glu Phe Arg Leu Glu Gly Glu Pro Val Ala Leu
         35                  40                  45

Arg Cys Pro Gln Val Pro Tyr Trp Leu Trp Ala Ser Val Ser Pro Arg
     50                  55                  60

Ile Asn Leu Thr Trp His Lys Asn Asp Ser Ala Arg Thr Val Pro Gly
 65                  70                  75                  80

Glu Glu Glu Thr Arg Met Trp Ala Gln Asp Gly Ala Leu Trp Leu Leu
                 85                  90                  95

Pro Ala Leu Gln Glu Asp Ser Gly Thr Tyr Val Cys Thr Thr Arg Asn
            100                 105                 110

Ala Ser Tyr Cys Asp Lys Met Ser Ile Glu Leu Arg Val Phe Glu Asn
        115                 120                 125

Thr Asp Ala Phe Leu Pro Phe Ile Ser Tyr Pro Gln Ile Leu Thr Leu
    130                 135                 140

Ser Thr Ser Gly Val Leu Val Cys Pro Asp Leu Ser Glu Phe Thr Arg
145                 150                 155                 160

Asp Lys Thr Asp Val Lys Ile Gln Trp Tyr Lys Asp Ser Leu Leu Leu
                165                 170                 175

Asp Lys Asp Asn Glu Lys Phe Leu Ser Val Arg Gly Thr Thr His Leu
            180                 185                 190

Leu Val His Asp Val Ala Leu Glu Asp Ala Gly Tyr Tyr Arg Cys Val
        195                 200                 205

Leu Thr Phe Ala His Glu Gly Gln Gln Tyr Asn Ile Thr Arg Ser Ile
    210                 215                 220

Glu Leu Arg Ile Lys Lys Lys Glu Glu Thr Ile Pro Val Ile Ile
225                 230                 235                 240

Ser Pro Leu Lys Thr Ile Ser Ala Ser Leu Gly Ser Arg Leu Thr Ile
                245                 250                 255

Pro Cys Lys Val Phe Leu Gly Thr Gly Thr Pro Leu Thr Thr Met Leu
            260                 265                 270

Trp Trp Thr Ala Asn Asp Thr His Ile Glu Ser Ala Tyr Pro Gly Gly
        275                 280                 285

Arg Val Thr Glu Gly Pro Arg Gln Glu Tyr Ser Glu Asn Asn Glu Asn
    290                 295                 300

Tyr Ile Glu Val Pro Leu Ile Phe Asp Pro Val Thr Arg Glu Asp Leu
305                 310                 315                 320

His Met Asp Phe Lys Cys Val Val His Asn Thr Leu Ser Phe Gln Thr
                325                 330                 335
```

```
Leu Arg Thr Thr Val Lys Glu Ala Ser Ser Thr Phe Ser Glu Arg Cys
            340                 345                 350

Asp Asp Trp Gly Leu Asp Thr Met Arg Gln Ile Gln Val Phe Glu Asp
            355                 360                 365

Glu Pro Ala Arg Ile Lys Cys Pro Leu Phe Glu His Phe Leu Lys Phe
            370                 375                 380

Asn Tyr Ser Thr Ala His Ser Ala Gly Leu Thr Leu Ile Trp Tyr Trp
385                 390                 395                 400

Thr Arg Gln Asp Arg Asp Leu Glu Pro Ile Asn Phe Arg Leu Pro
            405                 410                 415

Glu Asn Arg Ile Ser Lys Glu Lys Asp Val Leu Trp Phe Arg Pro Thr
            420                 425                 430

Leu Leu Asn Asp Thr Gly Asn Tyr Thr Cys Met Leu Arg Asn Thr Thr
            435                 440                 445

Tyr Cys Ser Lys Val Ala Phe Pro Leu Glu Val Val Gln Lys Asp Ser
            450                 455                 460

Cys Phe Asn Ser Pro Met Lys Leu Pro Val His Lys Leu Tyr Ile Glu
465                 470                 475                 480

Tyr Gly Ile Gln Arg Ile Thr Cys Pro Asn Val Asp Gly Tyr Phe Pro
            485                 490                 495

Ser Ser Val Lys Pro Thr Ile Thr Trp Tyr Met Gly Cys Tyr Lys Ile
            500                 505                 510

Gln Asn Phe Asn Asn Val Ile Pro Glu Gly Met Asn Leu Ser Phe Leu
            515                 520                 525

Ile Ala Leu Ile Ser Asn Asn Gly Asn Tyr Thr Cys Val Val Thr Tyr
            530                 535                 540

Pro Glu Asn Gly Arg Thr Phe His Leu Thr Arg Thr Leu Thr Val Lys
545                 550                 555                 560

Val Val Gly Ser Pro Lys Asn Ala Val Pro Pro Val Ile His Ser Pro
            565                 570                 575

Asn Asp His Val Val Tyr Glu Lys Glu Pro Gly Glu Glu Leu Leu Ile
            580                 585                 590

Pro Cys Thr Val Tyr Phe Ser Phe Leu Met Asp Ser Arg Asn Glu Val
            595                 600                 605

Trp Trp Thr Ile Asp Gly Lys Lys Pro Asp Asp Ile Thr Ile Asp Val
            610                 615                 620

Thr Ile Asn Glu Ser Ile Ser His Ser Arg Thr Glu Asp Glu Thr Arg
625                 630                 635                 640

Thr Gln Ile Leu Ser Ile Lys Lys Val Thr Ser Glu Asp Leu Lys Arg
            645                 650                 655

Ser Tyr Val Cys His Ala Arg Ser Ala Lys Gly Glu Val Ala Lys Ala
            660                 665                 670

Ala Lys Val Lys Gln Lys Val Pro Ala Pro Arg Tyr Thr Val Ser Gly
            675                 680                 685

Glu Ser Lys Tyr Gly Pro Pro Cys Pro Pro Cys Pro Ala Pro Glu Phe
            690                 695                 700

Leu Gly Gly Pro Ser Val Phe Leu Phe Pro Pro Lys Pro Lys Asp Thr
705                 710                 715                 720

Leu Met Ile Ser Arg Thr Pro Glu Val Thr Cys Val Val Val Asp Val
            725                 730                 735

Ser Gln Glu Asp Pro Glu Val Gln Phe Asn Trp Tyr Val Asp Gly Val
            740                 745                 750
```

```
Glu Val His Asn Ala Lys Thr Lys Pro Arg Glu Glu Gln Phe Asn Ser
        755                 760                 765

Thr Tyr Arg Val Val Ser Val Leu Thr Val Leu His Gln Asp Trp Leu
    770                 775                 780

Asn Gly Lys Glu Tyr Lys Cys Lys Val Ser Asn Lys Gly Leu Pro Ser
785                 790                 795                 800

Ser Ile Glu Lys Thr Ile Ser Lys Ala Lys Gly Gln Pro Arg Glu Pro
                805                 810                 815

Gln Val Tyr Thr Leu Pro Pro Ser Gln Glu Glu Met Thr Lys Asn Gln
            820                 825                 830

Val Ser Leu Thr Cys Leu Val Lys Gly Phe Tyr Pro Ser Asp Ile Ala
        835                 840                 845

Val Glu Trp Glu Ser Asn Gly Gln Pro Glu Asn Asn Tyr Lys Thr Thr
    850                 855                 860

Pro Pro Val Leu Asp Ser Asp Gly Ser Phe Phe Leu Tyr Ser Arg Leu
865                 870                 875                 880

Thr Val Asp Lys Ser Arg Trp Gln Gly Asn Val Phe Ser Cys Ser
                885                 890                 895

Val Met His Glu Ala Leu His Asn His Tyr Thr Gln Lys Ser Leu Ser
            900                 905                 910

Leu Ser Leu Gly Lys
        915

<210> SEQ ID NO 51
<211> LENGTH: 2748
<212> TYPE: DNA
<213> ORGANISM: Homo sapiens

<400> SEQUENCE: 51
atggtgcttc tgtggtgtgt agtgagtctc tacttttatg gaatcctgca aagtgatgcc      60
tcagaacgct gcgatgactg gggactagac accatgaggc aaatccaagt gtttgaagat     120
gagccagctc gcatcaagtg cccactcttt gaacacttct tgaaattcaa ctacagcaca     180
gcccattcag ctggccttac tctgatctgg tattggacta gcaggaccg ggaccttgag      240
gagccaatta acttccgcct ccccgagaac cgcattagta aggagaaaga tgtgctgtgg     300
ttccggccca ctctcctcaa tgacactggc aactataccct gcatgttaag gaacactaca     360
tattgcagca agttgcatt tcccttggaa gttgttcaaa agacagctg tttcaattcc      420
cccatgaaac tcccagtgca taactgtat atagaatatg gcattcagag gatcacttgt      480
ccaaatgtag atggatattt tccttccagt gtcaaaccga ctatcacttg gtatatgggc      540
tgttataaaa tacagaattt taataatgta atacccgaag gtatgaactt gagttttctc      600
attgccttaa tttcaaataa tggaaattac acatgtgttg ttacatatcc agaaaatgga     660
cgtacgtttc atctcaccag gactctgact gtaaaggtag taggctctcc aaaaaatgca     720
gtgccccctg tgatccattc acctaatgat catgtggtct atgagaaaga accaggagag     780
gagctactca ttcctgtac ggtctatttt agttttctga tggattctcg caatgaggtt     840
tggtggacca ttgatggaaa aaaacctgat gacatcacta ttgatgtcac cattaacgaa     900
agtataagtc atagtagaac agaagatgaa acaagaactc agattttgag catcaagaaa     960
gttacctctg aggatctcaa gcgcagctat gtctgtcatg ctagaagtgc caaaggcgaa    1020
gttgccaaag cagccaaggt gaagcagaaa gtgccagctc aagatacac agtgcacaca    1080
ggggctgcca gaagctgccg gtttcgtggg aggcattaca gcggagtt caggctgaa       1140
```

```
ggggagcctg tagccctgag gtgccccag gtgccctact ggttgtgggc ctctgtcagc    1200
ccccgcatca acctgacatg gcataaaaat gactctgcta ggacggtccc aggagaagaa    1260
gagacacgga tgtgggccca ggacggtgct ctgtggcttc tgccagcctt gcaggaggac    1320
tctggcacct acgtctgcac tactagaaat gcttcttact gtgacaaaat gtccattgag    1380
ctcagagttt ttgagaatac agatgctttc ctgccgttca tctcataccc gcaaatttta    1440
accttgtcaa cctctggggt attagtatgc cctgacctga gtgaattcac ccgtgacaaa    1500
actgacgtga agattcaatg gtacaaggat tctcttcttt tggataaaga caatgagaaa    1560
tttctaagtg tgaggggac cactcactta ctcgtacacg atgtggccct ggaagatgct    1620
ggctattacc gctgtgtcct gacatttgcc catgaaggcc agcaatacaa catcactagg    1680
agtattgagc tacgcatcaa gaaaaaaaaa gaagagacca ttcctgtgat catttccccc    1740
ctcaagacca tatcagcttc tctggggtca agactgacaa tcccatgtaa ggtgtttctg    1800
ggaaccggca cacccttaac caccatgctg tggtggacgg ccaatgacac ccacatagag    1860
agcgcctacc cgggaggccg cgtgaccgag gggccacgcc aggaatattc agaaaataat    1920
gagaactaca ttgaagtgcc attgattttt gatcctgtca caagagagga tttgcacatg    1980
gattttaaat gtgttgtcca taatacctg agttttcaga cactacgcac cacagtcaag    2040
gaagcctcct ccacgttctc cggagacaaa actcacacat gcccaccgtg cccagcacct    2100
gaactcctgg gggaccgtc agtcttcctc ttccccccaa acccaagga caccctcatg    2160 atctcccgga cccctgaggt cacatgcgtg gtggtggacg tgagccacga agaccctgag    2220
gtcaagttca actggtacgt ggacggcgtg gaggtgcata atgccaagac aaagccgcgg    2280
gaggagcagt acaacagcac gtaccgtgtg gtcagcgtcc tcaccgtcct gcaccaggac    2340
tggctgaatg gcaaggagta caagtgcaag gtctccaaca aagccctccc agcccccatc    2400
gagaaaacca tctccaaagc caagggcag ccccgagaac cacaggtgta caccctgccc    2460
ccatcccggg atgagctgac caagaaccag gtcagcctga cctgcctggt caaaggcttc    2520
tatcccagcg acatcgccgt ggagtgggag agcaatgggc agccggagaa caactacaag    2580
accacgcctc ccgtgctgga ctccgacggc tccttcttcc tctatagcaa gctcaccgtg    2640
gacaagagca ggtggcagca ggggaacgtc ttctcatgct ccgtgatgca tgaggctctg    2700
cacaaccact acacgcagaa gagcctctcc ctgtctccgg gtaaatga                2748
```

<210> SEQ ID NO 52
<211> LENGTH: 915
<212> TYPE: PRT
<213> ORGANISM: Homo sapiens

<400> SEQUENCE: 52

```
Met Val Leu Leu Trp Cys Val Val Ser Leu Tyr Phe Tyr Gly Ile Leu
 1               5                  10                  15

Gln Ser Asp Ala Ser Glu Arg Cys Asp Asp Trp Gly Leu Asp Thr Met
                20                  25                  30

Arg Gln Ile Gln Val Phe Glu Asp Glu Pro Ala Arg Ile Lys Cys Pro
            35                  40                  45

Leu Phe Glu His Phe Leu Lys Phe Asn Tyr Ser Thr Ala His Ser Ala
        50                  55                  60

Gly Leu Thr Leu Ile Trp Tyr Trp Thr Arg Gln Asp Arg Asp Leu Glu
 65                  70                  75                  80

Glu Pro Ile Asn Phe Arg Leu Pro Glu Asn Arg Ile Ser Lys Glu Lys
                85                  90                  95
```

```
Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
            115                 120                 125

Leu Glu Val Val Gln Lys Asp Ser Cys Phe Asn Ser Pro Met Lys Leu
            130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
            195                 200                 205

Asn Tyr Thr Cys Val Val Thr Tyr Pro Glu Asn Gly Arg Thr Phe His
            210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
            275                 280                 285

Pro Asp Asp Ile Thr Ile Asp Val Thr Ile Asn Glu Ser Ile Ser His
            290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350

Ala Pro Arg Tyr Thr Val His Thr Gly Ala Ala Arg Ser Cys Arg Phe
            355                 360                 365

Arg Gly Arg His Tyr Lys Arg Glu Phe Arg Leu Glu Gly Glu Pro Val
            370                 375                 380

Ala Leu Arg Cys Pro Gln Val Pro Tyr Trp Leu Trp Ala Ser Val Ser
385                 390                 395                 400

Pro Arg Ile Asn Leu Thr Trp His Lys Asn Asp Ser Ala Arg Thr Val
                405                 410                 415

Pro Gly Glu Glu Glu Thr Arg Met Trp Ala Gln Asp Gly Ala Leu Trp
            420                 425                 430

Leu Leu Pro Ala Leu Gln Glu Asp Ser Gly Thr Tyr Val Cys Thr Thr
            435                 440                 445

Arg Asn Ala Ser Tyr Cys Asp Lys Met Ser Ile Glu Leu Arg Val Phe
450                 455                 460

Glu Asn Thr Asp Ala Phe Leu Pro Phe Ile Ser Tyr Pro Gln Ile Leu
465                 470                 475                 480

Thr Leu Ser Thr Ser Gly Val Leu Val Cys Pro Asp Leu Ser Glu Phe
                485                 490                 495

Thr Arg Asp Lys Thr Asp Val Lys Ile Gln Trp Tyr Lys Asp Ser Leu
            500                 505                 510
```

```
Leu Leu Asp Lys Asp Asn Glu Lys Phe Leu Ser Val Arg Gly Thr Thr
            515                 520                 525

His Leu Leu Val His Asp Val Ala Leu Glu Asp Ala Gly Tyr Tyr Arg
        530                 535                 540

Cys Val Leu Thr Phe Ala His Glu Gly Gln Gln Tyr Asn Ile Thr Arg
545                 550                 555                 560

Ser Ile Glu Leu Arg Ile Lys Lys Lys Glu Glu Thr Ile Pro Val
                565                 570                 575

Ile Ile Ser Pro Leu Lys Thr Ile Ser Ala Ser Leu Gly Ser Arg Leu
            580                 585                 590

Thr Ile Pro Cys Lys Val Phe Leu Gly Thr Gly Thr Pro Leu Thr Thr
        595                 600                 605

Met Leu Trp Trp Thr Ala Asn Asp Thr His Ile Glu Ser Ala Tyr Pro
    610                 615                 620

Gly Gly Arg Val Thr Glu Gly Pro Arg Gln Glu Tyr Ser Glu Asn Asn
625                 630                 635                 640

Glu Asn Tyr Ile Glu Val Pro Leu Ile Phe Asp Pro Val Thr Arg Glu
                645                 650                 655

Asp Leu His Met Asp Phe Lys Cys Val Val His Asn Thr Leu Ser Phe
            660                 665                 670

Gln Thr Leu Arg Thr Thr Val Lys Glu Ala Ser Ser Thr Phe Ser Gly
        675                 680                 685

Asp Lys Thr His Thr Cys Pro Pro Cys Pro Ala Pro Glu Leu Leu Gly
    690                 695                 700

Gly Pro Ser Val Phe Leu Phe Pro Pro Lys Pro Lys Asp Thr Leu Met
705                 710                 715                 720

Ile Ser Arg Thr Pro Glu Val Thr Cys Val Val Val Asp Val Ser His
                725                 730                 735

Glu Asp Pro Glu Val Lys Phe Asn Trp Tyr Val Asp Gly Val Glu Val
            740                 745                 750

His Asn Ala Lys Thr Lys Pro Arg Glu Glu Gln Tyr Asn Ser Thr Tyr
        755                 760                 765

Arg Val Val Ser Val Leu Thr Val Leu His Gln Asp Trp Leu Asn Gly
    770                 775                 780

Lys Glu Tyr Lys Cys Lys Val Ser Asn Lys Ala Leu Pro Ala Pro Ile
785                 790                 795                 800

Glu Lys Thr Ile Ser Lys Ala Lys Gly Gln Pro Arg Glu Pro Gln Val
                805                 810                 815

Tyr Thr Leu Pro Pro Ser Arg Asp Glu Leu Thr Lys Asn Gln Val Ser
            820                 825                 830

Leu Thr Cys Leu Val Lys Gly Phe Tyr Pro Ser Asp Ile Ala Val Glu
        835                 840                 845

Trp Glu Ser Asn Gly Gln Pro Glu Asn Asn Tyr Lys Thr Thr Pro Pro
    850                 855                 860

Val Leu Asp Ser Asp Gly Ser Phe Phe Leu Tyr Ser Lys Leu Thr Val
865                 870                 875                 880

Asp Lys Ser Arg Trp Gln Gln Gly Asn Val Phe Ser Cys Ser Val Met
                885                 890                 895

His Glu Ala Leu His Asn His Tyr Thr Gln Lys Ser Leu Ser Leu Ser
            900                 905                 910

Pro Gly Lys
        915
```

<210> SEQ ID NO 53
<211> LENGTH: 2754
<212> TYPE: DNA
<213> ORGANISM: Homo sapiens

<400> SEQUENCE: 53

```
atggtgcttc tgtggtgtgt agtgagtctc tactttatg gaatcctgca aagtgatgcc        60
tcagaacgct gcgatgactg gggactagac accatgaggc aaatccaagt gtttgaagat      120
gagccagctc gcatcaagtg cccactcttt gaacacttct tgaaattcaa ctacagcaca      180
gcccattcag ctggccttac tctgatctgg tattggacta gcaggaccg ggaccttgag        240
gagccaatta acttccgcct ccccgagaac cgcattagta aggagaaaga tgtgctgtgg      300
ttccggccca ctctcctcaa tgacactggc aactatacct gcatgttaag gaacactaca      360
tattgcagca agttgcatt tcccttggaa gttgttcaaa aagacagctg tttcaattcc      420
cccatgaaac tcccagtgca taaactgtat atagaatatg gcattcagag gatcacttgt      480
ccaaatgtag atggatattt tccttccagt gtcaaaccga ctatcacttg gtatatgggc      540
tgttataaaa tacagaattt taataatgta ataccccgaag gtatgaactt gagtttcctc      600
attgccttaa tttcaaataa tggaaattac acatgtgttg ttacatatcc agaaaatgga      660
cgtacgtttc atctcaccag gactctgact gtaaaggtag taggctctcc aaaaaatgca      720
gtgccccctg tgatccattc acctaatgat catgtggtct atgagaaaga accaggagag      780
gagctactca ttccctgtac ggtctatttt agttttctga tggattctcg caatgaggtt      840
tggtggacca ttgatggaaa aaacctgat gacatcacta ttgatgtcac cattaacgaa        900
agtataagtc atagtagaac agaagatgaa caagaactc agattttgag catcaagaaa       960
gttacctctg aggatctcaa gcgcagctat gtctgtcatg ctagaagtgc caaaggcgaa      1020
gttgccaaag cagccaaggt gaagcagaaa gtgccagctc aagatacac agtgcacaca       1080
ggggctgcca aagctgccg gtttcgtggg aggcattaca gcgggagtt caggctggaa        1140
ggggagcctg tagccctgag gtgcccccag gtgccctact ggttgtgggc ctctgtcagc      1200
cccgcatca acctgacatg gcataaaaat gactctgcta ggacggtccc aggagaagaa       1260
gagacacgga tgtgggccca ggacggtgct ctgtggcttc tgccagcctt gcaggaggac      1320
tctggcacct acgtctgcac tactagaaat gcttcttact gtgacaaaat gtccattgag      1380
ctcagagttt ttgagaatac agatgctttc ctgccgttca tctcataccc gcaaatttta      1440
accttgtcaa cctctggggt attagtatgc cctgacctga gtgaattcac ccgtgacaaa      1500
actgacgtga agattcaatg gtacaaggat tctcttcttt tggataaaga caatgagaaa      1560
tttctaagtg tgagggggac cactcactta ctcgtacacg atgtggccct ggaagatgct      1620
ggctattacc gctgtgtcct gacatttgcc catgaaggcc agcaatacaa catcactagg      1680
agtattgagc tacgcatcaa gaaaaaaaa gaagagacca ttcctgtgat catttccccc      1740
ctcaagacca tatcagcttc tctggggtca agactgacaa tcccatgtaa ggtgtttctg      1800
ggaaccggca cacccttaac caccatgctg tggtggacgg ccaatgacac ccacatagag      1860
agcgcctacc cgggaggccg cgtgaccgag gggccacgcc aggaatattc agaaaataat      1920
gagaactaca ttgaagtgcc attgattttt gatcctgtca agagagga tttgcacatg      1980
gatttttaaat gtgttgtcca taatccctg agttttcaga cactacgcac cacagtcaag     2040
gaagcctcct ccacgttctc cggagagtcc aaatacggtc cgccatgccc atcatgccca     2100
gcacctgagt tcctgggggg accatcagtc ttcctgttcc ccccaaaacc caaggacact     2160
```

-continued

```
ctcatgatct cccggacccc tgaggtcacg tgcgtggtgg tggacgtgag ccaggaagac    2220
cccgaggtcc agttcaactg gtacgtggat ggcgtggagg tgcataatgc caagacaaag    2280
ccgcgggagg agcagttcaa cagcacgtac cgtgtggtca gcgtcctcac cgtcctgcac    2340
caggactggc tgaacggcaa ggagtacaag tgcaaggtct ccaacaaagg cctcccgtcc    2400
tccatcgaga aaaccatctc caaagccaaa gggcagcccc gagagccaca ggtgtacacc    2460
ctgcccccat cccaggagga gatgaccaag aaccaggtca gcctgacctg cctggtcaaa    2520
ggcttctacc ccagcgacat cgccgtggag tgggagagca atgggcagcc ggagaacaac    2580
tacaagacca cgcctcccgt gctggactcc gacggctcct tcttcctcta cagcaggcta    2640
accgtggaca agagcaggtg gcaggagggg aatgtcttct catgctccgt gatgcatgag    2700
gctctgcaca accactacac acagaagagc ctctccctgt ctctgggtaa atga         2754
```

<210> SEQ ID NO 54
<211> LENGTH: 917
<212> TYPE: PRT
<213> ORGANISM: Homo sapiens

<400> SEQUENCE: 54

```
Met Val Leu Leu Trp Cys Val Val Ser Leu Tyr Phe Tyr Gly Ile Leu
 1               5                  10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270
```

```
Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
        290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Lys Val Lys Gln Lys Val Pro
        340                 345                 350

Ala Pro Arg Tyr Thr Val His Thr Gly Ala Ala Arg Ser Cys Arg Phe
        355                 360                 365

Arg Gly Arg His Tyr Lys Arg Glu Phe Arg Leu Glu Gly Pro Val
        370                 375                 380

Ala Leu Arg Cys Pro Gln Val Pro Tyr Trp Leu Trp Ala Ser Val Ser
385                 390                 395                 400

Pro Arg Ile Asn Leu Thr Trp His Lys Asn Asp Ser Ala Arg Thr Val
                405                 410                 415

Pro Gly Glu Glu Glu Thr Arg Met Trp Ala Gln Asp Gly Ala Leu Trp
        420                 425                 430

Leu Leu Pro Ala Leu Gln Glu Asp Ser Gly Thr Tyr Val Cys Thr Thr
        435                 440                 445

Arg Asn Ala Ser Tyr Cys Asp Lys Met Ser Ile Glu Leu Arg Val Phe
450                 455                 460

Glu Asn Thr Asp Ala Phe Leu Pro Phe Ile Ser Tyr Pro Gln Ile Leu
465                 470                 475                 480

Thr Leu Ser Thr Ser Gly Val Leu Val Cys Pro Asp Leu Ser Glu Phe
                485                 490                 495

Thr Arg Asp Lys Thr Asp Val Lys Ile Gln Trp Tyr Lys Asp Ser Leu
        500                 505                 510

Leu Leu Asp Lys Asp Asn Glu Lys Phe Leu Ser Val Arg Gly Thr Thr
        515                 520                 525

His Leu Leu Val His Asp Val Ala Leu Glu Asp Ala Gly Tyr Tyr Arg
        530                 535                 540

Cys Val Leu Thr Phe Ala His Glu Gly Gln Gln Tyr Asn Ile Thr Arg
545                 550                 555                 560

Ser Ile Glu Leu Arg Ile Lys Lys Lys Lys Glu Glu Thr Ile Pro Val
                565                 570                 575

Ile Ile Ser Pro Leu Lys Thr Ile Ser Ala Ser Leu Gly Ser Arg Leu
        580                 585                 590

Thr Ile Pro Cys Lys Val Phe Leu Gly Thr Gly Thr Pro Leu Thr Thr
        595                 600                 605

Met Leu Trp Trp Thr Ala Asn Asp Thr His Ile Glu Ser Ala Tyr Pro
        610                 615                 620

Gly Gly Arg Val Thr Glu Gly Pro Arg Gln Glu Tyr Ser Glu Asn Asn
625                 630                 635                 640

Glu Asn Tyr Ile Glu Val Pro Leu Ile Phe Asp Pro Val Thr Arg Glu
                645                 650                 655

Asp Leu His Met Asp Phe Lys Cys Val Val His Asn Thr Leu Ser Phe
        660                 665                 670

Gln Thr Leu Arg Thr Thr Val Lys Glu Ala Ser Ser Thr Phe Ser Gly
        675                 680                 685

Glu Ser Lys Tyr Gly Pro Pro Cys Pro Ser Cys Pro Ala Pro Glu Phe
```

```
                  690             695             700
Leu Gly Gly Pro Ser Val Phe Leu Phe Pro Pro Lys Pro Lys Asp Thr
705                 710                 715                 720

Leu Met Ile Ser Arg Thr Pro Glu Val Thr Cys Val Val Val Asp Val
                725                 730                 735

Ser Gln Glu Asp Pro Glu Val Gln Phe Asn Trp Tyr Val Asp Gly Val
            740                 745                 750

Glu Val His Asn Ala Lys Thr Lys Pro Arg Glu Gln Phe Asn Ser
        755                 760                 765

Thr Tyr Arg Val Val Ser Val Leu Thr Val Leu His Gln Asp Trp Leu
770                 775                 780

Asn Gly Lys Glu Tyr Lys Cys Lys Val Ser Asn Lys Gly Leu Pro Ser
785                 790                 795                 800

Ser Ile Glu Lys Thr Ile Ser Lys Ala Lys Gly Gln Pro Arg Glu Pro
                805                 810                 815

Gln Val Tyr Thr Leu Pro Pro Ser Gln Glu Met Thr Lys Asn Gln
            820                 825                 830

Val Ser Leu Thr Cys Leu Val Lys Gly Phe Tyr Pro Ser Asp Ile Ala
            835                 840                 845

Val Glu Trp Glu Ser Asn Gly Gln Pro Glu Asn Asn Tyr Lys Thr Thr
850                 855                 860

Pro Pro Val Leu Asp Ser Asp Gly Ser Phe Phe Leu Tyr Ser Arg Leu
865                 870                 875                 880

Thr Val Asp Lys Ser Arg Trp Gln Glu Gly Asn Val Phe Ser Cys Ser
                885                 890                 895

Val Met His Glu Ala Leu His Asn His Tyr Thr Gln Lys Ser Leu Ser
            900                 905                 910

Leu Ser Leu Gly Lys
        915
```

<210> SEQ ID NO 55
<211> LENGTH: 2754
<212> TYPE: DNA
<213> ORGANISM: Homo sapiens

<400> SEQUENCE: 55

```
atggtgcttc tgtggtgtgt agtgagtctc tacttttatg gaatcctgca aagtgatgcc      60
tcagaacgct gcgatgactg gggactagac accatgaggc aaatccaagt gtttgaagat     120
gagccagctc gcatcaagtg cccactcttt gaacacttct tgaaattcaa ctacagcaca     180
gcccattcag ctggccttac tctgatctgg tattggacta ggcaggaccg ggaccttgag     240
gagccaatta acttccgcct ccccgagaac cgcattagta ggagaaaga gtgctgtgtg     300
ttccggccca ctctcctcaa tgacactggc aactataccc tgcatgttaag gaacactaca     360
tattgcagca agttgcatt tcccttggaa gttgttcaaa agacagctg tttcaattcc     420
cccatgaaac tcccagtgca taaactgtat atagaatatg cattcagag gatcacttgt     480
ccaaatgtag atggatattt tccttccagt gtcaaaccga ctatcacttg gtatatgggc     540
tgttataaaa tacagaattt taataatgta atacccgaag gtatgaactt gagtttcctc     600
attgccttaa tttcaaataa tggaaattac acatgtgttg ttacatatcc agaaaatgga     660
cgtacgtttc atctcaccag gactctgact gtaaaggtag taggctctcc aaaaaatgca     720
gtgcccctg tgatccattc acctaatgat catgtggtct atgagaaaga accaggagag     780
gagctactca ttccctgtac ggtctatttt agttttctga tggattctcg caatgaggtt     840
```

```
tggtggacca ttgatggaaa aaaacctgat gacatcacta ttgatgtcac cattaacgaa      900
agtataagtc atagtagaac agaagatgaa acaagaactc agattttgag catcaagaaa      960
gttacctctg aggatctcaa gcgcagctat gtctgtcatg ctagaagtgc aaaggcgaa      1020
gttgccaaag cagccaaggt gaagcagaaa gtgccagctc aagatacac agtgcacaca      1080
ggggctgcca gaagctgccg gtttcgtggg aggcattaca agcgggagtt caggctggaa      1140
ggggagcctg tagccctgag gtgcccccag gtgccctact ggttgtgggc ctctgtcagc      1200
ccccgcatca acctgacatg gcataaaaat gactctgcta ggacggtccc aggagaagaa      1260
gagacacgga tgtgggccca ggacggtgct ctgtggcttc tgccagcctt gcaggaggac      1320
tctggcacct acgtctgcac tactagaaat gcttcttact gtgacaaaat gtccattgag      1380
ctcagagttt ttgagaatac agatgctttc ctgccgttca tctcataccc gcaaatttta      1440
accttgtcaa cctctggggt attagtatgc cctgacctga gtgaattcac ccgtgacaaa      1500
actgacgtga agattcaatg gtacaaggat tctcttcttt tggataaaga caatgagaaa      1560
tttctaagtg tgaggggggac cactcactta ctcgtacacg atgtggccct ggaagatgct      1620
ggctattacc gctgtgtcct gacatttgcc catgaaggcc agcaatacaa catcactagg      1680
agtattgagc tacgcatcaa gaaaaaaaa gaagagacca ttcctgtgat catttccccc      1740
ctcaagacca tatcagcttc tctggggtca agactgacaa tcccatgtaa ggtgtttctg      1800
ggaaccggca caccttaac caccatgctg tggtggacgg ccaatgacac ccacatagag      1860
agcgcctacc cgggaggccg cgtgaccgag gggccacgcc aggaatattc agaaaataat      1920
gagaactaca ttgaagtgcc attgattttt gatcctgtca caagagagga tttgcacatg      1980
gattttaaat gtgttgtcca aatacactg agttttcaga cactacgcac acagtcaag       2040
gaagcctcct ccacgttctc cggagagtcc aaatacggtc cgccatgccc accatgccca      2100
gcacctgagt tcctgggggg accatcagtc ttcctgttcc ccccaaaacc caaggacact      2160
ctcatgatct cccggacccc tgaggtcacg tgcgtggtgg tggacgtgag ccaggaagac      2220
cccgaggtcc agttcaactg gtacgtggat ggcgtggagg tgcataatgc caagacaaag      2280
ccgcgggagg agcagttcaa cagcacgtac cgtgtggtca gcgtcctcac cgtcctgcac      2340
caggactggc tgaacggcaa ggagtacaag tgcaaggtct ccaacaaagg cctcccgtcc      2400
tccatcgaga aaaccatctc caaagccaaa gggcagcccc gagagccaca ggtgtacacc      2460
ctgcccccat cccaggagga gatgaccaag aaccaggtca gcctgacctg cctggtcaaa      2520
ggcttctacc ccagcgacat cgccgtggag tgggagagca atgggcagcc ggagaacaac      2580
tacaagacca cgcctcccgt gctggactcc gacggctcct tcttcctcta cagcaggcta      2640
accgtggaca agagcaggtg gcaggagggg aatgtcttct catgctccgt gatgcatgag      2700
gctctgcaca accactacac acagaagagc ctctccctgt ctctgggtaa atga           2754
```

<210> SEQ ID NO 56
<211> LENGTH: 917
<212> TYPE: PRT
<213> ORGANISM: Homo sapiens

<400> SEQUENCE: 56

Met Val Leu Leu Trp Cys Val Val Ser Leu Tyr Phe Tyr Gly Ile Leu
 1               5                  10                  15

Gln Ser Asp Ala Ser Glu Arg Cys Asp Asp Trp Gly Leu Asp Thr Met
            20                  25                  30

-continued

```
Arg Gln Ile Gln Val Phe Glu Asp Glu Pro Ala Arg Ile Lys Cys Pro
             35                  40                  45
Leu Phe Glu His Phe Leu Lys Phe Asn Tyr Ser Thr Ala His Ser Ala
 50                  55                  60
Gly Leu Thr Leu Ile Trp Tyr Trp Thr Arg Gln Asp Arg Asp Leu Glu
 65                  70                  75                  80
Glu Pro Ile Asn Phe Arg Leu Pro Glu Asn Arg Ile Ser Lys Glu Lys
             85                  90                  95
Asp Val Leu Trp Phe Arg Pro Thr Leu Leu Asn Asp Thr Gly Asn Tyr
            100                 105                 110
Thr Cys Met Leu Arg Asn Thr Thr Tyr Cys Ser Lys Val Ala Phe Pro
            115                 120                 125
Leu Glu Val Val Gln Lys Asp Ser Cys Phe Asn Ser Pro Met Lys Leu
130                 135                 140
Pro Val His Lys Leu Tyr Ile Glu Tyr Gly Ile Gln Arg Ile Thr Cys
145                 150                 155                 160
Pro Asn Val Asp Gly Tyr Phe Pro Ser Ser Val Lys Pro Thr Ile Thr
            165                 170                 175
Trp Tyr Met Gly Cys Tyr Lys Ile Gln Asn Phe Asn Asn Val Ile Pro
            180                 185                 190
Glu Gly Met Asn Leu Ser Phe Leu Ile Ala Leu Ile Ser Asn Asn Gly
            195                 200                 205
Asn Tyr Thr Cys Val Val Thr Tyr Pro Glu Asn Gly Arg Thr Phe His
            210                 215                 220
Leu Thr Arg Thr Leu Thr Val Lys Val Val Gly Ser Pro Lys Asn Ala
225                 230                 235                 240
Val Pro Pro Val Ile His Ser Pro Asn Asp His Val Val Tyr Glu Lys
            245                 250                 255
Glu Pro Gly Glu Glu Leu Leu Ile Pro Cys Thr Val Tyr Phe Ser Phe
            260                 265                 270
Leu Met Asp Ser Arg Asn Glu Val Trp Trp Thr Ile Asp Gly Lys Lys
            275                 280                 285
Pro Asp Asp Ile Thr Ile Asp Val Thr Ile Asn Glu Ser Ile Ser His
            290                 295                 300
Ser Arg Thr Glu Asp Glu Thr Arg Thr Gln Ile Leu Ser Ile Lys Lys
305                 310                 315                 320
Val Thr Ser Glu Asp Leu Lys Arg Ser Tyr Val Cys His Ala Arg Ser
            325                 330                 335
Ala Lys Gly Glu Val Ala Lys Ala Ala Lys Val Lys Gln Lys Val Pro
            340                 345                 350
Ala Pro Arg Tyr Thr Val His Thr Gly Ala Ala Arg Ser Cys Arg Phe
            355                 360                 365
Arg Gly Arg His Tyr Lys Arg Glu Phe Arg Leu Glu Gly Glu Pro Val
            370                 375                 380
Ala Leu Arg Cys Pro Gln Val Pro Tyr Trp Leu Trp Ala Ser Val Ser
385                 390                 395                 400
Pro Arg Ile Asn Leu Thr Trp His Lys Asn Asp Ser Ala Arg Thr Val
            405                 410                 415
Pro Gly Glu Glu Glu Thr Arg Met Trp Ala Gln Asp Gly Ala Leu Trp
            420                 425                 430
Leu Leu Pro Ala Leu Gln Glu Asp Ser Gly Thr Tyr Val Cys Thr Thr
            435                 440                 445
Arg Asn Ala Ser Tyr Cys Asp Lys Met Ser Ile Glu Leu Arg Val Phe
```

-continued

```
                450                 455                 460
Glu Asn Thr Asp Ala Phe Leu Pro Phe Ile Ser Tyr Pro Gln Ile Leu
465                 470                 475                 480

Thr Leu Ser Thr Ser Gly Val Leu Val Cys Pro Asp Leu Ser Glu Phe
                485                 490                 495

Thr Arg Asp Lys Thr Asp Val Lys Ile Gln Trp Tyr Lys Asp Ser Leu
                500                 505                 510

Leu Leu Asp Lys Asp Asn Glu Lys Phe Leu Ser Val Arg Gly Thr Thr
                515                 520                 525

His Leu Leu Val His Asp Val Ala Leu Glu Asp Ala Gly Tyr Tyr Arg
                530                 535                 540

Cys Val Leu Thr Phe Ala His Glu Gly Gln Gln Tyr Asn Ile Thr Arg
545                 550                 555                 560

Ser Ile Glu Leu Arg Ile Lys Lys Lys Glu Thr Ile Pro Val
                565                 570                 575

Ile Ile Ser Pro Leu Lys Thr Ile Ser Ala Ser Leu Gly Ser Arg Leu
                580                 585                 590

Thr Ile Pro Cys Lys Val Phe Leu Gly Thr Gly Thr Pro Leu Thr Thr
                595                 600                 605

Met Leu Trp Trp Thr Ala Asn Asp Thr His Ile Glu Ser Ala Tyr Pro
610                 615                 620

Gly Gly Arg Val Thr Glu Gly Pro Arg Gln Glu Tyr Ser Glu Asn Asn
625                 630                 635                 640

Glu Asn Tyr Ile Glu Val Pro Leu Ile Phe Asp Pro Val Thr Arg Glu
                645                 650                 655

Asp Leu His Met Asp Phe Lys Cys Val Val His Asn Thr Leu Ser Phe
                660                 665                 670

Gln Thr Leu Arg Thr Val Lys Glu Ala Ser Ser Thr Phe Ser Gly
                675                 680                 685

Glu Ser Lys Tyr Gly Pro Pro Cys Pro Pro Cys Pro Ala Pro Glu Phe
                690                 695                 700

Leu Gly Gly Pro Ser Val Phe Leu Phe Pro Pro Lys Pro Lys Asp Thr
705                 710                 715                 720

Leu Met Ile Ser Arg Thr Pro Glu Val Thr Cys Val Val Val Asp Val
                725                 730                 735

Ser Gln Glu Asp Pro Glu Val Gln Phe Asn Trp Tyr Val Asp Gly Val
                740                 745                 750

Glu Val His Asn Ala Lys Thr Lys Pro Arg Glu Glu Gln Phe Asn Ser
                755                 760                 765

Thr Tyr Arg Val Val Ser Val Leu Thr Val Leu His Gln Asp Trp Leu
770                 775                 780

Asn Gly Lys Glu Tyr Lys Cys Lys Val Ser Asn Lys Gly Leu Pro Ser
785                 790                 795                 800

Ser Ile Glu Lys Thr Ile Ser Lys Ala Lys Gly Gln Pro Arg Glu Pro
                805                 810                 815

Gln Val Tyr Thr Leu Pro Pro Ser Gln Glu Glu Met Thr Lys Asn Gln
                820                 825                 830

Val Ser Leu Thr Cys Leu Val Lys Gly Phe Tyr Pro Ser Asp Ile Ala
                835                 840                 845

Val Glu Trp Glu Ser Asn Gly Gln Pro Glu Asn Asn Tyr Lys Thr Thr
                850                 855                 860

Pro Pro Val Leu Asp Ser Asp Gly Ser Phe Phe Leu Tyr Ser Arg Leu
865                 870                 875                 880
```

```
Thr Val Asp Lys Ser Arg Trp Gln Glu Gly Asn Val Phe Ser Cys Ser
            885                 890                 895

Val Met His Glu Ala Leu His Asn His Tyr Thr Gln Lys Ser Leu Ser
            900                 905                 910

Leu Ser Leu Gly Lys
        915
```

We claim:

1. A recombinant nucleic acid molecule encoding a fusion polypeptide which forms a multimer capable of binding interleukin-1 (IL-1) to form a nonfunctional complex, wherein the nucleic acid molecule comprises the nucleic acid sequence of SEQ ID NO:51.

2. The nucleic acid of claim 1 encoding a fusion polypeptide comprising the amino acid sequence of SEQ ID NO:52.

3. A vector comprising the nucleic acid molecule of claim 1.

4. A host-vector system for the production of a fusion polypeptide, comprising the vector of claim 3 in a suitable host cell.

5. A method of producing a fusion polypeptide, comprising growing cells of the host-vector system of claim 4, under conditions permitting production of the fusion polypeptide and recovering the fusion polypeptide so produced.

6. A recombinant nucleic acid molecule encoding a fusion polypeptide which forms a multimer capable of binding interleukin-1 (IL-1) to form a nonfunctional complex, wherein the nucleic acid molecule comprises the nucleic acid sequence of SEQ ID NO:53.

7. The nucleic acid of claim 6 encoding a fusion polypeptide comprising the amino acid sequence of SEQ ID NO:54.

8. A recombinant nucleic acid molecule encoding a fusion polypeptide which forms a multimer capable of binding interleukin-1 (IL-1) to form a nonfunctional complex, wherein the nucleic acid molecule comprises the nucleic acid sequence of SEQ ID NO:55.

9. The nucleic acid of claim 8 encoding a fusion polypeptide comprising the amino acid sequence of SEQ ID NO:56.

10. A fusion polypeptide comprising the amino acid sequence of SEQ ID NO:52.

11. A composition comprising a multimer of the fusion polypeptide of claim 10.

12. The composition of claim 11 wherein the multimer is a dimer.

13. A method of treating arthritis, comprising administering a therapeutically effective amount of the composition of claim 12.

* * * * *